United States Patent
Nadzan et al.

(10) Patent No.: US 11,396,659 B2
(45) Date of Patent: Jul. 26, 2022

(54) NUCLEOTIDE SEQUENCES AND CORRESPONDING POLYPEPTIDES CONFERRING MODIFIED PHENOTYPE CHARACTERISTICS IN PLANTS

(71) Applicant: CERES, INC., Thousand Oaks, CA (US)

(72) Inventors: Gregory Nadzan, Woodland Hills, CA (US); Richard Schneeberger, Carlsbad, CA (US); Han Suk Kim, Pinole, CA (US); David Van-dinh Dang, San Diego, CA (US); Kenneth A. Feldmann, Tucson, AZ (US); Roger Pennell, Malibu, CA (US); Shing Kwok, Fairfax, VA (US); Hongyu Zhang, Temple City, CA (US); Cory Christensen, Zionsville, IN (US); Jack Okamuro, Santa Cruz, CA (US); Fasong Zhou, Wuhan (CN); Wuyi Wang, Newbury Park, CA (US); Emilio Margolles-Clark, Miami, FL (US); Gerard Magpantay, Canoga Park, CA (US); Julissa Sosa, Northridge, CA (US); Nestor Apuya, Culver City, CA (US); Kerstin Piccolo, Fair Oaks, CA (US); Bonnie Hund, Pueblo, CO (US); Nickolai Alexandrov, Newbury Park, CA (US); Vyacheslav Brover, Rockville, MD (US); Peter Mascia, Thousand Oaks, CA (US)

(73) Assignee: Ceres, Inc, Thousand Oaks, CA (US)

( * ) Notice: Subject to any disclaimer, the term of this patent is extended or adjusted under 35 U.S.C. 154(b) by 250 days.

(21) Appl. No.: 16/554,116

(22) Filed: Aug. 28, 2019

(65) Prior Publication Data

US 2020/0056199 A1 Feb. 20, 2020

Related U.S. Application Data

(60) Division of application No. 14/627,544, filed on Feb. 20, 2015, now Pat. No. 10,428,344, which is a continuation-in-part of application No. 13/644,359, filed on Oct. 4, 2012, now Pat. No. 9,777,287, which is a continuation-in-part of application No. 13/465,846, filed on May 7, 2012, now abandoned, which is a division of application No. 10/572,827, filed as application No. PCT/US03/25997 on Aug. 18, 2003, now Pat. No. 8,193,409, said application No. 14/627,544 is a continuation-in-part of application No. 14/175,856, filed on Feb. 7, 2014, now abandoned, which is an application for the reissue of Pat. No. 8,110,724, filed as application No. PCT/US2007/006651 on Mar. 14, 2007, said application No. 13/644,359 is a continuation-in-part of application No. 11/779,266, filed on Jul. 17, 2007, now abandoned, which is a continuation-in-part of application No. 11/778,060, filed on Jul. 15, 2007, now abandoned, which is a continuation-in-part of application No. 11/248,547, filed on Oct. 12, 2005, now Pat. No. 7,244,879, said application No. 13/644,359 is a continuation-in-part of application No. 12/514,991, filed as application No. PCT/US2007/085007 on Nov. 16, 2007, now abandoned, said application No. 13/644,359 is a continuation-in-part of application No. 12/445,005, filed as application No. PCT/US2007/081301 on Oct. 12, 2007, now abandoned, said application No. 13/644,359 is a continuation-in-part of application No. 12/515,707, filed as application No.

(Continued)

(51) Int. Cl.
*C12N 15/82* (2006.01)
*C12Q 1/6895* (2018.01)
*C07K 14/415* (2006.01)

(52) U.S. Cl.
CPC ........ *C12N 15/8271* (2013.01); *C07K 14/415* (2013.01); *C12N 15/8261* (2013.01); *C12Q 1/6895* (2013.01); *Y02A 40/146* (2018.01)

(58) Field of Classification Search
CPC .................................................. C12N 15/8271
USPC ....................................................... 800/267
See application file for complete search history.

(56) References Cited

U.S. PATENT DOCUMENTS

| 7,635,800 B2 | 12/2009 | Ratcliffe et al. |
| 7,696,409 B2 | 4/2010 | Schneeberger et al. |

(Continued)

FOREIGN PATENT DOCUMENTS

| EP | 1033405 | 9/2000 |
| WO | WO 2004/031349 | 4/2004 |
| WO | 2009/105612 | 8/2009 |

OTHER PUBLICATIONS

Q9C9V8_ARATH (Jun. 1, 2001) (Year: 2001).*

(Continued)

*Primary Examiner* — Li Zheng
(74) *Attorney, Agent, or Firm* — Dentons US LLP

(57) ABSTRACT

Methods and materials for modulating low-nitrogen tolerance levels in plants are disclosed. For example, nucleic acids encoding low nitrogen tolerance-modulating polypeptides are disclosed as well as methods for using such nucleic acids to transform plant cells. Also disclosed are plants having increased low-nitrogen tolerance levels and plant products produced from plants having increased low-nitrogen tolerance levels.

11 Claims, 166 Drawing Sheets

Specification includes a Sequence Listing.

Related U.S. Application Data

PCT/US2007/085439 on Nov. 21, 2017, now abandoned, said application No. 13/644,359 is a continuation-in-part of application No. 12/615,920, filed on Nov. 10, 2009, now Pat. No. 8,471,099, which is a continuation of application No. 11/114,963, filed on Apr. 25, 2005, now Pat. No. 7,696,409, said application No. 13/644,359 is a continuation-in-part of application No. 12/605,261, filed on Oct. 23, 2009, now abandoned, which is a division of application No. 11/298,391, filed on Dec. 8, 2005, now Pat. No. 7,663,027, said application No. 13/644,359 is a continuation-in-part of application No. 12/377,106, filed as application No. PCT/US2007/075747 on Aug. 10, 2007, now abandoned, said application No. 13/644,359 is a continuation-in-part of application No. 12/541,607, filed on Aug. 14, 2009, now abandoned, which is a continuation of application No. 11/140,347, filed on May 27, 2005, now Pat. No. 7,576,260, said application No. 13/644,359 is a continuation-in-part of application No. 13/184,361, filed on Jul. 15, 2011, now Pat. No. 8,932,921, which is a division of application No. 11/140,450, filed on May 27, 2005, now Pat. No. 8,022,273, said application No. 13/644,359 is a continuation-in-part of application No. 11/654,357, filed on Jan. 16, 2007, now abandoned, said application No. 13/644,359 is a continuation-in-part of application No. 13/465,841, filed on May 7, 2012, now Pat. No. 9,765,355, which is a division of application No. 11/858,117, filed on Sep. 19, 2007, now abandoned, which is a continuation-in-part of application No. PCT/US2007/006544, filed on Mar. 14, 2007, said application No. 13/644,359 is a continuation-in-part of application No. 12/918,609, filed as application No. PCT/US2009/034638 on Feb. 20, 2009, now abandoned, said application No. 13/644,359 is a continuation-in-part of application No. 12/922,143, filed as application No. PCT/US2009/037025 on Mar. 12, 2009, now abandoned, said application No. 13/644,359 is a continuation-in-part of application No. 11/241,685, filed on Sep. 30, 2005, now Pat. No. 8,481,814, said application No. 13/644,359 is a continuation-in-part of application No. 12/863,773, filed as application No. PCT/US2009/031609 on Jan. 21, 2009, now abandoned, said application No. 13/644,359 is a continuation-in-part of application No. 12/282,342, filed as application No. PCT/US2007/006544 on Mar. 14, 2007, now Pat. No. 8,324,454.

(60) Provisional application No. 60/859,467, filed on Nov. 16, 2006, provisional application No. 60/851,585, filed on Oct. 12, 2006, provisional application No. 60/860,296, filed on Nov. 21, 2006, provisional application No. 60/564,659, filed on Apr. 23, 2004, provisional application No. 60/635,115, filed on Dec. 8, 2004, provisional application No. 60/635,140, filed on Dec. 8, 2004, provisional application No. 60/837,434, filed on Aug. 11, 2006, provisional application No. 60/575,309, filed on May 27, 2004, provisional application No. 60/575,253, filed on May 27, 2004, provisional application No. 60/778,568, filed on Mar. 1, 2006, provisional application No. 60/758,831, filed on Jan. 13, 2006, provisional application No. 60/782,735, filed on Mar. 14, 2006, provisional application No. 61/030,152, filed on Feb. 20, 2008, provisional application No. 61/036,396, filed on Mar. 13, 2008, provisional application No. 60/615,080, filed on Sep. 30, 2004, provisional application No. 61/022,786, filed on Jan. 22, 2008, provisional application No. 60/782,735, filed on Mar. 14, 2006, provisional application No. 60/583,621, filed on Jun. 30, 2004, provisional application No. 60/584,829, filed on Jun. 30, 2004, provisional application No. 60/584,800, filed on Jun. 30, 2004.

(56) References Cited

U.S. PATENT DOCUMENTS

| | | |
|---|---|---|
| 8,471,099 B2 | 6/2013 | Schneeberger et al. |
| 9,777,287 B2 | 10/2017 | Nadzan et al. |
| 10,428,344 B2 | 10/2019 | Nadzan et al. |
| 10,815,494 B2 | 10/2020 | Nadzan et al. |
| 2002/0160378 A1 | 10/2002 | Harper et al. |
| 2004/0009476 A9 | 1/2004 | Harper et al. |
| 2011/0061124 A1 | 3/2011 | Nadzan et al. |
| 2020/0048653 A1 | 2/2020 | Nadzan et al. |
| 2021/0079416 A1 | 3/2021 | Nadzan et al. |
| 2021/0087576 A1 | 3/2021 | Nadzan et al. |

OTHER PUBLICATIONS

Office Action regarding U.S. Appl. No. 15/689,941, dated May 30, 2019.
Response to Office Action regarding U.S. Appl. No. 15/689,941, filed Jul. 15, 2019.
Final Office Action regarding U.S. Appl. No. 15/689,941, dated Sep. 17, 2019.
Response to Final Office Action regarding U.S. Appl. No. 15/689,941, filed Dec. 17, 2019.
Advisory Action regarding U.S. Appl. No. 15/689,941, dated Jan. 7, 2020.
Supplemental Response to Final Office Action regarding U.S. Appl. No. 15/689,941, filed Jan. 14, 2020.
Kano-Murakami et al., "A rice homeotic gene, OSH1, causes unusual phenotypes in transgenic tobacco", FEBS 334(3):365-368, 1993.
U.S. Appl. No. 16/991,897 filed Aug. 12, 2020, Nadzan et al.
U.S. Appl. No. 16/991,904 filed Aug. 12, 2020, Nadzan et al.
USPTO: Corrected Notice of Allowability for U.S. Appl. No. 15/689,941, dated Aug. 25, 2020.
Bowie et al., "Deciphering the Message in Protein Sequences: Tolerance to Amino Acid Substitutions," Science 247:1306-1310, 1990.
Eddy, "What is a hidden Markov model?", Nature Biotechnology 22:1315-1316, 2004.
McConnell et al., "Role of PHABULOSA and PHAVOLUTA in determining radial patterning in shoots," Nature 411:709-713, 2001.
GenBank Accession No. DR750626, dated Feb. 15, 2011.
Yanagisawa, "The Dof family of plant transcription factors," TRENDS in Plant Science 7:555-560, 2002.
USPTO: Non-Final Office Action regarding U.S. Appl. No. 15/689,941, dated Apr. 29, 2020.
Falcon-Perez et al., Functional Domain Analysis of the Yeast ABC Transporter Ycf1p by Sited-Directed Mutagenesis, The Journal of Biological Chemistry 274(33):23584-23590, 1999.
Hill and Preiss, Functional Analysis of Conserved Histidines in ADP-Glucose Pyrophosphorylase from Escherichia coli, Biochemical and Biophysical Research Communications 244:573-577, 1998.
Guo et al., Protein Tolerance to Random Amino Acid Change, PNAS 101(25):9205-9210, 2004.
Lazar et al., Transforming Growth Factor alpha: Mutation of Aspartic Acid 47 and Leucine 48 Results in Different Biological Activities, Molecular and Cellular Biology 8(3):1247-1252, 1988.

(56) References Cited

OTHER PUBLICATIONS

Sweetlove et al., Starch Metabolism in Tubers of Transgenic Potato (*Solarium tuberosum*) with Increased ADPglucose Pyrophosphorylase, Biochemical Journal 320:493-498, 1996.
Fourgoux-Nicol et al., Isolation of Rapeseed Genes Expressed Early and Specifically During Development of the Male Gametophyte, Plant Molecular Biology 40:857-872, 1999.
Response to Non-Final Office Action regarding U.S. Appl. No. 15/689,941, dated Jun. 2, 2020.
USPTO: Notice of Allowance regarding U.S. Appl. No. 15/689,941, dated Jun. 24, 2020.

\* cited by examiner

Figure 1

| | | |
|---|---|---|
| SEQ_ID_NO_21 | ---------- --- MTNLYLT -........ ......... .......... | 8 |
| SEQ_ID_NO_36 | ---------- --- MNPLA-- ......... ......... .......... | 5 |
| SEQ_ID_NO_47 | ---------- --- MSLWIV F-....... ......... .......... | 8 |
| SEQ_ID_NO_4 | ----- MENRR SGGSGWWC VLP------L FTKDGPAYF HSSSDDVSAW | 39 |
| SEQ_ID_NO_46 | .......... .......... .......... .......... .......... | 0 |
| SEQ_ID_NO_39 | -- MDSSPST DCGGWLLYVS LAAKC---G GDPCRVVGFV ---------- | 34 |
| SEQ_ID_NO_40 | MDMDSSPST DCGGWLLYVS LAAKC---G GDPCRVVGFV ---------- | 36 |
| SEQ_ID_NO_27 | ----- MAPSE KC-GWLLYVS LAAKCCGNGD GKPYRVVGFV ---------- | 34 |
| SEQ_ID_NO_29 | ---- MAPPTE DC-GWLLYLS LAAKC---- GDPQRLGFA ---------- | 30 |
| SEQ_ID_NO_38 | ----- MAPSE DC-GWLLYLS LAAKC---- GDPHRLGFA ---------- | 29 |
| SEQ_ID_NO_3 | ------- MAT KLDTSSLLA LSKC---SL LTQTNLALSL ---------- | 30 |
| SEQ_ID_NO_25 | ------- MST NI-DNLWIFA LASKC---- -TQENIAYSL ---------- | 26 |
| SEQ_ID_NO_22 | ------- MTS HDDNLWIA LTSKC---- -TQENLAWL ---------- | 27 |
| SEQ_ID_NO_6 | ------- MGS DI-ESVMLFA LASKC--KA FSQQNTAWP ---------- | 29 |
| SEQ_ID_NO_10 | ------- MRT DI-DSFWIFA LASKC--RA FTQENAWSL ---------- | 29 |

| | | |
|---|---|---|
| SEQ_ID_NO_21 | ------LLPT FIFLIVLVLS .......... .......... ---RRRNNR | 28 |
| SEQ_ID_NO_36 | ------LIFC TALFCILLYH FL........ .......... ---TRRSVR | 27 |
| SEQ_ID_NO_47 | ------VTIV AALINRLLN LI........ .......... ---KKPTLP | 30 |
| SEQ_ID_NO_4 | RQWPLYALL IVANCAVLVS MLSPGGCAWA GRH------- ---KRGRVA | 78 |
| SEQ_ID_NO_46 | .......... .......... .......... .......... .......... | 0 |
| SEQ_ID_NO_39 | ------AVAV VAFAVTSLLH MLSPGGPAWG RYWW------ ---NRRGGLG | 69 |
| SEQ_ID_NO_40 | ------AVAV VAFAVTSLLH MLSPGGPAWG RYWW------ ---NRRGGLG | 71 |
| SEQ_ID_NO_27 | ------VVLL AAFVVTSLLH WASQGGAAWG RYWW------ ---RRKGLG | 68 |
| SEQ_ID_NO_29 | ------AVFV AACVVTSLLH MASPGGPAWG WYWW------ ---TRRAGLG | 65 |
| SEQ_ID_NO_38 | ------AVLA TAFVVTALLH WASPGGPAWG RYWW------ ---TRRAGLG | 64 |
| SEQ_ID_NO_3 | ------LVAS LASLALSLFF MSHPGGPAWG KYFL------ ---HRRRQTT | 65 |
| SEQ_ID_NO_25 | ------LIMA LLWITMFFY MSHPGGPAWG KYYYSSNYST TKTNNKNNLN | 70 |
| SEQ_ID_NO_22 | ------LIMG SLWLTMFYY MSHPGGPAWG KYYT------ ----YSPPLS | 61 |
| SEQ_ID_NO_6 | ------LIIA LAWLVMTIVY WHPGGPAWS KYRF------ ---KKCAIT | 63 |
| SEQ_ID_NO_10 | ------LIIG LAWIVVTLIY MAYPGGPAWG KYKL------ ---KNTSLT | 63 |

Figure 1 (continued)

| | | | | |
|---|---|---|---|---|
| SEQ_ID_NO_21 | YGITLQRAVP | LVVHPKLRLD | MSAYGLGSA | 511 |
| SEQ_ID_NO_36 | YGLTLQRAAP | LMVHPRPRLS | PQVFGK--- | 509 |
| SEQ_ID_NO_47 | YGLTLQRAVP | LAHPRPRLS | PHLYL---- | 510 |
| SEQ_ID_NO_4 | LKLSCEMARP | LHCVPVTRVP | FAKFSD--- | 553 |
| SEQ_ID_NO_46 | LKMSLEMKNP | LVCVAVPRFE | -------- | 426 |
| SEQ_ID_NO_39 | LKLSCEMATP | LEARLRPRRK | VMSV----- | 552 |
| SEQ_ID_NO_40 | LKLSCEMATP | LEARLRPRRK | V-------- | 551 |
| SEQ_ID_NO_27 | LRLSCEMAAP | LEARLRPRRA | V-------- | 552 |
| SEQ_ID_NO_29 | LRLSCEMAAP | LEARVVPRHA | VC------- | 543 |
| SEQ_ID_NO_38 | LRLSCEMAAP | LEARLVPRRA | V-------- | 548 |
| SEQ_ID_NO_3 | LRLSCEMANP | LAAKLRPRRS | FSV------ | 534 |
| SEQ_ID_NO_25 | LRLSCEMANP | LTVQVRPRR- | -------- | 546 |
| SEQ_ID_NO_22 | LKLSSEMANP | LIVKVRPRRG | -------- | 523 |
| SEQ_ID_NO_6 | LKLSCEMANP | LKVRIRPRRK | LT------ | 533 |
| SEQ_ID_NO_10 | LRLSCEMANP | LTVKVRPRRS | SQSPLY--- | 535 |

Figure 1 (continued)

| | | | | | | | |
|---|---|---|---|---|---|---|---|
| SEQ_ID_NO_21 | L--------- | ----PPGPNP | APIIGNLPHM | -GPKPHQTLA | AMVTT---YG | | 61 |
| SEQ_ID_NO_36 | L--------- | ----PPGPKP | APIVGNLPHL | -GPVPHRSIA | ALAKT---YG | | 60 |
| SEQ_ID_NO_47 | L--------- | ----PPGPSP | APIVGNLPHM | -GPVPHHALA | ALALK---HG | | 63 |
| SEQ_ID_NO_4 | --------- | ----IPGPKG | APIIGSLMDM | SVGLPHRKLE | SLARL-HGAK | | 113 |
| SEQ_ID_NO_46 | --------- | --------- | --------- | --------- | --------- | | 0 |
| SEQ_ID_NO_39 | AAA------ | ----IPGPRG | LPVLGSMSLM | -AGLAHRKLA | AAAGGSPARR | | 108 |
| SEQ_ID_NO_40 | AAA------ | ----IPGPRG | LPVLGSMSLM | -AGLAHRKLA | AAAGGSPARR | | 110 |
| SEQ_ID_NO_27 | GEAR----- | ----IPGPRG | FPVIGSMGLM | -TGLAHRKLA | AAAAGNVRRR | | 108 |
| SEQ_ID_NO_29 | VRAA----- | ----IPGPRG | LPVVGSMGLM | -TGLAHRKLS | AAAEROASRR | | 105 |
| SEQ_ID_NO_38 | GAA------ | ----IPGPRG | LPVLGSMGLM | -TGLAHRKLA | AAAGK--ARR | | 101 |
| SEQ_ID_NO_3 | V-------- | ----IPGPRG | LPEVGSMSLM | SNTLAHRCIA | ATAEK-FRAE | | 101 |
| SEQ_ID_NO_25 | SSTKPSTTTS | SSIFIPGPKG | YPLEGSMNLM | SSSLAHHRIA | STAKT-CKAT | | 119 |
| SEQ_ID_NO_22 | I--------- | ----IPGPKG | FPLIGSMGLM | -TGLAHHRIA | AAAAT-CRAK | | 96 |
| SEQ_ID_NO_6 | TINKP----- | ----IPGPRG | LPLIGSMNMV | ANSLAHHLIA | TIAKT-CKAK | | 103 |
| SEQ_ID_NO_10 | ISNP------ | ----IPGPRG | FPITGSMKLM | -TSLAHHKIA | AAADA-CKAR | | 101 |

| | | | | | | | |
|---|---|---|---|---|---|---|---|
| SEQ_ID_NO_21 | PILHLREGFA | DVVVAASKSV | AEQFLKVHDA | NFASRPPNSG | AKHMAYNYQD | | 111 |
| SEQ_ID_NO_36 | PLMHLRMGFV | DVVVAASASV | AAQFLKTHDA | NFSNRPPNSG | AKHIAYNYQD | | 110 |
| SEQ_ID_NO_47 | PLMHLQLGFV | DVIVAASASV | AEQFLKVHDA | NFSSRPPNSG | AKYIAYNYQD | | 113 |
| SEQ_ID_NO_4 | QLMSFSLGCT | PAVITSDPEV | ARELL-TBP | HFANRPLKQS | AQQLLFG-RA | | 160 |
| SEQ_ID_NO_46 | --MAFSVGLT | RFIVSSHPKT | AKEILL-SBP | AFADRPIKES | AYELLFN-RA | | 45 |
| SEQ_ID_NO_39 | RLMALSLGET | RVVVTADPGV | ARELL-ASA | AFADRPVKES | AYGMLFH-RA | | 155 |
| SEQ_ID_NO_40 | RLMALSLGET | RVVVTADPGV | ARELL-ASA | AFADRPVKES | AYGMLFH-RA | | 157 |
| SEQ_ID_NO_27 | RLMSFSMGET | RVVVTADPDV | ARELL-ASP | AFADRPVKES | AYGLMFH-RA | | 155 |
| SEQ_ID_NO_29 | RLMAFSLGET | RVVVTADLDV | ARELL-ASA | AFADRPVKES | AYGLLFH-RA | | 152 |
| SEQ_ID_NO_38 | RLMAFSLGET | RVVVTADPDV | ARELL-ASA | TFADRPVKES | AYGLLFH-RA | | 148 |
| SEQ_ID_NO_3 | RLMAFSLGET | RVIVTCNPDV | AKEILL-NSP | VFADRPVKES | AYSLMFN-RA | | 148 |
| SEQ_ID_NO_25 | RLMAFSLGDT | RAMVTCNPDV | AKEILL-HSS | VFADRPIKES | AYSLMFN-RA | | 166 |
| SEQ_ID_NO_22 | RLMAFSLGDT | RVIVTCHPDV | AKEILL-NSS | VFADRPVKES | AYSLMFN-RA | | 143 |
| SEQ_ID_NO_6 | RLMAFSLGDT | RVIVTCNPEV | AKEILL-NSS | VFADRPVKES | AYSLMFN-RA | | 150 |
| SEQ_ID_NO_10 | RLMAFSLGDT | RVIVTCNPDV | AKEILL-NSS | VFADRPVKES | AYSLMFN-RA | | 148 |

Figure 1 (continued)

| | | | | | | | |
|---|---|---|---|---|---|---|---|
| SEQ_ID_NO_21 | LVFAPYGDRW | RMLRKISSVH | LFSAKALEDF | KHVRQEEYGT | LMRE--LARA | | 159 |
| SEQ_ID_NO_36 | LVFAPYGPRW | RMLRKICSVH | LFSGDALDDF | RHIRQEEVLA | LMRA--LARE | | 158 |
| SEQ_ID_NO_47 | LVFAPYGPRW | RLLRKISYVH | MFSSKALDDF | RHIRQDEVAR | LIRN--LSNS | | 161 |
| SEQ_ID_NO_4 | IGFAPNGGYW | RLLRRIASAH | LFAPRRIAAH | EAGRQADVVA | MLDD--QKE | | 208 |
| SEQ_ID_NO_46 | MGFAPFGDYW | RNLRRISSTY | LFSPRRVSSF | EKQRSE GEG | MVRD--MKRM | | 93 |
| SEQ_ID_NO_39 | IGFAPYGTYW | RALRRVASTH | LFSPRQVSAS | AAQRAV ARD | MVEAMRSAAA | | 205 |
| SEQ_ID_NO_40 | IGFAPYGTYW | RALRRVASTH | LFSPRQVSAS | AAQRAV ARQ | MVEAMRSAAA | | 207 |
| SEQ_ID_NO_27 | IGFAPYGAYW | RTLRRVSSSH | LFSPRQVAAS | AAQRAV AHQ | MVDA--MRPV | | 203 |
| SEQ_ID_NO_29 | IGFAPHGAYW | RALRRVASAH | LFSPRQIAAS | AAQRAA ARQ | MVDA--TTTA | | 200 |
| SEQ_ID_NO_38 | IGFAPHGAYW | RALRRVASAH | LFSPRQIAAS | AAQRAV ARQ | MVDAMMMEQG | | 198 |
| SEQ_ID_NO_3 | IGFAPYGVYW | QTLRKIASNH | LFSPKQIKRS | ETQRSV ANQ | IVKC--LTKQ | | 196 |
| SEQ_ID_NO_25 | IGFAPYGVYW | RTLRKISTNH | LFSPMQIKSS | GPQRSE ATQ | MIDL--FRNR | | 214 |
| SEQ_ID_NO_22 | IGFASYGVYW | RSLRRIASNH | LFCPRQIKAS | ELQRSQ AAQ | MVHI--LNNK | | 191 |
| SEQ_ID_NO_6 | IGFAPYGVYW | RELRRIAATH | LFCPKQIKNS | EEQRRF ADE | MVNL--FGRH | | 198 |
| SEQ_ID_NO_10 | IGFAPYGVYW | RTLRKIASTH | LFCPKQIKAA | ESQRLQ ASQ | MVST--FNDR | | 196 |
| | | | | | | | |
| SEQ_ID_NO_21 | NTKP---VNL | GQLVNMCVLN | ALGREM GRR | LFGAD----- | ADHKAEEFRS | | 201 |
| SEQ_ID_NO_36 | GQTP---VKL | GQLLNVCTTN | ALGRVML GRR | VFGDGSGG-- | EDPKADEFKE | | 203 |
| SEQ_ID_NO_47 | GSKA---ANL | GQMLNVCTTN | ALARYMI GRR | VFNEGNGGCE | CDPRADEFKS | | 208 |
| SEQ_ID_NO_4 | YHSK-GVVRV | RRHLQGAALN | NIMGSVFGRR | FDMSH----- | ENEEVKKLRE | | 252 |
| SEQ_ID_NO_46 | MERN-GVVEV | RRMLHYGSLN | NIMLTVFGKK | FDF------- | AKDEGLELEL | | 135 |
| SEQ_ID_NO_39 | AAAG-GGVAA | RPFLKRASLH | NVMASVFGRK | YELAAP---- | ESEETAELRS | | 250 |
| SEQ_ID_NO_40 | AAAG-GGVAA | RPFLKRASLH | NVMASVFGRK | YELAAP---- | ESEETAELRS | | 252 |
| SEQ_ID_NO_27 | GGAGVKHVEA | RRFLKRASLH | NVMASVFGRR | YELDEA---- | GSGEAAELKS | | 249 |
| SEQ_ID_NO_29 | AAHA-PVVVA | RRFLKRASLH | NVMASVFGRR | YDLMA----- | DSREAEELKA | | 244 |
| SEQ_ID_NO_38 | AAAP-GVVTA | RRFLKRASLH | SVMASVFGRR | YELLQAAD-- | GGEEAAELQS | | 245 |
| SEQ_ID_NO_3 | SNTK-GLCFA | RDLIKTASLN | NMMCSVFGKE | YELEE----- | EHEEVSELRE | | 240 |
| SEQ_ID_NO_25 | HLHG-GFC-V | RDVLKKASLN | NMMCSVFGQR | FKIDE----- | VNERMMELSG | | 257 |
| SEQ_ID_NO_22 | RHRS---LRV | RQVLKKASLS | NMMCSVFGCE | YKLHD----- | PNSGMEDLGI | | 233 |
| SEQ_ID_NO_6 | GHER--SFIV | REVVKRASLN | NMMVSIFGRK | YKLDC----- | DNNEVDELRG | | 241 |
| SEQ_ID_NO_10 | EKSS---FSV | REVLKRASLN | NMMCSVFGRE | YKLDS----- | FNNEVEELRA | | 238 |

Figure 1 (continued)

| SEQ_ID_NO_21 | MVTEMMALAG VFNI GDFVPA DCLDLQGVA GKMKRLHKRF DAFLSSI LEE | 251 |
| SEQ_ID_NO_36 | MVVELMVLAG VFNI GDFVPA EWLDLQGVA SKMKKLHARF DAFLGAI VEE | 253 |
| SEQ_ID_NO_47 | MVVELMVLAG VFNI GDFVPS EWLDIQGVQ SKMKKLHKRF DSFLTSI IED | 258 |
| SEQ_ID_NO_4 | MVDEGFQLLG AFNWADHLPW RPLDPLRIH ARCARLVPRV TTFVSNI IEQ | 302 |
| SEQ_ID_NO_46 | LKEGYELLG IFNWGDHLPE GWLDLQGVR RRCRTLVAKV NVFVKKI IDE | 185 |
| SEQ_ID_NO_39 | MVDEGYDLLG QLNWSDHLPW LAPFDLQKTR SRCSSLVPRV NRFVTRI IDE | 300 |
| SEQ_ID_NO_40 | MVDEGYDLLG QLNWSDHLPW LAPFDLKKTR SRCSSLVPRV NRFVTRI IDE | 302 |
| SEQ_ID_NO_27 | LVDEGYDLLG QLNWSDHLPW LARFDLQKIR SRCSALVPRV NRFVGRI IDE | 299 |
| SEQ_ID_NO_29 | LVDEGYDLLG QLNWSDHLPW LARFDLQKTR ARCCALVPRV NRFVGNI IGE | 294 |
| SEQ_ID_NO_38 | LVDQGYDLLG QLNWSDHLPW LARFDLQRTR ARCAALVPRV NRFVGRI IDE | 295 |
| SEQ_ID_NO_3 | LVEEGYDLLG TLNWTDHLPW SEFDPQRIR SRCSNLVPKV NRFVNRI ISD | 290 |
| SEQ_ID_NO_25 | LVEQGYDLLG GLNWGDHLPF KDFDVQKIR FSCSELVPKV NRFVGS ISD | 307 |
| SEQ_ID_NO_22 | LVDQGYDLLG LFNWADHLPF LAHFDAQNI R FRCSNLVPMV NRFVGT IAE | 283 |
| SEQ_ID_NO_6 | LVDEGYDLLG TLNWSDHLPW LADFDPQNI R VRCSNLVPKV NGFVGG IAQ | 291 |
| SEQ_ID_NO_10 | LVEEGYDLLG TLNWSDHLPW LADFDPQKIR FRCSNLVPKV NRFVSRI IAE | 288 |

| SEQ_ID_NO_21 | HEAMK----N GQDQKHTDML STLISLK--- -STDFDGEG GTLTDTEI KA | 292 |
| SEQ_ID_NO_36 | HKI SG----S AGSERHVDLL STLISLKDNA DGEGG----- -KLTDVEI KA | 293 |
| SEQ_ID_NO_47 | HMVSK----- --SEKHNDLL STLLSLKEKV DEDGD----- -KLNDTEI KA | 295 |
| SEQ_ID_NO_4 | HRREE---QR RESGDQCDFV DVLLSLQ--- -GED----- -KLDEEDMI A | 338 |
| SEQ_ID_NO_46 | HKRRA-NGVG IDEGEGEDFV DVLLGLE--- -EKD----- -RLSESDMVA | 223 |
| SEQ_ID_NO_39 | HRARL----S LAVDAAVDFT DVLLSLH--- -GGD----- -KLSDADMVA | 335 |
| SEQ_ID_NO_40 | HRARL----S LAVDAAVDFT DVLLSLH--- -GGD----- -KLSDADMVA | 337 |
| SEQ_ID_NO_27 | HRAAL----N DDDDAVVDFT DVLLSLQ--- -GSD----- -KLSDADMI A | 334 |
| SEQ_ID_NO_29 | HRARL---GR GGDTAVMDFT DVLLSLQ--- -GDD----- -KLSDADMI A | 330 |
| SEQ_ID_NO_38 | HRAARLHLGG DGAAAVVDFT DVLLSLQ--- -GSD----- -RLSDADMI A | 334 |
| SEQ_ID_NO_3 | HREQT----- --RDSPSDFV DVLLSLD--- -GPD----- -KLSDPDI I A | 322 |
| SEQ_ID_NO_25 | HRADK----- --NGTNKDFV HVLLSLQ--- -EPD----- -KLSDSDMI A | 339 |
| SEQ_ID_NO_22 | HRASK----- --TETNRDFV DVLLSLP--- -EPD----- -QLSDSDMI A | 315 |
| SEQ_ID_NO_6 | HRART----- --NEEARDLV DVLLSLQ--- -GAD----- -KLSDSDMI A | 323 |
| SEQ_ID_NO_10 | HRALT----- --RSENPDFV DVLLSLQ--- -GHD----- -KLSDSDMI A | 320 |

Figure 1 (continued)

| | | | | | | | |
|---|---|---|---|---|---|---|---|
| SEQ_ID_NO_21 | LLLNMFTAGT | DTSASTVDWA | AELIRHPEI | MRKAQEELDS | VV- | GRGRPIN | 341 |
| SEQ_ID_NO_36 | LLLNLFTAGT | DTSSSTVEWA | AELIRHPEM | MAQAQQELDA | VV- | GRGRLVT | 342 |
| SEQ_ID_NO_47 | LLLNMFTAGT | DTSSSTTEWA | AELIKNPKL | MIRIQNELDT | VV- | GRDRLVT | 344 |
| SEQ_ID_NO_4 | VLWEMIFRGT | DTTALLTEWT | MAELVLHPEA | QKKAQAELDA | VV- | GHDRSVK | 387 |
| SEQ_ID_NO_46 | VLWEMIFRGT | DTVAILLEWT | LARMVLHPDI | QSKAQVEIDS | VV- | DSSRPVL | 272 |
| SEQ_ID_NO_39 | VLWEMIFRGT | DTVAVLIEWV | AARLVLHQDV | QARVHDELDR | VV- | GSDRAVT | 384 |
| SEQ_ID_NO_40 | VLWEMIFRGT | DTVAVLIEWV | AARLVLHQDV | QARVHDELDR | VV- | GSDRAVT | 386 |
| SEQ_ID_NO_27 | VLWEMIFRGT | DTVAVVIEWV | LARLMLHQDV | QARVHEELDR | VV- | GPNRAVT | 383 |
| SEQ_ID_NO_29 | VLWEMIFRGT | DTVAVLIEWV | LARLVLHQDV | QSKVQEELDR | VV- | GLGQAVT | 379 |
| SEQ_ID_NO_38 | VLWEMIFRGT | DTVAVLMEWV | LARLVLHQDV | QRRVQEELDR | VV- | GPGRAVT | 383 |
| SEQ_ID_NO_3 | VLWEMIFRGT | DTVAVLIEWV | LARMVLHPDI | QSIVHNELDQ | IV- | GRSRAVE | 371 |
| SEQ_ID_NO_25 | VLWEMIFRGT | DTVAVLIEWV | LARLVIHPDV | QKKVQTELDE | VASGESCAIT | | 389 |
| SEQ_ID_NO_22 | VLWEMIFRGT | DTVAVLIEWV | LARMALHPHV | QSKVQEELDA | VV- | GKARAVA | 364 |
| SEQ_ID_NO_6 | VLWEMIFRGT | DTVAVLIEWV | LARIVVHPDV | QSRVHDELDK | VV- | GKSKAVY | 372 |
| SEQ_ID_NO_10 | VLWEMIFRGT | DTVAVLIEWV | LARMVLHPDV | QSKVHDELYK | VV- | GRSRAVA | 369 |

| | | | | | | | |
|---|---|---|---|---|---|---|---|
| SEQ_ID_NO_21 | ESDLSQLPYL | QAVIKENFRL | HPPTPLSLP | HIASESCEI- | NGYHIPKGST | | 389 |
| SEQ_ID_NO_36 | DLDLPKLTYL | QAIVKETFRL | HPSTPLSLP | RMAAESCEI- | NGYHIPKNAT | | 390 |
| SEQ_ID_NO_47 | EQDLTHLPYL | EAVIKETFRL | HPSTPLSLP | RVATNSCEI- | FNYHIPKGAT | | 392 |
| SEQ_ID_NO_4 | DSDIPKLPYI | QAVVKEALRM | HPPGPLLSWA | RLSTEDVNMG | DGMCVPAGTT | | 437 |
| SEQ_ID_NO_46 | DSDIQRLPYL | QSIVKETLRM | HPPGPLLSWA | RLAIHDVPV- | DGHMWPAGTT | | 321 |
| SEQ_ID_NO_39 | ESDASKLMYL | QAVIKEVLRL | HPPGPLLSWA | RLATSDVHV- | GGFLIPSGTT | | 433 |
| SEQ_ID_NO_40 | ESDASKLMYL | QAVIKEVLRL | HPPGPLLSWA | RLATSDVHV- | GGFLIPSGTT | | 435 |
| SEQ_ID_NO_27 | ESDAASLVFL | QAVVKEVLRL | HPPGPLLSWA | RLATSDVHV- | DGLHVPAGTT | | 432 |
| SEQ_ID_NO_29 | ESDTASLPYL | QAVIKEVLRL | HPPGPLLSWA | RLATSDVYV- | SGYLVPAGTT | | 428 |
| SEQ_ID_NO_38 | EPDGASLAYL | HAVIREVLRL | HPPGPLLSWA | RLATSDVHV- | GGYLVPAGTT | | 432 |
| SEQ_ID_NO_3 | ESDVVSLVYL | TAVVKEVLRL | HPPGPLLSWA | RLAITDTI- | DGRRVPAGTT | | 420 |
| SEQ_ID_NO_25 | EEDVAAMYYL | PAVIKEVLRL | HPPGPLLSWA | RLAITDTTI- | DGYHVPAGTT | | 438 |
| SEQ_ID_NO_22 | EDDVAVWTYL | PAVVKEVLRL | HPPGPLLSWA | RLSINDTTI- | DGYHVPAGTT | | 413 |
| SEQ_ID_NO_6 | ESDVMNLTYL | MAVIKEVLRL | HPPGPLLSWA | RLAITDTTV- | DGYHVPKGTM | | 421 |
| SEQ_ID_NO_10 | ESDITAMVYL | QAVVKEVLRL | HPPGPLLSWA | RLAITDTTL- | DGYHVPKGTT | | 418 |

Figure 1 (continued)

| | | | | | | | |
|---|---|---|---|---|---|---|---|
| SEQ_ID_NO_21 | LLINIWAIAR | DPDQMSDPLT | FRPERFLPGG | EKA-G----- | VDVKGNDFEL | 433 |
| SEQ_ID_NO_36 | LLVNVWAIAR | DPEVWEEPLE | FRPNRFLPGG | ERP-N----- | ADVRGNDFEV | 434 |
| SEQ_ID_NO_47 | LLVNVWAISR | DPKEMTNPLE | FKPERFLPGG | EKF-D----- | VDIRGNDFEV | 436 |
| SEQ_ID_NO_4 | AMVNMWSITH | DPNIWESPYE | FRPERFVVFE | GGE-E----- | VDVRGNDLRL | 481 |
| SEQ_ID_NO_46 | AMVNMWAITH | DECNMAEPNK | FNPDRFIDED | ---------- | VNILGSDLRL | 361 |
| SEQ_ID_NO_39 | AMVNMWAITH | DPAVWPDPNE | FKPERFVAGP | SSDQA---AE | FPIMGSDLRL | 480 |
| SEQ_ID_NO_40 | AMVNMWAITH | DPAVWPDPNE | FKPERFVAGP | SSDQA---TE | FPIMGSDLRL | 482 |
| SEQ_ID_NO_27 | AMVNMWAITH | DPTVWKPAE | FKPERFLGGS | SSDHAAAGAE | FSVTGSDLRL | 482 |
| SEQ_ID_NO_29 | AMVNMWAITH | DPSLWPEPME | FRPERFMGPA | AED------- | VPIMGSDLRL | 471 |
| SEQ_ID_NO_38 | AMVNMWAITH | DPAVWPDPAE | FKPERFAAGS | PGDEA----- | FPVMGSDLRL | 477 |
| SEQ_ID_NO_3 | AMVNMWAIAH | DPHVWENPLE | FKPERFVAKE | GEV-E----- | FSVLGSDLRL | 464 |
| SEQ_ID_NO_25 | AMVNMWAISR | DPDVWRNPLE | FNPERFVSEG | AE-------- | FSVLGSDLRL | 480 |
| SEQ_ID_NO_22 | AMVNTWAICR | DPHVWKDPLE | FMPERFVTAG | GDA-E----- | FSILGSDPRL | 457 |
| SEQ_ID_NO_6 | AVVNMWAIAR | DPQEMADPTE | FVPDRFVAKT | GEV-E----- | FSVLGSDLRL | 465 |
| SEQ_ID_NO_10 | AMVNMWAISR | DPEFMEDPLE | FMPERFVVTK | EDVLE----- | FSVLGSDLRL | 463 |

| | | | | | | | |
|---|---|---|---|---|---|---|---|
| SEQ_ID_NO_21 | IPFGAGRRIC | AGLSLGLRTI | QLLTATLVHG | FEWELAGGVT | -PEKLNMEET | 482 |
| SEQ_ID_NO_36 | IPFGAGRRIC | AGMSLGLRMV | HLLTATLVHA | FNMELPEGDV | -AEKLNMDEA | 483 |
| SEQ_ID_NO_47 | IPFGAGRRIC | AGMSLGLRMV | QLLTATLAHA | YDWELENGLS | -PEKLNMDFA | 485 |
| SEQ_ID_NO_4 | APFGAGRRVC | PGKALGLATV | NLWAKLLHH | FEWLPHAE- | --HPVDLSEV | 527 |
| SEQ_ID_NO_46 | APFGSGKRVC | PGKTMALAAV | HLMLAQLLKS | FKLLPSR-- | --NGVDLSEC | 406 |
| SEQ_ID_NO_39 | APFGSGRRSC | PGKSLAIATV | GFWATLLHE | FDWLPLSDK- | -SRGVDLSEV | 528 |
| SEQ_ID_NO_40 | APFGSGRRSC | PGKSLAIATV | GFWATLLHE | FDWLPLSDK- | -SRGVDLSEV | 530 |
| SEQ_ID_NO_27 | APFGSGRRSC | PGKSLAIATV | GFWATLLHE | FEWTPPSSDG | -SGGVDLSEV | 531 |
| SEQ_ID_NO_29 | APFGSGRRSC | PGKSLAVATV | GFWATLLYE | FKWLPPSDEP | RGGGVDLSEV | 521 |
| SEQ_ID_NO_38 | APFGSGRRVC | PGKSLAMATV | AFWATLLHE | FEWLPASSDE | PPRGVDLSEV | 527 |
| SEQ_ID_NO_3 | APFGSGRRVC | PGKNLGLTTV | TFWIATLLHE | FEWLTPSDE- | --KTVGLSEK | 511 |
| SEQ_ID_NO_25 | APFGSGRRSC | PGKNLGLATV | TFWVAKLLHE | FEWLPLDE- | -VNGVDLTEV | 527 |
| SEQ_ID_NO_22 | APFGSGRRAC | PGKTLGMATV | NFWVASLLHE | FEW-PSDE- | --KGVDLTEV | 503 |
| SEQ_ID_NO_6 | APFGSGRRTC | PGKNLGLTTV | SFWVATLLHE | FEWLPSDQ- | --NSVDLSEV | 511 |
| SEQ_ID_NO_10 | APFGSGRRTC | PGKTLGITTV | TFWVASLLHE | YEWLPGEE- | --NNVDLSEV | 509 |

| | | | | |
|---|---|---|---|---|
| SEQ_ID_NO_21 | YGTTLQRAVP | LVVHPKLRLD | MSAYGLGSA | 511 |
| SEQ_ID_NO_36 | YGLTLQRAAP | LMVHPRPRLS | PQVFGK--- | 509 |
| SEQ_ID_NO_47 | YGLTLQRAVP | LAHPRPRLS | PHLYL---- | 510 |
| SEQ_ID_NO_4 | LKLSCEMARP | LHCVPVTRVP | FAKFSD--- | 553 |
| SEQ_ID_NO_46 | LKMSLEMKNP | LVCVAVPRFE | --------- | 426 |
| SEQ_ID_NO_39 | LKLSCEMATP | LEARLRPRRK | VMSV----- | 552 |
| SEQ_ID_NO_40 | LKLSCEMATP | LEARLRPRRK | V-------- | 551 |
| SEQ_ID_NO_27 | LRLSCEMAAP | LEARLRPRRA | V-------- | 552 |
| SEQ_ID_NO_29 | LRLSCEMAAP | LEARVVPRHA | VC------- | 543 |
| SEQ_ID_NO_38 | LRLSCEMAAP | LEARLVPRRA | V-------- | 548 |
| SEQ_ID_NO_3 | LRLSCEMANP | LAAKLRPRRS | FSV------ | 534 |
| SEQ_ID_NO_25 | LRLSCEMANP | LTVQVRPRR- | --------- | 546 |
| SEQ_ID_NO_22 | LKLSSEMANP | LTVKVRPRRG | --------- | 523 |
| SEQ_ID_NO_6 | LKLSCEMANP | LKVRIRPRRK | LT------- | 533 |
| SEQ_ID_NO_10 | LRLSCEMANP | LTVKVRPRRS | SQSPLY--- | 535 |

Figure 2

| | | | | | | | |
|---|---|---|---|---|---|---|---|
| SEQ_ID_NO_67 | ---------- | MQLQPAVAN- | --------P | NTPSGAA--- | ---------- | | 17 |
| SEQ_ID_NO_65 | MDTSHWPQGI | GLVKAVEPS- | -----KPVPT | ERKPRPQ--- | ----KEQ--- | | 34 |
| SEQ_ID_NO_63 | MGMDSSSGQQ | QQMSNQSLES | MLTCSKGE-Q | DKKPKPP--- | ----QPE--- | | 39 |
| SEQ_ID_NO_73 | ----MDQQQ | QEMSSQTLES | MLVCTKPDQD | QKKPRPA--- | ----EQQ--- | | 35 |
| SEQ_ID_NO_69 | -------MQEE | PGRRPVPPF- | -----AGVDL | RRPKGYP--- | -VAVAKEERP | | 34 |
| SEQ_ID_NO_70 | -------MQE | AGRRPAPQF- | -----AGVDL | RRPKGYPAAA | QLTPAAEEAA | | 37 |
| SEQ_ID_NO_71 | -------MQE | AGRRPAPQF- | -----AGVDL | RRPKGYPAAA | QLTPAAEEAA | | 37 |
| SEQ_ID_NO_64 | -----MPSSD | SGESRRS K- | ---------P | QNRPGAP--- | ---APEQE-- | | 27 |
| SEQ_ID_NO_75 | -------MEA | GQVPDGRAL- | -----MAAVT | TTGGGGR--- | ----EPE--- | | 27 |
| SEQ_ID_NO_51 | -------MQD | ----PTGFH- | ---------Q | MKAPAFQ--- | ----EQEQQ- | | 21 |
| SEQ_ID_NO_53 | -------MQD | ----PSTAF- | ---------H | TIKPQFP--- | ----EQE--- | | 19 |
| SEQ_ID_NO_60 | -------MQD | ----PLTLF- | ---------Q | PMKPHFP--- | ----EQE--- | | 18 |
| SEQ_ID_NO_58 | -------MQE | DLTSAAAYYH | HQSMIMTAKQ | QQQPELP--- | ----EQE--- | | 33 |
| SEQ_ID_NO_49 | -------MQD | ----PAAYY- | -QTMMAKQQQ | QQQPQFA--- | ----EQE--- | | 27 |

| | | | | | | | |
|---|---|---|---|---|---|---|---|
| SEQ_ID_NO_67 | ---REQCPRC | ASHDTKFCYY | NNYNLSQPRH | FCRACRRYWT | LGGSLRNVPI | | 64 |
| SEQ_ID_NO_65 | ---AINCPRC | NSTNTKFCYY | NNYSLSQPRY | FCKTCRRYWT | EGGSLRNVPV | | 81 |
| SEQ_ID_NO_63 | ---ALKCPRC | DSNNTKFCYY | NNYSLSQPRY | FCKSCRRYWT | KGGTLRNVPV | | 86 |
| SEQ_ID_NO_73 | ---PQKCPRC | DSANTKFCYY | NNYSLTQPRY | FCKSCRRYWT | KGGTLRNVPV | | 82 |
| SEQ_ID_NO_69 | APGGDPCPRC | GSRDTKFCYY | NNYNLSQPRH | LCKSCRRYWT | KGGSLRNVPV | | 84 |
| SEQ_ID_NO_70 | AGVGDPCPRC | ESRDTKFCYY | NNYNLSQPRH | FCKSCRRYWT | KGGSLRNVPV | | 87 |
| SEQ_ID_NO_71 | AGVGDPCPRC | ESRDTKFCYY | NNYNLSQPRH | FCKSCRRYWT | KGGSLRNVPV | | 87 |
| SEQ_ID_NO_64 | ---NLPCPRC | DSTNTKFCYY | NNYNYSQPRH | LCKACRRYWT | HGGTLRDIPV | | 74 |
| SEQ_ID_NO_75 | ---GLPCPRC | ESVNTKFCYY | NNYNLSQPRY | FCKTCRRYWT | RGGALRNVPV | | 74 |
| SEQ_ID_NO_51 | ---QLKCPRC | DSTNTKFCYY | NNYNLSQPRH | FCKNCRRYWT | KGGALRNIPV | | 68 |
| SEQ_ID_NO_53 | ---QLKCPRC | DSNNTKFCYY | NNYNLSQPRH | FCKNCRRYWT | KGGALRNIPV | | 66 |
| SEQ_ID_NO_60 | ---QLKCPRC | DSTNTKFCYY | NNYNLSQPRH | FCKNCRRYWT | KGGALRNIPV | | 65 |
| SEQ_ID_NO_58 | ---QLNCPRC | ASPNTKFCYY | NNYNLSQPRH | FCKNCRRYWT | KGGSLRNIPV | | 80 |
| SEQ_ID_NO_49 | ---QLKCPRC | DSPNTKFCYY | NNYNLSQPRH | FCKSCRRYWT | KGGALRNVPV | | 74 |

Figure 2 (continued)

| | | | | | | | |
|---|---|---|---|---|---|---|---|
| SEQ_ID_NO_67 | GGSTRKRLRP | APQQTMRRPP | VHFGAP--P | PPPMPA--- | ---------- | | 97 |
| SEQ_ID_NO_65 | GGGSRKNKRS | SSSSNNSSSS | ---TSS---S | YKKIPDLT-- | ---------- | | 113 |
| SEQ_ID_NO_63 | GGGCRKNKRS | SSASSKRSQD | ----QPFQTN | PNPLTCFPSL | SYDSNDLTLA | | 132 |
| SEQ_ID_NO_73 | GGGCRKNKKL | SSTTSAKRSS | QDNISPNISN | PIPSYDSSTD | LSLAFARLQK | | 132 |
| SEQ_ID_NO_69 | GGGTRKSSSS | SSSSSAAAAA | ----TTTTTS | TSPGAAPK-- | -ATKRSKNSK | | 127 |
| SEQ_ID_NO_70 | GGGSRKSSTS | SSSSSSAAAA | ----SS---S | SSPSSPAK-- | -SPKRSKNSK | | 127 |
| SEQ_ID_NO_71 | GGGSRKSSTS | SSSAAAAAAS | -----S---S | SSPSSPAK-- | -SPKRSKNSK | | 126 |
| SEQ_ID_NO_64 | GGGTRKNAKR | SRTHHVAVTS | ----SS---S | SSAVT----- | ---------- | | 102 |
| SEQ_ID_NO_75 | GGNTRKATPA | TGRRKRSTPA | -----P---V | NVTVPAP--- | ---------- | | 103 |
| SEQ_ID_NO_51 | GCGTRKGTKR | SSSSTNKPKR | ----QP---N | PSPDPTPNQK | -IPDPSPPPP | | 110 |
| SEQ_ID_NO_53 | GGGSRKNTKR | SSNTKRANPD | -----P---N | PDPVKPTR-- | ---------- | | 96 |
| SEQ_ID_NO_60 | GGGSRKNTKR | SSSSNNNTKR | ---------- | ASPSPPVS-- | ---------- | | 93 |
| SEQ_ID_NO_58 | GGGTRKNSSK | RSSVGSSSSA | ----PS---S | SSPKSKTV-- | ---------- | | 111 |
| SEQ_ID_NO_49 | GGGSRKNATK | RSTSSSSSAS | ----SP---S | NSSQNKKT-- | ---------- | | 105 |
| | | | | | | | |
| SEQ_ID_NO_67 | -QSHSQQAPQ | GGLLSSLFAF | GAAPLFEGRV | GF----D-- | LGLGLPGLSQ | | 139 |
| SEQ_ID_NO_65 | -IPTSSQNPK | IINEPHDLNL | AFNPSATSNF | SNISEFMA-- | LPLMNPNSTT | | 160 |
| SEQ_ID_NO_63 | LARLQKGHLG | FDHEHDFSIL | GNQTNTSCG | LNN------- | HGMNHSSNNQ | | 175 |
| SEQ_ID_NO_73 | QTNAHLEIDQ | EHDNNNMSMM | YNTGNNCTST | TELDALRGG- | FLENAPNHPG | | 181 |
| SEQ_ID_NO_69 | RRRVAPAPDP | AAPGTDASTA | DVASTAPSTV | ---------- | AASEKPSATE | | 167 |
| SEQ_ID_NO_70 | RRRVSPPPPQ | PAP------- | APPPPTTADA | ---------- | ADVAAPTAPE | | 160 |
| SEQ_ID_NO_71 | RRRVSPPPPQ | PVP------- | APPPPTTADA | ---------- | ADVAAPTAPE | | 159 |
| SEQ_ID_NO_64 | -SAPEQNYP | ---------- | SMTP1OGGSF | PY------- | GGVDGEGKQN | | 132 |
| SEQ_ID_NO_75 | -ATASPPPPP | ALHGGSLLRP | YGGGGGSGLL | SFAAPALASP | LAAADPDRRL | | 152 |
| SEQ_ID_NO_51 | KSSSSSMFPQ | QIVLNSGAQN | SDSDIDSTRM | -Y----L-- | LPVDHQDGKM | | 152 |
| SEQ_ID_NO_53 | -RVADSSSSS | ATSSTSGQQL | AGNGNQDPTR | VY------- | GVEADPDRKI | | 137 |
| SEQ_ID_NO_60 | -SAPAPEPDP | TRI------- | ---------- | ---------- | GPTPVVG--- | | 112 |
| SEQ_ID_NO_58 | -AVSDOESRT | TGN------- | SGQEMDPTRM | LY----G-- | LPVGDPS--- | | 143 |
| SEQ_ID_NO_49 | -KNPDPDPDP | RNS------- | QKPDLDPTRM | LY----G-- | FPLSDQDVKG | | 140 |

Figure 2 (continued)

| | | | | | | | |
|---|---|---|---|---|---|---|---|
| SEQ_ID_NO_67 | VGLGGGAG-- | ---E------ | --FGLHSLGL | RGGHAGT--- | -----SA--- | | 165 |
| SEQ_ID_NO_65 | SFMSSIMP-- | --QLSDSNNI | M-YSSSSTGL | PNLHDLK--- | -----PTLNF | | 197 |
| SEQ_ID_NO_63 | GFFEALMG-- | --SDNNVQNL | YYMGEVDNGN | ANGNGNGEMM | LPYDHEMSIA | | 221 |
| SEQ_ID_NO_73 | LFHHNMYNYA | NMGQLVENGE | MGMSYQQDQM | SIGTSTTMMT | TIVKQEMCNM | | 231 |
| SEQ_ID_NO_69 | HAAAAVAT-- | --EKPPAAPP | VSVGAFADTS | PAPDAGS--- | ---------- | | 200 |
| SEQ_ID_NO_70 | DTTKKAPE-- | --DLTAAAAT | QPAVALGLGV | ADGGGGG--- | -----K---- | | 194 |
| SEQ_ID_NO_71 | ATTKKAPE-- | --DLTAAAAT | QPAVALGLGV | ADGGGGG--- | ---------- | | 192 |
| SEQ_ID_NO_64 | MSVCGSFT-- | --SLLNNNPQ | QNSGFLALGG | FGLGLGH--- | -----GL--- | | 167 |
| SEQ_ID_NO_75 | LDFGGSFT-- | --SLIAPGVA | DYGVHFSAGF | LMGGLAP--- | -----AALPR | | 190 |
| SEQ_ID_NO_51 | MDIGGSFS-- | --SLLASTGQ | --FGNLLEGF | NSNGSGL--- | -----KT--L | | 186 |
| SEQ_ID_NO_53 | LDMGGSFS-- | --SLLASSGQ | --FGSIFEGL | DSGGSGL--- | -----KMVRM | | 173 |
| SEQ_ID_NO_60 | ---GGSFS-- | --SLLASSGH | LGLGNLLEGL | NSSGSNL--- | -----KTVQM | | 147 |
| SEQ_ID_NO_58 | ---GGRFS-- | --SLLVSNMQ | QIRGVNYET- | ---GSG---- | ---------- | | 168 |
| SEQ_ID_NO_49 | MEIGGSFS-- | --SLLANNMQ | --LGLGGGGI | MLDGSG---- | ---------- | | 170 |

| | | | | | | | |
|---|---|---|---|---|---|---|---|
| SEQ_ID_NO_67 | ---------- | ---------- | PMLH PTAFL | D--------- | -NGNVDTMKV | | 184 |
| SEQ_ID_NO_65 | SL--DGFDNN | -----NGYGS | LQGE-TAGKK | LFFPLDDLKN | VSTPNDDHEF | | 239 |
| SEQ_ID_NO_63 | TTQAVTVTTM | KQEMCNVREQ | NENRVLLGFP | WQFNNGDTNM | AEMDII---- | | 266 |
| SEQ_ID_NO_73 | ARSTEGHDLN | ----NSNNN | NKV--LCGFP | WQQMNGDHHV | NNMNTNDFEY | | 274 |
| SEQ_ID_NO_69 | ----GGVREL | -----LPHPS | RFEM PSGCN | LG-------- | ---------- | | 222 |
| SEQ_ID_NO_70 | ----EHLDTS | -----P---- | -FEM PSGCD | L--------- | ---------- | | 210 |
| SEQ_ID_NO_71 | ---KEHLDTS | -----P---- | -FEM PSGCD | L--------- | ---------- | | 209 |
| SEQ_ID_NO_64 | ----GDMGFG | -----IGR-- | --EMSFPGMM | DGSNMGVPVV | SSGIGNSMQL | | 204 |
| SEQ_ID_NO_75 | AP--GSVAAL | -----PPPPP | QQQP-TVSQA | L--------- | ---------- | | 213 |
| SEQ_ID_NO_51 | NHFGGNFDSG | -----CEMDQ | NSGR-DPLFG | E--------- | SSKNGESYLD | | 221 |
| SEQ_ID_NO_53 | GGFGEDLNAG | -----PSR-- | ------NPGLD | LQGSSNNNTT | NDGGGESY-- | | 209 |
| SEQ_ID_NO_60 | EEFGENVSSG | -----PVADP | DSGR-NPGLE | MD-------- | SNGNAENFLS | | 183 |
| SEQ_ID_NO_58 | ---------- | ---------- | ---M YPGME | LG-------- | ---------- | | 176 |
| SEQ_ID_NO_49 | ---------- | ---------- | ---MDHPGMG | LGL------- | ---------- | | 180 |

Figure 2 (continued)

| | | | | | | |
|---|---|---|---|---|---|---|
| SEQ_ID_NO_67 | ----SGGGAA | AMWAPEFSPA | PTVADVGGNG | MFHGGAQIMG | QL | 222 |
| SEQ_ID_NO_65 | D-----EQN | RGQAAESHGF | WNG------ | ML GGGS---- | -- | 262 |
| SEQ_ID_NO_63 | ------LGR | AGWNGLTSSW | GHGL------ | LNSPLM---- | -- | 289 |
| SEQ_ID_NO_73 | STN----KQS | WNGFGGSSNW | HGL------- | NSPLM---- | -- | 299 |
| SEQ_ID_NO_69 | ------PPY | WGWGTSVFAD | TDPA------ | LFLNLP---- | -- | 245 |
| SEQ_ID_NO_70 | ---------G | PYWPTGVFAD | TDPS------ | LFLNLP---- | -- | 231 |
| SEQ_ID_NO_71 | ---------G | PYWPTGVFAD | TDPS------ | LFLNLP---- | -- | 230 |
| SEQ_ID_NO_64 | EGGE---TGF | VGGGGDCFSW | PGLA------ | STPGNGLK- | -- | 234 |
| SEQ_ID_NO_75 | ------PEG | MVW----SMGW | PDLS------ | L--------- | -- | 228 |
| SEQ_ID_NO_51 | V---QGGRDT | SCWSGDSNGW | PDLS------ | YTPGSSLRR | -- | 252 |
| SEQ_ID_NO_53 | ------LQG | GEWGNSNNGW | PGLA------ | YTPGSSFQ- | -- | 235 |
| SEQ_ID_NO_60 | LQN----GDS | SCW-NGTSGW | SHLA------ | FTPGSSFQ- | -- | 211 |
| SEQ_ID_NO_58 | ------LGS | GIRRNDDAAL | TDLA------ | MNRVEKN--- | -- | 200 |
| SEQ_ID_NO_49 | ------RRT | EPGNNNNNPW | TDLA------ | WNRAEKN--- | -- | 204 |

Figure 3

| | | |
|---|---|---|
| SEQ_ID_NO_88 | MAST- - - - - - - - - - - - - - - - - - - RRVQ C- -LMRRFYR - - -QSRTFGV | 23 |
| SEQ_ID_NO_95 | MTSL- - - - - - - - -QSFLAI KPAAAGWAAG ARPAAAPDSR RARVSACLAA | 40 |
| SEQ_ID_NO_90 | MNSL- - - - - - - - -QSFLAV APVK- -PAAA A- -ARLPSSR RARVSACLAT | 36 |
| SEQ_ID_NO_93 | MNSL- - - - - - - - -QSFLAL NPPAAAAALG G- -ARLRPSR - - -VTACLAT | 35 |
| SEQ_ID_NO_80 | MGSL- - - - - - - - -KLFPSF SLSV- -SPAT N- -LRRPLNN GR-VNASLNM | 35 |
| SEQ_ID_NO_87 | MGAVYFSQSC YKPRQI FNLE REBTLVGRCP V- -VQI RCRR V- -VSACLNV | 46 |
| SEQ_ID_NO_77 | MASL- - - - - - - - -GQI TLPR APS- - -SEI G L- -LRRRFER PI -I RTRI GF | 35 |
| SEQ_ID_NO_92 | MASL- - - - - - - - -GQI TLPR APS- - -LQKG L- -LRRP- - - - - -I RTPI RF | 30 |
| SEQ_ID_NO_78 | MTSL- - - - - - - - -QYFSLN RPV- - -FPAT H- -LHRPGI R HLQVSACANV | 35 |
| SEQ_ID_NO_82 | MGSL- - - - - - - - -QHFLNS PI SVPFSPNL N- -HRRSFF- - - -LRACLNL | 34 |

| | | |
|---|---|---|
| SEQ_ID_NO_88 | ATQPNA- - - - - - - - - - - - - - -SSSSQT I I DKEFQHSA HNNHPLPI VF | 55 |
| SEQ_ID_NO_95 | PPPPPT- - - -TAASAVGPA RRELSAASRA VMDDEARYLV GTYKRSRVVF | 85 |
| SEQ_ID_NO_90 | PAPAPT- - - - - - - - -APAAA RRELSAASRA VMADEAKYI V GTYKRAQVVF | 77 |
| SEQ_ID_NO_93 | PTPTPPPPTS APLAPAAAAA RRELSAASRA VVEDEARYI V GTYNRSRVVL | 85 |
| SEQ_ID_NO_80 | DVEAPN- - - - - - - - - - -P LKLKSNGSNE VI EKDAKFI V GTYARAPVVL | 72 |
| SEQ_ID_NO_87 | DVDAPN- - - - - - - - -TGN TTSEKKKTKD VI EMEGMYLV GTYARTPVVL | 85 |
| SEQ_ID_NO_77 | NGRI AS- - - -VLTNAGDQA VSVKASVSQK VI EEEAKVI V GTYARAPVVL | 80 |
| SEQ_ID_NO_92 | NGRI AS- - - -VLTNAG- - - -SVKASVSQK VI EEEAKVLV GTYARAPVVL | 71 |
| SEQ_ID_NO_78 | EVQAPS- - - - - - - - - - - -SVKKDGVSKE VMEAAGRVLV GTYARVPVVL | 71 |
| SEQ_ID_NO_82 | DVHAPD- - - - - - - - - -SV KPKTHLKSRE VMEMEGKVLV GTYARNPVVI | 72 |

| | | |
|---|---|---|
| SEQ_ID_NO_88 | AHAKGSAVWD PEGNKYI DFL SGYSAVNQGH CHPKI LKALK NDAGRLTVSS | 105 |
| SEQ_ID_NO_95 | EYGRGCKLYD VDGREYLDMS AGI AVTALGH ADPDVCATI A EQSGKI VHVS | 135 |
| SEQ_ID_NO_90 | VAGRGCKLYD I DGREYLDMA AGI AVNALGH GDPDVDAAAA DQRGRLVHAS | 127 |
| SEQ_ID_NO_93 | VAGRGCKLYD ADGREYLDMA AGI AVNALGH ADPDWAAVS AQAATLVHAS | 135 |
| SEQ_ID_NO_80 | SSGKGCKLYD PEGREFLDCA AGI AVNALGH GDPDWLRAVT EQASI LTHVS | 122 |
| SEQ_ID_NO_87 | ERGEGCKLYD VEGNEYLDLS AGI AVNALGH GDADWLKAVV EQAGTLTHTS | 135 |
| SEQ_ID_NO_77 | SSGKGCKLFD PEGKEYLDCA SGI AVNALGH GDPDWLRAVT EQAGVLAHVS | 130 |
| SEQ_ID_NO_92 | SSGKGCKLMD AEGKEYLDCA SGI AVNALGH GDPDWLQAVT DQASVLSHVS | 121 |
| SEQ_ID_NO_78 | SRGKGCKLYD PEGREYLDLS AGI AVNVLGH ADSDWLRAVT EQAATLTHVS | 121 |
| SEQ_ID_NO_82 | SSGKGCKLYD PEGREYLDCT SGI AVNALGH GDPDWKAVV EQANLLTHVS | 122 |

Figure 3 (continued)

| | | | | | | | |
|---|---|---|---|---|---|---|---|
| SEQ_ID_NO_88 | RAFYNDRFPV | FAEYSTALFG | YDMVLPINTG | AEGVETALKL | ARKAGYDKKK | | 155 |
| SEQ_ID_NO_95 | NVFYTTPQVE | LAKRLVEVSF | ADRAFFASTG | TEANEAAIKF | SRK--FQRVA | | 193 |
| SEQ_ID_NO_90 | NVGYTVPQVE | LAKRLVEASF | ADRAFFANSG | TEANEAAIKF | ARK--YQRVA | | 175 |
| SEQ_ID_NO_93 | NVQYTVPQVA | LAKRLVEASF | ADRVFFANTG | TEANEAAIKF | ARK--FQRVA | | 183 |
| SEQ_ID_NO_80 | NAYYSIPQ- | ---------- | ---------- | ---------- | ---------- | | 130 |
| SEQ_ID_NO_87 | NIFHTIPQVE | LAKRLVASSF | ADRVFFANSG | TEANEAAIKF | ARK--YQRHT | | 183 |
| SEQ_ID_NO_77 | NVYYTIPQIE | LAKRLVASSF | ADRVFFCNSG | TEANEAAIKF | SRK--FQRFT | | 178 |
| SEQ_ID_NO_92 | NVYYTIPQIE | LAKRLVASSF | ADRVFFCNSG | TEANEAAIKF | SRK--FQRFT | | 169 |
| SEQ_ID_NO_78 | NVFYSIPQVE | LAKRLVASSF | ADRVFFSNSG | TEANEAAIKF | ARK--FQRFT | | 169 |
| SEQ_ID_NO_82 | NVFYSVPQVE | LAKRLVACSF | ADRVFFTNSG | TEANEAAIKF | ARK--YQRFT | | 170 |
| | | | | | | | |
| SEQ_ID_NO_88 | IPNDEAL--- | IVSCCGCFNG | RTLGVISMSC | DNEATRGFGP | LIPGHLKVDF | | 202 |
| SEQ_ID_NO_95 | HPDSDDPPME | FLAFSSSFHG | RTMGAVALTS | KSQYREPFAP | VMPGVTFVDY | | 233 |
| SEQ_ID_NO_90 | HPNGDAPPTE | FMSFTNCFHG | RTIGSLALTS | KVQYREPFEP | VMPGSTFVEY | | 224 |
| SEQ_ID_NO_93 | RPDGDAPPTE | FMSFTNCFHG | RTMGSLALTS | KVQYREPFAP | VMPGATFAEY | | 232 |
| SEQ_ID_NO_80 | ---------- | ---------- | ---------- | ---------- | ---------- | | 130 |
| SEQ_ID_NO_87 | TSNGKVPATE | FIAFSNCFHG | RTLGALALTS | KVQYRMPFEP | VMPGVTFLEY | | 233 |
| SEQ_ID_NO_77 | HPEDKEVATG | FIAFTNSFHG | RTLGALALTS | KEQYRTPFEP | IMPGVTFLEY | | 228 |
| SEQ_ID_NO_92 | HPEDKEVATS | FIAFTNSFHG | RTLGALALTS | KEQYRTPFEP | IMPGVTFLEY | | 219 |
| SEQ_ID_NO_78 | RPDEKQPATE | FVSFSNSFHG | RTMGSLALTS | KENYRSPFEP | VMPGVTFLEY | | 219 |
| SEQ_ID_NO_82 | NPEKQQA-TE | FISFSNSFHG | RTMGALALTS | KEQYRFPFEP | VMPGVNFLEY | | 219 |
| | | | | | | | |
| SEQ_ID_NO_88 | GDAEALEKIL | KEKGDAIAAF | ILEPIQGEAG | VKIPPDGYLK | AVRDLCSKYN | | 252 |
| SEQ_ID_NO_95 | GQLEAAKKF | --QSGRVAAV | FVEPVQGEGG | HSATQEFLQ | GLREACDEAG | | 281 |
| SEQ_ID_NO_90 | GNLEEAKKVI | --QSGKIAAV | FVEPVQGEGG | HSATNEFLQ | GLRDACDEAG | | 272 |
| SEQ_ID_NO_93 | GNLEEAKKVI | --QSGKIAAV | FVEPVQGEGG | HSATKEFLQ | GLRDACDEAG | | 280 |
| SEQ_ID_NO_80 | ---------- | ---------- | ---------- | ---------- | ---------- | | 130 |
| SEQ_ID_NO_87 | GNAQAAVELI | --KQGKIAAV | FVEPIQGEGG | YSATKEFLQ | SLRNACDETG | | 281 |
| SEQ_ID_NO_77 | GNIQAATDLI | --RSGKIAAV | FVEPIQGEGG | YSATKEFLQ | SLRSACDAAG | | 276 |
| SEQ_ID_NO_92 | GNTDAATDLI | --RSGKIAAV | FVEPIQGEGG | VYSATKEFLQ | SLRSACDAAG | | 267 |
| SEQ_ID_NO_78 | GNIEAATQLI | --QRRKIAAV | FVEPIQGEGG | VYSATKEFLY | ALRKACDDSG | | 267 |
| SEQ_ID_NO_82 | GDVQAATELI | --KSGRIAAV | FVEPIQGEGG | YSATKEFLQ | SLRSACDDAG | | 267 |

Figure 3 (continued)

| SEQ_ID | Sequence | Pos |
|---|---|---|
| SEQ_ID_NO_88 | VLMI ADEI QT GLARTGKMLA CEWEEVRPDV VVLGKALGGG I PVSAVLAD | 302 |
| SEQ_ID_NO_95 | ALLVFDEVQC GFGRTGYLWA HEAYGVEPDI MTLAKPLANG - PI GVVLVK | 330 |
| SEQ_ID_NO_90 | ALLVFDEVQC GLGRTGYLWA HEVYGVLPDI MTLAKPLANG - LPI GVALVT | 321 |
| SEQ_ID_NO_93 | ALLVFDEVQC GLGRTGYLWA YEAYGVLPDI MTLAKPLAGG - LPI GVVLVT | 329 |
| SEQ_ID_NO_80 | -------VQC GLGRTGYLWA HEAYGVFPDM MTLAKPLAGG - LPI GATLVS | 172 |
| SEQ_ID_NO_87 | ALLVFDEVQC GLGRSGFLWA HEAYGVFPDM MTLAKPLAGG - LPI GALLVT | 330 |
| SEQ_ID_NO_77 | SLLVFDEVQC GLGRTGLMWA YEAFGVTPDI MTVAKPLAGG - LPI GAVLVT | 325 |
| SEQ_ID_NO_92 | SLLVFDEVQC GLGRTGNLWA YEAFGVTPDI MTVAKPLAGG - LPI GAVLVT | 316 |
| SEQ_ID_NO_78 | TLLVFDEVQC GLGRTGYLWA HELYDVFPDI MTLAKPLAGG - LPI GAVLVT | 316 |
| SEQ_ID_NO_82 | SLLVFDEVQC GLGRTGYLWA HEAYGVVPDI MTLAKPLAGG - LPI GAALVS | 316 |

| SEQ_ID | Sequence | Pos |
|---|---|---|
| SEQ_ID_NO_88 | KEVMLCI KPG QHGSTFGGNP LASAVAI ABL EVI KEERLAE RSTKLGGELL | 352 |
| SEQ_ID_NO_95 | EKVAAAI NYG DHGTTFGGGP LACQTAI TVF DKI MKPGFLA EVSKKGENFK | 380 |
| SEQ_ID_NO_90 | EKVAAAI HYG DHGTTFGGGP FVCHAALATL DKI QKPGFLA EVTKKGEYFK | 371 |
| SEQ_ID_NO_93 | EKVASAI NFG DHGTTFGGGP LVCQAALTTL DKI QKPGFLA EVAKKGENFK | 379 |
| SEQ_ID_NO_80 | ERVASAI AHG DHGSTFAGSP FVCSAAI CVF NKI SNPSFLS SVLKKGDYMK | 222 |
| SEQ_ID_NO_87 | ERVASAI NYG DHGSTFAGSP LVCSAALAVL DKI SKPDFLS SVSKKGLYFK | 380 |
| SEQ_ID_NO_77 | EKVAETI NYG DHGSTFAGSP LVCSAAI AVM DKVSKPSFLS SVSNKGRYFR | 375 |
| SEQ_ID_NO_92 | EKVAETI KYG DHGSTFAGNP LVCSAAI AVF DKVSKSSFLA SVSSKGLYFK | 366 |
| SEQ_ID_NO_78 | ERVASAI TYG DHGTTFAGGP LVCKAALTVL DKI LRPGFLA SVSKKGHYFK | 366 |
| SEQ_ID_NO_82 | EKVAAAI KYG DHGSTFAGGP LVCNAAI AVL DKI SKPGFLA SVSEKGQYFK | 366 |

| SEQ_ID | Sequence | Pos |
|---|---|---|
| SEQ_ID_NO_88 | GLLEKI QKQY PDHVKEVRGR GLFI GVELNS ESLSPVSFFE LSEKLKDRGV | 402 |
| SEQ_ID_NO_95 | QLLRTKLGGN P-HVKEVRGV GLLVGI ELD ----VPAGP LVDACLDAGV | 423 |
| SEQ_ID_NO_90 | QLLKTKLGGN P-HVKEI RGA GLI VGI ELD ----VPAGP LVDACLDAGV | 414 |
| SEQ_ID_NO_93 | QLLSTKLSGN A-HVKEI RGI GLI VGI ELD ----VPAGP LVDACLDRGV | 422 |
| SEQ_ID_NO_80 | ELLNQKLGGN P-HVKEI RGW GLMI GI ELD ----VSASP LVDACRNSGL | 265 |
| SEQ_ID_NO_87 | ELLREKLGEN R-HVKEI RGV GLI I GI DLD ----VPASP LVDACRSSGL | 423 |
| SEQ_ID_NO_77 | DLLVKKLGGN S-YVKEVRGE GLI I GVELD ----VPASS LVDACRDSGL | 418 |
| SEQ_ID_NO_92 | DLLVKKLGGN L-HVKEVRGE GLI I GVELD ----VPAGP LVDACRDSGL | 409 |
| SEQ_ID_NO_78 | EML NKLGGN S-HVREVRGV GLI VGI ELD ----VSASP LVNACLNSGL | 409 |
| SEQ_ID_NO_82 | ELL HKLGGN S-HVREVRGL GLI I GI ELD ----VSASP LVDACRDSSL | 409 |

Figure 3 (continued)

| | | | | | | | |
|---|---|---|---|---|---|---|---|
| SEQ_ID_NO_88 | LAKST-HDT | RFTPPLCIS | ADEIQQGSKA | LADVLEIDLP | MLKKMKPKDA | | 451 |
| SEQ_ID_NO_95 | LVLTAGKGNV | VRLVPPLIIS | EKELEHA--- | -ADVIRDCLP | VLDVAAA--- | | 466 |
| SEQ_ID_NO_90 | FLLTAGKGNV | VRLVPALIVS | EKELEQA--- | -AEVIRECLP | ALEASTS--- | | 457 |
| SEQ_ID_NO_93 | IVLTAGKGNV | VRLVPPLIIS | EKELEQA--- | -AEVIRDCLP | ALDASTS--- | | 465 |
| SEQ_ID_NO_80 | LVLTAGKGNV | VRLVPPLIIS | EEELKHA--- | -AEILHECLP | ALDNSN---- | | 307 |
| SEQ_ID_NO_87 | LVLTAGKGNV | VRLVPPLIIT | EKELEQA--- | -AEILCQTLP | VLDN------ | | 463 |
| SEQ_ID_NO_77 | LILTAGKGNV | VRIVPPLVIS | EEEIERA--- | -VEIMAQNLT | ALD------- | | 457 |
| SEQ_ID_NO_92 | LILTAGKGNV | VRIVPPLIIS | EEEIERA--- | -VEIIFHDLT | ALD------- | | 448 |
| SEQ_ID_NO_78 | LVLTAGKGNV | VRIVPPLIIT | EQELEKA--- | -AEILLQCLP | ALDRHG---- | | 451 |
| SEQ_ID_NO_82 | LILTAGKGNV | VRLVPPLIIS | EQELERA--- | -AEIILECLP | ALDKTS---- | | 451 |

| | | | |
|---|---|---|---|
| SEQ_ID_NO_88 | APPAGPSACD | RCGRVVYG | 469 |
| SEQ_ID_NO_95 | ---------- | -------- | 466 |
| SEQ_ID_NO_90 | ---------- | -------- | 457 |
| SEQ_ID_NO_93 | ---------- | -------- | 465 |
| SEQ_ID_NO_80 | ---------- | -------- | 307 |
| SEQ_ID_NO_87 | ---------- | -------- | 463 |
| SEQ_ID_NO_77 | ---------- | -------- | 457 |
| SEQ_ID_NO_92 | ---------- | -------- | 448 |
| SEQ_ID_NO_78 | ---------- | -------- | 451 |
| SEQ_ID_NO_82 | ---------- | -------- | 451 |

Figure 4

```
SEQ_ID_NO_101    -MSETEAAPV VA-------- -----PAAEA APAAEAPK-- AKAPKAKAPK   34
SEQ_ID_NO_102    --MATTEAVE EP-------- ----VPVEAT ANEDAKPTE- EKPAKEKKPK   35
SEQ_ID_NO_150    --MASTDPPA DT-------V PAEPVANEDV KAAEEKP--- VKAPKEKKVK   38
SEQ_ID_NO_118    --MALDTPVS AP-------- -----VVPEV TERKSKRG-- TKAAAVKVPK   32
SEQ_ID_NO_145    --MATTVAIE TP-------- --------AFT PVAVDPPA-- AKPAKAKKAK   31
SEQ_ID_NO_149    --MSAAVAIE TP-------- -----AFAPV PVARDEPV-- AKPGKVTKAK   33
SEQ_ID_NO_144    --MATDETTD PR-------- ---------- ------PV-- AKSKKAKAPK   22
SEQ_ID_NO_125    --MSTDVAAD VP----APEV EVAADPVVET TAEAAAGD-- AKPAKETKAK   42
SEQ_ID_NO_137    --MATEVAET PA-------- ---PLAEAVP ETPAEAPA-- APAAEANST-   34
SEQ_ID_NO_146    --MATDVAAT EP-------- -----EVAAE EAAAAAPETT ATAGDSKPAK   35
SEQ_ID_NO_147    --MATDVAAT EP-------- -----EVAAE EAAAAAPETT ATAGDSKPAK   35
SEQ_ID_NO_119    -MAAVEDPIV PM-----EGV EEEVPVTVTE APEEAAPP-- AEDPAPKKGK   42
SEQ_ID_NO_100    --MSLEEENV PT-------T VDSGAADTTV KSPEKKPA-- AKGGKSKKTT   39
SEQ_ID_NO_113    --MSTEEETK VV-------- --VESGDAEA TVTEKKPA-- AKGGAKAKKT   36
SEQ_ID_NO_104    --MATEEPAV VA-------- -DPAPETEED KTAETKAT-- SKSGRAKKTK   37
SEQ_ID_NO_108    --MSSDEPTV AV-------- -DGSTEPTSA EPADDKPA-- AKPSRAKKTK   37
SEQ_ID_NO_116    MTSSVEEPTV SAVEQTIVEE PAAVDPLPPV VNESDEPT-- AAKPK-----  43
SEQ_ID_NO_117    --MASEEPTT VAVEQPIVEE PEAVDTFPPV VNESEEPT-- AKPKKAPK-   44
SEQ_ID_NO_122    --MATEEPLV VT-----EIV TEAVVVEAEP AKEENSPA-- AEPDEPKKEK   41
SEQ_ID_NO_120    --MATEEPVI VN-------E VVEEQAAPET VKDEANPP-- AKSGKAKKET   39

SEQ_ID_NO_101    QPKAPKAPKE PKAPKEKKPK AAPTHPPYI E MVKDAITTLK ERNGSSLPAL   84
SEQ_ID_NO_102    TP----KEKK PRAAKGS--K PPAAHPPYVQ MIAEAITALK ERGSSSPYAI   79
SEQ_ID_NO_150    TP----KEKK PKAAKGS--K PPPAHPPYFQ MISEAIVALK ERGSSSPYAI   82
SEQ_ID_NO_118    ------EKKK VIAAKKPKSK GTSSHPSFFE MISDAISTLK ERTGSSQYAI   76
SEQ_ID_NO_145    VP----KEKK ASVAK----- -PALHPTYLE MISEAIASLK ERTGSSQIAI   71
SEQ_ID_NO_149    AP----KEKK ASVAKKP--- --ALHPTYLE MISEAIASLK ERTGSSQYAI   74
SEQ_ID_NO_144    EA----RAKK AAAPRKP--- --SAHPPYAE MIKEAITTLK ERTGSSPYAI   63
SEQ_ID_NO_125    AA----KAKK PSAPRKP--R ATPAHPTYAE MYSEAITALK ERTGSSQYAI   86
SEQ_ID_NO_137    ------KAKK ASAPKK---R ANPTHPPYAE MISEAVTSLK ERTGSSQYAI   75
SEQ_ID_NO_146    EA----KAKK AAAPRKA--R STATHPPYAE MISEAIATLK ERTGSSQYAI   79
SEQ_ID_NO_147    EA----KAKK AAAPRKA--R STATHPPYAE MISEAIATLK ERTGSSQYAI   79
SEQ_ID_NO_119    EL----KPKK AAAPRKP--R SAPAHPPYLE MITDAITSLK ERTGSSQAI    86
SEQ_ID_NO_100    TAKATKKPVK AAAPTKK--K TTSSHPTYEE MIKDAIVTLK ERTGSSQYAI   87
SEQ_ID_NO_113    PA----KKKP AAAPRK---R TTSSHPYEE  MIKDAIVTLK ERTGSSQYAI   79
SEQ_ID_NO_104    EP----KTKK AAAPRKP--R AAPTHPPYEE MIKDAIVTLK ERTGSSQYAI   81
SEQ_ID_NO_108    EP----KAKK APAPKKPRHR TPSSHPPYEE MIKDAIVTLK EKTGSSQYAI   83
SEQ_ID_NO_116    -----KAPK  EPKPRKPASK NTRTHPTYEE MVTDAIVTLK EKNGSSQYAL   87
SEQ_ID_NO_117    ------EPKA KKAPAKP--- --RTHPTYEE MVKEAIVALK ERNGSSQYAI   83
SEQ_ID_NO_122    EI----EAKK PAAPRK---R NPPTHPSYFE MIKDAIVTLK DKTGSSQHAI   84
SEQ_ID_NO_120    ------KAKK PAAPRKR--S ATPTHPPYFE MIKDAIVTLK ERTGSSQHAI   81
```

Figure 4 (continued)

| | | | | | | | |
|---|---|---|---|---|---|---|---|
| SEQ_ID_NO_101 | KKFIENKYGK | DIHDKNFAKT | LSQVVKTFVK | GGKLVKVKGS | FKLSE---- | 129 |
| SEQ_ID_NO_102 | AKFLSDKY-K | ADLPPNFKKQ | LNVQLKNLTK | SGKLTKVKAS | YKLTA---- | 123 |
| SEQ_ID_NO_150 | AKFLSEKY-K | SDLPPVFKKK | LNVQLRNLTN | SGKLTKVKGS | YKLAE---- | 126 |
| SEQ_ID_NO_118 | NKFVEDKH-K | Q-LPSNFRKL | LLFHLKKLVA | SGKLVKVKNS | FKLPS---- | 119 |
| SEQ_ID_NO_145 | SKFVENKH-K | AHLPANFKKL | LLVQLRKLTA | AGKLTKVKNS | YKISA---- | 115 |
| SEQ_ID_NO_149 | AKFVEDKH-K | SHLPANFKKL | LLVQLQKLTA | AGKLTKVKNS | YKISA---- | 118 |
| SEQ_ID_NO_144 | GKFIEDKH-K | AHLPSNFRKI | LFLQLKKLAA | AGKLTKVKSS | YKLST---- | 107 |
| SEQ_ID_NO_125 | AKFVEDKH-K | AHLPANFRKI | LSVQLKKLVA | SGKLTKVKAS | YKLSA---- | 130 |
| SEQ_ID_NO_137 | AKFVEDKH-K | DKLPPNFRKL | LLSQLKKLVA | AGKLTKVKNS | YKLPA---- | 119 |
| SEQ_ID_NO_146 | GKFLEDKH-K | DHLPSNFRKQ | LLVQIKKLVA | AGKLTKVKNS | YKLPP---- | 123 |
| SEQ_ID_NO_147 | GKFLEDKH-K | DHLPSNFRKQ | LLVQIKKLVA | AGKLTKVKNS | YKLPP---- | 123 |
| SEQ_ID_NO_119 | QKFLEAKH-K | D-LPAVFRKM | LSNNLKKLVA | AGKLVKVKAS | YKLPS---- | 129 |
| SEQ_ID_NO_100 | QKFIEEKH-K | S-LPPTFRKL | LLVNLKRLVA | SEKLVKVKAS | FKIPS---A- | 131 |
| SEQ_ID_NO_113 | QKFIEEKQ-K | S-LPPTFRKL | LLVNLRRLVA | SGKLVKVKAS | FKIPS---- | 122 |
| SEQ_ID_NO_104 | AKFIEEKQ-K | N-LPGNFKKL | LLVHLKKLVA | AGKLVKVKAS | YKLPS---A- | 125 |
| SEQ_ID_NO_108 | TKFLEEKH-K | Q-LPSNFKKL | LLFHLKKLVL | SDKIVKVKGS | FKLPS---- | 126 |
| SEQ_ID_NO_116 | AKFIEEKH-K | N-LPANFKKI | LLVQIKKLVA | SGKLVKVKGS | YKLPA--KS | 132 |
| SEQ_ID_NO_117 | AKFIEEKH-K | Q-LPSNFKKL | LLVQIRKLVA | SGKLVKVKAS | YKLPA---- | 126 |
| SEQ_ID_NO_122 | TKFIEDKQ-K | N-LPSNFRKL | LLVQLKKLVA | SGKLVKVKSS | YKLPA-AR- | 129 |
| SEQ_ID_NO_120 | TKFIEEKQ-K | S-LPSNFKKL | LLTQLKKFVA | SEKLVKVKNS | YKLPSGSKP- | 128 |

| | | | | | | | |
|---|---|---|---|---|---|---|---|
| SEQ_ID_NO_101 | ---ALKAKAK | KSTPKK-AKA | DG----EAKP | KK-SE-AKPK | ----KAEAVK | 165 |
| SEQ_ID_NO_102 | -----PKAPA | APKPKK-EKK | TVAKKKAPKP | KV-PA-AKPK | -APAAKAAKP | 164 |
| SEQ_ID_NO_150 | ----KEKKAD | APKPKT-EKK | PA----AKKP | KA-PA-AKAP | -AKAPSKAS | 163 |
| SEQ_ID_NO_118 | ------ARA | APAPAL-AKK | PT----IPKP | KV-------- | --AAKPKTAK | 147 |
| SEQ_ID_NO_145 | ----KPTTAT | KPKKTS-AKS | TT----VAKP | KS-AA-AKPK | --STAAKVKK | 152 |
| SEQ_ID_NO_149 | ----KPTPAA | KPKSA----- | ------AVKP | KS-AA-TKLK | -SAAKKVKK | 149 |
| SEQ_ID_NO_144 | ---IVHAAPA | EPKS------ | ------AAGP | KK-PA-AVQT | --KLKAKAKP | 138 |
| SEQ_ID_NO_125 | --------AAA | KPKP------ | ------AAKK | KPAAK-KKAP | --AKKTATKT | 158 |
| SEQ_ID_NO_137 | ----RAPAAA | KPKPKS-KTA | ------VKKP | KA-------- | --GAKKPKAA | 148 |
| SEQ_ID_NO_146 | ---TRAPAAA | KPKAKP-AAA | A-----KPKP | KPAA-AKPK | --AAAKPKAK | 161 |
| SEQ_ID_NO_147 | ---TRAPAAA | KPKAKP-AAA | A-----KPKP | KPAA-AKPK | --AAAKPKAK | 161 |
| SEQ_ID_NO_119 | -AKSSAPAKK | KPAAAP-AKK | KA----AAAP | AKKKT-AAAP | --KKKAAAAP | 170 |
| SEQ_ID_NO_100 | -RSAATPKPA | APVKKK-ATV | VA----KPKG | KV-AA-AVAP | --AKAKAAAK | 171 |
| SEQ_ID_NO_113 | --AAKPAATT | KPVNKK-PAA | A-----VTKP | KG----KAP | --AKAKPAAK | 157 |
| SEQ_ID_NO_104 | -RSSKTATAA | SAPAKK-KTA | TT----KSKS | KP--A-SKPK | --EGKSTKAT | 164 |
| SEQ_ID_NO_108 | ---AKSSAPA | KPAASPAKK | KTATAAKPKA | KSKPAVSKAK | ETKSAKSTAK | 173 |
| SEQ_ID_NO_116 | AAPAKKPAAA | KPKPKPKAKA | PVAKAPAAKS | KAKA-PAKA | KAKAKAKAAP | 181 |
| SEQ_ID_NO_117 | -KSSAAKPAK | KPAAAK-SKA | KPKAKAATKS | KAKPA-AKAK | --PAAKAKPA | 171 |
| SEQ_ID_NO_122 | -SAAPKAAAT | APAKKK-PGA | KPKAT-KAKP | KPKPK-TVAP | --KAKTATKP | 173 |
| SEQ_ID_NO_120 | -AAAAVPAKK | KPAAAK-SKP | AAKPKAAVKP | KAKPA-AKAK | --PAAKAKPA | 173 |

Figure 4 (continued)

| | | | | | | | |
|---|---|---|---|---|---|---|---|
| SEQ_ID_NO_101 | KTKAPKEKVE | RPKKEKKEKV | EKKKATPKAE | KPKK----AA | TPKSAGKKK- | | 210 |
| SEQ_ID_NO_102 | KAAKKAAPAK | PAAPAPP--- | ------KKEE | KPAA-AA-PK | KAAPAAKPKK | | 203 |
| SEQ_ID_NO_150 | KPAAPKKAEK | PVAPKK---A | AAPKKAAKPA | APKAAAPKAK | KPAAAAKPL- | | 208 |
| SEQ_ID_NO_118 | IGAKPKAKAK | VAAKTKA--T | TKTVA----- | ---------- | KKIPAAKPKA | | 180 |
| SEQ_ID_NO_145 | A--------- | ---------A | VKPKPKSAAV | KPKAEPA-AP | KPKAVSKPKA | | 183 |
| SEQ_ID_NO_149 | AAVKPKPKSA | ---------A | VKPKAPAVNM | KSKP-A-AL | KPNTVTKSKT | | 187 |
| SEQ_ID_NO_144 | AAASKTKAK | IATTAKA--K | SKHVASTVKP | KPKA-A-AA | KPRVAPKRKS | | 183 |
| SEQ_ID_NO_125 | KAKAPAKKA | ---------A | AKPKA-KAPA | KPKA----AA | KPKAAAKPKA | | 193 |
| SEQ_ID_NO_137 | TKPKPKAKAK | SPAKAKP--A | AKPKA-AAKP | KPAA----A | KPKAAAKPKA | | 190 |
| SEQ_ID_NO_146 | APAKSKAAAK | PKAAAKP--A | AKPKAAAKPK | SPAK--P-AA | KPKAAPKAKA | | 206 |
| SEQ_ID_NO_147 | APAKSKAAAK | PKAAAKP--A | AKPKAAAKPK | SPAK--P-AA | KPKAAPKAKA | | 206 |
| SEQ_ID_NO_119 | KKKAPVAKAK | PAAKPKAKAV | VKPKA-KAAV | KPKA-KP-AA | KPAAKAKPA- | | 216 |
| SEQ_ID_NO_100 | GTKKPAAKVV | AKAKV----T | AKPKAKVTAA | KPKS----K | SVAAVSKTKA | | 212 |
| SEQ_ID_NO_113 | GAKKPAAKAK | PKAKT----T | ATTKA-AAKP | KPKT----K | SVAAVSKTKA | | 197 |
| SEQ_ID_NO_104 | PKAKAKTKTT | SKAKSKP--A | AKPKA---TS | KAKAAPA-KT | KAVASVKPKT | | 208 |
| SEQ_ID_NO_108 | SPAKSKAAAK | PKAKPKAA-A | AKPKV-TAKA | KPKA-AP-AK | AKTSVAKPKA | | 219 |
| SEQ_ID_NO_116 | AKAKPAAKAK | PAAKAKP--A | AKAKP-VAKA | KPKAKAP-VA | KANAVPVA-- | | 225 |
| SEQ_ID_NO_117 | AKAKPAAKAK | PAAKAKP--A | AKAKPAAKPV | KTAAAKP-AA | KAKPAAKPKA | | 218 |
| SEQ_ID_NO_122 | KAKQRQVKAK | LVAKAKP--A | VKPKA----- | -----AA-VA | VPKAAEKPK- | | 209 |
| SEQ_ID_NO_120 | AKAKPAAKAK | PAAKAKP--A | AKAKP-VAKA | KPKA-AA-AA | KPKAAVKPKA | | 218 |

| | | | | | | | |
|---|---|---|---|---|---|---|---|
| SEQ_ID_NO_101 | -ATPKPKAAP | ---------- | ---------- | -------K | SPAKKDAKPK | KATPSKKAAP | 240 |
| SEQ_ID_NO_102 | -PAAKPKKAA | ---------- | ---------- | ---TPKKPAP | KPKPAKKAAT | | 229 |
| SEQ_ID_NO_150 | -AAPKRSST- | ---------- | ---------- | ---RTAAKPA | APKAAKKPTP | | 233 |
| SEQ_ID_NO_118 | KTAGKPKTVA | ---------- | ---------A | KPAKVAKTAA | VASPGKKKAV | | 211 |
| SEQ_ID_NO_145 | -VAPKPKTAG | ---------- | ---------- | -PAKKAKTSA | KPSPSKKAAP | | 211 |
| SEQ_ID_NO_149 | -VALKGKTAG | ---------- | ---------- | RPAKAAKTSV | KAAPGKKAAP | | 216 |
| SEQ_ID_NO_144 | PVKPKPKPKP | ---------- | ---------- | RPTRAAKTAA | KDSPGKKAAK | | 213 |
| SEQ_ID_NO_125 | KAAAKPKAAA | ---------- | ----KPKG | RPAKAAKTSA | KDAPGKKAPA | | 227 |
| SEQ_ID_NO_137 | KPAAKAKPKA | ------VAA | KPKPAAKKAG | RPAKAAKTSA | KDTPGKKAAP | | 233 |
| SEQ_ID_NO_146 | KPAAKPKAKA | APKPKAAVVT | KTKATSAPAR | RPAKAAKTSA | KDTPSKKAAP | | 256 |
| SEQ_ID_NO_147 | KPAAKPKAKA | APKPKAAAVT | KTKATSAPAR | RPAKAAKTSA | KDTPSKKAAP | | 256 |
| SEQ_ID_NO_119 | -AKAKPAAKP | ---------- | -KAK-----A | KPAKVARTST | RTTPGKKAPA | | 249 |
| SEQ_ID_NO_100 | -VAAKPKAKE | ---------- | ---------- | RPAKASRTST | RTSPGKKVAA | | 241 |
| SEQ_ID_NO_113 | -VAAKPKAKE | ---------- | ---------- | RPVKASRTST | RTSPGKKAAA | | 226 |
| SEQ_ID_NO_104 | TAATKPKAAA | ---------- | -KPK-----D | KPVKASRTST | RTSPGKRAAA | | 242 |
| SEQ_ID_NO_108 | -APAKPKAKE | ---------- | ---------- | RPAKASRTST | RTSPGKKAAA | | 248 |
| SEQ_ID_NO_116 | -AKAKPAAKA | ---------- | KPAAKAKPAA | RPAKASRTST | RTSPGKRAAA | | 264 |
| SEQ_ID_NO_117 | AAKAKPAAKA | ---------- | KPAAKAKPAA | KPAKAARTST | RTSPAAAAAA | | 258 |
| SEQ_ID_NO_122 | -TPVKTKAAA | ---------- | KP--KAK--E | KPAKVARTAT | RSTPSRKAAP | | 244 |
| SEQ_ID_NO_120 | -APAKTKAAV | ---------- | KPNLKAK--T | TTAKVAKTAT | RTTPSRKAAP | | 255 |

Figure 4 (continued)

| | | | | | |
|---|---|---|---|---|---|
| SEQ_ID_NO_101 | --KKAPAKKS | T-PKAKEA- | | | 255 |
| SEQ_ID_NO_102 | ---------- | --PKKKAG-- | | ----RP--- | 237 |
| SEQ_ID_NO_150 | ---------- | ----KKAG-- | | ----GA--- | 239 |
| SEQ_ID_NO_118 | -----PVKKV | K-TVKSPA-- | | | 223 |
| SEQ_ID_NO_145 | ----VASKKA | K-PVKKATA- | | | 225 |
| SEQ_ID_NO_149 | ----VALKKA | K-AGKKVTT- | | | 230 |
| SEQ_ID_NO_144 | ----RSSSRS | A-PTKKPK-- | | ----PAVKKA | 232 |
| SEQ_ID_NO_125 | ----AAAPKK | A-AARKPPT- | ---------- | KRSTPVKKAA PAKKAAPAKK | 261 |
| SEQ_ID_NO_137 | -----AKKPA | A-AAKKAPA- | ---------- | KKAAPAKKA- ----PTPSRK | 261 |
| SEQ_ID_NO_146 | ----AAKKPA | A-AAKKAPA- | ---------- | KKAAPAKKA- ----AAPARK | 285 |
| SEQ_ID_NO_147 | ----AAKKPA | A-AAKKAPA- | ---------- | KKAAPAKKA- ----AAPARK | 285 |
| SEQ_ID_NO_119 | KPAAAPVKKA | T-PVKKATAT | PVKKAAPVKK | AAPAKGKSV- ----KTPVKR | 293 |
| SEQ_ID_NO_100 | -----PAKKV | A-VTKKAP-- | ---------- | ---AKSAKV- ----KSPAKR | 265 |
| SEQ_ID_NO_113 | ----PAKKAA | AAATKKAP-- | ---------- | ---AKSVKV- ----KSPAKR | 252 |
| SEQ_ID_NO_104 | --PKPAAKKA | P-AAKKAP-- | ---------- | AKSVKPKSV- ----KSPAKK | 272 |
| SEQ_ID_NO_108 | --TKVAPKKA | A-TPKKAP-- | ---------- | AKTVKLKSV- ----KTPTKK | 278 |
| SEQ_ID_NO_116 | --AKPAVKKA | ATPVKKAVPA | ---------- | KKAATPVKK- ----AAPARK | 297 |
| SEQ_ID_NO_117 | --PKPAAKKA | A-PVKKTPV- | ---------- | KAAAKAKTA- ----KSPAKK | 289 |
| SEQ_ID_NO_122 | ---KPVAKKV | P-VKKAAPA- | ---------- | AKSVKAKTA- ----KSPAKR | 274 |
| SEQ_ID_NO_120 | --KATPAKKE | --PVKKAP-- | ---------- | -----AKNV- ----KSPAKK | 279 |

| | | |
|---|---|---|
| SEQ_ID_NO_101 | ---KSKGKK | 261 |
| SEQ_ID_NO_102 | ---AKKAKK | 243 |
| SEQ_ID_NO_150 | ---AKKAKK | 245 |
| SEQ_ID_NO_118 | ---GKRTRK | 229 |
| SEQ_ID_NO_145 | ---PKKAKK | 231 |
| SEQ_ID_NO_149 | ---PKKAKK | 236 |
| SEQ_ID_NO_144 | AAAAKKAKK | 241 |
| SEQ_ID_NO_125 | APAAKKAKK | 270 |
| SEQ_ID_NO_137 | VP-SRKAKK | 269 |
| SEQ_ID_NO_146 | VP-ARKAKK | 293 |
| SEQ_ID_NO_147 | VP-ARKAKK | 293 |
| SEQ_ID_NO_119 | TSARKAGKK | 302 |
| SEQ_ID_NO_100 | AS-TRKAKK | 273 |
| SEQ_ID_NO_113 | ASTRKK--- | 258 |
| SEQ_ID_NO_104 | AT-SRRGKK | 280 |
| SEQ_ID_NO_108 | AA-VKKGKK | 286 |
| SEQ_ID_NO_116 | APAKRGGRK | 306 |
| SEQ_ID_NO_117 | AA-AKRGKK | 297 |
| SEQ_ID_NO_122 | AS-ARKGRK | 282 |
| SEQ_ID_NO_120 | AT-PKRGRK | 287 |

Figure 5

| | | | | | | | | |
|---|---|---|---|---|---|---|---|---|
| SEQ_ID_NO_164 | MENM----- | KMNNDERFA- | ------QKGV | PVHSQVMKIK | QEBEKIVDWS | | | 37 |
| SEQ_ID_NO_158 | MENN----- | SSNDDSRGRN | GDGDHGYVGF | PIHSQVIKIR | QEFDKIKHPS | | | 44 |
| SEQ_ID_NO_154 | MEQKKISSSS | SSNNNAVIRD | EDE---YKGV | PIHSQVMKIK | QEFEKIKHPS | | | 47 |
| SEQ_ID_NO_152 | MENK----- | TDNGN----- | ------EDGP | IIHSQVEKIK | KEFEKIRQPS | | | 33 |
| SEQ_ID_NO_162 | MENK----- | TNNGN----- | ------EDGI | PKHSQVVKIK | REFEKISQPS | | | 32 |

| | | | | | | |
|---|---|---|---|---|---|---|
| SEQ_ID_NO_164 | PGKPEIRSVL | REIS-RQLSR | SPLGISGDPI | SVGES | | 71 |
| SEQ_ID_NO_158 | LQQLEVRGVV | KCRINRQRSR | SPLGLAERPI | SVGN- | | 78 |
| SEQ_ID_NO_154 | LQQPDMRRVL | REIT-RQRSR | SPLGLAERPI | SVGNS | | 81 |
| SEQ_ID_NO_152 | LQQPEMRRVL | SEIKRRQRSR | SPLGLGERSI | SVGN- | | 67 |
| SEQ_ID_NO_162 | LKQPEMRRVL | SEITRRQRSR | SPLGLGERSI | SVGH- | | 66 |

Figure 6

```
SEQ_ID_NO_184   ------------------------ MG L------- ----------    3
SEQ_ID_NO_168   ------------------------ MS SLPTQVLQG LLGEFHSRRL   22
SEQ_ID_NO_177   ------------------------ ME YPRRTLLH-- ----------   10
SEQ_ID_NO_181   ------------------------ MG TPLRMPHMST CSNVAPAP--   20
SEQ_ID_NO_182   ------------------------ MA MSPHDQHEHE PDHAHRSP--   20
SEQ_ID_NO_183   ------------------------ MA MSPHDQHEHE PDHAHRSP--   20
SEQ_ID_NO_170   ------------------------ MR PAPLEAEAAA ANISHLSP--   20
SEQ_ID_NO_166   ------------------------ MR LLVAEAA--- ----------    9
SEQ_ID_NO_174   MWMMI SQEGQ RSNPIIYHNN IHLLCEVDQK REKASVIVLK IQTKHPNPES   50

SEQ_ID_NO_184   -----SSLP GPSEGMLCVI LVN------ TALSISFKG VRSVLHVLG   40
SEQ_ID_NO_168   LLTPL-TTAS PPSSEHHNS SDLYTRNNSF DANIVMVLSV LLCALICSLG   70
SEQ_ID_NO_177   --TPFSGHPS GPSQPIDGAT A---TDGSNF DANVVMILAV LLCALICALG   55
SEQ_ID_NO_181   --APEAPRAP PSSP------ ---------L DYDVVVILAA MLCALVCALG   53
SEQ_ID_NO_182   ------SNGT AATSTIATNR AGPYSGAGDF ASNMAVILAA LLAALALALA   64
SEQ_ID_NO_183   ------SNGT AATSTIATNR AGPYSGAGDF ASNMAVILAA LLAALALALA   64
SEQ_ID_NO_170   --PPLHSRAP SCDPQVHSCK WAPYSNSNDF GANTAMILII LLCALICALV   68
SEQ_ID_NO_166   --SPLSSLAA TPTCNSHTCR WKPYSNSTDF TANASVLLIL VISALICALS   56
SEQ_ID_NO_174   FKTSLEPLSP PLSPHSLCIR WKPYSNSSEF QANASVLLIL FVSALICGLS   99

SEQ_ID_NO_184   IRLSQSSSSP SSVTASSEIP ASEPFDFRVS HPESFLEEFR NKIPTLRYES   90
SEQ_ID_NO_168   LNSIIRCALR CSSLIASESG ATTSSRLANK ---GNKRKAL KTFPTVNYS  116
SEQ_ID_NO_177   LNSIVRCALR CSSRVVVGPE PNQVTRLVQS ---GLRRKAL RAMPVLVYS  101
SEQ_ID_NO_181   LNSMLQCVVR CTRRAVADPV GWAHRRASA  ---GLKREDV VALPVVTYS   99
SEQ_ID_NO_182   LNAAVRYLLR RHRRARQQPA AAAAAAEDPE KPPVQEADPP PPPPALVYSA  114
SEQ_ID_NO_183   LNAAVRYLLR RHRRARQQPA AAAAAAEDPE KPPVQEADPP PPPPALVYSA  114
SEQ_ID_NO_170   LNTAIRAFLR BNNNNSSDRL GELEEDRKPK --DEADMAIL VLATTQVYS  115
SEQ_ID_NO_166   LYAAIRCFLR -------PT  LETEDDHKPD --PEAAASST PTTPTLVYS   95
SEQ_ID_NO_174   LCAAIRCFLR PN-----L   QTDDNEHKPD --PEEDVSST VPTPTLVYS  139

SEQ_ID_NO_184   LCRCKKHEDN ECSVCLSKFE EDSEINKLK- -C----GHL  FHKTCLEKW  132
SEQ_ID_NO_168   ADLKLPGLDS ECITCLSDFT AGDRVRLLPK -C----NHG  FHVRCIDKW  159
SEQ_ID_NO_177   PGLRINAANP TCAICLSDFE AGEHVRVLPK -C----NHG  FHVRCIDRW  144
SEQ_ID_NO_181   -ASPPAAAAA GCAICLSDFA DGERMRVLPV -C----GHR  FHVVCIDRW  141
SEQ_ID_NO_182   AGTKLAGALA ECAICLAEFV DGDTVRVMPC WCDEIPLESG LRFAQIKVYQ  163
SEQ_ID_NO_183   AGTKLAGALA ECAICLAEFV DGDTVRVMPV -C----GHG  FHARCIERW  156
SEQ_ID_NO_170   AGMKLGGVEA DCAICLSEFV EGEGIRVLGR -C----DHG  FHVLCIEKW  158
SEQ_ID_NO_166   SDLELAGAEA ECAICLSEFE QGESIQVLEK -C----QHG  FHVKCIHKW  138
SEQ_ID_NO_174   SDLELAGAQA ECAICLSEFE PGESIHVLEK -C----HHG  FHIKCIHKW  182
```

Figure 6 (continued)

```
SEQ_ID_NO_184             ----------  -I-DYWN TC  PLCRT- PLVV  ----------  --------V     150
SEQ_ID_NO_168             ----------  -L-SAHSSC  PKCRH- CLVD  TCQKI VGCT-  --QASSSEPP    192
SEQ_ID_NO_177             ----------  -L--LARSTC PTCRQ- SLFG  VPQKASGCSE  ASRAAFPEPA    180
SEQ_ID_NO_181             ----------  -L--ASHKSC PTCRR- RLSS  ----------  --------ES    159
SEQ_ID_NO_182             TGPFNVEAAN  LL--PTPGIC TTCRF- VYRG  VVKHLHFL--  ---YGDWRD L   206
SEQ_ID_NO_183             ----------  -L-AGGRRSSC PTCRA- PAAT ----------  --------PP    176
SEQ_ID_NO_170             ----------  -L--SSHSSC PTCRRSCLAS  SPSSPEPDNC  SAGNGHDSNS    195
SEQ_ID_NO_166             ----------  -L--STRSSC PTCRT- SIFS  ----------  ----------    154
SEQ_ID_NO_174             ----------  -L--SSRSSC PTCRT- SIFS  ----------  --QNTLDSAT    206

SEQ_ID_NO_184    AAAEDQKQLS  SNVW------  ----    164
SEQ_ID_NO_168    PVQETILSII  TPVDREGFIH  SYR-    215
SEQ_ID_NO_177    PAPAPARSVL  VPLRPEGLVT  HYDF    204
SEQ_ID_NO_181    GGGHRHLQVL  TAV-------  ----    172
SEQ_ID_NO_182    ACFVKGKKNT  NS--------  ----    218
SEQ_ID_NO_183    GATATEPAAV  APL-------  ----    188
SEQ_ID_NO_170    SQSAEPERAA  DNLSTNGNIP  V---    216
SEQ_ID_NO_166    QHSETPSSHI  NA--------  ----    166
SEQ_ID_NO_174    SAVAPSTNEI  NA--------  ----    218
```

Figure 7

```
SEQ_ID_NO_194    MLKSKSCREE MRSSS AYK  YHCLTNGGTP EAVAAPSPTN PQLPVMLRSY   49
SEQ_ID_NO_199    -MAAADYDRA YRPYAPSSAA DYDRPYRNE- ---------- ------ VPY   32
SEQ_ID_NO_204    -MAAADADYE YRAYG-APA- DHDRPYHG-- ---------- RE--- VVPY    31
SEQ_ID_NO_186    ---MANYYE- -PPAS-GNRR DAVKGYNS-- -G-------- ------- SF    25
SEQ_ID_NO_201    ---MD--RS- -KSYA-GGR- MQI EPYYD-- -G----GGAR PD---FRSY    30
SEQ_ID_NO_203    ---MDDFRS- -RSFN-DGK  MQLEVYGSRR SGAVPAPPVL HD---YRSY    39
SEQ_ID_NO_188    ---MEHFRS- -KSCR-EGR- I EMEGYDEDK AA----PTNM QD---LRSY    35
SEQ_ID_NO_196    ---MEEFRS- -KSYG-DGR- MQI EAYRG- --------ANI QD---LRCY    30
SEQ_ID_NO_197    ---MEDYNKQ IRPYG-NSCM MQMEGYYG-- -A----TNPN YD---IRSY    35
SEQ_ID_NO_193    ---MEDYNRQ -RAYG-DTG- MQI QPYHG-- -G----GPGT GD---FRKY    33

SEQ_ID_NO_194    S-------- TSTYS----- ---------- ----PHKNPT TVRDNPNS-K   70
SEQ_ID_NO_199    G-------- DRRI DLVVKP PPP------- ----TRSPPP PLPVTKSG--   60
SEQ_ID_NO_204    G-------- DRRI DVVVKP PGTTTTTT-- ----TRSPPP PLPVTKVG-G   65
SEQ_ID_NO_186    D-------- DSSGDQSQ-- ---------- ----TNDYQL KI KKSKSVPN   50
SEQ_ID_NO_201    SYSAGGSGMG TSSYAYQYEY S--------- ----GAGAGE EMKRSKS---   64
SEQ_ID_NO_203    S-------- -ASYFYTYD- ---------- ----GSGVGY GDFKGKPDHG   64
SEQ_ID_NO_188    S-------- -VSYAVSVQP N--------- ----QSGKEG KMKKDKSN--   60
SEQ_ID_NO_196    S-------- -ASYASSVHP TTTTTTTTQT QMGGNNNNEA KFKKGKST--   68
SEQ_ID_NO_197    S-------- DFSYAQTQRG ---------- ----PNNKDL KLKKGKS-S   61
SEQ_ID_NO_193    S-------- -TSYA----- ---------- ----TENNI X NLKKEKS--   52

SEQ_ID_NO_194    SNGKVKKGL- --KEAEI QRK KRVAAYNVYG VEGKVKGSI R KNFKWFKETC   117
SEQ_ID_NO_199    GGGGI GSAWC F-SDPEVKRR RRVASYKAYS VEGKVKASFR RGFRWI KDKC   109
SEQ_ID_NO_204    GGGGMGSAWC F-SDPEMKRR RRVASYKAYS VEGKVKSSLR RGFRWI KAKC   114
SEQ_ID_NO_186    ADRAASRSWS F-SDPESRRK RRVAGYKVYS VEDKMKGSI R KSFKWFKD--   97
SEQ_ID_NO_201    -----KRRWL ALADPDMERK RRVAAYKAVG VEGKMKGSFR KSFKWI KDRY   109
SEQ_ID_NO_203    SSASNKGGRV F-KDPEFQRK RRVASYKAYA VEGKVKGSLR RSLRWFKDKY   113
SEQ_ID_NO_188    -LESSSKSWS F-NDPELQRK RRVANYKVYA I EGKMKGSLR KSFRWI KDTC   108
SEQ_ID_NO_196    -NGSTSKSWS F-SDPELQRK KRVASYKVYA VEGKLKGSLR KSFKWLKDRC   116
SEQ_ID_NO_197    SRSSI SKSWS FGDDPEFQRK KRVASYKMYS VEGKVKGSFR KSFKWLKNRY   111
SEQ_ID_NO_193    ---ARSKSWG I-TDPELQRK KRVASYKMYS VEGKVKGSFR KSFRWLKQRY   98
```

Figure 7 (continued)

| | | |
|---|---|---|
| SEQ_ID_NO_194 | SNAVNGLW- ........... ............ . | 125 |
| SEQ_ID_NO_199 | TGF HG- ... ............ ............ . | 115 |
| SEQ_ID_NO_204 | SELIHGWYGS LLLPLSFSLD DFIITSKQAL S | 145 |
| SEQ_ID_NO_186 | ---IGS- ............ ............ . | 102 |
| SEQ_ID_NO_201 | LNLVYGWS-- ............ ............ . | 117 |
| SEQ_ID_NO_203 | TRAVYGWW- ............ ............ . | 121 |
| SEQ_ID_NO_188 | TQVVYGWR-- ............ ............ . | 116 |
| SEQ_ID_NO_196 | NRVVYG- ............ ............ . | 122 |
| SEQ_ID_NO_197 | WHVVYSLW- ............ ............ . | 119 |
| SEQ_ID_NO_193 | TQVVYGWW- ............ ............ . | 106 |

Figure 8

| | | |
|---|---|---|
| SEQ_ID_NO_216 | MGKGEAWVNG QRIGRYWPTY VASDASCTDS CNYRGPYSAS KCRKNCEKPS | 50 |
| SEQ_ID_NO_208 | ---------- ---------- ----METLQ CRHQHVFIL- ---------- | 15 |
| SEQ_ID_NO_214 | ---------- ---------- ----MDTTHS CRRG--YIL- ---------- | 14 |

| | | |
|---|---|---|
| SEQ_ID_NO_216 | QTLYHVPRSW LKPSGNILVL FFERGGDPTQ ISIVTKQTES LCAHVSDSHP | 100 |
| SEQ_ID_NO_208 | LVLFHS-SL FVLASKIDVS DDARGIRIDG ---GQKRFLT NSPQHGKEHA | 60 |
| SEQ_ID_NO_214 | LVLSYS-SV FGLASNMSIS NDTSGNKTDS FFESQSTSTE WGTDMGDKY | 62 |

| | | |
|---|---|---|
| SEQ_ID_NO_216 | PPVDLWNSET ESGRKVGPVL SLTCPHDNQV SSIKFASYG TPLGTCGNFY | 150 |
| SEQ_ID_NO_208 | -------ACT NEEPDLGPLT RISCNEPEYV TKINFADYG NPTGTCGHFR | 103 |
| SEQ_ID_NO_214 | -------MCT ESNMEIPWM -ISCKKSKEV FTRINFADYG NPSGKCEHYR | 103 |

| | | |
|---|---|---|
| SEQ_ID_NO_216 | HGRCSSNKAL SIVQKACIGS SSCSVGVSGD TFGDP-CRGM AKSLAVEATC | 199 |
| SEQ_ID_NO_208 | RDNCGARATM RIVKKNCLGK EKCHLLVTDE MFGPSKCKGA PM-LAVETTC | 152 |
| SEQ_ID_NO_214 | HGNCGAKTTM EVAKKNCLGK HDCVFKVSDE MFGTSHCKKE AK-FFVQLTC | 152 |

| | | |
|---|---|---|
| SEQ_ID_NO_216 | A-- | 200 |
| SEQ_ID_NO_208 | TIA | 155 |
| SEQ_ID_NO_214 | TKA | 155 |

Figure 9

```
SEQ_ID_NO_218       ----MDEEAA KPRDSTVNQQ H--------- ----------QYY YGTFQGVANF    30
SEQ_ID_NO_225       ----MDEEAA KPRDTTVNQQ Q--------- ----------QYY YGTFQGVANY    30
SEQ_ID_NO_227       -MGDGEEDKS KGFADEAGTH H--------- -----------Q YGTFQGVSNY    31
SEQ_ID_NO_220       ----MSGDEK NPAVVVDHQH H--------- -----------Q YGTFQGVSNY    28
SEQ_ID_NO_222       ----MSDQEK NRGVVVDHRH HEDQPPPPPP -----PPDPQ YGTFQGVANY    40
SEQ_ID_NO_231       MAGEMPDADG KPRSASSGFQ PSAPPQPQ-- ------AQQYQ YGTFGA----    39
SEQ_ID_NO_230       -MGGGREEEA ASKL-VGYSS GDLPPSAPPH LQGQDPQQYQ YGTFQ-----   42
SEQ_ID_NO_229       -MGGGDEQEA DAGKSGGYSS SGLPPSEP-- -----SQQYG YGTFQG---    38
SEQ_ID_NO_1052      -MGGRHEAEA DGGKAGGYSS SGLPPSEAPH LQGQPSQEYG YGTFQG---    45

SEQ_ID_NO_218       PTPAPPPDFM QPQHPITTF- ---PGHAY-- ----------Q NLQGHG----    61
SEQ_ID_NO_225       PPPAPPP--- LPHQPIVTSP LLPP------ ----------- ----------    51
SEQ_ID_NO_227       PPPRP----- QNSPPVTGFP QPSAPPRV-- ----------Y D-SAPP---    60
SEQ_ID_NO_220       PPPPPP---- QHHGPAIGFP QPVPPPGL-- ----------H EPSAPP---    59
SEQ_ID_NO_222       PPPS------ --QSHVIGFP QPVPPPG--- ----------- --TAEP---    64
SEQ_ID_NO_231       PSSAPG---- EVPQPAVGFP QPAPPPGL-- ----------R HYPQPPPPSY    74
SEQ_ID_NO_230       PPPHHHAASG ELARPPVGFP QPAPPPGFAG ASGGGGHYHH HHQQQP---   88
SEQ_ID_NO_229       SRAGSG---- EFRKPPVGFP QPAPPPGF-- --GGGG----Y HNQQQP---    73
SEQ_ID_NO_1052      P--------- --RQPPVGFP QPAPPPGF-- --SGGG----Y HNQQKP---    73

SEQ_ID_NO_218       ---------- ---GGVNYAQ GFPVVVPDYT -VVEVRP---M IEHELPCCGL    95
SEQ_ID_NO_225       ---------- ---------VH GYQ-TLQEYT -VVEVRP---V REHDVPCCGF    79
SEQ_ID_NO_227       ---------- -----HYAH GYQ-TVPVHG -IAEGRPVHV RQRRLPCCGI    92
SEQ_ID_NO_220       ---------- ----PQYYPQ GYQ-TVPGYA -VAEGRP---V RERRLPCCGI    91
SEQ_ID_NO_222       ---------- -------YAQ GYQ-TVPGYA -VAEGRP---V RQRRLPCCGC    93
SEQ_ID_NO_231       AVYPPLPPQT YPAAAPYYAL GYQ-AVQGYL PVVEGRP---V RMRRLPFCGL   121
SEQ_ID_NO_230       ---------- YAPAEPYYAQ GYQ-TGPGYG SI AEGRP---V RMRRLPCCGL   125
SEQ_ID_NO_229       ---------- YTPEEPYYAQ GYQ-AVPGYG QVAEGRP---V RMRRLPCCGL   110
SEQ_ID_NO_1052      ---------- YAPAEPYYAQ GYQ-AVPGYG PVAEGRP---V RMRRLPCCGL   110

SEQ_ID_NO_218       GMGWFLFIMG FLFGGIPWYL GAFIVLVT-S VDHREKAGYV ACSIA-----   139
SEQ_ID_NO_225       GMGWFLFIMG FLFGGIPWYL GAVIILFT-S VDHREKAGYV ACSVA-----   123
SEQ_ID_NO_227       GLGWFLFIVG FFLGAIPWYV GMFIMIVGRR DHREKPGYI ACTIA-----   137
SEQ_ID_NO_220       GFGWFLFIIG FFLGAIPWYI GLFVLLCA-R DYREKPGYI ACTIA-----   135
SEQ_ID_NO_222       GVGWFLFIIG FFLGAIPWYI GLFIIACMLR DPREKPGYV ACTIALRKHL   142
SEQ_ID_NO_231       GMGWFLFIIG FFLAAIPWYI GAFVLICVRV HDYREKPGYV ACTIA-----   166
SEQ_ID_NO_230       GLGWLLFIAG FFLAAIPWYV GAFILICVRV HDYREKPGYV ACTVA-----   170
SEQ_ID_NO_229       GLGWCLFITG FFLAAIPWYI GAFIMICVRV HDHREKPGYV ACTIAVSS--   158
SEQ_ID_NO_1052      GLGWCLFITG FFLAAIPWYI GAFILICVRV HDQREKPGYV ACTIA-----   155
```

Figure 9 (continued)

| | | | | | | |
|---|---|---|---|---|---|---|
| SEQ_ID_NO_218 | ---------- -------- | S | VVYLI AVMLG | MTGD N | I W | 158 |
| SEQ_ID_NO_225 | ---------- -------- | S | VVYLI AVMLG | MAGN N | I W | 143 |
| SEQ_ID_NO_227 | ---------- -------- | A | I LATI AVI LG | VTKGAE | DW | 156 |
| SEQ_ID_NO_220 | ---------- -------- | A | VLATI AI I LG | VTKGI D | DF | 153 |
| SEQ_ID_NO_222 | VEHECHI EI R CLLHNLCVK | A | I LATI AI I LG | ATKGAD | EW | 180 |
| SEQ_ID_NO_231 | ---------- -------- | A | SLAAI AI LLG | VTRGEE | I W | 185 |
| SEQ_ID_NO_230 | ---------- -------- | A | VI AAI M PLG | LTKGAH | VW | 189 |
| SEQ_ID_NO_229 | ---------- -------- | F | LL QCN TVY | FTSGI | --- | 174 |
| SEQ_ID_NO_1052 | ---------- -------- | A | VVAAVAI LLG | VTKGTH | VW | 174 |

Figure 10

| | | | | | | |
|---|---|---|---|---|---|---|
| SEQ_ID_NO_244 | MEYDRTNNLS | LAFQFFRKAF | EMCDSDPLLF | NEYGVLRYRQ | G-NYEEAVEN | 49 |
| SEQ_ID_NO_234 | MEYMRTHSYK | LADQFFMQAK | AICPSDPLVY | NELGVVAYHM | K-EYGKAVRW | 49 |
| SEQ_ID_NO_236 | MEYMRTHSYK | LAEQFFMQAK | TICPSDPLVY | NELGVVAYNM | K-EYNKAVLW | 49 |
| SEQ_ID_NO_241 | MQYVRMHNFK | LAEQFFTQAK | SICPSDPLIH | NELGVVAYNM | KEEYQKAVSY | 50 |
| SEQ_ID_NO_242 | MQYLRMHNFK | LAEQFFTQAK | SICPSDPLIY | NEMGVVAYNM | K-EYQKAVQW | 49 |

| | | | | | | |
|---|---|---|---|---|---|---|
| SEQ_ID_NO_244 | FERALDLAPK | PVGSRWESLI | VNLAQAFRKI | GRYDEAIATF | QSALLISPRN | 99 |
| SEQ_ID_NO_234 | FEKTLAHIPS | ALTESWEPTV | VNLAHAYRKL | RKDREAISYY | ERALTLSTKS | 99 |
| SEQ_ID_NO_236 | FEKTLKHIPS | -LSQLWEPTV | INLAHAYRKL | KIYHEAISCY | ERALALSTRS | 98 |
| SEQ_ID_NO_241 | YAKALTFPTK | SLS----AF | AGLAYIYHLM | DDFEAAINYY | HKALWLKPDD | 95 |
| SEQ_ID_NO_242 | FELTLEHTSS | SLNEMWEPTL | VNLGHALRKL | KKYQKAISYY | EKALTFQTKS | 99 |

| | | | | | | |
|---|---|---|---|---|---|---|
| SEQ_ID_NO_244 | ASTYAALAFT | YQMKSRCSEP | VSLGLAIEYY | HKALSLRADD | AFSQHHLELA | 149 |
| SEQ_ID_NO_234 | LSTYSGLAYT | YHLQGNFS- | ----AAISYY | HKALWLKPDD | QFCTEMLNVA | 143 |
| SEQ_ID_NO_236 | LSTYAGLAYT | YHLQDNFT- | ----AAITCY | HKALWLKPDD | QFCTEMLSLA | 142 |
| SEQ_ID_NO_241 | QFCTDMLTYA | LESICQIT- | ---------- | ---------- | ---------A | 114 |
| SEQ_ID_NO_242 | LSAFAGLAYT | YHLMAMYH- | ----V----- | HRA------ | ----EVLQL- | 127 |

| | | | | | | |
|---|---|---|---|---|---|---|
| SEQ_ID_NO_244 | LIDQSAITIP | RHQQVEWDTM | FPKVEDINAV | TPTFGIASSP | OGGILFPTPS | 199 |
| SEQ_ID_NO_234 | LMDE------ | ---------- | ---------- | ---------- | ---------- | 147 |
| SEQ_ID_NO_236 | LVDE------ | ---------- | ---------- | ---------- | ---------- | 146 |
| SEQ_ID_NO_241 | RRKP------ | ---------- | ---------- | ---------- | ---------- | 118 |
| SEQ_ID_NO_242 | TKEP------ | ---------- | ---------- | ---------- | ---------- | 131 |

| | | | | | |
|---|---|---|---|---|---|
| SEQ_ID_NO_244 | PHSFQGTPTF | GQTPFSARVD | RMDESVDMDQ | SVDMDESE | 237 |
| SEQ_ID_NO_234 | ---------- | CQNGVDSKV- | ---------- | -----ELC | 159 |
| SEQ_ID_NO_236 | ---------- | GRRGIDPKI- | ---------- | -----EFR | 158 |
| SEQ_ID_NO_241 | ---------- | GRGLLTAIGG | ---------- | -----VTC | 131 |
| SEQ_ID_NO_242 | ---------- | GR-------- | ---------- | -------- | 133 |

Figure 11

| | | | | | | |
|---|---|---|---|---|---|---|
| SEQ_ID_NO_268 | ---MEEQCAA | AAGGG---GG | GEGASMCANG | CGFFGSEATK | KLCSKCYRDQ | 44 |
| SEQ_ID_NO_228 | ---MAER-QE | VSG------ | GMAAPMCANR | CGFFGSAATK | NLCSKCYK-- | 37 |
| SEQ_ID_NO_260 | ---MSEEQNN | STSFP---- | PTEPKLCDNG | CGFFGSPSNK | NLCSKCYR-- | 40 |
| SEQ_ID_NO_249 | ---MAEE-HR | CQA------ | P---DLCANN | CGFFGSPTTC | NLCSECYR-- | 34 |
| SEQ_ID_NO_255 | ---MAEEQHR | CQE------ | P---RLCVNN | CGFFGSPATC | NLCSKCYG-- | 35 |
| SEQ_ID_NO_265 | ---MAEE-HR | CQA------ | --ADRLCANN | CGFFGSPANN | DLCSKCYR-- | 35 |
| SEQ_ID_NO_262 | ---MAEE-HR | CQA------ | PEGHRLCSNN | CGFFGSPATM | NLCSKCYR-- | 37 |
| SEQ_ID_NO_251 | ---MAEE-HR | CQA------ | PEGHRLCVNN | CGFFGSSATM | NLCSKCYR-- | 37 |
| SEQ_ID_NO_248 | ---MAEE-HR | CET------ | PEGHRLCVNN | CGFFGSSATM | NLCSNCYG-- | 37 |
| SEQ_ID_NO_274 | ---MAEE-HP | CQT------ | PEGHRLCVNN | CGFFGSSATM | NLCSNCYG-- | 37 |
| SEQ_ID_NO_243 | MAQRDKEETE | MKV------ | SEGLSLCINN | CGFSGNPATK | NMCDSCYK-- | 41 |
| SEQ_ID_NO_279 | ---MAQESWK | QESEETRVHA | PEAPILCINN | CGFFGSSMTN | NMCSKCYR-- | 45 |
| SEQ_ID_NO_288 | ---MAQESWK | QESHA----- | PEAPILCINN | CGFFGSSMTN | NMCSKCYR-- | 40 |
| SEQ_ID_NO_270 | ---MQHDKTG | CQSP------ | PEGPKLCINN | CGFFGSAATM | NMCSKCHK-- | 39 |
| SEQ_ID_NO_267 | ---MEQNETG | CQVP------ | PDAPMLCVNN | CGFFGSAATM | NPCSKCHK-- | 39 |
| SEQ_ID_NO_277 | ---MEHEETG | CQPH------ | PEGPILCVNN | CGFFGSVATR | NMCSKCHK-- | 39 |
| SEQ_ID_NO_286 | ---MEHKETG | CQQ------ | PKGPILCINN | CGFFGSAATM | NMCSKCHK-- | 38 |
| SEQ_ID_NO_290 | ---MEHKETG | CQQ------ | PEGPILCINN | CGFFGSAATM | NMCSKCHK-- | 38 |

| | | | | | | |
|---|---|---|---|---|---|---|
| SEQ_ID_NO_268 | LKAAPSSPPA | APDLVANEEE | EASTAAAAAN | DEQLALCSSG | CGFFGSKETN | 94 |
| SEQ_ID_NO_228 | ---------- | --EHLIKTAK | DEASAAVVUG | GAIVKCAADE | CGFFGSSATN | 75 |
| SEQ_ID_NO_260 | ---------- | --SLRAEEDQ | TAVAKAAVEK | SLKLPSCSL | TAPAPKD-PL | 77 |
| SEQ_ID_NO_249 | ---------- | --GLQLKEQQ | SSSAKQAFNH | TLVPSSSSLP | --------SS | 64 |
| SEQ_ID_NO_255 | ---------- | --DLRDSCPL | NCLLAPSSSA | SVSSFSSPL- | ---------- | 61 |
| SEQ_ID_NO_265 | ---------- | --DLQMKEQR | SSSAKLVLNQ | TLIPDCSNSS | SLDTS--HP | 72 |
| SEQ_ID_NO_262 | ---------- | --DIRLKEEE | DAKTKSTIET | ALSGSSSATV | ---------T | 66 |
| SEQ_ID_NO_251 | ---------- | --DLCLKEQE | ASSLKSALSS | SPSSSSTVV- | ---------- | 64 |
| SEQ_ID_NO_248 | ---------- | --DLCLKQQQ | DASMKSTVES | SLSPVIAPV- | ---------- | 64 |
| SEQ_ID_NO_274 | ---------- | --DLCLKMQQ | DASMKSTVES | SLSAASPPS- | ---------- | 64 |
| SEQ_ID_NO_243 | ---------- | -----STGI | MTQPALTFSG | KEKARSSLR | --------LP | 68 |
| SEQ_ID_NO_279 | ---------- | --DFI----- | KLVEAPVVEK | KVTTSASSS- | ---------- | 67 |
| SEQ_ID_NO_288 | ---------- | --DFV---KL | MEMDAPVVDK | KLITTASS-- | ---------- | 63 |
| SEQ_ID_NO_270 | ---------- | --TLFDQEQ | GAKLASAVSG | SPSNLKET | --------TA | 69 |
| SEQ_ID_NO_267 | ---------- | --DLMLKQQQ | TELAASSIGS | ANGGSGPS | KEPDSALT- | 75 |
| SEQ_ID_NO_277 | ---------- | --DMMLKEEQ | AKLAASSFGN | VNGTSNSNG | NEPV----VA | 73 |
| SEQ_ID_NO_286 | ---------- | --EMINKQEQ | AKLAASSIDS | VNGGDSGKE | PIIAG--HA | 73 |
| SEQ_ID_NO_290 | ---------- | --EMINKQEQ | AKLAASSIDS | VNGGDSGKE | PIIAG--HA | 73 |

| SEQ_ID_NO_268 | HACTFDFKKS | DREKIAKENP | LIVAPK TKF | 224 |
| SEQ_ID_NO_298 | HACDFDFKAA | GREKIAKNNP | LVVAAK NKI | 193 |
| SEQ_ID_NO_260 | HECSFDFKEV | GRSAIAKANP | VVKADKVQRI | 175 |
| SEQ_ID_NO_249 | TCLCF.... | .......... | | 137 |
| SEQ_ID_NO_255 | HDCEFDFKSL | GKEQIAKANP | VVKGEKLQRI | 159 |
| SEQ_ID_NO_265 | HGCGFDFKGM | GREEIKKANP | VVKGEKLNKI | 170 |
| SEQ_ID_NO_262 | HACGFDFKAV | GREEIARANP | VIKGEKLRRI | 164 |
| SEQ_ID_NO_251 | HGCTFDFKKV | GREEIARANP | LVKAEKLEKI | 161 |
| SEQ_ID_NO_248 | HGCTFDFKSA | GREEIAKANP | LV AAKLQKI | 161 |
| SEQ_ID_NO_274 | HGCTFDFKSA | GREEIAKANP | LVVAAKLQKI | 160 |
| SEQ_ID_NO_249 | HDCSFDYKAA | GREEIARQNP | VVKAAK RL | 170 |
| SEQ_ID_NO_279 | HQCTFDYKKV | AREQIAKQNP | VVMAEK NKI | 163 |
| SEQ_ID_NO_288 | HECTFDYKKV | AREQIAKQNP | VV AEK NKI | 169 |
| SEQ_ID_NO_270 | HNCSFDYHVA | AQEAIAKANP | VVKADKLDKI | 168 |
| SEQ_ID_NO_287 | HDCPFDYRSA | AQDAIAKANP | VVKAEKLDKL | 173 |
| SEQ_ID_NO_277 | HDCPYDYHTA | ARDVAKANP | VVKADKLEKI | 173 |
| SEQ_ID_NO_289 | HDCQFDYRTA | ARDAIAKANP | VVKAEKLDKI | 171 |
| SEQ_ID_NO_290 | HDCQFDYRTA | ARDAIAKANP | VVKAEKLDKI | 171 |

Figure 12

| | | | | | | | |
|---|---|---|---|---|---|---|---|
| SEQ_ID_NO_310 | ------- MAE | AKGAAAPL- | --LAREDGRR | RGGMGGATWA | Q--TLGNVVV | | 37 |
| SEQ_ID_NO_316 | MGFGMG-NDG | ASSSSSRLDP | APLLPHHGSA | GGEIG--LSS | QPKTFANVFI | | 47 |
| SEQ_ID_NO_325 | MGFGMGNNNG | ASSSSSRLDP | APLLPHHGSG | SREVG--LSS | QPKTFANVFI | | 48 |
| SEQ_ID_NO_312 | MGF----DKE | ASSSSSRLDA | APLLPQHG-- | GGGACGHLSS | QPKTFANVFI | | 44 |
| SEQ_ID_NO_319 | MGL----HKE | ASSSSSRLDA | APLLPHHGHG | GGGAGHHLSS | QPKTFANVFI | | 46 |
| SEQ_ID_NO_321 | MGL----HKE | ASSSSSRLDA | APLLPHHGHG | GGGAGHHLSS | QPKTFANVFI | | 46 |
| SEQ_ID_NO_300 | MGF----QNE | ASSSSYTLKI | PPPAREDTPL | LGK-GPPLSS | QFKTFANVFI | | 45 |
| SEQ_ID_NO_302 | MGFG---RKK | ASSSAKTF-- | --PPREDTPL | IAK-STPLSS | QSKTFANVFI | | 42 |

| | | | | | | | |
|---|---|---|---|---|---|---|---|
| SEQ_ID_NO_310 | SIVGTGVLGL | PYAFRAAGWV | AGSLGVAAAG | FATLYCMLLL | VDCKDKLQEE | | 87 |
| SEQ_ID_NO_316 | AVVGAGVLGL | PYTFSHTGWA | AGSLLLFAVA | VLTFYCMMLL | VACRRRLAD- | | 96 |
| SEQ_ID_NO_325 | AVVGAGVLGL | PYTFSHTGWA | AGTLLLFSVA | ALTFYCMMLL | VACRRRLAD- | | 97 |
| SEQ_ID_NO_312 | AVVGSGVLGL | PYTFSRTGWA | AGTLLLLAVA | ALTFHCMMLL | VAARRRIAD- | | 93 |
| SEQ_ID_NO_319 | AVVGSGVLGL | PYTFSRTGWV | AGSVLLLAVA | ALTFHCMMLL | VACRRRLAY- | | 95 |
| SEQ_ID_NO_321 | AVVGSGVLGL | PYTFSRTGWV | AGSVLLLAVA | ALTFHCMMLL | VACRRRLAY- | | 95 |
| SEQ_ID_NO_300 | AVVGAGVLGL | PYAFKRTGWL | MGVLLLVSVS | VLTHHCMMLL | VYTRRKLDSF | | 95 |
| SEQ_ID_NO_302 | AIVGAGVLGL | PYAFKRTGWL | MSLIMLFSVA | GLTHYCMMLL | VNTRGKLQSF | | 92 |

| | | | | | | | |
|---|---|---|---|---|---|---|---|
| SEQ_ID_NO_310 | ETDEPKNYTY | GDFGEKCFGT | IGRCLTEILI | LISQAGGSMA | YLVFIGENLH | | 137 |
| SEQ_ID_NO_316 | --ERPKIASF | GDLGDAVFGA | HGRFAVDVML | VLSQASFCIG | YLIFISNTMA | | 144 |
| SEQ_ID_NO_325 | --EHPKIASF | GDLGDAVFGA | HGRFAVDVML | VLSQFSFCVG | YLIFISNTMA | | 145 |
| SEQ_ID_NO_312 | --AHPKIASF | GDLGHAIYGA | PGRHAVDAML | VLSQASFCVG | YLIFISNTMA | | 141 |
| SEQ_ID_NO_319 | --DHPKIASF | GDLGAAVCGP | AGRHVVDAML | VLSQASFCVG | YLIFISNTMA | | 143 |
| SEQ_ID_NO_321 | --DHPKIASF | GDLGAAVCGP | AGRHVVDAML | VLSQASFCVG | YLIFISNTMA | | 143 |
| SEQ_ID_NO_300 | NAGISKIGSF | GDLGFAVCGS | LGRIVVDLFI | ILSQAGFCVG | YLIFISTTLA | | 145 |
| SEQ_ID_NO_302 | SGGFSKITSF | GDVGFTVCGS | IGRFVVDVMI | VLSQAGFCIG | YLIFIANTLA | | 142 |

| | | | | | | | |
|---|---|---|---|---|---|---|---|
| SEQ_ID_NO_310 | SVFS------ | ---------- | -----QSMS | PAGFIFAVLL | PVQIALSFL | | 165 |
| SEQ_ID_NO_316 | HLYP----IF | APSSS----- | ------ALLS | PKALFIWAML | PFQLGLNSIK | | 179 |
| SEQ_ID_NO_325 | HLYP----IT | APSSS----- | ------ALLS | PKALVIWAML | PFQLGLNSIK | | 180 |
| SEQ_ID_NO_312 | HLYPIAIGAQ | SPAS------ | ------PLLT | AKALFIWAML | PFQLGLNSIR | | 179 |
| SEQ_ID_NO_319 | HLYP--VGDS | SPSS------ | ------PLLT | AKAIFIWVML | PFQLGLNSIK | | 179 |
| SEQ_ID_NO_321 | HLYP--VGDS | SPSS------ | ------PLLT | AKAIFIWVML | PFQLGLNSIK | | 179 |
| SEQ_ID_NO_300 | NLSD----PE | SPTSLRHQFT | RLGSEFLGVS | SKSLYIWGCF | PFQLGLNSIK | | 191 |
| SEQ_ID_NO_302 | NLFN----SP | SPNGLASQIL | A-----LSMS | AKSMYMWGCF | PFQLGLNSIA | | 183 |

Figure 12 (continued)

| | | | | | | |
|---|---|---|---|---|---|---|
| SEQ_ID_NO_310 | SLSSLSPFSI | FADVCNVLAA | AVVIRKDLDL | IDHPFANRSA | FNGVLAIPFA | 215 |
| SEQ_ID_NO_316 | TLTLLAPLSI | FADVVDLGAM | GVVLGQDVAA | MAMPPPVVA | FGGPAALLYG | 229 |
| SEQ_ID_NO_325 | TLTLLAPLSI | FADVVDLGAM | GVVLGQDVAA | WAKPVPVAA | FGGPAALLYG | 230 |
| SEQ_ID_NO_312 | TLTLLAPLSI | FADVVDLGAM | GVVLGQDABV | MLADRPPVFA | FAGPAQLLYG | 229 |
| SEQ_ID_NO_319 | TLTLLAPLSI | FADVVDLGAM | GVVLGQDVST | MLANKPPVFA | SAGPTELYG | 229 |
| SEQ_ID_NO_321 | TLTLLAPLSI | FADVVDLGAM | GVVLGQDVST | MLANKPPVFA | SAGPTELYG | 229 |
| SEQ_ID_NO_300 | TLTHLAPLSI | FADIVDLGAM | AVVIVEDSM | ILKQRPDVVA | FGGMSLFLYG | 241 |
| SEQ_ID_NO_302 | TLTHLAPLSI | FADVVDLAAM | GVVIVKDVFL | MVENRAEVRA | FGGLSVFFYG | 233 |

| | | | | | | |
|---|---|---|---|---|---|---|
| SEQ_ID_NO_310 | FGVAVFCFEG | FSMTLALESB | MAERRKFRW | LSDAVVGILV | VYACFGVCGY | 265 |
| SEQ_ID_NO_316 | LGVSVYAFEG | VGMVLPLEAE | AANKRKFGVT | LGLSMAFIAV | MYGLFGVMGY | 279 |
| SEQ_ID_NO_325 | LGVSVYAFEG | VGMVLPLEAE | AANKKKFGVT | LGLSMAFIAV | MYGLFGVMGY | 280 |
| SEQ_ID_NO_312 | LGVAVYAFEG | IGMVLPLEAE | AADKRRFGAT | LALSMAFIAV | MYGLFGAMGY | 279 |
| SEQ_ID_NO_319 | LGVAVYAFEG | IGMVLPLEAE | AADKRKFGGT | LALSMAFIAV | MYGLFGAMGY | 279 |
| SEQ_ID_NO_321 | LGVAVYAFEG | IGMVLPLEAE | AADKRKFGGT | LALSMAFIAV | MYGLFGAMGY | 279 |
| SEQ_ID_NO_300 | MGVAVYSFEG | VGMVLPLESE | MKDKDKFGKV | LALGNGFISL | YLAFGILGY | 291 |
| SEQ_ID_NO_302 | MGVAVYAFEG | IGMVLPIESE | MREREKFGRI | LGLSMGLSV | IYGAFGVLGY | 283 |

| | | | | | | |
|---|---|---|---|---|---|---|
| SEQ_ID_NO_310 | LAYGEATKDI | TLNLPNSNS | SAAVKVGLCI | ALAFTEPVMM | HPIHEIVETR | 315 |
| SEQ_ID_NO_316 | VAFGDATRDI | TTNLGAGWL | SAAVQLGLCI | NLFFTMPVMM | NPVYEVAERL | 329 |
| SEQ_ID_NO_325 | VAFGDATRDI | TTNLGAGWL | SAAVQLGLCI | NLFFTMPVMM | NPVYEVAERL | 330 |
| SEQ_ID_NO_312 | LAFGAATRDI | TTNLGTGWL | SVLVQLGLCI | NLFFTMPVMM | NPVYEVAERL | 329 |
| SEQ_ID_NO_319 | LAFGAATRDI | TTNLGTGWL | SVAVQLGLCI | NLFFTMPVMM | NPVYEVAERL | 329 |
| SEQ_ID_NO_321 | LAFGAATRDI | TTNLGTGWL | SVTVQLGLCI | NLFFTMPVMM | NPVYEVAERL | 329 |
| SEQ_ID_NO_300 | LAFGEDTMDI | TANLGAGLV | STVQLGLCI | NLFFTFPLMM | NPVFEIVERR | 341 |
| SEQ_ID_NO_302 | FAFGNDTQDI | TANLGPGL | SLLVQLGLCI | NLFFTFPLMM | NPVYEILERR | 333 |

| | | | | | | |
|---|---|---|---|---|---|---|
| SEQ_ID_NO_310 | LRSSGCFQKL | SHGVPGAEWL | GLHSSRLMV | TLLVMASCI | PAFGSFVSFV | 365 |
| SEQ_ID_NO_316 | L-------- | -HGKRYCWWL | -----RWLLV | VVVGLAAMYV | PNFTDFLALV | 364 |
| SEQ_ID_NO_325 | L-------- | -HGKRYCWWL | -----RWLLV | IVVGLAAMYV | PNFTDFLALV | 365 |
| SEQ_ID_NO_312 | L-------- | -CGKRYAWWL | -----RWILV | VLVGLLAMLV | PNFADFLSLV | 364 |
| SEQ_ID_NO_319 | L-------- | -CRKRYAWWL | -----RWLLV | MVVGLMAMLV | PNFADFLSLV | 364 |
| SEQ_ID_NO_321 | L-------- | -CRKRYAWWL | -----RWLLV | MVVGLMAMLV | PNFADFLSLV | 364 |
| SEQ_ID_NO_300 | F-------- | -SRGMYSAWL | -----RWVLV | LAMTLVALFV | PNFADFLSLV | 376 |
| SEQ_ID_NO_302 | F-------- | -WGGRYCLWL | -----RWSM | LLVTLVALMV | PNFADFMSLV | 368 |

Figure 12 (continued)

| | | | | | | | |
|---|---|---|---|---|---|---|---|
| SEQ_ID_NO_310 | GCTVCALLSF | VLPTFFHLN | VGSSMSLWRR | VLDYGFLLFG | LGFAGYGIFT | | 415 |
| SEQ_ID_NO_316 | GSSVCVLLGF | VLPASFHLKV | FGAEMAWPGV | LSDALLVVLG | LALAVFGTYT | | 414 |
| SEQ_ID_NO_325 | GSSVCVLLGF | VLPASFHLKV | FGGEMEWPGV | VSDVLVVIG | LSLAVFGTYT | | 415 |
| SEQ_ID_NO_312 | GSSVCVVLGF | VLPAVFHLKV | FGTEIGWAGL | VADVAIIVTG | IALAVSGTWT | | 414 |
| SEQ_ID_NO_319 | GSSVCVLLGF | VLPAAFHLKV | FGAEVGWPGL | AGDVAVIVVG | TALAVSGTWT | | 414 |
| SEQ_ID_NO_321 | GSSVCVLLGF | VLPAAFHLKV | FGAEVGWPGL | AGDVAVIVVG | TALAVSGTWT | | 414 |
| SEQ_ID_NO_300 | GSSICCVLGF | VLPALFHLLV | FKEEMGWLQW | SSDTAIVYLG | VVLAVSGTWS | | 426 |
| SEQ_ID_NO_302 | GSSVCCGLGF | VLPALFHLLV | FKEEMSWKGW | SIDVGIVALG | LVLAVSGTWY | | 418 |

| | | | |
|---|---|---|---|
| SEQ_ID_NO_310 | ALSSH----- | | 420 |
| SEQ_ID_NO_316 | SLLQIFHSSS | A | 425 |
| SEQ_ID_NO_325 | SLLQIFHSSS | A | 426 |
| SEQ_ID_NO_312 | SLVQIFSSSD | L | 425 |
| SEQ_ID_NO_319 | SLAQIFSSSD | V | 425 |
| SEQ_ID_NO_321 | SLAQIFSSSD | V | 425 |
| SEQ_ID_NO_300 | SLSEIFSVKV | - | 436 |
| SEQ_ID_NO_302 | ALMEIFAVKV | - | 428 |

Figure 13

| | | | | | | | |
|---|---|---|---|---|---|---|---|
| SEQ_ID_NO_368 | · · · · · | NEAEM | LYSALALTFA | LMVHRILSN | SQNK | · · · · · | RSLINLPPSP | 39 |
| SEQ_ID_NO_348 | · · · · · | NEAEM | LYSALALTFA | FMVYRILSN | SQDK | · · · · · | RSLTKLPPSP | 39 |
| SEQ_ID_NO_365 | · · · · · | NEAEM | LYSALALTFA | FMVYRILSN | SCEK | · · · · · | SSLIKLPPSP | 39 |
| SEQ_ID_NO_346 | · · · · · · · · | MV | LLSELAAATL | FLTTHFIS | TLLS | · · · · I | TNGRRLPPGP | 37 |
| SEQ_ID_NO_2546 | · · · | MAPKKSK | TTAMKPDTVS | PPYLSKKPR | NLKCSYSLKS | | HKKIHLPPSP | 47 |
| SEQ_ID_NO_332 | · · · · · · · · · · | · · · · · · · · · · | · · · · · · · · · · | · · · · · · · · · · | · · · · · · · · · · | · · · · · · · · · · | · · · · · · · · · · | 0 |
| SEQ_ID_NO_339 | · · · | MEALMV | DFDNCLILIL | LDLLSFLCVS | FFFK | · · · KP | KDGFNLPPSP | 43 |
| SEQ_ID_NO_341 | · · · · · · · · · · | | MEMIVFLFL | VLLISLLSS | SENN | · · · · · · | SLQLPKGP | 32 |
| SEQ_ID_NO_2549 | · · · · · | NSTFT | DLQNYTIFFI | LBFISTLLLR | SFLN | RTTP | TTRLRLPPSP | 44 |
| SEQ_ID_NO_2544 | · · · · · · · · | MLL | EIALGLLVLG | LFLHLRPTPS | AKSK | · · · · A | LRHLPNPPSP | 38 |
| SEQ_ID_NO_2541 | · · · · · · · · | MLL | ELALGLLVLA | LFLHLRPTPT | AKSK | · · · · A | LRHLPNPPSP | 38 |
| SEQ_ID_NO_358 | · · · · · · · · | MLL | ELALGLLVLA | LFLHLRPTPT | AKSK | · · · · A | LRHLPNPPSP | 38 |
| SEQ_ID_NO_360 | · · · · · · · · | MLL | ELALGLLVLA | LFLHLRPTPT | AKSK | · · · · A | LRHLPNPPSP | 38 |
| SEQ_ID_NO_339 | · · · · · · · · | MRLV | EIAVTLVLIA | LFIHFRPTPT | AKSK | · · · · A | LRHLPNPPSP | 39 |
| SEQ_ID_NO_2550 | · · · · · · · · | MLV | ELALALLAIA | LFLHLRPTPT | AKSK | · · · · A | LRHLPNPPSP | 38 |
| SEQ_ID_NO_2543 | · · · · · · · · · | ML | EIQGYVVLFL | LWFISSIFIR | SLFK | · · · · K | SVCYKLPPGP | 37 |
| SEQ_ID_NO_2551 | · · · · · · · · · | ML | DIQGYLVLFL | LWFISTILIR | SIFK | · · · · K | SQCYKLPPGP | 37 |
| SEQ_ID_NO_2548 | MEVATSRELI | NPTAFPILVL | VAGLTTVFYW | LRRR | · · CSG | NGGLRLPPSP | 47 |
| SEQ_ID_NO_353 | · · · · | MDHQL | VARGLFKPLL | LFVAGLIVLY | ALRR | RRHRR | SSDLRLPPSP | 44 |
| SEQ_ID_NO_354 | · · · · | MDHQL | VARGLFKPLL | LFVAGLIVLY | ALRR | RRHRR | SSGLRLPPSP | 45 |
| SEQ_ID_NO_374 | · · · · · · · · | MA | DIQGYIILFL | LWLLSTILVR | AILN | · · · KF | RAKPRLPPSP | 38 |
| SEQ_ID_NO_356 | · · · · | MEPCLV | AVSVLVSALI | CVFFFRPYFH | RYGK | · · · · · · | · · · NLPPSP | 36 |
| SEQ_ID_NO_349 | · · · · | MNIFEV | FQSVSPAIIA | FFISSLFIY | LVL | · · · · RH | QKSLSPPSP | 42 |
| SEQ_ID_NO_351 | · · · · · · | MNT | QLFLLFFFP | TLLFLYCLPY | KRNQ | · · · · · | NHRRLPPSP | 37 |
| SEQ_ID_NO_2553 | · · · | MNIFVL | FQSLSPAVIA | AVVLPSLFLY | LLSK | · · · · S | KQNHRLPPSP | 41 |
| SEQ_ID_NO_364 | · · · · · · · · · · | · · · · | MALYAA | LFLLSAAVVR | SVLD | · · · RK | RGRPPYPPGP | 32 |
| SEQ_ID_NO_347 | · · · · · · · · · · | · · | MSTLVYST | LFILSTLLLT | LLTR | · · · · · | TRRKTRPPGP | 32 |
| SEQ_ID_NO_359 | · · · · · · · · · | M | DTVLITLYTA | LFVITTFLL | LLRR | · · · · · | RGPPSPPGP | 34 |

Figure 13 (continued)

| | | | | | | | |
|---|---|---|---|---|---|---|---|
| SEQ_ID_NO_366 | PGWLPIIGH | -LHLIK NPL | HRTLYDCSQK | LGSIFSVWFG | ··SRLVVVVS | 84 |
| SEQ_ID_NO_349 | PGWLPVIGH | -AHLMK NLL | HRTLYDFSQK | LGPIFSIRFG | ··SRLVVVVS | 84 |
| SEQ_ID_NO_365 | PGWLPVIGH | -VHLMK NLL | HRTLYDFSQK | LGPIFSLRFG | ··TRLVVVVS | 84 |
| SEQ_ID_NO_346 | -RSLPVIGA- | -LPLLG AMP | HVSLAKMAKK | VGAMYLKVG | ··TCGMVVAS | 61 |
| SEQ_ID_NO_2548 | -PALPFIGH | -LHILG ELV | HQSFQKLALR | YGPFMLIHAE | ··ASTSYVVS | 91 |
| SEQ_ID_NO_332 | ·········· | ·········· | ·········· | ·········· | ·········· | 0 |
| SEQ_ID_NO_338 | -PSLPIIGH | -LHHLLSLFM | HRSLQKLSSK | YGPLLYLHVF | ··HVPLLVS | 88 |
| SEQ_ID_NO_341 | -PSIPLLGH | -LHHLT-PSL | YKSLYTLSSK | HGPLLLLRLG | PSRRLLLVS | 78 |
| SEQ_ID_NO_2549 | -PALPIIGHL | RLHFLS-SSI | YKSFHSLSTC | YGPLLYLHFG | ··ASRCLLVS | 90 |
| SEQ_ID_NO_2544 | KPRLPLIGH | -LHLLKDQLL | HHSLIDLSKR | YGPLYSLYFG | ··SMPTVVAS | 84 |
| SEQ_ID_NO_2541 | KPRLPFIGH | -LHLLKDKLL | HYALIDLSKK | HGPLFSLYFG | ··SMPTVVAS | 84 |
| SEQ_ID_NO_358 | KPRLPFIGH | -LHLLKDKLL | HYALIDLSKK | HGPLFSLYFG | ··SMPTVVAS | 84 |
| SEQ_ID_NO_360 | KPRLPFIGH | -LHLLKDKLL | HYALIDLSKK | HGPLFSLYFG | ··SMPTVVAS | 84 |
| SEQ_ID_NO_339 | KPRLPFVGH | -LHLLDHPLL | HQSLIRLGER | YGPLYSLYFG | ··SMPTIVAS | 85 |
| SEQ_ID_NO_2550 | KPRLPFVGH | -LHLLDDPLL | HHSLIKLGER | YGPLYSLYFG | ··SMPTVVAS | 84 |
| SEQ_ID_NO_2543 | PISFPLGH | -APYLR SLL | HKSLYKLSHR | YGPLMHIMLG | ··SQHVVVAS | 82 |
| SEQ_ID_NO_2551 | PISLPLIGH | -APYLR SLL | HQALYKLSTR | YGPLMHVLIG | ··SQHVIVAS | 82 |
| SEQ_ID_NO_2546 | -LALPVLGH | -FHLLA PLP | HQALHRLASR | HGPLLYLRLG | ··SMPAAAC | 91 |
| SEQ_ID_NO_353 | -FGLPILGH | -LHLLA PLP | HQALHRLAAR | HGPLLFLRLG | ··SVPCVAAC | 88 |
| SEQ_ID_NO_354 | -FGLPILGH | -LHLLA PLP | HQALHRLAAR | HGPLLFLRLG | ··SVPCVAAC | 88 |
| SEQ_ID_NO_334 | -LALPIIGH | -LHLLA PIP | HQALHKLSTR | YGPLIHLFLG | ··SVPCVVAS | 82 |
| SEQ_ID_NO_352 | FFRLPIIGH | -MHMLG PLL | HQSFHNLSHR | YGPLFSLNFG | ··SVLCVVAS | 81 |
| SEQ_ID_NO_349 | -PALPIIGH | -LHHLG PLI | HHSFHDLSTR | YGPLIHLRLG | ··SVPCVVAS | 88 |
| SEQ_ID_NO_351 | -PSFPIIGH | -LHHLG PLI | HQSFHALSTR | YGSLIHLRLG | ··SVPCVVVS | 81 |
| SEQ_ID_NO_2553 | -PSLPIIGH | -LHHLG PLI | HQSFHNLSTR | YGPLIHLRLG | ··SVPCVVAS | 86 |
| SEQ_ID_NO_364 | -FPLPIIGH | -LHLLG PRL | HQTFHDLSQR | YGPLMQLRLG | ··SIRCVIAA | 78 |
| SEQ_ID_NO_347 | -LALPLIGH | -LHLLG PKL | HHTFHQFSQR | YGPLIQLYLG | ··SVPCVVAS | 78 |
| SEQ_ID_NO_359 | -LSLPIIGH | -LHLLG PRL | HHTFHEFSLK | YGPLIQLKLG | ··SIPCVVAS | 78 |

Figure 13 (continued)

| | | | | | | | |
|---|---|---|---|---|---|---|---|
| SEQ_ID_NO_368 | SSSLVEECFT | KYD I VLANR | PDLHLDLRSL | GNSTLSVIGA | PYGDHWRNLR | 133 |
| SEQ_ID_NO_349 | SSSLVEECFT | KYD I VLANR | PCASVDRRSL | GFSTTSVIGA | PYGDHWRNLR | 133 |
| SEQ_ID_NO_365 | SSSLVEECFT | KYD I VLANR | PQPSVDRRSL | GFSTTSVIGA | PYGDHWRNLR | 133 |
| SEQ_ID_NO_348 | TPDAAKAFLK | TLD LNFSNR | PFNAGATHFL | AYGAQDWVFA | HYGPRWXLR | 129 |
| SEQ_ID_NO_2548 | NGAIAKEVFK | TND INFANR | PEFGSSEY-C | IYNDIMFSIM | DYNKLWFLK | 139 |
| SEQ_ID_NO_332 | .......... | .......... | .......... | .......... | .......... | 0 |
| SEQ_ID_NO_339 | SPSIAYEIFR | TLD VNVSSR | DFPTNEGS-L | LFGSFGFGTA | PYGEYWKFMK | 136 |
| SEQ_ID_NO_341 | SAAVATDVFK | THD LAFSSR | PAFAFAERL | PFGTSGFVTA | PYGPYWRFMK | 126 |
| SEQ_ID_NO_2542 | SAAMAAEIFK | TND LAFASR | PRLAFADKL | PYGTSSFITA | EYGDYWRFMK | 138 |
| SEQ_ID_NO_2544 | TPELFKLFLQ | THEAASFNTR | FQTSAIKRL | TYDNSIVAMV | PFGPYWKFIR | 132 |
| SEQ_ID_NO_2541 | TPELFKLFLQ | THEATSFNTR | FQTSAIRRL | TYDSSIVAMV | PFGPYWKFVR | 132 |
| SEQ_ID_NO_359 | TPELFKLFLQ | THEATSFNTR | FQTSAIRRL | TYDSSIVAMV | PGPYWKFVR | 132 |
| SEQ_ID_NO_360 | TPELFKLFLQ | THEATSFNTR | FQTSAIRRL | TYDSSIVAMV | PFGPYWKFVR | 132 |
| SEQ_ID_NO_333 | TPDLFKLFLQ | THEAVSFNTR | FQTSAIRRL | TYDNSIVAMV | PFAPYWKFIR | 133 |
| SEQ_ID_NO_2550 | TPELFKLFLQ | THEASSFNTR | FQTSAIRRL | TYDNSIVAMV | PFAPYWKFIR | 132 |
| SEQ_ID_NO_2543 | TAESAKOILK | TCEFESFTNR | PIMIASENL | TYGAADYFFI | PYGNYWRFLK | 130 |
| SEQ_ID_NO_2551 | SAEMAKOILK | TYEFESFCNR | PIMIASENL | TYGAADYFFI | PYGTYWRFLK | 130 |
| SEQ_ID_NO_2549 | SPDAAREVLK | THEAAFLDR | AMPTAVHRL | MYGGQDFIFS | AYGPYWRFMK | 139 |
| SEQ_ID_NO_353 | SPDAAREVLK | THEAAFLDR | PKPAAVHRL | TYGGQDFSFS | AYGPYWRFMK | 138 |
| SEQ_ID_NO_354 | SPDAAREVLK | THEAAFLDR | PKPAAVHRL | TYGGQDFSFS | AYGPYWRFMK | 137 |
| SEQ_ID_NO_334 | TPEIAKEFLK | THENSFCDR | PKSTAVDF- | TYGSADFSFA | PYGPYWKFMK | 130 |
| SEQ_ID_NO_355 | TPHFAKCLLQ | TNELAFNCR | IESTAVKKL | TYESSLAFA | PYGDYWRFIK | 128 |
| SEQ_ID_NO_342 | TPDLARDFLK | TNELAFSSR | KHSLAIDHV | TYGVSFAFA | PYGPYWKFIK | 133 |
| SEQ_ID_NO_351 | TPDLAKDFLK | TNELAFSSR | KHSLAIDHI | TYGVAFAFA | PYGTYWKFIK | 128 |
| SEQ_ID_NO_2553 | TPDLARDFLK | TNELAFSSR | KHSLAIDHI | TYGVAFAFA | PYGPYWKFIK | 132 |
| SEQ_ID_NO_364 | SPELAKECLK | THELVFSSR | KHSTAIDIV | TYDSSFAFS | PYGPYWKFIK | 123 |
| SEQ_ID_NO_347 | TPELAREFLK | THELDFSSR | KHSTAIDIV | TYDSSFAFA | PGPYWKFIK | 123 |
| SEQ_ID_NO_359 | TPELAREFLK | TNELAFSSR | KHSTAIDIV | TYDSSFAFS | PYGPYWKYIK | 125 |

Figure 13 (continued)

| SEQ_ID | | | | | | | |
|---|---|---|---|---|---|---|---|
| SEQ_ID_NO_366 | KLCDLEVFAP | TRLASFLSIR | RDERDRMISG | LYKSSAGLR | KVNLEAKIAE | | 183 |
| SEQ_ID_NO_348 | KLCDLEVFAP | TRLASFLSIR | LDERDRMISA | LYKSSAGFA | KVNLEAKIVE | | 183 |
| SEQ_ID_NO_365 | KLCDLEVFAP | TRLASFLSIR | LDERDRMISS | LYKSSAGFA | KVNLETKIVE | | 183 |
| SEQ_ID_NO_346 | KLSNLHMLGG | KALENWANVR | ANELSHMLKS | MFDMGREGE | RVWAEMLTF | | 178 |
| SEQ_ID_NO_2548 | KICMTEILSA | QQISKFADVR | KEEMKVLQF | F-LKCSEQGD | AFDVGQLMD | | 188 |
| SEQ_ID_NO_332 | ·········· | ·········· | ·········· | ·········· | ·······MK | | 2 |
| SEQ_ID_NO_338 | KLIVTKFLGP | QALERSQKVR | ····RSYYLN | L-DKAVKKE | SVEIAEEAMK | | 181 |
| SEQ_ID_NO_341 | KLCVTELLST | RQLERSRSIR | REEILRSKR | V-IDNAREFV | ALDLGSEFTK | | 175 |
| SEQ_ID_NO_2549 | KLCVTELLGV | KQLERSRMVR | REELDCFLKK | L-VESGENGE | AVDVRAEVMK | | 187 |
| SEQ_ID_NO_2544 | KLIMNDLLNA | TTVNKLRPLR | SHEIRKVLRV | L-AQSAEAQQ | PLNVTEELLK | | 181 |
| SEQ_ID_NO_2541 | KLIMNDLFNA | TTVNKLRPLR | TQQIRKFLRV | M-AQGAEAQK | PLDLTEELLK | | 181 |
| SEQ_ID_NO_359 | KLIMNDLLNA | TTVNKLRPLR | TQQIRKFLRV | M-AQGAEAQK | PLDLTEELLK | | 181 |
| SEQ_ID_NO_360 | KLIMNDLLNA | TTVNKLRPLR | TQQIRKFLRV | M-AQGAEAQK | PLDLTEELLK | | 181 |
| SEQ_ID_NO_339 | KLIMNDLLNA | TTVNKLRPLR | SQEIRKVLNM | M-AKSAQTQE | PLNVTEELLK | | 182 |
| SEQ_ID_NO_2550 | KIIMNDLLNA | TTVNKLRPLR | SQEIRKVLKA | K-AHSAESQQ | PLNVTEELLK | | 181 |
| SEQ_ID_NO_2543 | KLCMTELLSG | KTLEHFVHIR | EDEIKCFMGT | L-LEISKNGK | PIEMRHELIR | | 179 |
| SEQ_ID_NO_2551 | KLCMTELLSG | KTLEHFVNIR | EDEIQCFLRN | V-LEISKTGK | GVEMRQELIR | | 179 |
| SEQ_ID_NO_2545 | RACVHELLDS | RTLERLRHVR | REEVSRLVRS | L-RSAGDESA | AVDVDAALMG | | 189 |
| SEQ_ID_NO_353 | RACVHELLAG | RTLDRLRHVR | REEVARLVGS | L-RASADGGE | RVDVDAALMG | | 185 |
| SEQ_ID_NO_354 | RACVHELLAG | RTLDRLRHVR | REEVARLVGS | L-RASADGGE | RVDVDAALMG | | 186 |
| SEQ_ID_NO_334 | KICMTELLGG | RMLDQLLPVK | HEEIRQFLQF | L-LKKANARE | SIDVGSQLIR | | 179 |
| SEQ_ID_NO_358 | KLSMNELLGS | RSINNFQHLR | AQETHQLLRL | L-SNRARAFE | AVHITEELLK | | 177 |
| SEQ_ID_NO_349 | KTSIVELLGN | QNLSNFLPIR | TQEVHELLQT | L-MVKSKKNE | SVHLSEELLK | | 182 |
| SEQ_ID_NO_351 | KLFTVELLGT | QNLSHFLPIR | THEIRELLRT | L-MVKSRAKE | RVNLTEELLK | | 177 |
| SEQ_ID_NO_2553 | KLSTVELLGN | QNLGHFLPIR | TQEIHELLHT | L-MEKSKRKE | SVNLTEELLK | | 181 |
| SEQ_ID_NO_364 | KLCTYELLGA | RNLAHFQPIR | TLEVKSFLQI | L-MRKGESGE | SFNVTEELVK | | 172 |
| SEQ_ID_NO_347 | KLCTYELLGA | RNLSHFQPIR | ALEVMSFLRI | L-YEKFEQKQ | SVNVTEELVK | | 172 |
| SEQ_ID_NO_350 | KLCTYELLGA | RNLGHFQPIR | NLEVRSFLQL | L-MHKSFKGE | SVNVTDELVR | | 174 |

Figure 13 (continued)

| | | | | | | | |
|---|---|---|---|---|---|---|---|
| SEQ_ID_NO_366 | LTFNNLMRML | AGKYYGEEA | EDEEEAKRFR | DMTKEALELM | NTFNLAEIFP | 233 |
| SEQ_ID_NO_348 | LTFNNIMRMV | AAKRYYGEEA | EDDEEAKRFR | DLTKEALELT | SASNPGEIFP | 233 |
| SEQ_ID_NO_365 | LTFNNIMRMV | AGKRYYGEEA | EDDEEAKRFR | DLTKEALELT | SASNPGEIFP | 233 |
| SEQ_ID_NO_346 | ANANMIGQVI | LSKRVFVN-- | KGV-EVNEFK | DMVVELMTTA | GVFNIGDFIP | 225 |
| SEQ_ID_NO_2546 | MTNNLICRLI | MSTRTSFN-- | VN-ESAFIR | EIAKGVLLA | GQLSLGEIFG | 234 |
| SEQ_ID_NO_332 | LVNNTVCQMI | MGRSCSEE-- | HG-EAERVR | GLVTKTDALT | KKFILAGILR | 48 |
| SEQ_ID_NO_329 | LVNNTVCQMI | MGRSCSEE-- | HG-EAERVR | GLVTKTDALT | KKFILAGILR | 227 |
| SEQ_ID_NO_341 | FTNNVTCRTA | MSTSCAEK-- | CE-DAERIR | KLVKESFELA | AKLDFGDVLG | 221 |
| SEQ_ID_NO_2542 | LTNHSTCRVI | LSARCSED-- | HD-EAERLI | EMVTEWELA | VKMSFGDVFG | 233 |
| SEQ_ID_NO_2544 | WTNNTISMLM | LG------- | ----EAEEVR | DLARETVKIF | GEYSLTDFIW | 219 |
| SEQ_ID_NO_2541 | WTNSTISMMM | LG------- | ----EAEEIR | DIAREVLKIF | GEYSLTDFIW | 219 |
| SEQ_ID_NO_358 | WTNSTISMMM | LG------- | ----EAEEIR | DIAREVLKIF | GEYSLTDFIW | 219 |
| SEQ_ID_NO_360 | WTNSTISMMM | LG------- | ----EAEEIR | DIAREVLKIF | GEYSLTDFIW | 219 |
| SEQ_ID_NO_339 | WTNSTISRMM | LG------- | ----EAEEIR | DIARDVLKIF | GEYSLTDFIW | 220 |
| SEQ_ID_NO_2550 | WTNNTISRMM | LG------- | ----EAEEVR | DIAREVLKIF | GEYSLTDFIW | 219 |
| SEQ_ID_NO_2543 | HTNNIISRMT | MGKKSSGM-- | ND-EVGQLR | KVVREIGELL | GAFNLGDIIG | 225 |
| SEQ_ID_NO_2551 | HTNNIISRMT | MGKKSNGT-- | ND-EVGQVR | KLVREIGELL | GAFNLGDIIG | 225 |
| SEQ_ID_NO_2549 | VTGDIVSRMV | MSRRWTGD-- | DSATDTEEMR | GVIAETAVLT | GTFNLQDYIG | 237 |
| SEQ_ID_NO_353 | LTGDIVSRMV | MGRRWTGD-- | DN-DAEEMR | GVVAETAELT | GTFNLQDYIG | 231 |
| SEQ_ID_NO_354 | LTGDIVSRMV | MGRRWTGD-- | DN-DAEEMR | GVVAETAELT | GTFNLQDYIG | 232 |
| SEQ_ID_NO_324 | LTNNVISRMA | MSQRCSDH-- | DD-EADEVR | NLVREVADLT | GKFNLSDFIW | 225 |
| SEQ_ID_NO_355 | LTNNVISIVM | VG------- | ----EAEEAR | DVVRDVTEIF | GEFNVSDFIW | 215 |
| SEQ_ID_NO_349 | LTNNVICQMM | MSIRCSGT-- | HN-EADEAK | NLVREVTKIF | GEFNISDFIC | 228 |
| SEQ_ID_NO_351 | LTNNVISQMM | MSIRCSGT-- | NS-EADEAK | NLVREVTKIF | GQFNVSDFIW | 223 |
| SEQ_ID_NO_2552 | LTNNVICQMM | MSIRCSGT-- | NS-EADEAK | NLVREVTTIF | GQFNVSDFIW | 227 |
| SEQ_ID_NO_364 | LTSNVISHMM | LSIRCSET-- | ES-EAEAAR | TVIREVTQIF | GEFDVSDIIW | 218 |
| SEQ_ID_NO_347 | LTSNVISNMM | LGIRCSGT-- | EG-EAEVAR | TVIREVTQIF | GEFDVSEIVW | 218 |
| SEQ_ID_NO_352 | LTSNVISHMM | LSIRCSED-- | EG-DAEAAR | TVIREVTQIF | GEFDVTDIIW | 220 |

Figure 13 (continued)

| | | | | | | |
|---|---|---|---|---|---|---|
| SEQ_ID_NO_366 | -LRWLGCNG | FEKQLPVHSR | KTDEIMQGLL | DEHR- | ---------- | 266 |
| SEQ_ID_NO_346 | -LRWLGCNG | LEKKLAVHSR | KTDEFMQGLL | DEHR- | ---------- | 266 |
| SEQ_ID_NO_365 | -LRWLGFNG | LEKKLAVHAR | KTDEFMQGLL | DEHR- | ---------- | 266 |
| SEQ_ID_NO_346 | -CLAMMDLQG | EKEMKRLHK | KFDALLTKMF | DEHK- | ----ATSV | 262 |
| SEQ_ID_NO_2546 | -PLKKVDLQG | AGRKAKALLL | KFDKLMDGII | KKHE---DER | R------V | 272 |
| SEQ_ID_NO_322 | KPLQKIGISL | FKKELMDASC | KFNEVLEKIL | VEYK- | ----EKVE | 86 |
| SEQ_ID_NO_338 | KPLQKIGISL | FKKELMDASC | KFNEVLEKIL | VEYK- | ----EKVE | 265 |
| SEQ_ID_NO_341 | -PFKELEFVV | YGKKADMST | RYDELLEEVL | KEHE---HKRL | L----SRAN | 262 |
| SEQ_ID_NO_2549 | -PLKRLGFW | YGRKAVELTL | RYDEILEKML | KEHE---ER | .......... | 268 |
| SEQ_ID_NO_2544 | -PLKKLKFGK | YEKRIDEIFN | KFDPVIEKVI | KKRQEIVRRR | KN---GEVV | 264 |
| SEQ_ID_NO_2541 | -PLKHLKVGK | YEKRIDDILN | KFDPVVERVI | KKRREIVRRR | KN---GEVV | 264 |
| SEQ_ID_NO_359 | -PLKHLKVGK | YEKRIDDILN | KFDPVVERVI | KKRREIVRRR | KN---GEVD | 264 |
| SEQ_ID_NO_360 | -PLKHLKVGK | YEKRIDDILN | KFDPVVERVI | KKRREIVRRR | KN---GEVV | 264 |
| SEQ_ID_NO_339 | -PLKKLKVGK | YEKKIEEIFN | RFDPVIEKVI | KKRQDVRRRR | KERN-GELE | 267 |
| SEQ_ID_NO_2550 | -PLKKLKVGD | YEKRIDEIFN | KFDPVIEKVI | KKRQEILKRR | KERD-GELE | 266 |
| SEQ_ID_NO_2543 | -FMRPLDLQG | FGKRNKDTHH | KMDVMMEKVL | KEHE---EAR | AL----KEGA | 266 |
| SEQ_ID_NO_2551 | -FMRPFDLQG | FGKKNRDAHH | MMDVMMEKVL | KEHE---EAR | AKE--KGGA | 268 |
| SEQ_ID_NO_2545 | -VFKYWDMQG | LGKRIDAVHR | KFDAMMERIL | TARDALRRRR | RKEP--ADGA | 284 |
| SEQ_ID_NO_353 | -VFKYWDVQG | LGKRIDAVHR | KFDAMMERIL | TEREAKRKLR | RQ----AAAD | 276 |
| SEQ_ID_NO_354 | -VFKYWDVQG | LGKRIDAVHR | KFDAMMERIL | TAREAKRKLR | RQ----AAAD | 277 |
| SEQ_ID_NO_334 | -FCKNLDLQG | FGKRLKEVRK | RFDTMTERII | WEHE---EAR | KKK---KETG | 268 |
| SEQ_ID_NO_355 | -LFKKMDLQG | FGKRIEDLFQ | RFDTLVERII | GKREQTRKDR | RRNGKKGEIG | 264 |
| SEQ_ID_NO_349 | -LFKNIDLQG | FKKRYVDTHT | RYNALLEKMI | FERE---EKR | KQ----KKSE | 270 |
| SEQ_ID_NO_351 | -FCKNIDLQG | FKKRYEGTHR | RYDALLERII | WERE---ENR | RR----GKLK | 265 |
| SEQ_ID_NO_2553 | -FCKNLDLQG | FKKRYEDTHR | RYDALLEKII | GERE---EKR | RK----GGKR | 269 |
| SEQ_ID_NO_364 | -LCKNFDFQG | IRKRSEDIQR | RYDALLEKII | TDRE---KQR | RTH--GGGG | 261 |
| SEQ_ID_NO_347 | -FCKNLDLQG | IRKRSEDIRR | RYDALLEKII | SDRE---RLR | LRG---GGGG | 261 |
| SEQ_ID_NO_359 | -FCKKFDLQG | IKKRSEDIQR | RYDALLEKII | SDRE---RSR | RQNRDKHGGG | 266 |

Figure 13 (continued)

| | | | | | | | |
|---|---|---|---|---|---|---|---|
| SEQ_ID_NO_368 | RGERQNTMVG | HLLSL--QE | SQPDYYTDEI | TGLIISLII | AGTDASVVTT | 313 |
| SEQ_ID_NO_346 | RGERQNTMVD | HLLSL--QE | SQPEYYTDEI | TGLIVALII | AGTDASVVTT | 313 |
| SEQ_ID_NO_365 | RGERQNTMVD | HLLSL--QE | SQPEYYTDEI | TGLIVALII | AGTDASVVTT | 313 |
| SEQ_ID_NO_346 | ERKGKPDFLD | CVMENRD-NS | EGE-RLSTTN | KALLLNLFT | AGTDTSSSAI | 310 |
| SEQ_ID_NO_2546 | GGKERRDMMD | ILLEIAD-DE | HAEMKLTRNG | KGLFLDLFL | GGTDTTSVAL | 321 |
| SEQ_ID_NO_332 | EHHQGTDMMD | KLLEVYG-DE | KAEYKITRDH | KSLFVDLFF | AGTDTSTHAI | 135 |
| SEQ_ID_NO_338 | EHHQGTDMMD | KLLEVYG-DE | KAEYKITRDH | KSLFVDLFF | AGTDTVTHAI | 314 |
| SEQ_ID_NO_341 | GDCSERDLMD | ILLDVYH-DA | HAEFKITMAH | KAFFMDLFI | AGTHTSAEAT | 311 |
| SEQ_ID_NO_2542 | GKREDKDLMD | VLLEVYQ-DD | KAGMKLTRTH | KAFILDLFM | AGTNTSAESM | 317 |
| SEQ_ID_NO_2544 | EGEQSGIFLD | TLLEFAE-DE | TMEIKITKEC | KGLVVDFFS | AGTDSTAVAT | 313 |
| SEQ_ID_NO_2541 | EGEVSGVFLD | TLLEFAE-DE | TMEIKITKDH | KGLVVDFFS | AGTDSTPVAT | 313 |
| SEQ_ID_NO_359 | EGEVSGVFLD | TLLEFAE-DE | TTEIKITKDH | KGLVVDFFS | AGTDSTAVAT | 313 |
| SEQ_ID_NO_360 | EGEVSGVFLD | TLLEFAE-DE | TMEIKITKDH | KGLVVDFFS | AGTDSTAEAT | 313 |
| SEQ_ID_NO_339 | EGEQSVVFLD | TLLDFAE-DE | TMEIKITKEC | KGLVVDFFS | AGTDSTAVAT | 316 |
| SEQ_ID_NO_2550 | EGEQSVVFLD | TLLEFAE-DE | TMEIKITKEC | KGLVVDFFS | AGTDSTAVAT | 315 |
| SEQ_ID_NO_2543 | GSDRKKDLFD | ILNLIEADD | GAEBKLTRES | AKAFALDMFI | AGTNGPASVL | 316 |
| SEQ_ID_NO_2551 | ESDRKKDLFD | ILNLIE-AD | GADNKLTRES | AKAFALDMFI | AGTNGPASVL | 317 |
| SEQ_ID_NO_2545 | GEGAKKDLLD | MLFDMHE-DE | AAEMRLTRDN | KAFMLDIF3 | AGTDTTAITL | 333 |
| SEQ_ID_NO_353 | GEDDEKDLLD | MLFDMHE-DE | AAEMRLTRDN | KAFMLDIFA | AGTDTTTITL | 325 |
| SEQ_ID_NO_354 | GEDDEKDLLD | MLFDMHE-DE | AAEMRLTRDN | KAFMLDIFA | AGTDTTTITL | 328 |
| SEQ_ID_NO_334 | EGDPVKDLLD | ILLDISE-DD | SSEMKLTREN | KAFILDIFA | AGTDTSAVTM | 317 |
| SEQ_ID_NO_355 | SGDGLRDFLO | ILLDCTE-DE | NSEIKIDRVH | KALIMDFFT | AGTDTTAIST | 313 |
| SEQ_ID_NO_349 | DGIKGKDFLD | ILLDVLE-DE | NAEIKITRDH | KALILDFFT | AATDTTAISI | 318 |
| SEQ_ID_NO_351 | DGIEGKDFLD | MLLDVLE-DG | KAEIKITRDH | KALILDFLT | AGTDTTAIAI | 313 |
| SEQ_ID_NO_2553 | DDVKGTDFLD | MLLDVLE-DG | KAEIKITRDH | KALILDFFT | AATDTTAIAV | 318 |
| SEQ_ID_NO_364 | GGGEAKDFLD | MFLDIME-SG | KAEVKFTREH | LKALILDFFT | AGTDTTAIVC | 310 |
| SEQ_ID_NO_347 | GGGEVKDFLD | MLLDVME-SE | KSEVEFTREH | LKALILDFFT | AGTDTTAITT | 310 |
| SEQ_ID_NO_359 | NNEEAKDFLD | MLLDVME-SG | DTEVKFTREH | LKALILDFFT | AGTDTTAIAT | 315 |

Figure 13 (continued)

| | | | | | | |
|---|---|---|---|---|---|---|
| SEQ_ID_NO_366 | EWAMSLLLNH | PKVLEKARQE | MDTLVGHERM | VEEDDLPKLR | YLHV ILETL | 363 |
| SEQ_ID_NO_348 | EWAMSLLLNH | PKVLEKARKE | LDTLVGHERM | VDEHDLPKLR | YLHCI VLETL | 363 |
| SEQ_ID_NO_365 | EWAMSLI LNH | PQVLEKARKE | LDTLVGHERM | VDEHDLPKLR | YLHCI VLETL | 363 |
| SEQ_ID_NO_346 | EWALAEMMKN | PA LKKACGE | MDQVI GNNRR | LLESDI PNLP | YLRAI CKETF | 360 |
| SEQ_ID_NO_2546 | QWE AEVLNH | PKALKKLQEE | IDRVVGPNRL | VDDSDI PNLP | YLQAVVKETL | 371 |
| SEQ_ID_NO_332 | QWMAEI I NN | SYI LERLREE | IDSVVGKTRL | QETDLPNLP | CLQATVKEGL | 185 |
| SEQ_ID_NO_338 | QWMAEI I NN | SYI LERLREE | DSVVGKTRL | QETDLPNLP | CLQATVKEGL | 364 |
| SEQ_ID_NO_341 | QWAMAELLNH | PEAFQKVRKE | ELVFGNVRL | VDESDI TNLP | YLQAVVKETL | 361 |
| SEQ_ID_NO_2549 | QWT! AELI NH | PDVFKKVREE | DLAVGRTRL | VEESDI PNLP | YLQAVVKETL | 367 |
| SEQ_ID_NO_2544 | EWALAELI NN | PRVLQKAREE | VYSVVGKDRL | VDEVDTQNLP | YI RAI VKETF | 363 |
| SEQ_ID_NO_2541 | EWALAELI NN | PKVLEKAREE | VYSVVGKDRL | VDEVDTPNLP | YI GAI VKETF | 363 |
| SEQ_ID_NO_359 | EWALAELI NN | PKVLEKAREE | VYSVVGKDRL | VDEVDTQNLP | YI RAI VKETF | 363 |
| SEQ_ID_NO_360 | EWALAELI NN | PKVLEKAREE | VYSVVGKDRL | VDEVDTQNLP | YI RAI VKETF | 363 |
| SEQ_ID_NO_339 | QWQ SELI NN | PRVMKKAREE | VDSVVGKDRL | VDESDI QNLP | YI RAVVKETF | 366 |
| SEQ_ID_NO_2550 | QWALSELI NN | PRVLKKAREE | VESVVGKDRL | VDEADI QNLP | YI RAI VKETF | 365 |
| SEQ_ID_NO_2543 | EWALAELI RN | PHVFKKAREE | DSI VGKERL | FKESDI PNLP | YLQAVVKETL | 366 |
| SEQ_ID_NO_2551 | EWSLAELI RN | PQVFKKAREE | DSVVGKERL | VKESDI PNLP | YLQAVVKETL | 367 |
| SEQ_ID_NO_2548 | EWALSELI NN | PDI LRRAQAE | LDAI VGASRL | ADESDI PRLP | YLQAI AKETL | 363 |
| SEQ_ID_NO_353 | EWALSELI NN | PPVLRKLQAE | LDAVVGGARL | ADESDI PSLP | YLQAVAKETL | 375 |
| SEQ_ID_NO_354 | EWALSELI NN | PPVLRKLQAE | LDAVVGGARL | ADESDI PSLP | YLQAVAKETL | 376 |
| SEQ_ID_NO_324 | EWALAELI NN | PNI LERAREE | DSVVGQSRL | VQESDI ANLP | YVQAI LKETL | 367 |
| SEQ_ID_NO_352 | EWALVELVKK | PSVLQKVREE | DNVVGKDRL | VEESDCPNLP | YLQAI LKETF | 363 |
| SEQ_ID_NO_349 | EWTLVELTNN | PKVLENARKE | AEVVGDERL | VQESDI PNLP | YI QAI I KETL | 368 |
| SEQ_ID_NO_351 | EWALVELI NN | PNALEKARQE | DQVI GOERL | VQESDTPNLP | YI QAI I KEAL | 363 |
| SEQ_ID_NO_2553 | EWTMVELI NN | PKVLEKAKKE | VDNVI GNSRL | VOESDAPNLP | YI QAI I KETL | 368 |
| SEQ_ID_NO_364 | EWAI AEVI NN | PNVLKKAQEE | IANI VGFDRI | LQESDAPNLP | YLQALI KETF | 360 |
| SEQ_ID_NO_347 | EWAI AELI SN | PNVLKKAQEE | MDKVI GSQRL | LQESDAPNLP | YLNAI I KETF | 360 |
| SEQ_ID_NO_350 | EWAI AELI NN | PNVLKKAQEE | SRI I GTKRI | VQESDAPDLP | YLQAI I KETF | 365 |

Figure 13 (continued)

| | | | | | | | |
|---|---|---|---|---|---|---|---|
| SEQ_ID_NO_366 | RLFPSVPTLV | PHEPSEDCN | GGYNVPKGTM | LVNAWAIHR | DPKVW | DDPM | 412 |
| SEQ_ID_NO_346 | RLFPSVPTLV | PHEPSEDCKI | GGYNVPKGTM | VLVNAWAIHR | DPKVW | DDPL | 412 |
| SEQ_ID_NO_365 | RLFPSVPTLV | PHEPSEDCKI | GGYNVPKGTM | LVNAWAIHR | DPKVW | DDPL | 412 |
| SEQ_ID_NO_346 | RVHPSTPLNL | PRISNEPCIV | DGYYIPKNTR | LSVNIWAIGR | DPEVW | ENPL | 409 |
| SEQ_ID_NO_2546 | RVHPSLPLEI | FRKCREDCVV | NGYTIPKNSR | LVLNIYAINR | DPNEH | RDAD | 410 |
| SEQ_ID_NO_333 | RLHPPVPLV | LRTFKEGCTI | GGFYVPEKTT | LVVHGYAMMR | DPEYW | EDPQ | 233 |
| SEQ_ID_NO_338 | RLHPPVPLLV | LRTFKEGCTI | GGFYVPEKTT | LVVNGYAMMR | DPEYW | EDPQ | 412 |
| SEQ_ID_NO_341 | RLYPPAPLF | TRECROHCKI | NBFDVPPKTA | VAINLYAIMR | DPDSH | DNPN | 409 |
| SEQ_ID_NO_2542 | RLHPPAPLVA | TRECRKNCKI | GGFNIPEKTA | VAINLYAIMR | DPEIW | DDPT | 415 |
| SEQ_ID_NO_2544 | RMHPPLPLVV | KRKCVEECEI | EGCVIPEGAL | LFNVWAVGR | DPKYW | DRPS | 411 |
| SEQ_ID_NO_2541 | RMHPPLPLVV | KRKCTEECEI | NGYVIPEGAL | LFNVWQVGR | DPKYW | DRPS | 411 |
| SEQ_ID_NO_358 | RMHPPLPLVV | KRKCTEECEI | NGYVIPEGAL | LFNVWQVGR | DPKYW | DRPS | 411 |
| SEQ_ID_NO_360 | RMHPPLPLVV | KRKCTEECEI | NGYVIPEGAL | LFNVWQVGR | DPKYW | DRPS | 411 |
| SEQ_ID_NO_339 | RMHPPLPLVV | KRKCTEECEI | NGYVIPEGAL | VLFNVWAVGR | DPKYW | DRPL | 414 |
| SEQ_ID_NO_2550 | RMHPPLPLVV | KRKCVQECEL | NGYVIPEGAL | LFNVWAVQR | DPKYW | EBPS | 413 |
| SEQ_ID_NO_2543 | RMHPPTPLF | AREATRSCQV | DGYDVPAFSK | FINAWAIGR | DPHYW | DNPL | 414 |
| SEQ_ID_NO_2551 | RMHPPTPLF | AREAIRGCQV | DGYDIPANSK | FINAWAIGR | DPKYW | DNPQ | 415 |
| SEQ_ID_NO_2549 | RLHPAFPLLV | VRRSTEPCKV | SGYDVPAGST | VFVNVWAIGR | DPACW | PDPL | 432 |
| SEQ_ID_NO_353 | RLHPTGPLLV | VRRSLERATV | AGYDVPAGAT | VFVNVWAIGR | DAAW | PEPT | 423 |
| SEQ_ID_NO_354 | RLHPTGPLLV | VRRSLERATV | AGYDVPAGAT | VFVNVWAIGR | DAAW | PEPT | 424 |
| SEQ_ID_NO_334 | RLHPTGPLI | LRESSESCTI | NGYEIPARTR | LFVNVWAINR | DPNYW | ENPL | 415 |
| SEQ_ID_NO_352 | RLHPPVPLMV | TRRCVAECTV | ENYVIPEDL | LFVNVWSIGR | NPKFW | DNPL | 411 |
| SEQ_ID_NO_349 | RMHPPIPLMV | RKSIDNVTV | DGYDIRAGTM | LFVNIWSIGR | NPLYW | ESPL | 416 |
| SEQ_ID_NO_351 | RLHPPIPLML | IRKSTEHVIV | DGYDIPAGTL | LFVNIWSIGR | NPQCW | ETPL | 411 |
| SEQ_ID_NO_2553 | RLHPPIPLML | RKSIEKVTV | DGYEIPAGTM | LFVNIWSIGR | NAQYW | ESPL | 416 |
| SEQ_ID_NO_364 | RLHPPIPLML | ARKSISDCVI | DGYMPANTL | LFVNLWSMGR | NPKIW | DIPT | 408 |
| SEQ_ID_NO_347 | RLHPPIPLML | TRKSISDVVV | NGYTIPAKTL | LFVNLWSMGR | NPHYW | ENPM | 408 |
| SEQ_ID_NO_359 | RLHPPIPLML | SRKSTSDCTV | NGYRQAKSL | LFVNIWSIGR | NPHYW | ESPM | 413 |

Figure 13 (continued)

| SEQ_ID_NO_368 | SFKPDRFET | ---------- | ---------- | LE | VETHKLLPFG | MGRRGCPGAG | 443 |
|---|---|---|---|---|---|---|---|
| SEQ_ID_NO_349 | SFKPDRFEI | ---------- | ---------- | ME | VETHKLLPFG | MGRRACPGAG | 443 |
| SEQ_ID_NO_365 | SFKPDRFET | ---------- | ---------- | ME | VETHKLLPFG | MGRRACPGAG | 443 |
| SEQ_ID_NO_348 | EFVPERFLS | ···SRNSKI | ·D······ | PR | SNDFELIPFG | AGRR CAGTR | 447 |
| SEQ_ID_NO_2548 | EFIPERYLVN | SGGGEENQLA | EPDELEAMK | SQNFEYVPFG | GGRRGCPGAG | 469 |
| SEQ_ID_NO_332 | EFKPERFLAS | SRSSQND··· | ·E······ | R | DELLKYLPFG | NGRRACPGAN | 273 |
| SEQ_ID_NO_338 | EFKPERFLAS | SRSSQND··· | ·E······ | R | DELLKYLPFG | NGRRACPGAN | 452 |
| SEQ_ID_NO_341 | EFQPERFLQE | CDHEDLSD·· | ·D······ | GK | RMKFNFVPFG | GRRGCPGTA | 450 |
| SEQ_ID_NO_2542 | EFRPERFLVP | SKEDVDLD·· | ·Q······ | TK | GQNFNFVPFG | GRRGCPGTL | 468 |
| SEQ_ID_NO_2544 | EFRPERFLEN | GGECAVGPI | ·D······ | LR | GQHFQLLPFG | GRRMCPGVN | 453 |
| SEQ_ID_NO_2541 | EFRPERFLET | GAEGEAGPL | ·D······ | LR | GQHFQLLPFG | GRRMCPGVN | 453 |
| SEQ_ID_NO_355 | EFRPERFLET | GAEGEARPL | ·D······ | LR | GQHFQLLPFG | GRRMCPGVN | 453 |
| SEQ_ID_NO_360 | EFRPERFLET | GAEGEARPL | ·D······ | LR | GQHFQLLPFG | GRRMCPGVN | 453 |
| SEQ_ID_NO_339 | EFRPERFLEN | AGEGDAGSI | ·D······ | LR | GQHFQLLPFG | GRRMCPGVN | 458 |
| SEQ_ID_NO_2550 | EFRPERFLT | ·AEGGATSI | ·D······ | LR | GQNFELLPFG | GRRMCPGVN | 453 |
| SEQ_ID_NO_2543 | VFNPERFLQ | SDDPSKSKI | ·D······ | VR | GQYYQLLPFG | GRRSCPGSS | 455 |
| SEQ_ID_NO_2551 | VYSPERFLI | TDEPGKSKI | ·D······ | VR | GQYYQLLPFG | GRRSCPGSS | 458 |
| SEQ_ID_NO_2548 | AFRPERFLE | GGEGRGDSAG | LD······ | VR | GQHFHLLPFG | GRR CPGAS | 475 |
| SEQ_ID_NO_353 | AFRPERFVS | GGGGGGTAA | ·D······ | VR | GQHFHLLPFG | GRR CPGAS | 464 |
| SEQ_ID_NO_354 | AFRPERFVS | GGGGGGTAA | ·D······ | VR | GQHFHLLPFG | GRR CPGAS | 465 |
| SEQ_ID_NO_334 | EFEPERFLC· | AGENGKSQL | ·D······ | VR | GQHFHFLPFG | GRRGCPGTT | 456 |
| SEQ_ID_NO_356 | EFRPERFLK | LEGDSSDVV | ·D······ | VR | GCHFQLLPFG | GRRMCPGVS | 452 |
| SEQ_ID_NO_349 | EFKPHRFLD | ···HARHL | ·D······ | VK | GCCFQLLPFG | TGRRGCPG S | 454 |
| SEQ_ID_NO_351 | EFKPHRFLD | ·GGDLKSSL | ·D······ | K | GHNFQLLPFG | TGRRGCPGVN | 451 |
| SEQ_ID_NO_2553 | EFEPDRFFE | ·GDFLKSSL | ·D······ | K | SCSFQLLPFG | TGRRGCPG N | 458 |
| SEQ_ID_NO_364 | AFQPERFLE | ···KEKAAI | ·D······ | VX | GQHFELLPFG | TGRRGCPGML | 446 |
| SEQ_ID_NO_347 | EFRPERFLEK | GTSSI····· | ·D······ | VK | GQHFELLPFG | TGRRGCPGML | 448 |
| SEQ_ID_NO_359 | EFRPERFLEK | GRESI····· | ·D······ | VK | GQHFELLPFG | TGRRGCPGML | 451 |

Figure 13 (continued)

| SEQ_ID_NO | | | | | | | |
|---|---|---|---|---|---|---|---|
| SEQ_ID_NO_366 | LAKKFVGLAL | ASLIQCFDWE | RSA-EKI | ......DLK | EGA RI | TLPK | 483 |
| SEQ_ID_NO_349 | LAQKFVGLAL | GSLIQCFDWE | RTSP-EKI | ......DLN | EGSG | TLPK | 482 |
| SEQ_ID_NO_365 | LAQKFVGLAL | GSLIQCFEWE | RMSA-EKI | ......DLN | EGSG | TLPK | 482 |
| SEQ_ID_NO_346 | VGIVMVEYIL | GTLVHSFDWK | LPSEVEL | ......NME | EAFG | LALCK | 487 |
| SEQ_ID_NO_2542 | LARAVLHRTL | GVLIQCFDWK | KGA-EKL | ......NME | QGVG | FSEAM | 508 |
| SEQ_ID_NO_332 | LAYISVGTAI | GVMVQCFDWE | ---KGDKI | ......NMD | EAPGKI | TLTM | 312 |
| SEQ_ID_NO_338 | LAYISVGTAI | GVMVQCFDWE | ---KGDKI | ......NMD | EAPGKI | TLTM | 491 |
| SEQ_ID_NO_341 | LAFSLNNTAV | AAMVQCFDWK | GKDGKGEKV | ......DME | SGSG | NSLSM | 492 |
| SEQ_ID_NO_2549 | LAFAMNNTTV | AAIVQCFDWK | LGDGDGSKV | ......DMQ | SGPG | LTLSM | 498 |
| SEQ_ID_NO_2544 | LSTSGMATLL | ASVIQCFDLQ | VLDPQGHVL | KGDDAKVSME | ERAG | LTVPR | 501 |
| SEQ_ID_NO_2541 | LATSGMATLL | ASLIQCFDLQ | VLGPQGQIL | KGGDAKVSME | ERAG | LTVPR | 501 |
| SEQ_ID_NO_358 | LATSGMATLL | ASLIQCFDLQ | VLGPQGQIL | KGGDAKVSME | ERAG | LTVPR | 501 |
| SEQ_ID_NO_360 | LATSGMATLL | ASLIQCFDLQ | VLGPQGQIL | KGGDAKVSME | ERAG | LTVPR | 501 |
| SEQ_ID_NO_339 | LATAGMATLL | SSVLQCFELQ | VLAGPNGQIL | KGADAKVSMD | ERPG | LTVPR | 504 |
| SEQ_ID_NO_2550 | LATAGMATLL | ASVIQCFDLQ | VVGLKGKLL | KGSDAKVSME | ESPG | LTVPR | 501 |
| SEQ_ID_NO_2543 | LALLVIQATL | ASLIQCFDWW | VNDGKSHD | ......DMS | EVGR | VTVFL | 498 |
| SEQ_ID_NO_2551 | LALLVIQATL | ASLVQCFDWW | VNDGKNSEI | ......DMS | EEGR | VTVFL | 497 |
| SEQ_ID_NO_2548 | LAMLVVQAAL | AAMLQCFEWA | PVGG-ATM | ......DME | EGPG | TLPR | 514 |
| SEQ_ID_NO_353 | LAMLVVQAAL | AAMVQCFEWS | PVGG-APV | ......DME | EGPG | LLPR | 503 |
| SEQ_ID_NO_354 | LAMLVVQAAL | AAMVQCFEWS | PVGG-APV | ......DME | EGPG | LLPR | 504 |
| SEQ_ID_NO_324 | LALQMVQTG | AAMIQCFDWK | VNGM--- | ......DMQ | EGTG | TLPR | 493 |
| SEQ_ID_NO_352 | LAMQEVPALL | GAIIQCFDFH | VVGPKGEIL | KGDDVLNVD | ERPG | TAPR | 500 |
| SEQ_ID_NO_349 | LAMRELPVVI | AGLIQCFEWN | A-NDK-EVL | ......SMD | ERAG | TAPR | 493 |
| SEQ_ID_NO_351 | LAMRELSVVI | ANLIQCFDWD | VVGE-RLL | ......NTD | ERAG | TAPR | 490 |
| SEQ_ID_NO_2553 | LAMRELPVVI | AGLIQCFEWD | VNNK-ERL | ......ITD | ERAG | TAPR | 495 |
| SEQ_ID_NO_364 | LAIQEVVII | GTMIQCFDWK | LPDGSHV- | ......DMA | ERPG | LTAPR | 488 |
| SEQ_ID_NO_347 | LGMQELFSII | GAMVQCFDWK | LPDGVLKSV | ......DMT | ERPG | LTAPR | 488 |
| SEQ_ID_NO_359 | LAIQEVVSII | GTMVQCFDWK | LADGSGNNV | ......DMT | ERSG | LTAPR | 492 |

Figure 13 (continued)

```
SEQ_ID_NO_368   ATTLEAMCKP  RHVMEKVLRQ  VSNV                         507
SEQ_ID_NO_348   AKTLEAMCKP  RHVMEKVLRQ  VSNV                         506
SEQ_ID_NO_365   AKTLEAMCKP  RHIMERVLRQ  VSNV                         506
SEQ_ID_NO_346   AVPLEAMVTP  RLP DVYAPL  A                            508
SEQ_ID_NO_2546  VHPLICYPVV  R    VNPL   ETAN                         527
SEQ_ID_NO_332   AHPLNCTLVP  RTLIPVTSTV  QIPSS                        337
SEQ_ID_NO_338   AHPLNCTLVP  RTLIPVTSTV  QIPSS                        516
SEQ_ID_NO_341   VHPLICVPVV  H    FIPY   D                            509
SEQ_ID_NO_2549  LHPLKCHPIV  H    FNPF   EG                           515
SEQ_ID_NO_2544  KHNLVCLPLA  K  TTLAAKL  LSP                          522
SEQ_ID_NO_2541  AHSLVCVPLA  R   GVASKL  LS                           521
SEQ_ID_NO_359   AHSLVCVPLA  R   GVASKL  LS                           521
SEQ_ID_NO_360   AHSLVCVPLA  R   GVASKL  LS                           521
SEQ_ID_NO_339   AHNLVCYPLA  R  PGAAAKL  LSS                          525
SEQ_ID_NO_2550  AHNLMCVPLA  R   TNVTSE  LSS                          522
SEQ_ID_NO_2543  AKPLKCKPVP  H    FVPF   SSA                          514
SEQ_ID_NO_2551  AKPLKCKPVP  R    FVPF   SA                           514
SEQ_ID_NO_2548  KRPLVCTVKA  R    LHPV   PVPTAAAADN GVDGTLHCA         548
SEQ_ID_NO_353   KRPLVCTVSP  R    HPL    PAAASASLT                    527
SEQ_ID_NO_354   KRPLVCTVSP  R    HPL    PAAASASLT                    528
SEQ_ID_NO_334   AHPLICVPVA  R    LNPF   PSF                          511
SEQ_ID_NO_358   AHNLVCVPVD  RTSGGGPLKI  EC                           523
SEQ_ID_NO_349   AVDLEFVPLM  R  CNCPNIF  VSA                          514
SEQ_ID_NO_351   AVDFVCVPLE  R  GNTLKI   LGSN                         511
SEQ_ID_NO_2553  AVDFVCVPSM  R  ENCPKVF                               513
SEQ_ID_NO_364   ETDLFCRVVP  R    VDPL   VVSTD                        506
SEQ_ID_NO_347   ANDLVCQLVP  R    DPV    VVSGP                        506
SEQ_ID_NO_359   AFDLVCRLYP  R    VDPA   TLSGA                        512
```

Figure 14

| | | | | | | | |
|---|---|---|---|---|---|---|---|
| SEQ_ID_NO_475 | ---------- | --MSS- | ---- | -------- | -------RL | ------YVGN | 9 |
| SEQ_ID_NO_436 | MAFCNKLGNL | LRQGATQS- | -----SHAP | VSSMLNYLRH | MSSSKL | FIGG | 42 |
| SEQ_ID_NO_420 | MAFLSKVGKI | FRQTSAHVTA | SNSMLQSI-- | --------RC | MSSSKI | FVGG | 40 |
| SEQ_ID_NO_473 | ---------- | --MAASDV- | ------EF- | --------RC | ------ | FVGG | 14 |
| SEQ_ID_NO_369 | ---------- | --MAGGE- | ------EF- | --------RC | ------ | FVGG | 13 |
| SEQ_ID_NO_371 | ---------- | --MASADV- | ------EF- | --------RC | ------ | FVGG | 14 |
| SEQ_ID_NO_372 | ---------- | --MASADV- | ------EF- | --------RC | ------ | FVGG | 14 |
| SEQ_ID_NO_373 | ---------- | ----MAEV- | ------EY- | --------RC | ------ | FVGG | 12 |
| SEQ_ID_NO_458 | ---------- | ----MADV- | ------EY- | --------RC | ------ | FVGG | 12 |
| SEQ_ID_NO_597 | ---------- | ----MADV- | ------EY- | --------RC | ------ | FVGG | 12 |
| SEQ_ID_NO_455 | ---------- | --MAAADV- | ------EY- | --------RC | ------ | FVGG | 14 |
| SEQ_ID_NO_477 | ---------- | --MAAADV- | ------EY- | --------RC | ------ | FVGG | 14 |
| SEQ_ID_NO_465 | ---------- | --MAASDV- | ------EY- | --------RC | ------ | FVGG | 14 |
| SEQ_ID_NO_488 | ---------- | --MAAPDV- | ------EY- | --------RC | ------ | FVGG | 14 |
| SEQ_ID_NO_494 | ---------- | --MAAPDV- | ------EY- | --------RC | ------ | FVGG | 14 |
| SEQ_ID_NO_374 | ---------- | ---MDAEV- | ------EY- | --------RC | ------ | FVGG | 13 |
| SEQ_ID_NO_441 | ---------- | ----MAEV- | ------EY- | --------RC | ------ | FVGG | 12 |
| SEQ_ID_NO_444 | ---------- | --MASADV- | ------EY- | --------RC | ------ | FVGG | 14 |
| SEQ_ID_NO_451 | ---------- | ----MGDV- | ------EY- | --------RC | ------ | FVGG | 12 |
| SEQ_ID_NO_595 | ---------- | ----MAEV- | ------EY- | --------RC | ------ | FVGG | 12 |
| SEQ_ID_NO_474 | ---------- | ----MAEV- | ------EY- | --------RC | ------ | FVGG | 12 |
| SEQ_ID_NO_447 | ---------- | ----MAEV- | ------EY- | --------SC | ------ | FVGG | 12 |
| SEQ_ID_NO_450 | ---------- | ---MAAEV- | ------EY- | --------SC | ------ | FVGG | 13 |
| SEQ_ID_NO_434 | ---------- | --MGSSDV- | ------EY- | --------RC | ------ | FVGG | 14 |
| SEQ_ID_NO_437 | ---------- | --MAAADI- | ------EY- | --------RC | ------ | FVGG | 14 |
| SEQ_ID_NO_438 | ---------- | ---MSADI- | ------EY- | --------RC | ------ | FVGG | 13 |
| SEQ_ID_NO_454 | ---------- | ----MAE-- | ------EY- | --------RC | ------ | FVGG | 11 |
| SEQ_ID_NO_392 | ---------- | ---MSAEV- | ------EY- | --------RC | ------ | FVGG | 13 |
| SEQ_ID_NO_425 | ---------- | --MASAEV- | ------EF- | --------RC | ------ | FVGG | 14 |
| SEQ_ID_NO_504 | ---------- | --MASAEI- | ------EF- | --------RC | ------ | FVGG | 14 |
| SEQ_ID_NO_368 | ---------- | --MASGDV- | ------EY- | --------RC | ------ | FVGG | 14 |
| SEQ_ID_NO_422 | ---------- | --MASPDV- | ------EY- | --------RC | ------ | FVGG | 14 |
| SEQ_ID_NO_596 | ---------- | --MASADV- | ------EF- | --------RC | ------ | FVGG | 14 |
| SEQ_ID_NO_433 | ---------- | ---M--ADV- | ------ED- | --------RC | ------ | FVGG | 12 |
| SEQ_ID_NO_376 | ---------- | --MASADV- | ------EY- | --------RC | ------ | FVGG | 14 |
| SEQ_ID_NO_440 | ---------- | --MASADV- | ------EY- | --------RC | ------ | FVGG | 14 |

Figure 14 (continued)

| | | | | | | | |
|---|---|---|---|---|---|---|---|
| SEQ_ID_NO_475 | LSWNAKEEDL | RTYFGKFGEV | EEASIALDRE | SGRSRGFGFV | TLPADVALKD | 58 |
| SEQ_ID_NO_436 | LSYGVDDQSL | KDAFASYGEV | VEARVITDRD | TGRSRGFGFV | NFTSDESATS | 92 |
| SEQ_ID_NO_420 | ISYSTDEFGL | REAFSKYGEV | VDAKIIVDRE | TGRSRGFAFV | TFTSTEEASN | 90 |
| SEQ_ID_NO_473 | LAWATDDASL | ERAFSTYGDI | VESKIINDRE | TGRSRGFGFV | TFRDEQSMRD | 64 |
| SEQ_ID_NO_369 | LAWATTDGRL | EQAFRPFGEV | VQSKVISDRE | TGRSRGFGFV | TFADENSMNA | 63 |
| SEQ_ID_NO_371 | LAWSTDDRSL | QEAFSPYGEV | VESKIISDRE | TGRSRGFGFV | TFNDEQSMRD | 64 |
| SEQ_ID_NO_372 | LSWSTDDRSL | KDAFTAFGEV | MDSKVVSDRE | TGRSRGFGFV | TFMDEQSMRD | 64 |
| SEQ_ID_NO_373 | LSWGTDDRSL | AEAFNKFGEV | TDSKIINDRE | TGRSRGFGFV | TFANEQSMRD | 62 |
| SEQ_ID_NO_458 | LAWATDDQSL | DNAFSKYGDV | IDSKIITDRE | TGRSRGFGFV | TFASDEAMRD | 62 |
| SEQ_ID_NO_507 | LRWATDDQSL | DNAFSKYGDV | IDSKIITDRE | TGRSRGFGFV | TFASDEAMRD | 62 |
| SEQ_ID_NO_455 | LAWATNNETL | EQAFANFGQV | IDSKVITDRE | TGRSRGFGFV | TFSSEQSMLD | 64 |
| SEQ_ID_NO_477 | LAWATDNASL | QQAFASYGDV | LDSKVITDRE | TGRSRGFGFV | TFSSEQSMLD | 64 |
| SEQ_ID_NO_465 | LAWATDDHSL | HNAFSTYGEV | LESKIILDRE | TQRSRGFGFV | TFSTEEAMRN | 64 |
| SEQ_ID_NO_488 | LAWATDDRSL | EAAFSTYGEI | LDSKIINDRE | TGRSRGFGFV | TFSSEQSMRD | 64 |
| SEQ_ID_NO_494 | LAWATDDRSL | EAAFSTYGEI | LDSKIINDRE | TGRSRGFGFV | TFSSEQSMRD | 64 |
| SEQ_ID_NO_374 | LAWATDDQSL | ERAFSNYGQV | LESKIINDRE | TGRSRGFGFV | TFSSEQAMRD | 63 |
| SEQ_ID_NO_441 | LAWATNDESL | EQAFSQFGDI | TDSKIINDRE | TGRSRGFGFV | TFKDEKSMRD | 62 |
| SEQ_ID_NO_444 | LAWATTDQSL | SEAFSQYGEI | LESKIINDRE | TGRSRGFGFV | TFKDEQSMRD | 64 |
| SEQ_ID_NO_451 | LAWATTDNTL | SEAFSQYGEV | VESKIINDRE | TGRSRGFGFV | TFKDEQAMRD | 62 |
| SEQ_ID_NO_505 | LAWATTDQTL | GDAFSQFGEI | LDSKIINDRE | TGRSRGFGFV | TFKDEKAMRD | 62 |
| SEQ_ID_NO_474 | LAWATTDQTL | GDAFSQYGEI | LDSKIINDRE | TGRSRGFGFV | TFKDEQAMRD | 62 |
| SEQ_ID_NO_447 | LAWATTDRTL | ADAFGTYGEV | LDSKIINDRE | TGRSRGFGFV | TFKDEKCMRD | 62 |
| SEQ_ID_NO_450 | LAWATTDRTL | SDAFSTYGEV | VDSKIINDRE | TGRSRGFGFV | TFKDEKSMKE | 63 |
| SEQ_ID_NO_434 | LAWATDSDAL | EQAFSKFGEI | TDSKVINDRE | TGRSRGFGFV | TFAEEKSMRD | 64 |
| SEQ_ID_NO_437 | LAWATSDKAL | EEAFSAYGEV | LESKIINDRE | TGRSRGFGFV | TFNNEKSMRD | 64 |
| SEQ_ID_NO_438 | LAWATTDQSL | DEAFSPYGEI | LDSKIINDRE | TGRSRGFGFV | TFNNEKSMRD | 63 |
| SEQ_ID_NO_454 | LAWATNDQSL | EQAFSQFGEI | TDCKIINDRE | TGRSRGFGFV | TFSSSESMKN | 61 |
| SEQ_ID_NO_392 | LAWATTDQVL | QEAFSQYGEI | IDSKIINDRE | TGRSRGFGFV | TFGNEKAMRD | 63 |
| SEQ_ID_NO_425 | LAWATDHDAL | EKAFSQFGEI | VESKVINDRE | TGRSRGFGFV | TFATEQAMRD | 64 |
| SEQ_ID_NO_504 | LAWATDNDAL | ERAFSPFGEI | IESKIINDRE | TGRSRGFGFV | TFSNEKAMRD | 64 |
| SEQ_ID_NO_368 | LAWATDDRAL | ETAFAQYGDV | IDSKIINDRE | TGRSRGFGFV | TFKDEKAMKD | 64 |
| SEQ_ID_NO_422 | LAWATDDRAL | ETAFSQYGEV | LDSKIINDRE | TGRSRGFGFV | TFKDEKSMKD | 64 |
| SEQ_ID_NO_506 | LAWATTDSSL | HEAFSAYGDI | LESKIINDRE | TGRSRGFGFV | TFRDEKSMRD | 64 |
| SEQ_ID_NO_433 | LAWATDNDAL | EKAFSQYGEI | VDSKIINDRE | TGRSRGFGFV | TFANEKSMND | 62 |
| SEQ_ID_NO_376 | LAWATDDRAL | EEAFSVYGEI | VESKIINDRE | SGRSRGFGFV | TFRDEKSMRD | 64 |
| SEQ_ID_NO_440 | LAWATDDHAL | EQAFSQYGEV | VESKIINDRE | TGRSRGFGFV | TFSNEKSMND | 64 |

Figure 14 (continued)

```
SEQ_ID_NO_475   AI EKTNGAEF MGRNI KVNEA SPPGER-PPR TNN------Y GGGYGDFN--   99
SEQ_ID_NO_436   ALSAMDGQDL NGRNI RVSYA NDRPSA---- ----------  ----P----  119
SEQ_ID_NO_420   AMQLLDGQDL HGRFI RVNYA TERGSGFGGR G--------F GGP-------  124
SEQ_ID_NO_473   AI KGMNGQTL DGRNI TVNEA EVFAAA-VAA ---------G TAAAAEVAVT 104
SEQ_ID_NO_369   AI KEMNGQEL DGRNI TVNQA QSRGGG-GGG GG-------G GGGYGR----  101
SEQ_ID_NO_371   AI DAMNGKML DGRSI TVNPA QSRGNG-GGG GGG------G SRGYR-----  102
SEQ_ID_NO_372   AI EGMNGRDL DGRNI TVNRA QARGGG-GGG GG-------G GGGYRG----  102
SEQ_ID_NO_373   AI DEMNGKEL DGRSI TVNEA QSRGSG-GGG ---------G GGGYRS----   98
SEQ_ID_NO_458   AI EAMNGQDL DGRNI TVNEA HSRRBG-GGG GGFSGG---G GGGYGGQRRE 108
SEQ_ID_NO_507   AI EAMNGQDL DGRNI TVNEA QSRRSD-GGG GFGG-----G GGGYGGQRRE 106
SEQ_ID_NO_455   AI ENMNGKEL DGRNI TVNQA QSRGGG-GGG GGYGG----G GGGY------ 103
SEQ_ID_NO_477   AI EAMNGKDL DGRNI TVNQA QSRGGG---- ---------G GGGY------  95
SEQ_ID_NO_465   AI EGMNGKEL DGRNI TVNEA QSRGGR-GGL ---------G GGGYG-----  98
SEQ_ID_NO_488   AI EGMNGKEL DGRNI TVNEA QSRRSG-GGG ---------G GGGY------  98
SEQ_ID_NO_494   AI EGMNGKEL DGRNI TVNEA QSRRBG-GGG GGYGG----G GGGY------ 103
SEQ_ID_NO_374   AI EGMNGQDL DGRNI TVNEA QSRGSG-GGG GGYRGG---G GGGY------ 103
SEQ_ID_NO_441   AI EGMNGQEL DGRNI TVNEA QSRGSG-GGG GRREG----G GGGY------ 101
SEQ_ID_NO_444   AI EGMNGQTL DGRNI TVNEA QSRGSG-GN- ---------G GGGFRGPRRD 103
SEQ_ID_NO_451   AI EGMNGQDL DGRNI TVNEA QSRGGG-GGG GGR------G GGCYGGGRRE 105
SEQ_ID_NO_505   AI EGMKGQDL DGRNI TVNEA QSRGSG-GGG ---------G GGGYR-----  97
SEQ_ID_NO_474   AI EGMNGQDL DGRNI TVNEA QSRGSG-GGG GG-------Y RGG--R----  98
SEQ_ID_NO_447   AI EGMNGQEL DGRSI TVNEA QARGSG-GGG GG-------Y GGCRRE---- 100
SEQ_ID_NO_450   AI SGMNGSEL DGRNI TVNEA QARGSG-GGG G--------G GGGFGGGRRR 104
SEQ_ID_NO_434   AI EEMNGQDI DGRNI TVNEA QSRGSG-GGG RGGGGGGYGG GGGYGG---- 109
SEQ_ID_NO_437   AI EGMNGQNL DGRNI TVNEA QSRGGG-GGL ---------G GGGYR-----  98
SEQ_ID_NO_438   AI QGMNSDEL DGRNI TVNEA QSRGSG-GGG ---------G GGGYSR----  99
SEQ_ID_NO_454   AI EGMNGQDL DGRNI TVNEA QSRSGG---- ---------G GGGY------  92
SEQ_ID_NO_392   AI DGMNGQDL DGRNI TVNEA QSRGSG-GGG G--------G GGGYNR---- 100
SEQ_ID_NO_425   AI EGMNGQNL DGRNI TVNEA QSRGKGGGGG GGGYGG---G GGGY------ 105
SEQ_ID_NO_504   AI EGMNGQNL DGRNI TVNEA QSRGSG-GGG GG-------N GGGYSR---- 102
SEQ_ID_NO_368   AI EGMNGQDL DGRSI TVNEA QSRGSG-GGG GHRGG----G GGGYLR---- 104
SEQ_ID_NO_422   AI EGMNGQDL DGRSI TVNEA QSRGSG-GGG GGRG-----G GGGYR----- 103
SEQ_ID_NO_506   AI EGMNGQNL DGRNI TVNEA QSRGSG-GGG GGGYGSR--G GGGY------ 105
SEQ_ID_NO_433   VI EAMNGQDL DGRNI TVNQA QSRGSG-GGG GGR------G GGGY------  99
SEQ_ID_NO_376   AI EGMNGQNL DGRNI TVNEA QSRRBG-GGG GEGYGG---G SGGYKR---- 106
SEQ_ID_NO_440   AI EGMNGQNL DGRNI TVNEA QSRGSG-GGG GRREGG---G GGGYGR---- 106
```

Figure 14 (continued)

| | | | | | | |
|---|---|---|---|---|---|---|
| SEQ_ID_NO_475 | GNGGGRDYG | ---------- | RGGYGRG | ------ NGGY | GGRNAG | YGG | 128 |
| SEQ_ID_NO_436 | RGGG GGY- | ---------- | GGGY---- | ------------ ----G- | DGF | 134 |
| SEQ_ID_NO_420 | GGGNAGGYGA | P--------- | SGGYGGG | ------ GGY ----- G- | GGA | 149 |
| SEQ_ID_NO_473 | EVVG----- | ---------- | TAATAGTA- | ------------ -----V- | DRR | 120 |
| SEQ_ID_NO_369 | REQGGGY- | ---------- | GGGYGGSR- | ------ GGG ----- D- | REG | 124 |
| SEQ_ID_NO_371 | GGGG----- | ---------- | GGGYGGSRD | RG---- DRGY -----G- | GGG | 125 |
| SEQ_ID_NO_372 | GGGG----- | ---------- | SGGYGGG- | ------ SGGY ESRRSG- | GGG | 127 |
| SEQ_ID_NO_373 | GGGG----- | ---------- | GGGYGGG- | ------ GGGY GGRREG- | GGG | 122 |
| SEQ_ID_NO_458 | GGGGGGGY- | ---------- | GGGRSGG- | ------ GGGY GS---R- | EGG | 133 |
| SEQ_ID_NO_507 | GGGG- SYGG | G--------- | GGGYGGGR- | ------------ -----S- | GGG | 127 |
| SEQ_ID_NO_455 | GGREGGGYGG | G--------- | GGGYGGRRE | G----- GGGY GGGGYG- | GGG | 137 |
| SEQ_ID_NO_477 | GGGRQGGYGG | G--------- | GGGYGGGGG | ------ GGGY GG---G- | RRE | 125 |
| SEQ_ID_NO_465 | GGRGGGGYGG | GGRRDG---- | GGGYGGG- | ------ GGGY -------- | GGG | 128 |
| SEQ_ID_NO_488 | GGGG-GGYGG | GRG------- | GGGYGGGG | ------ GGGY GRREGGY | GGG | 132 |
| SEQ_ID_NO_494 | GGGGGGGYGR | R--------- | EGGYGGG- | ------------ -----G- | GYG | 125 |
| SEQ_ID_NO_374 | GGRREGGYNR | GG-------- | GGGYGGG- | ------ GGGY -----G- | GGG | 130 |
| SEQ_ID_NO_441 | -GGG GGYGG | RREGGG---- | GGGYGGRR- | ------------ -----E- | GGG | 127 |
| SEQ_ID_NO_444 | GGGG-GGYGG | GRR------- | DGGYGGN- | ------ GGY GG---G- | RRE | 131 |
| SEQ_ID_NO_451 | GGGG- GYGG | ---------- | GGGYGGGRR | E----------- -----G- | GGG | 127 |
| SEQ_ID_NO_505 | GGGG GGYGG | GGRR------ | EGGYGGG- | ------ GGY GG---G- | RRE | 126 |
| SEQ_ID_NO_474 | GGGG GGYGG | GGRR------ | EGGYGGG- | ------ GGGY GG---G- | RRE | 128 |
| SEQ_ID_NO_447 | GGGG- GYGG | G--------- | GGGYGGGRR | ------------ -----E- | GGG | 122 |
| SEQ_ID_NO_450 | EGGG GGYGG | ---------- | GGGYRGGG | ------ GGGY -------- | GGG | 128 |
| SEQ_ID_NO_434 | GGGCYGGGGC | RRDGGYSRSG | GGGGYGGGG | ------ DRGY G----G- | GGG | 147 |
| SEQ_ID_NO_437 | NGGG GGYGG | GRR------- | EGGYGGG- | ------ GGY -----S- | RGG | 124 |
| SEQ_ID_NO_438 | GGGG GGYGG | GGRR------ | EGGYGGG- | ------ GGGY NSRS-S- | GGG | 131 |
| SEQ_ID_NO_454 | SRGG----- | ---------- | ---------- | ------------ ---------- | -- | 96 |
| SEQ_ID_NO_392 | NSGG GGYGG | GGRREG---- | GGGYSRG- | ------ GGGY GG---G- | GGG | 132 |
| SEQ_ID_NO_425 | GGGG- GYSR | G--------- | GGGYGGGGG | RR---- EGGY NR---N- | GGG | 135 |
| SEQ_ID_NO_504 | GGGG GGYGG | ---------- | GGGYGGGGR | R----- EGCG GGYSRG- | GGG | 134 |
| SEQ_ID_NO_368 | SGGG GGYSG | --G------- | GGSYGGGG- | ------------ ---------- | -- | 122 |
| SEQ_ID_NO_422 | SGGG GGYGG | G--------- | GGGYGGGGR | ------ EGGY -----S- | GGG | 130 |
| SEQ_ID_NO_506 | GGGGRRESGG | ---------- | GGGYGGSR- | -------- GY -----G- | GGG | 129 |
| SEQ_ID_NO_433 | GGGG----- | ---------- | ---------- | ------------ ---------- | -- | 103 |
| SEQ_ID_NO_376 | SGGG GGYGR | --R------- | EGGYGGGRR | EGVFWNGGGY DG---G- | GGG | 141 |
| SEQ_ID_NO_440 | REGG GGYSR | GGG------- | GGGYGGG- | ------ GGGY G----G- | GNG | 134 |

Figure 14 (continued)

| | | | | | | | | |
|---|---|---|---|---|---|---|---|---|
| SEQ_ID_NO_475 | RGNFG | -GQG | | GYGD | NRFGNDNFGG | SYGGRGGYRG | -PRGPSAEEN | 169 |
| SEQ_ID_NO_436 | SNRGG | -GGG | | | | | | 142 |
| SEQ_ID_NO_420 | GGYGA | -PGG | | GYGX | ---WWWL-RR | RCWWLRC--- | | 174 |
| SEQ_ID_NO_473 | MGTGG | | | | ----AK | AVVRLPR--- | | 134 |
| SEQ_ID_NO_389 | SGYGG | -SRG | G----- | GYG- | --------GG | GGGGYGG | -R-GG------ | 148 |
| SEQ_ID_NO_371 | GGYGG | -GGG | ------ | GYG- | --------GG | GGSRYGG | ---GG------ | 147 |
| SEQ_ID_NO_372 | SGGGGYSGGG | RERSERGYGG | GSRN----GG | GYGGYSG | GG-GGGSRYGGG | 171 |
| SEQ_ID_NO_373 | GGYGG | -GSG | G----- | GYGG | ---RRE--GG | GGGGYGG | -G-GGGGYRG-- | 155 |
| SEQ_ID_NO_458 | GGYGG | -GGG | ------ | GYGG | SRGGS---GG | GGGGYGGSRG | -G-------- | 163 |
| SEQ_ID_NO_507 | GGYGSRDGGG | G----- | GYL- | --------GG | GGGGYGG | -S RGG------ | 153 |
| SEQ_ID_NO_455 | GGYGGREGGG | ------ | GYGG | --------GG | GYGGNRG | | 160 |
| SEQ_ID_NO_477 | GGYGG | -GGG | GGRREGGYG- | --------GG | GYGSRG | | 150 |
| SEQ_ID_NO_465 | GGYGG | -GGG | ------ | GYGG | --------GN | RGGGYGN--- | -R | 149 |
| SEQ_ID_NO_488 | GGYGGGRGGG | G----- | GYG- | --------GS | RGGGYGG | | 155 |
| SEQ_ID_NO_494 | GGRGG | -GGG | ------ | GYG- | --------GS | RGGGYGG | | 145 |
| SEQ_ID_NO_374 | GGYGG | -GGG | ------ | GYGG | --------GR | REGGYGG | -G-GGDRYARG- | 160 |
| SEQ_ID_NO_441 | GGYGG | -GGG | ------ | GYGG | RR------EG | GDGGYGG | | 150 |
| SEQ_ID_NO_444 | GGYGG | -GDR | ------ | GYG- | --------GG | GGGGSRYSRG | -GG------- | 156 |
| SEQ_ID_NO_451 | GGYSG | -GGG | ------ | GYGG | GRREGGY-GG | GGGGYGGGDR | YSDRSSRGGG | 168 |
| SEQ_ID_NO_505 | GGYGG | -GGG | G----- | GYCG | --------GR | REGYGG | | 148 |
| SEQ_ID_NO_474 | GGYGG | -GGG | ------ | YGG | --------GR | REGYGG | | 148 |
| SEQ_ID_NO_447 | GGYGG | -GRR | ------ | | --------EG | GGGGYGG | | 139 |
| SEQ_ID_NO_450 | RREGG | -GGG | ------ | GYGG | GRRE----GG | GGGGYGG | | 153 |
| SEQ_ID_NO_434 | GGYGG | -GRD | R----- | GYGG | --------GG | GDRGYGG | GG-GGDRYSRGG | 180 |
| SEQ_ID_NO_437 | GGYGG | -GGG | ------ | GYG- | --------GG | RDRGYGGGGD | -GGSRYSRGG | 156 |
| SEQ_ID_NO_438 | GGYGG | -GRD | Q----- | GYGG | --------GG | GGSRYSR--G | -GG------- | 156 |
| SEQ_ID_NO_454 | | GGG | | | | | | 99 |
| SEQ_ID_NO_392 | YGSGG | -GGG | ------ | GYG- | --------GG | RDRGYGD--- | ---GGSRYSSR | 160 |
| SEQ_ID_NO_425 | GGYGG | -GGG | GYGGGGGYGG | --------GG | RDRGYGG | -D-GGSRYSRGG | 172 |
| SEQ_ID_NO_504 | GGYGS | -GGG | ------ | GYGG | G-------GR | REGGYGGGEG | -GGARYSRGS | 168 |
| SEQ_ID_NO_368 | -GRRE | -GGG | ------ | GYG- | --------GG | EGGGYGG | -S-GG------ | 144 |
| SEQ_ID_NO_422 | GGYSRGGGG | G----- | GYGG | GGRRD---GG | EGGGYGG | -S-GG------ | 162 |
| SEQ_ID_NO_506 | GGYGGRREGG | YSRDG-GYG- | --------GD | GGSRYSR--S | -GA------- | 159 |
| SEQ_ID_NO_433 | | | | | | | | 103 |
| SEQ_ID_NO_376 | GGYGG | -GGG | ------ | GYG- | --------GG | GGGGY | | 159 |
| SEQ_ID_NO_440 | GGYGG | -GRE | QR---- | GYGD | --------SG | GGSRYSR--- | | 157 |

Figure 14 (continued)

| SEQ_ID_NO | Sequence | # |
|---|---|---|
| SEQ_ID_NO_475 | NSNNYGGY- | 177 |
| SEQ_ID_NO_436 | ----GGGW- | 146 |
| SEQ_ID_NO_420 | --SSWWLWRR WLQCSRWWLR RWLILWWKCC WWRLWR | 208 |
| SEQ_ID_NO_473 | ----SEGWAS | 140 |
| SEQ_ID_NO_369 | --PSSGNWRN DRQPEY--- | 162 |
| SEQ_ID_NO_371 | --SEGGSWRR | 155 |
| SEQ_ID_NO_372 | GVSDDGGWRS | 181 |
| SEQ_ID_NO_373 | --NSDGNWRN | 163 |
| SEQ_ID_NO_458 | --SGGNWRE | 171 |
| SEQ_ID_NO_507 | --SGGNWRE | 181 |
| SEQ_ID_NO_455 | --DSGGNWRN | 168 |
| SEQ_ID_NO_477 | --DSGGNWRN | 158 |
| SEQ_ID_NO_465 | ---SDGNWRN | 156 |
| SEQ_ID_NO_488 | --DSGGNWRN | 163 |
| SEQ_ID_NO_494 | --DSGGNWRN | 153 |
| SEQ_ID_NO_374 | --NSDSDWRN | 168 |
| SEQ_ID_NO_441 | ----GGGGSR W- | 157 |
| SEQ_ID_NO_444 | --ASDGNWRN | 164 |
| SEQ_ID_NO_451 | GGSSDGNWRN | 178 |
| SEQ_ID_NO_505 | --GSES--- | 152 |
| SEQ_ID_NO_474 | --GSEGNWRN | 156 |
| SEQ_ID_NO_447 | --GGYGGGR Y- | 148 |
| SEQ_ID_NO_450 | --GGYGGGDR Y- | 162 |
| SEQ_ID_NO_434 | GADSGGNWRD | 190 |
| SEQ_ID_NO_437 | G-ASEGNWRS | 165 |
| SEQ_ID_NO_438 | --ESDGNWKN | 164 |
| SEQ_ID_NO_454 | --DSGGNWRN | 107 |
| SEQ_ID_NO_392 | GESEGGSWRS | 170 |
| SEQ_ID_NO_425 | GCSDGGSWRN | 182 |
| SEQ_ID_NO_504 | GCSEGGSWRS | 178 |
| SEQ_ID_NO_366 | ----GGGW- | 148 |
| SEQ_ID_NO_422 | ----GGGW- | 166 |
| SEQ_ID_NO_506 | -SDGGSWRN | 167 |
| SEQ_ID_NO_433 | ----GG--- | 105 |
| SEQ_ID_NO_376 | ----GG--- | 161 |
| SEQ_ID_NO_440 | -DSDGGNWRS | 166 |

Figure 15

```
SEQ_ID_NO_527    ---MAGISVI VVVVAFLHI LAFVLAIGAE MRRST---- ----------   32
SEQ_ID_NO_529    MGDVGRSSIL VHILVIALCL AAFGFAIAAE RRRST---- ----------   35
SEQ_ID_NO_530    MGDTERSSIL VHILVIALCL TAFGFAIAAE RRRSTVKSTY LRYILNFVFE   50
SEQ_ID_NO_531    MGDTERSSIL VHILVIALCL TAFGFAIAAE RRRST---- ----------   35
SEQ_ID_NO_510    MGELGKASTL VFILVVALSL VAFGFSIAAE RRRSI---- ----------   34
SEQ_ID_NO_525    MGELGKGSTL VFILVIALCL VAFGFSIAAE RRRSI---- ----------   34
SEQ_ID_NO_521    MAELGRGSTL VHLLVVVLCL VAFGFAIAAE RRRSV---- ----------   34
SEQ_ID_NO_513    MGELGKGSTL VHLLVVVLSL VAFGFAIAAE RRRSV---- ----------   34
SEQ_ID_NO_517    MFELGKGSTL VHLLVVVLSL VAFGFAIAAE RRRS----- ----------   33
SEQ_ID_NO_511    ----MASKL LLIAVFVLDL IAFGLAVAAE QRRST---- ----------   30
SEQ_ID_NO_523    ----MASIL VQVSALLLNL LAFGLAVAAE QRRSK---- ----------   30

SEQ_ID_NO_527    ---------- ---GKVVPDE YDERTFCAYD SDASTAVGLS AFGLLLLSQA   69
SEQ_ID_NO_529    ---------- ---GSIVTDS S-NTTFCVYD SDIATGYGVG AFLFLLSGHS   71
SEQ_ID_NO_530    FMDGVFFTIY IVQGSIVTDS F-NSTFCVYD SDIATGYGVG AFLFLLSGDS   99
SEQ_ID_NO_531    ---------- ---GSIVTDS F-NSTFCVYD SDIATGYGVG AFLFLLSGQS   71
SEQ_ID_NO_510    ---------- ---GKSIQDP ITNTTFCVYD SDVATGYGVG AFLFLLSSES   71
SEQ_ID_NO_525    ---------- ---GKSIQDP ITNATYCVYS SDVATGYGVG AFLFLLSSES   71
SEQ_ID_NO_521    ---------- ---GTMHKIE GTNETFCSYS SDVATGYGVG AFLFLLSXES   71
SEQ_ID_NO_513    ---------- ---GTVVKDD ITNSTYCVYN SDVATGYGVG AFLFLLSGES   71
SEQ_ID_NO_517    ---------- ---------- ---------- ------YGVG AFLFLLSSES   47
SEQ_ID_NO_511    ---------- ---AKIVQDS EVNYNYCVYD SYSTGYGVG AFLFLMVSQA   67
SEQ_ID_NO_523    ---------- ---ATVTPDL AKEYDYCVYD SDVATGYGVG ALLLVAAQA   67

SEQ_ID_NO_527    VMSAATRCLC FGRGLSAGGP RTCAIASFVV GWISFLVAEV CLLAGSARNA   119
SEQ_ID_NO_529    LLMGLTKCMC FGAPLAPGGS RAWSIIYFAS SWTFAIAEA CLIAGATKNA   121
SEQ_ID_NO_530    LLMVVTKCMC FGKPLAPGGS RAWSIIYFAS SWTFMIAES CLIAGATKNA   149
SEQ_ID_NO_531    LLMVVTKCMC FGKPLAPGGS RAWSIIYFAS SWTFMIAES CLIAGATKNA   121
SEQ_ID_NO_510    LLMSVTKCMC FGRPLAPGSD RAWSIIYFIS SWMTFLVAEA CVIAGATKNA   121
SEQ_ID_NO_525    LLMGVTKCMC FGRPLSPGSD RAWSIIYFIS SWMTFLVAEA CLIAGATKNA   121
SEQ_ID_NO_521    LXMGVTKCMC FGRPLTPGVN RAKSIXYFLS SWTFXVAEA CLIAGATKNA   121
SEQ_ID_NO_513    LLMGVTKCMC FGRPLAPGSD RAWSIIYFVS SWLTFLVAEA CLIAGATRNA   121
SEQ_ID_NO_517    LLMGITKCMC FGRSLAPGGD RAWAIIYFVS SWATFLVAEG CLIAGAKKNA   97
SEQ_ID_NO_511    LIMAASKCFC CGKGLNPSGS RAWAVILFIV CWLFLIAEL CLLAGSVRNA   117
SEQ_ID_NO_523    VVMLASRCFC CGRGLKPGGS RACALMLFLF SWLTFLVAAA CLLAGSVRNA   117
```

Figure 15 (continued)

| | | | | | | | |
|---|---|---|---|---|---|---|---|
| SEQ_ID_NO_527 | YHTKYVGYYA | KKDLSSCTAL | RKGVFAAGAT | FVLLSMISSL | LYYMSVSKA- | 168 |
| SEQ_ID_NO_529 | YHTKYRDMVY | AGNW-TCQSL | RKGVFIAGAV | FVVFTMILDV | YFYMYYAKA- | 169 |
| SEQ_ID_NO_530 | YHTRYRHMVY | VGSW-TCESL | RKGVFIAGAV | FVVFTMILNV | YFYMYYTKS- | 197 |
| SEQ_ID_NO_531 | YHTRYRHMVY | VGSW-TCESL | RKGVFIAGAV | FVVFTMILNV | YFYMYYTKS- | 169 |
| SEQ_ID_NO_510 | YHTKY--LS | SCTF-SCASL | RKGIFIAGAV | FIVATMVLNV | YYYMYFTKSV | 167 |
| SEQ_ID_NO_525 | YHTKY--LS | AQAF-SCESL | RKGIFIAGAV | FTVATMILNV | YYYFHFTKFV | 167 |
| SEQ_ID_NO_521 | YHTKYRGMIY | AHNF-SCEAL | RKGXFIAGAV | FVVATMILNV | YYYMYFTKAM | 170 |
| SEQ_ID_NO_513 | YHTKYRGMIY | AGNF-SCETL | RKGVFIAGAV | FVVATMILNV | YYYMYFAKAT | 170 |
| SEQ_ID_NO_517 | YHTKYRGMIY | AGNF-TCETL | RKGVFIAGAV | FVVATMILNV | YYYMYFSKAT | 146 |
| SEQ_ID_NO_511 | YHTKYRTIFS | EQPP-SCETV | RKGVFGAGAA | FIFLNAIVNK | FYYICYSSA- | 185 |
| SEQ_ID_NO_523 | YHTRYRGIFN | GDPL-SCETL | RKGVFAAGAA | FTFFTALLSE | FYYISYSKS- | 185 |

| | | | | |
|---|---|---|---|---|
| SEQ_ID_NO_527 | -DMGGWVKHQ | NEGGVGMAEF | GPEKRGLGNT NG | 199 |
| SEQ_ID_NO_529 | TSQAAKKISK | TTPSVGMTGY | A-------- -- | 190 |
| SEQ_ID_NO_530 | TSQAAKKINK | TTPNVGMTGY | A-------- -- | 218 |
| SEQ_ID_NO_531 | TSQAAKKINK | TTPNVGMTGY | A-------- -- | 190 |
| SEQ_ID_NO_510 | SSPPAHKANR | SSSNIGMAGY | A-------- -- | 188 |
| SEQ_ID_NO_525 | FFPPTHKANR | SSSNIGMAGY | A-------- -- | 188 |
| SEQ_ID_NO_521 | TXPVXHKANR | VSSTVGMAGY | A-------- -- | 191 |
| SEQ_ID_NO_513 | TTMPAHKANR | TNSTVGMTGY | A-------- -- | 191 |
| SEQ_ID_NO_517 | ASKAAHKTNR | TSS-VGMTGN | P-------- -- | 166 |
| SEQ_ID_NO_511 | -RDKSFQAYG | GETGVGMGTY | K-------- -- | 185 |
| SEQ_ID_NO_523 | -RDAAGGAPY | GGSSIGMGPY | T-------- -- | 185 |

Figure 16

```
SEQ_ID_NO_546   ----MSSSLE RKKGKTVI-- ----------M LRSCSQCGSN GHN-------  28
SEQ_ID_NO_542   ---------- ---------- ----------M GRKCSHCGNI GHN-------  14
SEQ_ID_NO_547   ---------- ---------- ----------M TRRCSHCSTN GHN-------  14
SEQ_ID_NO_533   ----MESVVA T--------- ----------W SREEEKAFEN AIALHCV---  25
SEQ_ID_NO_539   ----MSSGGT I--------- ----------W SYDEEKAFEN AIAMHM---  25
SEQ_ID_NO_535   ----MAGSVS ---------- ----------W SREEEKAFEN AIAMHM---  24
SEQ_ID_NO_538   ----MASVGT ---------- ----------W TRDEEKTFEN AIAMHM---  24
SEQ_ID_NO_553   ----MTSQAA TTTTTAAAAA A--------W TREDDKAFEN ALAACAAPPP  38
SEQ_ID_NO_550   ----MAAEEA SSSGGGEEGS GAGAGG---W TREQEKAFEN ALATV-----  38
SEQ_ID_NO_552   ----MAVNEA SSSGGGEEGC GS-------W TREQEKAFEN AVATMGG---  36
SEQ_ID_NO_536   ----METLYP SSHLSSSAWF VLDNPS-TKW TKEENKMFES ALAIY-----  40
SEQ_ID_NO_543   MDRGEILSP ASYLQNSNWL FPETRA-TKW TPEENKFEN ALALY-----  44
SEQ_ID_NO_548   ----MEILAP SSYFSSSSWF LEESRSTTRW TAAENKAFEN ALAVF-----  41

SEQ_ID_NO_546   --SRTCGESS SAAGNGASDG EFMLFGVRVK VDPMRKSVSM NDLSD-YELP  75
SEQ_ID_NO_542   ---------- SR-TCNSLRG SGBFVGVRLF GVQLDLSSSC VSMKKSFSMD  53
SEQ_ID_NO_547   --SRTCPNRG VK-LFGVRLT -DGLRKSAS MGNLTHFASG SGGGS-TPLN  59
SEQ_ID_NO_533   -EEEITEDQW NK-MSSMVPS -KALEEVKKH YQLLEDVKA ENGQ-VPLP  71
SEQ_ID_NO_539   --EESSKEQW EK-IASAVPS -KSMEEVKQH YQVLVEDVSA EAGH-ISFP  70
SEQ_ID_NO_535   -DKEECEEQW EK-IASTVPI -KSLEELKLH YELLVEDVTA EAGH-VPLP  70
SEQ_ID_NO_538   --DEDSNEQW EK-IASMVPS -KSLEELKLH YKILVEDVCA EAGN-VPIP  69
SEQ_ID_NO_553   ADGGAPDDW FAALAASVPG ARSAEEVRRH YEALVEDVAA DAGR-VPLP  87
SEQ_ID_NO_550   -DEEEGEAMW DK-IADAVEG -KTPEEVRRH YELLVEDVDG EAGR-VPLL  84
SEQ_ID_NO_552   --EEDGDARW EK-LAEAVEG -KTPEEVRRH YELLVEDVDG ESGR-VPLP  81
SEQ_ID_NO_536   --DKETPDRW FK-VAAKIPG -KTVSDVIKQ YKELEEDVCE EAGR-FPVP  85
SEQ_ID_NO_543   --DKDEPDRW DK-VAAMIPG -KTVGDVIKQ YRELEEDVSD EAGL-IPIP  89
SEQ_ID_NO_548   --DENTPNRW ER-VAERVPG -KTVGDVMRQ YKELEDDVSS EAGF-VPVP  86
```

Figure 16 (continued)

| | | | | | | | |
|---|---|---|---|---|---|---|---|
| SEQ_ID_NO_546 | SNVN------ | QNGVDNSKNS | NDSDKVVADD | VVTAGAGYV- | ---------S | | 109 |
| SEQ_ID_NO_542 | SFPT------ | ---SSSSPTS | SFSSSRLTID | DRASIGYLSD | GL-------- | | 86 |
| SEQ_ID_NO_547 | GVVH------ | DSPGDTPDHP | A-VGGGSADG | YASEDFVAG- | ---------- | | 91 |
| SEQ_ID_NO_533 | RYHHRKGLIV | DEAAAAATSP | ANRDSHSSGS | SEKKPNPGTS | GIS------S | | 115 |
| SEQ_ID_NO_539 | NYAS------ | DETTSSNKD- | FHGSSKATSS | DKRSNCNYGS | GFSGLGLDST | | 113 |
| SEQ_ID_NO_535 | CYKG------ | EEPSSSAKDY | FHGPSMAPNS | DRRSNSGYGN | GFSGLTLDST | | 114 |
| SEQ_ID_NO_538 | NYEG------ | EEAASSTKD- | LHGLSGTMTT | VKKLNCGYGS | GFVGLGHESS | | 112 |
| SEQ_ID_NO_553 | RYAG------ | EESAAPPDGA | GAAAASKDG | GHRRDERKGG | G-------G | | 123 |
| SEQ_ID_NO_550 | VYAG------ | DGDEGGSGGG | AGGSGGGGGG | GGKKSGGGG | --------G | | 118 |
| SEQ_ID_NO_552 | AYAA------ | ---------- | -DGAAEEGGG | GGKKGSGGG | --------G | | 104 |
| SEQ_ID_NO_536 | GYDL------ | ----ASSFSF | EFVDDRNFDV | YRRKSSVG-- | ---------- | | 113 |
| SEQ_ID_NO_543 | GYSS------ | ---SDAFTLE | WFNNNQGYDG | FRHYYTPGG | ---------- | | 119 |
| SEQ_ID_NO_546 | GYST------ | ----SSPFTL | EWGSGHGFDG | FKQSYGTGG | ---------- | | 115 |

| | | | | | | | |
|---|---|---|---|---|---|---|---|
| SEQ_ID_NO_546 | ADDAVQHQ-- | STGGRERKRG | IPWTEEEHKL | FLLGLQKVGK | GDWRGI | SRNF | 157 |
| SEQ_ID_NO_542 | ---------- | IVRTQERKKG | VPWTEEEHRK | FLVGLEKLGK | GDWRGI | SRNY | 126 |
| SEQ_ID_NO_547 | ---------- | SSSSRERKKG | VPWTEEEHRM | FLLGLQKLGK | GDWRGI | ARNY | 131 |
| SEQ_ID_NO_533 | SNGGRSGG-- | SRAEQERRKG | IPWTEEEHRL | FLLGLDKFGK | GDWRSI | SRNF | 163 |
| SEQ_ID_NO_539 | THSSGKGGLS | RSSEQERRKG | IPWTEEEHRL | FLLGLDKFGK | GDWRSI | SRNF | 163 |
| SEQ_ID_NO_535 | GHGGKQS--- | SRSDQERRKG | IPWTEEEHRL | FLLGLDKFGK | GDWRSI | SRNF | 161 |
| SEQ_ID_NO_538 | GHGGKGA--- | SRSEQERRKG | IPWTEEEHRL | FLLGLDKFGK | GDWRSI | SRNF | 159 |
| SEQ_ID_NO_553 | GYDGGKSC-- | SKAEQERRKG | IPWTEEEHRL | FLLGLDKFGK | GDWRSI | SRNF | 171 |
| SEQ_ID_NO_550 | G-IGEKGSS- | KSAEQERRKG | AWTEDEHRL | FLLGLEKYGK | GDWRSI | SRNF | 166 |
| SEQ_ID_NO_552 | THGDKRSA-- | KSAEQERRKG | AWTEDEHRL | FLLGLEKYGK | GDWRSI | SRNF | 152 |
| SEQ_ID_NO_536 | ---------- | RGSEHERKKG | VPWTEEEHKQ | FLRGLLKYGK | GDWRNI | SRNF | 153 |
| SEQ_ID_NO_543 | ----KRTTAA | RSSEQERKKG | VPWTEEEHRQ | FLMGLQKYGK | GDWRNI | SRNF | 165 |
| SEQ_ID_NO_546 | ----RKSSSG | RPSEQERKKG | VPWTEEEHKL | FLMGLKKYGK | GDWRNI | SRNF | 161 |

Figure 16 (continued)

```
SEQ_ID_NO_546    VKTRTPTQVA SHAQKYYLRK NNLNRRRRRS SLFDITTDSV PGGLPMDDVK  207
SEQ_ID_NO_542    VTTRTPTQVA SHAQKYFIRL ATLNKKKRRS SLFDMVGSGK TN-KTVD---  172
SEQ_ID_NO_547    VISRTPTQVA SHAQKYFIRQ SNMSRRKRRS SLFDIVADES GDTPMVSR--  179
SEQ_ID_NO_533    VISRTPTQVA SHAQKYFIRL NSMNRDRRRS SIHDITTVNN QA--------  205
SEQ_ID_NO_539    VISRTPTQVA SHAQKYFIRL NSMNRDRRRS SIHDITSVNN GD--------  205
SEQ_ID_NO_535    VISRTPTQVA SHAQKYFIRL NSMNRDRRRS SIHDITSVNN GD--------  203
SEQ_ID_NO_538    VISRTPTQVA SHAQKYFIRL NSMNRDRRRS SIHDITSLNN GD--------  201
SEQ_ID_NO_553    VISRTPTQVA SHAQKYFIRL NSMNRDRRRS SIHDITSVTA GDQV------  215
SEQ_ID_NO_550    VISRTPTQVA SHAQKYFIRL NSMNRERRRS SIHDITSVNL GE--------  207
SEQ_ID_NO_552    VISRTPTQVA SHAQKYFIRL NSMNRERRRS SIHDITSVNN GD--------  194
SEQ_ID_NO_536    VNSKTPTQVA SHAQKYFMRQ LSGGKDKRRP SIHDITTVNL TE--------  195
SEQ_ID_NO_543    VTTRTPTQVA SHAQKYFIRQ STGGKDERRS SIHDITTVNL PDTKS-----  210
SEQ_ID_NO_548    VITRTPTQVA SHAQKYFIRQ LSGGKDKRRA SIHDITTVNL SDNQTPS---  208

SEQ_ID_NO_546    NHQDKSVPKV LQHSQVPHAE KPNMNGYTIA PFPLAVGPIL LPVQVHNPME  257
SEQ_ID_NO_542    ---------- ------PNNS SKSKSGDSVC RHDHEVEKDA TLSL---LIN  203
SEQ_ID_NO_547    ---------- ------DFLA DDPAQAEMQS ----NNLLPP TPAVDEECES  209
SEQ_ID_NO_533    ---------- ------PAVT GGGQQPQVVK ----HRPAQP QPQP---Q--  230
SEQ_ID_NO_539    ---------- ------VASS QAPITGLHSS ------TISSN TMGV------  228
SEQ_ID_NO_535    ---------- --------TSH QAPITGQQAN --------TN SPGA---AVM  225
SEQ_ID_NO_538    ---------- ------VSSH QAPITGQQAN ----TSPAGP APAM------  225
SEQ_ID_NO_553    ---------- ------AAQQ GAPITGHQAT ----GNPAAA ALGP---PGM  242
SEQ_ID_NO_550    ---------- ------ASAA QGPITG---- ----TNGQAA VPGK---S--  228
SEQ_ID_NO_552    ---------- ------PSTA QGPITGQ--- ----TNGQAA NPGK---P--  216
SEQ_ID_NO_536    ---------- ------PTAS ENEKLSSMDQ ---FSKLPSL QKSP---CYQ  223
SEQ_ID_NO_543    ---------- ------PSPD EKKSSPDHST TSLQSQPQQK MVGM---A--  239
SEQ_ID_NO_548    ---------- ------PDNK KPPSSPDHSM ----AQQQTS STSI---H--  233
```

Figure 16 (continued)

| | | | | | | |
|---|---|---|---|---|---|---|
| SEQ_ID_NO_546 | NKAFHWGDHQ | L-QNGPGMLL | RTVPFIPVAN | S--------- | -----SSAIR | 292 |
| SEQ_ID_NO_542 | SLQQQTKSDD | Y-DMQKIEDD | SEEAEHKDVP | D--------- | -----WLHPL | 238 |
| SEQ_ID_NO_547 | MGSAASANSI | DGEHALPIPE | SSQYQHPLVY | PAYVAPFYPM | PYPCWPGYTA | 259 |
| SEQ_ID_NO_533 | PQPQQHHPPT | --MAGLGMYG | GAPVGQPIIA | P--------- | -----PDHMG | 264 |
| SEQ_ID_NO_539 | GQSLKHRVQG | HIPPGLGMYG | TPVGHPVAA | P--------- | -----PGHMA | 263 |
| SEQ_ID_NO_535 | GQSVKHRAQP | H-LPGLGMYG | APVGRPIAA | A--------- | -----PGHIG | 259 |
| SEQ_ID_NO_538 | GPPVKHRTQA | H-MPGLAMYG | P-PLGHPVAP | P--------- | -----PGHMA | 259 |
| SEQ_ID_NO_553 | KHHHHHHPGG | A-PPPMPMYS | AAPMGHPVA- | ---------- | ------GHMV | 274 |
| SEQ_ID_NO_550 | PKQSPHQPGN | L-PPGVDAFG | T-TIGQPVGG | P--------- | -------LV- | 259 |
| SEQ_ID_NO_552 | SKQSP-QPAN | T-PPGVDAYG | T-TIGQPVGG | P--------- | -------LV- | 246 |
| SEQ_ID_NO_536 | KLLFDWNRSS | --NGGLLGLG | B-NYGDRLMS | F--------- | -----PSGIA | 256 |
| SEQ_ID_NO_543 | KGLIDWKPQN | EGGGAAGVFB | Q-ANGNLLMA | P--------- | -----LCGI- | 273 |
| SEQ_ID_NO_548 | KLPFQWDQTS | N-ETIMGFAS | SGHHGNMFQS | N--------- | -----PFGM- | 267 |

| | | | | | | |
|---|---|---|---|---|---|---|
| SEQ_ID_NO_546 | DLNLN-QRML | ----EGEPSS | P--------- | ---------LS | LKLSLSSSDN | 319 |
| SEQ_ID_NO_542 | TKSLN-MTLV | L-PNSSNVAP | P--------- | ---------DL | ELTLAGSKSN | 269 |
| SEQ_ID_NO_547 | EPAIAETHEM | LKPIAVHSKS | PINVDELVGM | SKLSLGESIG | DAAKPPSLSL | 309 |
| SEQ_ID_NO_533 | -SAVG-TPVM | LPPPMGTHHH | H--------- | ---------HH | HHLGVAPYAV | 295 |
| SEQ_ID_NO_539 | -SAVG-TPVM | LPPGPHPHPH | P--------- | ---------HH | HAHPHPPYVL | 294 |
| SEQ_ID_NO_535 | -SAVG-TPVM | L-PPAHHPHS | P--------- | ------------ | -----PPYIV | 282 |
| SEQ_ID_NO_538 | -SAVG-TPVM | LPPPGHHPH- | ---------- | ------------ | -----PPYVV | 281 |
| SEQ_ID_NO_553 | PAAVG-TPVV | F-PPGH---- | ---------- | ------------ | -----APYVV | 293 |
| SEQ_ID_NO_550 | -SAVG-TPVT | LLPVAAPPHM | G--------- | --------YA | MHAPVPGTVV | 289 |
| SEQ_ID_NO_552 | -SAVG-TPVT | LLPVSAPPHL | A--------- | --------YG | MRAPVPGAVV | 276 |
| SEQ_ID_NO_536 | ANGK-N--- | --EQDQELNS | A--------- | --------YY | GTYSKPHKSI | 283 |
| SEQ_ID_NO_543 | -SSYG-QRL | --QENLLRG | T--------- | --------LP | GYQFAPYNLI | 301 |
| SEQ_ID_NO_548 | -NSYG-FKM | --QGQQMQRG | G--------- | --------FC | DTYLGSQNMA | 295 |

Figure 16 (continued)

| | | | | |
|---|---|---|---|---|
| SEQ_ID_NO_546 | SQSSSTRHST | GFQAMAATSF | SKGGDSIISV A-- | 350 |
| SEQ_ID_NO_542 | NMEQDKTSSS | SFLIGFISVT | ........... ... | 289 |
| SEQ_ID_NO_547 | KLVEGSSRQS | AFHANPSSGS | SGMNSSHNPI HAV | 342 |
| SEQ_ID_NO_533 | PA-------- | -YPVPPLPQQ | HPAPSTMH-- --- | 314 |
| SEQ_ID_NO_539 | PLA------- | -YPMAPPTMH | Q--------- --- | 307 |
| SEQ_ID_NO_535 | PVA------- | -YPMAPPPMH | Q--------- --- | 295 |
| SEQ_ID_NO_538 | PVA------- | -YPTAPPKTA | ---------- --- | 293 |
| SEQ_ID_NO_553 | PVG------- | -YPAPPAKMH | Q--------- --- | 306 |
| SEQ_ID_NO_550 | PRAPM----- | -YPMPPPPSR | ---------- --- | 303 |
| SEQ_ID_NO_552 | PGAPVNIAPM | PYPMPPPPSH | G--------- --- | 297 |
| SEQ_ID_NO_536 | ---------- | -FQFEPSRYQ | IYG------- --- | 295 |
| SEQ_ID_NO_543 | ---------- | -FQMQPMQRQ | ---------- --- | 310 |
| SEQ_ID_NO_548 | ---------- | -FQMQSGLHF | PNA------- --- | 307 |

Figure 17

| | | | | | | |
|---|---|---|---|---|---|---|
| SEQ_ID_NO_559 | ------MENK | -------TPI | FFSLSIFLSL | LNCALGG--- | -------NDL | 27 |
| SEQ_ID_NO_586 | ------MQTA | ---------- | -LFFLVTICT | ITCTLGD--- | -------VNL | 23 |
| SEQ_ID_NO_591 | ---------- | ------MLG | ICILLVFLNN | FTCALID--- | -------DDL | 23 |
| SEQ_ID_NO_581 | ------MART | PRTTILHLVL | TLCCILWVQN | TPSLAST--- | ---ASAIDEF | 38 |
| SEQ_ID_NO_588 | ------MARA | PR--ILHLLL | ALCSLSSSSV | AVAVASA--- | ---SGAADAF | 36 |
| SEQ_ID_NO_589 | ------MTTT | SR-ALALVLL | SSCCLLVAVD | AAYAKKP--- | ---NLSKNDF | 37 |
| SEQ_ID_NO_590 | MARTSMTTTS | RA--LALVLL | SSCCLLVAVD | AAYAKKP--- | ---NLSKNDF | 42 |
| SEQ_ID_NO_584 | ------MANS | RA---FALVL | LFCALASSCQ | VAFSYFP--- | ---PPAAKEDF | 36 |
| SEQ_ID_NO_583 | ------MATS | RP---LALAL | LLCALSACSH | AAISYPPSAM | STAAPANNGF | 41 |
| SEQ_ID_NO_585 | ------MARS | RA--FAFAL | LICAVAASCH | VALSAPP--- | PYAKQVERDF | 38 |
| SEQ_ID_NO_560 | ------MNCS | A----FSFWF | VCKIIFFLS | FNIQISI--- | ---ANPQENF | 34 |
| SEQ_ID_NO_577 | ------MKTL | -----SCYYT | FATVIALLFS | FTPSSAD--- | ------THENF | 31 |
| SEQ_ID_NO_569 | ------MPNP | -----MRPYL | ILSVFFFNL | YHSMAVP--- | ---DPTHQAL | 33 |
| SEQ_ID_NO_575 | ------MEKS | -----NSLPF | LSVIVLLLHV | SNSLTTP--- | -TRESIHDTF | 35 |
| SEQ_ID_NO_576 | ------MDTM | GK---LFFLT | ATLTVLFNS | TTAATSP--- | ------IQHF | 32 |
| SEQ_ID_NO_578 | ------MAN | TSSFNMQTS | LTLLLLLST | QSSATSR--- | ----SITDRF | 37 |
| SEQ_ID_NO_579 | ------MAIT | YS-FNFKSY | FPLLVLLST | HSSATST--- | ----SIIDRF | 36 |
| SEQ_ID_NO_558 | ------MTS | -----LTTQT | LIITFLLT | PTSFASP--- | ---PSLEDVF | 32 |
| SEQ_ID_NO_571 | ------MKSP | -------FVF | FSVLLISVSL | PNSIALP--- | -------DNF | 27 |

| | | | | | | |
|---|---|---|---|---|---|---|
| SEQ_ID_NO_559 | LSCLTFNGVR | N------HT | VFSADSDSDF | NRFLHLSIQN | PLFQNSLISK | 70 |
| SEQ_ID_NO_586 | SSCLTSNGVS | N------FTA | LSTSSDS-DY | HRLLYVSMON | QIFTRPKYPR | 66 |
| SEQ_ID_NO_591 | PSCLTHGVH | N------YTT | HQSTSNSDAY | HRLLYVSMON | QIFTRSIFPD | 67 |
| SEQ_ID_NO_581 | LGCLSAD-IP | S------GL | QTPATPSSY | SALLLSTTRN | LRYVLPDTSK | 80 |
| SEQ_ID_NO_588 | VGCLTAAGVP | P------GL | QTPASP-SY | DALLRSSVRN | LRYVAPGTPW | 78 |
| SEQ_ID_NO_589 | LSCLAAG-IP | A------RQ | LYAKGSP-SY | GSVLTSTIRN | LRYLSSKTCN | 78 |
| SEQ_ID_NO_590 | LSCLAAG-IP | A------RQ | LYAKGSP-SY | GSVLTSTIRN | LRYLSSKTCN | 83 |
| SEQ_ID_NO_584 | LGCLVKE-IP | P------RL | LYAKSSP-AY | PSVLGQTIRN | SRWSSPDNVK | 77 |
| SEQ_ID_NO_583 | LSCLIKS-VP | P------RL | LHGKSSR-AY | GSIVESTVRN | VKFVSDKTVK | 82 |
| SEQ_ID_NO_585 | LTCLTKD-IP | P------RQ | LYAKSSP-AY | ASVWSSTVRN | IKFLSDKTVK | 79 |
| SEQ_ID_NO_560 | LKCFSEY-IP | NNPANP--KF | YTQHDQ-LY | MSVLNSTIQN | LRFTSDTTPK | 60 |
| SEQ_ID_NO_577 | LOCLYSYPHN | T---NSISSV | LYTQTNS-SY | FSVLDATMON | LRFI--SDSRK | 75 |
| SEQ_ID_NO_569 | LOCLTDS-IP | T---DTASSI | VSKSNP-SY | TSVLRAYLRN | ARFNTSSTPK | 78 |
| SEQ_ID_NO_575 | LHCLQSH-TT | NQPDH-VSNI | VYAQTNT-SY | TSVLRAFARN | ARFSAPSTCK | 82 |
| SEQ_ID_NO_576 | LNCLPHSLVS | E-------V | TYTPNNA-SF | STILNMKIQN | KRFKTATTPK | 73 |
| SEQ_ID_NO_578 | LQCLHDRADP | S---FPITGE | VYTPGNS-SF | PTVLQNYIRN | LRFNETTTPK | 83 |
| SEQ_ID_NO_579 | TQCLNNRADP | S---FPLSGQ | LYTPDNS-SF | PSVLQAYIRN | LRFNESTTPK | 82 |
| SEQ_ID_NO_558 | AQCVTDF-KP | SNPKSPIQNY | YTQRSP-NF | LTILNNYVRN | LRYFNNMTRK | 80 |
| SEQ_ID_NO_571 | LOCLTENSQP | T---NPISDA | IHTPDNP-SF | TTVLQSYARN | LRFLTLSTPK | 73 |

Figure 17 (continued)

| SEQ_ID | Sequence block 1 | Sequence block 2 | Sequence block 3 | Sequence block 4 | Sequence block 5 | Sequence block 6 | # |
|---|---|---|---|---|---|---|---|
| SEQ_ID_NO_559 | PSAILPGSK | EELSNTIRC | RKGSWTRLR | SGGHSYEGLS | YTS | ---DTP | 116 |
| SEQ_ID_NO_586 | PSMILPQSK | EELAASYVCS | NRGLWTRLR | SGGHSYEGLS | YVA | ---DTP | 112 |
| SEQ_ID_NO_591 | PRVILPESM | DQLANVISCC | TRGSWTRLR | SGGHSYEGLS | HIA | ---DNP | 113 |
| SEQ_ID_NO_581 | PLGIAATEH | AHAQTTVRCG | RRHGVRVRVR | SGGHDYEGLS | YASVHLHNRN | | 130 |
| SEQ_ID_NO_588 | PLAVAATEP | AHAQAAVRCG | RRHGVRVRTR | SGGHDYEGLS | YASL | ---DPR | 125 |
| SEQ_ID_NO_589 | PLYVTPTDV | KHIQVAVSCG | RRHNVRIRVR | SGGHDYEGLS | YRS | ---EIP | 124 |
| SEQ_ID_NO_590 | PLYVTPTDV | KHIQVAVSCG | RRHNVRIRVR | SGGHDYEGLS | YRS | ---EIP | 129 |
| SEQ_ID_NO_584 | PLYITPTNV | SHIQSAVVCG | RRHSVRIRVR | SGGHDYEGLS | YRS | ---LQP | 123 |
| SEQ_ID_NO_583 | PVYITPTEA | AHIQATVACG | RXHGLRVRVR | SGGHDYEGLS | YRS | ---AKP | 128 |
| SEQ_ID_NO_585 | PLYITPTNA | SHIQAAVVCG | RRHGMRIRVR | SGGHDYEGLS | YRS | ---EKP | 125 |
| SEQ_ID_NO_560 | PLVVTPSNV | SHIQASILCS | KKVGLQIRTR | SGGHDAEGLS | YIS | ---QVP | 126 |
| SEQ_ID_NO_577 | PLVVTPQVV | SHIQATIKCS | QRHGLQIRTR | SGGHDYEGLS | YVA | ---RVP | 121 |
| SEQ_ID_NO_569 | PLIITPLDE | SHVSAAVICS | QKLGFDLKIR | SGGHDYEGLS | YVE | ---DNP | 124 |
| SEQ_ID_NO_575 | PLLVTPLSE | NQVQATVVCA | KSIGLQLKIR | SGGHDFEGVS | YIS | ---QVP | 128 |
| SEQ_ID_NO_576 | PLAITAKDD | SHIQETIKCA | KSNNQIRLR | SGGHDYEGFS | YVS | ---DVP | 119 |
| SEQ_ID_NO_578 | PFLITAEHV | SHIQAAVVCG | KQNRLLKTR | SGGHDYEGLS | YLT | ---NTN | 129 |
| SEQ_ID_NO_579 | PILITALHP | SHIQAAVVCA | KTHRLLMKTR | SGGHDYEGLS | YVT | ---NSN | 128 |
| SEQ_ID_NO_558 | PVAVAAADV | THIQATITCA | KKLGLQLRIR | SGGHDYDGMS | YLS | ---TID | 126 |
| SEQ_ID_NO_571 | PLAIAAKHE | SHVQATIICS | KKLGLQIRIR | SGGHDYDGLS | YVS | ---DVA | 119 |

| SEQ_ID | Sequence block 1 | Sequence block 2 | Sequence block 3 | Sequence block 4 | Sequence block 5 | Sequence block 6 | # |
|---|---|---|---|---|---|---|---|
| SEQ_ID_NO_559 | --FLIDLMN | LNRVSIDLES | ETAWESGST | LGELYYATE | SSSKL | GFTA | 163 |
| SEQ_ID_NO_586 | --FVVIDLMN | LNRISIDLES | KTAWESGAT | LGEIYCASE | ASDTL | GFSG | 159 |
| SEQ_ID_NO_591 | --FVIIDLMN | LNGSIDLDT | QTAWESGAT | LGEIYHAGK | SSGTM | AFSA | 160 |
| SEQ_ID_NO_581 | EPFAVLDLAA | LRAIHVDAAR | AEAWESGAT | VGELYYAVGA | ASRSL | GFPA | 179 |
| SEQ_ID_NO_588 | ESFAVLDLAA | FREVRVDAAR | AEAWAGSGAT | LGEVYYAVGA | ASRAL | AFPA | 174 |
| SEQ_ID_NO_589 | EPFAIVDLVN | MRNVTVDGKA | RTAWWESGAQ | GELYYGSK | ASPTL | AFPA | 173 |
| SEQ_ID_NO_590 | EPFAIVDLVN | MRNVTVDGKA | RTAWWESGAQ | GELYYGSK | ASPTL | AFPA | 178 |
| SEQ_ID_NO_584 | ETFAVVDLNK | MRAVVVDGKA | RTAWWDSGAQ | LGELYYAYK | ASPTL | AFPA | 172 |
| SEQ_ID_NO_583 | ETFAVVDLSM | MRQVRIDGKA | ATAWWDSGAQ | LGELYYAVAK | MTPSL | GFPA | 177 |
| SEQ_ID_NO_585 | EPFAVVDMNK | MRAVSIDGKA | ATAWWDSGAQ | LGDLYYGAK | ASPKL | GFPA | 174 |
| SEQ_ID_NO_560 | --FAIVDLRN | MHTVKVDIHS | QTAWWEAGAT | LGEVYYMNE | MNENF- | SFPG | 173 |
| SEQ_ID_NO_577 | --FVILDLLN | FREIKVDVEN | RTAWWQVGAT | LGELYYTSQ | ASKTL | GFPA | 168 |
| SEQ_ID_NO_569 | --FFVLDMFN | LRSITVNMAD | ETAWGAGAT | LGELYYNVK | NSKVH- | GFPA | 171 |
| SEQ_ID_NO_575 | --FIILDMFN | FQDVTVDVQN | ELAVQAGAS | LGQVYYRWE | KSKVH- | GFPA | 175 |
| SEQ_ID_NO_576 | --FILDMFH | LNSVDINLQE | STAWWESGAT | LGKIYYNAN | KSNKL | AFPS | 166 |
| SEQ_ID_NO_578 | QPFFVDMFN | LRSINVDIEQ | ETAWQAGAT | LGEVYYRAE | KSNKH- | GFPA | 178 |
| SEQ_ID_NO_579 | QPFFVVDMFN | LRSINVSED | ETAWQAGAT | LGEVYYRAE | KSNGH- | AFPA | 177 |
| SEQ_ID_NO_558 | --FVYLDMFN | LRSINIDPKL | QTAWQSGAT | LGEIYYGVAN | KSNDLRGFPA | | 174 |
| SEQ_ID_NO_571 | --FILDMFN | LRSINIDIED | ESAWQAGAT | LGEVYYRAE | KSNVH- | GFPA | 166 |

Figure 17 (continued)

| SEQ_ID_NO_559 | GWCPTVGTGG | HISGGGFGMM | SRKYGLAADN | VVDAILIDAN | GALDRQAMG | 213 |
|---|---|---|---|---|---|---|
| SEQ_ID_NO_586 | GYCPTVGSGG | HISGGGFGMM | SRKYGLAADN | VIDALIVDAN | GAVLDRSSMG | 209 |
| SEQ_ID_NO_591 | GYCPTGSSGG | HIAPGGFGMM | SRKYGLAADN | VVDALLVDAN | GNVLDRESMG | 210 |
| SEQ_ID_NO_581 | GSCPTMGVGG | HLSGGGFGSL | ARKYGLSADN | VLDAVVVDAD | GRLVNRSTMG | 229 |
| SEQ_ID_NO_588 | GVCPTVGVGG | HLGGGGFGTL | MRRYGLAADN | VLDAVLVDAD | GRLLNRTTMG | 224 |
| SEQ_ID_NO_589 | GVCPTIGVGG | HFSGGGFGML | LRKFGLASDN | VLDVKVVDAN | GKVQDRKSMG | 223 |
| SEQ_ID_NO_590 | GVCPTIGVGG | HFSGGGFGML | LRKFGLASDN | VLDVKVVDAN | GKVQDRKSMG | 228 |
| SEQ_ID_NO_584 | GVCPTIGVGG | NFAGGGFGML | LRKYGIAAEN | VIDVKLVDAN | GKLHDKKSMG | 222 |
| SEQ_ID_NO_583 | GVCATIGVGG | HFSGGGFGML | LRKYGTAGDN | VIDAKVVDAN | GTLLDRKSMG | 227 |
| SEQ_ID_NO_585 | GVCITIGVGG | HFSGGGFGML | LRKYGTAADN | VIDAKVVDAQ | GRLLDRKAMG | 224 |
| SEQ_ID_NO_560 | GYCPTVGVGG | HFSGGGYGAL | MRNYGLAADN | IDAHLVNVD | GKVLDRKSMG | 223 |
| SEQ_ID_NO_577 | GVCYSVGAGG | HISGGGYGFL | MRKYGLAADN | VIDAHIDVN | GNLLDRKAMG | 218 |
| SEQ_ID_NO_569 | GVCPTVGVGG | HLSGAGYGTL | IRKYGLSVDH | VVDAKLVDVN | GKILDRKTMG | 221 |
| SEQ_ID_NO_575 | GACPTVGVGG | HLSGGGYGNM | IRKYGLSVDH | VVDAKIVDVK | GRILDKESMG | 225 |
| SEQ_ID_NO_576 | GVCFTLGAGG | HFSGGGYGNL | MRKFGLSVDN | IDAKMVDVK | GNLLDRKSMG | 216 |
| SEQ_ID_NO_578 | GVCPTVGVGG | HFSGGGYGNL | MRKYGLSVDN | VDAQIIDVN | GKLLDRKSMG | 228 |
| SEQ_ID_NO_579 | GVCPTVGVGG | HFSGGGYGNL | MGKYGLSVDN | VDAQLIDVN | GKLLNRKSMG | 227 |
| SEQ_ID_NO_558 | GICPGLGAGG | HFSGGGYGNM | MRKYGLSIDN | IDAKIVDAK | GKVLDRSSMG | 224 |
| SEQ_ID_NO_571 | GVCPTLGVGG | HFSGGGYGNM | MRKYGLSVDN | VDAQIIDVR | GRILDRKSMG | 216 |

| SEQ_ID_NO_559 | EDVFWAIRGG | GGGVMGAIYA | WKIKLLPVPE | KVTVFRVTKN | VAIDE--ATS | 261 |
|---|---|---|---|---|---|---|
| SEQ_ID_NO_586 | EDVFWAIRGG | GGGVMGAIYA | WKLQLLPVPK | QVTVFKLMKN | FDNIE-EASK | 258 |
| SEQ_ID_NO_591 | EDVFWAIRGG | GGGVMGAVYA | WKLQLVPVPK | NVTIFRLMKH | SEVED--ASK | 258 |
| SEQ_ID_NO_581 | EDHFWALCGG | GGESFGVVLS | AKVRLVPVPE | TVTVFSIVRS | RSDS---AVE | 276 |
| SEQ_ID_NO_588 | EDLFWAIRGG | GGESFGVVLS | AKLRLVPVPE | TVTVFTVRRS | RNQS---ASE | 271 |
| SEQ_ID_NO_589 | EDYLWAVRGG | GGSSFGIVVS | AKLRLLPVPA | TVTVLQMPKM | VNEG---AVD | 270 |
| SEQ_ID_NO_590 | EDYLWAVRGG | GGSSFGIVVS | AKLRLLPVPA | TVTVLQMPKM | VNEG---AVD | 275 |
| SEQ_ID_NO_584 | DDHFWAVRGG | GGESFGIVVA | WQVKLLPVPP | TVTIFKISKT | VSEG---AVD | 269 |
| SEQ_ID_NO_583 | EDYFWAIRGG | GGESFGIMVS | WQVQLVPVPP | KVTVFQIHRG | VKDG---AID | 274 |
| SEQ_ID_NO_585 | EDHFWAIRGG | GGESFGIVAS | WQVKLLPVPP | KVTVFQVHKG | IKES---AID | 271 |
| SEQ_ID_NO_560 | EDLFWAIRGG | GGENFGIIAA | WKIKLVVNPS | KAIIFSVKKN | MELHG--LVK | 271 |
| SEQ_ID_NO_577 | EDLFWAIRGG | GGASFGIVVS | AKIKLVPVPS | TVTVFNVERI | LEEN---ATE | 265 |
| SEQ_ID_NO_569 | EDLFWAIRGG | GAASFGVVLS | YKIKLVPVPE | TVTVFRIERL | LTEN---ATD | 268 |
| SEQ_ID_NO_575 | EDLFWAIRGG | GGASFGVILS | YITVKLVPVPE | NVTVFQIDKT | LEEN---ATD | 272 |
| SEQ_ID_NO_576 | EDLFWAIRGG | GGASFGVILS | AKLQLVPVTP | QVVFDVKRN | VSEG---ATD | 263 |
| SEQ_ID_NO_578 | EDLFWAITGG | GGVSFGVVLA | YKIKLVRVPE | VVTVFTIERR | EEQN---LST | 275 |
| SEQ_ID_NO_579 | EDLFWAITGG | GGVSFGVVVA | YKIKLVRVPT | TVTVFNVQRT | SEQN---LST | 274 |
| SEQ_ID_NO_558 | EDLFWALRGG | GAASFCVVLA | AKIKLVPVPA | KVTVFNIETF | GNTGSVNTTE | 274 |
| SEQ_ID_NO_571 | EDLFWAIRGG | GAASFGVILS | AKIKLVPVPE | IVTVFSVDRT | LEEG---VSD | 263 |

Figure 17 (continued)

| | | | | | | |
|---|---|---|---|---|---|---|
| SEQ_ID_NO_559 | LLHKWQFV-A | EELEEDFTLG | VLGGADEK-- | -------QVW | LTMLGFHFGL | 301 |
| SEQ_ID_NO_586 | MLHKWQVV-A | PALEDDFTLS | VLAGADTN-- | -------G W | FSFLGLYLGP | 298 |
| SEQ_ID_NO_591 | LLHKWQLV-A | PKLEDDFSLA | VLAGTNKDS- | -------SIW | LTFLGLYLGP | 299 |
| SEQ_ID_NO_581 | LITKWQEM-A | PASPQELYLR | VLVL------ | -------NDQ | ANFQALFLGR | 312 |
| SEQ_ID_NO_588 | LITKWQEI-A | PALPRDLLR  | VVVQ------ | -------GRH | AQFEALFLGR | 307 |
| SEQ_ID_NO_589 | LLTKWQSL-A | PTFPEDLM R | VMAQ------ | -------AQK | ANFEGLYLGT | 306 |
| SEQ_ID_NO_590 | LLTKWQSL-A | PTFPEDLM R | VMAQ------ | -------AQK | ANFEGLYLGT | 311 |
| SEQ_ID_NO_584 | INKWQVV-A  | PQLPADLM R | IAQ------- | -------GPK | ATFEAMYLGT | 305 |
| SEQ_ID_NO_583 | LINKWQQV-A | PSLPDDLM R | MAM------- | -------EQD | AMFEALYLGT | 310 |
| SEQ_ID_NO_585 | LVTKWQTV-A | PALPDDLM R | MAM------- | -------GQG | AMFEALYLGT | 307 |
| SEQ_ID_NO_560 | LFNKWQN--A | YKYDKDLMLT | THFRTRNITD | NHGKNKTTVH | GYFSSIFLGG | 320 |
| SEQ_ID_NO_577 | IEKWQLV-A  | NKLDERFLR  | MDLARANSS- | QHGKL--ALQ | ANFVAMFQGG | 311 |
| SEQ_ID_NO_569 | TFKWQT--A  | PTTDENLFMR | MLLQPVTRN- | --KKK--TAR | ISVIALYLGD | 312 |
| SEQ_ID_NO_575 | LVVQWQKV-A | PHTDDRLYLR | LVLQPVSSNF | VKGKK--TIR | ASVEALFLGE | 319 |
| SEQ_ID_NO_576 | VVKWQL--A  | PKLHKDLFIR | AQPNVVQIG- | QEGKK--VVQ | ISFIGQFLGK | 309 |
| SEQ_ID_NO_578 | AERWVQV-A  | DKLDRDLFLR | MTFSVINDT- | NGG-K--TVR | AFPTLYLGN  | 320 |
| SEQ_ID_NO_579 | AHRWIQV-A  | DKLDNDLFLR | MTFNVINNT- | NGE-K--TIR | GLFPTLYLGN | 319 |
| SEQ_ID_NO_558 | LVAKWQE--A | DKIDNDLFIR | LTLGSSNK-- | -------TVK | ASFMGMYLGN | 314 |
| SEQ_ID_NO_571 | LAWKWQQIAA | DKLDNDLFIR | LMLQPVNGT- | QEGKK--TIQ | ASFVAMFLGR | 310 |

| | | | | | | |
|---|---|---|---|---|---|---|
| SEQ_ID_NO_559 | KTYAKSTFDL | LFPELGLVEE | DYLEMSWGES | FAYLAGLE-- | -----TVSQL | 344 |
| SEQ_ID_NO_586 | KELAISSVDQ | NFPELNLVME | DCKEMSWVES | FAHLAGLN-- | -----SVEEM | 341 |
| SEQ_ID_NO_591 | KELASSSMHK | KFPELNLLLE | DCMEMSWVEA | TAELAGLK-- | -----SVSEL | 342 |
| SEQ_ID_NO_581 | CGGLHRLMQD | RFPELGMTEQ | DCEEVSWVQS | TAFFGFSTTS | V----PPEQL | 358 |
| SEQ_ID_NO_588 | CSRVLEHMRA | HFPELGVARA | DCEEISWIQS | TVYFAFYSSS | K----PPELL | 353 |
| SEQ_ID_NO_589 | CDALLPLVTS | RFPELGVNRS | HCNEMSWVQS | IAFIHLGKNA | T----VKDI  | 351 |
| SEQ_ID_NO_590 | CDALLPLVTS | RFPELGVNRS | HCNEMSWVQS | IAFIHLGKNA | T----VKDI  | 356 |
| SEQ_ID_NO_584 | CKTLTPLMSG | KFPELGMNPD | HCNEMSWIQS | IPFVHLGHRD | A----LEDDL | 351 |
| SEQ_ID_NO_583 | CKDLLPLMAS | RFPELGVKQE | DCNEMPWIQS | VAFIPMGKSA | T----VMDL  | 355 |
| SEQ_ID_NO_585 | CKDLVLLMTA | RFPELGMNAT | HCKEMTWIES | VPYLPMGPKG | T----VRDL  | 352 |
| SEQ_ID_NO_560 | VDSLVDLMNK | SFPELGIKKT | DCKELSWIDT | TIFYSGVVNY | NTANFKKEL  | 370 |
| SEQ_ID_NO_577 | VEELIPLMQK | NFPELGLKRK | DCTETSWIGS | AVFTNGALIG | SSGHEAPEVL | 361 |
| SEQ_ID_NO_569 | SDSLVSLLQK | DFPELSIGKS | NCNETTWIDS | VLWWANFNLG | T----PPTAL | 358 |
| SEQ_ID_NO_575 | ADELVKLLGQ | EFPLIGLKKE | LCHEMRWIDS | VVWWANYNDG | S----SVNAL | 365 |
| SEQ_ID_NO_576 | IERLLTLMNK | EFPELGLNKS | DCFSMPWINS | TLFWYGEPIG | T----PLEVL | 355 |
| SEQ_ID_NO_578 | SRNLVTLLNK | DFPELGLQES | DCTEMSWVES | VLYYTGFPSG | T----PTTAL | 366 |
| SEQ_ID_NO_579 | STALVALLNK | DFPELGVEIS | DCIEMSWIES | VLFYTNFPIG | T----PTTAL | 365 |
| SEQ_ID_NO_558 | SSNLLEIMNA | KFPELGLIKR | ECIEMKWIES | VLFWLGIPPG | TA---PTTSM | 361 |
| SEQ_ID_NO_571 | AERLLSVMNE | SFPELGLQAK | DCAEMRWIES | VLSAVGMPKG | T----PLEVL | 356 |

Figure 17 (continued)

| | | |
|---|---|---|
| SEQ_ID_NO_559 | NNRFLKFDER AFKTKVDLTK EPLPSKAFYG LL-ERLSK-- EPNGFIALNG | 391 |
| SEQ_ID_NO_586 | NNRFLKYDDR AFKTKVDFVK EPIPLEGIKG AL-TMLTK-- ELRGFMAFNG | 388 |
| SEQ_ID_NO_591 | KDRFLRYDDR AFKTKVDFPK FAIPLEGIQG AL-EILKK-- EQRGFMVMNG | 389 |
| SEQ_ID_NO_581 | LNRISSNPSY YLKAKSDHVQ EPIPRDVMES WTTWLEK-- PEAALLMLDP | 405 |
| SEQ_ID_NO_588 | LDRIIGETGR YVKAKSDYVQ EPIPRHAMES TMSWLEK-- PEAGLLILDP | 399 |
| SEQ_ID_NO_589 | LNRITSSIRA FGKYKSDYVT DPLSKATMDT YKDWFSK-- PGSGIMIMDP | 398 |
| SEQ_ID_NO_590 | LNRITSSIRA FGKYKSDYVT DPLSKATMDT YKDWFSK-- PGSGIMIMDP | 403 |
| SEQ_ID_NO_584 | LNRINNSFKP FAEYKSDYVY DPFPKTVMEQ LNTWLVK-- PGAGIMIFDP | 398 |
| SEQ_ID_NO_583 | LNRITSNIKA FGKYKSDYVK DPIPRDVMEK YITWLAK-- PGAGVMIMDP | 401 |
| SEQ_ID_NO_585 | LNRITSNIKA FGKYKSDYVL EPIPKSDMEK FITWLVK-- PGAGVMIMDP | 398 |
| SEQ_ID_NO_560 | LDRISAGKKT AFSIKLDYVK KLIPETAMVK L-EKLYEEE VGVSMYVLYP | 418 |
| SEQ_ID_NO_577 | LNRITQIRSG KYKGKSDYVR KPIPVDGLRG LW-RWLNDDK VQYSQLQFAP | 409 |
| SEQ_ID_NO_569 | LDRIDLNDAG FLKRKSDYVQ TPIPKSGLES LW-QKMIE-- LGKVGMVFNA | 404 |
| SEQ_ID_NO_575 | LDRINHYSVH SNKRKSDYYQ TPISKDGFTW W-KKMIE-- LGKYSIVFNP | 411 |
| SEQ_ID_NO_576 | LDEPKDPQPL YQKNKSDYVK KPIPREALES W-KLMIE-- GENFLMQANP | 402 |
| SEQ_ID_NO_578 | LSRITPQRLN PFKIKSDYVQ NPISKRQFEF FI-ERMKE-- LENQMLAFNP | 412 |
| SEQ_ID_NO_579 | LSRITPQRLN PFKIKSDYVK NTISKQGFES FI-ERMKE-- LENQMLAFNP | 411 |
| SEQ_ID_NO_558 | RNRIIPQKQI YLKRKSDYVQ KPISRTGLES FI-KIMTE-- NENVTMAFNP | 407 |
| SEQ_ID_NO_571 | LDRIIPKGVS YLKRKSDYVK EPISKEGLES W-KVMTE-- VGEYAMLWNP | 402 |

| | | |
|---|---|---|
| SEQ_ID_NO_559 | FGGQMSKISS DFTPFPHRSG TRLMVEYIVA ANDSEQKKKT EFLDWLEKVY | 441 |
| SEQ_ID_NO_586 | QGGLMSRISS DSTPFPHRKG TLMMMEYIVA ADRDEDAKSY EFIGMLHGFY | 438 |
| SEQ_ID_NO_591 | QGGMMDRIST DASPFPHRSG TLSMVEYIVA ADKHEDLHSN EFIHWLHQLF | 439 |
| SEQ_ID_NO_581 | YGGVMSSIPP SETPFPHRCG NLYQLQYYSF WYENGTAAAE KRMSWVRGLY | 455 |
| SEQ_ID_NO_588 | YGGRMASISP SATPFPHRKC NLYNLQYYSF WFENGTAAME KRMNWVRGLY | 449 |
| SEQ_ID_NO_589 | YGATISKPGE ADTPFPHRKC MLYNIQYITF WFGEGAPAEA -PIKMRDFY | 447 |
| SEQ_ID_NO_590 | YGATISKPGE ADTPFPHRKC MLYNIQYITF WFGEGAPAEA -PIKMRDFY | 452 |
| SEQ_ID_NO_584 | YGATISATPE SATPFPHRKC VLFNIQYVNY WFAPGAAAAL -PLSWSKDIY | 446 |
| SEQ_ID_NO_583 | YGARISSIPQ DATPFPHRQC VLFNIQYVBY WFGEGDGAAL -PTQMSRDMY | 449 |
| SEQ_ID_NO_585 | YGGIASVPE SATPFPRRSG VLFNIQYVVY WFGEGAAAL- -PTQNTRDIY | 446 |
| SEQ_ID_NO_560 | YGGLMDEISE SAIPFPHRAG IMYELMYTAT WEKQEDNEK- -HINWVRSVY | 466 |
| SEQ_ID_NO_577 | YGGKMDNISE SEIPFAHRSG YIFHIHYVVY WQEEGDEATQ RHVNMRRLY | 459 |
| SEQ_ID_NO_569 | YGGRMQQIKP DEIPFPHRAG NLYKIQYSVN WDQPGSEADK NFITQAKLLH | 454 |
| SEQ_ID_NO_575 | YGGKMNEVPS DATPFPHRAG NLYKIQYTVS WQEPGAAVEK SFLSDIRVLH | 461 |
| SEQ_ID_NO_576 | YGGRMEEILP SEIPFSHRAG NLFLIQYLNI WSNESSEVSE RHVNFSRSFF | 452 |
| SEQ_ID_NO_578 | YGGRMSEISE FAKPFPHRSG NIAKIQYEVN WEDLSDEAEN RYLNFITRLMY | 462 |
| SEQ_ID_NO_579 | YGGRMSEISE FAKPFPHRSG NIAKIQYEVN WDELGVEAAN RYLNFITRVMY | 461 |
| SEQ_ID_NO_558 | YGGRMSEIPS TETAFPHRAG NMFKIQYAAN WFVPGEAVAK DCLSQTERLF | 457 |
| SEQ_ID_NO_571 | YGGKMSEISE TETAFPHRAG NIFKIQYSVN WKQEGIDTTN HYVNLTRTLF | 452 |

Figure 17 (continued)

| | | | | | | | |
|---|---|---|---|---|---|---|---|
| SEQ_ID_NO_559 | EFMKPFVSKN | PRLGYVNHID | LDLGGIDW-- | -GNKTVVNN- | AIEISRS- | WG | 486 |
| SEQ_ID_NO_586 | NYMGQFLPSD | PRIAYVNHVD | LDLGRLDW-- | -TNSTIASN- | AIEIART- | WG | 483 |
| SEQ_ID_NO_591 | DYMGKFVSNN | PRVGYVNHVD | LDLGRIDW-- | -VNKTISSGR | AIELART- | WG | 485 |
| SEQ_ID_NO_581 | KEMEPYVSKN | PRAVYVNYRD | LDLGTNELD- | -GDVT----- | SYEKARVS | WG | 498 |
| SEQ_ID_NO_588 | REMEPYVSKN | PRTGYVNYRD | LDLGTNELE- | -GNVT----- | SYAKARI- | WG | 491 |
| SEQ_ID_NO_589 | AFMEPYVTKN | PRQAYVNYRD | LDLGVNAVEA | GANVS----- | CYQVGKV- | WG | 491 |
| SEQ_ID_NO_590 | AFMEPYVTKN | PRQAYVNYRD | LDLGVNAVEA | GANVS----- | CYQVGKV- | WG | 496 |
| SEQ_ID_NO_584 | NYMEPYVSKN | PRQAYANYRD | IDLGRNEVV- | -NDVS----- | TYASGKV- | WG | 488 |
| SEQ_ID_NO_583 | AFMEPYVSKN | PRQAYANYRD | LDLGVNEVV- | -GDVS----- | TYDSGRV- | WG | 491 |
| SEQ_ID_NO_585 | DFMTPYVSKN | PRQAYVNYRD | LDLGVNQVV- | -GNVS----- | TYASGKV- | WG | 488 |
| SEQ_ID_NO_580 | NFTTPYVSQN | PRLAYLNYRD | LDLGKTNP-- | -ESPN----- | NYTQARI- | WG | 507 |
| SEQ_ID_NO_577 | KYMEPYVSNS | PRAAYVNYRD | LDIGVNN--- | -NGYT----- | SYHQAS- | WG | 499 |
| SEQ_ID_NO_569 | DFMTPFVSKN | PRSAYFNYRD | DVG--S--- | -TKKW----- | SYEEGKV- | YG | 492 |
| SEQ_ID_NO_575 | NYMTPFVSKN | PRSAYFNYRD | LDIGINS--- | -HGKD----- | NFEDGKV- | YG | 501 |
| SEQ_ID_NO_576 | EFMTPYVSTS | PREAFLNYRD | ADIGANHP-- | -SNVT----- | RFDIAKT- | YG | 493 |
| SEQ_ID_NO_578 | DYMTPFVSKN | PREAFLNYRD | LDIGINS--- | -HGRN----- | AYTEGMV- | YG | 502 |
| SEQ_ID_NO_579 | DYMTPFVSKN | PREAFLNYRD | LDIGVNS--- | -HGKN----- | AYGEGMV- | YG | 501 |
| SEQ_ID_NO_558 | EAMSPYVSKN | PREAFLNYRD | VDIGK----- | -SLNS----- | TYEEGKV- | YG | 495 |
| SEQ_ID_NO_571 | EAMTPYVSKN | PREAFLNYRD | DIGSIGS-- | -HGNG----- | TFQEASV- | YG | 493 |

| | | | | | | |
|---|---|---|---|---|---|---|
| SEQ_ID_NO_559 | ESYFLS-NYE | RLIRAKTLID | PNNVFNHPDS | PPMANFDYL | EKTLGSDGGE | 535 |
| SEQ_ID_NO_586 | EKYFLS-NYE | RLVRAKTLID | PKNVFHHPDS | PPMPQDDLR | PNGIWRTEEM | 532 |
| SEQ_ID_NO_591 | EKYFMS-NYD | RLVRAKTMID | PKNVFNHPDS | PPLLEIMLD | NVKENDVIYK | 534 |
| SEQ_ID_NO_581 | DKYFKG-NFK | RLAAVKTMVD | PHDFFRNEQS | PPLPTAKMM | IDSI------ | 541 |
| SEQ_ID_NO_588 | EKYFRG-NFE | RLAAVKAMVD | PDDFFRNEQS | PPLPAAKGW | SSI------- | 533 |
| SEQ_ID_NO_589 | EKYFKG-NFE | RLARTKAKVD | PTDFFRNEQS | PPLLA---- | ---------- | 526 |
| SEQ_ID_NO_590 | EKYFKG-NFE | RLARTKAKVD | PTDFFRNEQS | PPLLA---- | ---------- | 531 |
| SEQ_ID_NO_584 | QKYFKG-NFE | RLAITKGKVD | PTDYFRNEQS | PPLIKKY-- | ---------- | 525 |
| SEQ_ID_NO_583 | EKYYNG-NFE | RLARTKAKVD | PCDYFRNEQS | PPLLK---- | ---------- | 526 |
| SEQ_ID_NO_585 | EKYFKG-NFE | RLARTKGKID | PEDYFRNEQS | PPLL----- | ---------- | 522 |
| SEQ_ID_NO_580 | EKYFGK-NFN | RLVKVKTKAD | PNNFFRNEQS | PPLPPHHH- | ---------- | 545 |
| SEQ_ID_NO_577 | LKYFSN-NFK | RLATVKTKVD | PHNFFRNEQS | PTLSKE--- | ---------- | 535 |
| SEQ_ID_NO_569 | ESYFNG-NYE | RLVDVKTAVD | ANNFFRNEQS | PPRSSKI-- | ---------- | 529 |
| SEQ_ID_NO_575 | IKYFNK-NFE | RLVKVKSAID | PENFFMNEQS | PTYPRSNA- | ---------- | 539 |
| SEQ_ID_NO_576 | SKFFKG-NFE | RLVSVKTKVD | PQNFFRYEQS | PTRSL---- | ---------- | 528 |
| SEQ_ID_NO_578 | HKYFKETNYK | RLVSVKTKVD | PDNFFRNEQS | PTLSS---- | ---------- | 538 |
| SEQ_ID_NO_579 | HKYFKETNYK | RLTMVKTRVD | PSNFFRNEQS | PTLSSWK-- | ---------- | 540 |
| SEQ_ID_NO_558 | FKYFKD-NFE | KLVKIKSRVD | PDNFFRYEQS | PVLSSH--- | ---------- | 531 |
| SEQ_ID_NO_571 | HKYFKD-NFD | RLVQIKTRVD | PDNFFGYEQS | PTQSSSYRP | DLCAWQQPRK | 542 |

Figure 17 (continued)

| | | |
|---|---|---|
| SEQ_ID_NO_559 | VVI- - - - - - - ........... ........... ........... ........... | 538 |
| SEQ_ID_NO_586 | FFLE- - - - - ........... ........... ........... ........... | 536 |
| SEQ_ID_NO_591 | L- - - - - - - - - ........... ........... ........... ........... | 535 |
| SEQ_ID_NO_581 | ........... ........... ........... ........... ........... | 541 |
| SEQ_ID_NO_588 | ........... ........... ........... ........... ........... | 533 |
| SEQ_ID_NO_589 | ........... ........... ........... ........... ........... | 526 |
| SEQ_ID_NO_590 | ........... ........... ........... ........... ........... | 531 |
| SEQ_ID_NO_584 | ........... ........... ........... ........... ........... | 525 |
| SEQ_ID_NO_583 | ........... ........... ........... ........... ........... | 526 |
| SEQ_ID_NO_585 | ........... ........... ........... ........... ........... | 522 |
| SEQ_ID_NO_560 | ........... ........... ........... ........... ........... | 545 |
| SEQ_ID_NO_577 | ........... ........... ........... ........... ........... | 535 |
| SEQ_ID_NO_569 | ........... ........... ........... ........... ........... | 529 |
| SEQ_ID_NO_575 | ........... ........... ........... ........... ........... | 539 |
| SEQ_ID_NO_576 | ........... ........... ........... ........... ........... | 528 |
| SEQ_ID_NO_578 | ........... ........... ........... ........... ........... | 538 |
| SEQ_ID_NO_579 | ........... ........... ........... ........... ........... | 540 |
| SEQ_ID_NO_558 | ........... ........... ........... ........... ........... | 531 |
| SEQ_ID_NO_571 | RTLGARTSER AWQQHQAADT WRRAVMPYGL GKLARLAKHP KRRFTGPPAW | 592 |

| | | |
|---|---|---|
| SEQ_ID_NO_559 | ........... ........... ........... ........... ........... | 538 |
| SEQ_ID_NO_586 | ........... ........... ........... ........... ........... | 536 |
| SEQ_ID_NO_591 | ........... ........... ........... ........... ........... | 535 |
| SEQ_ID_NO_581 | ........... ........... ........... ........... ........... | 541 |
| SEQ_ID_NO_588 | ........... ........... ........... ........... ........... | 533 |
| SEQ_ID_NO_589 | ........... ........... ........... ........... ........... | 526 |
| SEQ_ID_NO_590 | ........... ........... ........... ........... ........... | 531 |
| SEQ_ID_NO_584 | ........... ........... ........... ........... ........... | 525 |
| SEQ_ID_NO_583 | ........... ........... ........... ........... ........... | 526 |
| SEQ_ID_NO_585 | ........... ........... ........... ........... ........... | 522 |
| SEQ_ID_NO_560 | ........... ........... ........... ........... ........... | 545 |
| SEQ_ID_NO_577 | ........... ........... ........... ........... ........... | 535 |
| SEQ_ID_NO_569 | ........... ........... ........... ........... ........... | 529 |
| SEQ_ID_NO_575 | ........... ........... ........... ........... ........... | 539 |
| SEQ_ID_NO_576 | ........... ........... ........... ........... ........... | 528 |
| SEQ_ID_NO_578 | ........... ........... ........... ........... ........... | 538 |
| SEQ_ID_NO_579 | ........... ........... ........... ........... ........... | 540 |
| SEQ_ID_NO_558 | ........... ........... ........... ........... ........... | 531 |
| SEQ_ID_NO_571 | VCRHVLWQT PTSGSAATRA WGMCPALLTL QTWALGADSH ARVNCDPHLS | 642 |

Figure 17 (continued)

| | | |
|---|---|---|
| SEQ_ID_NO_559 | ........... ........... ........... ........... ........... | 538 |
| SEQ_ID_NO_586 | ........... ........... ........... ........... ........... | 536 |
| SEQ_ID_NO_591 | ........... ........... ........... ........... ........... | 535 |
| SEQ_ID_NO_581 | ........... ........... ........... ........... ........... | 541 |
| SEQ_ID_NO_588 | ........... ........... ........... ........... ........... | 533 |
| SEQ_ID_NO_589 | ........... ........... ........... ........... ........... | 526 |
| SEQ_ID_NO_590 | ........... ........... ........... ........... ........... | 531 |
| SEQ_ID_NO_584 | ........... ........... ........... ........... ........... | 525 |
| SEQ_ID_NO_583 | ........... ........... ........... ........... ........... | 526 |
| SEQ_ID_NO_585 | ........... ........... ........... ........... ........... | 522 |
| SEQ_ID_NO_560 | ........... ........... ........... ........... ........... | 545 |
| SEQ_ID_NO_577 | ........... ........... ........... ........... ........... | 535 |
| SEQ_ID_NO_569 | ........... ........... ........... ........... ........... | 529 |
| SEQ_ID_NO_575 | ........... ........... ........... ........... ........... | 539 |
| SEQ_ID_NO_576 | ........... ........... ........... ........... ........... | 528 |
| SEQ_ID_NO_578 | ........... ........... ........... ........... ........... | 538 |
| SEQ_ID_NO_579 | ........... ........... ........... ........... ........... | 540 |
| SEQ_ID_NO_558 | ........... ........... ........... ........... ........... | 531 |
| SEQ_ID_NO_571 | RTQEEYI KLG PAQQDPFKLG SALEGPKI AR LDPLALALVA LMGPVLSKTH | 692 |

| | | |
|---|---|---|
| SEQ_ID_NO_559 | ........... | 538 |
| SEQ_ID_NO_586 | ........... | 536 |
| SEQ_ID_NO_591 | ........... | 535 |
| SEQ_ID_NO_581 | ........... | 541 |
| SEQ_ID_NO_588 | ........... | 533 |
| SEQ_ID_NO_589 | ........... | 526 |
| SEQ_ID_NO_590 | ........... | 531 |
| SEQ_ID_NO_584 | ........... | 525 |
| SEQ_ID_NO_583 | ........... | 526 |
| SEQ_ID_NO_585 | ........... | 522 |
| SEQ_ID_NO_560 | ........... | 545 |
| SEQ_ID_NO_577 | ........... | 535 |
| SEQ_ID_NO_569 | ........... | 529 |
| SEQ_ID_NO_575 | ........... | 539 |
| SEQ_ID_NO_576 | ........... | 528 |
| SEQ_ID_NO_578 | ........... | 538 |
| SEQ_ID_NO_579 | ........... | 540 |
| SEQ_ID_NO_558 | ........... | 531 |
| SEQ_ID_NO_571 | QRSLKKKI SL M | 703 |

Figure 18

| | | |
|---|---|---|
| SEQ_ID_NO_603 | MAAAT--SSS AMAVSTPQGV AERRGIPAAS FVEDVETYLR QAGLEVNSAL | 48 |
| SEQ_ID_NO_605 | MAAAA------SASTPQGV AERRGIPAAA FVEDVENYLR QAGLDVNSAL | 43 |
| SEQ_ID_NO_610 | MAAAAASSSS SSAAATPQGV TERRGIPAAS FVEDVETYLR QAGLDVNSGL | 50 |
| SEQ_ID_NO_593 | MSSSS------PSGSGSDL TERRGIPAAK FIQDVETYLS QSGLDPNSAL | 43 |
| SEQ_ID_NO_595 | MASSS----S TAVATATETT TERRGIPGAQ FVEDVETYLN QSGLDVNSAL | 46 |
| SEQ_ID_NO_599 | MASSS----------SESAM SERRGIPGAQ FVEDVQTYLT QSGLDVSSAL | 40 |

| | | |
|---|---|---|
| SEQ_ID_NO_603 | AFLQERLQQY KMVEMKLLAQ QRELQAKIPD EKCLDIVAT LKAKKALGEA | 98 |
| SEQ_ID_NO_605 | AFLQERLQQY KIVEMKLLAQ QRDLQAKIPD EKCLDIVST LQAKKDLGEA | 93 |
| SEQ_ID_NO_610 | AFLQERLQQY KIVEMKLLAQ QRDLQAKIPD EKCLDIVAT LQAKKALGEA | 100 |
| SEQ_ID_NO_593 | AFHQERLQQY KVVEMKLLAQ QRDLQAKIPD EKCLEVVAT LEAKKGTGEA | 93 |
| SEQ_ID_NO_595 | SFLQERLQQY KLVEMKLLAQ QRDLQAKIPD EKCLDVVAT LQAKKGTGEP | 96 |
| SEQ_ID_NO_599 | AFLQERLQQY KVVEMKLLAQ QRDLQAKIPD EKCLDVVAT LKAKKGTGEE | 90 |

| | | |
|---|---|---|
| SEQ_ID_NO_603 | LIADFELSEG IYSRAKIEDS DSVCLWLGAN VMLEYSCDEA NELLKSNLEN | 148 |
| SEQ_ID_NO_605 | LIADFELSEG IYSQAKIEDT DSVCLWLGAN VMLEYSCDEA NALLKKNLEN | 143 |
| SEQ_ID_NO_610 | LTADFELSEG IYSRAKIEDT DSVCLWLGAN VMLEYSCDEA NALLKKNLEN | 150 |
| SEQ_ID_NO_593 | LLADFEVSEG IYSRACIEDT DSVCLWLGAN VMLEYSCEEA SALLKNNLEN | 143 |
| SEQ_ID_NO_595 | LIADFEVSEG IYSQARIEDA ESVCLWLGAN VMLEYSCEEA NDLLQKNLDN | 146 |
| SEQ_ID_NO_599 | LIADFEVSEG IYSRARIEET NSVCLWLGAN VMLEYSLEEA TGLLQKNLDN | 140 |

| | | |
|---|---|---|
| SEQ_ID_NO_603 | ARASLEVLVG DLHFLRDQQT TQVTIARIF NWDVHQ-RRS KQ----SVM | 192 |
| SEQ_ID_NO_605 | AKASLEVLVA DLQFLRDQQT TQVTIARVF NWDVHH-RRS KQ-----AV | 186 |
| SEQ_ID_NO_610 | AKASLEVLVA DLQFLRDQQT TQVTIARVF NWDVHQ-RRS KQ-----AI | 193 |
| SEQ_ID_NO_593 | AKASLEVLVA DLQFLRDQVT VTQVTIARVY NWDVHQ-RRV KQVTPTALAV | 192 |
| SEQ_ID_NO_595 | AKASLEVLVA DLLFLRDQVT TQVTIARVY NWDVHQKRRM RE---AVTAE | 193 |
| SEQ_ID_NO_599 | ARASLEVLIA DLQFLRDQVT TQVTIARVY NWDVHQ-RRV QQ---AVATT | 186 |

| | | |
|---|---|---|
| SEQ_ID_NO_603 | KET | 195 |
| SEQ_ID_NO_605 | KEP | 189 |
| SEQ_ID_NO_610 | KET | 196 |
| SEQ_ID_NO_593 | ADS | 195 |
| SEQ_ID_NO_595 | KDS | 196 |
| SEQ_ID_NO_599 | AQD | 189 |

Figure 19

| | | | | | | | |
|---|---|---|---|---|---|---|---|
| SEQ_ID_NO_622 | ----MAFSNA | LRSAAKLVAS | SESSLSNSVS | RGFHSTGMKR | M-GGGHGHDE | | 45 |
| SEQ_ID_NO_613 | ----MALSTS | RSVSKIISS | SEASVSRSVT | RSFHSTGVKK | MSGGGHGGYD | | 46 |
| SEQ_ID_NO_620 | ----MALNTG | RSISKIIAF | SEASVSRSVS | RSFHSTGAKK | M-SGGHGHDE | | 45 |
| SEQ_ID_NO_626 | ----MALNTG | RSVSRLIAS | SESSVSRSVS | RSFHSTGAKK | M-SGGHGHDE | | 45 |
| SEQ_ID_NO_643 | ----MAAAAA | --------AA | GEEE--GEAS | RGFHATGVKR | M--GGHGHDE | | 34 |
| SEQ_ID_NO_644 | MATATALNRG | LRSGIRLLAT | GAEAISKTDS | RGFHATGVKR | M--GGHGHDE | | 47 |
| SEQ_ID_NO_624 | --MATALNRG | LRSGIRLLAT | GAEAISKPAS | RGFHATGVKR | M--SGHGHDE | | 45 |
| SEQ_ID_NO_638 | --MATALNRG | LRSGIRLLAA | GAEAISKPAS | RGFHATGVKR | M--GGHGHDE | | 45 |
| SEQ_ID_NO_634 | ----MALSRG | RSGLKLLSH | SEAALPRSVT | HEFHATSMKR | M--GGHGHDE | | 44 |
| SEQ_ID_NO_615 | ----MAMIRG | LSSGIKLLTS | SEAALFRSVT | REFHATGMKR | M--GGHGHDE | | 44 |

| | | | | | | |
|---|---|---|---|---|---|---|
| SEQ_ID_NO_622 | PYYLHAKHMY | NLDRMKHQGL | KMSLAVFTAF | SIGVAVPVYA | VIFQQKKTAS | 95 |
| SEQ_ID_NO_613 | EYYLHAKHMY | NLDRMKYQAL | KMSLGVFTAF | SIGVGVPIFA | VVFQQRKTQS | 96 |
| SEQ_ID_NO_620 | PYYLHAKHMY | NLDRMKYQGL | KMSLGVFTAF | SIGVGVPIFA | VVFQQRKTAS | 95 |
| SEQ_ID_NO_626 | PYYLHAKHMY | NLDRMKFQGL | KMSLAVFTAF | SIGVGVPIFA | VVFQQRKTAS | 95 |
| SEQ_ID_NO_643 | PYYLHAKHMY | NLHRMKHQKP | KVYLSVLGAV | GIGIAVPVYA | VVFQQKKTAS | 84 |
| SEQ_ID_NO_644 | PYYLHAKHMY | NLHRMKHQKP | KVYLSVLGAV | GIGIAVPVYA | VVFQQKKTAS | 97 |
| SEQ_ID_NO_624 | PYYLHAKHMY | NLHRMKHQKL | TAWTSVLGAV | SIGIGVPVFA | VVFQQKKTSS | 95 |
| SEQ_ID_NO_638 | PYYLHAKHMY | NLHRMKHQGL | KVTLSVLGAV | SIGVGVPVYA | VIFQQKKTAS | 95 |
| SEQ_ID_NO_634 | PFYIHAKHMY | NLDRMKHQKL | KVTLGVLSAF | SIGVVPIYA | VIFQQKKAAS | 94 |
| SEQ_ID_NO_615 | PYYLHAKHMY | NLDQMKHQKL | KVALSVWSAF | GIGMAVPVYA | VMFQQKKAAS | 94 |

| | | |
|---|---|---|
| SEQ_ID_NO_622 | S | 96 |
| SEQ_ID_NO_613 | G | 97 |
| SEQ_ID_NO_620 | G | 96 |
| SEQ_ID_NO_626 | G | 96 |
| SEQ_ID_NO_643 | G | 85 |
| SEQ_ID_NO_644 | G | 98 |
| SEQ_ID_NO_624 | G | 96 |
| SEQ_ID_NO_638 | G | 96 |
| SEQ_ID_NO_634 | G | 95 |
| SEQ_ID_NO_615 | A | 95 |

Figure 20

| | | | | | | |
|---|---|---|---|---|---|---|
| SEQ_ID_NO_685 | MGFISFVGRV | LFASLFLLSA | YQEFLEFGND | GGPAAKTLKP | KFNLFVKLVS | 50 |
| SEQ_ID_NO_679 | MGFVSFAGRV | LFASVFLLSA | YQEFSEFGAD | GGPAAKALRP | KYNVFTKNIS | 50 |
| SEQ_ID_NO_681 | MGFVSFAGRV | LFASVFLLSA | YQEFSEFGAD | GGPAAKALRP | KYNVFTKNIS | 50 |
| SEQ_ID_NO_668 | MGFVSFVGRV | LFVAAFLLSA | YQEFNEFGAD | GGPAAKALRP | KFNVFVKNVS | 50 |
| SEQ_ID_NO_676 | MGFVSFVGRV | LFVAAFLLSA | YQEFNEFGTD | GGPAAKALQP | KFNVFVKNIS | 50 |
| SEQ_ID_NO_646 | MELASFLGRA | LFVSVFLLSA | WQEFNDFGED | GGRSAKSLKP | KFNAFVNHVT | 50 |
| SEQ_ID_NO_648 | MALVSFVGRV | LFASVFILSA | WQEFNEFGVD | GGPAAKALKP | KFNVFSKTVT | 50 |
| SEQ_ID_NO_656 | MAFTSFLGRV | LFASVFILSA | YQEFNEFGVD | GGPAAKALKP | KFGVFTSHVD | 50 |
| SEQ_ID_NO_660 | MAFASFLGRV | LFASVFILSA | YQEFNEFGVD | GGPAAKALRP | KFDAFTHRVH | 50 |

| | | | | | | |
|---|---|---|---|---|---|---|
| SEQ_ID_NO_685 | KNTGLGVPHI | DIKIVIAATM | FLKGFGGLLF | ESSSFGAFL | LLIYLAFMTP | 100 |
| SEQ_ID_NO_679 | AHLGVAVPHV | ELKHIVAATI | GLKGLGGLLF | LSSSFGAYL | LLIYLAFITP | 100 |
| SEQ_ID_NO_681 | AHLGVAVPHV | ELKHIVAATI | GLKGLGGLLF | LSSSFGAYL | LLIYLAFITP | 100 |
| SEQ_ID_NO_668 | AHLGVAVPHI | ELKHVIAATI | GLKGLGSLLF | LSSSLGAYL | LLLYLALITP | 100 |
| SEQ_ID_NO_676 | SHLGVAVPHI | ELKHVIAATI | ALKGLGGLLF | LSCSLGAYL | LLLYLAIVTP | 100 |
| SEQ_ID_NO_646 | THTGQQLPPV | DMKILVAAAI | ALKGIGGLLF | VFGSSLGAYL | LLHQAVATP | 100 |
| SEQ_ID_NO_648 | AHTGVEVPEF | DIKVLVAAAV | AFKGVGGILF | FGSTIGAYL | ALQOVVTT | 100 |
| SEQ_ID_NO_656 | SHAGIDVPEI | EIKHLVSAAI | FLKGIGGILF | IGSSLGAYL | LIIHDLAIP | 100 |
| SEQ_ID_NO_660 | SDVGFQLPEL | DLKFLIAGAI | ALKGLGGVLF | FGSSFGALL | LLLHDLATP | 100 |

| | | | | | | |
|---|---|---|---|---|---|---|
| SEQ_ID_NO_685 | IVYDFYNYEM | ESEQFVQLFF | KFTQNLAFLG | ALLFFLGMKN | SIPRIRRISK | 148 |
| SEQ_ID_NO_679 | VVYDFYNYNM | EKSEFVQLFM | KFTQNLALFG | ALLFFLGMKN | SIPKIRQIAK | 148 |
| SEQ_ID_NO_681 | VVYDFYNYDM | EKSEFVQLFM | KFTQNLALFG | ALLFFLGMKN | SIPKIRQIAK | 148 |
| SEQ_ID_NO_668 | IIHDFYNYDM | EKAEFAGLFA | KFTQDLALIG | ALLFFLGMKN | SIPKIROGGK | 149 |
| SEQ_ID_NO_676 | IVHDFYNYDM | EKAEFAQIFG | KFTQDLALIG | ALLFFLGMKN | SIPKIRQISK | 148 |
| SEQ_ID_NO_646 | ILYDFYNYDV | DRKEFGQLFS | KFTQSLALLG | GLLFFIGMKN | SRKHGRQILR | 149 |
| SEQ_ID_NO_648 | ILYDFYNYDT | EKKEFGLLFS | KFSQNLALLG | ALLFFIGMKN | SIPS-RQILK | 148 |
| SEQ_ID_NO_656 | ILYDFYNYDS | EEKEFNQLFI | KFTQNMALYG | ALLFFIGMKN | SFPRIRQIHK | 148 |
| SEQ_ID_NO_660 | IHYDFYNYDS | EDKEFTQLFI | KFTQNMALFG | ALLFFIGMKN | SIPRIRI-VP | 147 |

| | | |
|---|---|---|
| SEQ_ID_NO_685 | GRTTKTKTN | 157 |
| SEQ_ID_NO_679 | KKAPKSKTN | 157 |
| SEQ_ID_NO_681 | KKAPKSKTN | 157 |
| SEQ_ID_NO_668 | KKAPKAKTN | 158 |
| SEQ_ID_NO_676 | KKAPKAKTN | 157 |
| SEQ_ID_NO_646 | KKAPKAKAN | 158 |
| SEQ_ID_NO_648 | KKAPKTKTV | 157 |
| SEQ_ID_NO_656 | KKVPKTKTG | 157 |
| SEQ_ID_NO_660 | KKAPKTKTY | 156 |

Figure 21

| | | | | | | |
|---|---|---|---|---|---|---|
| SEQ_ID_NO_708 | MDEI MNKMGS | YWLGQRANKE | MSSAGDDIES | LSTSVGDGAK | MLVNKLKGKM | 50 |
| SEQ_ID_NO_728 | MDQIFNKVGS | YWLGQKANKE | FNSVGDDINS | MGSSIGDGTK | MLVNKLKGKM | 50 |
| SEQ_ID_NO_718 | MDQILNKVGS | YWNKRANKE | LSSVGDDLNS | LSSSIEGGAK | MLVNKLKGKM | 50 |
| SEQ_ID_NO_687 | MDQIFNKVGS | YWLGQKANKQ | FDSVGNDLNS | VSTSIEGGTK | MLVNKIKGKM | 50 |
| SEQ_ID_NO_699 | MDQVFXKVGS | YWLGQKANKQ | FDSVGKDVSS | LSTSIEGGTK | MLVNKFKGTM | 50 |
| SEQ_ID_NO_689 | MDQILNKVGS | YWLGQKANKE | LDSVGDDLNS | LSTSIEGGAK | MLVNKIKGKM | 50 |
| SEQ_ID_NO_691 | MDAVLNKVGS | YWLGQKASKE | FNSVGDDINS | LSTSIEGGTK | MLVNKLKGKM | 50 |
| SEQ_ID_NO_703 | MDQIFNKVGS | YWFNQKASSD | LNSVGDDINS | MTNSIXGGTK | MLVNKIKGKM | 50 |
| SEQ_ID_NO_706 | MDQVFNKVGS | YWFNQKASKE | LNSVGDEINS | LSNSIEGGTK | MLVNKVKGKM | 50 |
| SEQ_ID_NO_721 | MDQIMGKVGG | YWFKQNAGKE | NNIGDDINS | SSSIGDGAK | MMVNKIKGKM | 50 |
| SEQ_ID_NO_712 | MDQVLNKVGS | YWFSKRASKE | DSIGDDLNS | VSSSIGGGAK | MMVNKIKGKL | 50 |
| SEQ_ID_NO_724 | MDQVLNKVGS | YWFSKRASKE | DSIGDDISS | STSIGTGAK | MMVNKIKGKM | 50 |
| | | | | | | |
| SEQ_ID_NO_708 | QKPLAELLQE | HDLPAGLFPR | EATNYEFEPE | TRRLTVHIPA | VCEVGYRDGS | 100 |
| SEQ_ID_NO_728 | QKPLPELLKD | YDLAVGIFPR | DATHYEFDER | QGKLTVYVPQ | CEVGYKDSS | 100 |
| SEQ_ID_NO_718 | QKSLPELLRE | YDMPIGLFPQ | DATHYEFNEE | TGKLTVFIPS | CEVGYRDSS | 100 |
| SEQ_ID_NO_687 | QKPLPELLKE | YDLPIGIFPG | DATNYEFDEE | TKKLTVLIPS | CEVGYKDSS | 100 |
| SEQ_ID_NO_699 | QKPLAELLKD | YDLPVGIFPR | DATNYEFDEQ | TKKLTVLIPS | VCEVGYKDSS | 100 |
| SEQ_ID_NO_689 | QKPLPELLRE | YNLPIGIFPR | DATNYEFNEE | TGKLTVFIPA | CEVGYKDSS | 100 |
| SEQ_ID_NO_691 | QKPLPDLLKE | YDLPIGIFPR | DATNYEFNEE | TRKLTVFIPS | CEVGYKDSS | 100 |
| SEQ_ID_NO_703 | QKALPELLKE | YDLPIGIFPR | DATNYEFNEE | TGKLMVYIPQ | VCEVGYKDSS | 100 |
| SEQ_ID_NO_706 | QKPLPELLKE | YDLPIGIFPR | DATNYEFNEE | TGKLEVFIPQ | VCEVGYKDSS | 100 |
| SEQ_ID_NO_721 | QKPLPEFLKE | YDLPVGLFPQ | DATNYEFNEE | TKKLTVYISS | VCEVGYKDSS | 100 |
| SEQ_ID_NO_712 | QKALPDLLKE | YDMPAGLFPR | DTTNYEFNEE | TKKLTVYIPS | ACDVGYKDSS | 100 |
| SEQ_ID_NO_724 | QKALPDLLKE | YDMPAGLFPR | DATNYEFNEE | TKKLTVYIPS | ACDVGYKDSS | 100 |
| | | | | | | |
| SEQ_ID_NO_708 | ELRFDTTVTG | TLDKGSLTGV | EGLKAKVLVW | ARVTAVKADA | AKVYFAVGIK | 150 |
| SEQ_ID_NO_728 | VLRFFAIVTG | YLEKGKLADI | EGLKTKIIIW | VKVTAITSEG | SKLHFTAGVK | 150 |
| SEQ_ID_NO_718 | VLRFLNIVTG | YLEKGKLVDI | EGIKTKVLIW | SKVTRISTEG | SKIHFTTGVK | 150 |
| SEQ_ID_NO_687 | VLKFITTVTG | HLEKGKLTDV | EGIKTKVMIW | VKVTSISTDA | SKVYFTAGMK | 150 |
| SEQ_ID_NO_699 | VLKFITTVTG | RLEKGKLGDL | EGMKTKVMIW | VKVTSISADS | SKVYFTAGVK | 150 |
| SEQ_ID_NO_689 | F-----CASS | PLL------- | --------- | --------- | --------- | 107 |
| SEQ_ID_NO_691 | VVRFLTTVTG | YLEKGKIADI | EGMKTKVMIW | VKVTCIASTS | SKLNFTAGMK | 150 |
| SEQ_ID_NO_703 | VLRFXTTVTG | YLEKGKLADI | EGMKTKVLIW | VKVTTLSXS | XKAYVTAGXK | 150 |
| SEQ_ID_NO_706 | VLRFFTTVTG | YLEKGKLADI | EGMKTKVIIW | VKVTTFSEG | SKLYVTAGMK | 150 |
| SEQ_ID_NO_721 | VLRFSTTVTG | YLENGKLSEV | EGLKTKILIW | TKVTAVRTEA | TKVHFAAGMN | 150 |
| SEQ_ID_NO_712 | VVRFFTCVTG | YLEKGKLSDI | EGMKTKVLVW | TKVTSIKTEG | SKVHFTAGMK | 150 |
| SEQ_ID_NO_724 | VLRFFTCVTG | YLEKGKLSDI | EGLKTKVLVW | TKVTAIKTEG | SKVHFTAGVK | 150 |

Figure 21 (continued)

| | | | | |
|---|---|---|---|---|
| SEQ_ID_NO_708 | KSRSREAYEV | VRGAI | TVDEF | 170 |
| SEQ_ID_NO_728 | KTRSREAYQV | LRDGVL | VDKF | 170 |
| SEQ_ID_NO_718 | KTRSRDAYQV | LRAGI | TVDKF | 170 |
| SEQ_ID_NO_687 | KSRSRDAYEV | QRNGLR | VDKF | 170 |
| SEQ_ID_NO_699 | KSRNRDAYEV | LRDGVRA | DKF | 170 |
| SEQ_ID_NO_689 | ---------- | ---------- | | 107 |
| SEQ_ID_NO_691 | KTRDRGAYEV | LRDGVGI | DKF | 170 |
| SEQ_ID_NO_703 | KTRSREAYEV | TRXGVCI | DKF | 170 |
| SEQ_ID_NO_706 | KTRSREAYDV | TRDGVP | VDKF | 170 |
| SEQ_ID_NO_721 | KARNRDAYEV | VRDGVGI | DKF | 170 |
| SEQ_ID_NO_712 | KTRSRDAYEV | VRDGI I | LDKF | 170 |
| SEQ_ID_NO_724 | KTRSRDAYEV | VRDGI P | LDKF | 170 |

Figure 22

| | | | | | | | |
|---|---|---|---|---|---|---|---|
| SEQ_ID_NO_737 | ··MDEL GGGG | G····KKGKA | WPWWL GASAA | QI TGAL VWFR | RGKGG SDMTW | | 44 |
| SEQ_ID_NO_738 | ···MEE GGGG | E·····EAER | WPWWA GASAA | QVAAGVAWFR | RGRGG AAFAM | | 42 |
| SEQ_ID_NO_742 | ··MDDR GGGG | G····GEAER | WPWWA AASAA | QAAAGVAWFR | RGRGG TAVAM | | 44 |
| SEQ_ID_NO_735 | MKMEE AAGSG | N····SDGGN | KWWWG VASAA | QMGL GI RTFA | KGH GGDSRLM | | 46 |
| SEQ_ID_NO_730 | MEEQN AGTGA | GESSLL DGSG | HWWWAL GSGA | QI MWGI RLI R | RGY AGDVRLM | | 50 |
| SEQ_ID_NO_732 | ···MEN GDGG | G····I ETQW | WWWWAMASMA | KF GWGI SAYK | RGF AGDSRLM | | 43 |

| | | | | | | |
|---|---|---|---|---|---|---|
| SEQ_ID_NO_737 | PFRAFAVASL | FVGAGATTVT | AGVSAAGVGS | VEEMKGLGAR | RKWSRVPPR | 94 |
| SEQ_ID_NO_738 | PFKAFAI ATL | FVGAGATAVT | AGVL AAGVGS | VDEMKGVGAS | RRWMGAPPR | 92 |
| SEQ_ID_NO_742 | PFKAFAI ASL | FVGAGATAVS | AGVL AAGVGS | VEEMKGVGAS | RRWMGAPPR | 94 |
| SEQ_ID_NO_735 | PFKAFVVASL | FVSSAASASV | LLL QANGI HR | VEDL MKAGAN | LRAKL GLRPR | 96 |
| SEQ_ID_NO_730 | PLKAFGVASL | FVGSL ATSSV | ALVRATGI HT | VQDAI DLGAN | RTNL GVTPQ | 100 |
| SEQ_ID_NO_732 | PLKAFAVASL | FVGSAASASI | ASL QASGI HK | VQDLI ELGAN | RTGL GVPPR | 93 |

| | | |
|---|---|---|
| SEQ_ID_NO_737 | RVE GGE····· | 100 |
| SEQ_ID_NO_738 | RRVE GGGDP·· | 101 |
| SEQ_ID_NO_742 | RAGGSD····· | 100 |
| SEQ_ID_NO_735 | TQNKNMDDS·· | 105 |
| SEQ_ID_NO_730 | I PDKQI TERD G | 111 |
| SEQ_ID_NO_732 | VAKE······· | 97 |

Figure 23

| | | | | | | |
|---|---|---|---|---|---|---|
| SEQ_ID_NO_765 | MSPMSNPSFD | HSY---E--L | PLRRNLLLL | DLLGRLRFIA | EVLLDRLGVA | 45 |
| SEQ_ID_NO_763 | MMLSSAYSTP | AADELGGPPP | LPPPPGADVS | VIVGALTGVL | LGLFLFL--- | 47 |
| SEQ_ID_NO_758 | ------MGFP | VGY--PE--V | SVPNIFLYTL | SLLSFLRSLT | ISFLBLLHLS | 40 |
| SEQ_ID_NO_761 | ------MGFP | VGY--SE--L | LLPRLLLQVL | LLLGHLHRFL | LMAFHAVGLG | 40 |
| SEQ_ID_NO_762 | ------MGFP | VGY--SE--L | LLPRLLLQVL | LLLGHLHRFL | LMAFHAVGLG | 40 |
| SEQ_ID_NO_755 | ------MGFY | AEDPLSG--L | TIGQAIYEVA | LMIAVLRWVL | CLIFRV--- | 39 |
| SEQ_ID_NO_748 | ------MGFF | VEE--SG--L | VFHLLYKAA | LVLAVLRWAL | AMALRFK--- | 37 |
| SEQ_ID_NO_746 | ------MTFF | IED--TS--L | ISHVLYKTA | LIITVLRWIF | AIMLRYR--- | 37 |
| SEQ_ID_NO_751 | ------MTFF | IED--TS--L | IBHVLYKTA | LIITVLRWIF | AIMLRYR--- | 37 |
| SEQ_ID_NO_753 | ------MSFF | IQD--SG--L | VFQLLYQMA | VFTLLRWIF | SMLRYR--- | 37 |
| SEQ_ID_NO_760 | ------MSFF | LED--SG--L | VFQLLYQMA | VLITLLRWIF | TMLRYR--- | 37 |

| | | | | | | |
|---|---|---|---|---|---|---|
| SEQ_ID_NO_765 | SW-----QG | EVHLPGQLWG | WGGEHASDAT | LEHFLEARLW | ETGTRSPLTT | 89 |
| SEQ_ID_NO_763 | ---------- | --IYAKHCRQ | RGRGGARGAA | GGLGLGFRAS | STCDRCRSGV | 85 |
| SEQ_ID_NO_758 | DL-------- | ---------- | ---------L | DTDFSTTTLP | DSHIHRPTLS | 63 |
| SEQ_ID_NO_761 | DLIDNPPGLA | ATEQDMMLQG | RGGGMAEGWA | SSSALQHRRP | EFRAIPPM- | 88 |
| SEQ_ID_NO_762 | DLIDNPPGLA | ATEQDLMLQG | RGGGMAEGWA | SSSALQHRRP | EFRAIPPM- | 88 |
| SEQ_ID_NO_755 | ---------- | ---------- | ---------- | NDRRTCSDE | TPTPEPCSQM | 59 |
| SEQ_ID_NO_748 | ---------- | ---------- | ---------N | RTHLASPSND | SLRRSHPVPS | 58 |
| SEQ_ID_NO_746 | ---------- | ---------- | ---------- | SRSSSSSBS | SQSSSSPSIS | 57 |
| SEQ_ID_NO_751 | ---------- | ---------- | ---------- | --SRSSSSSS | SQSSSSPSIS | 55 |
| SEQ_ID_NO_753 | ---------- | ---------- | ---------- | ------SKS | RTSSAPPVLS | 49 |
| SEQ_ID_NO_760 | ---------- | ---------- | ---------- | ----SRSTSS | SSSSTPPIS | 52 |

| | | | | | | |
|---|---|---|---|---|---|---|
| SEQ_ID_NO_765 | TRYRRRRVAL | AQPADGKLAA | EGDAEGAA-- | AVCAICVAGL | ESGDLEIVVE | 137 |
| SEQ_ID_NO_763 | SLSVVDALPV | VRFGD---MG | GAAAAQP-- | -ECAVCLGTF | DPAADELLRV | 129 |
| SEQ_ID_NO_758 | ALLRQFLPI | ITFND---LA | EGDSSPPV-- | -GCAVCLNEF | --AGEEEIRC | 105 |
| SEQ_ID_NO_761 | --AIEEALPV | VRFDE---LV | ASAPAAVCGG | GDCAVCLSGI | --CGRDEVRR | 131 |
| SEQ_ID_NO_762 | --AIEEALPV | VRFDE---LV | ASAPAAVCGG | GDCAVCLSGI | --CGRDEVRR | 131 |
| SEQ_ID_NO_755 | TRDKDSILLL | TTFGE---IK | ERLPETE--- | ETCAVCLSQL | --SVEDEVRE | 101 |
| SEQ_ID_NO_748 | SQQRDGLIL | TTFGD---VT | ERMPLGVC-- | DTCAVCLSQL | --RDQDEVRE | 100 |
| SEQ_ID_NO_746 | SQTIKESLAV | FAFRD---AV | ERSPAAIN-- | DMCAVCLGDL | --EDEDEIRE | 100 |
| SEQ_ID_NO_751 | SQTIKESLAV | SAFRD---AV | ERSPAAIN-- | DMCAVCLGDL | --EDEDEIRE | 98 |
| SEQ_ID_NO_753 | SQAIKESLSV | TTFHD---AL | ERKPELIS-- | DTCAVCLGDL | --EDGDEVRE | 92 |
| SEQ_ID_NO_760 | SQTIKESLAV | TTFRD---AA | DRSPELIS-- | DTCAVCLGDL | --EDGDEVRE | 95 |

Figure 23 (continued)

| | | | | | | | |
|---|---|---|---|---|---|---|---|
| SEQ_ID_NO_765 | LCSCSHAFHD | ACIDAWRSG | D--------- | -DDAATCPLC | RAPCCFRRG- | | 176 |
| SEQ_ID_NO_763 | LPKCRHAFHA | DCVDTMLEA- | ---------- | ---HSTCPVC | RRRVGKEDA- | | 164 |
| SEQ_ID_NO_758 | MANCRHMFHR | TCVDRWIDHD | ---------- | ---QKTCPLC | RTHFVPYHK- | | 141 |
| SEQ_ID_NO_761 | LSNCRHVFHR | GCLDRWMAHE | ---------- | ---QRTCPLC | RAPLIPDELL | | 168 |
| SEQ_ID_NO_762 | LSNCRHVFHR | GCLDRWMAHE | ---------- | ---QRTCPLC | RAPLIPDELL | | 168 |
| SEQ_ID_NO_755 | LMNCYHVFHR | ECIDRWLEHE | HE-------- | -NHSATCPIC | RAPLLSSSC- | | 141 |
| SEQ_ID_NO_748 | LRNCCHVFHR | DCIDRWVDHD | HEHD------ | -ENHNTCPLC | RAPLLTTSQ- | | 142 |
| SEQ_ID_NO_746 | LRNCTHVFHR | DCIDRWLDYE | CCGGDD---- | -DNHRTCPLC | RTPLLPSFT- | | 144 |
| SEQ_ID_NO_751 | LRNCTHVFHR | DCIDRWLDYE | CCGGDD---- | -DNHRTCPLC | RTPLLPSFT- | | 142 |
| SEQ_ID_NO_753 | LRNCSHVFHR | ECIDRWLDYE | CCGGDGNEGE | EDNHRTCPLC | RTPLLAADT- | | 141 |
| SEQ_ID_NO_760 | LRNCSHVFHR | ECIDRWLDYE | CCGGDDNDGE | EDNHRTCPLC | RTPLLAANT- | | 144 |

| | | | | | | | |
|---|---|---|---|---|---|---|---|
| SEQ_ID_NO_765 | ---------- | ---------- | TTTGGEQSLS | R----VLKGV | CVSVP | 197 |
| SEQ_ID_NO_763 | ---------- | -----FAVIP | ELEAADADMY | PAREAEMQIV | VRRPA | 194 |
| SEQ_ID_NO_758 | -----MEDYN | QRLWNDAASE | DDIDDDVSLF | SHRHDYYY A | NASL- | 180 |
| SEQ_ID_NO_761 | PAASGLPDPS | DYDLSYYPSP | LPLAPTPTLL | RPHELLLNGL | GGFQ- | 212 |
| SEQ_ID_NO_762 | PAASGLPDPS | DYDLSYYPSP | LPLAPTPTLL | RPHELLLNGL | GGFQ- | 212 |
| SEQ_ID_NO_755 | ---------- | ----HHSSAT | CLPPPQPSWA | VERLLYLFGD | DLLPC | 172 |
| SEQ_ID_NO_748 | ---------- | --------SL | ARTRAEPSWA | VERILYLFGD | DLVM- | 168 |
| SEQ_ID_NO_746 | ---------- | ---------D | YSTVTQTSWA | VERLLYLFGD | DLLP- | 169 |
| SEQ_ID_NO_751 | ---------- | ---------D | YSTVTQTSWA | VERLLYLFGD | DLLP- | 167 |
| SEQ_ID_NO_753 | ---------- | -----SSCGD | WPVKTEPSWA | VERLLYLFGD | DLLV- | 170 |
| SEQ_ID_NO_760 | ---------- | -----SSCAD | WPVKNEPSWA | VERLLYLFGD | DLLV- | 173 |

Figure 24

```
SEQ_ID_NO_779   MVLESIL SS S--KSPSF-- ------RRQF AKHELGSWST LKRHRFLLF    39
SEQ_ID_NO_783   MVLDSIL SS PCLKSPSF-- ------SRQF ARHELGSWST LVKRHCFLLS    42
SEQ_ID_NO_769   MVLDGLV SS PSRRQCL--- ------KKQW --DELGSWST LIQRHQYLLT    39
SEQ_ID_NO_777   MVLDGIV SS PLRRHQSL-- ------KKQW --EDLGSCST VVNRHRYLLT    39
SEQ_ID_NO_773   MVLDSMI TS PHRRSPSF-- ------RKPF PRDELGSWST LLRRHRFLLT    41
SEQ_ID_NO_771   MVLDGIV SS PLRRSAST-- ------RRQS SRDEFGSWST LVERHRFLLT    41
SEQ_ID_NO_789   MVLDSL- SS PHRRSQNTVF LASPSKKQQS GFNEPGSWST IVERHRFLLT    48
SEQ_ID_NO_785   MVLDSL- SS PHRRSQNTFF VSSA-KKPQS SRDD--SWSA LVERHRFLLT    45
SEQ_ID_NO_790   MVLDSL- SS PHRRSQNTFF LSSP-KKLQS SKDDVGSWSA LVERHRFLLT    47

SEQ_ID_NO_779   ALALLTVLCT YLYFAVTFA AN--DSCSGL NGPLKDSCHM EHVKASVAKS    87
SEQ_ID_NO_783   ALALLTVLCT YLYFAVTFA AN--DSCSGL SGSLRDSCHM EHVMDSEAKS    90
SEQ_ID_NO_769   ALALLAFLCT VYLYFAVTLG ARH-SSCYGL TGKDKAMCCL -QLVQALSKG    87
SEQ_ID_NO_777   ALLLGFLCT VYLYFAVTLD ARHNSSCYGL AGKEKAMC-- ----QAISKG    83
SEQ_ID_NO_773   AFALLAFLCT YLYFAVTLG AT--ESCSGL TGTKKTLCRL ELAKDSVGNG    89
SEQ_ID_NO_771   ALGLLAFLCT YLYFAVTLG AT--DTCSGL KGTEKATCNL QHVSSTLSHG    89
SEQ_ID_NO_789   MLALLAFLCT YLYFAVTLG AT--GSCSGM SGAEKALC-- -QAKSSLHKG    93
SEQ_ID_NO_785   TLLVLAFLCT VYLYFAVTLG AS--DACTGL TGAERIEC-- -QARSVLQHG    90
SEQ_ID_NO_790   TLVLVFLCT VYLYFAVTLG AP--DACSGL AGTEKAVC-- -RAKSALRHG    92

SEQ_ID_NO_779   KLKGLRHF    95
SEQ_ID_NO_783   KLKGLRHL    98
SEQ_ID_NO_769   KLK---FF    92
SEQ_ID_NO_777   KLK---LF    88
SEQ_ID_NO_773   KLK---FF    94
SEQ_ID_NO_771   KLK---FL    94
SEQ_ID_NO_789   KLK---FF    98
SEQ_ID_NO_785   KLK---FR    95
SEQ_ID_NO_790   KLK---FF    97
```

Figure 25

```
SEQ_ID_NO_799    - -MI AE- SM LLNPTSHI ST N-DSLDDPSP A- - - - - - - - - - - - - - - - -   26
SEQ_ID_NO_819    MMMMGE- - -  - - -GVSSVPP W- - - -SHLPV SGMDVLGGGG G- - - - - - -GG     32
SEQ_ID_NO_821    MMMMGE- - -  - - -GVSSVPP W- - - -SHLPV SGMDVLGGGG G- - - - - - -GG     32
SEQ_ID_NO_810    MMMMGE- - -  - - -RAHAPP W- - - -QHSPA A- - - - - -SGV T- - - - - - -DA  25
SEQ_ID_NO_816    MMMMGE- - -  - - -GAHAPP WQQQQQQPAA S- - - - - - AGM V- - - - - - - -DG  29
SEQ_ID_NO_801    -MMI GELSHH RSNPTVQI PQ WDPYEEQTTT SPSLSPI PTS P- - - - - - - -F        41
SEQ_ID_NO_792    -MMI GE-SHR GFNPTVHI PP W-PLSEDLTV SDI YGSPDGG S- - - - - - - - -        38
SEQ_ID_NO_794    -MML GE-THR P-NPTVHVPP W-PDLDDDQT DVVYSPI HYN ATDNNLSSNG                  46
SEQ_ID_NO_808    -MML GEPPHR T-NPTVHVPP W-PTLNNPTA E- FSPLTSN D- - - - - - -DY            39
SEQ_ID_NO_805    -MML GE-THR P-NPTVHVPP W- - - - - - - -A PEL FSPYTGN A- - - - - - -DY   32

SEQ_ID_NO_799    - - - - -I SSYF GTAHVSPLDS PTAALMDFDS SL WEDPDLPA PVDAYSCDQF              71
SEQ_ID_NO_819    DEMTPY- VI A ALRDYLPAND VGVGA-DEEE EAAAMAA- - - AVDAYACDEF              77
SEQ_ID_NO_821    DEMTPY- VI A ALRDYLPAND VGVGA-DEEE EAAAMAA- - - AVDAYACDEF              77
SEQ_ID_NO_810    DDASPYALLA ALQHYLPSNE V- -AAFDEDD EEAALAAATA AVDAYACDEF                 73
SEQ_ID_NO_816    DDASPYSLLV ALRHFLPSNE AAAAAYDEDD EL- - - -EALA AVDAYACDEF               74
SEQ_ID_NO_801    TNFNALDSLT SLHRYLPSNE PDP- - -TFED ELDL- - - - - - PVDAFSCDHF           82
SEQ_ID_NO_792    - - -SMMEALA ELQRYLPSNE PDP- - -DSDP DLSGPDS- - - PI DAYTCDHF            79
SEQ_ID_NO_794    NPFYLHEALS ALQRYLPSNG PDV- - - -ELDS EFPGLDGPDS PVDAYSCDHF              93
SEQ_ID_NO_808    SQFYMQEALS AFQHYVNENN DS- - - - -DSDS EI FPTHE- - - SVDSYSNDHF           82
SEQ_ID_NO_805    SPYSMQEALS ALQHYESTDA - - - - - -ESDS EVPSREP- EV PVDAYSCDHF            75

SEQ_ID_NO_799    RMYEFKVRSC ARGRSHDWTK CPYAHTGEKA RRRDPRKFNY SGAECPDLRH                   121
SEQ_ID_NO_819    RMYEFKVRRC ARGRSHDWTE CPFAHPGEKA RRRDPRKYHY SGTACPDFRK                   127
SEQ_ID_NO_821    RMYEFKVRRC ARGRSHDWTE CPFAHPGEKA RRRDPRKYHY SGTACPDFRK                   127
SEQ_ID_NO_810    RMYEFKVRRC GRGRNHDWTA CPYAHPGEKA RRRDPRRYHY SGAACPDFRK                   123
SEQ_ID_NO_816    RMYEFKVRRC GRGRSHDWTD CPYAHPGEKA RRRDPRRYHY SGTACPDYRK                   124
SEQ_ID_NO_801    RMYEFKVKRC ARGRSHDWTE CPYAHPGEKA RRRDPRRYHY SGTACPEFRK                   132
SEQ_ID_NO_792    RMYEFKVRRC ARGRSHDWTE CPYAHPGEKA RRRDPRKFHY SGTACPEFRK                   129
SEQ_ID_NO_794    RMYEFKI RRC ARGRSHDWTE CPYAHPGEKA RRRDPRKYHY SGTACPDFRK                  143
SEQ_ID_NO_808    RMFEFKI RRC ARGRSHDWTE CPFSHPGEKA RRRDPRKYNY SGTSCPDFRK                  132
SEQ_ID_NO_805    RMFEFKVRRC ARCRSHDWTD CPYAHPGEKA RRRDPRKYHY SGTACPDFRK                   125
```

Figure 25 (continued)

| | | | | | | | |
|---|---|---|---|---|---|---|---|
| SEQ_ID_NO_799 | GCCKKGDACE | YAHGTFEL WL | HPDRYRTQPC | RDGTGCRRRV | CFFAHTSEQL | | 171 |
| SEQ_ID_NO_819 | GGCKRGDACE | YAHGVFECWL | HPARYRTQPC | KDGTACRRRV | CFFAHTPDQL | | 177 |
| SEQ_ID_NO_821 | GGCKRGDACE | YAHGVFECWL | HPARYRTQPC | KDGTACRRRV | CFFAHTPDQL | | 177 |
| SEQ_ID_NO_810 | GGCKRGDACE | LAHGVFECWL | HPSRYRTQPC | KDGTGCRRRV | CFFAHTPDQL | | 173 |
| SEQ_ID_NO_816 | GGCKRGDACE | FAHGVFECWL | HPSRYRTQPC | KDGTACRRRV | CFFAHTPDXL | | 174 |
| SEQ_ID_NO_801 | GGCKKGDACE | FAHGVFECWL | HPARYRTQPC | KDGPACRRRV | CFFAHTPEQL | | 182 |
| SEQ_ID_NO_792 | GCCKRGDACE | FSHGVFECWL | HPARYRTQPC | KDGGNCRRRV | CFFAHSPDQI | | 179 |
| SEQ_ID_NO_794 | GNCRKGDSCE | FAHGVFECWL | HPARYRTQPC | KDGSGCRRRV | CFFAHTPDQL | | 193 |
| SEQ_ID_NO_808 | GSCKKGDSCE | FAHGVFECWL | HPSRYRTQPC | KDGTSCRRPV | CFFAHTTEQL | | 182 |
| SEQ_ID_NO_805 | GSCKKGDACE | YAHGVFECWL | HPARYRTQPC | KDGTSCRRRV | CFFAHTPDQL | | 175 |

| | | | | | | | |
|---|---|---|---|---|---|---|---|
| SEQ_ID_NO_799 | RI-PGKQSVR | SPRAREM--- | ---------- | ---------- | ---APAVSS | | 194 |
| SEQ_ID_NO_819 | RVLPAQQS-- | SPRSVAS--S | PLAESYD-GS | PLRRQAFESY | LTKTI-MSSS | | 221 |
| SEQ_ID_NO_821 | RVLPAQQS-- | SPRSVAS--S | PLAESYD-GS | PLRRQAFESY | LTKTI-MSSS | | 221 |
| SEQ_ID_NO_810 | RVPPPRQS-- | SPRGAAAA-S | PLAESYD-GS | PLRRQAFESY | LTKSGIVSSP | | 219 |
| SEQ_ID_NO_816 | RVLPPQQSSA | SPRGAGAAPS | PLAESYD-GS | PLRRQAFESY | LTKTGIMSSS | | 223 |
| SEQ_ID_NO_801 | RLLPQQ---- | SPKGNGSGSG | LGGGEYDFGS | PV-IHPFDSY | MTKAGIFVSS | | 227 |
| SEQ_ID_NO_792 | RVLPNQ---- | SPDR------ | --VDSFDVLS | PTIRRAFQ-- | -----FS-S | | 209 |
| SEQ_ID_NO_794 | RLVSS----- | ---------- | --TDTYD-GS | PL-------- | CGKTLTFASS | | 216 |
| SEQ_ID_NO_808 | RAPTQQ---- | SPRSVPS--- | --VDSYD-GS | PL-RLAFESS | CVKTLQFMSS | | 221 |
| SEQ_ID_NO_805 | RVLPQQ---- | SPRS------ | --ADSYD-GS | PL-RHAFESS | CAKSHPEVAS | | 211 |

| | | | | | | | |
|---|---|---|---|---|---|---|---|
| SEQ_ID_NO_799 | PTS-LLSPSS | ------DSP | PLSPLSP--V | SGG------- | ESLSRLVALM | | 229 |
| SEQ_ID_NO_819 | PTSTLMSPPK | SPPS---ESP | PLSPDGAA-A | RRGSMPGVG | SPVNDYLASF | | 267 |
| SEQ_ID_NO_821 | PTSTLMSPPK | SPPS---ESP | PLSPDGAA-A | RRGSMPGVG | SPVNDYLASF | | 267 |
| SEQ_ID_NO_810 | PTSTLVSPPR | SPPS---ESP | PMSPDAAA-A | LRRGSMPGVG | SPVNEVLASM | | 265 |
| SEQ_ID_NO_816 | PTSTLVSPPR | SPPS---ESP | PMSPDAAAGA | LRRGSMPGVG | SPVNEVVASL | | 270 |
| SEQ_ID_NO_801 | PTSLLTSPPV | SPPS---DSP | PMSPGSP--Q | VIGGSGPGSL | NSMSALLASM | | 272 |
| SEQ_ID_NO_792 | PSSN--SPPV | SPRG------ | --DSDSSCSL | SRSLGSNLG | ---NDVVASL | | 246 |
| SEQ_ID_NO_794 | PGSS--SPPV | SPRAESCSSP | PVSPMAQ--S | LSRSLGSASI | NEM---VTSL | | 259 |
| SEQ_ID_NO_808 | PGSV--SPPV | ------ESP | PMSPMTR--S | LGRSVGS--- | SSVNEMVASL | | 257 |
| SEQ_ID_NO_805 | PGSA--SSPV | ------ESP | PMSPMT---- | ---------- | VSVNEMVASL | | 238 |

Figure 25 (continued)

| | | |
|---|---|---|
| SEQ_ID_NO_799 | HSLRLDELK·············· ·············· TNPGVSSF·· | 246 |
| SEQ_ID_NO_819 | RQLRLNKVK· ·SSPSGGWSY PSSS······ AVYGSPKAA· ··TGLYSLPT | 306 |
| SEQ_ID_NO_821 | RQLRLNKVK· ·SSPSGGWSY PSSS······ AVYGSPKAA· ··TGLYSLPT | 306 |
| SEQ_ID_NO_810 | RQLRLGGGS· PRSAPSGGSF LGGG······ YPFGSPKSP· ··AGLYSLPS | 305 |
| SEQ_ID_NO_816 | RQLRLGGGGS PRSAPSGGSF LVG······· YPFGSPKSP· ··AALYSLPS | 310 |
| SEQ_ID_NO_801 | RGLQVGKAK· MGSPVGSWGV QSG······· FRFGSPRGSS LRPGFCSLPS | 314 |
| SEQ_ID_NO_792 | RNLQLNKVK· ·SSLSSSYNN QTGGYG···· SGFGSPRGSV GPGFRSLPT | 290 |
| SEQ_ID_NO_794 | RNLQLGKGK· ······SWKT QVGCCSPSSP SSFGSPRAAM RPGFCSLPS | 302 |
| SEQ_ID_NO_808 | RNLQLGTMK· ··SLPSSWNV QMGS······ PRFGSPRGPV RPGFCSLPS | 298 |
| SEQ_ID_NO_805 | RNLQLGKVK· ··SLPSSWNV ·MGS······ SGFGSPRGPM RPGFFSLPT | 278 |

| | | |
|---|---|---|
| SEQ_ID_NO_799 | SPNL······ ·RRSSGAAF· ·DLMDRGL·N EEEPAMERVE SGRNLRAQMY | 285 |
| SEQ_ID_NO_819 | TPLASTATVT TASSFMPNL· ·EPLDLGLIG DEEPVLDRVE SGRALREKVF | 353 |
| SEQ_ID_NO_821 | TPLASTATVT TASSFMPNL· ·EPLDLGLIG DEEPVLDRVE SGRALREKVF | 353 |
| SEQ_ID_NO_810 | TPTRPSPVTV TTASGATVLT VERLNLGLIG DEEPVMERVE SGRALREKVF | 355 |
| SEQ_ID_NO_816 | TPTRPAAVTV TTPSGATVMT VERLNLGLIG DEEPVMERVE SGRALREMVF | 360 |
| SEQ_ID_NO_801 | TPTR···TM ASRSGLSQL· ·DIMGDGVTC EEEPAMERVE SGRDLRAKIY | 358 |
| SEQ_ID_NO_792 | TPTRP····· ······GFM ·NIMENG··L EEEPAMERVE SGRELRAQLF | 325 |
| SEQ_ID_NO_794 | TPTR····NL ·TRPGISYP· ·DSMDKA··C EEEPVMERVE SGRDLRAKMF | 343 |
| SEQ_ID_NO_808 | TPTQ·····V PSRGRVNHF· ·DLMDQS··C EEEPVMERVE SGRDIRVKMF | 339 |
| SEQ_ID_NO_805 | TPTQ·····A PTRGGVNYF· ·DDMDQS·CC EEEPVMERVE SGRSLRARMF | 320 |

| | | |
|---|---|---|
| SEQ_ID_NO_799 | AKLMRENSVD RVRPMISA· ············ GSLN······ ············ | 307 |
| SEQ_ID_NO_819 | ERLSRDGAIY GDATAFATAG ·····VGLDV DWSDLIN··· ············ | 386 |
| SEQ_ID_NO_821 | ERLSRDGAIS GDATAFATAG ·····VGLDV DWSDLIN··· ············ | 386 |
| SEQ_ID_NO_810 | ERLSKEATYP SDTAASANVE GAA··PAPDV GWSDLIN··· ············ | 391 |
| SEQ_ID_NO_816 | ERLSKEATYP NDAAASANAE GAAPAAAPDV GWSDLIN··· ············ | 399 |
| SEQ_ID_NO_801 | AKLSKENSVD RDRGDBGVSG ·······PDV GWSELVK··· ············ | 389 |
| SEQ_ID_NO_792 | EKLSKENCMG RIEPDPDQGA G····DTPDV GWSDLVM··· ············ | 359 |
| SEQ_ID_NO_794 | EKLSKENSLE RVNPDQSSGG ·······PDL NWSDLGKQA MGIIVMVDIV | 386 |
| SEQ_ID_NO_808 | EKLSKENSFN GSGMGSGSGL GEVV·EDPDV GWSELVSPF LGD······ | 381 |
| SEQ_ID_NO_805 | EKLSKENHLD GSGSGSSQIS ······VPDV GWSELVSR· ············ | 353 |

Figure 25 (continued)

| | | |
|---|---|---|
| SEQ_ID_NO_799 | - - - - - - | 307 |
| SEQ_ID_NO_819 | - - - - - - | 386 |
| SEQ_ID_NO_821 | - - - - - - | 386 |
| SEQ_ID_NO_810 | - - - - - - | 391 |
| SEQ_ID_NO_816 | - - - - - - | 398 |
| SEQ_ID_NO_801 | - - - - - - | 389 |
| SEQ_ID_NO_792 | - - - - - - | 359 |
| SEQ_ID_NO_794 | L F I K Y F | 392 |
| SEQ_ID_NO_808 | - - - - - - | 381 |
| SEQ_ID_NO_805 | - - - - - - | 353 |

Figure 26

```
SEQ_ID_NO_1705    MA PPLSSWP WASLG YKYF LLGPLVWKVA QEWAE -QGG AP -LGSRWL    45
SEQ_ID_NO_828     MA APLSSWP WTSLGDYKYA LLGPLAWKVV QEWREDGQGA LP VLGSWWL    48
SEQ_ID_NO_1713    MA PPLSSWP WASLGQYKYV LFGALVWKVV QEWRE -QGG LP -LGSWWL    45
SEQ_ID_NO_824     MAPPPLSSWP WASLGQYKYV LLGPLVWKVL QEWRE -QAG LP -LGSWWL    48

SEQ_ID_NO_1705    HLLLLFSARG LTYQFWFSYS NMLFLTRRRR VVPDGVDFRC VDHEWDW..    92
SEQ_ID_NO_828     HLLLLFVVRG LTYQFWFTYG NMLFFTRRRR VVADGVDFRC DAEWDW..     96
SEQ_ID_NO_1713    HLLVLFAVRG LTYQFWFTYG NMLFFTRRRR VVADGVDFRC DAEWDW..     92
SEQ_ID_NO_824     HLLLLFAARG LTYQFWFSYG NMLFFTRRRR VVADGVDFRC DAEWDWKKI    96

SEQ_ID_NO_1705    .......... .......... .......... ..........              92
SEQ_ID_NO_828     .......... .......... .......... ..........              96
SEQ_ID_NO_1713    .......... .......... .......... ..........              92
SEQ_ID_NO_824     LWIPPPNNQP WSPSDTGNAQ AHLAG GRLF FLRLVPAFG              136
```

Figure 27

| | | | | | | | |
|---|---|---|---|---|---|---|---|
| SEQ_ID_NO_828 | ---MGRKP-- | DAVAKSYHSG | GGGAAASS-- | ---------- | --PRAARKAS | | 31 |
| SEQ_ID_NO_845 | ---MGRKP-- | DPSKPHY--- | GGGAS----- | ---------- | --PRAARRTQ | | 25 |
| SEQ_ID_NO_847 | ---MGRKP-- | DPSKPHY--- | GGGAS----- | ---------- | --PRAARRTQ | | 25 |
| SEQ_ID_NO_832 | -MLSLLSE-- | KPNLALYNQS | NGKHYQYHQN | IYNDWRWWRS | SATQQHRRKV | | 47 |
| SEQ_ID_NO_837 | --MGVVAEVW | RSSVRLLTNS | PQLNGGSHKS | ALWKWRFF-- | --SAQPKRTV | | 44 |
| SEQ_ID_NO_840 | --MKRRKQ-- | RSHEKLFLVL | QIILHTLIF- | ---------- | --KRRRRHH | | 33 |
| SEQ_ID_NO_842 | ---MVLPR-- | RRGGHNHH-- | ---------- | ---------- | --PCPRRAVL | | 21 |
| SEQ_ID_NO_844 | ---MGSRR-- | RRHHHHHG-- | ---------- | ---------- | --PMLVPAVA | | 21 |
| SEQ_ID_NO_839 | MFMAPRRGLL | DGGEDRYGLM | SFGTKDI--- | ---------- | --FTMRRKIR | | 35 |
| SEQ_ID_NO_850 | ---MSEAEKF | IYHRKLMEVK | GISVGESKAE | KLRSY----- | --LVSRSRMK | | 40 |

| | | | | | | | |
|---|---|---|---|---|---|---|---|
| SEQ_ID_NO_828 | PSP------- | VFLGTALFVL | GFVSLFTGHV | VTDADW---- | AR RSRWRPK | | 70 |
| SEQ_ID_NO_845 | PSP------- | VFLGTALFVL | GFVSLFTGHI | VTDADW---- | SR RSRWRSK | | 64 |
| SEQ_ID_NO_847 | PSP------- | VFLGTALFVL | GFVSLFTGHI | VTDADW---- | SR LSRWRSK | | 64 |
| SEQ_ID_NO_832 | PWS------- | LVCGLMLFGL | GLVSLFTGHV | ASDLEW---- | YSQRLVKRSL | | 66 |
| SEQ_ID_NO_837 | MWT------- | WVCGFMLFSL | GVISLFTGHV | VSHLEW---- | YSQQLSKRSL | | 83 |
| SEQ_ID_NO_840 | LLP------- | LAALTGGL | FFFVLFSPPL | TSQHH----- | HL NPIWFNN | | 71 |
| SEQ_ID_NO_842 | PAA------- | ALLLL--FLL | AAVTLLYVSP | PPLSDHPALA | YSRRRSPHAL | | 62 |
| SEQ_ID_NO_844 | PAA------- | AAFAAAGLLL | VVWAFHCFLS | PPLGDGGGGA | RVVRRPNPPF | | 64 |
| SEQ_ID_NO_839 | YWQKQFKQRH | LFGGLMVLLL | MCVITKFILM | NMFSDQ---- | LDLDTAIPSN | | 81 |
| SEQ_ID_NO_850 | LWM------- | IRAVTILLLW | SCVV----HL | MALGEFWG-- | PRLLKGWPSC | | 77 |

| | | | | | | | |
|---|---|---|---|---|---|---|---|
| SEQ_ID_NO_828 | -----QHRNY | EP-------- | --------D | WESKYSSMY | YGCSERSASF | | 99 |
| SEQ_ID_NO_845 | -----QVRNN | EP-------- | --------N | WKSRYSNLY | YGCSRRSVNF | | 93 |
| SEQ_ID_NO_847 | -----QVRNN | EP-------- | --------N | WKSRYSNLY | YGCSRRSVNF | | 93 |
| SEQ_ID_NO_832 | FYSRLEGRRR | EA-------- | --------D | WKSKYSNLF | YGCSERGRNF | | 120 |
| SEQ_ID_NO_837 | ----LDMSRR | EP-------- | --------D | VWKSKYSKFF | YGCSERGRNF | | 113 |
| SEQ_ID_NO_840 | GTELQMNLQK | EH----VFRV | PMGGGSLSGD | WISKQSILY | HGCSNSSYKF | | 117 |
| SEQ_ID_NO_842 | LNSSGGGSLV | EPGRREISRV | PKGGWSATDG | LWGSKLASKF | YGCSNSSSKF | | 112 |
| SEQ_ID_NO_844 | LLKKPAEVAR | SVIGAVDFTV | PSGGSKHGQE | LWESKATGNF | FGCSNATKHF | | 114 |
| SEQ_ID_NO_839 | VVQDEPSPNN | WP-------- | --------TLE | IWKHPNSDNY | FNCMGRAK-- | | 114 |
| SEQ_ID_NO_850 | ---------- | ---------- | --------FN | HHDLPVAAET | ASLPMKA-- | | 97 |

Figure 27 (continued)

| | | | | | | | |
|---|---|---|---|---|---|---|---|
| SEQ_ID_NO_828 | RSAVPENSST | GYLLIATSGG | LNQQRIGITD | AVVVAWLNA | TLVVPELDHH | 149 |
| SEQ_ID_NO_845 | RSAVPENSST | GYLLIGTSGG | LNQQRIGITD | AVVVARILNA | TLVVPELDHH | 143 |
| SEQ_ID_NO_847 | RSAVPENSST | GYLLIGTSGG | LNQQRLGITD | AVVVARILNA | TLVVPELDHH | 143 |
| SEQ_ID_NO_832 | PPAVRERASN | GYLLIAASGG | LNQQRTGITD | AVVVARILNA | TLVVPELDHH | 170 |
| SEQ_ID_NO_837 | LPAVQEQSSN | GYLLIAASGG | LNQQRTGITD | AVVVARILNA | TLVVPELDHH | 163 |
| SEQ_ID_NO_840 | PSADVNTHPN | RYLMIATSGG | LNQQRTGIVD | AVVAAHILNA | VLVVPKLDQK | 167 |
| SEQ_ID_NO_842 | LDSGVMTHPD | RYLMIVTSGG | LNQQRTGIID | AVVAARILNA | TLVVPKLDQT | 162 |
| SEQ_ID_NO_844 | AOAKAVTKLD | RYLMIATSGG | LNQQRTGIID | AVVAARILNA | TLVIPKLDEE | 164 |
| SEQ_ID_NO_839 | KDIRQGNNTN | GYLLVHANGC | LNQMKTGISD | MVAIAKIMNA | TLVFPTLDHN | 164 |
| SEQ_ID_NO_850 | LPPKRVYKNN | GYLMVSCNGC | LNQMRAALCD | MVTLARYMNV | TLIVPELDKT | 147 |

| | | | | | | | |
|---|---|---|---|---|---|---|---|
| SEQ_ID_NO_828 | SFWKDDSDFS | DIFDVEWFIS | HLSKDVTIVK | RIPYEVMLSM | DKLPWTMRAP | 199 |
| SEQ_ID_NO_845 | SFWKDDSDFS | DIFDVDWFIS | YLSKDVTIVK | RIPYEVMMSM | DKLPWTMRAP | 193 |
| SEQ_ID_NO_847 | SFWKDDSDFS | DIFDVDWFIS | YLSKDVTIVK | RIPYEVMMSM | DKLPWTMRAP | 193 |
| SEQ_ID_NO_832 | SYWKDDSDFV | NIFDVDWFIS | YLAKDVTIVK | RVPDKVMRSM | EKPPYTMRVP | 220 |
| SEQ_ID_NO_837 | SYWKDDSDFS | DIFDVNWFIS | SLAKDVTIVK | RVPDRVMRAM | EKPPYTTRVP | 213 |
| SEQ_ID_NO_840 | SYWKDSSNFS | EIFDVDRFIS | HLSKDVKIIR | DIPR--GDK | VITPYTTRVP | 215 |
| SEQ_ID_NO_842 | SFWKDASDFA | EIFNADWFIS | FLSKDVRIVK | ELPK--GGK | LWAPHRMRVP | 210 |
| SEQ_ID_NO_844 | SFWNDASDFA | OIFDVDSFIY | SLSNDVKVIR | QLPD--MNGK | KLSPYKMRIP | 212 |
| SEQ_ID_NO_839 | SFWTDPSDFK | EIFNMKNFVE | VLNEDVCVVE | SLPPELAAIK | P----ALKAP | 210 |
| SEQ_ID_NO_850 | SFWSDPSEFD | DIFDVDHFIT | SLRDEVRLLK | ELPPRLKRRF | ELGMYYSFPP | 197 |

| | | | | | | | |
|---|---|---|---|---|---|---|---|
| SEQ_ID_NO_828 | RK-SMPEFYI | DEVLPILMRR | RALQLTKFDY | RLTSD-LDED | LQKLRCRVNF | 247 |
| SEQ_ID_NO_845 | RK-SMPDFYI | DEVLPILMRR | RALQLTKFDY | RLTNE-LDEE | LQKLRCRVNF | 241 |
| SEQ_ID_NO_847 | RK-SMPDFYI | DEVLPILMRR | RALQLTKFDY | RLTNE-LDEE | LQKLRCRVNF | 241 |
| SEQ_ID_NO_832 | RK-SPPEYYL | DQVLPILLRR | RVVQLTKFDY | RLASN-LDEE | LQKLRCRANY | 268 |
| SEQ_ID_NO_837 | RK-STLEYYL | DQVLPILTRR | HVLQLTKFDY | RLAND-LDED | MQKLRCRVNY | 261 |
| SEQ_ID_NO_840 | RK-CNAKCYQ | TRILPILKKK | HAVQLTKFDY | RLSNR-LDID | MQKLRCRVNF | 263 |
| SEQ_ID_NO_842 | RK-CTQRCYL | NRVLPALVKK | HVVRLTKFDY | RLANR-LDSD | LQKLRCRVNY | 258 |
| SEQ_ID_NO_844 | RK-CTPKCYE | NRVLPALLKK | HVVQLTKFDY | RVSNR-LETD | LQKLRCRVNY | 260 |
| SEQ_ID_NO_839 | VSWSKASYYR | TDMLQLLKKH | KVIKFTHTDS | RLVNNGLASS | IQRVRCRAMY | 260 |
| SEQ_ID_NO_850 | ISWSDISYYB | NQILPLVKKY | KVVHLNKTDT | RLANNGLSLD | LQKLRCRVNF | 247 |

Figure 27 (continued)

| | | | | | | |
|---|---|---|---|---|---|---|
| SEQ_ID_NO_828 | HALKFTSSH | AMGQKLVQKL | RLMNTRYVAI | HLRFEPDMLA | FSGCYYGGGE | 297 |
| SEQ_ID_NO_845 | HALRFTNSQ | TLGEKLVRKL | RSMSSRYVAV | HLRFEPDMLA | FSGCYYGGGD | 291 |
| SEQ_ID_NO_847 | HALRFTNSQ | TLGEKLVRKL | RSMSSRYVAV | HLRFEPDMLA | FSGCYYGGGD | 291 |
| SEQ_ID_NO_832 | HALRFTKPIQ | EIGERLVTKM | RKMAKRYIAI | HLRFEPDMLA | FSGCYFGGGE | 318 |
| SEQ_ID_NO_837 | HALRFTKRQ | SVGMKVYKRM | RKMAKRFIAV | HLRFEPDMLA | FSGCDFGGGE | 311 |
| SEQ_ID_NO_840 | HALKFTDPI | EMGRKLVERI | RMKSKHFVAL | HLRFEPDMLA | FSGCYYGGGD | 313 |
| SEQ_ID_NO_842 | HALRFTDPIQ | EMGEKIIQRV | RERSTYFIAL | HLRFEPDMLA | FSGCYYGGGE | 308 |
| SEQ_ID_NO_844 | HALQFTDPIL | RMGELLVQRM | KEKSGRFIAL | HLRFEPDMLA | FSGCYYGGGD | 310 |
| SEQ_ID_NO_839 | EALRFAVPIE | ELGKKLVNRL | RENNTPYIAL | HLRYEKDMLA | FTGCSHNLTK | 310 |
| SEQ_ID_NO_850 | NALRFTPQE | ELGRRVVRL | REK-GPFLVL | HLRYEMDMLA | FSGCSHGCNP | 296 |

| | | | | | | |
|---|---|---|---|---|---|---|
| SEQ_ID_NO_828 | KERKELGEIR | ---KRWDTLP | ELSAEDERSR | GKCPLTPHEV | GLMLRALGFG | 344 |
| SEQ_ID_NO_845 | KERRELGEIR | ---KRWDTLP | ELSAEDERSR | GKCPLTPQEI | GLMLRALGFS | 338 |
| SEQ_ID_NO_847 | KERRELGEIR | ---KRWDTLP | ELSAEDERSR | GKCPLTPQEI | GLMLRALGFS | 338 |
| SEQ_ID_NO_832 | KERFELGEIR | ---KRWATLP | DLSPDSERER | GKCPLTPHEV | GLMLRALGFA | 365 |
| SEQ_ID_NO_837 | KERAELAEIR | ---KRWDTLP | DLDPLEERKR | GKCPLTPHEV | GLMLRALGFT | 358 |
| SEQ_ID_NO_840 | KETKELGKIR | ---KRWKTLH | ATNPDKERRH | GKCPLTPEEI | GLMLRALGFG | 360 |
| SEQ_ID_NO_842 | KEKRELGVR | ---KRWKTLH | ASNPEKERRH | GRCPLTPEEV | GLMLRALGYR | 355 |
| SEQ_ID_NO_844 | IERRELGEIR | ---KRWKTLH | ASNPDRERRH | GKCPLTPEEV | GLMLRALGFG | 357 |
| SEQ_ID_NO_839 | EETQELKKMR | YSVKHMKE-K | EIDSKSKRLK | GSCPNTPREV | AVFLEALGYP | 359 |
| SEQ_ID_NO_850 | DEEEELTRMR | YAYPWMKE-K | VLNSELKRKD | GLCPLTPEET | ALALNALGD | 345 |

| | | | | | | |
|---|---|---|---|---|---|---|
| SEQ_ID_NO_828 | NDTLLYVASG | EIYGGDSTLQ | PLRGLFPNFY | TKEKLAG-DD | LNPFLPFSSR | 393 |
| SEQ_ID_NO_845 | NDTYLYVASG | EIYGGEETLQ | PLRDLFPNYY | TKEMLAG-ND | LKLFLPFSSR | 387 |
| SEQ_ID_NO_847 | NDTYLYVASG | EIYGGEETLQ | PLRDLFPNYY | TKEMLAG-ND | LKPFLPFSSR | 387 |
| SEQ_ID_NO_832 | NDTYLYVASG | EIYGGEETLR | PLRELFPNFY | TKEMLAL-EE | LKSFFPFSSR | 414 |
| SEQ_ID_NO_837 | NDTYIYVASG | EIYGGEKTLK | PLRELFPNFY | TKEMLAN-DE | LKPLLPYSSR | 407 |
| SEQ_ID_NO_840 | NDVHIYVASG | EIYGGEETLA | PLKALFPNFY | SKETIASKEE | LAPFSSFSSR | 410 |
| SEQ_ID_NO_842 | KNVHIYVASG | DIYGGAKTLA | PLKALFPNLH | TKETVTSKDE | LAPFSKYSSR | 405 |
| SEQ_ID_NO_844 | KDVHLYVASG | DVYGGEETLA | PLKALFPNFH | SKETLASKEE | LAPFLPYSSR | 407 |
| SEQ_ID_NO_839 | VDTKIYVAAG | VIYGSEG-MK | PLQKKFPNLL | WHSSLATKEE | LQPFEGHLNQ | 408 |
| SEQ_ID_NO_850 | RNVQIYIAAG | EIYGGERRMK | ALAEAFPNVV | RKETLLEPSD | LKFFQNHSSQ | 395 |

Figure 27 (continued)

| | | | | | | |
|---|---|---|---|---|---|---|
| SEQ_ID_NO_828 | LAAIDFIVCD ESDVFVTNNN GNMAKVLAGR RRYMGHKRTI RPNAKKLNVL | 443 |
| SEQ_ID_NO_845 | LAAIDFIVCD GSDVFVTNNN GNMAKVLAGR RRYMGHKRTI RPNAKKLNLL | 437 |
| SEQ_ID_NO_847 | LAAIDFIVCD GSDVFVTNNN GNMAKVLAGR RRYMGHKRTI RPNAKKLNLL | 437 |
| SEQ_ID_NO_832 | MAAIDYIVCD ESDVFVTNNN GNMAKILAGR RRYAGHKRTI RPNAKKLSAL | 464 |
| SEQ_ID_NO_837 | LAAIDYIVSD ESDVFITNNN GNMAKILAGR RRYMGHKRTI RPNAKKLSAL | 457 |
| SEQ_ID_NO_840 | MAALDFMVCD ESDVFVSNNN GNMARMLAGR RRYFGHKPTI RPNAKKLYKL | 460 |
| SEQ_ID_NO_842 | MAALDFIVCD GSDAFVTNNN GNMAKILAGR RRYLGHKRTI RPNARKLYSL | 455 |
| SEQ_ID_NO_844 | MAALDFIVCD RSDVFVTNNN GNMARMLAGR RRYFGHRRTI RPNAKKLYSL | 457 |
| SEQ_ID_NO_839 | LAALDYYTV ESDVFVYSYD GNMAKAARGH RKFDGFKKTI SPDKORFVRL | 458 |
| SEQ_ID_NO_850 | MAALDYLVSL ESDIFVPTYD GNMAKVVEGH RRFLGFKKTI LLDRKLLVNL | 445 |

| | | | | | | |
|---|---|---|---|---|---|---|
| SEQ_ID_NO_828 | FQTRNQ-LS WDTFSRKVQR VQRGLMGEPD DI----RPK QDD-FHEFP- | 484 |
| SEQ_ID_NO_845 | FKRRKQ-MG WDIFSQKVKK VQRGLMGEPD DI----RPG RDD-FNEFP- | 478 |
| SEQ_ID_NO_847 | FKRRKQ-MG WDIFSQKVKK VQRGLMGEPD DI----RPG RDD-FNEFP- | 478 |
| SEQ_ID_NO_832 | FKARDR-MD WDTFAKKVKA SQRGFMGEPD EV----RPG RGD-FHEYP- | 505 |
| SEQ_ID_NO_837 | FMDREK-ME WQTFAKKVKS CQRGFMGDPD EF----KPG RGE-FHEYP- | 498 |
| SEQ_ID_NO_840 | FLSRNN--MT WEEFASQVRT SQIGFMGEPM EV----KPG RGE-FHENP- | 501 |
| SEQ_ID_NO_842 | FLSRGN--MS WDAFSSKVHM AQKGFMGEPK EL----RPG RGE-FHENP- | 496 |
| SEQ_ID_NO_844 | FLNRTS--MS WDTFASKVLT FQKGFMGEPN EI----KPG RGE-FHEHP- | 498 |
| SEQ_ID_NO_839 | IDQLDNGLIS WNDFSTKVKS HAKKKGAPQ AR-KIHRHPK FEE-TFYANPF | 507 |
| SEQ_ID_NO_850 | IDQYTEGLLS WDEFSSTVKE VHEDRMGSPK KRLVIPDKPK EEDYFYANPL | 494 |

| | | | | | | |
|---|---|---|---|---|---|---|
| SEQ_ID_NO_828 | SSCICSRK-- ---------- ---------- ---------- ---------- | 492 |
| SEQ_ID_NO_845 | SSCICQR--- ---------- ---------- ---------- ---------- | 486 |
| SEQ_ID_NO_847 | SSCICQR--- ---------- ---------- ---------- ---------- | 486 |
| SEQ_ID_NO_832 | -SCICEKPFT DDENRKGEDL LSDRIHMNLK ENVDSKYVGE NQGDKSLQRL | 554 |
| SEQ_ID_NO_837 | QSCICQRP-- ---------- ---------- ---------- ------FSYD | 510 |
| SEQ_ID_NO_840 | SACICADS-- ---------- ---------- ---------- ---------- | 509 |
| SEQ_ID_NO_842 | TTCICENT-- --------D PKTPTKPNPR SEQGLINGTE GRKAITEPTV | 535 |
| SEQ_ID_NO_844 | MDCICAKA-- ---------- ---------- -NGKIGQSRH HQIKRAGKGA | 525 |
| SEQ_ID_NO_839 | PGCICQK--- ---------- ---------- ---------- ---------- | 514 |
| SEQ_ID_NO_850 | HECLQLL--- ---------- ---------- ---------- ---------- | 501 |

Figure 27 (continued)

| | | | | | | |
|---|---|---|---|---|---|---|
| SEQ_ID_NO_828 | ---------- | ---------- | ---------- | ---------- | ---------- | 492 |
| SEQ_ID_NO_845 | ---------- | ---------- | ---------- | ---------- | ---------- | 486 |
| SEQ_ID_NO_847 | ---------- | ---------- | ---------- | ---------- | ---------- | 486 |
| SEQ_ID_NO_832 | KKRSIEEPIS | LRENKDVTVI | GSANELGLCT | GDRYVKVNGT | CLVASTKSDL | 604 |
| SEQ_ID_NO_837 | KTSTDDEEED | MSEENHNSTS | PGHVHLSS-- | ---------- | ---------- | 538 |
| SEQ_ID_NO_840 | DANDREDASL | FGTHSIISEI | DTGSSTNSAR | RDMVEVTDGQ | ASEEEQEWS- | 558 |
| SEQ_ID_NO_842 | ANHTNEELVG | SSAEEDDASV | EKEDDTSAEK | EDDTSEEKEE | IADPEAEDDA | 585 |
| SEQ_ID_NO_844 | ENHSSDGDLD | WRDLDYGEHT | PLGRDSSNES | ESDDIRVGGS | ---------- | 565 |
| SEQ_ID_NO_839 | ---------- | ---------- | ---------- | ---------- | ---------- | 514 |
| SEQ_ID_NO_850 | ---------- | ---------- | ---------- | ---------- | ---------- | 501 |

| | | | |
|---|---|---|---|
| SEQ_ID_NO_828 | -------PG | NISATT---- | 500 |
| SEQ_ID_NO_845 | -------PV | NRSVTARAEN | 499 |
| SEQ_ID_NO_847 | -------PV | NRSVTARAEN | 499 |
| SEQ_ID_NO_832 | LCHHVLSFST | PFLDETGSGM | 625 |
| SEQ_ID_NO_837 | -------AD | NERDEVFPD- | 549 |
| SEQ_ID_NO_840 | -------DT | EYMETELEI- | 569 |
| SEQ_ID_NO_842 | LVRP----DD | PELEEVLSD- | 600 |
| SEQ_ID_NO_844 | -------DI | PELEDMMSD- | 576 |
| SEQ_ID_NO_839 | -------PT | HLMAETNHES | 527 |
| SEQ_ID_NO_850 | -------DE | PLRTTRLSMF | 514 |

Figure 28

| | | | | | | | | |
|---|---|---|---|---|---|---|---|---|
| SEQ_ID_NO_876 | ----MGPVVL | TQLATGLGML | AGAALVKSVM | DQN--TMMGP | GSD---RF-- | | | 39 |
| SEQ_ID_NO_855 | ----MSPIVI | TQLATGISVL | AGAVFIKSVM | DQK-----P | MAG---QF-- | | | 35 |
| SEQ_ID_NO_862 | ----MGPIVL | TQLATGLSVL | AGAVLVKSVM | DQK-----P | MAG------ | | | 33 |
| SEQ_ID_NO_858 | ----MVPIVL | TQMATGLGVL | AGAVFVKSVM | DQK-----P | MAG---PF-- | | | 35 |
| SEQ_ID_NO_856 | ----MFPAVL | TQVATGLSVL | AGAVLVKSVM | DQK-----P | MAG---PF-- | | | 35 |
| SEQ_ID_NO_885 | MVVVVAPIAV | A--SAGLGML | AGVAMASRSS | NSSSSSGRTS | SPAALLRWGA | | | 48 |
| SEQ_ID_NO_868 | ---MVSPVVI | A--SAGLGML | AGVALASRGT | GDG-----LP | ASS---RWDA | | | 37 |
| SEQ_ID_NO_886 | ---MVGPIVI | A--SAGLGML | AGVAMANRTM | GGGGDGRQLP | AAS---RWDA | | | 42 |
| SEQ_ID_NO_870 | ---MVAPVVI | A--SAGLGML | AGVAMANRSL | GNG-----LP | AAS---RWDA | | | 37 |
| SEQ_ID_NO_878 | ---MVAPVYI | T--SAGLGML | AGLAMANRSL | GDG-----LP | AAS---RWDA | | | 37 |

| | | | | | | | | |
|---|---|---|---|---|---|---|---|---|
| SEQ_ID_NO_876 | ----PRCSRC | NGTGRVSC-L | CNRWSD--GD | -RGCRTCAGS | GRMVCSSCGG | | | 81 |
| SEQ_ID_NO_855 | ----PRCPTC | NGTGRVTC-F | CSRWSD--GD | -VGCRRCSGS | GRAACSNCGG | | | 77 |
| SEQ_ID_NO_862 | ----PLCPSC | NGTGRVAC-L | CSRWSD--GD | -AGCRACSGS | GRMACSSCGG | | | 75 |
| SEQ_ID_NO_858 | ----QRCPTC | NGTGRVSC-L | CSRWSD--GD | -VGCRTCSGS | GRRACSSCGG | | | 77 |
| SEQ_ID_NO_856 | ----QRCPTC | NGTGRITC-L | CTRWSD--GD | -IGCRTCAGS | GRMACSSCGG | | | 77 |
| SEQ_ID_NO_885 | PEPAPRCAAC | GGTGREECRL | CARWSDARGD | CSGCRACAGT | RRAPCRSCGG | | | 98 |
| SEQ_ID_NO_868 | R---PRCSTC | SGTGREEC-L | CSRWSD--GD | -VGCGTCSGS | GRKRCRSCGG | | | 80 |
| SEQ_ID_NO_886 | R---PRCATC | GGSGRVDC-L | CNRWSD--GD | -SGCRTCAGS | GRMPCRSCGG | | | 85 |
| SEQ_ID_NO_870 | R---PRCATC | GGSGRVEC-L | CNRWSD--GD | -SGCRTCAGS | GRMPCRSCGG | | | 80 |
| SEQ_ID_NO_878 | R---PRCATC | GGSGRVEC-L | CNRWSD--GD | -SGCRTCAGS | GRMPCRSCGG | | | 80 |

| | | | | | |
|---|---|---|---|---|---|
| SEQ_ID_NO_876 | TGTGRPLPVQ | SVR------ | ---PPNQS-- | ---Y- | 101 |
| SEQ_ID_NO_855 | SGTGRPLPAQ | TVQ------ | ---PPNRP-- | ---Y- | 97 |
| SEQ_ID_NO_862 | TGTGRPIPVQ | SMR------ | ---SPNRP-- | ---PS | 96 |
| SEQ_ID_NO_858 | SGTGRPIPVQ | LIVR------ | ---QPTNR-- | --SF | 98 |
| SEQ_ID_NO_856 | SGTGRPIPVQ | SVR------ | ---QPTNR-- | ---NS | 98 |
| SEQ_ID_NO_885 | SGTGRRAPVR | VSSS------ | ---APPSR-- | ------ | 117 |
| SEQ_ID_NO_868 | SGTGRPLPAR | LVQ------ | EQKLPTAPGR | RGDYN | 109 |
| SEQ_ID_NO_886 | SGTGRPLPAR | LLARGHHHHHH | NPPPSSAPGR | GGDYS | 120 |
| SEQ_ID_NO_870 | SGTGRPLPAR | LTVQ---HQ | KPPPPPPG- | ---YN | 107 |
| SEQ_ID_NO_878 | SGTGRPLPAR | LTVQ---HH | K--PPPPAG- | ---YN | 105 |

Figure 29

```
SEQ_ID_NO_907  ------MAV- ---------D SMHVVMFPFL AFGHISPFVQ LARKLVAAG-  33
SEQ_ID_NO_912  ---MAAAVVE AD------DE AMHVALFPFL AFGHISPFAQ LARSLGAVG-  40
SEQ_ID_NO_911  MGSAGAAPVA TAAGGGGGDG DLHVVMFPFL AFGHISPFAQ LARKMAGVGA  50
SEQ_ID_NO_896  ----MPSELA MN-----ND ELHVVMFPFL AFGHISPFVQ LSNKLFSH--  38
SEQ_ID_NO_913  ------MSLK GN-----DK ELHLVMFPFF AFGHITPFVQ LSNKISSLYP  38
SEQ_ID_NO_901  ----MENEMK HS-----ND ALHVVMFPFF AFGHISPFVQ LANKLSSY--  38
SEQ_ID_NO_915  ----MENE-- --------K VLHVVMFPFF AFGHISPFAQ LANKLSSH--  33
SEQ_ID_NO_904  ---MGSQA-- ---------T THHMAMYPWF GVGHLTAFFR LANKLASK--  34
SEQ_ID_NO_905  ---MGSQA-- ---------T TYHMAMYPWF GVGHLTGFFR LANKLAGK--  34
SEQ_ID_NO_908  ---MGSQA-- ---------T TYHMAMYPWF GVGHLTGFFR LANKLAGK--  34
SEQ_ID_NO_891  ------ME-- ---------P TFHAFMFPWF AFGHMIPFLH LANKLAEK--  31
SEQ_ID_NO_893  MSDLISKR-- ---------S SFRILMFPWF AVGHLTPFLH LSNKLAEK--  37

SEQ_ID_NO_907  GVRVTLLSAA ANVPRVEAML GPAAGAV--A VAPLRLQRVP GLPEGAESTA  81
SEQ_ID_NO_912  GVRVTFLSAA ANVARVEAML PADGTAV--- VAALHLPRVP GLPVGAESTA  87
SEQ_ID_NO_911  GVRVTFLSAA ANVPRVEAML GGTGGTS--T VAALELPRVP GLPEGAESTA  98
SEQ_ID_NO_898  GVHNTFLSAA SNIPRIRSTL NLNPAIN--- VISLKFPN-- ----GITNTA  79
SEQ_ID_NO_913  GVKITFLAAS ASVSRIETML NPSTNTK--- VIPLTLPRVD GLPEGVENTA  85
SEQ_ID_NO_901  GVKVSFFTAS GNASRVKSML NSAPTTH--- -VPLTLPHVE GLPPGAESTA  85
SEQ_ID_NO_915  GVKVSFFTAS GNASRLRSML NSAPTTTHID LVPLTLPHVE GLPPGSESTA  83
SEQ_ID_NO_904  GHRISFLIPK NTQSKLASIF NLHPHLV--S FVPITVPSIP GLPPGAETTS  81
SEQ_ID_NO_905  GHRISFLIPK NTQSKLESIF NLHPHLI--S FVPIVVPSIP GLPPGAETTS  81
SEQ_ID_NO_908  GHRISFLIPK NTQSKLESIF NLHPHLI--S FVPIVVPSIP GLPPGAETTS  81
SEQ_ID_NO_891  GHQITFLLPK KAQKQLEH-H NLFPDSI--V FHPLTIPHVN GLPAGAETTS  78
SEQ_ID_NO_893  GCTISFLLPN KAIKLLQH-F NLYPDHI--T FHPVKVPHVE GLPLGTETAS  84

SEQ_ID_NO_907  EVSADGAELL KVAVDGTRPQ VAALLAELRP DALLFDFATP WVTELAAPLR  131
SEQ_ID_NO_912  EVDADGAELL KLALDGTRPQ VEALLARLRP DVVLFDFATP WVADVARQLG  137
SEQ_ID_NO_911  EVSADGAELL KLAVDGTRPQ VEALLARLRP DVVLFDFATP WVDVARPLG   148
SEQ_ID_NO_898  ELPPHLAGNL IHALDLTQDQ VKSLLLELKP HYVFFDFAQH MLPKLASEVG  129
SEQ_ID_NO_913  DASPATIGLL VVAIDLMQPQ KTLLANLKP  DFVIFDFVHW MLPEIASELG  135
SEQ_ID_NO_901  ELTPASAELL KVALDLMQPQ KTLLSHLKP  HFVLFDFAQE MLPKMANGLG  135
SEQ_ID_NO_915  ELTPVTAELL KVALDLMQPQ KTLLSHLKP  HFVLFDFAQE MLPKMADELG  133
SEQ_ID_NO_904  DVPFSSTHLL MEAMDKTQTD EIILKNLEV  DVVFFDFTH- MLPGLARKIG  130
SEQ_ID_NO_905  DVPFPSTHLL MEAMDKTQND EIILKDLKV  DVVFYDFTH- MLPSLARKIG  130
SEQ_ID_NO_908  DVPFPSTHLL MEAMDKTQND EIILKDLKV  DVVFYDFTH- MLPSLARKIG  130
SEQ_ID_NO_891  DISISMDNLL SEALDLTRDQ VEAAVRALRP DLIFFDFAH- MPEIAKEHM   127
SEQ_ID_NO_893  DIPIHLTHFL CVAMDRTRDQ VEKIIRDQKP DFVMYDMAY- MPEVARPLG   133
```

Figure 29 (continued)

| | | | | | | | |
|---|---|---|---|---|---|---|---|
| SEQ_ID_NO_907 | IKALQFSVFS | AVSGAYLMNP | ARRLGAGGQL | --PTADDLTS | PPAGFPPSSS | | 179 |
| SEQ_ID_NO_912 | ARAAHFSVFT | AVTSAYLTVP | ARRRLHHGAA | SCPTVDDLAT | APVGFPPSSS | | 187 |
| SEQ_ID_NO_911 | VKAALFSVFA | AVSGAYVMAP | ARRRLPGPWR | --PTVDDLAS | APEGFPPSSP | | 195 |
| SEQ_ID_NO_898 | IKSVHFSVYS | AISDAYITVP | SRFADVEGRN | --ITFEDLKK | PPPGYPQNSN | | 177 |
| SEQ_ID_NO_913 | IKTIYFSVYM | ----ANIVMP | STSKLTGNKP | --STVEDIK- | ---ALQQSDG | | 175 |
| SEQ_ID_NO_901 | IKTVYYSVVV | ALSTAFLTCP | ARVLE-PKKY | --PSLEDMKK | PPLGFPQTSV | | 182 |
| SEQ_ID_NO_915 | IKTVFYSVFV | ALSTAFLTCP | ARVTE-PKKY | --PTLEDMKK | PPLGFPHTSI | | 180 |
| SEQ_ID_NO_904 | IKSVFYSTIS | PLMHGFALSP | ERRVA--GKQ | --LTEADMMK | APASFPDPSI | | 176 |
| SEQ_ID_NO_905 | IKSVFYSTIS | PLMHGYALSP | ERRVV-GKQ | --LTEADMMK | APASFPDPSI | | 176 |
| SEQ_ID_NO_908 | IKSVFYSTIS | PLMHGYALSP | ERRVV-GKQ | --LTEADMMK | APASFPDPSI | | 176 |
| SEQ_ID_NO_891 | IKSVSYMVS | ATTIAYTFAP | G--------- | -----GVLGV | PPPGYPSSKV | | 163 |
| SEQ_ID_NO_893 | IKTIKYSVVS | AAAIAIVLVP | ARNVV-EGKA | --ITAAELSV | PPTGYPSTSV | | 180 |

| | | | | | | | |
|---|---|---|---|---|---|---|---|
| SEQ_ID_NO_907 | ITVPAYQAA | DFSYVFTSFH | GEP-CVYDRV | LAGVQASDAL | VIKTCFEMEG | | 228 |
| SEQ_ID_NO_912 | LATVPTYQAA | DFTYVFTSFH | GMP-SAYDRV | AACDKASDVL | VFKTCAEMEG | | 236 |
| SEQ_ID_NO_911 | LATVPAYQAA | DFSYVFESFH | GMP-CVYDRV | AACHNACDAL | VIKTCAEMEG | | 245 |
| SEQ_ID_NO_898 | I-SLKAFEAM | DFMFLFTRFG | EKNLTGYERV | LQSLGECSFI | VFKTCKEIEG | | 226 |
| SEQ_ID_NO_913 | I-PVKTFEAI | SLMNVFKSFH | -------DRM | DKCINGCNLM | LIKSCREMEG | | 217 |
| SEQ_ID_NO_901 | T-SVRTFEAR | DFLYVFKSFH | NGP-TLYDRI | QSGLRGCSAI | LAKTCSQMEG | | 230 |
| SEQ_ID_NO_915 | T-SVKTFEAQ | DFLYIFKSFN | NRP-TVYDRV | LSGLKGCSAI | LAKTCSQMEG | | 228 |
| SEQ_ID_NO_904 | K--LHAHEAR | GFTARTVMKF | GGDITFFDRI | FTAVSESDGL | AYSTCREIEG | | 224 |
| SEQ_ID_NO_905 | K--LHAHEAR | GFTARTVMKF | GGDITFFDRI | FTAVSESDGL | AYSTCREIEG | | 224 |
| SEQ_ID_NO_908 | K--LHAHEAR | GFTARTVMKF | GGDITFFDRI | FTAVSESDGL | AYSTCREIEG | | 224 |
| SEQ_ID_NO_891 | L--YRENDAH | ALATLSIFYK | ----RLYHDI | TTGFKSCDI | ALRTCNEIEG | | 207 |
| SEQ_ID_NO_893 | V--LRGHEVR | SLLFVSQPYG | EGT-TFYERA | CIGMKGCDAI | AIRSCYEMEE | | 227 |

| | | | | | | | |
|---|---|---|---|---|---|---|---|
| SEQ_ID_NO_907 | PYINYLTAQH | GKPVLVTGPV | VPEPPQGE-L | EERWARMLSS | FPDNAVVFAS | | 277 |
| SEQ_ID_NO_912 | PYIEYVATQY | DKPILVTGPL | VPEPPHGE-L | EERWETMLSS | FPDNAVVFAS | | 285 |
| SEQ_ID_NO_911 | PYIDYIAAEH | GKPVLVTGPI | VPEPPRGE-L | EERWATMLSS | FPDNSVVFAS | | 294 |
| SEQ_ID_NO_898 | PYLDYIETQF | RKPVLLSGPL | VPEPSTDV-L | EEKWSKMLDG | FPAKSVILCS | | 275 |
| SEQ_ID_NO_913 | SRIDDVTKQS | TRPVFLTGPV | VPEPHSGE-L | DETWANMLNR | FPAKSVIYCS | | 266 |
| SEQ_ID_NO_901 | PYIKYVEAQF | NKPVFLIGPV | VPDPPSGK-L | EEKWATMLNK | FEGGTVIYCS | | 279 |
| SEQ_ID_NO_915 | PYIEYVKSQF | KKPVLLVGPV | VPDPPSGK-L | EEKWDAMLNK | FEAGTVIYCS | | 277 |
| SEQ_ID_NO_904 | QFCDYIETQF | KKPVLLAGPA | LPVPSKST-M | EQKWSDMLGK | FKEGSVIYCA | | 273 |
| SEQ_ID_NO_905 | QFCDYIETQF | QKPVLLAGPA | LPVPSKST-M | EQKWSDMLGK | FKEGSVIYCA | | 273 |
| SEQ_ID_NO_908 | QFCDYIETQF | QKPVLLAGPA | LPVPSKST-M | EQKWSDMLGK | FKEGSVIYCA | | 273 |
| SEQ_ID_NO_891 | KFCDYISSQY | HKKVLLTGPM | LPEQDTSKPL | EEQLSHFLSR | FPPRSVVFCA | | 257 |
| SEQ_ID_NO_893 | KLCDYIGRQY | GKPVFLTGPV | LPESARTP-L | EDRWAQMLNR | FEAGSVVFCS | | 276 |

Figure 29 (continued)

| SEQ_ID_NO_907 | FGSETFLPAA AATELLLGLE STNRPFFVVL NFPKGTDTEA ELAKCTPPGF | 327 |
| SEQ_ID_NO_912 | FGSETFLPTA AATELLLGLE ATGQPFVAVL NFPRSVDAEA EVKKCMAPGF | 335 |
| SEQ_ID_NO_911 | FGSETFLLHA AATELLLGLE ATALPFLAVL NFPKGTDAEA ELRKLTPPGL | 344 |
| SEQ_ID_NO_898 | FGSETFLSDY QIKELASGLE LTGLPFILVL NFPSNLSAKA ELERALPKGY | 325 |
| SEQ_ID_NO_913 | FGSETFLTDD QIRELALGLE LTGLPFFLVL NFPANVDKSA ELKRTLPDGF | 316 |
| SEQ_ID_NO_901 | FGSETFLTDD QVKELALGLE QTGLPFFLVL NFPANVDVSA ELNRALPEGF | 329 |
| SEQ_ID_NO_915 | FGSETFLKDD QIKELALGLE QTGLPFFLVL NFPANVDASA ELNRGLPEGF | 327 |
| SEQ_ID_NO_904 | FGSECTLRKE QFQELLMGLE LTGMPFFAAL KAPFGTDS-- -IEAAIPEEL | 320 |
| SEQ_ID_NO_905 | FGSECTLRKD KFQELLMGLE LTGMPFFAAL KPPFETES-- -VEAAIPEEL | 320 |
| SEQ_ID_NO_908 | FGSECTLRKD KFQELLMGLE LTGMPFFAAL KPPFEAES-- -IEAAIPEEL | 320 |
| SEQ_ID_NO_891 | LGSQIVLEKD QFQELCLGME LTGLPFLIAV KPPRGSST-- -VEEGLPEGF | 304 |
| SEQ_ID_NO_893 | FGSQLILEKE QLQELVLGFE STGLPFLVVL KPPVGSST-- -IEEALPEGF | 323 |

| SEQ_ID_NO_907 | AERTKGRGVV HTGWQQQHI LRHRGVGCFV NHAGLSSVVE GLVAGCRLVL | 377 |
| SEQ_ID_NO_912 | EERVKGRGVV HSGWQQQHI LRHRGYGCYV NHAGFSSVVE GLVAGCRLVL | 385 |
| SEQ_ID_NO_911 | EERVKGRGIL HTGWQQQHI LRHRBVGCFV NHSGLSSVVE GLIAGCRLVL | 394 |
| SEQ_ID_NO_898 | LERVKNRGVV HSGWFQQQLV LKHSGVGCYV CHGGFSSVIE AMVNECQLVL | 375 |
| SEQ_ID_NO_913 | LERVKDKGIV HSGWQQRHI LAHDGVGCYV FHAGYGSVIE GLVNDCQLVM | 366 |
| SEQ_ID_NO_901 | LERVKDKGII HSGWQQQNI LAHSGVGCYV CHAGFSSVIE ALVNDCQVVM | 379 |
| SEQ_ID_NO_915 | RERVKEKGVI HSGWQQQHI LAHTSVGCYV CHAGFSSVIE AFMNDCQVVM | 377 |
| SEQ_ID_NO_904 | REKIHGKGIV HGGWQQQLF LQHPGVGCFV SHCGWASLSE ALVNDCQIVL | 370 |
| SEQ_ID_NO_905 | KEKIQGRGIV HGEWQQQLF LQHPGVGCFV SHCGWASLSE ALVNDCQIVL | 370 |
| SEQ_ID_NO_908 | KEKIQGRGIV HGEWQQQLF LQHPGVGCFV SHCGWASLSE ALVNDCQIVL | 370 |
| SEQ_ID_NO_891 | QERVKGRGVV WGGWQQPLI LDHPSIGCFV NHCGPGTIVE CLMTDCQMVL | 354 |
| SEQ_ID_NO_893 | EERVKGRGVV WGGWQQLEI LDHPSIGCFV NTCGFGSMAE SLMSDCQIVL | 373 |

| SEQ_ID_NO_907 | LPMKGDQYLN AALFARDLRV GAEVARRDGD GWFGRGDVSD AVDTAMAD-- | 425 |
| SEQ_ID_NO_912 | LPMKSDQFFN AALLARELRV GTEVARRDGD GWFGHDAVRD AVNAAVAD-- | 433 |
| SEQ_ID_NO_911 | LPMKGDQYLN AALFARELRV GTEVARRARD GWFGREDVRD ALAAAFAG-- | 442 |
| SEQ_ID_NO_898 | LPFKGDQFFN SKLIANDLKA GVEVNRSDED GFFHKEDILE ALKTVMLEDN | 425 |
| SEQ_ID_NO_913 | LPMKVDQFTN SKVIALELKA GVEVNRRDED GYFGKDDVFE AVESVMNDTE | 416 |
| SEQ_ID_NO_901 | LPQKGDQILN AKLVSGDMEA GVEINRRDED GYFGKEDIKE AVEKVMVDVE | 429 |
| SEQ_ID_NO_915 | LPQKGDQLLN AKLVSGDMKA GVEVNRRDED GYFSKDDIEE AVEKVMVEL- | 425 |
| SEQ_ID_NO_904 | LPQVGDQIIN ARIMSVSLKV GVEVEKGEED GVFSRESVCK AVKAVM-DEK | 419 |
| SEQ_ID_NO_905 | LPQVGDQIIN ARIMSVSLKV GVEVEKGEED GVFSRESVCK AVKAVM-DEK | 419 |
| SEQ_ID_NO_908 | LPQVGDQIIN ARIMSVSLKV GVEVEKGEED GVFSRESVCK AVKAVM-DEK | 419 |
| SEQ_ID_NO_891 | LPFLGDQVLF TRLMTEEFKV SVEVSR-EKT GWFSKEBLSD AIKSVM-DKD | 402 |
| SEQ_ID_NO_893 | VPHLGDQILN TRLMAEELKV AVEVER-DEK GWFTKENLSN AIKCVM-DKD | 421 |

Figure 29 (continued)

| | | | | | | | |
|---|---|---|---|---|---|---|---|
| SEQ_ID_NO_907 | ---GMEGQG- | -IKWRDFLMD | DAVQKRLADD | FVRDFKKFVR | A--- | 461 |
| SEQ_ID_NO_912 | ---AGGGDDD | ERKWREFLTD | DAVQRRFVEE | FVRELRKLVL | ---- | 470 |
| SEQ_ID_NO_911 | ---GEDGGGE | EKKWREFLMD | DAVQRRFVRE | FVAGLRRLKG | ---- | 479 |
| SEQ_ID_NO_898 | KEQGKQIREN | HMQWSKFLSN | KEIQNKFITD | LVAQLKSMA- | ---- | 464 |
| SEQ_ID_NO_913 | NEPAKSIREN | HRKLKEFLQN | DEIQKKYIAD | FVENLKAL-- | ---- | 454 |
| SEQ_ID_NO_901 | KDPGKLIREN | QKKWKEFLLN | KDIQSKYIGN | LVNEMTAMAK | VSTT | 473 |
| SEQ_ID_NO_915 | ----KVIREN | QKKWKEFLLN | KDTHSKFVED | LVHDMMAMAK | LSTT | 465 |
| SEQ_ID_NO_904 | SEIGREVRGN | HDKLRGFLLN | ADLDSKYMDS | FNQKLQDLLG | ---- | 459 |
| SEQ_ID_NO_905 | SEIGREVRGN | HDKLRGFLMN | ADLDSKYMDS | FNQKLQDLLG | ---- | 459 |
| SEQ_ID_NO_908 | SEIGREVRGN | HDKLRGFLLN | ADLDSKYMDS | FNQKLQDLLG | ---- | 459 |
| SEQ_ID_NO_891 | SDLGKLVRSN | HAKLKETLGS | HGLLTGYVDK | FVEELQEYLI | ---- | 442 |
| SEQ_ID_NO_893 | SEVGSMKKN | HTEWRKLLRS | EGFMSSYFDK | FFQNMQELVD | HK-- | 463 |

Figure 30

| | | | | | | | |
|---|---|---|---|---|---|---|---|
| SEQ_ID_NO_935 | MAY--DRRRS | -SLEDAFTLS | PLPYPVLLIL | LMVFLLLSLS | WFFDHESFME | 47 |
| SEQ_ID_NO_917 | MSYYGDRRAE | SSIVEAFTLS | PLPYPVILVL | LMVTLLLGAS | WFFTYDDFIE | 50 |
| SEQ_ID_NO_925 | MSYY-DRRGE | SSVLEAFTLS | PLPYPVILIL | MMVTLLLGAS | WFFSYEDFME | 49 |
| SEQ_ID_NO_940 | MAY--QRGET | SSVVEAFTLS | PLPYPVILIL | LMVMLLGVS | WFFTYEDFME | 48 |
| SEQ_ID_NO_937 | MAYYGDRRPE | SSIVEAFTLS | PLPYPVILIL | LMVSLLLGVS | WFFTYEDFIE | 50 |
| SEQ_ID_NO_921 | MAY--EERRS | -SILDSFSLS | PLPYPVLLIL | AVASVFLSS | WYFSLEEAAE | 47 |
| SEQ_ID_NO_919 | MHY--YRRRS | DSIFDAFTLN | PLPYPVLLIL | AVLSIFLGMS | WFFSYEDMVE | 48 |
| SEQ_ID_NO_923 | MGY--GRSRA | SSVLDGFSLN | PVPYPVLLIL | SLILFLGIS | WYLSYEEVVE | 48 |

| | | | | | | | |
|---|---|---|---|---|---|---|---|
| SEQ_ID_NO_935 | ETEEQMSWVL | LTLPVVLILV | RWLSSIERL | DDTLMGLFRY | DRRRPSVYGY | 97 |
| SEQ_ID_NO_917 | EASQQLSWAL | LGVPIALVLL | RWISSVDSF | EGYLGFYPR | ESRWKGRYE- | 98 |
| SEQ_ID_NO_925 | EASEQFSWFL | LGVPIALVLL | RWISSVDTF | EGYFGFYPT | ESRWRG-YP- | 96 |
| SEQ_ID_NO_940 | EAAEQLSWAL | LLVPVALVLL | RWISSVDTF | DGYFSFYPT | ERRWNRVDP- | 96 |
| SEQ_ID_NO_937 | EAAEQFSWAL | LVVPIALVLL | RWISSVDSF | DGYFFGFYPS | ERRWRPGVG- | 99 |
| SEQ_ID_NO_921 | SAEEQINFAL | LLIPLFLIVL | VRWLSSMENP | DAL-LGMFSS | SRRTTYVSPG | 96 |
| SEQ_ID_NO_919 | TTEEQMGWML | LVVPLVLIVI | VRWLSSMENP | DMI-FVMSPW | DKRRRTHHR- | 96 |
| SEQ_ID_NO_923 | AAEEQLGWML | LATPVVLILV | VRWLSSVDTS | EMFFFNSSPW | ERRRRTHHF- | 97 |

| | | | | | | | |
|---|---|---|---|---|---|---|---|
| SEQ_ID_NO_935 | SDPQEGSSPW | GIAAVLVLLL | VMVYF----- | ---------- | ---------- | 122 |
| SEQ_ID_NO_917 | RGPAEGSSPW | GVALLVLLLL | VLARAGCGKV | VYGNPGRLGR | KRRGGDKVKE | 148 |
| SEQ_ID_NO_925 | AAPSEGSSPW | GVAMVVVLLL | LLASF----- | ---------- | ---------- | 121 |
| SEQ_ID_NO_940 | -GPAEGSSPW | GVAMVVLLLL | VLASF----- | ---------- | ---------- | 120 |
| SEQ_ID_NO_937 | SAPAEGSSPW | GVAMLVLLLI | VLASF----- | ---------- | ---------- | 124 |
| SEQ_ID_NO_921 | AGGDQGSSPW | GVAALIVLLL | VLLQY----- | ---------- | ---------- | 121 |
| SEQ_ID_NO_919 | --PSEGSSPW | GVAAFIVLLL | VLVKF----- | ---------- | ---------- | 119 |
| SEQ_ID_NO_923 | --PSEGSSPW | GVAALILLVL | VLLHY----- | ---------- | ---------- | 120 |

| | | | | | | | |
|---|---|---|---|---|---|---|---|
| SEQ_ID_NO_935 | ---HSSIQDM | AGP------- | ---------- | ---------- | ---------- | 132 |
| SEQ_ID_NO_917 | QAGDEAAKFP | ASGMRLATEK | RRRVRRSPSK | KGIVLKQKSR | KVSLQHRSKK | 198 |
| SEQ_ID_NO_925 | ---HSTFQDM | AKP------- | ---------- | ---------- | ---------- | 131 |
| SEQ_ID_NO_940 | ---HSTFQDM | AKP------- | ---------- | ---------- | ---------- | 130 |
| SEQ_ID_NO_937 | ---HETIRDM | ARP------- | ---------- | ---------- | ---------- | 134 |
| SEQ_ID_NO_921 | ---QSSFLEM | ASG------- | ---------- | ---------- | ---------- | 131 |
| SEQ_ID_NO_919 | ---QSTFLDS | ALV------- | ---------- | ---------- | ---------- | 129 |
| SEQ_ID_NO_923 | ---HSTFLDA | AFV------- | ---------- | ---------- | ---------- | 130 |

Figure 30 (continued)

| | | |
|---|---|---|
| SEQ_ID_NO_935 | - - - | 132 |
| SEQ_ID_NO_917 | L K A | 201 |
| SEQ_ID_NO_925 | - - - | 131 |
| SEQ_ID_NO_940 | - - - | 130 |
| SEQ_ID_NO_937 | - - - | 134 |
| SEQ_ID_NO_921 | - - - | 131 |
| SEQ_ID_NO_919 | - - - | 129 |
| SEQ_ID_NO_923 | - - - | 130 |

Figure 31

| | | | | | | | |
|---|---|---|---|---|---|---|---|
| SEQ_ID_NO_947 | MGI KFSQGPS | NTTI HNRS- - | -HQDGEDQRN | ETATKL NHDK | PQNQSS- -SF | | 45 |
| SEQ_ID_NO_972 | MGSL- GPSTI | SSMNMAKAAS | VVGGKTGVVA | VADQQKEVPP | KTMNCSSYAF | | 49 |
| SEQ_ID_NO_967 | MGSL- GPAVV | VSASAAKM- - | - - -AGGGQQP | STERKETSSA | FGGGCCGGGF | | 44 |
| SEQ_ID_NO_964 | MGSLL GPTVT | VNVSMTKPDA | AAAGGGQQPP | - -ERKEGGGR | CGVLGC- -GF | | 46 |
| SEQ_ID_NO_944 | MGSL- GPTVS | LSI -MARP- - | - - - -GGQQPA | EMERKKDSGV | FFGGGC- -GF | | 40 |
| SEQ_ID_NO_946 | - - -MSGVSCP | SSVSSAMP- - | - - - - -KDLRP | NGYNQHDASK | RGTCSC- - -F | | 37 |
| SEQ_ID_NO_962 | MGSI SQPVAN | LSLAASAQ- - | - - - - - - - - - - | - -AKQQQRDL | H- - - -C- - -F | | 29 |
| SEQ_ID_NO_950 | MESVTTRPSP | NVVGVANS- - | - - - - - - - - - - | - - - - - - - - -K | HGVEWCG- HF | | 28 |

| | | | | | | | |
|---|---|---|---|---|---|---|---|
| SEQ_ID_NO_947 | QI PLHYPKYT | KSDYEKMPEW | QLDRLLREYG | LPVLGDSYEK | RKFAI GAFLW | | 95 |
| SEQ_ID_NO_972 | QMPLHYPRYK | KADYESMPEW | RVDCLLREYG | LPADGDLDSK | RKFAMGAFLW | | 99 |
| SEQ_ID_NO_967 | QMPLHYPRYK | KADYEAMPEW | RVDCLLREYG | LPVDGGVEEK | RRFAMGAFLW | | 94 |
| SEQ_ID_NO_964 | RMPLHYPRYK | KEDYEGMPEW | RVDSLLREYG | LPADGDLDSK | RRFAMGAFLW | | 95 |
| SEQ_ID_NO_944 | RMPLHYPRYK | KADYESMPEW | RVDCLLREYG | LPADGDVDSK | RRFAMGAFLW | | 90 |
| SEQ_ID_NO_946 | QMPLHYPRYK | KSDYETMPEW | RLDCLLKEYG | LPAI GDANQK | RKFAMGAFLW | | 87 |
| SEQ_ID_NO_962 | RMPLHYPRYT | RADYESMPEW | KLDCLLREYG | LPVTGDVDHK | RSFAMGAFLW | | 79 |
| SEQ_ID_NO_950 | QMPLHYPRYT | QADYEAMPEW | RLDCLLKEYG | LPI FGDVESK | RKFAMGAFLW | | 78 |

| | | |
|---|---|---|
| SEQ_ID_NO_947 | SSENEH | 101 |
| SEQ_ID_NO_972 | PDQY- - | 103 |
| SEQ_ID_NO_967 | PDQY- - | 98 |
| SEQ_ID_NO_964 | PDQY- - | 100 |
| SEQ_ID_NO_944 | PDQY- - | 94 |
| SEQ_ID_NO_946 | PSENE- | 92 |
| SEQ_ID_NO_962 | PAH- - - | 82 |
| SEQ_ID_NO_950 | I K- - - - | 80 |

Figure 32

```
SEQ_ID_NO_976    ------MALH LNTVIDLTVD NYVLFRIPPI TIDFLNKLPQ QSEAPTPASA    44
SEQ_ID_NO_980    MAPSTIYQYH MRQDFSTNVD SN---NSTAP TTDAIIHLQ FSHVLELCYP     47
SEQ_ID_NO_978    ---------- ---------- ---------- MARLLFRLLQ ETNSPTPATP    20

SEQ_ID_NO_976    VTAQLTRRFT CSTGDFL-VL YRQPQRVEEM VTAAGLPLEC APSVAEFISL    92
SEQ_ID_NO_980    ETIQIPLNTT NESHLFPRQL FSBHVNRESI VKEILSSMGC SSDFIESAAP    97
SEQ_ID_NO_978    SP-------- --------AL YSDLVF--VM LAALLCALIC VLGLLAVSF-    49

SEQ_ID_NO_976    SVRSNSYRKL ---------- --PVVMTVEV GAPVDEDEDE DEEL------   123
SEQ_ID_NO_980    DISSFALDMV TNPCNASSSE VLTMVLAIHV TTPYDEREEI DRALSESLMQ   147
SEQ_ID_NO_978    --RCVWLRRI ANR------- ---------- SATNSDQPPA NKGLKKKVLK    80

SEQ_ID_NO_976    ---------- ---------- -PPGAVFEEC AICYKEYLVG GATSVKLACS   152
SEQ_ID_NO_980    EASRFKPASK SCIDGLKRMS LEGSCSMKEC MVCLEEFLMG SEVLVCLPCG   196
SEQ_ID_NO_978    SLPKLTYSPD SI-------- -PPAEKFAEC AICLMEFAAG DELRVLSQCG   120

SEQ_ID_NO_976    HTFHRKCLDR ATAVNRTCPY CRAPVPVEQD YWDDEDACDN GESESDDIPS   202
SEQ_ID_NO_980    HIFHGDCIVR MLETSHLCPL CRFAMP---- ---------- ---------   222
SEQ_ID_NO_978    HGFHVSCIDT MLGSHSSCPS CRQILV---- ---------- GIARCQKCGG   156

SEQ_ID_NO_976    EEGDDEESEY DDIPSEGGDD EETEHDDIPS EEGDDWESEY EDVPNEEDDG   252
SEQ_ID_NO_980    ---------- ---------- ---------- ---------- ---------   222
SEQ_ID_NO_978    LPGSSSSGPE PDTRIKQDDP NSNNNDNXSX LN-------- ---------   188

SEQ_ID_NO_976    SSPAPDGSSQ EITAASPEFV SSVRDLSLSC LRLD    286
SEQ_ID_NO_980    ---------- ---------- ---------- ----    222
SEQ_ID_NO_978    ---------- ---------- ---------- ----    188
```

Figure 33

| SEQ_ID | Block 1 | Block 2 | Block 3 | Block 4 | Block 5 | Block 6 | Block 7 | # |
|---|---|---|---|---|---|---|---|---|
| SEQ_ID_NO_991 | -MAMGMLEVH | LISGKGLRAH | DPLN----- | ------KPID | PYVEINYKGD | | | 37 |
| SEQ_ID_NO_1032 | -MAMGMLEVH | LISGKGLQAH | DPLN----- | ------KPID | PYVEINYKGQ | | | 37 |
| SEQ_ID_NO_985 | -MGMGMLEVH | LISGKGLQAH | DPLN----- | ------KPID | PYVDINYKGQ | | | 37 |
| SEQ_ID_NO_992 | -MAMGMLEVH | LISGKGLQAH | DPLN----- | ------KPID | PYVEINYKGQ | | | 37 |
| SEQ_ID_NO_1008 | MAGSGVLEVH | LVDAKGLTGN | DFL------ | ------GKID | PYVVVQYRSQ | | | 37 |
| SEQ_ID_NO_1001 | -MPRGTLEVV | LISAKGLEDN | DFL------ | ------SSID | PYVILSYRAQ | | | 36 |
| SEQ_ID_NO_1003 | -MAQGTLEVL | LVGAKGLENT | DYL------ | ------CNMD | PYAVLKCTSQ | | | 36 |
| SEQ_ID_NO_1028 | -MVQGTLEVL | LVGAKGLENT | DYL------ | ------CNMD | PYAVLKCRSQ | | | 36 |
| SEQ_ID_NO_984 | -MPQGKLQVV | LVSAKGLENT | DFL------ | ------CNMD | PYVLLTCRTQ | | | 36 |
| SEQ_ID_NO_995 | -MPEGTIQVV | LVGAKGLENT | DFFNYRVPCN | DVKTYPSNID | PYVLLTCRSQ | | | 49 |
| SEQ_ID_NO_982 | -MPHGTLEVV | LVSAKGLEDS | DFL------ | ------NSMD | PYVLLTCRTQ | | | 36 |
| SEQ_ID_NO_996 | -MPHGTLEVV | LVSAKGLEDA | DFL------ | ------NNMD | PYVQLTCRTQ | | | 36 |
| SEQ_ID_NO_1011 | -MVRGKLEVL | LVSAKGLDDS | DFF------ | ------NSMD | PYVILTCRSH | | | 36 |
| SEQ_ID_NO_1023 | -MVHGKLEVL | LVSAKGLEDT | DFL------ | ------NNMD | PYVILTCRTQ | | | 36 |
| SEQ_ID_NO_1026 | ---------- | ---------- | ---------- | --------MD | PYVILTCRTQ | | | 12 |

| SEQ_ID | Block 1 | Block 2 | Block 3 | Block 4 | Block 5 | Block 6 | # |
|---|---|---|---|---|---|---|---|
| SEQ_ID_NO_991 | ERMSKVAKNA | GPDPVWNEKF | KFLAEYPGSG | SDFLILFKVM | DHDVIDGDDY | | 87 |
| SEQ_ID_NO_1032 | ERMSKVAKNA | GPDPVWNEKF | KFLAEYPGSG | SDFLILFKVM | DHDVIDGDDY | | 87 |
| SEQ_ID_NO_985 | ERMSGVAKNG | GPNPLWDEKF | KFLAEYPGSG | SDFHILFKVM | DHDAIDGDDY | | 87 |
| SEQ_ID_NO_992 | ERMSKVAKNA | GPDPLWDEKF | KFLAEYPGSG | SDFHVLFKVM | DHDAIDGDDY | | 87 |
| SEQ_ID_NO_1008 | ERKSSVARDQ | GKNPSWNEVF | KFDINSTAAT | GDHKLFLRLM | DHDTFSRDDF | | 87 |
| SEQ_ID_NO_1001 | EHKSTVQEGA | GSNPQWNETF | LFTV---SD | SASELNLRIM | EKDNFNNDDN | | 82 |
| SEQ_ID_NO_1003 | EQKSTVASGK | GSDPEWNETF | VFTV---SE | NATELVKLL | DSDGGTDDDS | | 82 |
| SEQ_ID_NO_1028 | EQKSSVASGK | GSDPEWNETF | MFSV---TH | NATELIKLM | DSDSGTDDDF | | 82 |
| SEQ_ID_NO_984 | EQKSSVASGK | GSEPEWNEDF | IFNI---SE | GASELALKIM | DSDAGSQDDF | | 82 |
| SEQ_ID_NO_995 | EQRSSVASGQ | GSEPEWNETF | VFTI---SE | GTSELVLKIV | DHDTLTDDDY | | 95 |
| SEQ_ID_NO_982 | DQKSNVASGD | GTTPEWNETF | FNY---SE | GTTELKAKIF | DTDVGTEDDP | | 82 |
| SEQ_ID_NO_996 | DQKSNVAEGM | GTTPEWNETF | LFTV---SE | GTTELKAKIF | DKDVGTEDDA | | 82 |
| SEQ_ID_NO_1011 | EQKSTVASGA | GSEPEWNETF | FFAV---SS | DSPELRVKIM | DSDALSADDL | | 82 |
| SEQ_ID_NO_1023 | EQKSSVANGE | GSEPEWNETF | FTV---SD | DIPQLNLKIM | DSDFVTNDDF | | 81 |
| SEQ_ID_NO_1026 | EQKSSVAKGA | GSEPEWNETF | VFTV---SD | DVPQLNVKIM | DSDAFSADDF | | 58 |

Figure 33 (continued)

```
SEQ_ID_NO_991     GDVSIDVKD LLVEGVRKGW SELPPRMYQV AHKLYFKGE EVGVSFKRQ   137
SEQ_ID_NO_1032    GDVSIDVKD LLVEGVRKGW SELPPRMYQV AHKLYFKGE EVGVSFKRQ   137
SEQ_ID_NO_985     GDVKIDVKD LLAEGVRKGW SEIPPRMYHV AHKIHFKGE EVGVSFKLQ   137
SEQ_ID_NO_992     GDVKIDVKD LLAEGVRKGW SEIRPRMYHV AHKIHFKGE EVGVSFKLQ   137
SEQ_ID_NO_1008    LGEATINVTD LISLGMEHGT WEMSESKHRV LADKIVHGE RVSLTFTAS   137
SEQ_ID_NO_1001    LGEAIIPLEA VFEEG----  SLAENAYKL VKEQEYCGE KVALTFTPE    125
SEQ_ID_NO_1003    VGEATIPLDG VYTEG----  SIPPTVYNV VKDEEYRGE KIGLTFTPE    125
SEQ_ID_NO_1028    VGEATISLEA IYTEG----  SIPPTVYNV VKEEEYRGE KVGLTFTPE    125
SEQ_ID_NO_984     VEEVAIPLEP VFIER----  NIPLTPYTV VKDGEYRGE KFGLTFTPE    125
SEQ_ID_NO_995     LGKASIPLEP LFIEG----  NLPITAYNV VKDEEYRGE RVGLSFTPE    138
SEQ_ID_NO_982     LGEATIPLEA VFLEG----  DIPPAAYNV VKDEEFKGE AALSFKPS     125
SEQ_ID_NO_996     VGEATIPLEP VFMEG----  SIPPTAYNV VKDEEYKGE AWALSFKPS    125
SEQ_ID_NO_1011    VGEACIPLEA VLQEG----  SLPPAVHRV VKDEEYRGE KIALTFTPA    125
SEQ_ID_NO_1023    VGEASIPLEA VFQEG----  SLPPTVHPV VKEEKYCGE KLALTFTPA    124
SEQ_ID_NO_1026    VGEANIPLEP VFLEG----  SLPPAVHRV VKEEKYCGE KVALTFTPA    101

SEQ_ID_NO_991     ---------- ---------- ---------- ---------- ----------       137
SEQ_ID_NO_1032    ---------- ---------- ---------- ---------- ----------       137
SEQ_ID_NO_985     ---------- ---------- ---------- ---------- --GGGGCGGC    145
SEQ_ID_NO_992     ---------- ---------- ---------- ---------- --GGGGCAGC    145
SEQ_ID_NO_1008    ---------- ---------- ---------- ---------- AKAQDHAEQV    147
SEQ_ID_NO_1001    ---------- ---------- ---------- ---------- --RNDEEETC    133
SEQ_ID_NO_1003    --E------- ---------- ---------- ---------A RDEDQPEENY    137
SEQ_ID_NO_1028    --D------- ---------- ---------- ---------D RDRGLSEEDI    137
SEQ_ID_NO_984     ERE------- ---------- ---------- ---------S RDFEV-EESF    138
SEQ_ID_NO_995     RRT------- ---------- ---------- ---------S RTFDAGEESY    152
SEQ_ID_NO_982     --E------- ---------- ---------- ---------N RSRGFEEESY    137
SEQ_ID_NO_996     --E------- ---------- ---------- ---------N RSRGMDEESY    137
SEQ_ID_NO_1011    ---------- ---------- ---------- ---------- -EENEEEESY    134
SEQ_ID_NO_1023    -VE------- ---------- ---------- ---------T RRPDNEEGTY    137
SEQ_ID_NO_1026    AVKTLTSVSC NIDGVVAIVS EHLVGVCDAN VLDTRISSGN SPSSQPRERG    151
```

Figure 33 (continued)

| SEQ_ID_NO_991  | -G-------  -- | 138 |
|---|---|---|
| SEQ_ID_NO_1032 | -G-------  -- | 138 |
| SEQ_ID_NO_985  | NPWEN----  -- | 150 |
| SEQ_ID_NO_992  | YPWEN----  -- | 150 |
| SEQ_ID_NO_1008 | GGWAHSFRQ- -- | 156 |
| SEQ_ID_NO_1001 | GGWKESTRDF -- | 143 |
| SEQ_ID_NO_1003 | GGWNQSS---  -- | 144 |
| SEQ_ID_NO_1028 | GGWKQSS---  -- | 144 |
| SEQ_ID_NO_984  | GGWKQSSYTD -- | 148 |
| SEQ_ID_NO_995  | GGWKESAYTD -- | 162 |
| SEQ_ID_NO_982  | GGWKNSEASY -- | 147 |
| SEQ_ID_NO_996  | GGWKNSEASY -- | 147 |
| SEQ_ID_NO_1011 | GGWNQST---  -- | 141 |
| SEQ_ID_NO_1023 | SSWN-----  -- | 141 |
| SEQ_ID_NO_1026 | GGLQQLELIA CY | 163 |

Figure 34

```
SEQ_ID_NO_1058   MHRFASGLAS ---------- ------KARL ARKGANQIAS RSSMSRN---   31
SEQ_ID_NO_1077   ---MASTFAG MSSAGPLAAP STSSNKLSSM ANISSTSFGS KRNVALRKSR   47
SEQ_ID_NO_1078   ---MASTFAG MSSAGPLAAP STSSNKLSSM ANISSTSFGS KRNVALRKSR   47
SEQ_ID_NO_1075   ---MNTQIHP --HTSLLFFP PN---RFNF ISSFSSF--- -----RRRNP   33
SEQ_ID_NO_1095   ---MTTARGL ---------- ------SART TRGA------ -----SNRRV   20
SEQ_ID_NO_1055   ---MAQSQLA ---------- ------KGSR QTTGRPFQNK P----ARAAR   27
SEQ_ID_NO_1080   ---MATIPTT --GSASLLRG SA---ALQRD GRSTRPSSAA RPLPGRRARS   42
SEQ_ID_NO_1086   ---MATMPST CASSSSLFLL LR---KDRR SRSASL--- -----PGPAR   35
SEQ_ID_NO_1085   ---MATIPTT --DSALLLGS SA---LHRA RRASAARLPG A----NRRRP   37
SEQ_ID_NO_1097   ---MATIPTT --DSGLLLGS ------SALL RRTRRAASSA RLPAAARRRP   39
SEQ_ID_NO_1054   ---MASANAI --STASPFRP LS---QGRL ---------- -----ATRSQ   25
SEQ_ID_NO_1088   ---MASANAI --STASLLRS FS---SQGRV RRAK------ -----NGRAQ   31
SEQ_ID_NO_1068   ---MASANAL --SSASVLCS SR---QSKL G-GGNQQGQ RVSYNKRITLR   40
SEQ_ID_NO_1072   ---MATANAL --SSPSVLCS SR---QCKL SLGGSQQKGQ RVSY-RKANR   39
SEQ_ID_NO_1057   ---MASANAL --SSASILCS PN---KGSL RRKGNQRQNQ RVNY-RQGNN   40
SEQ_ID_NO_1061   ---MATSNAL --STASILCS PK---QGGL RRRGNQNNS RLNY-GLSSR   40
SEQ_ID_NO_1076   ---MASTNAL --SSTSILRS PTN--QADT SLSKKVKQHG RVNF-RQKPN   41
SEQ_ID_NO_1092   ---MASTNAL --SSTSILRS PTNN-QADT SLSKKAKQHG RVNY-RQNPN   42
SEQ_ID_NO_1074   ---MASTNAL --SSASILRS PN---RQSL TRRANH--NG RVNY-RKPNN   38
SEQ_ID_NO_1083   ---MASTNAL --SSASILRS PN---HQSL SRRANQ--NG RVNY-RQPNH   38

SEQ_ID_NO_1058   ------YAAK DVKFGVEARG --LMLKGVED LADAVKVTMG PKGRNVVIEQ   73
SEQ_ID_NO_1077   RLTIL-AAAK ELHFNKDGSA IKKLQNGVNK LADLVGVTLG PKGRNVVLES   96
SEQ_ID_NO_1078   RPTIL-AAAK ELHFNKDGSA IKKLQNGVNK LADLVGVTLG PKGRNVVLES   96
SEQ_ID_NO_1075   QFAVR-ASPK KISFGKECRE --NLQVGIDK LADAVSLTVG PKGRNVILSE   80
SEQ_ID_NO_1095   QVQVR-AEAK KLTFDMASRR --KIQAGIDK LADAVGVTLG PRGRNVVLEE   67
SEQ_ID_NO_1055   RLVIRAADAK EIVFDQESRR --RLQAGINK VADAVGVTLG PRGRNVVLEQ   75
SEQ_ID_NO_1080   LSVVR-ASAK DIAFDQASRS --ALQAGVEK LAAAVGVTLG PRGRNVVLDE   89
SEQ_ID_NO_1086   RLGVVRASAK EIAFDQGSRS --SLQAGVEK LAAAVTLG PRGRNVVLDE   83
SEQ_ID_NO_1085   QALVR-ASAK EIAFDQGARA --SLQAGVEK LAAAVGVTLG PRGRNVVLDE   84
SEQ_ID_NO_1097   QLLVR-ASAK EIAFDQSSRA --SLQAGVEK LAAAVGVTLG PRGRNVVLDE   86
SEQ_ID_NO_1054   RFVVR-ANAK DIAFDQKSRA --ALQAGVEK LANAVGVTLG PRGRNVVLDE   72
SEQ_ID_NO_1088   RLVVR-ADAK DIAFDQKSRA --ALQAGVEK LANAVGVTLG PRGRNVVLDE   78
SEQ_ID_NO_1068   RFSVR-ANVK EIAFDQHSRA --ALQAGIDK LADCVGLTLG PRGRNVVLDE   87
SEQ_ID_NO_1072   RFSLR-ANVK EIAFDQSSRA --ALQAGIDK LADAVGLTLG PRGRNVVLDE   86
SEQ_ID_NO_1057   RFGVK-ACAK EIAFDQSSRA --AMQAGIDK LADAVGLTLG PRGRNVVLDE   87
SEQ_ID_NO_1061   RFSVR-ANAK DIAFDQKSRA --ALQSGIDK LADAVGLTLG PRGRNVVLDE   87
SEQ_ID_NO_1076   RFVVK-AAAK DIAFDQHSRS --AMQAGIDK LADAVGLTLG PRGRNVVLDE   88
SEQ_ID_NO_1092   RFMVK-AAAK DIAFDQHSRR --AMQAGIDK LADAVGLTLG PRGRNVVLDE   89
SEQ_ID_NO_1074   RFSVK-ASAK EIAFDQHSRS --AMQAGIDK LADAVGLTLG PRGRNVVLDE   85
SEQ_ID_NO_1083   RFAVK-ASAK EIAFDQSSRA --AIQAGIDK LADAVGLTLG PRGRNVVLDE   85
```

Figure 34 (continued)

| SEQ_ID_NO | | | | | | |
|---|---|---|---|---|---|---|
| SEQ_ID_NO_1058 | SYGAPKVTKD | GVTVAKSI EF | KDKVKNVGAS | LVKQVANATN | DVAGDGTTCA | 123 |
| SEQ_ID_NO_1077 | KYGAPKI VND | GVTVAREVEL | EDPVKNI GAK | LVRQAAAKTN | DLAGDGTTTS | 146 |
| SEQ_ID_NO_1078 | KYGAPKI VND | GVTVAREVEL | EDPVENI GAK | LVRQAAAKTN | DLAGDGTTTS | 146 |
| SEQ_ID_NO_1075 | -SGKLKVI ND | GVTI ARSI EL | SDAI ENAGAM | LI QEVASKMN | DLAGDGTSTA | 129 |
| SEQ_ID_NO_1095 | KFGMPQVI ND | GVTI ARAI EL | PDPVENAGAQ | LI KEVAGRTN | DSAGDGTTTA | 117 |
| SEQ_ID_NO_1055 | KFGVPQVI ND | GVSI RRAI EL | KDPVENAGAQ | LI KEVAGRTN | DAAGDGTTTA | 125 |
| SEQ_ID_NO_1080 | -FGSPKVVND | GVTI ARAI EL | ADPMENAGAA | LI REVASKTN | DSAGDGTTTA | 138 |
| SEQ_ID_NO_1086 | -FGSPKVVND | GVTI ARAI EL | ADPMENAGAA | LI REVASKTN | DSAGDGTTTA | 132 |
| SEQ_ID_NO_1085 | -FGTPKVVND | GVTI ARAI EL | ADPMENAGAS | LI REVASKTN | DSAGDGTTTA | 133 |
| SEQ_ID_NO_1097 | -FGTPKVVND | GVTI ARAI EL | ADPMENAGAA | LI REVASKTN | DSAGDGTTTA | 135 |
| SEQ_ID_NO_1054 | -YGNPKVVND | GVTI ARAI EL | YDPMENAGAA | LI REVASKTN | DSAGDGTTTA | 121 |
| SEQ_ID_NO_1088 | -YGSPKVVND | GVTI ARAI EL | YDPMENAGAA | LI REVASKTN | DSAGDGTTTA | 127 |
| SEQ_ID_NO_1068 | -FGSPKVVND | GVTI ARAI EL | PNAMENAGAA | LI REVASKTN | DSAGDGTTTA | 136 |
| SEQ_ID_NO_1072 | -FGSPKVVND | GVTI ARAI EL | PDAMENAGAA | LI REVASKTN | DSAGDGTTTA | 135 |
| SEQ_ID_NO_1057 | -FGSPKVVND | GVTI ARAI EL | PNAMENAGAA | LI REVASKTN | DSAGDGTTTA | 136 |
| SEQ_ID_NO_1061 | -FGSPKVVND | GVTI ARAI EL | PDPMENAGAA | LI REVASKTN | DSAGDGTTTA | 136 |
| SEQ_ID_NO_1076 | -FGSPKVVND | GVTI ARAI EL | PDPMENAGAA | LI REVASKTN | DSAGDGTTTA | 137 |
| SEQ_ID_NO_1092 | -FGSPKVVND | GVTI ARAI EL | PDPMENAGAA | LI REVASKTN | DSAGDGTTTA | 138 |
| SEQ_ID_NO_1074 | -FGSPKVVND | GVTI ARAI EL | PDPMENAGAA | LI REVASKTN | DSAGDGTTTA | 134 |
| SEQ_ID_NO_1083 | -FGSPKVVND | GVTI ARAI EL | PDAMENAGAA | LI REVASKTN | DSAGDGTTTA | 134 |

| SEQ_ID_NO | | | | | | |
|---|---|---|---|---|---|---|
| SEQ_ID_NO_1058 | TI LTRAFTE | GCKSVAAGMN | AMDLRRGI SM | AVDSVVTNLK | SRARMSTSE | 173 |
| SEQ_ID_NO_1077 | VVLAQGLI AE | GVKVVAAGAN | PVLI TRGI EK | TAKALVAELK | NMSKEVEDS- | 195 |
| SEQ_ID_NO_1078 | VVLAQGLI AE | GVKVVAAGAN | PVLI TRGI EK | TAKALVAELK | NMSKEVEDS- | 195 |
| SEQ_ID_NO_1075 | I I LARAMI KG | GLSAVAFGAN | PI SLKKGMEK | TVKDLVKFLK | KRSI PVEGRD | 179 |
| SEQ_ID_NO_1095 | SVLAREMI KY | GLQSVAAGAN | PVTVKRGMDK | TSEFCRKKLD | ELTI PVRNAA | 167 |
| SEQ_ID_NO_1055 | SVLAREMI HY | GLQSVTAGAN | PI AVKRGLDK | TAEYLVAKLK | EHAKPVKGRD | 175 |
| SEQ_ID_NO_1080 | SVLAREI I KL | GLLSVTSGAN | PVSI KKGI DK | TVQSLVEELE | KKSRPVKGSG | 188 |
| SEQ_ID_NO_1086 | SVLAREI I KL | GLLSVTSGAN | PVSI KKGI DK | TVHSLVEELE | KKSRPVKGSG | 182 |
| SEQ_ID_NO_1085 | SVLAREI I KL | GMLSVTSGAN | PVSI KKGI DK | TVQKLVEELE | KKSRPVKGGG | 183 |
| SEQ_ID_NO_1097 | SVLAREI I KL | GMLSI TSGAN | PVSVKKGI DK | TVQKLVEELE | KKSRPVKGSG | 185 |
| SEQ_ID_NO_1054 | CVLAREI I KL | GLLSVTSGAN | PVSLKKGI DK | TVQGLI QELE | NKSRPI KGGG | 171 |
| SEQ_ID_NO_1088 | SVLAREI I KL | GLLSVTSGAN | PVSLKKGI DK | TVHGLI EELE | KKARPVKGSG | 177 |
| SEQ_ID_NO_1068 | SI LAREI I KH | GLLSVTSGAN | PVSLKRGI DK | TVQGLI EELQ | KKARPVKGRD | 186 |
| SEQ_ID_NO_1072 | SVLAREI I KH | GLLSVTSGAN | PVSLKRGI DK | TVQALI EELE | KRSRPVKGGR | 185 |
| SEQ_ID_NO_1057 | SVLAREI I KL | GLLTVTSGAN | PVSVKRGI DK | TVQSLI EELE | KKARPVKGRD | 186 |
| SEQ_ID_NO_1061 | SVLAREI I KL | GLLSVTSGAN | PVSI KRGI DK | TVQGLVEELE | KKARPVKGRD | 186 |
| SEQ_ID_NO_1076 | SI LAREI I KL | GLLNVTSGAN | PVSI KKGI DK | TVAALVEELE | KLARPVKGGD | 187 |
| SEQ_ID_NO_1092 | SI LAREI I KL | GLLSVTSGAN | PVSI KKGI DK | TVAGLI EELE | KLARPVKGGD | 188 |
| SEQ_ID_NO_1074 | SVLAREI I KL | GLLSVTSGAN | PVSLKRGI DK | TVQGLVEELE | KKARPVKGGD | 184 |
| SEQ_ID_NO_1083 | SVLAREI I KL | GLLSVTSGAN | PVSLKRGI DK | TVQGLVEELE | KRARPVKGGD | 184 |

Figure 34 (continued)

| | | | | | | |
|---|---|---|---|---|---|---|
| SEQ_ID_NO_1058 | EI AQVGTI SA | NGERE GELI | AKAMEKVGKE | GVI TI SDGKT | LFNELEVVEG | 223 |
| SEQ_ID_NO_1077 | ELPDVAAVSA | GNNLEVGSMI | AEPMSTVGRK | GVVTLEEGKS | AENSLRVVEG | 245 |
| SEQ_ID_NO_1078 | ELADVAAVSA | GNNLEVGSMI | AEAMSKVGRK | GVVTLEEGKS | AENSLRVVEG | 245 |
| SEQ_ID_NO_1075 | HI KAVASI SA | GNDEYVGNLI | AEAI EKI GFD | GVI TI ESSRS | SETSVVI EEG | 229 |
| SEQ_ID_NO_1095 | DI RAVASI SA | GNNEE GNMI | AEAI EKVGPD | GVLSI ETGSG | LETVVEVEEG | 217 |
| SEQ_ID_NO_1055 | DI KNVASI SA | GNDNAI GEMI | ADALDKVGSN | GVLSI ETSNS | TETVVEVQEG | 225 |
| SEQ_ID_NO_1080 | DI KAI AAI SA | GNDDF GTMI | AEAI NKVGPD | GVLSI ESSSS | FETTVEVEEG | 238 |
| SEQ_ID_NO_1086 | DI KAVAAI SA | GNDDFVGTMI | AEAI DKVGPD | GVLSI ESSSS | FETTVEVEEG | 232 |
| SEQ_ID_NO_1085 | DI KAVAAI SA | GNDEFVGTMI | AEAI DKVGPD | GVLSI ESSSS | FETTVEVEEG | 233 |
| SEQ_ID_NO_1097 | DI KAVAAI SA | GNDEFVGTMI | AEAI DKVGPD | GVLSI ESSSS | FETTVEVEEG | 235 |
| SEQ_ID_NO_1054 | DI KAVASI SA | GNDEFI GSMI | AEAI DKVGPD | GVLSI ESSSS | FETTVEVEEG | 221 |
| SEQ_ID_NO_1088 | DI KAVASI SA | GNDEL GSMI | ADAI DKVGPD | GVLSI ESSSS | FETTVDVEEG | 227 |
| SEQ_ID_NO_1068 | DI RAVASI SA | GNDDL GSMI | ADAI DKVGPD | GVLSI ESSSS | FETTVEVEEG | 236 |
| SEQ_ID_NO_1072 | DI KAVATI SA | GNDEL GAMI | ADAI DKVGPD | GVSP ESSSS | FETTVEVEEG | 235 |
| SEQ_ID_NO_1057 | DI KAVASI SA | GNDDL GTMV | ADAI DKVGPD | GVLSI ESSSS | FETTVDVEEG | 236 |
| SEQ_ID_NO_1061 | DI KAVASI SA | GNDEL GTMI | ADAI DKVGPD | GVLSI ESSSS | FETVVEVEEG | 236 |
| SEQ_ID_NO_1076 | DI KAVATI SA | GNDEL GKMI | AEAI DKVGPD | GVLSI ESSNS | FETTVEVEEG | 237 |
| SEQ_ID_NO_1092 | DI KAVASI SA | GNDEL GKMI | AEAI DKVGPD | GVLSI ESSSS | FETTVEVEEG | 238 |
| SEQ_ID_NO_1074 | DI KAVASI SA | GNDEL GQMI | AEAI DKVGPD | GVLSI ESSSS | FETTVEVEEG | 234 |
| SEQ_ID_NO_1083 | DI KAVASI SA | GNDEL GKMI | AEAI DKVGPD | GVLSI ESSSS | FETTVEVEEG | 234 |

| | | | | | | |
|---|---|---|---|---|---|---|
| SEQ_ID_NO_1058 | MKLDRGYI SP | YFI TNQKNQK | CELDDPLI LI | HEKKI SSI NS | VVKVLELALK | 273 |
| SEQ_ID_NO_1077 | MQFDRGYFAP | YFVTDSEKMS | VEYDNCKLLL | VDKKI TNAKD | LVNVLKDAI R | 295 |
| SEQ_ID_NO_1078 | MQFDRGYVSP | YFVTDSEKMS | VEYENCKLLL | VDKKI TNARD | LVNVLEDAI R | 295 |
| SEQ_ID_NO_1075 | MKI DRGYMSP | HFI TNQEKSI | VEFDNAKVLV | TDQKI SSVRE | I VPLLEKAMQ | 279 |
| SEQ_ID_NO_1095 | MEI DRGYI SP | QFVNDNERLM | VEYEGCRI LI | TDEKI EQVQM | LVPLLEEVSQ | 267 |
| SEQ_ID_NO_1055 | MEI DRGYI SP | QFVTNQERLL | VEYDNCRVLV | TDQKI DAI RD | I I PI LEQVTR | 275 |
| SEQ_ID_NO_1080 | MEI DRGYI SP | QFVTNSEKSV | VEFENARVLV | TDQKI SSI KE | I LPLLEQTTQ | 288 |
| SEQ_ID_NO_1086 | MEI DRGYI SP | QFVTNPEKSL | VEFENARI LV | TDQKI SSI KE | I I PLLEQTTQ | 282 |
| SEQ_ID_NO_1085 | MELDRGYI SP | QFVTNPEKST | VEFENARI LV | TDQKI SSI KE | I LPLLEQTTQ | 283 |
| SEQ_ID_NO_1097 | MELDRGYI SP | QFVTNPEKST | VEFENARI LV | TDQKI SSI KE | I I PLLEQTTQ | 285 |
| SEQ_ID_NO_1054 | MEI DRGYI SP | QFVTNLEKSI | VEFENCKYLI | TDQKI TSI KE | I LPI LEKTTQ | 271 |
| SEQ_ID_NO_1088 | MEI DRGYI SP | QFVTNLEKSI | VEFENAKVLI | TDQKI TSI KE | I LPI LEKTTQ | 277 |
| SEQ_ID_NO_1068 | MEI DRGYI SP | QFVTNPEKLL | AEFENARVLI | TDQKI TAI KD | I I PI LEKTTQ | 286 |
| SEQ_ID_NO_1072 | MEI DRGYI SP | QFVTNPEKLL | VEFENARVLI | TDQKI TAI KD | I I PI LEKTTQ | 285 |
| SEQ_ID_NO_1057 | MEI DRGYI SP | QFVTNPEKL | CEFENARVLV | TDQKI TAI KD | I I PLLEKTTQ | 286 |
| SEQ_ID_NO_1061 | MEI DRGYI SP | QFVTNPEKL | CEFENARVLI | TDQKI TAI KD | I I PLLEKTTQ | 286 |
| SEQ_ID_NO_1076 | MEI DRGYI SP | QFVTNPEKSI | VEFENARVLI | TDQKI SAI KD | I I PLLEKTTQ | 287 |
| SEQ_ID_NO_1092 | MEI DRGYI SP | QFVTNLEKSI | VEFENARVLI | TDQKI SAI KD | I PLLEKTTQ | 288 |
| SEQ_ID_NO_1074 | MEI DRGYI SP | QFVTNPEKL | VEFENARVLI | TDQKI SAI KD | I I PLLEKTTQ | 284 |
| SEQ_ID_NO_1083 | I EI DRGYI SG - FVTNLEKSI | VEFENARVLV | TDQKI SAI KD | I I PLLEKTTQ | | 283 |

Figure 34 (continued)

| SEQ_ID_NO | col1 | col2 | col3 | col4 | col5 | col6 | col7 | num |
|---|---|---|---|---|---|---|---|---|
| SEQ_ID_NO_1058 | RQ- | RPLLIVS | EDVESDALAT | LILNKLRAG | KVCAIKAPGF | GENRKAGLHD | | 322 |
| SEQ_ID_NO_1077 | NG- | SPTLIIA | ENIDQEALAT | LVVNKLRGAL | KVAALKAPGF | GERKSQYLDD | | 344 |
| SEQ_ID_NO_1078 | NG- | YPILIIA | EDIEQEALAT | LVVNKLRGAL | KVAALKAPGF | GERKSQYLDD | | 344 |
| SEQ_ID_NO_1075 | LS- | APLLIIA | EDVTAQVLET | LIVNKMQGLL | RVAAVKCPGL | GDGKKALLQD | | 328 |
| SEQ_ID_NO_1095 | AGSP | PLLIIA | EDITGEALAT | LVVNKMRGVL | KVAAIKAPGF | GERRKALLQD | | 317 |
| SEQ_ID_NO_1055 | LN- | APLLIIA | EDVSGEALAT | LVVNKLRGVL | NVCAIKAPGF | GERRKSLLQD | | 324 |
| SEQ_ID_NO_1080 | LR- | APLLIIA | EDVSGEALAT | LVVNKLRGIL | NVAAIKAPGF | GERRKALLQD | | 337 |
| SEQ_ID_NO_1086 | LR- | APLLIIA | EDVAGEALAT | LVVNKLRGIL | NVAAIKAPGF | GERRKALLQD | | 331 |
| SEQ_ID_NO_1085 | LR- | APLLIIA | EDVSGEALAT | LVVNKLRGIL | NVAAIKAPGF | GERRKALLQD | | 332 |
| SEQ_ID_NO_1097 | LR- | APLLIIA | EDVSGEALAT | LVVNKLRGIL | NVAAIKAPGF | GERRKALLQD | | 334 |
| SEQ_ID_NO_1054 | LR- | APLFIIA | EDITGEALAT | LVVNKLRGIL | NVAAIKAPSF | GERRKAVLQD | | 320 |
| SEQ_ID_NO_1088 | LR- | APLFIIA | EDITGEALAT | LVVNKLRGIL | NVAAIKAPSF | GERRKAVLQD | | 326 |
| SEQ_ID_NO_1068 | LR- | APLLIIA | EDVTGEALAT | LVVNKLRGVL | NVVAVKAPGF | GERRKAMLQD | | 335 |
| SEQ_ID_NO_1072 | LR- | APLLIIA | EDVTGEALAT | LVVNKLRGVL | NVVAVKAPGF | GERRKAMLQD | | 334 |
| SEQ_ID_NO_1057 | LR- | APLLIIA | EDVTGEALAT | LVVNKLRGIL | NVAAIKAPSF | GERRKAVLQD | | 335 |
| SEQ_ID_NO_1061 | LR- | APLLIIA | EDVTGEALAT | LVVNKLRGVL | NVAAIKAPGF | GERRKAMLQD | | 335 |
| SEQ_ID_NO_1076 | LR- | APLLIIS | EDITGEALAT | LVVNKLRGIL | NVAAIKAPGF | GERRKALLQD | | 336 |
| SEQ_ID_NO_1092 | LR- | APLFIIA | EDITGEALAT | LVVNKLRGIL | NVAAIKAPGF | GERRKALLQD | | 337 |
| SEQ_ID_NO_1074 | LR- | APLLIIA | EDVTGEALAT | LVVNKLRGIL | NVAAIKAPGF | GERRKALLQD | | 333 |
| SEQ_ID_NO_1083 | LR- | APLIIIA | EDVTGEALAT | LVVNKLRGIL | NVAAIKAPSF | GERRKAVLQD | | 332 |

| SEQ_ID_NO | col1 | col2 | col3 | col4 | col5 | col6 | num |
|---|---|---|---|---|---|---|---|
| SEQ_ID_NO_1058 | LAVLTGGQLI | TEELGMNLEK | VDLDMLGSCK | KITISKDDTV | LDGAGDKKS | | 372 |
| SEQ_ID_NO_1077 | IATLTGGTVI | REELGLTLDK | ADKEVLGHAA | KVVLTKDATT | VGDGSTQEA | | 394 |
| SEQ_ID_NO_1078 | IATLTGGTVI | REELGLTLDK | ADKEVLGHAA | KVVLTKDATT | VGDGSTQEA | | 394 |
| SEQ_ID_NO_1075 | IALMTGADFL | CGDLGLTLES | TTSDQLGSAL | KVKITSNATT | FADPNTKAE | | 378 |
| SEQ_ID_NO_1095 | IAIVTGAQYI | AKDLGLSVQR | ATMDSLGYAR | KVSIAQTTTT | LIADGASKED | | 367 |
| SEQ_ID_NO_1055 | IAIVTGAEFL | AKDLGMKVED | AVVEQLGVAR | KVTVANNTTT | LIADAASKDE | | 374 |
| SEQ_ID_NO_1080 | IAIVTGAEFQ | AKDLGQLIEQ | TTVEQLGIAR | KVTISGSSTT | IIADVATKDE | | 387 |
| SEQ_ID_NO_1086 | IAIVTGAEFQ | AKDLGLLVES | TTVEQLGIAR | KVTISQSSTT | IIADVATKDE | | 381 |
| SEQ_ID_NO_1085 | IAIVTGAEYQ | SKDLGLLVEK | TTVEQLGIAR | KVTISSSSTT | IIADAASKDD | | 392 |
| SEQ_ID_NO_1097 | IAIVTGAEYQ | SKDLGLLVEN | TTVEQLGIAR | KVTISSSSTT | IIADAASKDD | | 394 |
| SEQ_ID_NO_1054 | IAIVTGAEFL | AKDLGLLVEN | ATEEQLGTAR | KVTIHQTTTT | LIADAASKDE | | 370 |
| SEQ_ID_NO_1088 | IAIVTGAEFL | AKDLGLLVEN | ATEEQLGTAR | KVTIHQTTTT | LIADAASKDE | | 376 |
| SEQ_ID_NO_1068 | IAILTGAEYL | AMDMSLLVEN | ATIDQLGIAR | KVTISKDSTT | LIADAASKDE | | 385 |
| SEQ_ID_NO_1072 | IAILTEPS-T | ALDMGLLVEN | TTIDQLGIAR | KVTISKDSTT | LIADAASKAE | | 383 |
| SEQ_ID_NO_1057 | IAILTGAEFQ | ANDLGLLIEN | TSVEQLGIAR | KVITKDSTD | IIADAASKDE | | 385 |
| SEQ_ID_NO_1061 | IAILTGAEFQ | ASDLGLSEN | TSIEQLGLAR | KVTISKDSTT | IIADAASKDE | | 385 |
| SEQ_ID_NO_1076 | IAILTGAEFQ | ASDLGLLVEN | TTIEQLGLAR | KVTISKDSTT | IIADAASKDE | | 386 |
| SEQ_ID_NO_1092 | IAILTGAEYQ | ASDLGLLVEN | TSIEQLGLAR | KVTISKDSTT | IIADAASKDE | | 387 |
| SEQ_ID_NO_1074 | IAILTGAEFQ | ASDLGLLVEN | TSVEQLGLAR | KITISKDSTT | VIADAATKDE | | 383 |
| SEQ_ID_NO_1083 | IAILTGAEFQ | ASDLGLLVEN | TSIEQLGLAR | KVTISKDSTT | IIADAASKDE | | 382 |

Figure 34 (continued)

| SEQ_ID_NO | | | | | | |
|---|---|---|---|---|---|---|
| SEQ_ID_NO_1058 | IEERCEQIRS | AIELSTSDYD | KEKLDERLAK | LSGGVAVLKI | GGASEAEVGE | 422 |
| SEQ_ID_NO_1077 | VNKRVAQIKN | LIEAADQDYE | KEKLNERIAK | LSGGVAVIQV | GAQTETELKE | 444 |
| SEQ_ID_NO_1078 | VNKRVAQIKN | LIEAADQDYE | KEKLNERIAK | LSGGVAVIQV | GAQTETELKE | 444 |
| SEQ_ID_NO_1075 | IQARILQIKK | DLIETDNANH | SRKLSERIAK | LTGGIAVIKV | GAHITELFLED | 428 |
| SEQ_ID_NO_1095 | DMRVAQLKQ | ELAETDSVYD | TEKLSERIAK | LAGGVAVIKV | GAATETEMEE | 417 |
| SEQ_ID_NO_1055 | EMRIAQLKK | ELAETDSVYD | TEKLSERIAK | LSGGVAVIKV | GAATEAELED | 424 |
| SEQ_ID_NO_1080 | IQARIAQLKR | ELSQTDSTYD | SEKLAERIAK | LSGGVAVIKV | GAATETELED | 437 |
| SEQ_ID_NO_1086 | IQARIAQLKR | ELSQTDSAYD | SEKLAERIAK | LSGGVAVIKV | GAATETELED | 431 |
| SEQ_ID_NO_1085 | IQARIAQLKR | ELSQTDSTYD | SEKLAERIAK | LSGGVAVIKV | GASTEAELED | 432 |
| SEQ_ID_NO_1097 | IQARIAQLKR | ELSQTDSAYD | SEKLAERIAK | LSGGVAVIKV | GASTEAELED | 434 |
| SEQ_ID_NO_1054 | IQARIAQLKK | ELAETDSVYD | TEKLAERIAK | LAGGVAVIKV | GAATETELED | 420 |
| SEQ_ID_NO_1088 | IQARVAQLKK | ELSETDSIYD | TEKLAERIAK | LSGGVAVIKV | GAATETELED | 426 |
| SEQ_ID_NO_1068 | LQARIAQLKK | ELFETDSVYD | SEKLAERIAK | LSGGVAVIKV | GAATETELED | 435 |
| SEQ_ID_NO_1072 | LQARISQLKK | ESFETDSVYD | SEKLAERIAK | LSGGVAVIKV | GAATETELED | 433 |
| SEQ_ID_NO_1057 | LQARVDQLKK | ELAETDSVYD | TEKLAERIAK | LSGGVAVIKV | GAATETELED | 435 |
| SEQ_ID_NO_1061 | LQARIAQLKK | ELSETDSVYD | SEKLAERIAK | LSGGVAVIKV | GAATETELED | 435 |
| SEQ_ID_NO_1076 | LQSRVAQLKK | ELSETDSIYD | SEKLAERIAK | LSGGVAVIKV | GAATETELED | 436 |
| SEQ_ID_NO_1092 | LQSRVAQLKK | ELSETDSVYD | SEKLAERIAK | LSGGVAVIKV | GAATETELED | 437 |
| SEQ_ID_NO_1074 | LQARVAQLKK | ELSQTDSVYD | TEKLAERIAK | LSGGVAVIKV | GAATETELED | 433 |
| SEQ_ID_NO_1083 | LQARVAQLKK | ELAETDAVYD | SVKLAERITK | LSGGVAVIKV | GAATETELED | 432 |

| SEQ_ID_NO | | | | | | |
|---|---|---|---|---|---|---|
| SEQ_ID_NO_1058 | KKDRVTDALN | ATKAAVEEGI | VPGGGVALLY | ASKELDKLL | STANFDQKIG | 470 |
| SEQ_ID_NO_1077 | KKLRVEDALN | ATKAAVERGI | VVGGGCTLLR | LAAKVDAIKG | TLANDEEKVG | 494 |
| SEQ_ID_NO_1078 | KKLRVEDALN | ATKAAVEEGI | VVGGGCTLLR | LAAKVDAIKG | TLANDEEKVG | 494 |
| SEQ_ID_NO_1075 | RKLRIEDAKN | ATFAAINEGL | VPGGGATYVH | LDLIPAIKN | SMEDLDEQIG | 478 |
| SEQ_ID_NO_1095 | RKLRIEDAKN | ATFAAVEEGI | VPGGGAALVH | LSKMDEFIP | TLTSAEERLG | 467 |
| SEQ_ID_NO_1055 | RKLRIEDAKN | ATFAAVEEGI | VPGGGAALLH | LSELVPAFKE | TLIDAEEKLG | 474 |
| SEQ_ID_NO_1080 | RKLRIEDAKN | ATFAAIEEGI | VPGGGAAYVH | LSTFVPAIKE | KLDDPEERLG | 487 |
| SEQ_ID_NO_1086 | RKLRIEDAKN | ATFAAIEEGI | VPGGGAAYVH | LSKFVPAIKE | KLDDPEERLG | 481 |
| SEQ_ID_NO_1085 | RKLRIENAKN | ATFAAIEEGI | VPGGGAAYVH | LSTFVPAIKE | KLDDPEERLG | 482 |
| SEQ_ID_NO_1097 | RKLRIEDAKN | ATFAAIEEGI | VPGGGAAYVH | LSTFVPAIKE | TLDDPEERLG | 494 |
| SEQ_ID_NO_1054 | RQLRIEDAKN | ATFAAIEEGI | VPGGGAAYVH | LSTVVPKIKE | AIEDPDERLG | 470 |
| SEQ_ID_NO_1088 | RQLRIEDAKN | ATFAAIEEGI | VPGGGTAYVH | LSTTVPAIKE | TIEDHDERLG | 476 |
| SEQ_ID_NO_1068 | RKLRIEDAKN | ATFAAIEEGI | VPGGGAALVH | LSTVIPAIKE | TFEDADERLG | 485 |
| SEQ_ID_NO_1072 | RKLRIEDAKN | ATFAAIEEGI | VPGGGATLVH | LSTVIPAIKE | TFEDADVRLG | 483 |
| SEQ_ID_NO_1057 | RKLRIEDAKN | ATFAAIEEGI | VPGGGAALVH | LSTCVPAIKD | KLEDPEERIG | 485 |
| SEQ_ID_NO_1061 | RKLRIEDAKN | ATFAAIEEGI | VPGGGAALVH | LSTCVPAIKD | KIEDADERLG | 485 |
| SEQ_ID_NO_1076 | RKLRIEDAKN | ATFAAIEEGI | VPGGGTALVH | LSGYVPAIKE | KLEDADERLG | 486 |
| SEQ_ID_NO_1092 | RKLRIEDAKN | ATFAAIEEGI | VPGGGTALVH | LSAYVPAIKE | KLEDADERLG | 487 |
| SEQ_ID_NO_1074 | RKLRIEDAKN | ATFAAIEEGI | VPGGGTALVH | LSTHVPAIKD | KLEDADERLG | 483 |
| SEQ_ID_NO_1083 | RKLRIEDAKN | ATFFAIEVGI | VL-VDTALLH | LSTHVPAIKD | KLEDADERLG | 480 |

Figure 34 (continued)

| | | | | | | | |
|---|---|---|---|---|---|---|---|
| SEQ_ID_NO_1058 | VQIQNALKT | PVHTIASNAG | VEGAVVYGKL | LEDDNPDLGY | DAAKGEYVDM | 520 |
| SEQ_ID_NO_1077 | ADIVQRALSY | PLKLIAKNAG | VNGSVVSEKV | LSSDDPKFGY | NAATGNYEDL | 544 |
| SEQ_ID_NO_1078 | ADIVKRALSY | PLKLIAKNAG | VNGSVVSEKV | LSSDDPKFGY | NAATGNYEDL | 544 |
| SEQ_ID_NO_1075 | ADIVAKALVE | PAKSIAANAG | VDGDVVEKT | RTFID-VRIGY | NAMTGTYEDL | 527 |
| SEQ_ID_NO_1095 | AEIVQKALLA | PCRLIGNNAG | VEGDVIVQHV | MEGD-FNYGY | DAMVGEYGDL | 516 |
| SEQ_ID_NO_1055 | ADIVMKSLRA | PCRLIADNAG | VEGEVIVQRL | LGKP-FEVGY | NAMDKVENL | 523 |
| SEQ_ID_NO_1080 | ADIIQKALVA | PASLIAHNAG | VEGEVIVEKI | KDSE-MEFGY | NAMTDKHENL | 536 |
| SEQ_ID_NO_1086 | ADIIQKALVA | PAALIAHNAG | VEGEVIVEKI | KESE-MEVGY | NAMADRHENL | 530 |
| SEQ_ID_NO_1085 | ADIIQKALVA | PAALIAHNAG | VEGEVIVDKI | KESE-MEYGY | NAMADKHENL | 531 |
| SEQ_ID_NO_1097 | ADIIQKALVA | PAALIAHNAG | VEGEVIVDKI | RESE-MEFGY | NAMADKHENL | 533 |
| SEQ_ID_NO_1054 | ADIIQKALVA | PASLIAHNAG | VEGVVVEKI | KOSD-MEVGY | NAMTDKYENL | 519 |
| SEQ_ID_NO_1088 | ADIIQKALVA | PASLIAHNAG | VEGVVVEKI | KOGE-MEVGY | NAMNDKYENL | 525 |
| SEQ_ID_NO_1069 | ADIVQKALLS | PAALIAQNAG | VEGEVVVEKI | MFSD-MENGY | NAMTDTYENL | 534 |
| SEQ_ID_NO_1072 | ADIVQKALVA | Q-SLIAQNAG | IEGEVVVEKI | MFSE-MELGY | NAMTDTYENL | 531 |
| SEQ_ID_NO_1057 | ADIVQKALVA | PASLIAQNAG | MEGEVVVEKV | KNSE-MEIGY | NAMTDTYENL | 534 |
| SEQ_ID_NO_1061 | ADIVQKALYS | PASLIAQNAG | IEGEVVVEKL | KASE-MEIGY | NAMTDKYENL | 534 |
| SEQ_ID_NO_1076 | ADIVQKALVA | PAALIAQNAG | IEGEVVVEKI | KNGE-MEVGY | NAMTDTYENL | 535 |
| SEQ_ID_NO_1092 | ADIVQKALVA | PASLIAQNAG | IEGEVVVEKI | RNGE-MEVGY | NAMTDTYENL | 536 |
| SEQ_ID_NO_1074 | ADIVQKALIA | PAALIAQNAG | IEGEVVVEKI | KSGE-MEVGY | NAMADRYENL | 532 |
| SEQ_ID_NO_1083 | ADIVQKALIA | PASLIAQNAG | IEGEVVVEKV | KNGE-MEVGY | NAMTDRYENL | 529 |

| | | | | | | | |
|---|---|---|---|---|---|---|---|
| SEQ_ID_NO_1058 | -IKAGIIDPL | KVIRTALVDA | ASVSGLMTTT | EAIVVELPKD | E---KEVPA | 565 |
| SEQ_ID_NO_1077 | IMAAGIIDPT | KVWRCCLEHA | ASVAKTFLMS | DCVVVEIKEP | E---AAVAG | 590 |
| SEQ_ID_NO_1078 | -MAAGIIDPT | KVWRCCLEHA | ASVAKTFLMS | DCVVVEIKEP | E---AAVAG | 589 |
| SEQ_ID_NO_1075 | -LNAGVADPS | RVARCALQSA | VSIAGVVLTT | QAILVDKYL- | -----GSN-K | 569 |
| SEQ_ID_NO_1095 | -IEKGVIDPK | KVTRSGVQNS | CSIAGMVLTT | QAVITEIPKK | KRAIGANAGP | 565 |
| SEQ_ID_NO_1055 | -LDAGVIDPA | KVTRNGLLNS | VSIAGIMLTT | QAVMVEKHKP | SEIPGGMT-A | 571 |
| SEQ_ID_NO_1080 | -VEAGVIDPA | KVTRCALQNA | ASVAGMVLTT | QAIVVEKPSK | K---APA-P | 580 |
| SEQ_ID_NO_1086 | -VQAGVIDPA | KVTRCALQNA | ASVAGMVLTT | QAIVVEKPKK | K---ASA-A | 574 |
| SEQ_ID_NO_1085 | -VEAGVIDPA | KVTRCALQNA | ASVAGMVLTT | QAIVVEKPKK | K---APA-A | 575 |
| SEQ_ID_NO_1097 | -VEAGVIDPA | KVTRCALQNA | ASVAGMVLTT | QAIVVEKPQK | -----APA-A | 576 |
| SEQ_ID_NO_1054 | -MEAGVIDPA | KVTRCALQNA | ASVAGMVLTT | QAIVVEKPKP | K---PQV-A | 563 |
| SEQ_ID_NO_1088 | -IEAGVIDPA | KVTRCALQNA | ASVAGMVLTT | QAIVVEKPKP | K---APV-A | 569 |
| SEQ_ID_NO_1069 | -FEAGVIDPA | KVTRCALQNA | ASVAGMVLTT | QAIVVDKPKP | K---APA-A | 578 |
| SEQ_ID_NO_1072 | -LEAGVIDPA | KVTRCALQNA | ASVAGMVLTT | QAIVVDKPKP | K---APA-A | 575 |
| SEQ_ID_NO_1057 | -LAAGVIDPA | KVTRCALQNA | ASVAGMVLTT | QAIVVEKAKP | K---APA-A | 578 |
| SEQ_ID_NO_1061 | -MEAGVIDPA | KVTRCALQNS | ASVAGMVLTT | QAIVVEKPKP | K---TPA-A | 578 |
| SEQ_ID_NO_1076 | -VESGVIDPA | KVTRCALQNA | ASVAGMVLTT | QAIVVEKPKP | K---AAV-A | 579 |
| SEQ_ID_NO_1092 | -IESGVIDPA | KVTRCALQNA | ASVAGMVLTT | QAIVVEKPKP | R---APV-P | 580 |
| SEQ_ID_NO_1074 | -VEAGVIDPA | KVTRCALQNA | ASVAGMVLTT | QAIVVEKPKP | K---APV-A | 576 |
| SEQ_ID_NO_1083 | -VEAGVIDPA | KVTRCALQNA | ASVAGMVLTT | QAIVVEKPKP | K---APT-A | 573 |

Figure 34 (continued)

| | | | |
|---|---|---|---|
| SEQ_ID_NO_1058 | MGGGMGGMDY | | 575 |
| SEQ_ID_NO_1077 | NPMDNSGYGY | | 600 |
| SEQ_ID_NO_1078 | NPMDNSGYGY | | 599 |
| SEQ_ID_NO_1075 | NALTNGKVTV | AVSYSWGMMK PMYYKA | 595 |
| SEQ_ID_NO_1095 | MADEEGNFSL | | 575 |
| SEQ_ID_NO_1055 | SGMPSG-MTI | | 580 |
| SEQ_ID_NO_1080 | AGMPQGMM- | | 588 |
| SEQ_ID_NO_1086 | SGAPEGSLAM | | 584 |
| SEQ_ID_NO_1085 | AGAPEGSFAM | | 585 |
| SEQ_ID_NO_1097 | AAAP- | | 580 |
| SEQ_ID_NO_1054 | -EPPEGALTV | | 572 |
| SEQ_ID_NO_1088 | -EPAEGTLTV | | 578 |
| SEQ_ID_NO_1068 | -AAPEG-LMV | | 586 |
| SEQ_ID_NO_1072 | -AAPEG-LMV | | 583 |
| SEQ_ID_NO_1057 | -AAPEG-LTI | | 586 |
| SEQ_ID_NO_1061 | -AATQGQYAV | | 587 |
| SEQ_ID_NO_1076 | -AAPQG-LTI | | 587 |
| SEQ_ID_NO_1092 | -GAPQG-LTV | | 588 |
| SEQ_ID_NO_1074 | -GAPQG-LTV | | 584 |
| SEQ_ID_NO_1083 | -AAPQG-LTI | | 581 |

Figure 35

| | | |
|---|---|---|
| SEQ_ID_NO_1106 | MAELNVAPSP PPSTILTLED MLRKLPLPSD ETIRSPATTK MCKIVSHRSS | 50 |
| SEQ_ID_NO_1105 | ·········· ·········· ·········· ·········· ·········M | 1 |
| SEQ_ID_NO_1108 | ·········· ·········· ·········· ·········· ······MREY | 4 |
| SEQ_ID_NO_1109 | ··MAAVAPIA MPARVHHHHH HHRRALAASP AALAAAGNGL SATRRVRRSP | 48 |
| SEQ_ID_NO_1101 | ·········· ······MPFA SSSSLIKRRP LL········ ······RHAN | 20 |
| SEQ_ID_NO_1099 | ·········· ·········· MTRHVILTSE E········· ······RNSP | 15 |
| SEQ_ID_NO_1103 | ·········· ·········· MTRHVILKSP LLVSSEESTM ······RNSP | 24 |

| | | |
|---|---|---|
| SEQ_ID_NO_1106 | PRHPTTKANK G······FQC AEVAGGTTAG CAALVCC·PC GIVGLLVLAT | 93 |
| SEQ_ID_NO_1105 | TRQNQLQNRR R······SV GEVAGNALAE CAAICCCVPC AVVDMVALAT | 44 |
| SEQ_ID_NO_1108 | GRGHEEEEGE E··HEPQPGC GEGACDAAAN CAAVCCCCPL ALLDVLLLVT | 52 |
| SEQ_ID_NO_1109 | AVEMRRERER RRAREQQPRC GEVAGGTAAE CAAVFCCFPE AVVELVVLAA | 98 |
| SEQ_ID_NO_1101 | SSGSSCCSGR F········· GEIAGGTTAE CAAICCCCPC GLVNLLVLTI | 61 |
| SEQ_ID_NO_1099 | PTTMIKHAER R······KV GEVAGGAAAE CAAVMCCGPC AVVNLVVLAV | 58 |
| SEQ_ID_NO_1103 | PSTTSLSKER R······KV GEVAGGAAAE CAAVMCCCPC AVVNLMVLAV | 67 |

| | | |
|---|---|---|
| SEQ_ID_NO_1106 | VKLPAGLCRR ALSQKRRKRV KKR······· ······STTL RSRAMSFVSD | 130 |
| SEQ_ID_NO_1105 | YKVPASLKKK AAINNRKKRL LKQ······· ·········· MKKDMKNFLE | 77 |
| SEQ_ID_NO_1108 | VKLPAGVMRR VRRRRRHRD RVS·····RK KRSAAAAVE PASPSGSSGK | 97 |
| SEQ_ID_NO_1109 | VRAPAALCRR AVRGGRRRRV RST·····KP KETGAMDIAS PRGLAAAAAK | 143 |
| SEQ_ID_NO_1101 | YKIPAGICRR ALKRKQRKKL IKKGLFPPRG RGYGCGSCDD PELHIHPMAR | 111 |
| SEQ_ID_NO_1099 | YRVPAAVCKK AMRQTKRQRF MRR·····RH GLLASAAA·· ·ESTVHARLK | 100 |
| SEQ_ID_NO_1103 | YKVPAAVCKK AVRRSKRRRF TRK·····RH GLLASATAEG SESTVHARLN | 112 |

| | | |
|---|---|---|
| SEQ_ID_NO_1106 | DEDFGVPSFV PRTPETWPSK SPSVEVAEK· EEEMVLAEFY SAGFWRSPSQ | 178 |
| SEQ_ID_NO_1105 | HEKPGGP··G PETVVVGPTM EELLAQEELP EEDLW·ARFS VNGFWRSSSS | 124 |
| SEQ_ID_NO_1108 | AMIGAAP··S PLEAEEEEAR GEAAAAAEL· EREIMSSRFY GAGFWRSVSS | 144 |
| SEQ_ID_NO_1109 | ARKVDAD··F PAT····PKA EHLVDM···· EKEVW·ASFY GGGFWRSPSQ | 182 |
| SEQ_ID_NO_1101 | VEDSLRE··F DGEIEIAVKK EEL·AMLRL· EKEMW·ETFY GTGFWRSPSQ | 153 |
| SEQ_ID_NO_1099 | EEDPTAE··I VFEIEINVVN VELNDVVVL· EDEMF·ERFY GAGFWRSPSQ | 144 |
| SEQ_ID_NO_1103 | EEDLTAE··I VFEIECHVSG GELNDVVRL· ENEML·DRFY GAGFWRSPSQ | 157 |

Figure 35 (continued)

| | | |
|---|---|---|
| SEQ_ID_NO_1106 | ·········· KESN····· ············ ············ ··· | 182 |
| SEQ_ID_NO_1105 | ·····QKHEP DELQTGEN·· ············ ············ ·NR | 139 |
| SEQ_ID_NO_1108 | ·········· GCSSSASMRY Q··········· ············ ··· | 155 |
| SEQ_ID_NO_1109 | REDRRCI AAG DGAAAAALFF FSFTTVVGFL AFLLPFLGKR EDR | 225 |
| SEQ_ID_NO_1101 | RELPAKRSSP RETPNARL·· ············ ············ ··· | 171 |
| SEQ_ID_NO_1099 | ·········· RDTSSGSI·· ············ ············ ··· | 152 |
| SEQ_ID_NO_1103 | ·········· KDTSSGSL·· ············ ············ ··· | 165 |

Figure 36

| | | | | | | |
|---|---|---|---|---|---|---|
| SEQ_ID_NO_1112 | MAQNKMVMV | LLSTFLVVA | RSLWPEEPS | NADD-IRGAC | IEECTKE-NK | 48 |
| SEQ_ID_NO_1113 | MAQNKTIAVA | LLATLVAV- | ----MGKEPE | TLEETLRAGC | KEECSEQKKK | 45 |
| SEQ_ID_NO_1114 | MAQNKTIAVA | LLATLVAV- | ----MGKEPE | TLEEAVRAGC | KEECSEQKKK | 45 |

| | | | | | | |
|---|---|---|---|---|---|---|
| SEQ_ID_NO_1112 | APGDKKTCEV | LC-------- | ---------- | ---------- | ---------T | 61 |
| SEQ_ID_NO_1113 | APIDEKQCED | FCFIKTKSIF | EAHKGVKDLK | ADRFIDFCNN | ECNAVYKEDP | 95 |
| SEQ_ID_NO_1114 | APIDEKQCED | FCFIKTKSIF | EAHKGVKDLK | ADRFIDFCNN | ECNAVYKEDP | 95 |

| | | | | | |
|---|---|---|---|---|---|
| SEQ_ID_NO_1112 | KLTKKPSEEG | KHD------- | ---------- | ---- | 74 |
| SEQ_ID_NO_1113 | ATSKKCAESC | EADAKEAEVF | LDKVVAYMQT | MKQA | 129 |
| SEQ_ID_NO_1114 | ATSKKCAESC | EADAKEAEVF | LDKVVAYIQT | TKQA | 129 |

Figure 37

```
SEQ_ID_NO_1138    M---KRSREA EEEEEQAA-- --GAELLLLL SLSRGDKPA- ----------  32
SEQ_ID_NO_1141    M------TKH PRDGEVIS-- --LSLSLTLG AAADSGERK- ----------  29
SEQ_ID_NO_1143    -MAMKR-MRS EDIVGDKDSL DDMAKCLMLL S--HGGGLT- ----------  35
SEQ_ID_NO_1120    MLLSKVGQAD HEILTNYR-- --SAAAAAAA A--TAGA--- ----------  31
SEQ_ID_NO_1147    MAKRERAAWE VEAGAAAD-- --TARLLMLL A--QAQQHL  LQQHAHHHHH  44
SEQ_ID_NO_1132    -----MAMKR QRSNEGID-- --YANCLMLL S--CPQQ--- ----------  26
SEQ_ID_NO_1134    MSAMKR-SRE DRQVEAAA-- --MANCLMLL S--KLNDKS- ----------  32
SEQ_ID_NO_1136    ---------- ---------- --MARILLLF SGHHQHHAH- ----------  17
SEQ_ID_NO_1145    ---------- ---------- --MPMPMPVA A--RGHR--- ----------  13
SEQ_ID_NO_1144    WAI---SE KSTVETTA-- --AANCLMLL S--RVGQEN- ----------  30
SEQ_ID_NO_1116    WAI---SE NPTVEAT--- --AANCLMLL S--RVGQK-- ----------  28
SEQ_ID_NO_1123    WAI---SE KSTVDVT--- --AANCLMLL S--RVGQEN- ----------  29
SEQ_ID_NO_1140    -MTIKRSWED DREVENLA-- --MANCLMLL S--RVGQS-- ----------  31
SEQ_ID_NO_1133    WMINIPMKR TREANDFDSI TTMANCLMLL SQNRSGEFI- ----------  39
SEQ_ID_NO_1118    -------MKR GRDIDAMD-- --MADCLMLL S--RVGET-- ----------  25
SEQ_ID_NO_1129    -------MKR GREESKLD-- --MANCLMLL T--KVGES-- ----------  25

SEQ_ID_NO_1138    ------TVRK K---VRAAEG ---VFECKIC SRQFPTFQAL GGHRISHNRP  70
SEQ_ID_NO_1141    ------KPRR GSSPAASGSG ---DFVCKTC SRAFPSFQAL GGHRTSHLRG  70
SEQ_ID_NO_1143    ------TDTK ----PKTCPH PVDVFECKTC NRQFSSFQAL GGHRASHKRP  75
SEQ_ID_NO_1120    ---------- ----GAGAGR ---SFSCKTC NKNFPSFQAL GGHRASHKKP  64
SEQ_ID_NO_1147    HHHGVGVPPF PAGRAAVHGR ---VFECKTC SRQFPTFQAL GGHRASHKRP  91
SEQ_ID_NO_1132    ---------- ----KSYENG ---EVECKTC NKKFSSFQAL GGHRASHKRM  59
SEQ_ID_NO_1134    ------TSTT TT--NQDHHN ---DFECKTC NKRFSSFQAL GGHRASHKRP  71
SEQ_ID_NO_1136    ------YG-- ----PSSPER ---VFECKTC NRRFPSFQAL GGHRASHKKP  52
SEQ_ID_NO_1145    ---------- --------APER ---VFVCKTC DRVFPSFQAL GGHRASHKKP  44
SEQ_ID_NO_1144    ------VD-- ----GGSAKR ---VFTCKTC LKEFHSFQAL GGHRASHKKP  65
SEQ_ID_NO_1116    ---------- ----GGDQKR ---VFTCKTC LKEFHSFQAL GGHRASHKKP  61
SEQ_ID_NO_1123    ------VD-- ----GGDQKR ---VFTCKTC LKQFHSFQAL GGHRASHKKP  64
SEQ_ID_NO_1140    ---------- ----GSTPDR ---VFHCKTC DKEFKSFQAL GGHRASHKRP  64
SEQ_ID_NO_1133    ------DSTT SNSSNLNSNR ---VFECKTC NRQFPSFQAL GGHRASHKRP  80
SEQ_ID_NO_1118    ---------- ----DRVAGR ---VFACKTC NKKFSSFQAL GGHRASHKKP  58
SEQ_ID_NO_1129    ------ETNY PISKGSDIG- ---DFKCKTC NRRFSSFQAL GGHRASHKKP  65
```

Figure 37 (continued)

| | | | | | |
|---|---|---|---|---|---|
| SEQ_ID_NO_1138 | RVDRS- - - - - - - - - - TS- - - - - - - - - - - - - - - - - - - - - - - - - - - - RRSVHQCS | 85 |
| SEQ_ID_NO_1141 | RHGLA- - - - L GLAAATAKET TKKVQEKPA- - - - - - - - - - - - - AAATHECH | 103 |
| SEQ_ID_NO_1143 | RLMGE- - - - - - - - - EHKVD RTKLCSSGN- - - - - - - - - - - - KPKMHECS | 102 |
| SEQ_ID_NO_1120 | KLKES- - - - - - - - - T- - - - - GNLKLPNS PS- - - - - - - - - - - KPKTHQCS | 89 |
| SEQ_ID_NO_1147 | RVLQQQQLQQ QQTVVADHAG QLCLGRQPLQ LPLPTTTTPQ QAKPRVHECP | 141 |
| SEQ_ID_NO_1132 | KLAEG- - - - - - - - - - - - EELKEQAKS LSLWN- - - - - - KPKMHECS | 86 |
| SEQ_ID_NO_1134 | KLLIG- - - - - - - - A- - - - GEFLVQPS- - - - - - - - - - - - SKKMHECS | 93 |
| SEQ_ID_NO_1136 | RLADG- - - - - - - - - - - - - - AGAEPP- - - - - - - - - - - - - KPKVHGCS | 71 |
| SEQ_ID_NO_1145 | RLDDG- - - - - - - - - - - - - - - GDL- - - - - - - - - - - - - - - - KPKLHGCS | 60 |
| SEQ_ID_NO_1144 | NNENL- - - - - - - - - S- - - - GLMKKTK- - - - - - - - - - - - ASSSHPCP | 88 |
| SEQ_ID_NO_1116 | NNNES- - - - - - - - - - - L SGLVKKAK- - - - - - - - - - - - APSSHPCP | 83 |
| SEQ_ID_NO_1123 | NNDAL- - - - - - - - - SS- - - GLMKKV- - - - - - - - - - - - - KTSSHPCP | 85 |
| SEQ_ID_NO_1140 | KTSDG- - - - - - - - - - - - - SEARTPP- - - - - - - - - - - - - KPKTHECP | 84 |
| SEQ_ID_NO_1133 | RLGGD- - - - - - - - - - - - - LTLSQIPVA AA- - - - - - - - - KPKTHECS | 104 |
| SEQ_ID_NO_1118 | KLTVG- - - - - - - - DN- - - EGLAVSP- - - - - K- - - - KPKTHECS | 61 |
| SEQ_ID_NO_1129 | KLMVT- - - - - - - - DL- - - SCHQELPNP TMKQ- - - - - - QPRMHPCP | 93 |

| | | | | | |
|---|---|---|---|---|---|
| SEQ_ID_NO_1138 | CGVEFAMGQ ALGGHMRRHK PMAEDSKRSD PKK- - - - - - - - - - - - - - - - | 118 |
| SEQ_ID_NO_1141 | CGQGFEMGQ ALGGHMRRHR EEAAAAAAAV H- - - - - - - - - - - - - - - - - | 134 |
| SEQ_ID_NO_1143 | LCGQKFSMGQ ALGGHMRRHR A- - NEGLSSI MNPLDHA- - - - - - - KVPM | 141 |
| SEQ_ID_NO_1120 | CGLEFPLGQ ALGGHMRRHR APNNVDTTST SSKDHELAVT QPPFLPAVPV | 139 |
| SEQ_ID_NO_1147 | VCGLEFAVGQ ALGGHMRRHR AEAEAEATEA PSKVMMR- - - - - - - - - PA | 180 |
| SEQ_ID_NO_1132 | CGMGFSLGQ ALGGHMRKHR AVINEGVSSI NQIIEKF- - - - - - - - - PV | 125 |
| SEQ_ID_NO_1134 | CGMEFSLGQ ALGGHMRRHR AAIDEKSKAA TKAMMIP- - - - - - - - - - V | 131 |
| SEQ_ID_NO_1136 | CGLEFAVGQ ALGGHMRRHR AVAAAGPGVG LGLSLGL- - - - GLGPNEDG | 116 |
| SEQ_ID_NO_1145 | VCGLEFAIGQ ALGGHMRRHR AMAAGGGGGM MPMTPPT- - - - - AAALKE | 103 |
| SEQ_ID_NO_1144 | CGVEFPMGQ ALGGHMRRHR NESG-GAGAL VTRELLP- - - - - EAALMT | 128 |
| SEQ_ID_NO_1116 | CGVEFPMGQ ALGGHMRRHR NEIG-GGAAL VTRALLP- - - - - EPTMTT | 125 |
| SEQ_ID_NO_1123 | CGVEFPMGQ ALGGHMRRHR NESGAAGGAL VTRALLP- - - - - EPTVTT | 128 |
| SEQ_ID_NO_1140 | VCGLEFAIGQ ALGGHMRRHR DVGNEK- - BG RPVAARP- - - - - - - - - - - | 119 |
| SEQ_ID_NO_1133 | CGLEFAIGQ ALGGHMRRHR AAMSDSASGN SASPPRDDRT VVVKKSNIV- | 153 |
| SEQ_ID_NO_1118 | CGLEFAIGQ ALGGHMRRHR AALNDG- - -L VTRDLLP- - - - - - - - - - E | 116 |
| SEQ_ID_NO_1129 | CGLEFAIGQ ALGGHMRKHR TAINDGLLCG KPSSSLS- - - - - - - - ILKE | 134 |

Figure 37 (continued)

```
SEQ_ID_NO_1138   .......... .......... M DLT MADPEF- .......... G DL HR VR ---   135
SEQ_ID_NO_1141   .......... .......... .... APPV- .......... ..........           138
SEQ_ID_NO_1143   L KRSNS- --- --- TRVV CSL DLN -LTPL .......... E N - DLK- L F    170
SEQ_ID_NO_1120   L KRSNS S--- --- KRVL C-L DLS LAL PMY- .......... Q NDS ELQ- LEK 171
SEQ_ID_NO_1147   HDKT CDV- --- --- AGG C-L DLN -LTPS- .......... E NCAKC RS VMV   211
SEQ_ID_NO_1132   L KRL NS- --- --- KRI MG-L DLN -LTPL .......... E ND- DLM- FG    153
SEQ_ID_NO_1134   L KKSNS S- --- --- KRI FC-L DLN -LTPR- .......... N EDV DLK- L MP 161
SEQ_ID_NO_1136   NKK AAA- --- --- AAE LA-L DLN -EPAL .......... E EEP ADR- AM     145
SEQ_ID_NO_1145   HGES GDDDAV VGMKRGL W-L DLN -HPP CD EYGAGSESDD ECGH VD- AAA      149
SEQ_ID_NO_1144   L KKSSS- --- --- GRL AC-L DLS -LGMW .......... E NL- NLK- LEL    156
SEQ_ID_NO_1116   L KKSSS G--- --- KRVAC-L DLS -LGMW .......... E NL- NLK- LEL     154
SEQ_ID_NO_1123   L KKSSS G--- --- KRVAC-L DLS -LGMW .......... D NL- NLK- LEL     157
SEQ_ID_NO_1140   --- ES VT- --- --- KRGLF-M DLN -LTPL .......... E N - DLK- L WS  144
SEQ_ID_NO_1133   -- DDDN D--- --- RRV MG-L DLN -LTPF- .......... E N - HLE- FQL   179
SEQ_ID_NO_1118   MN KST GD- --- --- GRDPS- DLG -LTSW- .......... G VDLELK- L -    144
SEQ_ID_NO_1129   SSK DGDQ- --- --- KLNLR-L DLN -LTPL .......... E ED- DLK- LNL    163

SEQ_ID_NO_1138   ------- RTG SHCQL LQL FV         148
SEQ_ID_NO_1141   .......... ---- LL EL FV        144
SEQ_ID_NO_1143   ------- GKM APKVDL RLM           183
SEQ_ID_NO_1120   .......... --- VARPM L RCF I    181
SEQ_ID_NO_1147   LGAAAGQ GVH KTLAM L DCSL         231
SEQ_ID_NO_1132   ------- KSP PTPI PL SLF          165
SEQ_ID_NO_1134   ------- TAP ISSPV L RI F         174
SEQ_ID_NO_1136   ------- GLA VGFRPRGG--          156
SEQ_ID_NO_1145   AGYTFHQF MD TGTMA V DCV-        168
SEQ_ID_NO_1144   ------- GRP VC --------          161
SEQ_ID_NO_1116   ------- GRT VC --------          159
SEQ_ID_NO_1123   ------- GRT VY --------          162
SEQ_ID_NO_1140   ------- NTV NTAL AM ---         153
SEQ_ID_NO_1133   ------- GKI APT-- V DCFL        190
SEQ_ID_NO_1118   ------- GKV TPTPV H CFI         157
SEQ_ID_NO_1129   .......... - RTPVL NCFI         172
```

Figure 38

| | | | | | | |
|---|---|---|---|---|---|---|
| SEQ_ID_NO_1162 | MATKIFALLV | LLALSASATT | AMIPQCSLA | PTAAIIPRFL | PPVSAIGFEH | 50 |
| SEQ_ID_NO_1163 | MATKIFVLLA | LLALSVSTTT | AMIPQCSLA | PNAFLISQFL | PPLTLVGFEH | 49 |
| SEQ_ID_NO_1161 | MAAKIFAILA | LLALSASVAT | ATIIPQCSQF | -------QYL | SPVTAARFEY | 42 |
| SEQ_ID_NO_1159 | MATKIFSLLM | LLALSACVAN | ATIFPQCSQA | PIASLLPPYL | PSMIASVCEN | 50 |
| SEQ_ID_NO_1164 | MAAKIFCFLM | LLGLSASVAT | ATIFPQCSQA | PIASLLPPYL | SPAVSSMCEN | 50 |

| | | | | | | |
|---|---|---|---|---|---|---|
| SEQ_ID_NO_1162 | PAVQAYRLQQ | ALAASIL-- | ----QQPLAD | LQQQSSAHLT | IQTIAAQQIQ | 92 |
| SEQ_ID_NO_1163 | PALQAYRLQQ | ALANSIL-- | ----QQPFPQ | LQQQSSAHLT | VQTIAAQQQQ | 92 |
| SEQ_ID_NO_1161 | PTIQSYRLQE | AIAASILRSL | ALTVQQPYAL | LQQPSLMNLY | LQRIAAQQLQ | 92 |
| SEQ_ID_NO_1159 | PALQPYRLQQ | AIAASNIPLS | PLLFQQSPAL | ----SLVQSL | VQTIRAQQLQ | 96 |
| SEQ_ID_NO_1164 | PIVQPYRIQQ | AIATGLPLS | PLFLQQPSAL | LQQLPLVHLV | AQNIRAQQLQ | 100 |

| | | | | | | |
|---|---|---|---|---|---|---|
| SEQ_ID_NO_1162 | QQFLPSLSQL | AAANPTAYLQ | QQLLASNPLA | VANAIAYQHQ | QQLQQLLPAL | 142 |
| SEQ_ID_NO_1163 | QQFLPALSQL | ALANPVAYLQ | QQLLASNPLA | LVNNAAYQ-Q | QQLQQVLPVI | 141 |
| SEQ_ID_NO_1161 | QQLLPTINQV | VAANLAAYLQ | Q--------- | ---------- | ---QQFLPFF | 119 |
| SEQ_ID_NO_1159 | QLVLPVINQV | ALANLSPYSQ | Q--------- | ---------- | ---QQFLPFF | 123 |
| SEQ_ID_NO_1164 | ------QL | VLANLAAYSQ | Q--------- | ---------- | ---HQFLPFF | 119 |

| | | | | | | |
|---|---|---|---|---|---|---|
| SEQ_ID_NO_1162 | SQLAVANPAA | YLQ-SQLFPS | NPLV-ANAAA | YLQQQQLQQI | LPVLSQLAVA | 190 |
| SEQ_ID_NO_1163 | SQVAMANPAA | YLQ-QQQLAY | NPLVAANAAA | YLQQQQLQQI | LPALSQLALV | 190 |
| SEQ_ID_NO_1161 | NQLAGVNPAA | YLQAQQLLPF | NQLV-RSPAA | FLLQQQL--- | LP-FHLQVVA | 164 |
| SEQ_ID_NO_1159 | NQLSTLNPAA | YLQ-QQLLPF | SQLA----TA | YSQQQQL--- | LP-FNQLAAL | 164 |
| SEQ_ID_NO_1164 | NQLAALNSAA | YLQ-QQ-LPF | SQLV----RA | YP--RQF--- | LP-FNQLAAL | 157 |

| | | | | | | |
|---|---|---|---|---|---|---|
| SEQ_ID_NO_1162 | DPNSYL-QQQ | QLLPFNQVAV | ANNAVYEQQH | QLLQVNPLA- | -----AAFLQ | 233 |
| SEQ_ID_NO_1163 | NPAAYL-QQQ | QLLPFNQLAV | TNTAAYLQQQ | QLLRVNPVVA | ANPLAAAFLQ | 239 |
| SEQ_ID_NO_1161 | NIAAFLQQQQ | QLLPFYPQVV | GNINAFLQQQ | QLLPFYPQDV | ANN--VAFLQ | 212 |
| SEQ_ID_NO_1159 | NPAAYL-QQQ | ILLPFSQLAA | ANRASFLTQQ | QLLPFYQQFA | ANP--ATLLQ | 211 |
| SEQ_ID_NO_1164 | NSAAYL-QQQ | QLLPFSQLAD | VSPAAFLTQQ | QLLPFYLHAM | PNA--GTLLQ | 204 |

| | | | | | |
|---|---|---|---|---|---|
| SEQ_ID_NO_1162 | QQQRQLLPFN | QMSLMNPALS | WQQPIVGGVG | F- | 264 |
| SEQ_ID_NO_1163 | QQ--QLLPFN | DISLMNPAFS | WQQPIVGSAI | F- | 268 |
| SEQ_ID_NO_1161 | QQ--QLLPFN | QLALTNPTTL | LQQPTIGGAI | F- | 241 |
| SEQ_ID_NO_1159 | LQ--QLLPFV | QLALTDRAAS | YQQHIGGAL | F- | 240 |
| SEQ_ID_NO_1164 | LQ--QLLPFN | QLALTNSTVF | YQQPIIGGAL | FD | 234 |

Figure 39

| | | | | | | |
|---|---|---|---|---|---|---|
| SEQ_ID_NO_1167 | MAK------ | -NGINNSVAV | GIAVQSDWDN | RHFSSSLSLN | VRRLFEFLLQ | 42 |
| SEQ_ID_NO_1182 | MGR----GG | --GMGNPVNV | GIAVQADWGN | REFISNISLN | VRRLFDFLLR | 43 |
| SEQ_ID_NO_1166 | MGR----GG | --GMGNPVNV | GIAVQADWEN | REFISNISLN | VRRLFDFLLR | 43 |
| SEQ_ID_NO_1183 | MAR----AG | GHGMGNPVNV | GIAVQADWEN | REFISNISLN | VRRLFDFLLR | 45 |
| SEQ_ID_NO_1173 | MARAGGGGGG | GGGITNAVNV | GIAVQADWEN | REFISHISLN | IRRLFDFLIQ | 50 |
| SEQ_ID_NO_1169 | MSR----GG | GVGITNAVNV | GIAVQADWEN | REFISNISIN | VRRLFDFLIN | 45 |
| SEQ_ID_NO_1177 | MAR----AG | --GITNAVNV | GIAVQADWEN | REFISHISLN | VRRLFDFLVQ | 43 |
| SEQ_ID_NO_1180 | MAR----AG | --GITNAVNV | GIAVQADWEN | REFISHISLN | VRRLFDFLVQ | 43 |
| SEQ_ID_NO_1171 | MAR----AG | --GITNAVNV | GIAVQADWEN | REFISHISLN | VRRLFEFLLQ | 43 |
| SEQ_ID_NO_1175 | MAK----AG | --GITNAVNV | GIAVQADWEN | REFISHISLN | VRRLFEFLVQ | 43 |

| | | | | | | |
|---|---|---|---|---|---|---|
| SEQ_ID_NO_1167 | FESSTRSKLA | TLNEKLTVLE | RQLEFLEADF | STALINPV-- | -------- | 79 |
| SEQ_ID_NO_1182 | FEATTKSKLA | SLNEKLDILE | RKLEVLEVQV | SSATTNPSVF | N------- | 84 |
| SEQ_ID_NO_1166 | FEATTKSKLA | SLNEKLDILE | RKLEVLEVQV | GSATTNPSVF | N------- | 84 |
| SEQ_ID_NO_1183 | FEATTKSKLA | SLNEKLDILE | RKLEVLEVQV | SSATTNPSVF | N------- | 86 |
| SEQ_ID_NO_1173 | FESTTKSKLS | SLNLKLDTLE | RRLQLLELQV | STATSNPSLF | TSTTTTTA | 98 |
| SEQ_ID_NO_1169 | FEATTKSKLA | SLNEKLDTLE | RRLELLEVQV | GTASANPSLF | T------- | 86 |
| SEQ_ID_NO_1177 | FEATTKSKLA | SLNEKLDVLE | RRLELLEVQV | GNASANPSLF | AT------ | 85 |
| SEQ_ID_NO_1180 | FEATTKSKLA | SLNEKLDVLE | RRLELLEVQV | GNASANPSLF | AT------ | 85 |
| SEQ_ID_NO_1171 | FEATTKSKLA | SLNEKLDTLE | RRLELLEVQV | GTASANPSLF | ST------ | 85 |
| SEQ_ID_NO_1175 | FESTTKSKLA | SLNEKLDLLE | RRLEMLEVQV | STATANPSLF | AT------ | 85 |

Figure 40

| | | | | | | |
|---|---|---|---|---|---|---|
| SEQ_ID_NO_1187 | MFSWLRGCR | DECSATDQLK | Q---------- ---------A | RDVFVAKEAV | | 32 |
| SEQ_ID_NO_1185 | MFAWLRGCR | DECSASDQLK | Q---------- ---------A | HDVFKAKEVV | | 32 |
| SEQ_ID_NO_1189 | MFSWLRGCR | DECSASDQLK | Q---------- ---------A | RDVFMAKEAV | | 32 |
| SEQ_ID_NO_1190 | MFAWLLRGCR | DECSASDQLK | QGVVKEKNRC | WFWGAFSVNA | RDVFVAKEAV | 50 |
| SEQ_ID_NO_1191 | MFAWLLRGCR | DECSASDQLK | Q---------- ---------A | RDVFVAKEAV | | 32 |

| | | | | | | |
|---|---|---|---|---|---|---|
| SEQ_ID_NO_1187 | LQKKISQEME | RAKEFKKSGN | KQAAMQCLKR | KRYYESQMNQ | VGSVRLRIDT | 82 |
| SEQ_ID_NO_1185 | LQKKISQEVE | RAKEFTKSGN | KQAAMQCLKR | KRYYESQMNQ | VGSVQLRINT | 82 |
| SEQ_ID_NO_1189 | LQKKISQEME | RAKEFTKSGN | KQAAMQCLKR | KKYYESQMSQ | VGSVQLRINT | 82 |
| SEQ_ID_NO_1190 | LQKKISQEME | RAKEFTKSGN | KQAAMQCLKR | KKYYESQMNQ | VGSVQLRINT | 100 |
| SEQ_ID_NO_1191 | LQKKISQEME | RAKEFTKSGN | KQAAMQCLKR | KKYYESQMNQ | VGSVQLRINT | 82 |

| | | | |
|---|---|---|---|
| SEQ_ID_NO_1187 | KEKMIADNMV | N---K | 94 |
| SEQ_ID_NO_1185 | KERMIADHTG | N---K | 94 |
| SEQ_ID_NO_1189 | KEKMIADHMG | N---K | 94 |
| SEQ_ID_NO_1190 | KEKMIADHSG | NKEDK | 115 |
| SEQ_ID_NO_1191 | KEKMIADHSG | NKEDK | 97 |

Figure 41

| | | | | | | | |
|---|---|---|---|---|---|---|---|
| SEQ_ID_NO_1204 | ........MVK | TRAAATPR.. | ............. | ..... | PSGGG | GAGAADI TAG | 26 |
| SEQ_ID_NO_1203 | MGEQSLSDPK | PQPLSPFPSP | PASAAL---- | ----- | PPPAS | ASASASASAA | 41 |
| SEQ_ID_NO_1205 | MESPNPQQVN | SMGDQSPLSP | NLHPLS---- | ------ | PSPSA | AAAAAA.... | 37 |
| SEQ_ID_NO_1196 | MGEDTPSQPQ | PQVQSQPPND | SSTTTQAQVQ | NQSGDPSNTS | TAAVSTVTTA | 50 |
| SEQ_ID_NO_1202 | MGEQTLGQAQ | SLIEPQPL.. | ............. | ..... | PAPSS | TAVPDGATVD | 33 |
| SEQ_ID_NO_1194 | ---MSLRKIL | TAVNQSSL-- | ............. | ..... | PPDSL | ISAGNLTVSE | 30 |
| SEQ_ID_NO_1200 | MGKPVTRSHS | LLLHEPSS-- | ............. | ..... | PPLS- | .......... | 22 |

| | | | | | | | |
|---|---|---|---|---|---|---|---|
| SEQ_ID_NO_1204 | .......... | .......... | ....KISFRS | RKIVKSTPAK | GKSVATTTTA | 52 |
| SEQ_ID_NO_1203 | .......... | .......... | ........S | TSRTTSAAAS | RPKKKVTN-P | SPDRNPAKKP | 71 |
| SEQ_ID_NO_1205 | .......... | .......... | ........T | PTPAAAAASS | RSSRSKKPPH | SSDPNQSKKP | 68 |
| SEQ_ID_NO_1196 | CTAIVACGPT | ELVNVPLPTS | SPPSKIPSRP | RKIRKLSPDL | SFDPNASQDA | 100 |
| SEQ_ID_NO_1202 | ........S | ELNNVPRPTT | SPATKIPLRP | RKIRKVSPDP | STSESQTETP | 74 |
| SEQ_ID_NO_1194 | .......... | .......... | ........VS | GSSSRIRFRP | RKIRKVSSDP | SPRIIITASP | 62 |
| SEQ_ID_NO_1200 | .......... | .......... | ........T | TTSSKISFQS | RKIRKLSTNK | TTTTTTAITS | 53 |

| | | | | | | | |
|---|---|---|---|---|---|---|---|
| SEQ_ID_NO_1204 | .......... | .VLS...... | .......... | ...PP----P | LSSPGELAAA | 68 |
| SEQ_ID_NO_1203 | .......... | .RLT...... | .......... | ...FSIPGRP | LSAVGEVGVA | 91 |
| SEQ_ID_NO_1205 | .......... | -RLT...... | .......... | ...LTVPGRP | LSADGEVAAA | 88 |
| SEQ_ID_NO_1196 | TTSSSTSLTE | QRKTVGRTSK | TKLSQHRALA | VVAPRIIARS | LSDEGEVETA | 150 |
| SEQ_ID_NO_1202 | .......... | .KPAKTGGRN | TTKAAPPRAL | TVVPRIVARS | LSDDGEVEIA | 113 |
| SEQ_ID_NO_1194 | .......... | .......... | .......... | ..........P | LSTKSTVDIA | 73 |
| SEQ_ID_NO_1200 | .......... | .TSI...... | .......... | ...PPL--KP | LSHKGEIELA | 71 |

| | | | | | | | |
|---|---|---|---|---|---|---|---|
| SEQ_ID_NO_1204 | LSHLRTADPL | LSEVIASTGA | PAFISSPSRP | AFHSLAHSIL | HQQLAPSAAA | 118 |
| SEQ_ID_NO_1203 | IRYLRAADPA | LAAVIDAH-E | PPVFQCPHRP | -FHSLVRSIL | YQQLAFKAAA | 139 |
| SEQ_ID_NO_1205 | IQHLRAADPA | LATVIDAH-D | PPAFQCPHRP | -FHSLVRSIL | YQQLAFKAAA | 136 |
| SEQ_ID_NO_1196 | IRHLRDADPL | LASLIDLH-P | PPTFDTFHAP | -FLALTRSIL | YQQLAFKAGT | 198 |
| SEQ_ID_NO_1202 | LRYLRNADPV | LSPLIDIH-Q | PPTFDNFHTP | -FLALTRSIL | YQQLAYKAGT | 161 |
| SEQ_ID_NO_1194 | LRHLQSSDEL | LGALITTHND | PPVFDSSNTP | -FLSLARSIL | YQQLATKAAK | 122 |
| SEQ_ID_NO_1200 | LDHLSKSDPL | LAPLLNSH-E | PPALNPCTSP | -FLSLTKSIL | FQQLATNAAK | 119 |

Figure 41 (continued)

| | | | | | | | |
|---|---|---|---|---|---|---|---|
| SEQ_ID_NO_1204 | AIYARFLAL | PAAADPDAAV | VNPAAVLALS | AADLRAIGVS | ARKAAYLHDL | | 168 |
| SEQ_ID_NO_1203 | SVYSRFLALL | ----G-GESC | VAPDAVLALT | PHQLRQIGVS | PRKASYLHDL | | 184 |
| SEQ_ID_NO_1205 | SVYSRFLSLL | ----G-GEHN | VLPEAVLALT | TQDLRQIGVS | PRKASYLHDL | | 181 |
| SEQ_ID_NO_1196 | SIYTRFISLC | ----G-GENG | VVPETVLSLT | SQQLRQIGVS | GRKASYLHDL | | 243 |
| SEQ_ID_NO_1202 | SIYTRFIALC | ----G-GENG | VVPETVLALT | PQQLRQIGVS | GRKASYLHDL | | 206 |
| SEQ_ID_NO_1194 | CIYDRFISLF | ----NGGEAG | VFPESVISLS | AVDLRKIGVS | GRKASYLHDL | | 168 |
| SEQ_ID_NO_1200 | SIYTRFLTLC | ----D-GESD | VNPDTVLSLS | APKLREIGVS | GRKASYLHDL | | 164 |

| | | | | | | | |
|---|---|---|---|---|---|---|---|
| SEQ_ID_NO_1204 | AGRFAAGELS | ESAVAAMDEA | ALLAELTKVK | GVGEWIVHMF | MIFSLHRPDV | | 218 |
| SEQ_ID_NO_1203 | ARKYASGILS | DAAIVNMDDR | SLAAMLTMVK | GIGSWSVHMF | MIFSLARPDV | | 234 |
| SEQ_ID_NO_1205 | ARKYASGILS | DAAVVNMDDR | SLAAMLTMVK | GIGAWSVHMF | MIFSLNRPDV | | 231 |
| SEQ_ID_NO_1196 | ARKYQTGILS | DSAIVNMDDK | SLFTMLTMVN | GIGSWSVHMF | MIFSLHRPDV | | 293 |
| SEQ_ID_NO_1202 | ARKYQNGILS | DSAIVNMDDK | SLLTMLTMVN | GIGSWSVHMF | MIFSLHRPDV | | 256 |
| SEQ_ID_NO_1194 | ADKYNNGVLS | DELILKMSDE | ELIDRLTLVK | GIGVWTVHMF | MIFSLHRPDV | | 218 |
| SEQ_ID_NO_1200 | AEKYRNGSLS | DSSILEMNDD | MLLNRLTEVK | GIGVWSVHMF | MLFSLHRPDV | | 214 |

| | | | | | | | |
|---|---|---|---|---|---|---|---|
| SEQ_ID_NO_1204 | LPSGDLGVRK | GVQELYGLPA | LPKPEEMAAL | CERWRPYRSV | GAWYMWRLME | | 268 |
| SEQ_ID_NO_1203 | LPSADLGVRK | GVQMLYALED | VPRPSQMDKL | CERWRPYRSV | GAWYMWRLIE | | 284 |
| SEQ_ID_NO_1205 | LPAADLGVRK | GVQHLYGLDA | VPRPSQMEKL | CEQWRPYRSV | GAWYMWRLIE | | 281 |
| SEQ_ID_NO_1196 | LPINDLGVRK | GVQLLYNLEE | LPRPSQMDQL | CEKWRPYRSV | ASWYLWRYVE | | 343 |
| SEQ_ID_NO_1202 | LPINDLGVRK | GVQLLYNLED | LPRPSQMDQL | CDKWRPYRSV | ASWYMWRFVE | | 306 |
| SEQ_ID_NO_1194 | LPVGDLGVRK | GVKDLYGLKN | LPGPLQMEQL | CEKWRPYRSV | GSWYMWRLIE | | 268 |
| SEQ_ID_NO_1200 | LPVGDLGVRK | GVQSLYGLKD | LPQALEMEQI | CEKWKPYRSV | GSWYMWRLME | | 264 |

| | | | | | | | |
|---|---|---|---|---|---|---|---|
| SEQ_ID_NO_1204 | SKGAAAKKAK | SNAIATLPS- | -------SC- | ---------- | ---QQQQTVIQM | | 289 |
| SEQ_ID_NO_1203 | SKVPQPAPAI | PVGSLAFPS- | ---------P | DGQSMLQQQE | QQQQQTVIQM | | 324 |
| SEQ_ID_NO_1205 | SKAPPPPPAI | PVGPPALTE- | -------HGD | ELMLQQQQHQ | QQQQQSVIQM | | 323 |
| SEQ_ID_NO_1196 | AKGAPSSAAA | VAAGASLPP- | ---------- | ----LQQQEE | PQQHQQQPPL | | 378 |
| SEQ_ID_NO_1202 | AKGTPSSAVA | VATGAGLQQQ | QHHQHHHQHQ | QQEQQQQQQQ | QQQHPPQPQL | | 356 |
| SEQ_ID_NO_1194 | SRKTK----- | ---------- | ---------- | ---------- | ---------- | | 273 |
| SEQ_ID_NO_1200 | AKALANKAAK | KA-------- | ---------- | ---------- | ---------- | | 276 |

Figure 41 (continued)

| SEQ_ID_NO_1204 | | 289 |
|---|---|---|
| SEQ_ID_NO_1203 | IDPLQMLPGMG------ | 335 |
| SEQ_ID_NO_1205 | IDPLQMLPGMG------ | 334 |
| SEQ_ID_NO_1196 | MDPINSILNLG-ACAWGQ | 395 |
| SEQ_ID_NO_1202 | LDPINSMFNLGAACAWGQ | 374 |
| SEQ_ID_NO_1194 | | 273 |
| SEQ_ID_NO_1200 | | 276 |

Figure 42

| | | | | | | | |
|---|---|---|---|---|---|---|---|
| SEQ_ID_NO_1241 | MFL VDWF YGV | LASL GLWQKD | AKI LFL GLDN | AGKTTLLHML | KDERL VQHQP | 50 |
| SEQ_ID_NO_1229 | MFV LDWF YGV | LASL GLWQKE | AKI LFL GLDN | AGKTTLLHML | KDERL VQHQP | 50 |
| SEQ_ID_NO_1249 | MFL WDWF YGV | LASL GLWQKE | AKI LFL GLDN | AGKTTLLHML | KDERL VQHQP | 50 |
| SEQ_ID_NO_1264 | - - - MGI VFTR | LFSSVFGNRE | ARI LVLGLDN | AGKTTI LYRL | QMGEVVSTI P | 47 |
| SEQ_ID_NO_1251 | - - - MGI VFTR | LFSSVFGNRE | ARI LVLGLDN | AGKTTI LYRL | QMGEVVSTI P | 47 |
| SEQ_ID_NO_1265 | - - - MGI VFTR | LFSSVFGNRE | ARI LVLGLDN | AGKTTI LYRL | QMGEVVSTI P | 47 |
| SEQ_ID_NO_1253 | - - - MGI VFTK | LFSSVFGNKE | ARI LVLGLDN | AGKTTI LYRL | QMGEVVSTI P | 47 |
| SEQ_ID_NO_1210 | - - - MGI LFTR | MFSSVFGNKE | ARI LVLGLDN | AGKTTI LYRL | QMGEVVSTI P | 47 |
| SEQ_ID_NO_1267 | - - - MGI LFTR | MFSSVFGNKE | ARI LVLGLDN | AGKTTI LYRL | QMGEVVSTI P | 47 |
| SEQ_ID_NO_1213 | - - - MGI LFTK | MFSNLFGNRE | ARI LVLGLDN | AGKTTI LYRL | QMGEVVSTI P | 47 |
| SEQ_ID_NO_1218 | - - - MGI LFSK | MFSSVFGNKE | ARI LVLGLDN | AGKTTI LYRL | QMGEVVSTI P | 47 |
| SEQ_ID_NO_1232 | - - - MGL VFTK | LFSSLFGNKE | ARI LVLGLDN | AGKTTI LYRL | QMGEVVSTI P | 47 |
| SEQ_ID_NO_1234 | - - - MGL VFTR | LFSSVFGNKE | ARI LVLGLDN | AGKTTI LYRL | QMGEVVSTI P | 47 |
| SEQ_ID_NO_1272 | - - - MGL SFTK | LFSRLFAKKE | MRI LMVGLDA | AGKTTI LYKL | KLGEI VTTI P | 47 |
| SEQ_ID_NO_1268 | - - - MGI TFAK | LFQRLFSKKE | MRI LMVGLDA | AGKTTI LYKL | KLGEI VTTI P | 47 |
| SEQ_ID_NO_1211 | - - - MGL RFTK | ALSRLFSKKE | MRI LMVGLDA | AGKTTI LYKL | KLGEI VTTI P | 47 |
| SEQ_ID_NO_1216 | - - - MGL SFTK | LLGRLFSEKE | MRI LMVGLDA | AGKTTI LYKL | KLGEI VTTI P | 47 |
| SEQ_ID_NO_1269 | - - - MGL SFTK | LLGRLFSKKE | MRI LMVGLDA | AGKTTI LYKL | KLGEI VTTI P | 47 |
| SEQ_ID_NO_1239 | - - - MGL SFTK | LFSRLFAKKE | MRI LMVGLDA | AGKTTI LYQL | KLGEI VTTI P | 47 |
| SEQ_ID_NO_1259 | - - - MGL TFTK | LFSRLFAKKE | MRI LMVGLDA | AGKTTI LYKL | KLGEI VTTI P | 47 |
| SEQ_ID_NO_1233 | - - - MGL TFTK | LFSRLFAKKE | MRI LMVGLDA | AGKTTI LYKL | KLGEI VTTI P | 47 |
| SEQ_ID_NO_1235 | - - - MGL SFTK | LFSRLFAKKE | MRI LMVGLDA | AGKTTI LYKL | KLGEI VTTI P | 47 |
| SEQ_ID_NO_1243 | - - - MGL SFTK | LFSRLFAKKE | MRI LMVGLDA | AGKTTI LYKL | KLGEI VTTI P | 47 |
| SEQ_ID_NO_1270 | - - - MGL SFTK | LFSRLFAKKE | MRI LMVGLDA | AGKTTI LYKL | KLGEI VTTI P | 47 |
| SEQ_ID_NO_1242 | - - - MGL SFGK | LFSRLFAKKE | MRI LMVGLDA | AGKTTI LYKL | KLGEI VTTI P | 47 |
| SEQ_ID_NO_1238 | - - - MGL SFTK | LFSRLFAKKE | MRI LMVGLDA | AGKTTI LYKL | KLGEI VTTI P | 47 |
| SEQ_ID_NO_1236 | - - - MGL SFTK | LFSRLFAKKE | MRI LMVGLDA | AGKTTI LYKL | KLGEI VTTI P | 47 |
| SEQ_ID_NO_1240 | - - - MGL SFGK | LFSRLFAKKE | MRI LMVGLDA | AGKTTI LYKL | KLGEI VTTI P | 47 |

Figure 42 (continued)

| SEQ ID | | | | | | | |
|---|---|---|---|---|---|---|---|
| SEQ_ID_NO_1241 | T | - - - - - - - - - | - - - - - QYPT | SEELSIGNIK | FKAFDLGGHQ | IARRVWRDYY | 85 |
| SEQ_ID_NO_1229 | T | - - - - - - - - - | - - - - - QHPT | SEELSIGKIK | FKAFDLGGHQ | IARRVWKDYY | 85 |
| SEQ_ID_NO_1249 | T | - - - - - - - - - | - - - - - QHPT | SEELSIGKIK | FKAFDLGGHQ | IARRVWKDYY | 85 |
| SEQ_ID_NO_1264 | SGFPAPDSLI | FFLPFA | GFN | VETVQYNNIK | FQVWDLGGQT | SIRPYMRCYF | 97 |
| SEQ_ID_NO_1251 | T | - - - - - - - - - | - - - - - - | GFN VETVQYNNIK | FQVWDLGGQT | SIRPYMRCYF | 82 |
| SEQ_ID_NO_1265 | T | - - - - - - - - - | - - - - - - | GFN VETVQYNNIK | FQVWDLGGQT | SIRPYMRCYF | 82 |
| SEQ_ID_NO_1253 | T | - - - - - - - - - | - - - - - - | GFN VETVQYNNIK | FQVWDLGGQT | SIRPYMRCYF | 82 |
| SEQ_ID_NO_1210 | T | - - - - - - - - - | - - - - - - | GFN VETVQYNNIK | FQVWDLGGQT | SIRPYMRCYF | 82 |
| SEQ_ID_NO_1267 | T | - - - - - - - - - | - - - - - - | GFN VETVQYNNIK | FQVWDLGGQT | SIRPYMRCYF | 82 |
| SEQ_ID_NO_1213 | T | - - - - - - - - - | - - - - - - | GFN VETVQYNNIK | FQVWDLGGQT | SIRPYMRCYF | 82 |
| SEQ_ID_NO_1218 | T | - - - - - - - - - | - - - - - - | GFN VETVQYNNIK | FQVWDLGGQT | SIRPYMRCYF | 82 |
| SEQ_ID_NO_1232 | T | - - - - - - - - - | - - - - - - | GFN VETVQYNNIK | FQVWDLGGQT | SIRPYMRCYF | 82 |
| SEQ_ID_NO_1234 | T | - - - - - - - - - | - - - - - - | GFN VETVQYNNIK | FQVWDLGGQT | SIRPYMRCYF | 82 |
| SEQ_ID_NO_1272 | T | - - - - - - - - - | - - - - - - | GFN VETVEYKNIS | FTVWDVGGQD | KIRPLWRHYF | 82 |
| SEQ_ID_NO_1268 | T | - - - - - - - - - | - - - - - - | GFN VETVEYKNIS | FTVWDVGGQD | KIRPLWRHYF | 82 |
| SEQ_ID_NO_1211 | T | - - - - - - - - - | - - - - - - | GFN VETVEYKNIS | FTVWDVGGQD | KIRPLWRHYF | 82 |
| SEQ_ID_NO_1216 | T | - - - - - - - - - | - - - - - - | GFN VETVEYKNIS | FTVWDVGGQD | KIRPLWRHYF | 82 |
| SEQ_ID_NO_1269 | T | - - - - - - - - - | - - - - - - | GFN VETVEYKNIS | FTVWDVGGQD | KIRPLWRHYF | 82 |
| SEQ_ID_NO_1239 | T | - - - - - - - - - | - - - - - - | GFN VETVEYQYS | FTVWDVGGQD | KIRPLWRHYF | 82 |
| SEQ_ID_NO_1259 | T | - - - - - - - - - | - - - - - - | GFN VETVEYKNIS | FTVWDVGGQD | KIRPLWRHYF | 82 |
| SEQ_ID_NO_1233 | T | - - - - - - - - - | - - - - - - | GFN VETVEYKNIS | FTVWDVGGQD | KIRPLWRHYF | 82 |
| SEQ_ID_NO_1235 | T | - - - - - - - - - | - - - - - - | GFN VETVEYKNIS | FTVWDVGGQD | KIRPLWRHYF | 82 |
| SEQ_ID_NO_1243 | T | - - - - - - - - - | - - - - - - | GFN VETVEYKNIS | FTVWDVGGQD | KIRPLWRHYF | 82 |
| SEQ_ID_NO_1270 | T | - - - - - - - - - | - - - - - - | GFN VETVEYKNIS | FTVWDVGGQD | KIRPLWRHYF | 82 |
| SEQ_ID_NO_1242 | T | - - - - - - - - - | - - - - - - | GFN VETVEYKNIS | FTVWDVGGQD | KIRPLWRHYF | 82 |
| SEQ_ID_NO_1238 | T | - - - - - - - - - | - - - - - - | GFN VETVEYKNIS | FTVWDVGGQD | KIRPLWRHYF | 82 |
| SEQ_ID_NO_1236 | T | - - - - - - - - - | - - - - - - | GFN VETVEYKNIS | FTVWDVGGQD | KIRPLWRHYF | 82 |
| SEQ_ID_NO_1240 | T | - - - - - - - - - | - - - - - - | GFN VETVEYKNIS | FTVWDVGGQD | KIRPLWRHYF | 82 |

Figure 42 (continued)

| | | | | | | | |
|---|---|---|---|---|---|---|---|
| SEQ_ID_NO_1241 | AKVDAVVYLV | DANDRERFPE | AKKELDGLLS | DESLTNVPFL | LGNKI DI PY | 135 |
| SEQ_ID_NO_1229 | AKVDAVVYLV | DAYDKERFAE | SKKELDALLS | DESLATVPFL | LGNKI DI PY | 135 |
| SEQ_ID_NO_1249 | AKVDAVVYLV | DAYDKERFAE | SKKELDALLS | DDSLANVPFL | LGNKI DI PY | 135 |
| SEQ_ID_NO_1264 | PNTQAI IYVV | DSSDTDRLVT | AKEEFHAI LE | EDELKGAVVL | VYANKQDLPG | 147 |
| SEQ_ID_NO_1251 | PNTQAI IYVV | DSSDTDRLVT | AKEEFHSI LE | EDELKGAVVL | VYANKQDLPG | 132 |
| SEQ_ID_NO_1265 | PNTQAI IYVV | DSSDTDRLVT | AKEEFHAI LE | EDELKGAVVL | VYANKQDLPG | 132 |
| SEQ_ID_NO_1253 | PNTQAVI YVV | DSSDTDRI GV | AKEEFHAI LE | EELKGAMVL | IFANKQDLPG | 132 |
| SEQ_ID_NO_1210 | PNTQAVI YVV | DSSDTDRI GV | AKEEFHAI LE | EDELKGAVVL | IFANKQDLPG | 132 |
| SEQ_ID_NO_1267 | PNTQAVI YVV | DSSDTDRI GV | AKEEFHAI LE | EELKGAVVL | IFANKQDLPG | 132 |
| SEQ_ID_NO_1213 | PNTQAI IYVV | DSSDTDRLV | AKEEFHAI LE | EELRGAAVL | IFANKQDLPG | 132 |
| SEQ_ID_NO_1218 | PNTQAI IYVV | DSSDVDRLV | AKDEFHAI LE | EELRGAI VL | IFANKQDLPG | 132 |
| SEQ_ID_NO_1232 | PNTQAI IYVV | DSSDVDRLV | AKEEFHAI LE | EELKGAVVL | IFANKQDLPG | 132 |
| SEQ_ID_NO_1234 | PNTQAI IYVV | DSSDTDRLV | AREEFHAI LE | EELKGAVVL | IFANKQDLPG | 132 |
| SEQ_ID_NO_1272 | QNTQGLI FVV | DSNDRDRVVE | ARDELHRMLN | EDELRDAVLL | VFANKQDLPN | 132 |
| SEQ_ID_NO_1268 | QNTQGLI FVV | DSNDRDRVSE | ARDELHRMLN | EDELRDAVLL | VFANKQDLPN | 132 |
| SEQ_ID_NO_1211 | QNTQGLI FVV | DSNDRERVVE | ARDELHRMLN | EDELRDAVLL | VFANKQDLPN | 132 |
| SEQ_ID_NO_1216 | QNTQGLI FVV | DSNDRDRVGE | AREELHRMLN | EDELRDAVLL | VFANKQDLPN | 132 |
| SEQ_ID_NO_1269 | QNTQGLI FVV | DSNDRDRVGE | ARDELHRMLN | EDELRDAVLL | VFANKQDLPN | 132 |
| SEQ_ID_NO_1239 | QNTQGLI FVV | DSNDRDRVVE | ARDELHRMLN | EDELRDAVLL | VFANKQDLPN | 132 |
| SEQ_ID_NO_1259 | QNTQGLI FVV | DSNDRDRI VE | AKDELHRMLN | EDELRDAVLL | VFANKQDLPN | 132 |
| SEQ_ID_NO_1233 | QNTQGLI FVV | DSNDRDRVVE | ARDELHRMLN | EDELRDAVLL | VFANKQDLPN | 132 |
| SEQ_ID_NO_1235 | QNTQGLI FVV | DSNDRDRVVE | ARDELHRMLN | EDELRDAVLL | VFANKQDLPN | 132 |
| SEQ_ID_NO_1243 | QNTQGLI FVV | DSNDRDRVVE | ARDELHRMLN | EDELREAVLL | VFANKQDLPN | 132 |
| SEQ_ID_NO_1270 | QNTQGLI FVV | DSNDRDRVVE | ARDELHRMLN | EDELRDAVLL | VFANKQDLPN | 132 |
| SEQ_ID_NO_1242 | QNTQGLI FVV | DSNDRDRVVE | ARDELHRMLN | EDELREAVLL | VFANKQDLPN | 132 |
| SEQ_ID_NO_1238 | QNTQGLI FVV | DSNDRDRVVE | AKDELHRMLN | GDELRDAVLL | VFANKQDLPN | 132 |
| SEQ_ID_NO_1236 | QNTQGLI FVV | DSNDRDRVVE | ARDELHRMLN | EDELRDAVLL | VFANKQDLPN | 132 |
| SEQ_ID_NO_1240 | QNTQGLI FVV | DSNDRDRVVE | ARDELHRMLN | EDELRDAVLL | VFANKQDLPN | 132 |

Figure 42 (continued)

| | | | | | | | | |
|---|---|---|---|---|---|---|---|---|
| SEQ_ID_NO_1241 | AASEDELRYH | LGLTGVTTGK | GNINLAGTNV | RP--IEVFMC | SIVRK-- | MGY | | 181 |
| SEQ_ID_NO_1229 | AASEDELRYH | LGLSNFTTGK | GKVDLVGSNV | RP--LEVFMC | SIVRK-- | MGY | | 181 |
| SEQ_ID_NO_1249 | AASEEELRYH | LGLSSFTTGK | GKVSLCDSNV | RP--LEVFMC | SVVRK-- | MGY | | 181 |
| SEQ_ID_NO_1264 | ALDDAAITES | LELHKIKS-- | ---------- | RQ--WAIFKT | SAIKG- | EGL | | 181 |
| SEQ_ID_NO_1251 | ALDDAAITES | LELHKIKS-- | ---------- | RQ--WAIFKT | SAIKG- | EGL | | 166 |
| SEQ_ID_NO_1265 | ALDDAAITES | LELHKIKS-- | ---------- | RQ--WAIFKT | SAIKG- | EGL | | 166 |
| SEQ_ID_NO_1253 | ALDDAAVTEA | LELHKIKS-- | ---------- | RQ--WAIFKT | CAVKG- | EGL | | 166 |
| SEQ_ID_NO_1210 | ALDDAAVTEA | LELHKIKS-- | ---------- | RQ--WAIFKT | CAVKG- | EGL | | 166 |
| SEQ_ID_NO_1267 | ALDDAAVTEA | LELHKIKS-- | ---------- | RQ--WAIFKT | CAVKG- | EGL | | 166 |
| SEQ_ID_NO_1213 | ALDDAAVTES | LELHKIKN-- | ---------- | RQ--WAIFKT | SAIKG- | EGL | | 166 |
| SEQ_ID_NO_1218 | ALDDAAVTEA | LELHKIKN-- | ---------- | RQ--WAIFKT | SAIKG- | EGL | | 166 |
| SEQ_ID_NO_1232 | ALDDAAVTEA | LELHKIKN-- | ---------- | RQ--WAIFKT | SAIKG- | EGL | | 166 |
| SEQ_ID_NO_1234 | ALDDAAVTES | LELHKIKN-- | ---------- | RQ--WAIFKT | SAIKG- | EGL | | 166 |
| SEQ_ID_NO_1272 | AMNAAEITDK | LGLHSLRQ-- | ---------- | RPNLWGLINS | PKEVPLVANL | | | 170 |
| SEQ_ID_NO_1268 | AMSAAEITDK | LGLHSLRQ-- | ---------- | RH--WFIQST | CATSG- | EGL | | 166 |
| SEQ_ID_NO_1211 | AMNAAEITDK | LGLHSLRQ-- | ---------- | RH--WYIQST | CATSG- | EGL | | 166 |
| SEQ_ID_NO_1216 | AMNAAEITDK | LGLHSLRQ-- | ---------- | RH--WYIQST | CATSG- | EGL | | 166 |
| SEQ_ID_NO_1269 | AMNAAEITDK | LGLHSLRQ-- | ---------- | RH--WYIQST | CATSG- | EGL | | 166 |
| SEQ_ID_NO_1239 | AMNAAEITDK | HGLHSLRQ-- | ---------- | RH--WYIQST | CATSG- | EGL | | 166 |
| SEQ_ID_NO_1259 | AMNAAEITDK | LGLHSLRQ-- | ---------- | RH--WYIQST | CATSG- | EGL | | 166 |
| SEQ_ID_NO_1233 | AMNAAEITDK | LGLHSLRQ-- | ---------- | RH--WYIQST | CATSG- | EGL | | 166 |
| SEQ_ID_NO_1235 | AMNAAEITDK | LGLHSLRQ-- | ---------- | RH--WYIQST | CATSG- | EGL | | 166 |
| SEQ_ID_NO_1243 | AMNAAEITDK | LGLHSLRQ-- | ---------- | RH--WYIQST | CATSG- | EGL | | 166 |
| SEQ_ID_NO_1270 | AMNAAEITDK | LGLHSLRQ-- | ---------- | RH--WYIQST | CATSG- | EGL | | 166 |
| SEQ_ID_NO_1242 | AMNAAEITDK | LGLHSLRQ-- | ---------- | RH--WYIQST | CATSG- | EGL | | 166 |
| SEQ_ID_NO_1238 | AMNAAEITDK | LGLHSLRQ-- | ---------- | RH--WYIQST | CATSG- | EGL | | 166 |
| SEQ_ID_NO_1236 | AMNAAEITDK | LGLHSLRQ-- | ---------- | RH--WYIQST | CATSG- | EGL | | 166 |
| SEQ_ID_NO_1240 | AMNAAEITDK | LGLHSLRQ-- | ---------- | RH--WYIQST | CATSG- | EGL | | 166 |

Figure 42 (continued)

| SEQ_ID_NO_1241 | GEGFK----- | ---------- | ---------- | ----- | -----WMSQY | K-------- | 193 |
|---|---|---|---|---|---|---|---|
| SEQ_ID_NO_1229 | GEGFK----- | ---------- | ---------- | ----- | -----WLSQY | K-------- | 193 |
| SEQ_ID_NO_1249 | GDGFK----- | ---------- | ---------- | ----- | -----WVSQY | N-------- | 193 |
| SEQ_ID_NO_1264 | FEGLDCSVLQ | HIILQFLPDE | CIWEYLMELT | YKSLMYLHIE | KNRFVENDE | | 231 |
| SEQ_ID_NO_1251 | FEGLN----- | ---------- | ---------- | ----- | -----MLSNA | KSGGS---- | 182 |
| SEQ_ID_NO_1265 | FEGLD----- | ---------- | ---------- | ----- | -----MLSNA | KSKSS---- | 182 |
| SEQ_ID_NO_1253 | FEGLD----- | ---------- | ---------- | ----- | -----MLSNT | KSGTG---- | 182 |
| SEQ_ID_NO_1210 | FEGLD----- | ---------- | ---------- | ----- | -----MLSNT | KSGSG---- | 182 |
| SEQ_ID_NO_1267 | FEGLD----- | ---------- | ---------- | ----- | -----MLSNT | KSGSG---- | 182 |
| SEQ_ID_NO_1213 | FEGLD----- | ---------- | ---------- | ----- | -----MLSNT | KSGSG---- | 182 |
| SEQ_ID_NO_1218 | FEGLD----- | ---------- | ---------- | ----- | -----MLSNT | KSGGG---- | 182 |
| SEQ_ID_NO_1232 | FEGLD----- | ---------- | ---------- | ----- | -----MLSNT | KSGGG---- | 182 |
| SEQ_ID_NO_1234 | FEGLD----- | ---------- | ---------- | ----- | -----MLSNT | KSGGG---- | 182 |
| SEQ_ID_NO_1272 | FLG------ | ---------- | ---------- | ----- | -----AKGVL | LGGGPKNLG | 188 |
| SEQ_ID_NO_1268 | YEGLD----- | ---------- | ---------- | ----- | -----MLSSN | SQRA----- | 181 |
| SEQ_ID_NO_1211 | YEGLD----- | ---------- | ---------- | ----- | -----MLSNN | ANKT----- | 181 |
| SEQ_ID_NO_1216 | YEGLD----- | ---------- | ---------- | ----- | -----MLSNN | ASKA----- | 181 |
| SEQ_ID_NO_1269 | YEGLD----- | ---------- | ---------- | ----- | -----MLSNN | SSKA----- | 181 |
| SEQ_ID_NO_1239 | YEGLD----- | ---------- | ---------- | ----- | -----MLSNN | ANKA----- | 181 |
| SEQ_ID_NO_1259 | YEGLD----- | ---------- | ---------- | ----- | -----MLSNN | ASKA----- | 181 |
| SEQ_ID_NO_1233 | YEGLD----- | ---------- | ---------- | ----- | -----MLSNN | ASKA----- | 181 |
| SEQ_ID_NO_1235 | YEGLE----- | ---------- | ---------- | ----- | -----MLSNN | ASKA----- | 181 |
| SEQ_ID_NO_1243 | YEGLD----- | ---------- | ---------- | ----- | -----MLSNN | ASKA----- | 181 |
| SEQ_ID_NO_1270 | YEGLD----- | ---------- | ---------- | ----- | -----MLSNN | ASKG----- | 181 |
| SEQ_ID_NO_1242 | YEGLD----- | ---------- | ---------- | ----- | -----MLSNN | SNKA----- | 181 |
| SEQ_ID_NO_1238 | YEGLD----- | ---------- | ---------- | ----- | -----MLSNN | ANKA----- | 181 |
| SEQ_ID_NO_1236 | YEGLD----- | ---------- | ---------- | ----- | -----MLSNN | ANKA----- | 181 |
| SEQ_ID_NO_1240 | YEGLD----- | ---------- | ---------- | ----- | -----MLSNN | ANKA----- | 181 |

Figure 42 (continued)

| | | |
|---|---|---|
| SEQ_ID_NO_1241 | - - - - - - - - - - - - - | 193 |
| SEQ_ID_NO_1229 | - - - - - - - - - - - - - | 193 |
| SEQ_ID_NO_1249 | - - - - - - - - - - - - - | 193 |
| SEQ_ID_NO_1264 | QTVRTLGHWW LYP | 244 |
| SEQ_ID_NO_1251 | - - - - - - - - - - - - - | 182 |
| SEQ_ID_NO_1265 | - - - - - - - - - - - - - | 182 |
| SEQ_ID_NO_1253 | - - - - - - - - - - - - - | 182 |
| SEQ_ID_NO_1210 | - - - - - - - - - - - - - | 182 |
| SEQ_ID_NO_1267 | - - - - - - - - - - - - - | 182 |
| SEQ_ID_NO_1213 | - - - - - - - - - - - - - | 182 |
| SEQ_ID_NO_1218 | - - - - - - - - - - - - - | 182 |
| SEQ_ID_NO_1232 | - - - - - - - - - - - - - | 182 |
| SEQ_ID_NO_1234 | - - - - - - - - - - - - - | 182 |
| SEQ_ID_NO_1272 | LLSPKPK- - - - - - | 195 |
| SEQ_ID_NO_1268 | - - - - - - - - - - - - - | 181 |
| SEQ_ID_NO_1211 | - - - - - - - - - - - - - | 181 |
| SEQ_ID_NO_1216 | - - - - - - - - - - - - - | 181 |
| SEQ_ID_NO_1269 | - - - - - - - - - - - - - | 181 |
| SEQ_ID_NO_1239 | - - - - - - - - - - - - - | 181 |
| SEQ_ID_NO_1259 | - - - - - - - - - - - - - | 181 |
| SEQ_ID_NO_1233 | - - - - - - - - - - - - - | 181 |
| SEQ_ID_NO_1235 | - - - - - - - - - - - - - | 181 |
| SEQ_ID_NO_1243 | - - - - - - - - - - - - - | 181 |
| SEQ_ID_NO_1270 | - - - - - - - - - - - - - | 181 |
| SEQ_ID_NO_1242 | - - - - - - - - - - - - - | 181 |
| SEQ_ID_NO_1238 | - - - - - - - - - - - - - | 181 |
| SEQ_ID_NO_1236 | - - - - - - - - - - - - - | 181 |
| SEQ_ID_NO_1240 | - - - - - - - - - - - - - | 181 |

Figure 43

| | | | | | | | |
|---|---|---|---|---|---|---|---|
| SEQ_ID_NO_1285 | .......... | ........ | ----MVGNAF | VEQYYS LHR | DPDQVHRFYH | 26 |
| SEQ_ID_NO_1297 | MAVSDGVQTP | TP------- | ---DVVGNAF | VEQYYS LHQ | DPDQVHKFYH | 39 |
| SEQ_ID_NO_1284 | MALQ-TATPP | TT------- | PSAQVVGNAF | VEQYYHI LHH | SPGSVYRFYQ | 41 |
| SEQ_ID_NO_1300 | MAAP- QPAAP | AP-----EAP | PSAQVVGNAF | VQQYLVLHQ | SPDLVYRFYQ | 44 |
| SEQ_ID_NO_1294 | MAAP- Q- ASP | S--------- | PSAQVVGNAF | VQQYYQ LHQ | SPDLVYRFYQ | 39 |
| SEQ_ID_NO_1295 | MAAP- Q- ASP | S--------- | PSAQVVGNAF | VQQYYQ LHQ | SPDLVYRFYQ | 39 |
| SEQ_ID_NO_1287 | MAAP- TPPPA | AAPAAAPGPT | PPAQVVGNAF | VQQYYNI LHQ | SPELVFRFYQ | 49 |
| SEQ_ID_NO_1289 | -MAS- QPPPP | AA- AAASGAP | PPAQVVGNAF | VHQYYNI LHQ | SPELVYRFYQ | 47 |
| SEQ_ID_NO_1291 | MASP- PPPPP | AG- AAAPGSP | PPAQVVGNAF | VNQYYNI LHQ | SPELVHRFYQ | 48 |
| SEQ_ID_NO_1274 | MAML GAQQVP | AA-----ACT | PL- DMVGNAF | VPQYYHI LHQ | SPEHVHRFYQ | 43 |
| SEQ_ID_NO_1276 | MASV- EQQVP | AG-----IAT | PTSDVVGNAF | VHQYYL LHQ | SPELVHRFYH | 44 |
| SEQ_ID_NO_1280 | MAAP- VTQLP | V--------- | PTADVVGNAF | AHQYYHI LQQ | SPDLVHRFYQ | 40 |

| | | | | | | | |
|---|---|---|---|---|---|---|---|
| SEQ_ID_NO_1285 | DSSVMSRP-- | -EEDGTMTTV | TTTAEI DKKI | QSLEYTSFRV | EVLSADAQPS | 73 |
| SEQ_ID_NO_1297 | ESSVLSRP-- | -EEDGTMTTV | TTTAEI DKKI | QSFDYTSYRV | EVLSADAQPS | 86 |
| SEQ_ID_NO_1284 | DSSVI SRP-- | -DSSGVMTSV | TTMKGI NEKI | LSLNFKEFKA | EIKTADAQKS | 88 |
| SEQ_ID_NO_1300 | DASRLARPAS | AAGAAGMDSV | TTMEAI SEKI | MEMDVS- KA | EIRTVDSQES | 92 |
| SEQ_ID_NO_1294 | DASRLGRP- P | ADRYGDWVSV | TTMEAI NEKI | MAMDNS- RA | EIKTVDSQES | 86 |
| SEQ_ID_NO_1295 | DASRLGRP- P | ADRYGDWVSV | TTMEAI NEKI | MAMDNS- RA | EIKTVDSQES | 86 |
| SEQ_ID_NO_1287 | EASRI GRPAT | TGADL- MDTV | TTMEAI NEKI | MSMDI A- RA | EIRGVDAQES | 95 |
| SEQ_ID_NO_1289 | EASCLGRPAG | TGADG- MDTV | TTMDAI NDKI | VSMGI D-- RA | KIKAVDAQES | 94 |
| SEQ_ID_NO_1291 | DASRLGRPAG | AGADG- MDTV | TTMDAI SDKI | VSMGI TI- RA | EIKAVDAQES | 95 |
| SEQ_ID_NO_1274 | ELSKLGRP-- | -EENGLMSI T | STLQAI DKKI | MALGYGVI SA | EISTVDTQES | 90 |
| SEQ_ID_NO_1276 | DSSKLGRP-- | -EENGGMSI T | TTMQAI NEKI | LSLGYGEFTA | EITTVDAQDS | 91 |
| SEQ_ID_NO_1280 | DGSKFGRP-- | -GEDGVMSTT | TTMNAI NEKI | LSLGYGQVRA | EIVTVDSQES | 87 |

| | | | | | | | |
|---|---|---|---|---|---|---|---|
| SEQ_ID_NO_1285 | YNNGVWVVT | GQLTGTDNIK | RKFAQSFFLA | PQDKGFYVLN | DVFRYVDAY- | 122 |
| SEQ_ID_NO_1297 | YNSGVVVVVT | GQLTGTDNVK | RKFAQSFFLA | PQDKGFYVLN | DVFRYVDAY- | 135 |
| SEQ_ID_NO_1284 | YKEGVTVLVT | GQLTGKDNLR | RKFAQSFFLA | PQDNGYFVLN | DVFRYVEDH- | 137 |
| SEQ_ID_NO_1300 | LGGGVTVLVT | GHLTGRDSVR | REFSQSFFLA | PQEKGYFVLN | DI FRFYGDL- | 141 |
| SEQ_ID_NO_1294 | LGGGVTVLVT | GHLTVRDGVC | REFSQSFFLA | PQEKGYFVLN | DMFRYVGDG- | 135 |
| SEQ_ID_NO_1295 | LGGGVTVLVT | GHLTVRDGVC | REFSQSFFLA | PQEKGYFVLN | DMFRYVGDG- | 135 |
| SEQ_ID_NO_1287 | LCGGVTVLVT | GHLTGKDDVC | REFAQSFFLA | PQEKGYFVLN | DI LRYVGQG- | 144 |
| SEQ_ID_NO_1289 | LCGGVSVLVM | GHLTGRNSVS | RQFVQSFFLA | PQEKGYFVLN | DI LRYVGEG- | 143 |
| SEQ_ID_NO_1291 | LGGGVTVLVM | GHLTGRTSVG | REFVQSFFLA | PQEKGYFVLN | DI LRYVGDGX | 145 |
| SEQ_ID_NO_1274 | HGGGYI VLVT | GYLTGKDSVR | RTFSQTFFLA | POETGYFVLN | DMFRFI DEG- | 139 |
| SEQ_ID_NO_1276 | HNGGVLVLVT | GYLTGKDKVK | RKFTQSFFLA | PQDKGYFVLN | DVFRFVDDT- | 140 |
| SEQ_ID_NO_1280 | YKGGVLVLVT | GYLNGNDNLR | QKFTQSFFLA | PQDKGYFVLN | DVFRYVDDS- | 136 |

Figure 43 (continued)

| SEQ_ID_NO_1285 | ........KS | IDIESVPAND | ADESAPSEA | TPEPEPVHV | PEVIPPTQTV | 164 |
| SEQ_ID_NO_1297 | .........K | SVDIETVPAN | DADESAPSEA | FTPDPEPIHV | A......ED | 169 |
| SEQ_ID_NO_1284 | ........EP | SELPPVTGDG | DSAAVTVTPE | LEPSHVAD.. | ........SC | 169 |
| SEQ_ID_NO_1300 | .......PA | PTAVEAQPEA | DAVVPPVAAP | LANGTATPAV | EPAIPDDHDA | 183 |
| SEQ_ID_NO_1294 | .......PTP | AAAAAAAVEV | QPEADAVAPP | LANGTATAPL | QPAAPDY-DG | 177 |
| SEQ_ID_NO_1295 | .........P | TPAAAAAAEV | QPEADAVAPP | LANGTATAPL | QPAAPDY-DA | 175 |
| SEQ_ID_NO_1287 | ..EADPSLPP | PQQQPPAPEL | DAVVAP-AAA | LANGTVAP-- | VETVPREQEA | 189 |
| SEQ_ID_NO_1289 | ....GGDEGA | EKOPAPEVAA | DAEKTTSAPI | LANGTVGGDA | TTVPQ---DA | 186 |
| SEQ_ID_NO_1291 | GEEGAGHPPP | PPQQPVQETV | TGAEAVPAPI | LANGTVGG-D | NETLPCEQDA | 194 |
| SEQ_ID_NO_1274 | .......... | ....TVVHGN | QIPVNNVQAP | VNTYQDTAAA | KEIPDDFVQE | 175 |
| SEQ_ID_NO_1276 | .......... | ....KHQPGG | ODPVNGFEAS | LTHEQGHS-- | .......... | 164 |
| SEQ_ID_NO_1280 | .......... | ....THQNGN | QEPASNFEAP | VAPDQDTP-- | .......... | 160 |

| SEQ_ID_NO_1285 | IPTAQTVPP | TQTVIADTET | IISKEVSLPL | ENGKLSVT-- | .......... | 202 |
| SEQ_ID_NO_1297 | IPTIQPVAD | TDTNISK--- | ----EVSLPL | ENGKLSVT-- | .......... | 200 |
| SEQ_ID_NO_1284 | APEPTNSHVN | KGQTVAEL-- | ----NAVELS | NNHERQIPV- | .......... | 201 |
| SEQ_ID_NO_1300 | VPQQENHVVD | RSPPQPEEED | EA--EVYNPP | PEEVV----- | .......... | 216 |
| SEQ_ID_NO_1294 | MPQEEPDVVE | HAAVPPEEEE | ----EVYNPP | LEEVEGGAV- | .......... | 212 |
| SEQ_ID_NO_1295 | MPHEEPDVVE | NVAVPPEEEE | ----EVYNPP | LEEVEGGAV- | .......... | 210 |
| SEQ_ID_NO_1287 | SPQPELDLSE | SVPHTNEEED | PKE-EVYNPP | NDVEVPV--- | .......... | 225 |
| SEQ_ID_NO_1289 | SPQPECQVAE | PALNPKEEVL | NG--EVCNBL | SDVEKPV--- | .......... | 221 |
| SEQ_ID_NO_1291 | SPQPEQPAAE | SAPPTPEEED | LYGEEVYNPP | NDMEKPV--- | .......... | 231 |
| SEQ_ID_NO_1274 | KYVQENHAVK | QTEVLSKSTN | EPE-KVFTPS | EDEQVSA--- | .......... | 211 |
| SEQ_ID_NO_1276 | -PVPENHIEQ | PAA-LPEECN | GP--EVYNSS | ENGDGSE--- | .......... | 198 |
| SEQ_ID_NO_1280 | -HTQETHISE | PTAALSEEVI | GG--EVYNPS | ESGDVSVEVE | EEESGDVSFE | 207 |

| SEQ_ID_NO_1285 | ENVIPVNHVK | ESSHHVKEPE | QPTSEKVAS | NTQEDTPKKS | FASIVNALKD | 252 |
| SEQ_ID_NO_1297 | ENVIPVNHVK | ESSHQEQMAS | IEKV----PS | NTQEDTPKKS | FASIVSAYKD | 246 |
| SEQ_ID_NO_1284 | ENEGNVESHF | QSNGNDDSQA | TELA-----S | SAQDDAPKKS | YASIVKVQKG | 246 |
| SEQ_ID_NO_1300 | DEEQPVPEVI | NEVPNNVAPV | AATT---VAP | VLQEEAPKKS | YASIVKVMKE | 263 |
| SEQ_ID_NO_1294 | EEEQSVPEVI | NEVPNNVVPV | VAPA---AAP | VSHEEAPKKS | YASIVKVMKE | 259 |
| SEQ_ID_NO_1295 | EEEQSVPEVI | NEVPNNVVPV | VAPA---DAP | VSHEEAPKKS | YASIVKVMKE | 257 |
| SEQ_ID_NO_1287 | VEETLVPEVI | DEVPNNVAAS | IPVS---APP | VPHEEAPKKS | YASIVKVMKA | 272 |
| SEQ_ID_NO_1289 | AEETPVPDVI | NEVPNNVAVA | PPIS---SPP | VPLKEAPKKS | YASIVKVMKE | 268 |
| SEQ_ID_NO_1291 | VDETPVAEVI | NEVPNNVAVA | APSS---SPS | LPIEEAPKKS | YASIVKVMKE | 278 |
| SEQ_ID_NO_1274 | AEEVLVTETV | NEAPIEVQKV | GESD------ | SRTGEIPKRS | YASIVKVMKE | 255 |
| SEQ_ID_NO_1276 | EEESPVAEVV | DEIPDDSKMV | SDSK------ | PEMEELPKKS | YASILKVLKE | 242 |
| SEQ_ID_NO_1280 | EEEEPMPEVV | DEIPPDSQLV | ADSDVVVESS | AKIEDTPKKS | YASVVKVQKE | 257 |

Figure 43 (continued)

| | | | | | | | |
|---|---|---|---|---|---|---|---|
| SEQ_ID_NO_1285 | NSAPFHL--- | -RASPAKPAV | HPP- -RVHSV | PAPEAPTPNM | D-P-EKNN- - | | 294 |
| SEQ_ID_NO_1297 | NSAPFLS--- | -RTSPAKPAV | QPP- -RVHSV | PAPEAPAPNM | D-PSEKNN- - | | 288 |
| SEQ_ID_NO_1284 | SSVPTKVYV- | -PTNTLKSGP | NKT- -ESKVV | ES-VESTEVP | EAALESVSNP | | 291 |
| SEQ_ID_NO_1300 | VPLPA----- | -PAPPTRPAP | PKP- -EKQS- | -P-PAPTPVT | DVPPFSSN- P | | 301 |
| SEQ_ID_NO_1294 | APVPAPIPAT | RPAPAARPAP | PKP- -EKQSP | AP-PAPAPVA | DATPFSSN- A | | 305 |
| SEQ_ID_NO_1295 | APVPAPIPAT | RPAPAARPAP | PKP- -EKQSP | AP-PAPAPVA | DATPFSSN- A | | 303 |
| SEQ_ID_NO_1287 | VLPPN----- | -STVPYRPAP | PKP- -EKQA- | -PAPAQSVAV | DAPTFSPN- P | | 311 |
| SEQ_ID_NO_1289 | HRPLA----- | -PAVPSRPAP | P-T- -EKQA- | -S-PAPTPVT | EAPAFSPN- P | | 306 |
| SEQ_ID_NO_1291 | YPPPA----- | -PAVPSRPAP | PKP- -EKQA- | -P-PAPSLVA | DAPAFSPN- T | | 316 |
| SEQ_ID_NO_1274 | NAAPMSA--- | -SRTPTKVEP | KKD- -EDDAI | HI-PLPTPLS | EKSDSGANVA | | 296 |
| SEQ_ID_NO_1276 | NAVPVSAP-- | -TQSPVKSAV | KSQGHPRI AA | PP- SAPMPAS | DAQVSSNNVT | | 288 |
| SEQ_ID_NO_1280 | YTAPFSSP-- | -TPSPLRSAP | KI Q- -EQVTA | AV-SQP-PAA | ESHVSSSNTF | | 300 |

| | | | | | | | |
|---|---|---|---|---|---|---|---|
| SEQ_ID_NO_1285 | ENAGR----- | --AHAIFVAN | LPMSATVEQL | DRAFKKFGP- | KRDGIQVRSN | | 337 |
| SEQ_ID_NO_1297 | ENGGR----- | --AHAIFVAN | LPMTATVEQL | DRVFKKFGTI | KRDGIQVRSN | | 331 |
| SEQ_ID_NO_1284 | ESSDAHE-EV | E-GHSIYIRN | LPLNVTVADL | ELFFKKFGP- | KPGGIQVRNN | | 339 |
| SEQ_ID_NO_1300 | DNSN-QEPEV | D-AHAIYVRN | LPLNATETQL | EDEFKKFGTI | KQNGIQVRSN | | 350 |
| SEQ_ID_NO_1294 | ESSNTHEPEV | D-AHAIYVRS | LPLNATTTQL | EDEFKKFGTI | KPDGIQVRSH | | 354 |
| SEQ_ID_NO_1295 | ESSNTHEPEV | D-AHAIYVRS | LPLNATTTQL | EDEFKKFGTI | KPDGIQVRSH | | 352 |
| SEQ_ID_NO_1287 | ESSN-QDQEV | D-ALAVYVKN | LPLHATPSQL | EEEFKRFGTI | KHDGIQVRSH | | 360 |
| SEQ_ID_NO_1289 | QSGGFQDPEV | D-AHAIYVRS | LPLNATPQDL | EEEFKRFGTI | KHEGIQVRSN | | 355 |
| SEQ_ID_NO_1291 | QGGSFQDPEV | D-AHAIYVRN | LPLNATPQDL | EEEFKRFGTI | KHEGIQVRSN | | 365 |
| SEQ_ID_NO_1274 | VNENNQENER | ALGPSIYLKG | LPLDATPAL- | ENEFQKFGL- | RTNGIQVRSQ | | 348 |
| SEQ_ID_NO_1276 | ENGNNQDAEA | E-GPSIYVKG | LPLNATPSML | EVEFKKFGPI | KSGGIQVRSQ | | 337 |
| SEQ_ID_NO_1280 | ENGNAQESE- | E-GPSIYVKG | LPLDATTTLL | ENEFKKFGPI | RNGGVQVRFQ | | 348 |

| | | | | | | | |
|---|---|---|---|---|---|---|---|
| SEQ_ID_NO_1285 | K- -GSCFGFV | EFESAASMQS | ALEASPPVML | DNRRLS-EER | RGR------ | | 378 |
| SEQ_ID_NO_1297 | K- -GSCFGFV | EFESAASLQS | ALEASPPVML | DNRRLS-EER | RGR------ | | 372 |
| SEQ_ID_NO_1284 | KQQGYCFGFV | EFLSLNSMNS | AIQAS-PVP- | GGRQAVVE-K | RTTTRVGSGI | | 388 |
| SEQ_ID_NO_1300 | KIQGFCYGFV | EFEDSTVQS | AIEAS-PVT- | GGRQCYVEEK | RTP- - -GSR- | | 395 |
| SEQ_ID_NO_1294 | KIQGFCYGFV | EFEEATAVQS | AIEAS-PVMI | GGRQCFVEEK | RTP- - -GSR- | | 399 |
| SEQ_ID_NO_1295 | KIQGFCYGFV | EFEEATAVQS | AIEAS-PVMI | GGRQCFVEEK | RTP- - -GSR- | | 397 |
| SEQ_ID_NO_1287 | KIQGFCYGFI | EFEDASSVQS | ALAAS-PVT- | DDRPCHVEEK | RTP- - -GS- | | 404 |
| SEQ_ID_NO_1289 | KIQGFCYGFV | EFEDASAVQA | AIEAS-PVT- | GERQCFVEEK | RTT- - -GSRG | | 401 |
| SEQ_ID_NO_1291 | KIQGFCYGFV | EFEDANAVQT | AIEAS-PVMI | SERQCYVEEK | RTT- - -GSR- | | 410 |
| SEQ_ID_NO_1274 | K- -GFCFGFV | EFESASSMQS | AIEAS-PVML | NGHKVVEEK | RST- - -A- - - | | 389 |
| SEQ_ID_NO_1276 | K- -GFCFGFV | EFEMASSVQS | AIEAS-PIN- | GGRKAVVEEK | RST- - -S- - - | | 378 |
| SEQ_ID_NO_1280 | K- -GFCFGFV | EFEVASAVQS | ALEL-YLFLF | T--------- | --------- | | 377 |

Figure 43 (continued)

| | | |
|---|---|---|
| SEQ_ID_NO_1285 | SGYR- - - - - - - - - -NDRND NFRGRGNFGG GRGGGFNGRN DF-ERRGGEF | 416 |
| SEQ_ID_NO_1297 | GGYR- - - - - - - - - -NDRND NFRGRGNFGG GRGGGFNGRN DF-DRRG-EF | 409 |
| SEQ_ID_NO_1284 | NGTGRPR-PS GRG-GLRND SFRGRGNYVG GR-G--YGRN DY-VSRG-GF | 431 |
| SEQ_ID_NO_1300 | GSSRGGRFAP GRGN-NFRSE GTRGRGNYGG GR-G--YGRG EF-SYRS-DY | 439 |
| SEQ_ID_NO_1294 | GSSRGGRFAP GRGNNNFRAD GMRGRGNYSG GR-S--YGRG DF-SYRS-DY | 444 |
| SEQ_ID_NO_1295 | GSSRGGRFAP GRGNNNFRAD GMRGRGNYSG GR-S--YGRG DF-SYRS-DY | 442 |
| SEQ_ID_NO_1287 | RGSSRGRFPP GRGG-NFRGE GMRGRGSYTS GR-G--YGRG EYNNYRS-DF | 449 |
| SEQ_ID_NO_1289 | GGSRGGRFPP GRGG-NFRGE GIRGRGTYNG GR-G--YGRG EF-SYRS-DY | 445 |
| SEQ_ID_NO_1291 | GSNRGGRFAP GRGG-NFRGE GLRGRGTYNG GR-G--YGRG EF-SYRS-DY | 454 |
| SEQ_ID_NO_1274 | RGNYRGRSTF GVNT-GYRNE GGRGRGSFGG GRGG--YGRT DFNGYGN- - | 433 |
| SEQ_ID_NO_1276 | RGN-KGKSSS VSGA-GYRNE GARGRGNYGG GR-G--YSRG EF- - - - - - - | 415 |
| SEQ_ID_NO_1280 | TGNNRGRFPS GSGA-GYKSE GMRGRGNL-G GK-V--YGR- EF-GIRT-EF | 420 |

| | | |
|---|---|---|
| SEQ_ID_NO_1285 | SGRSRGG-QN AGR- - - - - - - - - - - - - - - - - - - - - - - - - -S | 429 |
| SEQ_ID_NO_1297 | SGRPRGG-NN TGR- - - - - - - - - - - - - - - - - - - - - - - - - -S | 422 |
| SEQ_ID_NO_1284 | SGRGRGH- - - - - - - - - - - - - - - - - - - - - - - - - - - - - - | 438 |
| SEQ_ID_NO_1300 | GGRSGGR-GG PAR- - - - - - - - - - - - - - - - - - - - - - - - - -G | 452 |
| SEQ_ID_NO_1294 | GGRGGGR-GG SAR- - - - - - - - - - - - - - - - - - - - - - - - - -G | 457 |
| SEQ_ID_NO_1295 | GGRGGGR-GG SAR- - - - - - - - - - - - - - - - - - - - - - - - - -G | 455 |
| SEQ_ID_NO_1287 | GGRGGGR-GG SGR- - - - - - - - - - - - - - - - - - - - - - - - - -G | 462 |
| SEQ_ID_NO_1289 | GGRGGGR-GG SLH- - - - - - - - - - - - - - - - - - - - - - - - - -G | 458 |
| SEQ_ID_NO_1291 | GGRGGGR-GG SSR- - - - - - - - - - - - - - - - - - - - - - - - - -G | 467 |
| SEQ_ID_NO_1274 | -NRGNNR-GG YANRAN- - - - - - - - - - - - - - - - - - - - - -G | 448 |
| SEQ_ID_NO_1276 | GNRSSNR-GG YSS- - - - - - - - - - - - - - - - - - - - - - - - - -R | 428 |
| SEQ_ID_NO_1280 | GNRGGSRGGG YSNRGGDGYS NRGGGGGGGG DGYSNRGGGG GGDGYSNRGG | 470 |

| | | |
|---|---|---|
| SEQ_ID_NO_1285 | NGDAVPRSYQ NG--GGKVAA RQPPVKVQ- - - - - - - - - - - - - - - - | 455 |
| SEQ_ID_NO_1297 | NGDAAPRSYQ NG--GGKV-A RQPPVKAQ- - - - - - - - - - - - - - - - | 447 |
| SEQ_ID_NO_1284 | -GEGYHOG-- - - - -RGRG-G RSSGQKQNAV SN- - - - - - - - - - - - | 462 |
| SEQ_ID_NO_1300 | ADVGYQRVDH AGYAGGRG-G RTAAAGAPAK - - - - - - - - - - - - | 481 |
| SEQ_ID_NO_1294 | PDVGYQRVD- - - - -GGRG-G RTSAGPGAPA K- - - - - - - - - - - - | 482 |
| SEQ_ID_NO_1295 | PDVGYQRVD- - - - -GGRG-G RTSAGPGAPA K- - - - - - - - - - - - | 480 |
| SEQ_ID_NO_1287 | GDVGYQRVDH SGT-GGRGGA RAAAK- - - - - - - - - - - - - - - - - | 486 |
| SEQ_ID_NO_1289 | GDVGYQRVDY SGTSSGRG-A RAPSAAAAMA K- - - - - - - - - - - - | 488 |
| SEQ_ID_NO_1291 | -EVGYQRVDH SGTAGGRG-T RPASAATAAK - - - - - - - - - - - - - | 495 |
| SEQ_ID_NO_1274 | DGGGFPRANG NF--NGRV-R RGGGIDANRA TKPVDDAPHV SVTA | 488 |
| SEQ_ID_NO_1276 | GGDGYQRGEH MGGNGGRV-S RSGEATFNAS TKNV--APRV SAPA | 469 |
| SEQ_ID_NO_1280 | GGDGYRRADK MGNNGGRA-N RSGGLGLNGT AKTT--APRV SATA | 511 |

Figure 44

| | | | | | | |
|---|---|---|---|---|---|---|
| SEQ_ID_NO_1327 | MVVTVAATG- | PDTAETLHST | TFASRYVRDQ | LPRYRMPENS | PKEAAYQII | 49 |
| SEQ_ID_NO_1333 | MVVSVAATGA | GTDAEPVTST | FFASRYVRDP | LRRYRMPERS | PREAAYQII | 50 |
| SEQ_ID_NO_1336 | MVVSVAATDS | DTAQPVQYST | FFASRYVRDP | LPRFRMPEQS | PREAAYQII | 50 |
| SEQ_ID_NO_1319 | MVLTTTS-- | RDSEESLHCT | -FASRYVQEP | LPKFKMPKKS | MPKEAAYQIV | 47 |
| SEQ_ID_NO_1302 | MVLATN--- | SDSDEHLHST | -FASRYVRAV | VPRFKMPDHC | MPKDAAYQVI | 45 |
| SEQ_ID_NO_1311 | MVISTAA-- | TDSDENLYST | -FASRYVRTA | LPRFKMPENS | MPKDAAYQVI | 46 |
| SEQ_ID_NO_1317 | MVLTSTATHP | DEQDQSLNYT | -FASRYVREP | PKFKMPEKS | PKDAAYQII | 49 |
| SEQ_ID_NO_1305 | MLAAT---- | NPTEEHVHST | -FASRYVRAP | VPRFKMPEKS | PKDAAYQVI | 44 |
| SEQ_ID_NO_1339 | MALSSA---- | TDSDGSIHST | -FASRYVQES | LPRFQIPSRS | PKDAAYQII | 45 |
| SEQ_ID_NO_1318 | MVLSETA-- | THMDASVHST | -FASRYVRTS | LPRFKMGENS | PKEAAYQII | 46 |
| SEQ_ID_NO_1331 | MVLSNTASSG | SESDLSIHST | -FASRYVRTS | LPRFKMPQES | PKEAAYQII | 49 |
| SEQ_ID_NO_1313 | MVLSKTA-- | SESDVSIHST | -FASRYVRTS | LPRFEMPENS | PKEAAYQII | 46 |
| SEQ_ID_NO_1303 | MVLSKTF--- | SESDESIHST | -FASRYVRNS | LPRFTMPENS | PKEAAYQII | 46 |
| SEQ_ID_NO_1340 | MVLSKTA-- | SESDVSVHST | -FASRYVRAS | LPRFKMPENS | PKEAAFQII | 46 |
| SEQ_ID_NO_1320 | MVLSKTA-- | SESDVSIHST | -FASRYVRTS | LPRFKMPENS | PKEAAYQII | 46 |
| SEQ_ID_NO_1326 | MVLSKTV--- | SQSDVSIHST | -FASRYVRTS | LPRFKMPDNS | PKEAAYQII | 46 |
| SEQ_ID_NO_1334 | MVLSKAV--- | SESDMSVHST | -FASRYVRAS | LPRYRMPENS | PKEAAYQII | 46 |
| SEQ_ID_NO_1330 | MVLSHGV--- | GGSDESVHST | -FASRYVRTS | LPRYRMPEQS | PKEAAYQII | 46 |

| | | | | | | |
|---|---|---|---|---|---|---|
| SEQ_ID_NO_1327 | SDELMLDGNP | RLNLASFVTT | MMEPECGKLI | NDSVNKNYVD | MDEYPVTTEL | 99 |
| SEQ_ID_NO_1333 | NDELMLDGNP | RLNLASFVTT | MMEPECDKLI | NGSINKNYVD | MDEYPVTTEL | 100 |
| SEQ_ID_NO_1336 | NDELMLDGNP | RLNLASFVTT | MMEPECDKLI | NDSVNKNYVD | MDEYPVTTEL | 100 |
| SEQ_ID_NO_1319 | NDELMLDGNP | RLNLASFVST | MMEPECDKLI | MSSINKNYVD | MDEYPVTTEL | 97 |
| SEQ_ID_NO_1302 | NDELMLDGNP | RLNLASFVTT | MMEPECDKLI | NDSVNKNYVD | MDEYPVTTEL | 95 |
| SEQ_ID_NO_1311 | NDELMLDGNP | RLNLASFVTT | MMEPECNDLI | MASINKNYVD | MDEYPVTTEL | 96 |
| SEQ_ID_NO_1317 | NDELMLDGAP | RLNLASFVTT | MMEPECDKLI | MASLNKNYVD | MDEYPVTTEL | 99 |
| SEQ_ID_NO_1305 | HDELMLDGNP | RLNLASFVTT | MMEPECDKLM | MAAINKNYVD | MDEYPVTTEL | 94 |
| SEQ_ID_NO_1339 | SDELMLDGNP | RLNLASFVTT | MMEPECDKLI | NQAINKNYVD | MDEYPVTTEL | 95 |
| SEQ_ID_NO_1318 | NDELMLDGNP | RLNLASFVTT | MMEPECDKLI | MASINKNYVD | MDEYPVTTEL | 96 |
| SEQ_ID_NO_1331 | NDELMLDGNP | RLNLASFVTT | MMEPECDKLI | MASINKNYVD | MDEYPVTTEL | 99 |
| SEQ_ID_NO_1313 | NDELMLDGNP | RLNLASFVTT | MMEPECDKLM | NESINKNYVD | MDEYPVTTEL | 96 |
| SEQ_ID_NO_1303 | NDELMLDGNP | RLNLASFVTT | MMEPECDKLM | MAAINKNYVD | MDEYPVTTEL | 96 |
| SEQ_ID_NO_1340 | NDELMLDGNP | RLNLASFVTT | MMEPECDKLI | ASINKNYVD | MDEYPVTTEL | 96 |
| SEQ_ID_NO_1320 | NDELMLDGNP | RLNLASFVTT | MMEPECNKLM | NDSINKNYVD | MDEYPVTTEL | 96 |
| SEQ_ID_NO_1326 | NDELMLDGNP | RLNLASFVTT | MMEPECDKLM | NDSINKNYVD | MDEYPVTTEL | 96 |
| SEQ_ID_NO_1334 | NDELMLDGNP | RLNLASFVTT | MMEPECDKLI | MAAINKNYVD | MDEYPVTTEL | 96 |
| SEQ_ID_NO_1330 | NDELMLDGNP | RLNLASFVTT | MMEPECDKLI | GASVNKNYVD | MDEYPVTTEL | 96 |

Figure 44 (continued)

| | | | | | | | |
|---|---|---|---|---|---|---|---|
| SEQ_ID_NO_1327 | QDRCVNMI AH | LFNAPI GEDE | TAI GVSTVGS | SEAI MLAGLA | FKRKWANKMK | 149 |
| SEQ_ID_NO_1333 | QNRCVNMI AH | LFNAPI KEDE | TAVGVGTVGS | SEAI MLAGLA | FKRKWQNKRK | 150 |
| SEQ_ID_NO_1336 | QNRCVNMI AH | LFNAPI KEDE | TAI GVGTVGS | SEAI MLAGLA | FKRKWQNKRK | 150 |
| SEQ_ID_NO_1319 | QNRCVNMLAH | LFHAPVGDDE | TAVGVGTVGS | SEAI MLAGLA | FKRKWQSKRK | 147 |
| SEQ_ID_NO_1302 | QNRCVNMI AN | FFHAPVGEDE | AAI GEGTVGS | SEAI MLAGLA | FKRKWQHRRK | 145 |
| SEQ_ID_NO_1311 | QNRCVNI I AH | LFNAPVGEKE | TAVGVGTVGS | SEAI MLAGLA | FKRKWQNKRK | 146 |
| SEQ_ID_NO_1317 | QNRCVNI I AN | LFHAPI SDDE | TAVGVGTVGS | SEAI MLAGLA | FKRKWQTKRK | 149 |
| SEQ_ID_NO_1305 | QNRCVNMI AN | LFHAPVGEEE | TAVGVGTVGS | SEAI MLAGLA | FKRRWQHKRK | 144 |
| SEQ_ID_NO_1339 | QNRCVNI I AN | LFNAPLGDGE | EAVGVGTVGS | SEAI MLAGLA | FKRKWQNKRK | 145 |
| SEQ_ID_NO_1318 | QNRCVNMI AH | LFNAPLEDSE | PAVGVGTVGS | SEAI MLAGLA | FKRKWQNRRK | 146 |
| SEQ_ID_NO_1331 | QNRCVNMI AH | LFNAPLGDSD | T--VGTVGS | SEAI MLAGLA | FKRTWQNRRK | 146 |
| SEQ_ID_NO_1313 | QNRCVNMI AR | LFNAPLGDGE | AAVGVGTVGS | SEAI MLAGLA | FKRQWQNKRK | 146 |
| SEQ_ID_NO_1303 | QNRCVNI I AR | LFNAPLEDSE | TAVGVGTVGS | SEAI MLAGLA | FKRKWQNKRK | 146 |
| SEQ_ID_NO_1340 | QNRCVNMI AH | LFNAPLGDSE | TAVGVGTVGS | SEAI MLAGLA | FKRKWQNKRK | 146 |
| SEQ_ID_NO_1320 | QNRCVNMI AH | LFNAPLGDGE | TAVGVGTVGS | SEAI MLAGLA | FKRKWQNKMK | 146 |
| SEQ_ID_NO_1326 | QNRCVNMI AH | LFNAPLEDGE | TAVGVGTVGS | SEAI MLAGLA | FKRKWQNKMK | 146 |
| SEQ_ID_NO_1334 | QNRCVNMI AH | LFHAPLGEDE | TAVGVGTVGS | SEAI MLAGLA | FKRRWQNKRK | 146 |
| SEQ_ID_NO_1330 | QNRCVNMI AH | LFNAPLGDAE | TAVGVGTVGS | SEAI MLAGLA | FKRRWQNKMK | 146 |

| | | | | | | | |
|---|---|---|---|---|---|---|---|
| SEQ_ID_NO_1327 | EQGKPCDKPN | VTGANVQVC | WEKFARYFEV | ELKEVKLTEG | YYVMDPKKAV | 199 |
| SEQ_ID_NO_1333 | EQGKPYDKPN | VTGANVQVC | WEKFARYFEV | ELKEVKLSEG | YYVMDPVKAV | 200 |
| SEQ_ID_NO_1336 | EQGKPCDKPN | VTGANVQVC | WEKFARYFEV | ELKEVKLSEG | YYVMDPVKAV | 200 |
| SEQ_ID_NO_1319 | AEGKPFDKPN | VTGANVQVC | WEKFARYFEV | ELKEVKLKEG | YYVMDPAKAV | 197 |
| SEQ_ID_NO_1302 | AQGLPIDKPN | VTGANVQVC | WEKFARYFEV | ELKEVKLSED | YYVMDPAKAV | 195 |
| SEQ_ID_NO_1311 | AEGKPYDKPN | VTGANVQVC | WEKFARYFEV | ELKEVKLTEG | YYVMDPVKAV | 196 |
| SEQ_ID_NO_1317 | AEGKPYDKPN | VTGANVQVC | WEKFARYFEV | ELKEVKLKEG | YYVMDPAKAV | 199 |
| SEQ_ID_NO_1305 | TEGKPTDNPN | VTGANVQVC | WEKFARYFEV | GLKEVKLKEG | YYVMDPEQAV | 194 |
| SEQ_ID_NO_1339 | AEGKPYDKPN | VTGANVQVC | WEKFARYFEV | ELKEVKLKKD | YYI MDPVKAV | 195 |
| SEQ_ID_NO_1318 | SEGKSCENPN | VTGANVQVC | WEKFARYFEV | ELKEVKLRDG | YYVMDPEKAA | 196 |
| SEQ_ID_NO_1331 | AEGKPHDKPN | VTGANVQVC | WEKFARYFEV | ELKEVKLSEG | YYVMDPQKAV | 196 |
| SEQ_ID_NO_1313 | AQGLPYDKPN | VTGANVQVC | WEKFARYFEV | ELKEVKLREG | YYVMDPEKAV | 196 |
| SEQ_ID_NO_1303 | AEGKPFDKPN | VTGANVQVC | WEKFARYFEV | ELKEVKLSEG | YYVMDPAKAV | 196 |
| SEQ_ID_NO_1340 | AEGKPYDKPN | VTGANVQVC | WEKFARYFEV | ELKEVKLSDG | YYVMDPEKAV | 196 |
| SEQ_ID_NO_1320 | AQGKPCDKPN | VTGANVQVC | WEKFARYFEV | ELKEVKLSDG | YYVMDPEKAV | 196 |
| SEQ_ID_NO_1326 | AQGKPCDKPN | VTGANVQVC | WEKFARYFEV | ELKEVKLSEG | YYVMDPEKAV | 196 |
| SEQ_ID_NO_1334 | AEGKPFDKPN | ITGANVQVC | WEKFARYFEV | ELKEVKLRDG | YYVMDPEKAV | 196 |
| SEQ_ID_NO_1330 | AAGKPCDKPN | VTGANVQVC | WEKFARYFEV | ELKEVKLSDG | YYVMDPQKAV | 196 |

Figure 44 (continued)

| | | | | | | | |
|---|---|---|---|---|---|---|---|
| SEQ_ID_NO_1327 | EMVDENTI CV | AAI LGSTLTG | EYEDVKLLND | LLVEKNKETG | MNVPI HVDAA | 249 |
| SEQ_ID_NO_1333 | DMVDENTI CV | AAI LGSTLTG | EFEDVKQLND | LLTEKNKETG | MDVPI HVDAA | 250 |
| SEQ_ID_NO_1336 | EMVDENTI CV | AAI LGSTLTG | FFEDVKLLNN | LLTEKNKETG | MDVPI HVDAA | 250 |
| SEQ_ID_NO_1319 | EI VDENTI CV | AAI LGSTLTG | EFEDVKLLNE | LLTKKNKETG | METPI HVDAA | 247 |
| SEQ_ID_NO_1302 | EMVDENTI CV | AAI LGSTLTG | EFEDVKQLND | LLAEKNAETG | METPI HVDAA | 245 |
| SEQ_ID_NO_1311 | EMVDENTI CV | AAI LGSTLTG | EFEDVKLLND | LLSKKNKETG | MNTPI HVDAA | 246 |
| SEQ_ID_NO_1317 | EMVDENTI CV | AAI LGSTMTG | EFEDVKLLDE | LLTKKNNETG | MDTPI HVDAA | 249 |
| SEQ_ID_NO_1305 | ELVDENTI CV | AAI LGSTLTG | EFEDVKTLND | LLMKKNEETG | MGTPI HVDAA | 244 |
| SEQ_ID_NO_1339 | EMVDENTI CV | AAI LGSTYNG | EFEDVKLVND | LLI QKNKETG | MDTPI HVDAA | 245 |
| SEQ_ID_NO_1318 | EMVDENTI CV | AAI LGSTLNG | EFEDVKRLND | LLVEKNAETG | MDTPI HVDAA | 246 |
| SEQ_ID_NO_1331 | DLVDENTI CV | AAI LGSTLNG | EFEDVKRLND | LLI EKNKETG | MDTPI HVDAA | 246 |
| SEQ_ID_NO_1313 | EMVDENTI CV | AAI LGSTLTG | EFEDVKLLND | LLVEKNKQTG | MDTG HVDAA | 246 |
| SEQ_ID_NO_1303 | EMVDENTI CV | AAI LGSTLNG | EFEDVKLLND | LLTEKNKETG | MDTPI HVDAA | 246 |
| SEQ_ID_NO_1340 | QMVDENTI CV | AAI LGSTLNG | EFEDVKLLND | LLVEKNKSTG | MDTPI HVDAA | 246 |
| SEQ_ID_NO_1320 | EMVDENTI CV | AAI LGSTLNG | EFEDVKRLND | LLI EKNKETG | MDTPI HVDAA | 246 |
| SEQ_ID_NO_1326 | EMVDENTI CV | AAI LGSTLNG | EFEDVKRLND | LLVEKNKETG | MDTPI HVDAA | 246 |
| SEQ_ID_NO_1334 | DMVDENTI CV | AAI LGSTLNG | EFEDVKLLND | LLDKKNKETG | METPI HVDAA | 246 |
| SEQ_ID_NO_1330 | DMVDENTI CV | AAI LGSTLNG | EFEDVKLLND | LLTKKNAETG | MDTPI HVDAA | 246 |

| | | | | | | | |
|---|---|---|---|---|---|---|---|
| SEQ_ID_NO_1327 | SGGFI APFLQ | PELEWDFRLP | LVKSI NVSGH | KYGLVYPGVG | WI WRSKDDL | 299 |
| SEQ_ID_NO_1333 | SGGFI APFLY | PELEWDFRLP | LVKSI NVSGH | KYGLVYAGVG | WI WRSKKDL | 300 |
| SEQ_ID_NO_1336 | SGGFI APFLY | PELEWDFRLP | LVKSI NVSGH | KYGLVYPGVG | WI WRSKEDL | 300 |
| SEQ_ID_NO_1319 | SGGFI APFLW | PDLEWDFRLP | LVKSI NVSGH | KYGLVYAGVG | WI WRSKEDL | 297 |
| SEQ_ID_NO_1302 | SGGFI APFLY | PDLEWDFRLP | WKSI NVSGH | KYGLVYAGVG | WVVWRTKDDL | 295 |
| SEQ_ID_NO_1311 | SGGFI APFI W | PDLEWDFRLP | LVKSI NVSGH | KYGLVYAGVG | WVVWRTKEDL | 296 |
| SEQ_ID_NO_1317 | SGGFI APFLY | PDLEWDFRLP | LVKSI NVSCH | KYGLVYPGVG | WVVWRSKDDL | 299 |
| SEQ_ID_NO_1305 | SGGFI APFLY | PDLEWDFRLP | LVKSI NVSGH | KYGLVYAGVG | WVWRNKEDL | 294 |
| SEQ_ID_NO_1339 | SGGFI APFLY | PELEWDFRLP | LVKSI NVSGH | KYGLVYAGI G | WI WRAKQDL | 295 |
| SEQ_ID_NO_1318 | SGGFI APFLY | PELVWDFRLS | LVKSI NVSGH | KYGLVYAGI G | MI WRSKEDL | 296 |
| SEQ_ID_NO_1331 | SGGFI APFI Y | PELEWDFRLP | LVKSI NVSGH | KYGLVYAGI G | WI WRNKEDL | 296 |
| SEQ_ID_NO_1313 | SGGFI APFLY | PELEWDFRLP | LVKSI NVSGH | KYGLVYAGI G | WVVWRTKSDL | 296 |
| SEQ_ID_NO_1303 | SGGFI APFLY | PELEWDFRLP | LVKSI NVSGH | KYGLVYAGI G | WVVWRNKEDL | 296 |
| SEQ_ID_NO_1340 | SGGFI APFI Y | PELEWDFRLP | LVKSI NVSGH | KYGLVYAGI G | WI WRNKEDL | 296 |
| SEQ_ID_NO_1320 | SGGFI APFLY | PELEWDFRLP | LVKSI NVSGH | KYGLVYAGI G | WA WRNKEDL | 296 |
| SEQ_ID_NO_1326 | SGGFI APFI Y | PELEWDFRLP | LVKSI NVSGH | KYGLVYAGI G | WVVWRNKDDL | 296 |
| SEQ_ID_NO_1334 | SGGFI APFLY | PELEWDFRLP | WKSI NVSGH | KYGLVYAGI G | WC WRNKEDL | 296 |
| SEQ_ID_NO_1330 | SGGFI APFLY | PELEWDFRLP | LVKSI NVSGH | KYGLVYAGI G | WC WRTKVDL | 296 |

Figure 44 (continued)

| | | | | | | |
|---|---|---|---|---|---|---|
| SEQ_ID_NO_1327 | PEELIFHINY | LGADQPTFTL | NFSKGQ-QII | AQYYQLIRLG | FEGYKHIMEN | 348 |
| SEQ_ID_NO_1333 | PEELIFHINY | LGTDQPTFTL | NFSKGSSQII | AQYYQLIRLG | FQGYKNIMEN | 350 |
| SEQ_ID_NO_1336 | PEELIFHINY | LGTDQPTFTL | NFSKGSSQII | AQYYQLIRLG | FEGYKNIMQN | 350 |
| SEQ_ID_NO_1319 | PDELVFHINY | LGSDQPTFTL | NFSKGSYQII | AQYYQLIRLG | FEGYKNVMKN | 347 |
| SEQ_ID_NO_1302 | PEELVFHINY | LGADQPTFTL | NFSKGSSQII | AQYYQFIRLG | FEGYKNIMEN | 345 |
| SEQ_ID_NO_1311 | PDELIFHINY | LGSDQPTFTL | NFSKGSGQII | AQYYQFIRLG | FEGYKRIMEN | 346 |
| SEQ_ID_NO_1317 | PDELVFHINY | LGSDQPTFTL | NFSKGSSQII | AQYYQLIRLG | FEGYKNIMEN | 349 |
| SEQ_ID_NO_1305 | PDDLVFHINY | LGSDQPTFTL | NFSKGSSQII | AQYYQFLRLG | FEGYKNIIEN | 344 |
| SEQ_ID_NO_1339 | PEELIFHINY | LGADQPTFTL | NFSKGASQII | AQYYQLIRLG | FEGYRNIMGN | 345 |
| SEQ_ID_NO_1318 | PEELIFHINY | LGADQPTFTL | NFSKGSSQVI | AQYYQLIRLG | YEGYRNVMEN | 346 |
| SEQ_ID_NO_1331 | PEELIFHINY | LGADQPTFTL | NFSKGSSQII | AQYYQLIRLG | YEGYKHVMEN | 346 |
| SEQ_ID_NO_1313 | PDELIFHINY | LGADQPTFTL | NFSKGSSQVI | AQYYQLIRLG | FEGYRNVMDN | 346 |
| SEQ_ID_NO_1303 | PEELIFHINY | LGADQPTFTL | NFSKGSSQVI | AQYYQLIRLG | FEGYRNVMEN | 346 |
| SEQ_ID_NO_1340 | PEELIFHINY | LGADQPTFTL | NFSKGSSQVI | AQYYQLIRLG | YEGYKNVMEN | 346 |
| SEQ_ID_NO_1320 | PDELIFHINY | LGADQPTFTL | NFSKGSSQVI | AQYYQLIRLG | FEGYKNVMEN | 346 |
| SEQ_ID_NO_1326 | PDELIFHINY | LGADQPTFTL | NFSKGSSQVI | AQYYQLIRLG | YEGYKNVMEN | 346 |
| SEQ_ID_NO_1334 | PEELIFHINY | LGADQPTFTL | NFSKGSSQVI | AQYYQLIRHG | FEGYRNIMEN | 346 |
| SEQ_ID_NO_1330 | PEELIFHINY | LGADQPTFTL | NFSKGSSQVI | AQYYQLIRLG | FEGYKNIMEN | 346 |

| | | | | | | |
|---|---|---|---|---|---|---|
| SEQ_ID_NO_1327 | CKLNAAVLKE | GIDATGRFDV | LSKADGVPLV | ALRLKDSTNF | SVFDISENLR | 398 |
| SEQ_ID_NO_1333 | CMENAAILRE | GIAATGRFDI | LSKDAGVPLV | AFSLKDSSRF | SVFDISENLR | 400 |
| SEQ_ID_NO_1336 | CMENTAILRE | GIEATGRFEI | LSKEAGVPLV | AFSLKDSGRY | TVFDISEHLR | 400 |
| SEQ_ID_NO_1319 | CLSNAKVLTE | GIIKMGRFDI | VSKDVGVPYV | AFSLRDSSKY | TVFEVSEHLR | 397 |
| SEQ_ID_NO_1302 | CMDNARRLRE | GIEMTGKFNI | VSKDIGVPLV | AFSLKDSSKH | TVFEIAESLR | 395 |
| SEQ_ID_NO_1311 | CLENARVLRE | GLEKTGRFDI | VSKDKGVPLV | AFSLKDSSKH | TVFEIAESLR | 396 |
| SEQ_ID_NO_1317 | CWENARVLKE | GIERTGRFNI | ISKDIGVPLV | AFSLQDSSQH | TVFEIADHLR | 399 |
| SEQ_ID_NO_1305 | CMENMKVLKQ | GIENTGRFNI | LSKDIGVPLV | AFSLKDSSKH | TVFEIAENLR | 394 |
| SEQ_ID_NO_1339 | CAANAKALSD | GLVRTGRFNI | LSKEIGVPLV | AFSLKDSSRH | DEYEISDHLR | 395 |
| SEQ_ID_NO_1318 | CRDNMMVLKD | GLEKTERFEI | VSKDEGVPLV | AFTLKDHNNF | NEFQISDMLK | 396 |
| SEQ_ID_NO_1331 | CRDNMLVLKE | GLQKTGRFEI | VSKDNGVPLV | AFTLKDHTHY | NEFQISDSLF | 395 |
| SEQ_ID_NO_1313 | CRENMMVLRE | GLEKTGRFNI | VSKENGVPLV | AFSLKDSSRH | DEFEVAETLR | 396 |
| SEQ_ID_NO_1303 | CHENAMVLKE | GLEKTGRFNI | VSKDEGVPLV | AFSLKDNKRH | DEFEVAELLR | 396 |
| SEQ_ID_NO_1340 | CRDNMLVLKQ | GLEKTGKFNI | VSKDKGVPLV | AFSLKDNSLH | NEFEVSDMLR | 396 |
| SEQ_ID_NO_1320 | CQENARVLRE | GLEKSGRFNI | ISKEIGVPLV | AFSLKDNSQH | NEFEISETLR | 396 |
| SEQ_ID_NO_1326 | CQENASVLRE | GLEKTGRFNI | ISKEIGVPLV | AFSLKDNRQH | NEFEISETLR | 396 |
| SEQ_ID_NO_1334 | CHENAMVLKE | GLVKTGRFDI | VSKDEGVPLV | AFSLKDRSRH | DEFEISDMLR | 396 |
| SEQ_ID_NO_1330 | CQENATVLKQ | GLEKTGKFNI | VSKDNGVPLV | AFSLKDSSRH | SEFEISDFLR | 396 |

Figure 44 (continued)

```
SEQ_ID_NO_1327   RFGW VPAYT MPADAEHVAV LRIVIREDFN RSLAQRLLAD FNKIIGELDA   448
SEQ_ID_NO_1333   RFGW VPAYT MPADAEHVAV LRVVIREDFS RTLLERLVGD VLKILRELDA   450
SEQ_ID_NO_1336   RFGW VPAYT MPANAEHVAV LRVVIREDFS RSLAERLVSD VKILHELDA    450
SEQ_ID_NO_1319   RFGW VPAYT MPPDAEHIAV LRVVIREDFS HSLAERLVSD EKILSELDT    447
SEQ_ID_NO_1302   KFGW IPAYT MPADAQHIAV LRVVIREDFS RGLADRLITH DVLKEIEG     445
SEQ_ID_NO_1311   RFGW IPAYT MPANAQHIAV LRVVVREDFN RSLAERLVSH DQVMKETDS    446
SEQ_ID_NO_1317   KFGW VPAYT MPPDAQHIAV LRVVIREDFS RGLAERLAAD EKVVKLLDT    449
SEQ_ID_NO_1305   RFGW LPAYT MPANAQHVAV LRAVIREDFS HGLAKRLVAH EQVLKEMDG    444
SEQ_ID_NO_1339   RFGW VPAYT MAPDAQEVKL LRVVVREDFN RSLAERLVHD EKVLHELDT    445
SEQ_ID_NO_1318   RHGW IPAYT MPPDAEHVTV LRVVIREDFS RTFAERLVID TRVIHELD     446
SEQ_ID_NO_1331   .......... ........A. LRV....... .......... .......DS    401
SEQ_ID_NO_1313   RFGW VPAYT MPADAQHVTV LRVVIREDFS RTLAERLVAD FEKVLHELDT   446
SEQ_ID_NO_1303   RFGW VPAYT MPADAQHITV LRVVIREDFS RTLAERLVLD TKVLHELDS    446
SEQ_ID_NO_1340   RFGW VPAYT MPPDAQHVTV LRVVIREDFS RTLAERLVID GKVLHELET    446
SEQ_ID_NO_1320   RFGW IPAYT MPPNAQHVTV LRVVIREDFS RTLAERLVID EKVLHELDT    446
SEQ_ID_NO_1326   RFGW VPAYT MPPNAQHITV LRVVIREDFS RTLAERLVRD EKVLHELDT    446
SEQ_ID_NO_1334   RFGW VPAYT MPPDAQHVTV LRVVIREEFS RTLAERLVLD EKVMYQLDA    446
SEQ_ID_NO_1330   RFGW VPAYT MPPDAQHVTV LRVVIREDFS RTLAERLVLD EKVLHELDA    446

SEQ_ID_NO_1327   HAVHAIKLST AAAGGDG--- .......... .......... ASKSAVDAATE   476
SEQ_ID_NO_1333   CATHAVRVAT ATAAVQSGDG GGVVARK--- .......... SILELEREVAS   488
SEQ_ID_NO_1336   HSAQVLKISS AIAKQQSGDD GVVTKK---- .......... SVLETEREIFA   487
SEQ_ID_NO_1319   QPPRLPTKAV RVTAEEVRDD KGDGLHHFHM .........D TVETQKDIIK   488
SEQ_ID_NO_1302   LPSRIAHLAA AAAVSGDDEE VKVK------ .......... TAKMSLEDITK   480
SEQ_ID_NO_1311   LPSRVAVQAS RIVTVDETQD NMDGKKTVKK .......... SSRELDEFVTL   487
SEQ_ID_NO_1317   LPSPLTTKAV HITAITSETG EKIKK----- .......... AAETQKEIAF   485
SEQ_ID_NO_1305   LPSGLDHKK- .......... .......... .......... AERETQEEVFR   464
SEQ_ID_NO_1339   LPSKIAREVV ASLYDGHPEL KEVKDLGIDV TQFKSSAVFN EIYNSQKAVK   495
SEQ_ID_NO_1318   VPSRVVSTNT ITVTGGEEDA DNDGTVTIAN Q-........ SVLETQRKITT   488
SEQ_ID_NO_1331   AGIQHAPKYS A--------- .......... .......... ..........   412
SEQ_ID_NO_1313   LPARVQAKMA NGNANGVKK- .......... .......... TEEETTREYTA   476
SEQ_ID_NO_1303   LPSKVLVPAS EQNGRNGKK- .......... .......... TELETQREVTT   476
SEQ_ID_NO_1340   LPSRISAKIV LANEEKDAVA AGKEKK---- .......... DVQNETREIIT   483
SEQ_ID_NO_1320   LPARVNAKLA VAEANGSGVH KK-------- .......... TDREVQLEITT   479
SEQ_ID_NO_1326   LPARVNAKLA VAEEQAAANG SEVHKK---- .......... TDSEVQLEMIT   493
SEQ_ID_NO_1334   LPSRLMPPVP PAPLLVVAKK .......... .......... SELETQRSVTE   477
SEQ_ID_NO_1330   LPARVPSGDL AALAAAESSE .......... .......... REMEKQRQVIS   477
```

Figure 44 (continued)

| | | |
|---|---|---|
| SEQ_ID_NO_1327 | AFKDLAGK- --KKAGVC- | 490 |
| SEQ_ID_NO_1333 | RMRDAVSK- --KKTGPC- | 502 |
| SEQ_ID_NO_1336 | YMRDQVKK- --KDTGIC- | 501 |
| SEQ_ID_NO_1319 | HMRKIAGK- --KTSGVC- | 502 |
| SEQ_ID_NO_1302 | YMKRLVEH- --KRNIVC- | 494 |
| SEQ_ID_NO_1311 | YMRRLASE- --KRTGAC- | 501 |
| SEQ_ID_NO_1317 | YMKRLVDG- --KRLGAC- | 499 |
| SEQ_ID_NO_1305 | CMKRLVDR- --KIAGVC- | 478 |
| SEQ_ID_NO_1339 | AMKKFVAQ- --KANRVC- | 509 |
| SEQ_ID_NO_1318 | AMKKFVMNRK --KTNGVC- | 504 |
| SEQ_ID_NO_1331 | --------- --RDRGPCSH | 420 |
| SEQ_ID_NO_1313 | YMKKFVEAKK -SNKNRIC- | 493 |
| SEQ_ID_NO_1303 | YMRKFVSERK ANNKNKIC- | 494 |
| SEQ_ID_NO_1340 | AMRKLVVQRK --KLNGVC- | 499 |
| SEQ_ID_NO_1320 | AMKKFVADKK K-KTNGVC- | 496 |
| SEQ_ID_NO_1326 | AMKKFVEEKK K-KTNRVC- | 500 |
| SEQ_ID_NO_1334 | AMKKFVLAK- --RTNGVC- | 492 |
| SEQ_ID_NO_1330 | LMKRAVLAKK --KTNGVC- | 493 |

Figure 45

| SEQ_ID_NO | Sequence | # |
|---|---|---|
| SEQ_ID_NO_1363 | ........... ........... ........... ---MSKTTNQ NRRPSFTSST | 17 |
| SEQ_ID_NO_1373 | ........... ........... ........... ........... ........MVD | 3 |
| SEQ_ID_NO_1342 | ........... ........... ........... ........... ........... | 0 |
| SEQ_ID_NO_1381 | ........... ........... ........... ........... ........... | 0 |
| SEQ_ID_NO_1382 | ........... ........... ........... ........... ........... | 0 |
| SEQ_ID_NO_1371 | ........... ........... ........... ........... ........... | 0 |
| SEQ_ID_NO_1366 | ........... ........... ........... ........... ..........M | 1 |
| SEQ_ID_NO_1370 | ........... ........... ........... ........... ........... | 0 |
| SEQ_ID_NO_1346 | ........... ........... ........... ........... ........... | 0 |
| SEQ_ID_NO_1372 | ........... ........... ........... ........... ........... | 0 |
| SEQ_ID_NO_1374 | ........... ........... ........... ........... --MKKQEKEA | 8 |
| SEQ_ID_NO_1355 | ........... ........... ........... ........... ........... | 0 |
| SEQ_ID_NO_1364 | ........... ........... ........... ........... ........... | 0 |
| SEQ_ID_NO_1378 | MGSRHQVVQQ QNRGDVVPGA IKQKSMAVEK KNRRALGDIG NVV-TVRGVE | 49 |
| SEQ_ID_NO_1377 | ---MNTNRAV LVPHRGEVGG KQKNGQADGR NNRRVLGDIG NLVTGAPYIE | 47 |
| SEQ_ID_NO_1379 | MGSRAVVVPD QQPRGR--GG KQKNGQAEGR -NRRVLRDIG NLV-PVPTVE | 46 |
| SEQ_ID_NO_1380 | ........... ........... ........... ---MAGADEN HGAVKLANFR | 17 |
| SEQ_ID_NO_1383 | ........... ........... ........... ........... ........... | 0 |

| SEQ_ID_NO | Sequence | # |
|---|---|---|
| SEQ_ID_NO_1363 | ESSMRKRHGP SSSSSAVK- PISNTAVMVA KKRAPLGNIT .......... | 55 |
| SEQ_ID_NO_1373 | EENKVPAFAA ASRGSNKR- AFDSJ AI TNE NDPLQISERP .......... | 41 |
| SEQ_ID_NO_1342 | ........... ........... ........... ........... ........... | 0 |
| SEQ_ID_NO_1381 | -MADKENSTP ASAARLTRSS AAAGAQAKRS AAAGVADGGA .......... | 39 |
| SEQ_ID_NO_1382 | -MADKENSTP ASAARLTRSS AAAGAQAKRS AAAGVADGGA .......... | 39 |
| SEQ_ID_NO_1371 | ........... .......... -APSMTTPF- .......... .......... | 8 |
| SEQ_ID_NO_1366 | ATSENNSSAR PQREAKKR- AAAI SQI HG N......... .......... | 30 |
| SEQ_ID_NO_1370 | MADQDNSTRR PQREAKKR- AVAAL CE--- .......... .......... | 25 |
| SEQ_ID_NO_1346 | -MAEQENCTR VTRAAKKR- AAAL ASTEDQ .......... .......... | 27 |
| SEQ_ID_NO_1372 | -MADKENCIR VTRLAKKR- AVEAMAASEQ Q-......... .......... | 28 |
| SEQ_ID_NO_1374 | IMADLENCGR VTRLAKKR- AAEAMASHQQ Q-......... .......... | 37 |
| SEQ_ID_NO_1355 | MADEKENCVR MTRAATKRKA SMEAAIDKE- .......... .......... | 29 |
| SEQ_ID_NO_1364 | -MAENQNSTR MTRAAAKR- KASVTDEN-- .......... .......... | 25 |
| SEQ_ID_NO_1378 | GKALPQVSRP ITRGFCAQLI ANAEAAAAEN NKNSLAVNAK GADGALPIKR | 99 |
| SEQ_ID_NO_1377 | GKPKAQI SRP ATRSFCAQLL ANAQAEKNKV KPLAEVVNKV .......... | 87 |
| SEQ_ID_NO_1379 | EKPQNQI SRP VTRSLCVQ- PAAAAEKKNK KPLAEVVNGG GEVKAAAAAH | 94 |
| SEQ_ID_NO_1380 | ETTNRRALKD IKNFVGAP-- SFPCAANKRD LKEVVCGNND .......... | 55 |
| SEQ_ID_NO_1383 | -MITGAQGVR QTRSKTTY-- EVPQQQQQQS FEW-...... .......... | 30 |

Figure 45 (continued)

| | | | | | | | |
|---|---|---|---|---|---|---|---|
| SEQ_ID_NO_1363 | -----NQRKD | SRIFPNSSSA | DSAHCPNKSA | KLKLAAPTQP | VCVNACETKS | | 100 |
| SEQ_ID_NO_1373 | -----YPANK | KRVVLGELNN | LGNV------ | --IVSTQNSD | LTETHESKRK | | 78 |
| SEQ_ID_NO_1342 | ------MGYL | WRVRLSSFAA | GAAT------ | --ASAAGFFL | LYKDHLLARA | | 36 |
| SEQ_ID_NO_1381 | -----PPAKR | KRVALSDLPT | LSNA------ | --VVVAPRQP | HHPVVIKPSS | | 76 |
| SEQ_ID_NO_1382 | -----PPAKR | KRVALSDLPT | LSNA------ | --VVVAPRQP | HHPVVIKPSS | | 76 |
| SEQ_ID_NO_1371 | ------PASK | RRVVLGEISN | NSSA------ | --VSGNEDLL | CREFEVPKCV | | 44 |
| SEQ_ID_NO_1366 | ------AAKK | KRVVLGDVTN | VSSS------ | ---------- | -----DVAVS | | 53 |
| SEQ_ID_NO_1370 | ------QRKR | KRVALGDITN | DVVS------ | --ETEKLVSD | SHSHTQKKKK | | 61 |
| SEQ_ID_NO_1346 | ------PLNK | KRVVLGELPN | LSNA------ | --IVSS---- | -NEPQKDKAK | | 58 |
| SEQ_ID_NO_1372 | ------RPSK | KRVVLGELKN | LSSN------ | ---ISSQTY  | DFSSGPDKQQ | | 63 |
| SEQ_ID_NO_1374 | ------HPSK | KRVVLGEIQN | FSNL------ | --GVSQIKGL | NTEPKKDPKS | | 73 |
| SEQ_ID_NO_1355 | ------RINK | KRVVLGELPN | LSNI------ | ---------- | ----KKSRKA | | 53 |
| SEQ_ID_NO_1364 | ------PVSK | KRVVLGELPN | NGNV------ | ----PAPLIP | LQFRETQKPK | | 59 |
| SEQ_ID_NO_1378 | AVAR--VPVQ | KKTVKSKPQE | IEISPDTEK  | KKAPVLEKEI | TGEKSLKKKA | | 147 |
| SEQ_ID_NO_1377 | ------PAKK | KASDKPAVQE | AVIVISPDEE | VKKKTIEKSP | LSKRKAKKTG | | 131 |
| SEQ_ID_NO_1379 | KKHYDPPKPE | TVIVISSDEE | LESE------ | --EKKKPVAV | IARKSRVGSS | | 136 |
| SEQ_ID_NO_1380 | -----SVIPR | RPITRQFAST | LASK------ | --SQQSHGET | SNKHGQITGN | | 92 |
| SEQ_ID_NO_1383 | ------GRTS | QRTSHGKPRR | GSVM------ | --------GGT | MTTAGADVDM | | 61 |

| | | | | | | | |
|---|---|---|---|---|---|---|---|
| SEQ_ID_NO_1363 | TCEEVVPIE | RKAFSNLCIT | PSSDTTTNVM | SETENKEEKF | MNDNKDDAD | | 150 |
| SEQ_ID_NO_1373 | IKLRKTRNVV | KETVELKTSA | NSSPK----- | ---------- | --------DN | | 105 |
| SEQ_ID_NO_1342 | ADAESNSASY | SPPLATADTA | FSAPP----- | ---------- | RAVAP---AD | | 68 |
| SEQ_ID_NO_1381 | KQPEPAAEAA | APSGGGGGSP | VSSAST---- | ---------- | STASPSSGWD | | 112 |
| SEQ_ID_NO_1382 | KQPEPAAEAA | APSGGGGGSP | VSSAST---- | ---------- | STASPSSGWD | | 112 |
| SEQ_ID_NO_1371 | AQKKRKRGVK | EDVGVDFGEK | F--------- | ---------- | ---------DD | | 67 |
| SEQ_ID_NO_1366 | VSKKPVQTHK | NVKLEKPAAP | VAIPE----- | ---------- | ---KVEERHD | | 85 |
| SEQ_ID_NO_1370 | RNIAKSPVPE | KL-------- | ---------- | ---------- | ---------ED | | 75 |
| SEQ_ID_NO_1346 | AKPKARKGAS | TKKEGVLKED | VDGNP----- | ---------- | ---------ED | | 85 |
| SEQ_ID_NO_1372 | KNKNKRKAKE | SLGFEVKEKK | VEEAG----- | ---------- | IDVFSQS-DD | | 97 |
| SEQ_ID_NO_1374 | KQQSKRKLK  | RAVTSKIDKE | ELNVD----- | ---------- | -NVDANY-DD | | 106 |
| SEQ_ID_NO_1355 | TTKQKKKSVS | IPTIETLNSD | IDTRS----- | ---------- | --------DD | | 80 |
| SEQ_ID_NO_1364 | STLFAAKKQT | KTPPIPQTVD | FESGS----- | ---------- | ---------SD | | 86 |
| SEQ_ID_NO_1378 | PTLTSTLTAR | SKAASVVRTK | PKEQI----- | ---------- | VDDAADVNN | | 182 |
| SEQ_ID_NO_1377 | KTLTSTLTAR | SKAACGLSNR | PKNEI----- | ---------- | DDDAADAAN | | 166 |
| SEQ_ID_NO_1379 | RTMTSILTAR | SKALCGPTTK | PKVPI----- | ---------- | ADDAADVDN | | 171 |
| SEQ_ID_NO_1380 | EKHNPIIIDE | DVPMVEESEE | MEECELVEEI | TMEDIVIDSA | QDDIGDVGN  | | 142 |
| SEQ_ID_NO_1383 | RESYSTYLER | SSAADVMTDA | L--------- | ---------- | PDDLYDHDN  | | 92 |

Figure 45 (continued)

| | | | | | | | | |
|---|---|---|---|---|---|---|---|---|
| SEQ_ID_NO_1363 | PQLYATFACD | YNHLRAAE- | -AKKQPAVDY | METVQKDVNS | TMRGILVDWL | 198 |
| SEQ_ID_NO_1373 | LDKCS-YGPL | YQHLHSLEV | EERRRPLSNY | MEKVQNNVIP | SMRTVLVDWL | 154 |
| SEQ_ID_NO_1342 | LDLSGSYASD | YTYLRSLEV | DPQRRSRSDY | ERVQADVTA | HMRSILVDWL | 118 |
| SEQ_ID_NO_1381 | PQ---YASD | YTYLRSMEV | EARRQSAADY | ESVQVDVTA | NMRAILVDWL | 158 |
| SEQ_ID_NO_1382 | PQ---YASD | YTYLRSMEV | EARRQSAADY | EAVQVDVTA | NMRAILVDWL | 158 |
| SEQ_ID_NO_1371 | PQMCSAYVSD | VYEYLKQMEM | ETKRRPMMNY | EQVQKDVTS | NMRGVLVDWL | 117 |
| SEQ_ID_NO_1368 | PQLCGPYVSD | YEYLRGMEV | DPSKRPLMDY | VQKIQRDVNA | NMRGVLVDWL | 135 |
| SEQ_ID_NO_1370 | PQLCEPYVSD | HDYLRNLEV | DPSKRPLPDY | QKVQRDINA | NMRGVLVDWL | 125 |
| SEQ_ID_NO_1346 | PQMCAPYASD | YEYLHKMEV | DPKRRPLPDY | EKVQKDVSP | NMRGILVDWL | 135 |
| SEQ_ID_NO_1372 | PQMCGAYVSD | YEYLHKMEM | ETKRRPLPDY | LDKVQKDVTA | NMRGVLIDWL | 147 |
| SEQ_ID_NO_1374 | PQMCSAYVSD | YDYLRKMEI | EEKRRPLPDY | LEKVQKDLSP | NMRGVLVDWL | 156 |
| SEQ_ID_NO_1355 | PQMCGPYVTS | FEYLRQLE- | -VKSRPLVDY | EKIQKDVTS | NMRGVLVDWL | 128 |
| SEQ_ID_NO_1364 | PQMCGPFVAD | CAYLREMEG | KLKQRPLHDY | EKVQSDLTP | SMRGVLMDWL | 136 |
| SEQ_ID_NO_1378 | DLAVVEYVED | MYKFYKSAE- | -NDSRPH-DY | MDFSQPEINE | KMRAILIDWL | 228 |
| SEQ_ID_NO_1377 | HLAVVEYVED | YNFYKLTE- | -DESRVN-NY | MEFFQPELNH | KMRAILVDWL | 212 |
| SEQ_ID_NO_1379 | ELAVVEYVED | YKFYKLTE- | -GESRVH-DY | MDFSQPEINS | KMRSILIDWL | 217 |
| SEQ_ID_NO_1380 | PLAVVDYVDD | YNVYRRVE- | -ASSCVHPDY | MS-NQFDIND | KMRAILIDWL | 189 |
| SEQ_ID_NO_1383 | PLAVTQYVND | YQYWYKVE- | -PDTRVSETY | ML-QGDINY | KMRAILIDWL | 139 |

| | | | | | | | |
|---|---|---|---|---|---|---|---|
| SEQ_ID_NO_1363 | VEVSEEYRLV | PETLYLTVNY | DRYLSGNV | SRQKLQLLGV | ACMMIAA-KY | 247 |
| SEQ_ID_NO_1373 | VEVTEEYKLV | SDTLYLAVSY | DRFLSSHVL | AMEKLQLLGV | SCMLVAS-KY | 203 |
| SEQ_ID_NO_1342 | VEVAEEYKLV | ADTLYLTISY | VDRFLSVNAL | GRDKLQLLGV | ASMLIAA-KF | 167 |
| SEQ_ID_NO_1381 | VEVADEYKLV | ADTLYLAVSY | LDRYLSAHPL | RRNRLQLLGV | GAMLIAA-KY | 207 |
| SEQ_ID_NO_1382 | VEVADEYKLV | ADTLYLAVSY | LDRYLSAHPL | RRNRLQLLGV | GAMLIAA-KY | 207 |
| SEQ_ID_NO_1371 | VEVSLEYKLL | PETLYLAISY | VDRYLSVNVL | NRQKLQLLGV | SSFLIAS-KY | 166 |
| SEQ_ID_NO_1366 | VEVAEEYKLV | SDTLYFSVAY | DRFLSLNIL | SRQRLQLLGV | ASMLIAS-KY | 184 |
| SEQ_ID_NO_1370 | VEVAEEYKLV | ADTLYFSVSY | DRFLSLNDL | SRQKLQLLGV | SSMLIAS-KY | 174 |
| SEQ_ID_NO_1346 | VEVAEEYKLV | SETLYLTVSY | VDRFLSFNVL | SRQRLQLLGV | SSMLLAS-KY | 184 |
| SEQ_ID_NO_1372 | VEVAEEYKLL | PDTLYLTVSY | DRFLSMNAL | SRQKLQLLGV | SSMLIAS-KY | 196 |
| SEQ_ID_NO_1374 | VEVAEEYKLL | SDTLYLAVSY | DRFLSTNV | TRQKLQLLGV | SSMLISA-KY | 205 |
| SEQ_ID_NO_1355 | VEVAEEYKLL | SDTLYLAVSY | DRFLSLKTV | NKQRLQLLGV | TSMLIAS-KY | 177 |
| SEQ_ID_NO_1364 | VEVAEEYKLV | SDTLYLTVSY | VDRFLSAKPL | NRQRLQLVGV | SAMLIASRKY | 186 |
| SEQ_ID_NO_1378 | VQVHYKFELS | PETLYLTIN | VDRYLASKTT | SRRELQLLGM | SSMLIAS-KY | 277 |
| SEQ_ID_NO_1377 | LEVHRKFELM | PESLYLTIN | LDRFLSMKTV | PRKELQLVGI | SAMLIAC-KY | 261 |
| SEQ_ID_NO_1379 | TEVHRKFELM | PETLYLTIN | VDRYLSMNAV | PRRELQLVGI | SSMLIAC-KY | 266 |
| SEQ_ID_NO_1380 | VEVHYKFELM | EETLYLTVN | DRFLSRQAV | VRKKLQLVGV | TAMLLAC-KY | 238 |
| SEQ_ID_NO_1383 | VEVHLKFKLM | PETLFLTTN | DRFLELKTV | TRRNLQLVGV | TAMLVAS-KY | 188 |

Figure 45 (continued)

| | | | | | | | |
|---|---|---|---|---|---|---|---|
| SEQ_ID_NO_1363 | EEVCAPQVEE | FCYITDNTYL | KDEVLDMESA | VLNYLKFEMS | APTVKCFLRR | 297 |
| SEQ_ID_NO_1373 | EEISPPHVED | FCYITDNTYT | REEVVNMERD | LLSFLNFEIS | SPTTITFLRI | 253 |
| SEQ_ID_NO_1342 | EEISPPHPED | FCYITDNTYT | KEELLKMESD | ILKLLKFELG | NPTIKTFLRR | 217 |
| SEQ_ID_NO_1381 | EEISPPHVED | FCYITDNTYT | RQEVVKMESD | LKLLEFEMG | NPTIKTFLRR | 257 |
| SEQ_ID_NO_1382 | EEISPPHVED | FCYITDNTYT | RQEVVKMESD | LKLLEFEMG | NPTIKTFLRR | 257 |
| SEQ_ID_NO_1371 | EEIKPKNVAD | FVDITDNTYS | QQEVVKMEAD | LLKTLKFEMG | SPTVKTFL-G | 215 |
| SEQ_ID_NO_1365 | EEIKPPEVED | FCYITDNTYS | KEEVVNMEAE | ILKALKFELG | GPTVKTFLRR | 234 |
| SEQ_ID_NO_1370 | EEIKPPEVED | FCYITDNTYS | KEEVLSMEAE | LKTLKFELG | GPTIKTFLRR | 224 |
| SEQ_ID_NO_1346 | EEINPPHVED | FCYITDNTYT | KEEVVKMEAD | LKSLKFEMG | NPTIKTFLRR | 234 |
| SEQ_ID_NO_1372 | EEISPPHVED | FCYITDNTYK | KEEVVKMEAD | VLKFLKFEMG | NPTIKTFLRR | 246 |
| SEQ_ID_NO_1374 | EEISPPHVED | FCYITDNTYT | KEEVVKMEAD | VLKTLNFEMG | NPTVKTFLRR | 255 |
| SEQ_ID_NO_1355 | EEITPPNVDD | FCYITDNTYT | KQEIVKMEAD | LLALQFELG | NPTSNTFLRR | 227 |
| SEQ_ID_NO_1364 | EEISPPKVED | FMYITDNTFT | RQDVVSMEAD | LLALQFELG | CPTIKTFLRR | 236 |
| SEQ_ID_NO_1378 | EEIWAPEVND | LVCISDGSYS | NEQVLRMEKK | LGALEWYLT | VPTPYVFLVR | 327 |
| SEQ_ID_NO_1377 | EEIWAPEVND | FNHISDNMYT | RDHILQMEKA | LGKLEWYLT | VPTPYVFLVR | 311 |
| SEQ_ID_NO_1379 | EEIWAPEVSD | FIVISDNAYV | REQILIMEKA | LGKLEWYLT | VPTPYVFLVR | 316 |
| SEQ_ID_NO_1380 | EEVSVPVVDD | LVTISDRAYT | RKEVLDMEKS | IVKTLQFNTS | VPTPFVFLRR | 288 |
| SEQ_ID_NO_1383 | EEIWAPEVRD | FMYISDRAYT | RQQILEMEKQ | MLNTLGFHLT | VPTPYCFLNR | 238 |

| | | | | | | | |
|---|---|---|---|---|---|---|---|
| SEQ_ID_NO_1363 | LF-SGCPRVH | EAPCMQLECM | ASYIAELSLL | EY-TMLSHPP | SLVAASAIFL | 345 |
| SEQ_ID_NO_1373 | FL-KAAQDNL | SFLTLQFEFL | SCYLAELSLL | DY-SCVRFLP | SMTAASAIFL | 301 |
| SEQ_ID_NO_1342 | FI-RSAHEDK | KGSILLMEFL | GSYLAELSLL | DY-GCLRFLP | SVVAASVMFV | 265 |
| SEQ_ID_NO_1381 | FT-RSCQEDK | KRSSLLLEFM | GSYLAELSLL | DY-SCLRFLP | SVVAASVVFV | 305 |
| SEQ_ID_NO_1382 | FT-RSCQEDK | KRSSLLLEFM | GSYLAELSLL | DY-GCLRFLP | SVVAASVVFV | 305 |
| SEQ_ID_NO_1371 | FI-RAVQENP | DVPKLKFEFL | ANYLAELSLL | DY-GCLEFVP | SLIAASVTFL | 263 |
| SEQ_ID_NO_1366 | FS-RVGQEGV | DTSDLQFEFL | SCYLAELSLL | DY-NCIKFLP | SLVAASVVFL | 282 |
| SEQ_ID_NO_1370 | FITKVGQEGV | DASELQFEFL | CCYLAELSLL | DY-NCVKFLP | SMVAASVVFL | 273 |
| SEQ_ID_NO_1346 | FT-RVALEDY | KTSNLQLEFL | GFYLAELSLL | DY-NCVKFLP | SLVAASVIFL | 282 |
| SEQ_ID_NO_1372 | LT-RVVQDGD | KNPNLQFEFL | GYYLAELSLL | DY-GCVKFLP | SLIASSVIFL | 294 |
| SEQ_ID_NO_1374 | FT-GVAQEDY | KTPNLQLEFL | GYYLAELSIL | DY-SCVKYVP | SLLAAAVVFL | 303 |
| SEQ_ID_NO_1355 | FT-RMAQEDF | EMSHLQMEFL | CSYLSELSML | DY-QSVKFLP | STVAASAVFL | 275 |
| SEQ_ID_NO_1364 | FT-RMAQEDF | NESLLQIECL | CCYLSELSLL | DY-SCVKFLP | SMLAASAVFL | 284 |
| SEQ_ID_NO_1378 | FI-KASLPDS | DI---VEKNM | VYFLAELGMM | NYATIIMYCP | SMIAAAAVYA | 372 |
| SEQ_ID_NO_1377 | YI-KAAMPSD | DQ---EIQNM | AFFFAELGLM | NYTTTISYCP | SMLAASAVYA | 357 |
| SEQ_ID_NO_1379 | FI-KASVPSN | DHRE-EMENM | VFFLAELGLM | HYPTIILYCP | SMIAASAVYA | 364 |
| SEQ_ID_NO_1380 | FL-KAAGSEK | K----LELL | SSFIIELSLV | EY-QMLKFQP | SLLAAAAIYT | 331 |
| SEQ_ID_NO_1383 | FF-KAAGGDR | Q----FQLY | ASYAVECALP | EY-GMLKYSG | STLAAGVYI | 281 |

Figure 45 (continued)

| | | | | | | |
|---|---|---|---|---|---|---|
| SEQ_ID_NO_1363 | AKYTLDPTRR | PWNSTLRHYT | QYEAMELRGC | VMDLQRLCSN | AHV---STLP | 392 |
| SEQ_ID_NO_1373 | SRFTVLPEVC | PWTLALQQCT | GYKPSELKDC | VLVIHELQSS | LME---ATGR | 348 |
| SEQ_ID_NO_1342 | ARLTIDPNTN | PWNTKLQKMT | GYKVSELKDC | VAIHDLQLN | RKC---PSLT | 312 |
| SEQ_ID_NO_1381 | AKLNIDPYTN | PWSKKMQKLT | GYKVSELKDC | LAIHDLQLR | KKC---SNLT | 352 |
| SEQ_ID_NO_1382 | AKLNIDPYTN | PWSKKMQKLT | GYKVSELKDC | LAIHDLQLR | KKC---SNLT | 352 |
| SEQ_ID_NO_1371 | ARFTIRPNVN | PWSIALQKCS | GYKSKDLKEC | VLLLHDLQMG | RRG---GSLS | 310 |
| SEQ_ID_NO_1366 | ARFMFSTKTH | PWNSALHQLT | RYKPADLKEC | VLNLHDLYLS | RRG---ASLQ | 329 |
| SEQ_ID_NO_1370 | ARFMLNPKSR | PWNSAICQFT | SYKPADLKEC | VLNMHDLYLS | RKG---ATLQ | 320 |
| SEQ_ID_NO_1346 | TRFLMRPKTN | PWSSTLQQYT | GYKAADLREC | VLIIHDLYLS | RRG---GGLQ | 329 |
| SEQ_ID_NO_1372 | SRFTLQPKVH | PWNSLLQHNS | GYKPADLKEC | VLIIHDLQLS | KRG---SSLV | 341 |
| SEQ_ID_NO_1374 | SRFTLQPNTH | PWSLALQQYS | GYKAADLKEC | LILHDLQLS | RRG---GSLA | 350 |
| SEQ_ID_NO_1355 | ARFIIRPKQH | PWNVMLEEYT | RYKAGDLKEC | VAMIHDLYLS | RKC---GALE | 322 |
| SEQ_ID_NO_1364 | ARFIIRPKQR | PWNQMLEEYT | KYKASDLGQP | VGIIHDLYLS | RRG---NSLE | 331 |
| SEQ_ID_NO_1378 | ARCTLNKMPI | -WNETLRMHT | GFSEVQLMDC | AKLLDFHGG | STD---QKLQ | 418 |
| SEQ_ID_NO_1377 | ARGTLNKGPL | -WTPTLQHHT | GYSEEQLMEC | TKQLVSYHKG | AAE---SKLK | 403 |
| SEQ_ID_NO_1379 | ARCTLNSNPL | -WTETLKHHT | GYSEDQLGDC | AKMLARFHSD | GGGVEKSKLK | 413 |
| SEQ_ID_NO_1380 | AQCSLKGFKF | -WTRTCEQYT | MYTEDQLLEC | SKMMVGFHRN | AGS---GKLT | 377 |
| SEQ_ID_NO_1383 | AIRGLQTGS- | -WNHTMEAHT | RLSESEVYPC | ACDMAELMRK | APT---ATLT | 326 |

| | | | | | |
|---|---|---|---|---|---|
| SEQ_ID_NO_1363 | AVRDKYSQHK | YKFVAKKFCP | SIIPPDFFK | ---NSLY- | 425 |
| SEQ_ID_NO_1373 | ALREKYMNHK | YKCVAALHPP | -DIPSCFFD | ---DR--- | 378 |
| SEQ_ID_NO_1342 | AIRDKYKQHK | FKCYSLILVP | VVIPTSYFE | ---DLAE- | 345 |
| SEQ_ID_NO_1381 | AIRDKYKQHK | FKCVSTLLPP | VDIPASYLQ | ---DLTE- | 385 |
| SEQ_ID_NO_1382 | AIRDKYKQHK | FKCVSTLLPP | VDIPASYLQ | ---DLTE- | 385 |
| SEQ_ID_NO_1371 | AVRDKYKKHK | FKCVSTLSPA | PEIPESIFN- | ---DV-- | 341 |
| SEQ_ID_NO_1366 | AVREKYKQHK | FKCVATTPSP | PEIPLSFFEF | EGQILRQL | 367 |
| SEQ_ID_NO_1370 | AVRDKYKQHK | FKCVATTPSP | PEISLSFFEF | RGADP--- | 355 |
| SEQ_ID_NO_1346 | AVREKYKQHK | FKCVANMPSP | PELPALYFE | ---EVI-- | 360 |
| SEQ_ID_NO_1372 | AVRDKYKQHK | FKCVSTLTAP | PSIPDEFFE | ---DI--- | 372 |
| SEQ_ID_NO_1374 | AVRDKYKQHK | FKCVSSLTSP | VEIPASFFE | ---DMRQL | 384 |
| SEQ_ID_NO_1355 | AIREKYKQHK | FKCVATMPVS | PELPLTNFE | ---DVNI- | 355 |
| SEQ_ID_NO_1364 | AVRNKYKQHK | FKCVATMPVS | PELPQAFFE | ---DVTIR | 365 |
| SEQ_ID_NO_1378 | GIYRKYSRLE | KGAVALLPQP | LLA------ | -------- | 441 |
| SEQ_ID_NO_1377 | AIYRKFSSPD | RGAVALFPPA | RNLLPTTTT- | ---TTTSS | 437 |
| SEQ_ID_NO_1379 | AVYKKFSSSD | RSSVALFPPA | RSLLLVL--- | -------- | 440 |
| SEQ_ID_NO_1380 | GVHRKYSTSK | FGFAGKSYPA | LFLLDNRL-- | -------- | 405 |
| SEQ_ID_NO_1383 | AVYKKYSSEK | FMKIATLPVP | HDLRL----- | -------- | 351 |

Figure 46

| | | | | | | | |
|---|---|---|---|---|---|---|---|
| SEQ_ID_NO_1404 | -MA------ | ---SEWSKEE | NKLFEQAIAY | YGEGAPDLMH | KVSRAMGGIK | | 39 |
| SEQ_ID_NO_1401 | -MSGSRSSSP | NSKSEWSRKE | NKMFEEALAY | YGEDTPNRWD | KVASAMGGIK | | 49 |
| SEQ_ID_NO_1400 | -MAGSCSSSP | NSNSTWSLKE | NKMFEEALAY | YGESTPNLAD | KVSSAIGGIK | | 49 |
| SEQ_ID_NO_1385 | -MSASRSSSP | NSISQWSQKE | NKMFEEALAY | YGESTSNRWD | KVSRAMGGIK | | 49 |
| SEQ_ID_NO_1407 | -MSASRSSSP | NSMSKWSPKE | NKMFEQALAY | YGESTPNRWD | KVSSAMGGIK | | 49 |
| SEQ_ID_NO_1387 | -MSSSHQTPR | NSSSSWTPRE | NKLFEKALAL | FDKDTPDRWQ | NIAKAVGGVK | | 49 |
| SEQ_ID_NO_1393 | MASSSLSKQK | ASDSSWTPKQ | NKLFEKALAK | YDKDTPDRWQ | NVAKAYGGIK | | 49 |
| SEQ_ID_NO_1390 | MASSSMSSQ- | -SSGSWTAKQ | NKAFEQALAT | YDQDTPNRWQ | NVAKVVGGIK | | 47 |
| SEQ_ID_NO_1395 | --MSSMSSQH | GSSGSWTAKQ | NKAFEKALAV | YDKETRDRWS | NVAKAVGGIK | | 47 |
| SEQ_ID_NO_1398 | MASGSMS--- | ---SSWTAKE | NKMFEKALAV | YDRDTPDRWH | KIARAIGGIK | | 43 |
| SEQ_ID_NO_1396 | -MASTRGSG- | ---RPWSAKE | NKAFERALAV | YDKDTPDRWA | NVARAVEGIR | | 44 |
| SEQ_ID_NO_1394 | MASSSMSAS- | ---GSWSVKE | NKAFERALAV | YDKDTPDRWY | NVAHAVGGIK | | 45 |

| | | | | | | | |
|---|---|---|---|---|---|---|---|
| SEQ_ID_NO_1404 | TADEVRLHFE | LVDDIKLIE | ARRVPFPKYN | TQGAIN---- | ---------- | | 75 |
| SEQ_ID_NO_1401 | SAEEIRCHYE | DLTDDVKTIE | SGRVQFPKYK | TQGYWT---- | ---------- | | 85 |
| SEQ_ID_NO_1400 | SAEEVRCHYE | DLVDDVKMIE | SGRVTYPKYK | TQGFWTRG-- | ---------- | | 87 |
| SEQ_ID_NO_1385 | SAEEVRCHYE | DLDYDVKME | SGHVPYPKYK | THGFWT---- | ---------- | | 85 |
| SEQ_ID_NO_1407 | SAEEVRCHYE | DLDYDVKME | SGHVPYPQYK | TQGFWTRGSL | MPTNYVGSNP | | 99 |
| SEQ_ID_NO_1387 | SAEEMKRHYE | LIEDLKHIE | SGRVPLPNYK | SSRSYSNTNE | EER------- | | 92 |
| SEQ_ID_NO_1393 | SADEVKRHYE | ILEDLRHIE | SGHVPLPKYK | STGSSTNVEE | EERLLKYLKL | | 99 |
| SEQ_ID_NO_1390 | TTEEVKRHYE | LLVQDINSIE | NGHVPFPNYR | TSGGCINGRL | SQEEKRYVLS | | 97 |
| SEQ_ID_NO_1395 | TAEEVKRHYE | LLRDVFFID | NGMVPFPKYK | TTGSSHNSTS | D--------- | | 88 |
| SEQ_ID_NO_1398 | TADEVKRYYD | LLVEDVRRIE | AGQMPYANYR | SSNGRG---- | ---------- | | 79 |
| SEQ_ID_NO_1396 | TPEEVKKHYE | ILVEDIKYIE | SGKVPFPNYR | TTGGNMKTDE | KRFRNLKIR- | | 93 |
| SEQ_ID_NO_1394 | TPEEVKKHYE | LLVEDIKHIE | SGKVPFPNYK | KISVSHEEKR | MRNMSLH--- | | 92 |

| | | |
|---|---|---|
| SEQ_ID_NO_1404 | ---------- | 75 |
| SEQ_ID_NO_1401 | ---------- | 85 |
| SEQ_ID_NO_1400 | ---------- | 87 |
| SEQ_ID_NO_1385 | ---------- | 85 |
| SEQ_ID_NO_1407 | SIMTKISYFQ | 109 |
| SEQ_ID_NO_1387 | ---------- | 92 |
| SEQ_ID_NO_1393 | N--------- | 100 |
| SEQ_ID_NO_1390 | ---------- | 97 |
| SEQ_ID_NO_1395 | ---------- | 88 |
| SEQ_ID_NO_1398 | ---------- | 79 |
| SEQ_ID_NO_1396 | ---------- | 93 |
| SEQ_ID_NO_1394 | ---------- | 92 |

Figure 47

```
SEQ_ID_NO_1419  ---------- -----MSFYL F--------- ---------- --FLFITMPL   14
SEQ_ID_NO_1421  ---------- -----MAC-- F--------- ---------- --RSRSRAAA   12
SEQ_ID_NO_1409  ---------- -----MSQRR F--------- ---------- --EDERAALA   14
SEQ_ID_NO_1425  ---------- -----MADC- ---------- ---------- ---TTMRLAS   11
SEQ_ID_NO_1424  MEPWRWQICL VTPRSFLFQA FVRTGFRAMR VSSASSTPPP PAFAAAAMAV   50
SEQ_ID_NO_1413  ---------- -----MNRRF L--------- ---------- --FVLSSLSF   14
SEQ_ID_NO_1418  ---------- -----MRMEH I--------- ---------- --YKFQHWLF   14
SEQ_ID_NO_1415  MEGELKMRGG DLIRPGRFCI L--------- ---------- --SVATISS    29

SEQ_ID_NO_1419  IVFCDF---- ---------- --EMPSGSST QFHSFHE--- ----------   36
SEQ_ID_NO_1421  VVVVTM---- ---------- -LLLQACSEV SASSSPQF-- ----RKM---   38
SEQ_ID_NO_1409  TVASLL---- ---------- -LILTTAQAA AAAASGRH-- ----LSLPT-   42
SEQ_ID_NO_1425  SMTLIL---- ---------- -LLLVASQAL VVSGESSS-- ----SAM---   37
SEQ_ID_NO_1424  VLLAML---- -------RSD VALAAASSN DDTGLSPLMP PPPPLAAPVP   89
SEQ_ID_NO_1413  AVLFLF---- ---------- -LVALFSGQGK NINGSFGL-- ----KLLR--   42
SEQ_ID_NO_1418  FIGLGY---- ---------L LSLSLSVKAN DFEGSNDR-- ----RSIALK   45
SEQ_ID_NO_1415  LLAVFFEDIY HSSMHASSLV SLLLNPVQTQ SLTELFHL-- ----KAVSEI   73

SEQ_ID_NO_1419  -------DKN GSLTVSEKVE HAH------- ---------- -------YTPR   56
SEQ_ID_NO_1421  ---------- -LVSVNASSM SSS------- ---------- -GG-GGHSAE   58
SEQ_ID_NO_1409  --QKAAAARM NDTSSSDMQV ITP------- ---------- -APLAISTAA   72
SEQ_ID_NO_1425  --QSKTLNMN KLLNISED-- HSP------- ---------- -NG-GRHWMQ   64
SEQ_ID_NO_1424  AAVSPAPATP PAVLSPRKLL RPPGADVVGV GFVSGSGGGG GGGGGGDGVR  139
SEQ_ID_NO_1413  --LRINQGNH TLLTPHRKLL RTA------- ---------- -------LAEPN  68
SEQ_ID_NO_1418  A-RSFVSINE NRTALSRKLL LSP------- ---------- -DI--GDGTN   74
SEQ_ID_NO_1415  GSKKPVFYKE NNTNFARKLL QLP------- ---------- -DA---GSTN  102

SEQ_ID_NO_1419  KFWFHGSCTK -RDISISDSK GST--SGIPQ YLVQIVNTCV SG-------   95
SEQ_ID_NO_1421  PLE-LEECSK -DLLEVFQNN APSMAGGMPT YSVEITNTCI -D-------   97
SEQ_ID_NO_1409  RMG-PDGCSG -EDVAVYQSS ANPLPSGIPA YTVRINVCS GG-------  112
SEQ_ID_NO_1425  RMQ-PDSCSE -QNVVVYQNN AEHLPSGIPT YSVEIINVCT -A-------  103
SEQ_ID_NO_1424  TRRVDDGCAG ADDIAIYQGR ATPLPSGVPA YTVDVMNRCA GGGGGGGDEE 189
SEQ_ID_NO_1413  RIW-GEKCSK -ADIVNQGP TAPLPSGIPT YTVEILNVCV SG-------  108
SEQ_ID_NO_1418  RIG--QDCSK -DDIVLFQGS TNPLPSGVPS YTVEIFNSCV SD-------  113
SEQ_ID_NO_1415  RIG--AACSK -DGIDIVQGS TAPLPNGIPS YTVQILNVCV SG-------  141
```

Figure 47 (continued)

| | | | | | | | |
|---|---|---|---|---|---|---|---|
| SEQ_ID_NO_1419 | CAPYDIHLHC | GWFASARIIN | PKLFKRLSYD | DCLVHGGKPL | TSNQIRFIY | | 145 |
| SEQ_ID_NO_1421 | CAVCDVHIAC | GDFASNDVID | PDKFRRLGFN | DCLVNGGGSI | EPSFPVSFQY | | 147 |
| SEQ_ID_NO_1409 | CTVYDVHVSC | GDFASTELVD | PAKFQRVGFN | DCVVKGGGAL | EPSETVSFQY | | 162 |
| SEQ_ID_NO_1425 | CTVYDVHISC | GEFASAELVD | PSQFQRIGFN | DCLVKGGGRL | GPSEAVSFQY | | 153 |
| SEQ_ID_NO_1424 | CAIAGIHVRC | GWFSSVSLVD | PRVFRRLGHD | DCLLNDGRPL | LAGETVSFEY | | 239 |
| SEQ_ID_NO_1413 | CDISGIHLTC | GWFSSARLIN | PKIFKRLRYN | DCLVNDGKPL | INGGTLSFQY | | 158 |
| SEQ_ID_NO_1418 | CNIAEIHVSC | GWFSSVRLVN | PRVFRRLDYD | DCLVNDGQPL | GPGQSLSFQY | | 163 |
| SEQ_ID_NO_1415 | CSISNIHVSC | GWFSSAKLIN | PSVFRRIYYD | DCLVNDGEPL | GPGETLSFQY | | 191 |

| | | | | |
|---|---|---|---|---|
| SEQ_ID_NO_1419 | SNSFMYPLAE | KSARFC---- | ---------- ---------- ---------- ---------- | 161 |
| SEQ_ID_NO_1421 | GNSFPYPMTV | ASASCDCN-- | ---------- ---------- ---------- ---------- | 165 |
| SEQ_ID_NO_1409 | SNSFSYHLSV | ASVACR---- | ---------- ---------- ---------- ---------- | 178 |
| SEQ_ID_NO_1425 | SNSFAYPLAV | ANVACFHYSI | VWASMIPCLP EHACHTASSV KGLGPRPHA | 202 |
| SEQ_ID_NO_1424 | TNSFPYKLSV | SVATCVVDPA | AP-------- ---------- ---------- ---------- | 261 |
| SEQ_ID_NO_1413 | ANTFLYPLSV | SRVVCS---- | ---------- ---------- ---------- ---------- | 174 |
| SEQ_ID_NO_1418 | ANSFSYPLSV | ASVSCF---- | ---------- ---------- ---------- ---------- | 179 |
| SEQ_ID_NO_1415 | ANSFLYPLSV | SSVACC---- | ---------- ---------- ---------- ---------- | 207 |

Figure 48

```
SEQ_ID_NO_1436              ..........  ..MTRPARFL  ETAATPPQPS  EQ........  ........MLA   23
SEQ_ID_NO_1444              .........M  GVHARAMSWY  TSPPGSPAPG  SAAEA.QHAL  SSSPRGGDTS    40
SEQ_ID_NO_1452              .........M  GVHGRSMGWY  LGPPGSPAPG  SAVAEAQHAL  SSSPGGGDAS    41
SEQ_ID_NO_1428              ..........  ..MHRL..LL  ESHGGGNETS  GSGGG.....  ..DGYTRDMN    29
SEQ_ID_NO_1430  MMQAKTAMVT  TLYHRPHRLL  DTQPNASPS   LPNGS....R  TRNAFANEAN    46
SEQ_ID_NO_1432              ..........  ..MHR..RHL  DTVPLDVAPA  NGN......R  THDSY1NETN    30
SEQ_ID_NO_1439              ..........  ..........  .......MPP  SVGGG....N  TSDTFISDAN    19
SEQ_ID_NO_1442              ..........  ..MRRLSDAG  EATPLVTPA   AAAAAGGTLA  SPAAAGSNAN    37
SEQ_ID_NO_1453              ..........  ..MRRLGDVV  EAPALVLTPA  SMQQA.....  .GGRGSSGA     31
SEQ_ID_NO_1457              ..........  ..MRRLVDVV  EAPALVLTPA  WAATA....S  MQQAGGSSGA    34

SEQ_ID_NO_1436  AESDMVVILS  ALLCALICVA  GLAAVVRCAL  .MLRRFTTGE  NSPSANK...    68
SEQ_ID_NO_1444  FDTNMVVVLA  ALLFALLFAL  GINSLARCLI  RWARRAPAAE  GGGG......    84
SEQ_ID_NO_1452  FDTNMVIILA  ALLFALLFAL  GLNQLARCLI  RWARRASEGE  AGARGG....    87
SEQ_ID_NO_1428  FDANMVIILA  ALLCALILAL  GLNSILRCAM  RCGFGLSSSA  AAGTVADRAL    78
SEQ_ID_NO_1430  FDTNMVIILA  ALLCALICAL  GLNSIMRCTF  RCGRRFGLDA  TEETAARLAA    96
SEQ_ID_NO_1432  FDTNMVIILA  ALLCALIGAL  GLNSIVRCLL  RCSSRFALET  TEEAAARLAA    80
SEQ_ID_NO_1439  FDTNMVIILA  ALLCALICAL  GLNSIARCAL  RCGRPFGNET  AEDAAARLAG    69
SEQ_ID_NO_1442  FDANMVIILA  ALLCVLIFAL  GLNSVIRCVL  HCGRRLAPSS  SLAASATTAR    87
SEQ_ID_NO_1453  LDASMVVILA  ALLCVVICAL  GLTSLIRCAL  HCARGLSPTT  ATPTPSVSTA    81
SEQ_ID_NO_1457  LDANMVIVLA  ALLCVVICSL  GLSSLIRCAL  HCARGLSPSP  AMATPAAATT    84

SEQ_ID_NO_1436  ........G   LKKKALQSLP  RSTFTAAEST  SGTAAEDG..  .GDSTECAI    105
SEQ_ID_NO_1444  ........G   FEKRVLRSMP  VEVY......  GAAAV.....  .TVADVCAI    112
SEQ_ID_NO_1452  ........G   LKRRALRSIP  VEVY......  GACGADGAA   A.VAADVCAI   120
SEQ_ID_NO_1428  ........G   LKKRELKKFP  VAEV......  GSGEVK...   .AATECAI     107
SEQ_ID_NO_1430  AT......G   LKKSALRRLP  VAVY......  GSGMD.....  .WATECPI     126
SEQ_ID_NO_1432  T.......G   LKKRDLRQIP  VAIY......  GAGGS.....  .SATECPI     109
SEQ_ID_NO_1439  TL......G   LKRRELSRIP  VAVY......  GAAGENT..   .PATECPI     100
SEQ_ID_NO_1442  TTTSVHVQAG  LKRKALRKIP  VEVY......  GGAKSSGGA   LPATATECAX   130
SEQ_ID_NO_1453  AT......AG  LKKTELRRIP  VEVY......  GAKQAG...   .VPDGECAI    113
SEQ_ID_NO_1457  TG......G   LKKKELRRIT  VEVY......  GAKQAG...   .VPDAECAI    115
```

Figure 48 (continued)

| | | | | | | | |
|---|---|---|---|---|---|---|---|
| SEQ_ID_NO_1436 | CLSDFADGEE | IRVLPLCGHS | FHVECIDKML | VSRSSCPXCR | XILRPV--X | 152 |
| SEQ_ID_NO_1444 | CLGEFADGEK | VRVLPRCTHG | FHVRCVDTWL | LSHDSCPTCR | ASVLDG---- | 158 |
| SEQ_ID_NO_1452 | CLGEFADGEK | VRVLPRCAHG | FHVRCVDTWL | LSHDSCPTCR | GTVLEAAAPG | 170 |
| SEQ_ID_NO_1428 | CLGEFADGER | VRVLPPCNHS | FHMSCIDTWL | VSHSSCPNCR | HSLIEV--- | 153 |
| SEQ_ID_NO_1430 | CLGEFMGGEK | VRVLPKCNHG | FHVRCIDTWL | LSHSSCPTCR | QSLLDQA--T | 174 |
| SEQ_ID_NO_1432 | CLGEFVDGEK | VRVLPKCNHG | FHVRCIDTWL | LSHSSCPNCR | HSLLEH---T | 156 |
| SEQ_ID_NO_1439 | CLGEFEKGDR | VRMLPKCNHG | FHVRCIDTWL | LSHSSCPNCR | HSLLEK---- | 146 |
| SEQ_ID_NO_1442 | CLGEFADGEK | VRVLPRCHHG | FHVRCIDMML | ATHTSCPNCR | ASLAED---- | 176 |
| SEQ_ID_NO_1453 | CLGDFADGDK | VRVLPRCHHG | FHVRCIDTWL | AAHTSCPTCR | DSILSV--- | 159 |
| SEQ_ID_NO_1457 | CLGDFADGDK | VRVLPRCHHG | FHVGCIDTWL | AAHTSCPTCR | DSILSV--- | 161 |

| | | | | | | |
|---|---|---|---|---|---|---|
| SEQ_ID_NO_1436 | CDRCGHASXA | GSQMKDHQHX | QHXSDLTSXX | XTFXP | 187 |
| SEQ_ID_NO_1444 | --AKAATPAG | GGSRMQGSEA | AAIAVVIR-- | ----- | 184 |
| SEQ_ID_NO_1452 | KDKAAASAPA | GGSRRQGSEA | AAIAVVIG-- | ----- | 198 |
| SEQ_ID_NO_1428 | -------HVA | GSE------- | ---------- | ----- | 159 |
| SEQ_ID_NO_1430 | SSSDGAVEIE | NGIRPHGNSS | GGDQADVPVP | ADEVG | 209 |
| SEQ_ID_NO_1432 | TDSGAAQEVT | GAARPGENDP | GRQARGWP- | -EHGG | 188 |
| SEQ_ID_NO_1439 | ---PAAAPES | GSGRRSEVVV | VVEQAS---- | ----- | 169 |
| SEQ_ID_NO_1442 | ----GAAAAN | GGGR------ | ---------- | ----- | 186 |
| SEQ_ID_NO_1453 | -----HGVVA | GGQT------ | ---------- | ----- | 168 |
| SEQ_ID_NO_1457 | -----HAGVT | GGQT------ | ---------- | ----- | 170 |

Figure 49

| | | | | | | | |
|---|---|---|---|---|---|---|---|
| SEQ_ID_NO_1473 | ----------  | ---MKLVWCP | ETASQAFIAG | VSALSDAEHG | PAGSAG-VAE | 36 |
| SEQ_ID_NO_1474 | ----------  | ----------MASKAYIDG | VRALAG--HD | LAGAAADVAE | | 27 |
| SEQ_ID_NO_1476 | MAPPPPPAAQ | VVRMKLVWCP | EMASKAYIDG | VRALAG--HD | LAGAAADVAE | 48 |
| SEQ_ID_NO_1471 | ---------- | ---MKLAWSP | ERASKAYIDT | VQSCDV--FR | ESG---VAE | 31 |
| SEQ_ID_NO_1463 | ---------- | ---MKLVWSP | ETASDAYIDT | VKSCKS--DK | ESG---VAE | 31 |
| SEQ_ID_NO_1465 | ---------- | ---MKLVWTP | DTALKAYVCN | VKTCED--FK | ESS---VAE | 31 |

| | | | | | | | |
|---|---|---|---|---|---|---|---|
| SEQ_ID_NO_1473 | LVSAMVGGWN | AQLVVEAPEV | SAPDSATMSL | ALAAAAGRTG | GRYARVLPDE | 86 |
| SEQ_ID_NO_1474 | LVSAMAGGWN | ARLVVEAPDS | AAPAAAATSL | ALAAVARRTG | GRYALVLPDR | 77 |
| SEQ_ID_NO_1476 | LVSAMAGGWN | ARLIVEAPDS | AAPAAAATSL | ALAAAARRTG | GRYALVLPDR | 98 |
| SEQ_ID_NO_1471 | FISAMAAGWN | SQLIVETWSQ | GGL--ATSV | GLALARSHTC | GRHVCVVPDE | 79 |
| SEQ_ID_NO_1463 | FLSATAAGWN | ARLIVETWSR | GDP--TTSV | GLAVAATHTG | GRHVCIVPDE | 79 |
| SEQ_ID_NO_1465 | LLSAMAAGWN | AKLIVESWSK | AGP--ATSI | GLAVAAKHTC | GRHVCVVPDE | 79 |

| | | | | | | | |
|---|---|---|---|---|---|---|---|
| SEQ_ID_NO_1473 | DA-------- | ---------- | ----DRAMA | ELEGVDFLVV | DARRRDGAAV | 113 |
| SEQ_ID_NO_1474 | DAAASAAET | -------AEV | VVGEADEAMA | GLHGVDLLVV | DARRRDAAAV | 120 |
| SEQ_ID_NO_1476 | DAAASAAET | -------AEV | VVGEADEAMA | GLHGVDLLVV | DARRRDAAAV | 141 |
| SEQ_ID_NO_1471 | RARSEYAERM | GEAGVT-AEI | VVGEPEEVME | GLVGVDFLVV | DSRRKDFTRV | 128 |
| SEQ_ID_NO_1463 | QSKLEYVLAM | RGFVTTEVVH | VGESVFNTME | EFPGVDFLVV | DSKRREFVRT | 129 |
| SEQ_ID_NO_1465 | GSRSEYVKAM | HGAGMRETEV | LVGEAEEVMA | GLVGVDFLVA | DCRRRDFVRV | 129 |

| | | | | | | | |
|---|---|---|---|---|---|---|---|
| SEQ_ID_NO_1473 | LAAARPGPRG | MVVV-RHGDE | RRPGIKALEA | SMAAGT-RV | VRSVYLPVDK | 160 |
| SEQ_ID_NO_1474 | LRAARPGARG | MVVV-RHGDG | RQRGAKDLAA | SMAAGT-RV | VRSVYLPIGK | 167 |
| SEQ_ID_NO_1476 | LRAARPGARG | MVVVLRHGDG | RQRGAKDLAA | SMAAGT-RV | VRSVYLPIGK | 188 |
| SEQ_ID_NO_1471 | LRLAKLSNKG | AVLLCKNANS | NSKG-FIARS | LVAKGSRRV | VRSAFLPVGK | 177 |
| SEQ_ID_NO_1463 | LRFAKLSNKG | AVLVCKNAMH | RAISGFKMHD | VLKRGT-RV | VRSVFLPVGS | 177 |
| SEQ_ID_NO_1465 | LRFAKLSHKG | AVLACKNAFQ | QSVSGFKMHG | VLERGT-RV | VKTAYLPVGQ | 177 |

| | | | | | | | |
|---|---|---|---|---|---|---|---|
| SEQ_ID_NO_1473 | GVEVLHVGV | GKGPSLQCRR | SRSASSRWIR | HVDHKTGEEH | LFRRP | 204 |
| SEQ_ID_NO_1474 | GVEVLHVGV | GKGPSLQNHR | DRRSTSRWIR | HVDHDTGEEH | VFRRQ | 211 |
| SEQ_ID_NO_1476 | GVEVLHVGV | GKGPSLQNHR | DRRSTSRWIR | HVDHDTGEEH | VFRRQ | 232 |
| SEQ_ID_NO_1471 | GLDMAHVSAS | GIG---N-- | -NSSGHRWIK | HVDQHSGDVH | FIRR- | 213 |
| SEQ_ID_NO_1463 | GLDIVHVGAT | GRG-----D | SRNLRSRWIR | HVDHLSGEEH | LFRR- | 215 |
| SEQ_ID_NO_1465 | GLDMAHIGSN | GIG---DKR | SRGGPSRWIK | HIDRKSGEEH | VFRE- | 216 |

Figure 50

| | | |
|---|---|---|
| SEQ_ID_NO_1493 | MTFLMPSPEV ---STAFAKI FSNPT-PRHK FLKSCAISKN DDEKVWSKTN | 46 |
| SEQ_ID_NO_1503 | MAFLLPKLTT ---PSCKLPP S--PL-LKPQ LAQPVHGGGK IQGSVFGSVA | 44 |
| SEQ_ID_NO_1508 | MAFLLPKLTT PSGPSCKLPP S--PL-LKPQ LAQPGHSGGK IQGSVSGAGA | 47 |
| SEQ_ID_NO_1501 | MAFLLPKLTT ---PPCRSPP P--SP-LKPQ LGLPSHGGGR ----LHGAGS | 40 |
| SEQ_ID_NO_1504 | MAFLLPKLTT ---PSCKSPP S--P--LKSD LGLPGGGKLQ ---------P | 34 |
| SEQ_ID_NO_1505 | MAFLLPKLTT ---PSCKSPP S--P--LKSD LGLPGGGKLQ ---------P | 34 |
| SEQ_ID_NO_1495 | MAFLLPNLS- ---PSLLINS KSFKDREKPV LYQTQTLPSH ---------- | 36 |
| SEQ_ID_NO_1499 | MAFLLPNLSL ---PSFLLQT GKSLK-EKPI STHSLSISSS -----SSSSN | 40 |
| SEQ_ID_NO_1491 | MAFLLSNLSS ---PSIHLQT GKYPN-LKPI FSQSLSSSSS ---------V | 37 |
| | | |
| SEQ_ID_NO_1493 | ARVGVKDVGS TVSGLSQNLR LYVQFSAPVK ------RGS KSSKEEEEKQ | 89 |
| SEQ_ID_NO_1503 | AQVAAPGHLS LLLLLSASQQ AAAP-AAKST ATKNR---- CKGGGDPQRS | 89 |
| SEQ_ID_NO_1508 | AQVAAPGHLS LLLLLSAPQQ AADP-ASKST ATKNR---- CKGGCDPQRS | 91 |
| SEQ_ID_NO_1501 | AQAAAPTHLN LPLLLSASQQ EAIP-TAKSA ETRNRAASGG GGGGDPRRS | 88 |
| SEQ_ID_NO_1504 | AQAVAPSHLN LLLLLGASQQ EAAAVPTPKS RSKNGGGRSG GGGGEDPRRS | 84 |
| SEQ_ID_NO_1505 | AQAVAPSHLN LLLLLGASQQ EAAAVPTPKS RSKNGGGRSG GGGGEDPRRS | 84 |
| SEQ_ID_NO_1495 | -YQTTTTTTS TTTKKPTNTN SSMPPPLQVK T-----PPG AQDKEQHQRD | 79 |
| SEQ_ID_NO_1499 | SYEFEEGSLS LLSLPVQAP- ----PAPGA QVKTM--PSE QDKHQQHGKD | 82 |
| SEQ_ID_NO_1491 | SYEFVEENLS TLSLLSIQS- ---PIPLKDI QVQTR--HSS QDKHNNHDRD | 80 |
| | | |
| SEQ_ID_NO_1493 | DYYVNMGYAI RTLRKELPD- FYRELSFDIY RDDIVFKDPL NTFLGIDNYK | 139 |
| SEQ_ID_NO_1503 | DFYLNLGTAV RTLRDDLPDV FVREPNYDIY REDITFVDPL NTFHGIDNYK | 138 |
| SEQ_ID_NO_1508 | DFYLNLGTAV RTLRDDLPDV FDREPNYDIY REDITFVDPL NTFHGIDNYK | 141 |
| SEQ_ID_NO_1501 | DFYLNLGAAV RALRDDLPAV FLREPNYDIY REDITFVDPL NTFHGIDNYK | 138 |
| SEQ_ID_NO_1504 | DYYLNLGTAV RTLRDDLPAV FVREPNYDIY REDITFVDPL NTFHGIDNYK | 134 |
| SEQ_ID_NO_1505 | DYYLNLGTAV RTLRDDLPAV FVREPNYDIY REDITFVDPL NTFHGIDNYK | 134 |
| SEQ_ID_NO_1495 | EFYVNLGLAV RTLREDLPVL FTEDLNYDIY RDDITFIDPL NTFTGIDNYK | 129 |
| SEQ_ID_NO_1499 | EFYINLGLAI RTLREDLPLL FSKDLNYDIY RDDITLVDPA NTFSGIENYK | 132 |
| SEQ_ID_NO_1491 | EFYINLGVAV RTLREDLPLL FTRDLNYDIY RDDITFVDPM NTFTGMDNYK | 130 |
| | | |
| SEQ_ID_NO_1493 | SFFSAPRFHG RIFFKALWLD VSVWQPMEN VIMVRWIIHG IPRVPWESHG | 189 |
| SEQ_ID_NO_1503 | TIFWALRFHG RLLFREIGLD VSRIWQLTEN SIVVRWELWG TPRVPWESYG | 188 |
| SEQ_ID_NO_1508 | TIFWALRFHG RLLFREIGLD VSRIWQLTET SIVVRWELWG TPRVPWESYG | 191 |
| SEQ_ID_NO_1501 | TIFWALRFHG RLLFSEIGLD VSRIWQLTET SIVVRWELWG TPRVPWESYG | 188 |
| SEQ_ID_NO_1504 | TIFWALRFHG RLLFREIGLD ISRIWQLTEN SIVVRWELWG TPRVPWESYG | 184 |
| SEQ_ID_NO_1505 | TIFWALRFHG RLLFREIGLD ISRIWQLTEN SIVVRWELWG TPRVPWESYG | 184 |
| SEQ_ID_NO_1495 | LIFWALRFHG KMLFREISLE MYRIWQPSEN VLLIRWNLKG VPRVPWEAKG | 179 |
| SEQ_ID_NO_1499 | LIFWALRFHG KILFRDXXXE XYRVWQPSEN MLLIRWNXKG VPRVPWEAKG | 182 |
| SEQ_ID_NO_1491 | IIFWALRFHG KILFRDISLE IFRVWQPSEN MLLIRWNLKG VPRVPWEAKG | 180 |

Figure 50 (continued)

| | | | | | | | | |
|---|---|---|---|---|---|---|---|---|
| SEQ_ID_NO_1493 | RFDGTSEYKL | DKKGKIYEHR | VDNTALNSPP | KF-HMLAVED | LIRSVGCPST | | | 238 |
| SEQ_ID_NO_1503 | CFSGTSRYKV | DRNGKIYEHK | VDNLALDFPR | SVAKVGSIAD | MV-VATP--S | | | 235 |
| SEQ_ID_NO_1508 | CFSGTSRYKV | DRNGKIYEHK | VDNLALDFPR | SVAKVGSIAD | MV-VATP--S | | | 238 |
| SEQ_ID_NO_1501 | CFSGTSRYKV | DRNGKIYEHK | VDNLALDFPR | PAVKVSSITN | LV-VAAYPPS | | | 237 |
| SEQ_ID_NO_1504 | CFSGTSRYKV | DRNGKIYEHK | VDNLALDFPR | PAAKVGSIAD | IV-VATCPPS | | | 233 |
| SEQ_ID_NO_1505 | CFSGTSRYKV | DRNGKIYEHK | VDNLALDFPR | PAAKVGSIAD | IV-VASCPPS | | | 233 |
| SEQ_ID_NO_1495 | EFQGTSRYKL | DRNGKIYEHK | VDNLAFNFPQ | QLKPAASVLD | LV--AACPAS | | | 227 |
| SEQ_ID_NO_1499 | EFQGTSRYKL | DRNGKIYEHK | VDNLAFNFPH | QLKPATSVLD | LV--TACPAS | | | 230 |
| SEQ_ID_NO_1491 | EFQGTSRYKL | DRNGKIYEHK | VDNLAFNFPQ | QLKPAASVLD | LVTASPASS | | | 229 |

| | | | | | | | |
|---|---|---|---|---|---|---|---|
| SEQ_ID_NO_1493 | PRPTY----- | ---------- | ---------F | ELSSASPPEK | NI-----IKP | 259 |
| SEQ_ID_NO_1503 | PNLTF-MNVV | G-TGDGCSWT | KLYEAVLEAV | EREEHSSTGI | GVGALGPVGC | 283 |
| SEQ_ID_NO_1508 | PNLTF-MNVV | G-PGDGCSWT | KLYEAVVEAV | EREEHGSTGI | GVGGL-PVPC | 285 |
| SEQ_ID_NO_1501 | PNPTF-MDVV | G-TGDGCSWT | KLYRAVLETV | EREGDIPAGI | CMEGL--LTC | 283 |
| SEQ_ID_NO_1504 | PNLTF-MDMV | GSTGDGCSWA | NLYQAVVETV | EQEGNDPAGI | AIEGL--LTC | 280 |
| SEQ_ID_NO_1505 | PNLTF-MDMV | GSTGDGCSWA | NLYQAVVETV | EREGNDPAGI | AIEGL--LTC | 280 |
| SEQ_ID_NO_1495 | PNPTFLMGPA | D--VYSSSW | EFYRAVRETL | DXEN---STN | CFCKM-ATC | 270 |
| SEQ_ID_NO_1499 | PNPTFVFGS- | ---SYSSSW | EFYQAVQRTL | DKQQDQI--M | MQDRF--VLC | 272 |
| SEQ_ID_NO_1491 | PNPTFFSPV | D--SYSSSW | KFYQAVRGTL | ETEDMFVTTD | CL----VTC | 272 |

| | | |
|---|---|---|
| SEQ_ID_NO_1493 | P--------- | 260 |
| SEQ_ID_NO_1503 | G----CGCSF | 289 |
| SEQ_ID_NO_1508 | SFGCGCGSSF | 295 |
| SEQ_ID_NO_1501 | S--------- | 284 |
| SEQ_ID_NO_1504 | S--------- | 281 |
| SEQ_ID_NO_1505 | S--------- | 281 |
| SEQ_ID_NO_1495 | S--------- | 271 |
| SEQ_ID_NO_1499 | L--------- | 273 |
| SEQ_ID_NO_1491 | S--------- | 273 |

Figure 51

```
SEQ_ID_NO_1520    MDSLPKLR-- ---------- -HPSPFPTPL SSSLSFRSLP PPHFPSSSFR      37
SEQ_ID_NO_1510    MESLGKLQLH HQPFHLSFTH TSSSTFPKNL -----FKSSI QPISSL--LK      42
SEQ_ID_NO_1512    MESLTKLHCR LQPLHLSFNH QRPSFAKPI SSSVSFRTS- ---SSSSPFK       45
SEQ_ID_NO_1516    MESVAKLHCR HQPFNLSLNP HRPSFPKPI -ISLSFKTPP PSSSSPFKLS       48

SEQ_ID_NO_1520    LPSIRASSSP SQNDPAFRTP RNTPSLPPLL QTLTSFLSPL LETTCIMLA       86
SEQ_ID_NO_1510    SASIKASSSK FQNS---TP LPK------ ST----PFRL FKSTCITLTT       78
SEQ_ID_NO_1512    LTSIRALSSS SSS---SVP LHQTPKPSLL QT----LAPL LKTTCITITA      87
SEQ_ID_NO_1516    STSIRASSSS SSR----TP LN-------- KN----LGTI IKITSITLTA      62

SEQ_ID_NO_1520    AAAFFMRFH HT-PAVIAAP LTSPAAETDT -----AFTQE EAERLLEERL      130
SEQ_ID_NO_1510    AAALLLANLH LKSPAIAAPI APPPSVESKE -----NVTLE EEERALDEHL     123
SEQ_ID_NO_1512    GAALLFMRFH QK-PALAATP TVTPTVEPAQ TDS--NVSLE DOEKTIEEHL     134
SEQ_ID_NO_1516    AAALFFTRLN IK-PAIASPL TASSTVDPTE ESSKENVSYE EQERALQDYL     131

SEQ_ID_NO_1520    STNPRDTEAL HALMEVKIKA RKMDEAFEVL NRLIELEPEE QEWPLLKANM     180
SEQ_ID_NO_1510    ITHPSDVDAL RSLMEVKIKS RKLTEAVEVI DRLIKLEPEE KEWPVLKANI     173
SEQ_ID_NO_1512    TQYPNDVEAL QSLMEVRIKS RKLPQAIEVI DRLIQLEPED TEWPMLRAQI     184
SEQ_ID_NO_1516    SQNPNDIEAL RSLMEVRIKS KKLVEAIEVV DRLIELEPNE DEWPLLKSQI     181

SEQ_ID_NO_1520    HIYNDDHASA RKLFEEILKK DPLRVEAFHG LVMATAQSNE PLKSLLKRVE     230
SEQ_ID_NO_1510    FTYSGDLDLA KTGFEEILAK DPLRVEAYHG LLMAYSDAGL DLKEVESRIE      223
SEQ_ID_NO_1512    HSYSGDFALA KNEFEEILAK DPVRVEAFHG LVMASSESGQ KLKELEKRIE     234
SEQ_ID_NO_1516    YTYSGDFESA KDGFEAILKK DPLRVEAYHG LVMANSESGG SLEVVLKRIE     231

SEQ_ID_NO_1520    EAIEVCKKQK KDSDVRDFRL LIAQIKVMEG DYTEALKAYQ ELVKEEPRDF     280
SEQ_ID_NO_1510    EAMLKCKKEN NQNDFRDFKL LVAQIRVIEG KHSEALKLYQ ELVKEEPRDF     273
SEQ_ID_NO_1512    GAMEKCKKEK KNKDFRDFKL LIAQIRVIEG DHLEALKVYE GLVKEEPRDF     284
SEQ_ID_NO_1516    SAMDKCKKEK KTSDLRDFKL LVAQVRVMEE KYLDALKVYE ELVKEEPRDF     281

SEQ_ID_NO_1520    RPYLCQGIIY TLLRKKDEAD KQFNKFRRLV PKDHPYKDYF EDNMFATKFF     330
SEQ_ID_NO_1510    RPYLCQGIIY TLLKKKDKAE EQFDNFRKLV PKNHPYREYF MDNMIATKLF     323
SEQ_ID_NO_1512    RPYLCMGIIY SLMKKKDEAE KHFEKVRKLV PRNHPYREYF VDNMWATKLF     334
SEQ_ID_NO_1516    RPYLCQGIIY TLLRKKDEAE KKFEQFKKLV PKNHPYREYL VDNMFATKFF     331
```

Figure 51 (continued)

```
SEQ_ID_NO_1520      SQKLEREGA---GARG     343
SEQ_ID_NO_1510      SEKAQRENAE EMAGSTS   340
SEQ_ID_NO_1512      SERAEREGA-------     343
SEQ_ID_NO_1516      SDKVERERS-------     340
```

Figure 52

| | | | | | | | |
|---|---|---|---|---|---|---|---|
| SEQ_ID_NO_1525 | ---------- | MAFPQRKRTP | SFSSSVLDSV | YRSIDESDG | LQSDLKGS | N | 39 |
| SEQ_ID_NO_1535 | ---------- | MALPQRQRTQ | SFSSSVLDSI | YRSIDESDG | LQSDLRGT | N | 39 |
| SEQ_ID_NO_1527 | MYKKERSSRE | STFHPRRRTP | SFSSTLLDSI | YRSIDESNG | -EEQHVLGI | K | 48 |
| SEQ_ID_NO_1534 | MHERSMKEAA | GTCPQRRRTP | SFSSSLLDAI | YRSIDESKSN | LHDDQLGLH | | 50 |

| | | | | | | |
|---|---|---|---|---|---|---|
| SEQ_ID_NO_1525 | EN----VSS | SSSSPSPNKK | DDKLTTLRRA | MDEEHWLYA | RSS------ | 77 |
| SEQ_ID_NO_1535 | SNNNENVSSS | SSSSPSPNKK | DDKLTTLRRA | MDEEHWLYG | RSS---TTT | 85 |
| SEQ_ID_NO_1527 | KQSCNSVSTT | RRDTSFLEEE | KEVSTTLRRA | VR-TESWMEK | KST-RGSMQ | 95 |
| SEQ_ID_NO_1534 | HHD---QTT | HSFTSEKGGK | KERMNLRRA | VMLEDWMEK | HGSHSLNAQL | 94 |

| | | | | | | |
|---|---|---|---|---|---|---|
| SEQ_ID_NO_1525 | ·TTTTNSSDS | SS-------- | --FSSSEAES | -----YRTKR | RLRKLAEQGK | 111 |
| SEQ_ID_NO_1535 | TTTTTNSSDS | SA-------- | --FSSSEAES | -----FRTKR | RLRKLAEQGN | 120 |
| SEQ_ID_NO_1527 | YNSTSSSSDS | SSAGGGGSGG | GVFSSSENES | ------SVR | GNSSSCQQRT | 138 |
| SEQ_ID_NO_1534 | LNSSSSSSED | SSA-----G | GIFSSSETDT | TTTLTLKKQR | PARLTSEKKK | 138 |

| | | | | | | |
|---|---|---|---|---|---|---|
| SEQ_ID_NO_1525 | RSGDERQRTK | RTVMDNDSRL | FSKSDDDKKP | KAVKIEEL | KRSKQPVSPG | 160 |
| SEQ_ID_NO_1535 | RLGEERQRT | ---------- | --KSDDDIKV | KAVKMFEEL | KRSKQPVSPG | 156 |
| SEQ_ID_NO_1527 | KPLSDKPHQK | PKCEG----- | --GGFHKTKL | RALKIYGEL | KKVKQPISPG | 180 |
| SEQ_ID_NO_1534 | KKQDRIMSSE | KQNKE----- | --SGFTRTKL | RALKIYGELN | QRVKQPISPG | 181 |

| | | | | | | |
|---|---|---|---|---|---|---|
| SEQ_ID_NO_1525 | ARLTSFLNSI | FQSN-·AKKV | KLCSVGKTTD | VK------ | ------SSS | 193 |
| SEQ_ID_NO_1535 | ARLTSFLNSI | FQSN-·AKKV | KFCSVGKTTD | VK------ | ------SSSS | 190 |
| SEQ_ID_NO_1527 | GRIASFLNSI | FNSASAAKKV | KMCSIGAMDD | VSFERKSKSA | CSSA-TSFS | 228 |
| SEQ_ID_NO_1534 | SRIASFLSSI | FNSON-VKKA | KMCYAGAVED | VSFEHKSNGP | CFSSPSSFS | 230 |

| | | | | | | |
|---|---|---|---|---|---|---|
| SEQ_ID_NO_1525 | SKSCFSRTRN | KTDNNNNNC- | --KKLERSIR | FYPVRVTIDG | DCRDYAQKH | 239 |
| SEQ_ID_NO_1535 | SRSCFSRTRN | KTNNNNNNNN | NFKKLERSIR | FYPVRVTIDG | DCRDYAHKN | 239 |
| SEQ_ID_NO_1527 | -RSCLSKTPP | PRGKPSNG-- | ----TKRSVR | FYPVGVIVDE | DSRPCGHKS- | 270 |
| SEQ_ID_NO_1534 | RRSCMSKTPS | SAKKSNNNE- | ----VKRSVR | FYPVSVILGE | DSEPQSSYHK | 275 |

| | | | | | | |
|---|---|---|---|---|---|---|
| SEQ_ID_NO_1525 | ---TRVRK- | --PIPEFTAK | -KSVKE---· | EIKTNDHHTE | FTCITRNI- | 276 |
| SEQ_ID_NO_1535 | ---TR---- | --PIPTKVHQ | TELMKE---· | EIKTVHQTE | LTCITRK- | 274 |
| SEQ_ID_NO_1527 | ---YEDDPG | LMPTPRKVVK | SSSVKELEVA | KGAAADYLRS | YH-QRKNV- | 314 |
| SEQ_ID_NO_1534 | CNILYE--- | --SEPNLGVR | SSSIKELKKN | TARGNENGAE | EAAARGFVKG | 319 |

Figure 52 (continued)

```
SEQ_ID_NO_1525       ------GLKD FVRSNKY EG KEEEGDAWSH SSSDLFELDS YRIGMGRYLK    319
SEQ_ID_NO_1535       ------GLKD YVRSSNI DEG KEEEDDVWSY SSSDLFELDH YRIGMGRYLK    318
SEQ_ID_NO_1527       ------SEFD FRGFHNYVAD DSDSDDEF SC TSSDLFELDH LF GIGRYRE      356
SEQ_ID_NO_1534       YRNSGQSEFD FRGF--YDDD DEDDDDDVSC SSSDLFELDH LF GAARYDE       366

SEQ_ID_NO_1525       ELPVYETTDF KTNQAIARSL LL    341
SEQ_ID_NO_1535       ELPVYETTDF KENQAIARGL LL    340
SEQ_ID_NO_1527       ELPVYETTNF KTNQAIANGF FP    378
SEQ_ID_NO_1534       ELPVYETTNL ETNKAIASGL CL    388
```

Figure 53

```
SEQ_ID_NO_1550    MDMNESSEKG ME----GNGS SGPGGGI PVE MQSQFS---G GGFS-A---    38
SEQ_ID_NO_1552    MYSGQQSDQC PS----ANS- ---------- -------G REFSEA---    22
SEQ_ID_NO_1537    MLEGLVSQES LSLNS-MDMS VLER----LK WVQQQDQLQ QVVSHS---    41
SEQ_ID_NO_1543    MLESLVSLES MSLSS-MDVS VLER----LK WLQQQ----Q QQVLST---    37
SEQ_ID_NO_1545    MLGYANPSGN LAVD--GDMT VLERQRARMK WQEEQEYFSG NSFNGV----   44
SEQ_ID_NO_1539    MLHC------ ------TDIT VLERQRACIK WQQEQQQQQQ VQLQQQEISY   38
SEQ_ID_NO_1548    MLHCLNTSGN LVGGIISDMT VLERQRARKK FQHEHQD-Q QFFMVG----   45

SEQ_ID_NO_1550    HQHQQHPHMM DSFGSGMWS- --------AA SQHGAGFLAP VPGFLPPPGL   79
SEQ_ID_NO_1552    NRNTVTMHQK MGYNSG---- ---------- ---------- ------PYGF   42
SEQ_ID_NO_1537    SNNSPELLQ LGFHGSN--- --------ND ELLESSFSQF Q---MLGSGF    77
SEQ_ID_NO_1543    TNASPELLQF HGTN------ --------ND ELLQNTFSHF Q---MLRSGF   70
SEQ_ID_NO_1545    FSSSSSLHVP DSIMVAADS- ---------G CALAEVVAQA QPRSINKPSA   84
SEQ_ID_NO_1539    FTELTGVFQQ AGFHEGGLSE VVTRSVKPDP GLVDNGAWND H---VVGLGV   85
SEQ_ID_NO_1548    CDSALGEVVA NSMKPG---- ---------- ---------- ----------   61

SEQ_ID_NO_1550    GGHFPVDSG- -FIE----RA ARSSCFVGPG AGGGMVGAGA FGGAGDQQMG   123
SEQ_ID_NO_1552    GP---YNKG -LEE----RP GLYQSSSGTF SQNIQM--- ---------S    70
SEQ_ID_NO_1537    GPNYNMGFGP PHES----IS RTSSCHMEPV DTMEVL--- ------LKTG   113
SEQ_ID_NO_1543    GPNYSMGFGP SHEAMDGC-S ITNSCQMDQA DTVGVM--- ------LKNS   110
SEQ_ID_NO_1545    AP------G- -LHANSSS-S RTFSCPPALV DPEPKPT--- ---------D   114
SEQ_ID_NO_1539    GPLYDNGSG- -FELNYGA-S RISSCPPAAV AAVAAATVKG SESVVSDK S   133
SEQ_ID_NO_1548    ------DLG- -FEN------ ---------- ---------- ----------    87

SEQ_ID_NO_1550    SAFGEGYLDH RRKEGGDKAE PELAGSGGVP SSEAAGGDCS SKGSDSKKRR   173
SEQ_ID_NO_1552    DEHSGGVKKR KGMD------ ---------- ------DCV AMLQNAGDQQ    97
SEQ_ID_NO_1537    EETRAVALKN KRKP------ ---------- ------EVK TREEQKTEKK   140
SEQ_ID_NO_1543    EENITISLKN KRKS------ ---------- ------EVK TREEEKTEKK   137
SEQ_ID_NO_1545    SSIGKDSFKK RKTD------ ---------- -KPHN-PKV VAENENKDKR   145
SEQ_ID_NO_1539    SGVGRESSKK RKVD------ ---------- -NKQNNSKV DAEEDTRDKR   165
SEQ_ID_NO_1548    ---VEFTVKK RKAD------ ---------- ------H KVDMKSKDKR    89
```

Figure 53 (continued)

```
SEQ_ID_NO_1550      RPSEVMGGDQ VQSSNVAADS ANESAQSKDK GEESSPATGT TTGGKSKGKG   223
SEQ_ID_NO_1552      ----TEGSSQ PE-------- ----RNSLEG NRKISPKMQS ---KEDSSDG   128
SEQ_ID_NO_1537      ----IKVEAE TESSMK---- ----GKSNMG NTEASSDTSK ---ETSKGAS   175
SEQ_ID_NO_1543      ----IKVEAE TELNMK---- ----VKSNLS NTEASSETSK ---QKSKAAS   172
SEQ_ID_NO_1545      ----IKVGAD DGESKITKCN T---INTNTN NKETCTDTSN ---SKQNSKA   185
SEQ_ID_NO_1539      ----IKGCAE EGESKITEKN NNKNSRNNNT NKNNNSNKES SA-GNSKDNS   210
SEQ_ID_NO_1548      ----IKVSVE EGESKITEQI KGN-KNTKLK NRENCDDVGS ----KENSKG   130

SEQ_ID_NO_1550      AKESSEKEDY HVRARRGQA  TNSHSLAERL RREKISERMK LLQDLVPGCS   273
SEQ_ID_NO_1552      DG---TKEDY VHVRAKQGQA TNSHSLAERL RRKKISERMK LLQDLVPGCS   175
SEQ_ID_NO_1537      EN---QKLDY HVRARRGQA  TDRHSLAERA RREKISKKMK YLQDIVPGCN   222
SEQ_ID_NO_1543      EN---QKLDY HVRARRGQA  TDRHSLAERA RREKISKKMK YLQDLVPGCN   219
SEQ_ID_NO_1545      S----EKPDY HVRARRGQA  TDSHSLAERV RREKISERMK YLQDLVPGCN   231
SEQ_ID_NO_1539      KVTEVQKPDY HVRARRGQA  TDSHSLAERV RREKISERMK YLQDLVPGCN   260
SEQ_ID_NO_1548      SEIQNHKPDY HVRARRGQA  TDSHSLAERV RREKISERMK YLQDLVPGCN   180

SEQ_ID_NO_1550      KVTGKAVMLD EIINYVQSLQ RQVEFLSMKL ATVNPRLDLN IEGLLSKDLL   323
SEQ_ID_NO_1552      KITGKAVMLD EIINYVQSLQ RQVEFLSMKL ATVNPELSFD IEDILSKQMM   225
SEQ_ID_NO_1537      KVTGKAGMLD EIINYVQCLQ RQVEFLSMKL AVLNPELELA VEDVSVKQAY   272
SEQ_ID_NO_1543      KVTGRAGMLD EIINYVQSLQ RQVEFLSMKL AVLNPELELA MEDLSVKQLF   268
SEQ_ID_NO_1545      KVTGKAGMLD EIINYVQSLQ RQVEFLSMKL AAVNPRLDFS MDDLFDKDVF   281
SEQ_ID_NO_1539      KITGKAGMLD EIINYVQSLQ RQVEFLSMKL AAVNPRLDFN FDNLFAREAF   310
SEQ_ID_NO_1548      KIAGKAGMLD EIINYVQSLQ RQVEFLSMKL AAVNPRLDFN IDELFAKEVF   230

SEQ_ID_NO_1550      RF-------- ---PGVSSSS MGFSPEMMHP QLQLSQPGLM QGGAAAMANS   362
SEQ_ID_NO_1552      LSQDRHFAFY GVDPGSSSLA SQFSDGIMQP QM-------- --MCNISNPA   265
SEQ_ID_NO_1537      FTNV------ --------VA SKQSIMVDVP LFPLDQQGSL --DLSAINPN   306
SEQ_ID_NO_1543      QAYFTNLPVV --------VA SKPSLMVDAP LFPLDQQGSL --DLSVINPN   308
SEQ_ID_NO_1545      PTCAANFPNI GMSSTSSDIT NPAYLPFNSP QQIFQYDGL- --DTGINPSD   328
SEQ_ID_NO_1539      PACSVNFPTI GM---SSDMT NPAYLDFNPA QQQLVTCCGL --DMGTDPPD   355
SEQ_ID_NO_1548      TQNFQMM--- -----QSEMS NPAYLDFNSA QQQVSCCGGL INNMGILPPE   272
```

Figure 53 (continued)

| | | | | | | | |
|---|---|---|---|---|---|---|---|
| SEQ_ID_NO_1550 | DVFRRIMDAD | ········L | GAKDCSHSQM | AHALNGPFSD | HVAQMAYPSM | | 403 |
| SEQ_ID_NO_1552 | DVLQGTIHDV | ···· | ····STMNQI | PAMAEG-LQN | -LPQNNFNPG | | 299 |
| SEQ_ID_NO_1537 | QT········ | ·········· | ····TSIEAP | SGSWETQSQS | -LYN····· | | 327 |
| SEQ_ID_NO_1543 | QA········ | ·········· | ····TTIEAP | SASWETQSQS | -LYN····· | | 329 |
| SEQ_ID_NO_1545 | YGLRRTISAP | VS--MPETYL | QSSCFTQMLP | SSTWEGDFQN | -LCNFDVDQA | | 375 |
| SEQ_ID_NO_1539 | MGLKRTTSSP | ES--IPETFL | DSSCFTQAHP | PPAWDADLQN | -LYNVAFDQG | | 402 |
| SEQ_ID_NO_1548 | IGVRRNINAP | ASASLPEIFL | DPSCFTHILP | SSTWEGDFQN | -LHSVDFDQG | | 321 |

| | | | | |
|---|---|---|---|---|
| SEQ_ID_NO_1550 | GSSHSHSQDL | S·······L | RPSQDAYQM | 424 |
| SEQ_ID_NO_1552 | VAADSSANN· | ·········· | -SGSMKIED | 316 |
| SEQ_ID_NO_1537 | ·········· | ·········· | -TSSLGFHY | 335 |
| SEQ_ID_NO_1543 | ·········· | ·········· | -TSSLGFDY | 337 |
| SEQ_ID_NO_1545 | RATSFPSQLL | SGL·····V | EASNLKMEM | 398 |
| SEQ_ID_NO_1539 | RQTSFPTQPF | TGKIKLSCS | EASNLKMEM | 431 |
| SEQ_ID_NO_1548 | RSTSFPSQPF | TGM······ | EASNLKMEM | 344 |

Figure 54

```
SEQ_ID_NO_1571   MAVEAVS...   ......GNGG  EAVAPAPA..  ..........  ..........    19
SEQ_ID_NO_1567   MAEEPQ...    ......PQAA  AAPAAAAT.   ..........  .EVVMAEKAP    27
SEQ_ID_NO_1572   MAEEPQ...    ......PEAA  PAAVAATT.   ..........  .EVAMAEKAP    27
SEQ_ID_NO_1574   MAEEPQ...    ......PEAA  PAAVAATT.   ..........  .EVAMAEKAP    27
SEQ_ID_NO_1555   MAEETDK...   ......PAAA  EAPTSTQP.   ..........  YPEEPAVVPP    29
SEQ_ID_NO_1563   MSQEQDVVVV   TDV...PQAE  KTAPVPPT.   ..........  MPVVMEKEPP    35
SEQ_ID_NO_1575   MAEEPQK...   ......PTEQ  VATTPATS.   ..........  .ETTLEKTPP    28
SEQ_ID_NO_1554   MAEEPTTTTL   VTPEKLPSPS  LTPSEVSEST  QDALPTETET  LEKVTETNPP    50
SEQ_ID_NO_1565   MAQNDSN...   ......PTPP  PEPHVAAE.   ..........  ..........P   20

SEQ_ID_NO_1571   ..........   ..........  PV  KEVSAK.    ..........  ....VEAKEA    33
SEQ_ID_NO_1567   ..AEVEKKAE   E.....PA    AEAEAE.     ..........  .ETAAVADDG    53
SEQ_ID_NO_1572   VEAEKEKKVE   EET...PA    VEAEAK.     ..EEKKDEAA  ...AAGGDEA    63
SEQ_ID_NO_1574   VEAEKEKKVE   EET...PA    VEAEAK.     ..EEKKDEAA  AAAAAGGDEA    66
SEQ_ID_NO_1555   PVPAAEIQLP   DSAPAPPQPE  ASPAKP...   ..DSVAEVAE  DEKPKASEEF    73
SEQ_ID_NO_1563   V........    ..........PV PETEEEPMKP  KQVEEGAVET  QVLKPSGGDD    68
SEQ_ID_NO_1575   PQAEEVVAAA   DADAVVVPPV  VAEETE...   ..KPAEDVKP  ADETAAATDK    72
SEQ_ID_NO_1554   ETADTTTKPE   EETAAEHHPP  TVTETETAST  EKQEVKDEAS  QKEVAEEKKS   100
SEQ_ID_NO_1565   ITEDLVQDKE   EEDDSSKIVI  PVPESE...   ..........  ..........    46

SEQ_ID_NO_1571   AAVTKNASFR   EESNFLDDLK  ESERKALAEL  RDKVEAATLE  GKLFDDGKPE    83
SEQ_ID_NO_1567   GAVEATGSFK   EESNLVADLP  DPEKKALDEF  KELIVAALAA  GEFNLPPPPP   103
SEQ_ID_NO_1572   GAIEGTGSFK   EESNLVADLP  DPEKKALDEF  KQLIAAALAA  CEFNLPPPPP   113
SEQ_ID_NO_1574   GAIEGTGSFK   EESNLVADLP  DPEKKALDEF  KQLIAAALAA  CEFNLPPPPP   116
SEQ_ID_NO_1555   EKISQSVSFK   EESNVVGELP  ESQRKALADL  KVLIQEALNK  HEFTAPPAPL   123
SEQ_ID_NO_1563   EKMPQLVSFK   EESTKVADLL  DSEKKALDEF  KQLVQEALN.  ..........   107
SEQ_ID_NO_1575   KILQ.SVSFK   EETNVVSELP  ESQKKALDEL  KQLIQEALNK  HEFTAPPPPP   121
SEQ_ID_NO_1554   MIPQNLGSFK   EESSKLSDLS  NSEKKSLDEL  KHLVREALDN  HQFTN.....   145
SEQ_ID_NO_1565   ....SLSLK    EDSNRVSD.   .SEKNAIDEL  KKLLKEELED  ..........    78

SEQ_ID_NO_1571   ..........   ..........  VKEKREAKKK  AEKAPEEKKE  EEEEGKKEPE   113
SEQ_ID_NO_1567   PPKAKTEAAA   EETKTEAPAK  EEAKTEEPAK  AEEPAKEEPK  AEEPAKAEAA   153
SEQ_ID_NO_1572   PPKAKVEAAV   EETKA.....  EESKAEEEPK  AEEPAKEEEP  KAEVAAAAAA   158
SEQ_ID_NO_1574   PPKAKVEAAV   EETKA.....  EETKAEEEPK  AEEPAKEEEP  KAEVAAAAAA   161
SEQ_ID_NO_1555   PPK.....E    EEKPA.....  EEKKEDTEKP  AEQPQIDE.P  AKEPVIEEPP   161
SEQ_ID_NO_1563   ..........   ..........  ..........  ..........  ..........   107
SEQ_ID_NO_1575   PTKAVAEVAE   EKKPE.....  EEEKKTEEVV  AEEKKVEEVV  AEEKKVEEAV   166
SEQ_ID_NO_1554   ..........   ..........  ..........  ..........  ..........   145
SEQ_ID_NO_1565   ..........   ..........  ..........  ..........  ..........    78
```

Figure 54 (continued)

```
SEQ_ID_NO_1571    AVEKKGEEDD KKEAEVEGKE EEEESKKEAE KEMEQEE--- ----------   150
SEQ_ID_NO_1567    AAEPAAEEPK AVVA------ ----AEAAAE EPAKEEPK-- ---AEEAKPA   188
SEQ_ID_NO_1572    PPEAGTEEPK AEASSEEAKT EEPKAEAAAD EPAKQESKAE AAPAEEAKPA   208
SEQ_ID_NO_1574    PPEAGTEEPK AEASSEEAKT EEPKAEAAAD EPAKEESKAE AAPAEEAKPA   211
SEQ_ID_NO_1555    KTEAEPEPVT ETVTVKVEET ITPHPAPETS LAPEADFKAA EPSTVVEKVA   211
SEQ_ID_NO_1563    ---------- ---------- ---------- ---------- ----------   107
SEQ_ID_NO_1575    AEEKKVEEVE KKEEEKGSSS EEPKTEAKIE AEPEAKKEFT VLEVVEKIAT   216
SEQ_ID_NO_1554    ---------- ---------- ---------- ---------- ----------   145
SEQ_ID_NO_1565    ---------- ---------- ---------- ---------- ----------   78

SEQ_ID_NO_1571    ---------- ---------- ---------- --AGEAEKVA AAAEEKPAET   168
SEQ_ID_NO_1567    EPKKEEEAVV VAEE--GTKT ------AEPV EEAAAAATTT EQAAAPEPEA   230
SEQ_ID_NO_1572    EPEPEEKTVV VTEEEAATKT VEAIEETVVP AAAAPAAAAT EEAAAPEPEV   258
SEQ_ID_NO_1574    EPEPGGED-- ---------- ------RRGH RGRGGHQDGG SDRGNRRARC   243
SEQ_ID_NO_1555    VIDEDGAKTV EAIEESVVAV ------STPP PEESAPSKEE AEVEVEAAEA   255
SEQ_ID_NO_1563    ---------- ---------- ---------- ---------- ----------   107
SEQ_ID_NO_1575    STEEDGAKTV EAIQESIVSV ------TVTD GEQPVTETVG EAVAVAEVEF   259
SEQ_ID_NO_1554    ---------- ---------- ---------- ---------- ----------   145
SEQ_ID_NO_1565    ---------- ---------- ---------- ---------- ----------   78

SEQ_ID_NO_1571    AAVVVDKDIA LWGVPLLPSK GDEF ATDVVL LKFLRARDFK AGAAFEMLRR   217
SEQ_ID_NO_1567    E-AAAPEPVF IWGVPLV--- GDDERTDAVL LKFLRAREFK VKEAMAMLRS   276
SEQ_ID_NO_1572    QAAAAPEPVL IWGVPLV--- GDDERTDFVL LKFLRAREFK VKEAMAMLRS   305
SEQ_ID_NO_1574    CCACCRRHGG SRGAGTG--- GDDERTDFVL LKFLRAREFK VKEAMAMLRS   290
SEQ_ID_NO_1555    VPPPPPEEVF IWGIPLL--- GDEFRSDVIL LKFLRARDFK VKDAFTMIKN   301
SEQ_ID_NO_1563    ---------- ---------- ----KSDVIL LKFLRARDFK VKDAFTMLKS   133
SEQ_ID_NO_1575    VTPTTPEEVE IWGIPLL--- ADEFRSDVIL LKFLRARDFK VKEAYTMIKQ   305
SEQ_ID_NO_1554    ----TPEEVK IWGIPLL--- EDDFRSDVVL LKFLRAREFK VKDSFAMLKN   187
SEQ_ID_NO_1565    ------EEVS IWGVPLF--- KDDFRTDVIL LKFLRAREFK VKDALVMFQN   118

SEQ_ID_NO_1571    TLRWRRDWPG FDADADADLP -EELAGACVL DGADREGHPV CYNALRVFAD   266
SEQ_ID_NO_1567    AVLWRKRF-G IESLLEADLA FPELEKVVFY RGADREGHPV CYNYYGEFQD   325
SEQ_ID_NO_1572    AVLWRKRF-G IESLLDADLA LPELDSVVFY RGADREGHPV CYNVYGEFQD   354
SEQ_ID_NO_1574    AVLWRKRF-G IESLLDADLA LPELDSVVFY RGADREGHPV CYNVYGEFQD   339
SEQ_ID_NO_1555    TVRWRKQF-D IEALLDEDLG -NQMDKVVFS HGVDREGHPV CYNVFGEFEN   349
SEQ_ID_NO_1563    TIRWRKEF-G DELLEQDLG FDDLGKVVFM HGLDKEGHPV CYNVYGEFQN   182
SEQ_ID_NO_1575    TVLWRKEF-G IEALLQEDLG -TDMDKVVFT DGYDKEGHPV YYNVFGEFEN   353
SEQ_ID_NO_1554    TIKWRKEF-K DELVEEDLV -DDLDKVVFM HGHDREGHPV CYNVFGEFQN   235
SEQ_ID_NO_1565    TLRWRKDF-N DALLDEDLG -DHLEKVVFM HGHGREGHPV CYNVYGEFQN   166
```

Figure 54 (continued)

| SEQ_ID_NO_1571 | DAVYKKAL GT | EEGKARFLRW | RVRAMERHV- | AELDLKP- GG | AASLLQVTDL | 314 |
| SEQ_ID_NO_1567 | KEVYEKAFGD | EEKRERFLKW | RICLLERGL | SQLDFAP- SG | ICSMVQVTDL | 374 |
| SEQ_ID_NO_1572 | KDLYEKAFGD | EEKRERFLKW | RICLLERGL | SQLDFSP- SG | ICSMVQVTDL | 403 |
| SEQ_ID_NO_1574 | KDLYEKAFGD | EEKRERFLKW | RICLLERGL | SQLDFSP- SG | ICSMVQVTDL | 388 |
| SEQ_ID_NO_1555 | KDLYQITFSD | DEKSLKFLRW | RVQFLEKSI- | RKLDFSP- NG | ISTIVQVNDL | 397 |
| SEQ_ID_NO_1563 | KELYKNSFSD | EEKRQRFLRW | RIQFLEKSI- | RTLDFSP- GG | ISTIVQVNDL | 230 |
| SEQ_ID_NO_1575 | KELYQNTFSD | DEKRTKFIRW | RICSLEKSI- | RKLDFTP- SG | ISTIVQVNDL | 401 |
| SEQ_ID_NO_1554 | KELYNKTFSD | EEKRKHFLRT | RIQFLERSI- | RKLDFSS- GG | VSTIFQVNDM | 283 |
| SEQ_ID_NO_1565 | KDLYHKAFSS | QDNRNKFLRW | RICLLERSI- | RHLDFTPSSG | INTIFQVNDL | 215 |

| SEQ_ID_NO_1571 | KNSPGPAKKD | FRVAVKQMLD | LFQDNYPELV | ARNILJNVPF | WYYAFSTLFY | 364 |
| SEQ_ID_NO_1567 | KNSPPMLGKH | -RAVTRQAVA | LLQDNYPEFI | AKKVFINVPW | WYLAANKMMS | 423 |
| SEQ_ID_NO_1572 | KNSPPMLGKH | -RAVTRQAVA | LLQDNYPEFI | AKKVFINVPW | WYLAANKMMS | 452 |
| SEQ_ID_NO_1574 | KNSPPMLGKH | -RAVTRQAVA | LLQDNYPEFI | AKKVFINVPW | WYLAANKMMS | 437 |
| SEQ_ID_NO_1555 | KNSPGLTKME | LRNATKRALQ | LFQDNYPEFA | AKQVFINVPW | WYLAVNRMIS | 447 |
| SEQ_ID_NO_1563 | KNSPGPAKRE | LRQATRQALQ | LLQDNYPEFV | AKQIFINVPW | WYLTVNRMIS | 280 |
| SEQ_ID_NO_1575 | KNSPGLGKKE | LRQATNKALQ | LLQDNYPEFV | AKQVFINVPW | WYLAFSRFLS | 451 |
| SEQ_ID_NO_1554 | KNSPGLGKKE | LRSATKQAVE | LLQDNYPEFV | FKQAFINVPW | WYLVFYTVIG | 333 |
| SEQ_ID_NO_1565 | KNSPGPAKRE | LRLATKQALQ | LLQDNYPEFV | AKQVFINVPW | WYLAFYTMIN | 265 |

| SEQ_ID_NO_1571 | PFLTQRTKSK | FVLARPSKVT | ETLLKYIPIE | AIPVKYGGLK | RDD---DTEF | 411 |
| SEQ_ID_NO_1567 | PFLTQRTKSK | FVFASQAKSP | ETLFRYIAPE | QVPVQFGGLF | KED---DPDF | 470 |
| SEQ_ID_NO_1572 | PFLTQRTKSK | FIFASPAKSA | ETLFRYIAPE | QVPVQFGGLF | KED---DPEF | 499 |
| SEQ_ID_NO_1574 | PFLTQRTKSK | FIFASPAKSA | ETLFRYIAPE | QVPVQFGGLF | KED---DPEF | 484 |
| SEQ_ID_NO_1555 | PFFTQRTKSK | FVFAGPSKTA | ETLFKYVTPE | QVPVQYGGLS | REG---EQEF | 494 |
| SEQ_ID_NO_1563 | PFLTQRTRSK | FVFVGPSKSA | ETLIRYIAAE | QIPVKYGGLS | KDG-----EF | 325 |
| SEQ_ID_NO_1575 | AFLTQRTKSK | FVFAGPSKSA | DTLFKYIAPE | QVPVQYGGLS | REG---EQEF | 498 |
| SEQ_ID_NO_1554 | PFMTPRSKSK | LVFAGPSRSA | ETLFKYISPE | QVPVQYGGLS | VDPCDCNPDF | 383 |
| SEQ_ID_NO_1565 | PFLTSRTKSK | FVFAGPSKSP | DTLFKYIFPE | QVPVQYGGLS | VDFCDCNPDF | 315 |

| SEQ_ID_NO_1571 | SSADDGEVAE | LTVKGSSTET | IEIEAAEADA | TLTMDLIVLG | MEVNYKEEFV | 461 |
| SEQ_ID_NO_1567 | TTSD--SVTE | LTIKASSKET | IEIPVTE-NS | TIVWELRVLG | MEVSHGAEFT | 517 |
| SEQ_ID_NO_1572 | TTSD--AVTE | LTIKPSSKET | VEIPVTE-NS | TIGMELRVLG | MEVSYGAEFT | 546 |
| SEQ_ID_NO_1574 | TTSD--AVTE | LTIKPSSKET | VEIPVTE-NS | TIGMELRVLG | MEVSYGAEFT | 531 |
| SEQ_ID_NO_1555 | SIDD--PVTE | VAIKAATKHT | VEFPISE-PS | LLVWELRVVG | MDVSYGAEFL | 541 |
| SEQ_ID_NO_1563 | GSAD--AVTE | ITVKPAAKHT | VEFPVTE-TC | LLTMEVRVAG | MDVSYSAEFV | 372 |
| SEQ_ID_NO_1575 | TTAD--PATE | VTIKPATKHA | VEFPISE-KS | TLVMEVRVVD | MSVNYGAEFV | 545 |
| SEQ_ID_NO_1554 | SLED--SASE | ITVKPGTKQT | VEIIYE-KC | ELVWEIRVTG | MEVSYKAEFV | 430 |
| SEQ_ID_NO_1565 | TMSD--PVTE | LPIKPTTKQT | VEIALYE-KC | IIVWELRVVG | MEVSYNAEFK | 362 |

Figure 54 (continued)

| | | | | | | | |
|---|---|---|---|---|---|---|---|
| SEQ_ID_NO_1571 | PADEGSYTII | VRKGKKMGAG | EERVLRNSFR | AGEPGKVVLT | VENTSH-KKK | 509 |
| SEQ_ID_NO_1567 | PDAEGAYTVI | VQKTRKVPAN | EEPIMKGSFK | AGEAGKIVLT | VSNAAS-KKK | 566 |
| SEQ_ID_NO_1572 | PDAEGGYTVI | VQKTRKVPAN | EEPIMKGSFK | VGEPGKIVLT | INNPAS-KKK | 595 |
| SEQ_ID_NO_1574 | PDAEGGYTVI | VQKTRKVPAN | EEPIMKGSFK | VGEPGKIVLT | INNPAS-KKK | 580 |
| SEQ_ID_NO_1555 | PSAEGGYTVI | VQKTAKLGPA | DEPVISNSYR | VGEAGKIVLT | IDNLSSKKKK | 591 |
| SEQ_ID_NO_1563 | PSAEDSYTVI | IQKARKVAAT | EEPVVCNSFK | IGEPGKVVLT | IDNSTSKKKK | 422 |
| SEQ_ID_NO_1575 | PSAEDGYTVI | QKNRKVAPA | DETIISNTFK | IGEPGKVILT | IDNQSS-KKK | 594 |
| SEQ_ID_NO_1554 | PEEKDAYTVV | IQKPRKMRPS | DEPVLTHSFK | VNELGKVLLT | VDNPTS-KKK | 479 |
| SEQ_ID_NO_1565 | PDVEDAYTVI | QKATKMSPT | DEPVVSNSFK | VVELGKLLLT | IDNPTL-KKK | 411 |

| | | | |
|---|---|---|---|
| SEQ_ID_NO_1571 | KVLFRHKSKS | AEAKKC----- | 525 |
| SEQ_ID_NO_1567 | KLLYRSKVKC | STGESVEADI P | 587 |
| SEQ_ID_NO_1572 | KLLYRSKVKS | TSESV------ | 610 |
| SEQ_ID_NO_1574 | KLLYRSKVKS | TSESV------ | 595 |
| SEQ_ID_NO_1555 | ILLYRSKTKP | ISD-------- | 604 |
| SEQ_ID_NO_1563 | KLLYRLKTKP | ASSD------- | 436 |
| SEQ_ID_NO_1575 | KLLYRSKTIP | ISE-------- | 607 |
| SEQ_ID_NO_1554 | KLVYRFNVKP | L---------- | 490 |
| SEQ_ID_NO_1565 | RLLYRFKIKP | YSD-------- | 424 |

Figure 55

| SEQ_ID | Part 1 | Part 2 | Part 3 | Part 4 | Part 5 | Part 6 | # |
|---|---|---|---|---|---|---|---|
| SEQ_ID_NO_1578 | ---------- | ---------- | ---------- | ---------- | -MSFYRGTAS | | 9 |
| SEQ_ID_NO_1607 | MADNKDGVTP | KSSAAFPLR- | ---------- | N PNVTLNERNF | AAFTNRSAAA | | 40 |
| SEQ_ID_NO_1440 | MDEEMNAVAE | MNAVASKVKE | EY-------- | R RAPKLNQRII | SSMSRRSVAA | | 43 |
| SEQ_ID_NO_1648 | ----MSEEAA | TETGSSSVK- | ---------- | R TTPKLNERIL | SSLSRRSVAA | | 36 |
| SEQ_ID_NO_1651 | ---MSQENGA | TNGHLAEEQQ | DVWMEVEPKR | RAPRLNERIL | SSLSRRSVAA | | 47 |
| SEQ_ID_NO_1487 | MSSENGENGH | GAADEVVEPY | QQTP-----R | PGPKLNERIL | SSLSRRSVAA | | 45 |
| SEQ_ID_NO_1040 | --MSQEDSTS | AAAQQPTS- | ---------- | R PAPKLNERIL | SSLSRRGGGA | | 38 |
| SEQ_ID_NO_1465 | ---MSEEDTN | AAAGQP---- | ---------- | R RAPKLNERIL | SSLSRRSVAA | | 34 |
| SEQ_ID_NO_1580 | ----MSEEDK | NEAKVLETP- | ---------- | R KPPRLNERIL | SSMSRRSVAA | | 36 |
| SEQ_ID_NO_1623 | --------MS | NENDDLSPQ- | ---------- | R RAPRLNERIL | SSISRRSVAA | | 32 |
| SEQ_ID_NO_1622 | MSEHDDEVQE | VQENVQEIH- | ---------- | R PVPRLNERIL | SSLSRRSVAA | | 40 |
| SEQ_ID_NO_1041 | ----MSDVTK | TQENEVETK- | ---------- | H QAPRLNERIL | SSLSRRTVAA | | 36 |
| SEQ_ID_NO_1590 | ---MSDETKT | QENEVVEAK- | ---------- | R QAPRLNERIL | SSLSRRTVAA | | 37 |
| SEQ_ID_NO_1577 | ---MNGEEVK | TSQPQKKLQ- | ---------- | N PTPRLNERIL | SSLSKRSVAA | | 37 |
| SEQ_ID_NO_1611 | ---MSEEVKE | NQSDKLQ--- | ---------- | R TAPRLNERIL | SSLSRKSVAA | | 35 |
| SEQ_ID_NO_1637 | ---MSEEVKE | NQSGKLQ--- | ---------- | K PTPRLNERIL | SSLSKRSVAA | | 35 |
| SEQ_ID_NO_1627 | -MAPSQEVAA | ATKEPSTNGN | GTQAAAAPKT | KTPALNERIL | SSITRRSVAA | | 49 |
| SEQ_ID_NO_1608 | MAPPLETVQK | VQPPPNAIEP | HVTYHHQH-S | SHPPLNERIL | SSMTRRSIAA | | 49 |
| SEQ_ID_NO_1609 | ---MSPPLES | PAKVAITQH- | ---------S | KPPPLNERII | SSMTRRSVAA | | 37 |
| | | | | | | | |
| SEQ_ID_NO_1578 | HPWHDLHPGN | DAPNFVSCVI | EIPRGSKVKY | ELDKDTGLCF | VDRILYSSVV | | 59 |
| SEQ_ID_NO_1607 | HPWHDLEIGP | EAPAVFNCVV | EISKGGKVKY | ELDKNSGLIK | VDRVLYSSIV | | 90 |
| SEQ_ID_NO_1440 | HPWHDLEIGP | NAPEICNCVV | EIPKGSKVKY | ELDKKTGLIM | VDRILYSSVV | | 93 |
| SEQ_ID_NO_1648 | HPWHDLEIGP | GAPSVVNAVV | EITKGSKVKY | ELDKKTGMIK | VDRVLYSSVV | | 86 |
| SEQ_ID_NO_1651 | HPWHDLEIGP | EAPAVFNVVV | EITKGSKVKY | ELDKKTGLIK | VDRVLYSSVV | | 97 |
| SEQ_ID_NO_1487 | HPWHDLEIGP | DAPAVFNVVV | EITKGSKVKY | ELDKKTGLIK | VDRILYSSVV | | 95 |
| SEQ_ID_NO_1040 | HPWHDLEIGP | GAPAVFNVVV | EITKGSKVKY | ELDKKTGLIK | VDRVLYSSVV | | 88 |
| SEQ_ID_NO_1465 | HPWHDLEIGP | GAPAVFNVVV | EITKGSKVKY | ELDKKTGLIK | VDRVLYSSVV | | 84 |
| SEQ_ID_NO_1580 | HPWHDLEIGP | GAPAIFNCVV | EIPKGSKVKY | ELDKKTGLIK | VDRVLYSSVV | | 86 |
| SEQ_ID_NO_1623 | HPWHDLEIGP | EAPSVFNVVI | EISKGSKVKY | ELDKKTGLIK | VDRILYSSVV | | 82 |
| SEQ_ID_NO_1622 | HPWHDLEIGP | GAPHIFNCVV | EITKGSKVKY | ELDKKTGLIK | VDRILYSSVV | | 90 |
| SEQ_ID_NO_1041 | HPWHDLEIGP | GAPHIFNVVV | EITKGSKVKY | ELDKKTGLIK | VDRILYSSVV | | 86 |
| SEQ_ID_NO_1590 | HPWHDLEIGP | GAPHIFNVVV | EITKGSKVKY | ELDKKTGLIK | VDRILYSSVV | | 87 |
| SEQ_ID_NO_1577 | HPWHDLEIGP | GAPVIFNVVI | EISKGSKVKY | ELDKKTGLIK | VDRILYSSVV | | 87 |
| SEQ_ID_NO_1611 | HPWHDLEIGP | GAPSIFNVVI | EISKGSKVKY | ELDKKTGLIK | VDRILYSSVV | | 85 |
| SEQ_ID_NO_1637 | HPWHDLEIGP | GAPVIFNVVV | EISKGSKVKY | ELDKKTGLIK | VDRILYSSVV | | 85 |
| SEQ_ID_NO_1627 | HPWHDLEIGP | DAPTIFNCVI | EIPKGSKVKY | ELDKKTGLIK | VDRVLYSSVV | | 99 |
| SEQ_ID_NO_1608 | HPWHDLEIGP | GAPKIFNCVI | EIPKGSKVKY | ELDKKTGLIK | GDRILDSSVV | | 99 |
| SEQ_ID_NO_1609 | HPWHDLEIGP | EAPKIFNCVV | EIGKGSKVKY | ELDKKTGLIK | VDRVLYSSVV | | 67 |

Figure 55 (continued)

| | | | | | | |
|---|---|---|---|---|---|---|
| SEQ_ID_NO_1578 | YPHNYGFVPK | TLCEDGDPLD | VLVLMQEPVV | PMCFLRAKPI | GVMQMLDQGE | 109 |
| SEQ_ID_NO_1607 | YPHNYGFIPR | TICEDSDPID | VLVLMQEPVL | TGSFLRARAI | GLMPMIDQGE | 140 |
| SEQ_ID_NO_1440 | YPHNYGFIPR | TLCEDGDPMD | VLVLMQEPVV | PGRFLRARAI | GLMPMIDQGE | 143 |
| SEQ_ID_NO_1648 | YPHNYGFIPR | TLCEDNDPLD | VLILMQEPVL | PGCFLRARAI | GLMPMIDQGE | 136 |
| SEQ_ID_NO_1651 | YPHNYGFIPR | SLCEDNDPMD | VLVLMQEPVL | PGAFLRARAI | GLMPMIDQGE | 147 |
| SEQ_ID_NO_1487 | YPHNYGFIPR | TLCEDNDPMD | VLVLMQEPVL | PGSFLRARAI | GLMPMIDQGE | 145 |
| SEQ_ID_NO_1040 | YPHNYGFIPR | TLCEDNDPMD | VLVLMQEPVI | PGSFLRARAI | GLMPMIDQGE | 138 |
| SEQ_ID_NO_1485 | YPHNYGFIPR | TLCEDNDPMD | VLVLMQEPVI | PGSFLRARAI | GLMPMIDQGE | 134 |
| SEQ_ID_NO_1580 | YPHNYGFIPR | TLCEDNDPLD | CLVIMQEPVL | PGCFLRARAL | GLMPMIDQGE | 136 |
| SEQ_ID_NO_1623 | YPQNYGFIPR | TLCEDNDPMD | VLVLMQEPVL | PGCFLRARAI | GLMPMIDQGE | 132 |
| SEQ_ID_NO_1622 | YPHNYGFIPR | TLCEDNDPID | VLVLMQEPVL | PGCFLRARAI | GLMPMIDQGE | 140 |
| SEQ_ID_NO_1041 | YPHNYGFIPR | TLCEDNDPLD | VLVLMQEPVL | PGCFLRARAI | GLMPMIDQGE | 136 |
| SEQ_ID_NO_1590 | YPHNYGFIPR | TLCEDNDPLD | VLVLMQEPVL | PGCFLRARAI | GLMPMIDQGE | 137 |
| SEQ_ID_NO_1577 | YPHNYGFVPR | TLCEDNDPID | VLVIMQEPVL | PGCFLRARAI | GLMPMIDQGE | 137 |
| SEQ_ID_NO_1611 | YPHNYGFIPR | TLCEDNDPLD | VLVIMQEPVL | PGCFLRARAI | GLMPMIDQGE | 135 |
| SEQ_ID_NO_1637 | YPHNYGFIPR | TLCEDNDPLD | VLVIMQEPVL | PGCFLRARAI | GLMPMIDQGE | 135 |
| SEQ_ID_NO_1627 | YPHNYGFIPR | TLCDDSDPID | VLVIMQEPVV | PGCFLRAKAI | GLMPMIDQGE | 149 |
| SEQ_ID_NO_1608 | YPHNYGFIPR | TLCEDNDPLS | CLDIMQEPVV | PGCFLRAKAI | GLMPMIDQGE | 149 |
| SEQ_ID_NO_1609 | YPHNYGFIPR | TICEDSDPMD | VLVIMQEPVL | PGCFLRAKAI | GLMPMIDQGE | 137 |

| | | | | | | |
|---|---|---|---|---|---|---|
| SEQ_ID_NO_1578 | RDDKLIAVHA | DDPEYKGFTD | ISQLPPHRLA | EIKRFFEDYK | KNEHKEVVVD | 159 |
| SEQ_ID_NO_1607 | KDDKIIAVCA | DDPEFRHYRD | IKELPPHRLA | EIRRFFEDYK | KNENKKVAVE | 190 |
| SEQ_ID_NO_1440 | KDDKIIAVCA | DDPEVRHYTD | INQLPPHRLA | EIRRFFEDYK | KNENKEVAVN | 193 |
| SEQ_ID_NO_1648 | KDDKIIAVCA | DDPEYRHYTD | IKQLAPHRLA | EIRRFFEDYK | KNENKEVAVN | 186 |
| SEQ_ID_NO_1651 | KDDKIIAVCA | DDPEYRHYND | ISELSPHRLQ | EIRRFFEDYK | KNENKEVAVN | 197 |
| SEQ_ID_NO_1487 | KDDKIIAVCA | DDPEYRHFNN | LSELSPHRLQ | EIRRFFEDYK | KNENKEVAVN | 195 |
| SEQ_ID_NO_1040 | KDDKIIAVCA | DDPEYRHYSI | SVSLLPFRLQ | ELKRFLEDYK | KNENKEVAVD | 186 |
| SEQ_ID_NO_1485 | KDDKIIAVCA | DDPEYRHYND | IN--------- | ---------K | KNENKEVAVD | 167 |
| SEQ_ID_NO_1580 | KDDKIIAVCV | DDPEYKHYTD | IKDLPPHRLT | EIRRFFEDYK | KNENKEVAVD | 186 |
| SEQ_ID_NO_1623 | KDDKIIAVCA | DDPEYRHYTD | IKQLPPHRLA | EIRRFFEDYK | KNENKDVAVD | 182 |
| SEQ_ID_NO_1622 | KDDKIIAVCA | DDPEYKHFTD | YKELAPHRIM | EIRRFFEDYK | KNENKEVAVN | 190 |
| SEQ_ID_NO_1041 | KDDKIIAVCA | DDPEYKHYTD | IKELAPHRLS | EIRRFFEDYK | KNENKEVAVN | 186 |
| SEQ_ID_NO_1590 | KDDKIIAVCA | DDPEYKHYTD | IRELAPHRLS | EIRRFFEDYK | KNENKEVAVN | 187 |
| SEQ_ID_NO_1577 | KDDKIIAVCV | DDPEYKHITN | INELPPHRLS | EIRRFFEDYK | KNENKEVAVN | 187 |
| SEQ_ID_NO_1611 | KDDKIIAVCV | DDPEYKHYTD | IKELPPHRLS | EIRRFFEDYK | KNENKEVAVN | 185 |
| SEQ_ID_NO_1637 | KDDKIIAVCV | DDPEYKHYTD | IKELPPHRLT | EIRRFFEDYK | KNENKEVAVN | 185 |
| SEQ_ID_NO_1627 | ADDKIIAVCA | DDPEYRHFND | IKELPPHRLA | EIRRFFEDYK | KNENKEVAVN | 199 |
| SEQ_ID_NO_1608 | KDDQIIAVCA | DDPEYRHYND | IKELPPHRLA | EIRRFFEDYK | KNENKEVAVD | 199 |
| SEQ_ID_NO_1609 | KDDKIIAVCA | DDPEYRHYND | IKELPPHRLA | EIRRFFEDYK | KNENKEVEVH | 187 |

Figure 55 (continued)

| SEQ_ID | Sequence | Pos |
|---|---|---|
| SEQ_ID_NO_1578 | DFLGAEEAKK VVKDSLNMYQ EHYVPRKLRN VYE | 192 |
| SEQ_ID_NO_1607 | GFLPAQAAID AIKDSMDLYA A- YIKAGLQR --- | 219 |
| SEQ_ID_NO_1440 | EFLPAQIAHD AIQHSMDLYA E- YILQTLRR --- | 222 |
| SEQ_ID_NO_1648 | DFLPSATAHE AIQYSMDLYA E- YIMMSLRR --- | 215 |
| SEQ_ID_NO_1651 | EFLPAEAARE AIQYSMDLYG Q- YIMQTLRR --- | 226 |
| SEQ_ID_NO_1487 | DFLPAPTARE AIQYSMDLYA Q- YILQSLKR --- | 224 |
| SEQ_ID_NO_1040 | AFLPATTARE AIQYSMDLYA Q- YILQSLRQ --- | 215 |
| SEQ_ID_NO_1485 | AFLPANTARD AIQYSMDLYA Q- YILQSLRQ --- | 196 |
| SEQ_ID_NO_1580 | KFLPATAAVE AVQYSMDLYA E- YIMQTLRR --- | 215 |
| SEQ_ID_NO_1623 | DFLPPNSAVN AIQYSMDLYA E- YILHSLRK --- | 211 |
| SEQ_ID_NO_1622 | DFLPPSTAVE AIQYSMDLYA E- YILHTLRR --- | 219 |
| SEQ_ID_NO_1041 | DFLPSNTAVE AIQYSMDLYA E- YILHTLRR --- | 215 |
| SEQ_ID_NO_1590 | DFLPSNSAVE AIQYSMDLYA E- YILHTLRR --- | 216 |
| SEQ_ID_NO_1577 | DFLQPGPAIE AIQYSMDLYA E- YILHTLRR --- | 216 |
| SEQ_ID_NO_1611 | DFLPNGPAVE AIQYSMDLYA E- YILHTLRR --- | 214 |
| SEQ_ID_NO_1637 | DFLPNGPAVE AIQYSMDLYA E- YILHTLRR --- | 214 |
| SEQ_ID_NO_1627 | DFLPSEDAYE AIQHSMDLYA T- YICEGLRR --- | 228 |
| SEQ_ID_NO_1608 | DFLPASTAFD AIQHSMNLYA D- YIVESLRR --- | 228 |
| SEQ_ID_NO_1609 | DFLLATTAMR AIKHSMTLYA D- YIVESLRR --- | 216 |

Figure 56

```
SEQ_ID_NO_361     --MNGGIGDA LMQP--QHVQ V-MSS---- --------S LPMVASTFVA   31
SEQ_ID_NO_443     MDDPGASADP AARHHLSPQQ LGGQP---- --------P VPRSPTPLDL   36
SEQ_ID_NO_212     -MDDPGAADP GARPL-HHLS PGQPP---- --------V VPRSPTPLDL   33
SEQ_ID_NO_421     ---------- ---------- ---------- ---------- ----------    0
SEQ_ID_NO_1437    MGGGGDTTDT NMMQRVNSSS GTSSS---- --------S PKHNLHLNP    36
SEQ_ID_NO_740     -MGDTEEANS EMIQRLQSSF GTTQSSSTTM AKQPFSLINQ DVSQLSLNP    49
SEQ_ID_NO_173     -MEDTEAASS FKMN--NHME QLTIP---- --------Q FNASSQSQMR   33
SEQ_ID_NO_1461    -MEDTEAASS FKMN--NHME QLTIP---- --------Q FNASSQSQMR   33

SEQ_ID_NO_361     EPAAAAAA-- ---------- ---------- -ANKP-RAAG ----LPPTP    52
SEQ_ID_NO_443     ASAAAASG-- -YRRLSPS-- ----RPPAHP QARLP-SPYG ----QIPSP    72
SEQ_ID_NO_212     SSAAAAAAAA SYRRLSPS-- ----RPPAHP QARLP-SPYP ----QIPSSS   73
SEQ_ID_NO_421     ---------- ---------- ------MADS NSKPPMSSQN ----------   14
SEQ_ID_NO_1437    ALIRSHHH-- -----FRH-- ----PFTGAPP PPIPPISPYS ----QIPATL   69
SEQ_ID_NO_740     TQMRARHFTN FSQNFSGDSN KRVGFPPSHP NQIPPISPYS ----QIPVSR   95
SEQ_ID_NO_173     TVTRNHHH-- ---NQRGG-- ----GIPPSHP HQIPPISPYS HMNNQIPVSR   73
SEQ_ID_NO_1461    TVTRNHHH-- ---NQRGG-- ----GIPPSHP HQIPPISPYS HMNNQIPVSR   73

SEQ_ID_NO_361     ---------- ---------- ----P-QVFA AQRAAAAA-- ----------   65
SEQ_ID_NO_443     ---------- -GAGA-HHAR SLSQP-LFFS LDSLPPPP-- ----------   97
SEQ_ID_NO_212     S-----APA AGSSG-HHAR SLSQP-LFFS LDSLPPLP-- ----------  103
SEQ_ID_NO_421     ---------- FGVGAVSHVR SLSQS-SIFS NSCLPPLSPF PPSEPGMVSG   53
SEQ_ID_NO_1437    ---------- --LQP-RHSR SMSQPSSFFS FDSLPPLNPS APL-------   98
SEQ_ID_NO_740     PVNQQMGPQS FSLGP-THSR SLSQPSSFFS LDSLPPLSPA PFRDSSSPSV  144
SEQ_ID_NO_173     P---QMPSHS TSPTP-SHTR SLSQP-SFFS LDSLPPLSPC TFRESSSTSD  118
SEQ_ID_NO_1461    P---QMPSHS TSPTP-SHTR SLSQP-SFFS LDSLPPLSPC TFRESSSTSD  118

SEQ_ID_NO_361     ----GGDVCM EESAQGGGG- ---------- ---------- --GLPPRKA    87
SEQ_ID_NO_443     ----YADL-- ------GAAP AVPPSPPP-- --STSDPPPL --GLPPRRAG  129
SEQ_ID_NO_212     ----YADL-- ------AAPP AIPPSPPS- --SSSDPPPP --GLPPRKGG  135
SEQ_ID_NO_421     RSS-LKDISM EEADVNSQCV GVVSS---- --FTRD--- --GLPPRKG    88
SEQ_ID_NO_1437    ----SVSVSV EEKTGAGFSP SLPPSPFTMC HSSSSRNAGD GENLPPRKS   143
SEQ_ID_NO_740     SDPISTDVFM EEKDGGSHSL -LPPSPF--- -NRGNAPRN VESLPPRKA   187
SEQ_ID_NO_173     ----HADVSM EDRDVTSHSP -LPP------ --FAARNP-- --SLPPRKS   150
SEQ_ID_NO_1461    ----HADVSM EDRDVTSHSP -LPP------ --FAARNP-- --SLPPRKS   150
```

Figure 56 (continued)

| | | |
|---|---|---|
| SEQ_ID_NO_361 | HRRSSSDVPF GYL-----A GQHQLLPP------------ ---------- | 109 |
| SEQ_ID_NO_443 | HRRSQSDIPF GFA-----Q LSPPLPPP------------ ---------- | 151 |
| SEQ_ID_NO_212 | HRRSQSDIPF GFS-----H LSPPLPPP------------ ---------- | 157 |
| SEQ_ID_NO_421 | HRRSNSDVPL GFSAMI--Q SSPQLMPI------------ ---------S | 114 |
| SEQ_ID_NO_1437 | HRRSNSDVTF GFSSMMSQNQ KSPPLSSLER SISGEDT---- -------SD | 182 |
| SEQ_ID_NO_740 | HRRSNSDIPF GLANVL--Q CSPPLIPS-R GSSGLERSMS GRENLGMAKP | 233 |
| SEQ_ID_NO_173 | HRRSNSDIPF GFSTVL--Q SSPPLIPL-R GREGV----- --------KP | 183 |
| SEQ_ID_NO_1461 | HRRSNSDIPF GFSTVL--Q SSPPLIPL-R GREGV----- --------KP | 183 |

| | | |
|---|---|---|
| SEQ_ID_NO_361 | -----KVEAG A-----GHL GACA----GG AAADDLFNA YLNLDGLDGL | 144 |
| SEQ_ID_NO_443 | --APVKREVT A-----AAD GCRSDGGGGD DAALYDLVNA YMDLDGLDPL | 193 |
| SEQ_ID_NO_212 | --APVKREAA T-----AAE GCRSD---GD DFALYDLVNS YMDLDGMEAL | 196 |
| SEQ_ID_NO_421 | GDKVLGRAVS LG----DSN GKIDERKPKG ELVTDELLFS YMNLENIETL | 158 |
| SEQ_ID_NO_1437 | WSNLVKKE-- ------PRE GFYKGRKPEV EAAMDDVFTA YMNLDNIDVL | 223 |
| SEQ_ID_NO_740 | ADSVKK---E MERGCDSNAE GMGERKS-EG ELVVDDLFSA YMNLDNIDVL | 278 |
| SEQ_ID_NO_173 | NSSVVKRETN MEHG--NVE GSGEKKSPEG ELVVDDLFSA YMNLDSFDTL | 229 |
| SEQ_ID_NO_1461 | NSSVVKRETN MEHG--NVE EKIKSLSPEG ELVVDDLFSA YMNLDNIDAI | 228 |

| | | |
|---|---|---|
| SEQ_ID_NO_361 | NSSDDRH-DE GD------- SRGSSI-KTN GADSSENESE ECADDTRGGI | 184 |
| SEQ_ID_NO_443 | NSSEDRH-DD RD------- SRASGTRAGS AAESSENEAE S-------- | 225 |
| SEQ_ID_NO_212 | NSSEERH-ED RD------- SRASGTRTGS VADSSENEAE S-------- | 228 |
| SEQ_ID_NO_421 | NGSGTKD-RD KD------- SIVSGT-KVT GSESSNNEAE SVMKGNNVS- | 197 |
| SEQ_ID_NO_1437 | NSFGGEDGKN GNENVFEMES SRGSGTKKTN GGDSSDSEGD SSASGNVK-- | 271 |
| SEQ_ID_NO_740 | NSSGTDD-KN GNENREDLD- SRASGT-KTN GGDSSDNEAE SSVNESGGNL | 325 |
| SEQ_ID_NO_173 | NSSGTDD-KN GNENRDDLD- SRADGT-KTN GGDSSDNEAE SSVNESGH-- | 274 |
| SEQ_ID_NO_1461 | NDDKNAATDD --------- SRASGT-KTN GGDSSDNEAE SSVNESG--- | 264 |

| | | |
|---|---|---|
| SEQ_ID_NO_361 | RLWS-ADGGE RREGVKRNAA GEPATAPLAR HARSLSMDS- LIGKFNFTAG | 232 |
| SEQ_ID_NO_443 | ---------- QSTSADRKDG GK-----BR HCRSLSIDS- FMGKLSFAAG | 258 |
| SEQ_ID_NO_212 | ---------- HSTPVERKDG GG----KSR HCRSLSVDS- FIEKLNF--- | 259 |
| SEQ_ID_NO_421 | -----IQPTN LREGTKRSAD AN---APAAR HFRSLSMDS- AIGNFHY-G | 237 |
| SEQ_ID_NO_1437 | -----VALSS SSSGVKRRAG GD-IAPTGR HYRSVSMDSC FMGKLNF--G | 312 |
| SEQ_ID_NO_740 | PRAGLSSSTE KREGIKRSAG GD-IAPTTR HYRSVSMDS- FMGKLNF--G | 370 |
| SEQ_ID_NO_173 | ------GGSE KREGMKRSAG GE-IAPTTR HYRSVSMDS- FIGKLNF--G | 313 |
| SEQ_ID_NO_1461 | ------DSMQ RREGNKRSAG GD-IAPTTR HYRSVSMDS- FIGKLNF--N | 303 |

Figure 56 (continued)

| | | | | | | | |
|---|---|---|---|---|---|---|---|
| SEQ_ID_NO_361 | TA------- | AAAGNGVALG | PN------- | RFSLEFGSGE | FTPSEMKKIM | 266 |
| SEQ_ID_NO_443 | EESP-KLPLP | SPGGSLTRSG | SGSLEGGAVA | LFNMEFTNGE | FTDSEKKKIM | 307 |
| SEQ_ID_NO_212 | DESP-KLPLP | SPSGGLSRSG | SGSLDGGAAS | LFSAEFANGE | FTEAEKKKIM | 308 |
| SEQ_ID_NO_421 | DESP-NLP-T | SLMMRSGQLS | PSNSGNESSS | KHNLDFGNSE | FSEAEMKKIM | 285 |
| SEQ_ID_NO_1437 | DESSLKLP-P | SSSA---KVS | PTNSGEGNSS | AYSVEFGNSE | FTAAEMKKIA | 358 |
| SEQ_ID_NO_740 | NESP-KLP-P | SPGTRPGQLS | PTDSIDGNL- | AFSLDFGNGE | FSGAELKKIM | 416 |
| SEQ_ID_NO_173 | DESP-KLP-P | SPGDRGRLMS | PAGGDGNSA | AFSLEFGSGE | FSGPELKKIM | 361 |
| SEQ_ID_NO_1461 | DESL-KMP-P | SPGG---LMS | PGNSGDGNNA | AFSLEFGNGE | FSGPELKKIM | 348 |

| | | | | | | | |
|---|---|---|---|---|---|---|---|
| SEQ_ID_NO_361 | ADEKLAEMAL | ADPKRVKRVL | ANRQSAARSK | ERKMRYIAEL | EQKVQLQSE | 316 |
| SEQ_ID_NO_443 | ANERLAEIAL | TDPKRVKRIL | ANRQSAARSK | ERKMRYIQEL | EHKVQVLQTE | 357 |
| SEQ_ID_NO_212 | ANERLAEIAL | TDPKRVKRIL | ANRQSAARSK | ERKMRYIQEL | EHKVQVLQTE | 358 |
| SEQ_ID_NO_421 | ADERLAEIAV | LDPKRAKRIL | ANRLSAARSK | ERKTRYISEL | EHKVQKLQTE | 335 |
| SEQ_ID_NO_1437 | ADEKLAEIVM | ADPKRVKRIL | ANRVSAARSK | ERKTRYMAEL | EHKVQTLQTE | 408 |
| SEQ_ID_NO_740 | ANEKLAEIAL | ADPKRAKRIL | ANRQSAARSK | ERKMRYISEL | EHKVQTLQTE | 466 |
| SEQ_ID_NO_173 | ANEKLAEIAL | TDPKRAKRIL | ANRQSAARSK | ERKMRYISEL | EHKVQTLQTE | 411 |
| SEQ_ID_NO_1461 | ANEKLAEIAM | ADPKRAKRIL | ANRQSAARSK | ERKMRYISEL | EHKVQTLQTE | 398 |

| | | | | | | | |
|---|---|---|---|---|---|---|---|
| SEQ_ID_NO_361 | ATNLSAQLTM | MQRDSAGLAT | QNNELKFRLH | AMEQQAQLRD | ALNEALTIEV | 366 |
| SEQ_ID_NO_443 | ATTLSAQLTM | LQRDSAGLAT | QNNELKIRLQ | AMEQQAQLRD | ALNEALTAEV | 407 |
| SEQ_ID_NO_212 | ATTLSAQLTM | LQRDSTGLAT | QNNELKIRLQ | AMEQQAQLRD | ALNEALTAEV | 408 |
| SEQ_ID_NO_421 | TTTLSTQVTI | LQKNFVESS | LNSELKFRIQ | AMEQQAQLRD | ALHEALTAEV | 385 |
| SEQ_ID_NO_1437 | ATTLSAQLTH | LQRDSMGLTN | QNSELKFRLQ | AMEQQAQLRD | ALSEKLNEFV | 458 |
| SEQ_ID_NO_740 | ATTLSAQLTL | LQRDSVGLTN | QNNELKFRIQ | AMEQQAQLRD | ALNEALTAEV | 516 |
| SEQ_ID_NO_173 | ATTLSAQLTL | LQRDSAGLTN | QNSELKFRLQ | SMEQQAKLRD | ALNEALTAEV | 461 |
| SEQ_ID_NO_1461 | ATTLSAQLTL | LQRDSVGLTN | QNSELKFRLQ | SMEQQAKLRD | ALNEALTAEV | 448 |

| | | | | | | | |
|---|---|---|---|---|---|---|---|
| SEQ_ID_NO_361 | QRLKLATAEL | GDSCSSSSLA | QQLQLNAQNQ | MFQL----- | -------QQQ | 403 |
| SEQ_ID_NO_443 | QRLKLATGEV | T-DGRMPKGL | QQQM--NSQ | MLQL----- | -------QQL | 440 |
| SEQ_ID_NO_212 | QRLKLATGEI | T-DGRMSKGL | QQQM--NSQ | LIQL----- | ---------- | 438 |
| SEQ_ID_NO_421 | QRLKLAAGEH | REEGRLPNNW | TQQT-PVKHN | FQM----- | ---------- | 418 |
| SEQ_ID_NO_1437 | QRLKLVIGEP | NRRQSGSSSS | ESKMSLNPE | MFQQ----- | ---------L | 492 |
| SEQ_ID_NO_740 | RRLKIATAEQ | GGDSDPSKSM | VQQQLSINPQ | MYLQQPRPSQ | LGMHQLQQQS | 566 |
| SEQ_ID_NO_173 | QRLKIATAEL | SSDSHGSSCL | PQH-SVNPL | MFQQ----- | -------QPP | 497 |
| SEQ_ID_NO_1461 | QRLKIVTAEL | NGESLPSNCM | PQH-SVNPM | MFQQ----- | ---------- | 481 |

Figure 56 (continued)

| | | | | | | | |
|---|---|---|---|---|---|---|---|
| SEQ_ID_NO_361 | QATQLPFYQL | QQSQ | | | Q | NGAAKNNESK | E | 429 |
| SEQ_ID_NO_443 | QVQQQAPQAQ | QQGQ | | | | RQQQQQPQKS | A | 465 |
| SEQ_ID_NO_212 | --QQLQIQQQ | QSSQ | | | | ----TTQDDR | L | 457 |
| SEQ_ID_NO_421 | --QRQQPSQM | QQLS | | | VGK | ASAASATPAS | A | 444 |
| SEQ_ID_NO_1437 | SLSQLQHQQM | QHSN | | | QC | STMKAKHTSN | D | 519 |
| SEQ_ID_NO_740 | SASQFNMHQR | QRQQQQQQQQ | QSSQPQPQQN | GNTTPKPDSN | Q | 607 |
| SEQ_ID_NO_173 | SASQQNIHLQ | QQQH | | | RQN | GNANSNSDLK | Q | 525 |
| SEQ_ID_NO_1461 | ---QHQHQQH | QQQQ | | | QQN | GNANSKNELK | Q | 506 |

Figure 57

```
SEQ_ID_NO_97     ----MGKKSP NVAAFMLPLL LILFTLSSQL KVVESTGRKL -AWGFSSTPI  46
SEQ_ID_NO_2013   MKKKMGSKSP NVGAFVLPLL LILFTLSSQA RLIESTGRKL AAWGFGGAPI  50
SEQ_ID_NO_2015   ----MGSKSP NVAALVLPLL LILFSLSSQA RLVESSGRKL AAWGFGGAPI  46

SEQ_ID_NO_97     VYTPPSRSCG TSPAVFTSKW RRPRPCRLPP GSYPASDQS P    86
SEQ_ID_NO_2013   WTPPSNSCG  ASPAVWYPKP TKRGPCRGPP GIGPTSYQS P    91
SEQ_ID_NO_2015   GTPSSNSCG  ASPAVWYPKP TKPRPCRRTP GIGPTSHQS P    87
```

NUCLEOTIDE SEQUENCES AND CORRESPONDING POLYPEPTIDES CONFERRING MODIFIED PHENOTYPE CHARACTERISTICS IN PLANTS

CROSS REFERENCE TO RELATED APPLICATIONS

This application is a Divisional of application Ser. No. 14/627,544, filed Feb. 20, 2015 which application is a Continuation-in-Part of application Ser. No. 13/644,359 filed on Oct. 4, 2012 (now U.S. Pat. No. 9,777,287), which is a Continuation-in-Part of application Ser. No. 13/465,846 filed on May 7, 2012 (abandoned), and for which priority is claimed under 35 U.S.C. § 120. Application Ser. No. 13/465,846 is a Division of application Ser. No. 10/572,827 filed on Mar. 7, 2007 (now U.S. Pat. No. 8,193,409). Application Ser. No. 10/572,827 is a national phase under 35 U.S.C. § 371 of PCT International Application No. PCT/US2003/025997 which has the International filing date of Aug. 18, 2003, which designated the United States of America. The entire contents of each of the above-identified applications are hereby incorporated by reference, including their sequence listings.

Application Ser. No. 14/627,544, filed Feb. 20, 2015 (pending), is a Continuation-in-Part of application Ser. No. 14/175,856 filed on Feb. 7, 2014 (abandoned), which is a Reissue of application Ser. No. 12/281,616 filed on Dec. 5, 2008 (now U.S. Pat. No. 8,110,724). Application Ser. No. 12/281,616 is a national phase under 35 U.S.C. § 371 of PCT International Application No. PCT/US2007/006651 which has the International filing date of Mar. 14, 2007, which designated the United States of America, and which claims priority under 35 U.S.C. § 119(e) of U.S. Provisional Application No. 60/821,639 filed on Aug. 7, 2006, and U.S. Provisional Application No. 60/782,428 filed on Mar. 14, 2006. The entire contents of each of the above-identified applications are hereby incorporated by reference, including their sequence listings.

Application Ser. No. 13/644,359 filed on Oct. 4, 2012 (now U.S. Pat. No. 9,777,287) is a Continuation-in-Part of application Ser. No. 11/779,266 filed on Jul. 17, 2007 (abandoned) and for which priority is claimed under 35 U.S.C. § 120. Application Ser. No. 11/779,266 is a Continuation-in-Part of application Ser. No. 11/778,060 filed Jul. 15, 2007 (abandoned). Application Ser. No. 11/778,060 is a Continuation-in-Part of application Ser. No. 11/248,547 filed Oct. 12, 2005 (now U.S. Pat. No. 7,244,879). The entire contents of each of which are hereby incorporated by reference, including their sequence listings.

Application Ser. No. 13/644,359 filed on Oct. 4, 2012 (now U.S. Pat. No. 9,777,287) is a Continuation-in-Part of application Ser. No. 12/514,991 filed on Jan. 8, 2010 (abandoned), and for which priority is claimed under 35 U.S.C. § 120. Application Ser. No. 12/514,991 is a national phase under 35 U.S.C. § 371 of PCT International Application No. PCT/US2007/085007 which has the International filing date of Nov. 16, 2007, which designated the United States of America, and which claims priority under 35 U.S.C. § 119(e) of U.S. Provisional Application No. 60/859,467 filed Nov. 16, 2006. The entire contents of each of which are hereby incorporated by reference, including their sequence listings.

Application Ser. No. 13/644,359 filed on Oct. 4, 2012 (now U.S. Pat. No. 9,777,287) is a Continuation-in-Part of application Ser. No. 12/445,005 filed on Jul. 13, 2011 (abandoned), and for which priority is claimed under 35 U.S.C. § 120. Application Ser. No. 12/445,005 is a national phase under 35 U.S.C. § 371 of PCT International Application No. PCT/US2007/081301 which has the International filing date of Oct. 12, 2007, which designated the United States of America, and which claims priority under 35 U.S.C. § 119(e) of U.S. Provisional Application No. 60/851,585 filed Oct. 12, 2006. The entire contents of each of which are hereby incorporated by reference, including their sequence listings.

Application Ser. No. 13/644,359 filed on Oct. 4, 2012 (now U.S. Pat. No. 9,777,287) is a Continuation-in-Part of application Ser. No. 12/515,707 filed on Dec. 16, 2009 (abandoned) and for which priority is claimed under 35 U.S.C. § 120. Application Ser. No. 12/515,707 is a national phase under 35 U.S.C. § 371 of PCT International Application No. PCT/US2007/085439 which has the International filing date of Nov. 21, 2007, which designated the United States of America, and which claims priority under 35 U.S.C. § 119(e) of U.S. Provisional Application No. 60/860,296 filed Nov. 21, 2006. The entire contents of each of which are hereby incorporated by reference, including their sequence listings.

Application Ser. No. 13/644,359 filed on Oct. 4, 2012 (now U.S. Pat. No. 9,777,287) is a Continuation-in-Part of application Ser. No. 12/615,920 filed on Nov. 10, 2009 (now U.S. Pat. No. 8,471,099), and for which priority is claimed under 35 U.S.C. § 120. Application Ser. No. 12/615,920 is a Continuation of application Ser. No. 11/114,963 filed on Apr. 25, 2005 (now U.S. Pat. No. 7,696,409). Application Ser. No. 11/114,963 claims priority under 35 U.S.C. § 119(e) of U.S. Provisional Application No. 60/564,659 filed Apr. 23, 2004. The entire contents of each of which are hereby incorporated by reference, including their sequence listings.

Application Ser. No. 13/644,359 filed on Oct. 4, 2012 (now U.S. Pat. No. 9,777,287) is a Continuation-in-Part of application Ser. No. 12/605,261 filed on Oct. 23, 2009 (abandoned), and for which priority is claimed under 35 U.S.C. § 120. Application Ser. No. 12/605,261 is a Division of application Ser. No. 11/298,391 filed on Dec. 8, 2005 (now U.S. Pat. No. 7,663,027). Application Ser. No. 11/298,391 claims priority under 35 U.S.C. § 119(e) of U.S. Provisional Application Nos. 60/635,115, filed Dec. 8, 2004 and 60/635,140 filed on Dec. 8, 2004. The entire contents of each of which are hereby incorporated by reference, including their sequence listings.

Application Ser. No. 13/644,359 filed on Oct. 4, 2012 (now U.S. Pat. No. 9,777,287) is a Continuation-in-Part of application Ser. No. 12/377,106 filed on Aug. 13, 2010 (abandoned) and for which priority is claimed under 35 U.S.C. § 120. Application Ser. No. 12/377,106 is a national phase under 35 U.S.C. § 371 of PCT International Application No. PCT/US2007/075747 which has the International filing date of Aug. 10, 2007, which designated the United States of America, and which claims priority under 35 U.S.C. § 119(e) of U.S. Provisional Application No. 60/837,434 filed Aug. 11, 2006. The entire contents of each of which are hereby incorporated by reference, including their sequence listings.

Application Ser. No. 13/644,359 filed on Oct. 4, 2012 (now U.S. Pat. No. 9,777,287) is a Continuation-in-Part of application Ser. No. 12/541,607 filed on Aug. 14, 2009 (abandoned), and for which priority is claimed under 35 U.S.C. § 120. Application Ser. No. 12/541,607 is a Continuation of application Ser. No. 11/140,347 filed on May 27, 2005 (now U.S. Pat. No. 7,576,260). Application Ser. No. 11/140,347 claims priority under 35 U.S.C. § 119(e) of U.S. Provisional Application No. 60/575,309 filed May 27, 2004.

The entire contents of each of which are hereby incorporated by reference, including their sequence listings.

Application Ser. No. 13/644,359 filed on Oct. 4, 2012 (now U.S. Pat. No. 9,777,287) is a Continuation-in-Part of application Ser. No. 13/184,361 filed on Jul. 15, 2011 (now U.S. Pat. No. 8,962,921), and for which priority is claimed under 35 U.S.C. § 120. Application Ser. No. 13/184,361 is a Division of application Ser. No. 11/140,450 filed on May 27, 2005 (now U.S. Pat. No. 8,022,273). Application Ser. No. 11/140,450 claims priority under 35 U.S.C. § 119(e) of U.S. Provisional Application No. 60/575,253 filed May 27, 2004. The entire contents of each of which are hereby incorporated by reference, including their sequence listings.

Application Ser. No. 13/644,359 filed on Oct. 4, 2012 (now U.S. Pat. No. 9,777,287) is a Continuation-in-Part of application Ser. No. 11/654,357 filed on Jan. 16, 2007 (abandoned), and for which priority is claimed under 35 U.S.C. § 120. Application Ser. No. 11/654,357 is a Non-Provisional which claims priority under 35 U.S.C. § 119(e) of U.S. Provisional Application Nos. 60/778,568 filed Mar. 1, 2006 and 60/758,831 filed on Jan. 13, 2006. The entire contents of each of which are hereby incorporated by reference, including their sequence listings.

Application Ser. No. 13/644,359 filed on Oct. 4, 2012 (now U.S. Pat. No. 9,777,287) is a Continuation-in-Part of application Ser. No. 13/465,841 filed on May 7, 2012 (now U.S. Pat. No. 9,765,355) and for which priority is claimed under 35 U.S.C. § 120. Application Ser. No. 13/465,841 is a Division of application Ser. No. 11/858,117 filed on Sep. 19, 2007 (abandoned). Application Ser. No. 11/858,117 is a Continuation-in-Part of Application No. PCT/US2007/006544 which has the International filing date of Mar. 14, 2007, and which claims priority under 35 U.S.C. § 119(e) of U.S. Provisional Application No. 60/782,735 filed Mar. 14, 2006. The entire contents of each of which are hereby incorporated by reference, including their sequence listings.

Application Ser. No. 13/644,359 filed on Oct. 4, 2012 (now U.S. Pat. No. 9,777,287) is a Continuation-in-Part of Application Ser. No. 12/918,609 filed on Nov. 22, 2010 (abandoned) and for which priority is claimed under 35 U.S.C. § 120. Application Ser. No. 12/918,309 is a national phase under 35 U.S.C. § 371 of PCT International Application No. PCT/US2009/034638 which has the International filing date of Feb. 20, 2009, which designated the United States of America, and which claims priority under 35 U.S.C. § 119(e) of U.S. Provisional Application No. 61/030, 152, filed Feb. 20, 2008. The entire contents of each of which are hereby incorporated by reference, including their sequence listings.

Application Ser. No. 13/644,359 filed on Oct. 4, 2012 (now U.S. Pat. No. 9,777,287) is a Continuation-in-Part of application Ser. No. 12/922,143 filed on Feb. 1, 2011 (abandoned), and for which priority is claimed under 35 U.S.C. § 120. Application Ser. No. 12/922,143 is a national phase under 35 U.S.C. § 371 of PCT International Application No. PCT/US2009/037025 which has the International filing date of Mar. 12, 2009, which designated the United States of America, and which claims priority under 35 U.S.C. § 119(e) of U.S. Provisional Application No. 61/036, 396, filed Mar. 13, 2008. The entire contents of each of which are hereby incorporated by reference, including their sequence listings.

Application Ser. No. 13/644,359 filed on Oct. 4, 2012 (now U.S. Pat. No. 9,777,287) is a Continuation-in-Part of application Ser. No. 11/241,685 filed on Sep. 30, 2005 (now U.S. Pat. No. 8,481,814), and for which priority is claimed under 35 U.S.C. § 120. Application Ser. No. 11/241,685 is a non-provisional which claims priority under 35 U.S.C. § 119(e) of U.S. Provisional Application No. 60/615,080, filed on Sep. 30, 2004. The entire contents of each of which are hereby incorporated by reference, including their sequence listings.

Application Ser. No. 13/644,359 filed on Oct. 4, 2012 (now U.S. Pat. No. 9,777,287) is a Continuation-in-Part of application Ser. No. 12/863,773 filed on Nov. 23, 2010 (abandoned), and for which priority is claimed under 35 U.S.C. § 120. Application Ser. No. 12/863,773 is a national phase under 35 U.S.C. § 371 of PCT International Application No. PCT/US2009/031609 which has the International filing date of Jan. 21, 2009, which designated the United States of America, and which claims priority under 35 U.S.C. § 119(e) of U.S. Provisional Application No. 61/022, 786 filed Jan. 22, 2008. The entire contents of each of which are hereby incorporated by reference, including their sequence listings.

Application Ser. No. 13/644,359 filed on Oct. 4, 2012 (now U.S. Pat. No. 9,777,287) is a Continuation-in-Part of application Ser. No. 12/282,342 filed on Nov. 17, 2008 (now U.S. Pat. No. 8,324,454), and for which priority is claimed under 35 U.S.C. § 120. Application Ser. No. 12/282,342 is a national phase under 35 U.S.C. § 371 of PCT International Application No. PCT/US2007/06544 which has the International filing date of Mar. 14, 2007, which designated the United States of America, and which claims priority under 35 U.S.C. § 119(e) of U.S. Provisional Application No. 60/782,735, filed Mar. 14, 2006. The entire contents of each of which are hereby incorporated by reference, including their sequence listings.

Application Ser. No. 13/644,359 filed on Oct. 4, 2012 (now U.S. Pat. No. 9,777,287) is a Continuation-in-Part of application Ser. No. 12/776,319 filed on May 7, 2010 (abandoned), and for which priority is claimed under 35 U.S.C. § 120. Application Ser. No. 12/776,319 is a Division of application Ser. No. 11/324,093 filed on Dec. 29, 2005 (now U.S. Pat. No. 7,803,983). Application Ser. No. 11/324, 093 is a Continuation-in-Part of application Ser. No. 11/172, 740 filed on Jun. 30, 2005 (now U.S. Pat. No. 7,396,979). Application Ser. No. 11/172,740 claims priority under 35 U.S.C. § 119(e) of U.S. Provisional Application Nos. 60/584,829, 60/583,621, and 60/584,800, all filed on Jun. 30, 2004. The entire contents of each of which are hereby incorporated by reference, including their sequence listings.

Application Ser. No. 13/644,359 filed on Oct. 4, 2012 (now U.S. Pat. No. 9,777,287) is a Continuation-in-Part of application Ser. No. 12/911,698 filed on Oct. 25, 2010 (now U.S. Pat. No. 9,914,935), and for which priority is claimed under 35 U.S.C. § 120. Application Ser. No. 12/911,698 is a Division of application Ser. No. 11/324,098 filed on Dec. 29, 2005 (now U.S. Pat. No. 7,884,261). Application Ser. No. 11/324,098 is a Continuation-in-Part of application Ser. No. 11/172,740 filed on Jun. 30, 2005 (now U.S. Pat. No. 7,396,979). Application Ser. No. 11/172,740 claims priority under 35 U.S.C. § 119(e) of U.S. Provisional Application Nos. 60/584,829, 60/583,621, and 60/584,800, all filed on Jun. 30, 2004. The entire contents of each of which are hereby incorporated by reference, including their sequence listings.

Application Ser. No. 13/644,359 filed on Oct. 4, 2012 (now U.S. Pat. No. 9,777,287) is a Continuation-in-Part of application Ser. No. 13/609,176 filed on Sep. 10, 2012 (abandoned) and for which priority is claimed under 35 U.S.C. § 120. Application Ser. No. 13/609,176 is a Division of application Ser. No. 12/139,269 filed on Jun. 13, 2008 (abandoned). Application Ser. No. 12/139,269 is a Division of application Ser. No. 11/172,740 filed on Jun. 30, 2005 (now U.S. Pat. No. 7,396,979). Application Ser. No. 11/172,740 claims priority under 35 U.S.C. § 119(e) of U.S. Provisional Application Nos. 60/584,829, 60/583,621, and 60/584,800, all filed on Jun. 30, 2004. The entire contents of each of which are hereby incorporated by reference, including their sequence listings.

TECHNICAL FIELD

The present invention relates to methods and materials involved in tolerance of a plant to limiting exogenous nitrogen sources. For example, this document provides plants having increased low-nitrogen tolerance levels as well as materials and methods for making plants and plant products having increased low-nitrogen tolerance levels.

BACKGROUND

Nitrogen is often the rate-limiting element in plant growth, and all field crops have a fundamental dependence on exogenous nitrogen sources.

According to a recent study published in Field Crops Research (Volume 100, Issues 2-3, 1 Feb. 2007, Pages 210-217), Nitrogenous fertilizer, which is usually supplied as ammonium nitrate, potassium nitrate, or urea, typically accounts for 40% of the costs associated with crops, such as corn and wheat in intensive agriculture.

Improving nitrogen use efficiency of crop plants is an important goal towards reducing input costs and reducing the environmental consequences of intensive nitrogen fertilization on the environment. Increased efficiency of nitrogen use by plants should enable the production of higher yields with existing fertilizer inputs and/or enable existing yields of crops to be obtained with lower fertilizer input, or better yields on soils of poorer quality. Also, higher amounts of proteins in the crops could also be produced more cost-effectively.

Plants have a number of means to cope with nutrient deficiencies, such as poor nitrogen availability. One important mechanism senses nitrogen availability in the soil and respond accordingly by modulating gene expression while a second mechanism is to sequester or store nitrogen in times of abundance to be used later. The nitrogen sensing mechanism relies on regulated gene expression and enables rapid physiological and metabolic responses to changes in the supply of inorganic nitrogen in the soil by adjusting nitrogen uptake, reduction, partitioning, remobilization and transport in response to changing environmental conditions. Nitrate acts as a signal to initiate a number of responses that serve to reprogram plant metabolism, physiology and development (Redinbaugh et al. (1991) *Physiol. Plant.* 82, 640-650; Forde (2002) *Annual Review of Plant Biology* 53, 203-224). Nitrogen-inducible gene expression has been characterized for a number of genes in some detail. These include nitrate reductase, nitrite reductase, 6-phosphoglucante dehydrogenase, and nitrate and ammonium transporters (Redinbaugh et al. (1991) *Physiol. Plant.* 82, 640-650; Huber et al. (1994) Plant Physiol 106, 1667-1674; Hwang et al. (1997) *Plant Physiol.* 113, 853-862; Redinbaugh et al. (1998) *Plant Science* 134, 129-140; Gazzarrini et al. (1999) *Plant Cell* 11, 937-948; Glass et al. (2002) *J. Exp. Bot.* 53, 855-864; Okamoto et al. (2003) *Plant Cell Physiol.* 44, 304-317).

In the fields of agriculture and forestry, efforts are constantly being made to produce plants with an increased growth potential in order to feed the ever-increasing world population and to guarantee the supply of reproducible raw materials. There is a need for methods of increasing nitrogen use efficiency in plants, which leads to better growth potential and more biomass. This is done conventionally through plant breeding. The breeding process is, however, both time-consuming and labor-intensive. Furthermore, appropriate breeding programs must be performed for each relevant plant species. In addition, although great progresses that have been made about nitrogen utilization and the components involved in nitrogen use efficiency, such as nitrogen uptake, nitrogen assimilation and nitrogen partitioning or remobilization, much is still unknown about many of these complex interactions. Therefore, there is a continuing need for generally applicable processes that improve forest or agricultural plant growth to suit particular needs depending on specific environmental conditions. For example, genes that confer tolerance to growth on low nitrogen supply are valuable product prototypes for manipulating nitrogen use efficiency in plants (Good et al., 2004). One strategy to achieve such desirable traits involves genetic manipulation of plant characteristics through the introduction of exogenous nucleic acids conferring increased efficiency of nitrogen use by plants, which in turn should enable the production of higher yields with existing fertilizer inputs and/or enable existing yields of crops to be obtained with lower fertilizer input, or better yields on soils of poorer quality. Such approaches have the advantage of not usually being limited to one plant species, but instead being transferable among plant species. The present invention relates to a method for increasing growth potential, and/or increasing levels of nitrogen use efficiency in plants, characterized by expression of recombinant DNA molecules stably integrated into the plant genome

SUMMARY

The present invention provides methods and materials related to plants having modulated levels of low-nitrogen tolerance. For example, the present invention provides transgenic plants and plant cells having increased levels of low-nitrogen tolerance, nucleic acids (i.e. isolated polynucleotides), polypeptides encoded thereby used to generate transgenic plants and plant cells having increased levels of low-nitrogen tolerance, and methods for making plants and plant cells having increased levels of low-nitrogen tolerance. Such plants and plant cells can be grown under limiting exogenous nitrogen without stunted growth and diminished yields. Plants having increased low-nitrogen tolerance levels may be useful to produce biomass which may be converted to a liquid fuel or other chemicals and/or to produce food and feed on land that is currently marginally productive, resulting in an overall expansion of arable land.

Methods of producing a plant tissue are provided herein. In one aspect, a method comprises growing a plant cell comprising an exogenous nucleic acid. The exogenous nucleic acid comprises a regulatory region operably linked to a nucleotide sequence encoding a polypeptide. The Hidden Markov Model (HMM) bit score of the amino acid sequence of the polypeptide is greater than about 20, using an HMM generated from the amino acid sequences depicted in one of FIGS. 1-57. The tissue has a difference in the level of low-nitrogen tolerance as compared to the corresponding level in tissue of a control plant that does not comprise the exogenous nucleic acid.

In another aspect, a method comprises growing a plant cell comprising an exogenous nucleic acid. The exogenous nucleic acid comprises a regulatory region operably linked to a nucleotide sequence encoding a polypeptide having 80 percent or greater sequence identity to an amino acid sequence set forth in SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, or SEQ ID NO:1577. A plant and/or plant tissues produced from the plant cell has a difference in the level of low-nitrogen tolerance as compared to the corresponding level of low-nitrogen tolerance of a control plant that does not comprise the exogenous nucleic acid.

In another aspect, a method comprises growing a plant cell comprising an exogenous nucleic acid. The exogenous nucleic acid comprises a regulatory region operably linked to a nucleotide sequence having 80 percent or greater sequence identity to a nucleotide sequence, or a fragment thereof, set forth in SEQ ID NO:1, SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, or SEQ ID NO:1576. A plant and/or plant tissues produced from the plant cell has a difference in the level of low-nitrogen tolerance as compared to the corresponding level low-nitrogen tolerance of a control plant that does not comprise the exogenous nucleic acid.

In another aspect, the invention provides a method of producing a plant, the method comprising growing a plant cell comprising an exogenous nucleic acid that is effective for downregulating an endogenous nucleic acid in the plant cell, wherein the endogenous nucleic acid encodes a polypeptide, and wherein the HMM bit score of the amino acid sequence of the polypeptide is greater than about 20, said HMM based on the amino acid sequences depicted in one of FIGS. 1-57.

Methods of modulating the level of low-nitrogen tolerance in a plant are provided herein. In one aspect, a method comprises introducing into a plant cell an exogenous nucleic acid, that comprises a regulatory region operably linked to a nucleotide sequence encoding a polypeptide. The HMM bit score of the amino acid sequence of the polypeptide is greater than about 20, using an HMM generated from the amino acid sequences depicted in one of FIGS. 1-57. A plant and/or plant tissue produced from the plant cell has a difference in the level of low-nitrogen tolerance as compared to the corresponding level of low-nitrogen tolerance of a control plant that does not comprise the exogenous nucleic acid.

In certain embodiments, the HMM bit score of the amino acid sequence of the polypeptide is greater than about 40, using an HMM generated from the amino acid sequences depicted in one of FIGS. 1-57, wherein the polypeptide comprises a Pfam domain having 70 percent or greater sequence identity to a Pfam domain of any one of the polypeptides in the sequence listing.

In another aspect, a method comprises modulating the level of low-nitrogen tolerance in a plant by introducing into a plant cell an exogenous nucleic acid that comprises a regulatory region operably linked to a nucleotide sequence encoding a polypeptide having 80 percent or greater sequence identity to an amino acid sequence set forth in SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, or SEQ ID NO:1577, or a fragment thereof. A plant and/or plant tissue produced from the plant cell has a difference in the level of low-nitrogen tolerance as compared to the corresponding level of low-nitrogen tolerance of a control plant that does not comprise the exogenous nucleic acid.

In another aspect, a method comprises modulating the level of low-nitrogen tolerance in a plant by introducing into a plant cell an exogenous nucleic acid, that comprises a regulatory region operably linked to a nucleotide sequence having 80 percent or greater sequence identity to a nucleotide sequence set forth in SEQ ID NO:1, SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, or SEQ ID NO:1576, or a fragment thereof. A plant and/or plant tissue produced from the plant cell has a difference in the level of low-nitrogen tolerance as compared to the corresponding level of low-nitrogen tolerance of a control plant that does not comprise the exogenous nucleic acid.

Plant cells comprising an exogenous nucleic acid are provided herein. In one aspect, the exogenous nucleic acid comprises a regulatory region operably linked to a nucleotide sequence encoding a polypeptide. The HMM bit score of the amino acid sequence of the polypeptide is greater than about 20, using an HMM based on the amino acid sequences depicted in one of FIGS. 1-57. The plant has a difference in the level of low-nitrogen tolerance as compared to the corresponding level of low-nitrogen tolerance of a control plant that does not comprise the exogenous nucleic acid. In another aspect, the exogenous nucleic acid comprises a regulatory region operably linked to a nucleotide sequence encoding a polypeptide having 80 percent or greater sequence identity to an amino acid sequence selected from the group consisting of SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, and SEQ ID NO:1577. A plant and/or plant tissue produced from the plant cell has a difference in the level of low-nitrogen tolerance as compared to the corresponding level of low-nitrogen tolerance of a control plant that does not comprise the exogenous nucleic acid. In another aspect, the exogenous nucleic acid comprises a regulatory region operably linked to a nucleotide sequence having 80 percent or greater sequence identity to a nucleotide sequence selected from the group consisting of SEQ ID NO:1, SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, and SEQ ID NO:1576, or a fragment thereof. A plant and/or plant tissue of a plant produced from the plant cell has a difference in the level of low-nitrogen tolerance as compared to the corresponding level of low-nitrogen tolerance of a control plant that does not comprise the exogenous nucleic acid. A transgenic plant comprising such a plant cell is also provided.

Isolated nucleic acids are also provided. In one aspect, an isolated nucleic acid comprises a nucleotide sequence having 80% or greater sequence identity to the nucleotide sequence set forth in SEQ ID NO:1, SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, or SEQ ID NO:1576. In another aspect, an isolated nucleic acid comprises a nucleotide sequence encoding a polypeptide having 80% or greater sequence identity to the amino acid sequence set forth in SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, or SEQ ID NO:1577.

In another aspect, methods of identifying a genetic polymorphism associated with variation in the level of low-nitrogen tolerance are provided. The methods include providing a population of plants, and determining whether one or more genetic polymorphisms in the population are genetically linked to the locus for a polypeptide selected from the group consisting of the polypeptides depicted in FIGS. 1-57, SEQ ID NO:556, SEQ ID NO:853, SEQ ID NO:1157, and functional homologs thereof, such as those in the Sequence Listing. The correlation between variation in the level of low-nitrogen tolerance in a tissue in plants of the population and the presence of the one or more genetic polymorphisms in plants of the population is measured, thereby permitting identification of whether or not the one or more genetic polymorphisms are associated with such variation.

In another aspect, the invention provides a method of making a plant line, said method comprising:

a) determining whether one or more genetic polymorphisms in a population of plants is associated with the locus for a polypeptide selected from the group consisting of the polypeptides depicted in FIGS. 1-57, SEQ ID NO: 556, SEQ ID NO: 853, and SEQ ID NO: 1157 and functional homologs thereof;

b) identifying one or more plants in said population in which the presence of at least one allele at said one or more genetic polymorphisms is associated with variation in a trait;

c) crossing each said one or more identified plants with itself or a different plant to produce seed;

d) crossing at least one progeny plant grown from said seed with itself or a different plant; and e) repeating steps c) and d) for an additional 0-5 generations to make said plant line, wherein said at least one allele is present in said plant line.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 1 is an alignment of Ceres SEEDLINE No. ME00919 (SEQ ID NO:3) with homologous and/or orthologous amino acid sequences GI No. 5921925 (SEQ ID NO:4), CeresClone:1929222 (SEQ ID NO:6), CeresAnnot:1471370 (SEQ ID NO:10), GI No. 84380741 (SEQ ID NO:21), GI No. 5921926 (SEQ ID NO:22), GI No. 84514161 (SEQ ID NO:25), CeresClone:779234 (SEQ ID NO:27), CeresClone:1600726 (SEQ ID NO:29), GI No. 78183420 (SEQ ID NO:36), CeresClone:1877346 (SEQ ID NO:38), GI No. 125562440 (SEQ ID NO:39), GI No. 115477665 (SEQ ID NO:40), GI No. 1173624 (SEQ ID NO:46), and GI No. 84468276 (SEQ ID NO:47). In all the alignment figures shown herein, a dash in an aligned sequence represents a gap, i.e., a lack of an amino acid at that position. Identical amino acids or conserved amino acid substitutions among aligned sequences are identified by boxes. FIG. 1 and the other alignment figures provided herein were generated using the program MUSCLE version 3.52.

FIG. 2 is an alignment of ME01312 (SEQ ID NO:49) with homologous and/or orthologous amino acid sequences CeresClone:1869410 (SEQ ID NO:51), CeresAnnot:1540549 (SEQ ID NO:53), CeresClone:978708 (SEQ ID NO:58), CeresClone:1623097 (SEQ ID NO:60), GI No. 92873064 (SEQ ID NO:63), GI No. 37051131 (SEQ ID NO:64), GI No. 3341468 (SEQ ID NO:65), CeresClone:937560 (SEQ ID NO:67), CeresClone:456844 (SEQ ID NO:69), GI No. 125564100 (SEQ ID NO:70), GI No. 52077334 (SEQ ID NO:71), GI No. 113205234 (SEQ ID NO:73), and CeresAnnot:6100272 (SEQ ID NO:75).

FIG. 3 is an alignment of ME01463 (SEQ ID NO:77) with homologous and/or orthologous amino acid sequences GI No. 2811029 (SEQ ID NO:78), CeresClone:1853284 (SEQ ID NO:80), CeresAnnot:1476446 (SEQ ID NO:82), CeresClone:527024 (SEQ ID NO:87), GI No. 27527063 (SEQ ID NO:88), CeresClone:913632 (SEQ ID NO:90), CeresClone:1386710 (SEQ ID NO:92), GI No. 115461885 (SEQ ID NO:93), and CeresAnnot:6054519 (SEQ ID NO:95)

FIG. 4 is an alignment of ME01910 (SEQ ID NO:100) with homologous and/or orthologous amino acid sequences GI No. 585238 (SEQ ID NO:101), GI No. 90704789 (SEQ ID NO:102), CeresClone:1895729 (SEQ ID NO:104), CeresAnnot:1442808 (SEQ ID NO:108), CeresClone:1104700 (SEQ ID NO:113), GI No. 32966575 (SEQ ID NO:116), GI No. 4996567 (SEQ ID NO:117), GI No. 62286644 (SEQ ID NO:118), GI No. 2623960 (SEQ ID NO:119), GI No. 585241 (SEQ ID NO:120), GI No. 790929 (SEQ ID NO:122), CeresClone:579112 (SEQ ID NO:125), CeresClone:244199 (SEQ ID NO:137), CeresClone:1725848 (SEQ ID NO:144), GI No. 6474950 (SEQ ID NO:145), GI No. 125546057 (SEQ ID NO:146), GI No. 115455945 (SEQ ID NO:147), GI No. 2641211 (SEQ ID NO:149), and GI No. 30024108 (SEQ ID NO:150).

FIG. 5 is an alignment of ME02538 (SEQ ID NO:152) with homologous and/or orthologous amino acid sequences CeresClone:1843642 (SEQ ID NO:154), CeresAnnot:1459112 (SEQ ID NO:158), CeresClone:953633 (SEQ ID NO:162), and CeresClone:587957 (SEQ ID NO:164).

FIG. 6 is an alignment of ME02603 (SEQ ID NO:166) with homologous and/or orthologous amino acid sequences CeresClone:1857256 (SEQ ID NO:168), CeresAnnot:1442042 (SEQ ID NO:170), GI No. 89257469 (SEQ ID NO:174), CeresClone:389818 (SEQ ID NO:177), CeresClone:2019147 (SEQ ID NO:181), GI No. 125537720 (SEQ ID NO:182), GI No. 115443697 (SEQ ID NO:183), and GI No. 20340241 (SEQ ID NO:184).

FIG. 7 is an alignment of ME02613 (SEQ ID NO:186) with homologous and/or orthologous amino acid sequences CeresAnnot:1490274 (SEQ ID NO:188), CeresClone:873093 (SEQ ID NO:193), GI No. 6635384 (SEQ ID NO:194), CeresClone:663726 (SEQ ID NO:196), GI No. 92881411 (SEQ ID NO:197), CeresClone:686525 (SEQ ID NO:199), CeresClone:1524364 (SEQ ID NO:201), CeresClone:1742159 (SEQ ID NO:203), and GI No. 125543535 (SEQ ID NO:204).

FIG. 8 is an alignment of ME02801 (SEQ ID NO:208) with homologous and/or orthologous amino acid sequences CeresClone:981621 (SEQ ID NO:214) and CeresClone:564714 (SEQ ID NO:216).

FIG. 9 is an alignment of ME03123 (SEQ ID NO:218) with homologous and/or orthologous amino acid sequences CeresClone:1899168 (SEQ ID NO:220), CeresAnnot:1494669 (SEQ ID NO:222), CeresClone:1017441 (SEQ ID NO:225), CeresClone:1065937 (SEQ ID NO:227), CeresClone:1822919 (SEQ ID NO:229), GI No. 125553329 (SEQ ID NO:230), GI No. 115439053 (SEQ ID NO:231), and CeresAnnot:6040744 (SEQ ID NO:1052).

FIG. 10 is an alignment of ME04204 (SEQ ID NO:234) with homologous and/or orthologous amino acid sequences CeresAnnot:1519952 (SEQ ID NO:236), CeresClone:

234768 (SEQ ID NO:241), GI No. 108707052 (SEQ ID NO:242), and GI No. 55978030 (SEQ ID NO:244).

Figure 11:
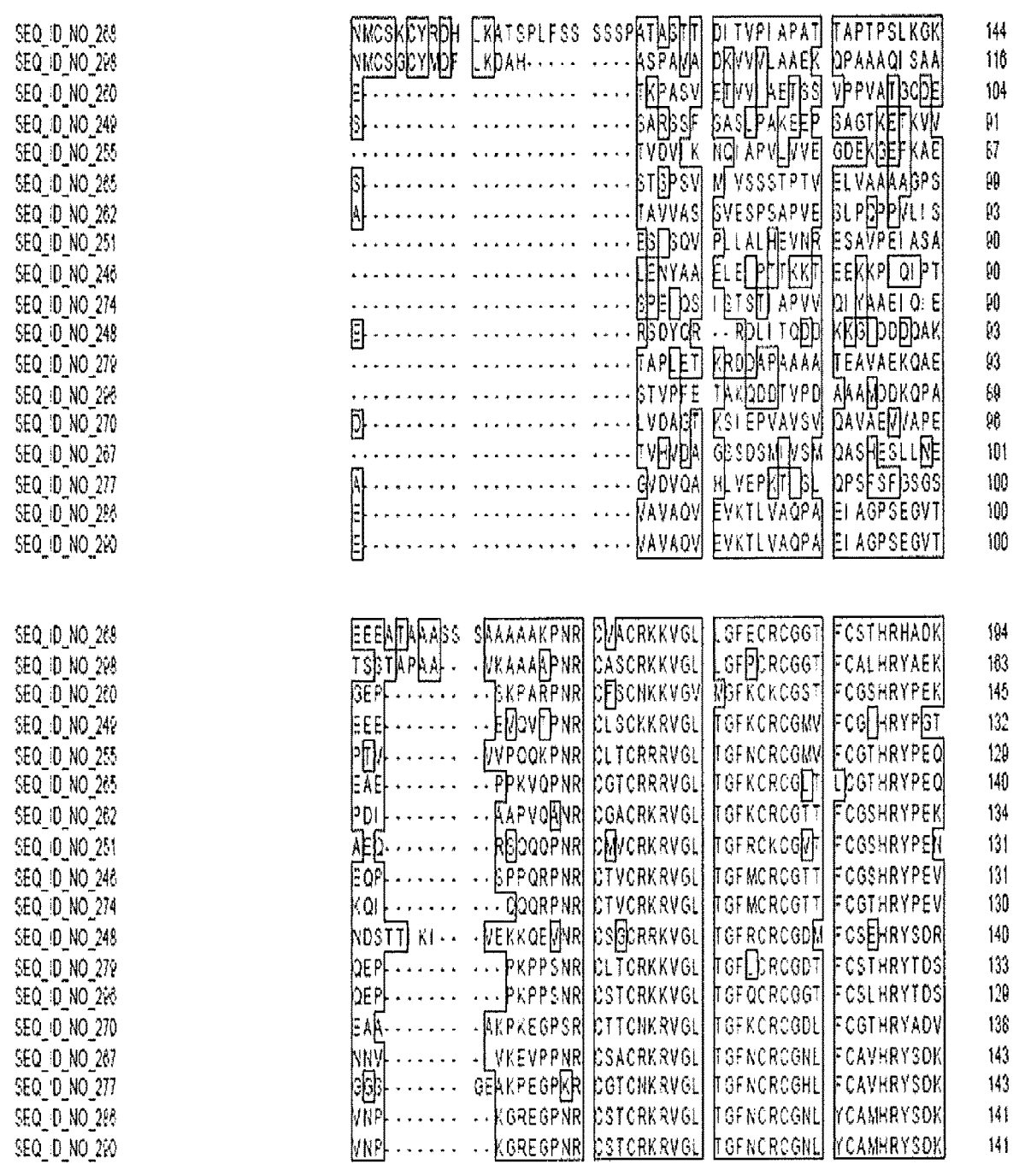

FIG. 11 s an alignment of ME04477 (SEQ ID NO:246) with homologous and/or orthologous amino acid sequences CeresClone:1620215 (SEQ ID NO:248), GI No. 38016527 (SEQ ID NO:249), CeresClone:1798756 (SEQ ID NO:251), CeresAnnot:1460527 (SEQ ID NO:255), GI No. 119720772 (SEQ ID NO:260), CeresClone:708446 (SEQ ID NO:262), GI No. 92896423 (SEQ ID NO:265), GI No. 113196593 (SEQ ID NO:267), GI No. 75133829 (SEQ ID NO:268), CeresClone:1030374 (SEQ ID NO:270), CeresClone:1387149 (SEQ ID NO:274), GI No. 5031281 (SEQ ID NO:277), CeresClone:1775820 (SEQ ID NO:279), GI No. 35187687 (SEQ ID NO:286), GI No. 115468934 (SEQ ID NO:290), GI No. 118424243 (SEQ ID NO:296), and CeresAnnot:6063957 (SEQ ID NO:298).

FIG. 12 is an alignment of ME04507 (SEQ ID NO:300) with homologous and/or orthologous amino acid sequences CeresAnnot:1513514 (SEQ ID NO:302), CeresClone:923483 (SEQ ID NO:310), CeresClone:304357 (SEQ ID NO:312), CeresClone:1902716 (SEQ ID NO:316), GI No. 116309713 (SEQ ID NO:319), GI No. 38345408 (SEQ ID NO:321), and CeresAnnot:6017635 (SEQ ID NO:325).

FIG. 13 is an alignment of ME04587 (SEQ ID NO:332) with homologous and/or orthologous amino acid sequences Ceres ANNOT ID no. 1474882 (SEQ ID NO:334), Ceres ANNOT ID no. 553243 (SEQ ID NO:338), Public GI ID no. 5514645 (SEQ ID NO:339), Ceres CLONE ID no. 464376 (SEQ ID NO:341), Public GI ID no. 1345643 (SEQ ID NO:346), Public GI ID no. 5832707 (SEQ ID NO:347), Public GI ID no. 81157968 (SEQ ID NO:348), Public GI ID no. 6118407 (SEQ ID NO:349), Public GI ID no. 5081817 (SEQ ID NO:351), Public GI ID no. 125556057 (SEQ ID NO:353), Public GI ID no. 115468946 (SEQ ID NO:354), Public GI ID no. 5915860 (SEQ ID NO:356), Public GI ID no. 6979544 (SEQ ID NO:358), Public GI ID no. 5832709 (SEQ ID NO:359), Public GI ID no. 6979542 (SEQ ID NO:360), Public GI ID no. 14278923 (SEQ ID NO:364), Public GI ID no. 81157970 (SEQ ID NO:365), Public GI ID no. 81157972 (SEQ ID NO:366), Public GI ID no. 169793907 (SEQ ID NO:2541), Public GI ID no. 84514153 (SEQ ID NO:2543), Public GI ID no. 184202209 (SEQ ID NO:2544), Ceres ANNOT ID no. 8459850 (SEQ ID NO:2546), Ceres ANNOT ID no. 8743452 (SEQ ID NO:2548), Public GI ID no. 157327290 (SEQ ID NO:2549), Public GI ID no. 148839039 (SEQ ID NO:2550), Public GI ID no. 197209782 (SEQ ID NO:2551), Public GI ID no. 171906244 (SEQ ID NO:2553).

FIG. 14 is an alignment of ME04753 (SEQ ID NO:368) with homologous and/or orthologous amino acid sequences GI No. 21388658 (SEQ ID NO:369), GI No. 4704605 (SEQ ID NO:371), GI No. 90704785 (SEQ ID NO:372), GI No. 115529229 (SEQ ID NO:373), GI No. 20152613 (SEQ ID NO:374), CeresClone:1916226 (SEQ ID NO:376), CeresAnnot:1460836 (SEQ ID NO:392), GI No. 83032218 (SEQ ID NO:420), GI No. 1346180 (SEQ ID NO:422), CeresClone:621487 (SEQ ID NO:425), GI No. 6273331 (SEQ ID NO:433), GI No. 92874469 (SEQ ID NO:434), GI No. 1778374 (SEQ ID NO:436), GI No. 18076086 (SEQ ID NO:437), GI No. 2674201 (SEQ ID NO:438), GI No. 2267567 (SEQ ID NO:440), GI No. 544426 (SEQ ID NO:441), GI No. 6911144 (SEQ ID NO:444), GI No. 469071 (SEQ ID NO:447), GI No. 1934994 (SEQ ID NO:450), GI No. 82623423 (SEQ ID NO:451), GI No. 90265701 (SEQ ID NO:454), GI No. 544423 (SEQ ID NO:455), CeresClone:1320097 (SEQ ID NO:458), CeresClone:1469740 (SEQ ID NO:465), CeresClone:1740834 (SEQ ID NO:473), GI No. 2226370 (SEQ ID NO:474), GI No. 27527723 (SEQ ID NO:475), CeresClone:1762613 (SEQ ID NO:477), GI No. 125545195 (SEQ ID NO:488), GI No. 108710322 (SEQ ID NO:494), GI No. 34851124 (SEQ ID NO:504), GI No. 111162637 (SEQ ID NO:505), GI No. 7024451 (SEQ ID NO:506), and GI No. 1229138 (SEQ ID NO:507).

FIG. 15 is an alignment of ME04772 (SEQ ID NO:510) with homologous and/or orthologous amino acid sequences GI No. 38016521 (SEQ ID NO:511), CeresClone:1895044 (SEQ ID NO:513), CeresAnnot:1512198 (SEQ ID NO:517), CeresClone:682503 (SEQ ID NO:521), CeresClone:685324 (SEQ ID NO:523), CeresClone:1384414 (SEQ ID NO:525), CeresClone:1739919 (SEQ ID NO:527), CeresClone:2002832 (SEQ ID NO:529), GI No. 125531563 (SEQ ID NO:530), and GI No. 115478344 (SEQ ID NO:531).

FIG. 16 is an alignment of ME04909 (SEQ ID NO:533) with homologous and/or orthologous amino acid sequences CeresClone:1839156 (SEQ ID NO:535), GI No. 56605378 (SEQ ID NO:536), CeresAnnot:1467946 (SEQ ID NO:538), GI No. 110931704 (SEQ ID NO:539), GI No. 92869601 (SEQ ID NO:542), GI No. 12005328 (SEQ ID NO:543), GI No. 119331596 (SEQ ID NO:546), GI No. 7705206 (SEQ ID NO:547), GI No. 18874263 (SEQ ID NO:548), CeresClone:753605 (SEQ ID NO:550), CeresClone:291733 (SEQ ID NO:552), and GI No. 21902114 (SEQ ID NO:553).

FIG. 17 is an alignment of ME05194 (SEQ ID NO:558) with homologous and/or orthologous amino acid sequences GI No. 400972 (SEQ ID NO:559), GI No. 81158002 (SEQ ID NO:560), CeresClone:1834135 (SEQ ID NO:569), CeresAnnot:1467218 (SEQ ID NO:571), CeresClone:1104143 (SEQ ID NO:575), GI No. 87240745 (SEQ ID NO:576), GI No. 13161397 (SEQ ID NO:577), GI No. 18652400 (SEQ ID NO:578), GI No. 18652398 (SEQ ID NO:579), CeresClone:778892 (SEQ ID NO:581), CeresClone:222523 (SEQ ID NO:583), GI No. 82492267 (SEQ ID NO:584), GI No. 41393750 (SEQ ID NO:585), GI No. 4335857 (SEQ ID NO:586), CeresClone:1776394 (SEQ ID NO:588), GI No. 125555681 (SEQ ID NO:589), GI No. 115468460 (SEQ ID NO:590), and GI No. 51980210 (SEQ ID NO:591).

FIG. 18 is an alignment of ME05267 (SEQ ID NO:593) with homologous and/or orthologous amino acid sequences CeresAnnot:1511954 (SEQ ID NO:595), CeresClone:560687 (SEQ ID NO:599), CeresClone:579724 (SEQ ID NO:603), CeresClone:286197 (SEQ ID NO:605), and GI No. 115489090 (SEQ ID NO:610).

FIG. 19 is an alignment of ME05300 (SEQ ID NO:613) with homologous and/or orthologous amino acid sequences CeresAnnot:6431448 (SEQ ID NO:615), CeresClone:969084 (SEQ ID NO:620), CeresClone:471052 (SEQ ID NO:622), CeresClone:733048 (SEQ ID NO:624), CeresClone:1062332 (SEQ ID NO:626), CeresClone:1743166 (SEQ ID NO:634), CeresClone:1778589 (SEQ ID NO:638), GI No. 125548354 (SEQ ID NO:643), and GI No. 115458464 (SEQ ID NO:644).

FIG. 20 is an alignment of ME05341 (SEQ ID NO:646) with homologous and/or orthologous amino acid sequences CeresClone:1808421 (SEQ ID NO:648), CeresAnnot:1452653 (SEQ ID NO:656), CeresClone:1660955 (SEQ ID NO:660), CeresClone:1287179 (SEQ ID NO:668), CeresClone:1770929 (SEQ ID NO:676), GI No. 125542421 (SEQ ID NO:679), GI No. 115450741 (SEQ ID NO:681), and CeresAnnot:6063505 (SEQ ID NO:685).

FIG. 21 is an alignment of ME05392 (SEQ ID NO:687) with homologous and/or orthologous amino acid sequences CeresClone:1841531 (SEQ ID NO:689), CeresAnnot:1507382 (SEQ ID NO:691), CeresClone:978410 (SEQ ID NO:699), CeresClone:527314 (SEQ ID NO:703), GI No. 92893019 (SEQ ID NO:706), CeresClone:638935 (SEQ ID NO:708), CeresClone:1437744 (SEQ ID NO:712), Ceres-Clone:1728293 (SEQ ID NO:718), GI No. 125526460 (SEQ ID NO:721), GI No. 115463325 (SEQ ID NO:724), and GI No. 40642817 (SEQ ID NO:728).

FIG. 22 is an alignment of ME05429 (SEQ ID NO:730) with homologous and/or orthologous amino acid sequences CeresAnnot:1539629 (SEQ ID NO:732), CeresClone: 682471 (SEQ ID NO:735), CeresClone:729869 (SEQ ID NO:737), GI No. 115459766 (SEQ ID NO:738), and CeresAnnot:6026765 (SEQ ID NO:742).

FIG. 23 is an alignment of ME05493 (SEQ ID NO:746) with homologous and/or orthologous amino acid sequences CeresAnnot:1455092 (SEQ ID NO:748), GI No. 15229284 (SEQ ID NO:751), CeresClone:961796 (SEQ ID NO:753), CeresClone:706956 (SEQ ID NO:755), GI No. 87162911 (SEQ ID NO:758), CeresClone:1061446 (SEQ ID NO:760), GI No. 125540686 (SEQ ID NO:761), GI No. 115447931 (SEQ ID NO:762), GI No. 20152976 (SEQ ID NO:763), and CeresAnnot:6007280 (SEQ ID NO:765).

FIG. 24 is an alignment of ME05885 (SEQ ID NO:769) with homologous and/or orthologous amino acid sequences CeresClone:1808741 (SEQ ID NO:771), CeresAnnot: 1437729 (SEQ ID NO:773), CeresClone:952789 (SEQ ID NO:777), CeresClone:724313 (SEQ ID NO:779), Ceres-Clone:791239 (SEQ ID NO:783), CeresClone:208975 (SEQ ID NO:785), CeresClone:1727075 (SEQ ID NO:789), and GI No. 115475611 (SEQ ID NO:790).

FIG. 25 is an alignment of ME07344 (SEQ ID NO:792) with homologous and/or orthologous amino acid sequences CeresClone:1843695 (SEQ ID NO:794), GI No. 56605376 (SEQ ID NO:799), CeresAnnot:1508502 (SEQ ID NO:801), CeresClone:1239229 (SEQ ID NO:805), GI No. 92893962 (SEQ ID NO:808), CeresClone:327364 (SEQ ID NO:810), CeresClone:1820378 (SEQ ID NO:816), GI No. 125524748 (SEQ ID NO:819), and GI No. 115435036 (SEQ ID NO:821).

FIG. 26 is an alignment of ME07859 (SEQ ID NO:824) with homologous amino acid sequence Fragment_of_Ceres ANNOT ID no. 6007357 (SEQ ID NO:826), Fragment_of_Ceres CLONE ID no. 771707 (SEQ ID NO:1708), and Fragment_of_Ceres CLONE ID no. 1790436 (SEQ ID NO:1713).

FIG. 27 is an alignment of ME08464 (SEQ ID NO:828) with homologous and/or orthologous amino acid sequences CeresAnnot:1499777 (SEQ ID NO:832), GI No. 22328730 (SEQ ID NO:837), GI No. 92886131 (SEQ ID NO:839), GI No. 559921 (SEQ ID NO:840), CeresClone:910787 (SEQ ID NO:842), CeresClone:1797432 (SEQ ID NO:844), GI No. 116310135 (SEQ ID NO:845), GI No. 38345464 (SEQ ID NO:847), and GI No. 90657544 (SEQ ID NO:850).

FIG. 28 is an alignment of ME11735 (SEQ ID NO:855) with homologous and/or orthologous amino acid sequences GI No. 35187445 (SEQ ID NO:856), CeresClone:1798230 (SEQ ID NO:858), CeresAnnot:1500963 (SEQ ID NO:862), CeresClone:567542 (SEQ ID NO:868), CeresClone:702251 (SEQ ID NO:870), CeresClone:1606777 (SEQ ID NO:876), CeresClone:1789146 (SEQ ID NO:878), GI No. 116309500 (SEQ ID NO:885), and GI No. 115446281 (SEQ ID NO:886).

FIG. 29 is an alignment of ME12910 (SEQ ID NO:891) with homologous and/or orthologous amino acid sequences CeresAnnot:1466353 (SEQ ID NO:893), CeresClone: 519143 (SEQ ID NO:898), GI No. 2501497 (SEQ ID NO:901), GI No. 119394507 (SEQ ID NO:904), GI No. 62857206 (SEQ ID NO:905), CeresClone:766529 (SEQ ID NO:907), GI No. 62857204 (SEQ ID NO:908), GI No. 125534279 (SEQ ID NO:911), GI No. 115485437 (SEQ ID NO:912), GI No. 23955910 (SEQ ID NO:913), and GI No. 22759895 (SEQ ID NO:915).

FIG. 30 is an alignment of ME12927 (SEQ ID NO:917) with homologous and/or orthologous amino acid sequences CeresAnnot:1503548 (SEQ ID NO:919), CeresClone:37778 (SEQ ID NO:921), CeresClone:681297 (SEQ ID NO:923), CeresClone:575835 (SEQ ID NO:925), CeresClone: 1714750 (SEQ ID NO:935), CeresClone:1721907 (SEQ ID NO:937), and GI No. 115451923 (SEQ ID NO:940).

FIG. 31 is an alignment of ME12929 (SEQ ID NO:944) with homologous and/or orthologous amino acid sequences CeresAnnot:1447562 (SEQ ID NO:946), GI No. 98962139 (SEQ ID NO:947), CeresClone:641607 (SEQ ID NO:950), CeresClone:1715150 (SEQ ID NO:962), CeresClone: 1873767 (SEQ ID NO:964), GI No. 115468306 (SEQ ID NO:967), and CeresAnnot:6059980 (SEQ ID NO:972).

FIG. 32 is an alignment of ME12954 (SEQ ID NO:976) with homologous and/or orthologous amino acid sequences CeresClone:957229 (SEQ ID NO:978) and CeresAnnot: 1496202 (SEQ ID NO:980).

FIG. 33 is an alignment of ME12970 (SEQ ID NO:982) with homologous and/or orthologous amino acid sequences CeresClone:1935438 (SEQ ID NO:984), GI No. 117573664 (SEQ ID NO:985), GI No. 68349002 (SEQ ID NO:991), GI No. 68348998 (SEQ ID NO:992), CeresAnnot:1497170 (SEQ ID NO:995), GI No. 15221718 (SEQ ID NO:996), GI No. 3860331 (SEQ ID NO:1001), CeresClone:1075911 (SEQ ID NO:1003), GI No. 2920839 (SEQ ID NO:1008), CeresClone:698452 (SEQ ID NO:1011), CeresClone: 2019456 (SEQ ID NO:1023), GI No. 90399071 (SEQ ID NO:1026), GI No. 115459588 (SEQ ID NO:1028), and GI No. 68349016 (SEQ ID NO:1032).

FIG. 34 is an alignment of ME13021 (SEQ ID NO:1054) with homologous and/or orthologous amino acid sequences GI No. 2493647 (SEQ ID NO:1055), CeresClone:1924252 (SEQ ID NO:1057), GI No. 461736 (SEQ ID NO:1058), CeresAnnot:1542060 (SEQ ID NO:1061), GI No. 15226314 (SEQ ID NO:1068), GI No. 464727 (SEQ ID NO:1072), CeresClone:480644 (SEQ ID NO:1074), GI No. 124301264 (SEQ ID NO:1075), GI No. 1710807 (SEQ ID NO:1076), GI No. 110349923 (SEQ ID NO:1077), GI No. 1762130 (SEQ ID NO:1078), CeresClone:706098 (SEQ ID NO:1080), GI No. 3790441 (SEQ ID NO:1083), Ceres-Clone:1795282 (SEQ ID NO:1085), GI No. 125546535 (SEQ ID NO:1086), GI No. 115488160 (SEQ ID NO:1088), GI No. 84468456 (SEQ ID NO:1092), GI No. 116060917 (SEQ ID NO:1095), and CeresAnnot:6039555 (SEQ ID NO:1097).

FIG. 35 is an alignment of ME13064 (SEQ ID NO:1099) with homologous and/or orthologous amino acid sequences CeresAnnot:1528508 (SEQ ID NO:1101), CeresClone:9248 (SEQ ID NO:1103), GI No. 87240560 (SEQ ID NO:1105), GI No. 19453 (SEQ ID NO:1106), CeresClone:1795329 (SEQ ID NO:1108), and GI No. 108862979 (SEQ ID NO:1109).

FIG. 36 is an alignment of ME13071 (SEQ ID NO:1112) with homologous and/or orthologous amino acid sequences GI No. 125541485 (SEQ ID NO:1113), and GI No. 115449245 (SEQ ID NO:1114).

FIG. 37 is an alignment of ME13087 (SEQ ID NO:1116) with homologous and/or orthologous amino acid sequences CeresClone:100062822 (SEQ ID NO:1118), CeresAnnot: 1440025 (SEQ ID NO:1120), GI No. 15238538 (SEQ ID NO:1123), GI No. 69111473 (SEQ ID NO:1129), GI No. 92873711 (SEQ ID NO:1132), GI No. 55734106 (SEQ ID NO:1133), GI No. 2346974 (SEQ ID NO:1134), Ceres-Clone:569852 (SEQ ID NO:1136), CeresClone:1715326 (SEQ ID NO:1138), CeresClone:1608104 (SEQ ID NO:1140), CeresClone:115456237 (SEQ ID NO:1141), GI No. 68655289 (SEQ ID NO:1143), GI No. 81022807 (SEQ ID NO:1144), GI No. 75706704 (SEQ ID NO:1145), and CeresAnnot:6016055 (SEQ ID NO:1147).

FIG. 38 is an alignment of ME13107 (SEQ ID NO:1159) with homologous and/or orthologous amino acid sequences CeresClone:1371824 (SEQ ID NO:1161), GI No. 22585 (SEQ ID NO:1162), GI No. 22208482 (SEQ ID NO:1163), and GI No. 16073 (SEQ ID NO:1164).

FIG. 39 is an alignment of ME13108 (SEQ ID NO:1166) with homologous and/or orthologous amino acid sequences GI No. 99109436 (SEQ ID NO:1167), CeresClone:1627939 (SEQ ID NO:1169), CeresClone:1840433 (SEQ ID NO:1171), CeresAnnot:1524198 (SEQ ID NO:1173), CeresClone:1650 (SEQ ID NO:1175), CeresClone:691979 (SEQ ID NO:1177), GI No. 92876897 (SEQ ID NO:1180), CeresClone:1774130 (SEQ ID NO:1182), and GI No. 115450018 (SEQ ID NO:1183).

FIG. 40 is an alignment of ME13110 (SEQ ID NO:1185) with homologous and/or orthologous amino acid sequences CeresClone:737317 (SEQ ID NO:1187), CeresClone:1880853 (SEQ ID NO:1189), GI No. 125558381 (SEQ ID NO:1190), and GI No. 115472157 (SEQ ID NO:1191).

FIG. 41 is an alignment of ME13125 (SEQ ID NO:1194) with homologous and/or orthologous amino acid sequences CeresClone:1938817 (SEQ ID NO:1196), CeresAnnot:1457245 (SEQ ID NO:1200), CeresClone:577910 (SEQ ID NO:1202), Public PUBLICCLONE ID no. 100736184 (SEQ ID NO:1203), GI No. 125553355 (SEQ ID NO:1204), and GI No. 5091600 (SEQ ID NO:1205).

FIG. 42 is an alignment of ME13149 (SEQ ID NO:1210) with homologous and/or orthologous amino acid sequences GI No. 1703374 (SEQ ID NO:1211), CeresClone:1846330 (SEQ ID NO:1213), GI No. 29124979 (SEQ ID NO:1216), CeresAnnot:1531725 (SEQ ID NO:1218), GI No. 3334321 (SEQ ID NO:1229), CeresClone:571410 (SEQ ID NO:1232), GI No. 39653273 (SEQ ID NO:1233), GI No. 92875403 (SEQ ID NO:1234), GI No. 11131026 (SEQ ID NO:1235), GI No. 77812440 (SEQ ID NO:1236), GI No. 89475524 (SEQ ID NO:1238), GI No. 3182919 (SEQ ID NO:1239), GI No. 7643794 (SEQ ID NO:1240), GI No. 1710851 (SEQ ID NO:1241), GI No. 115501471 (SEQ ID NO:1242), GI No. 77999251 (SEQ ID NO:1243), GI No. 3450893 (SEQ ID NO:1249), CeresClone:704589 (SEQ ID NO:1251), CeresClone:1384151 (SEQ ID NO:1253), CeresClone:1713894 (SEQ ID NO:1259), GI No. 125560752 (SEQ ID NO:1264), GI No. 115475543 (SEQ ID NO:1265), GI No. 3182922 (SEQ ID NO:1267), GI No. 145353078 (SEQ ID NO:1268), GI No. 11131023 (SEQ ID NO:1269), GI No. 47026845 (SEQ ID NO:1270), and GI No. 38353642 (SEQ ID NO:1272).

FIG. 43 is an alignment of ME13151 (SEQ ID NO:1274) with homologous and/or orthologous amino acid sequences CeresClone:1884601 (SEQ ID NO:1276), CeresAnnot:1445717 (SEQ ID NO:1280), CeresClone:527903 (SEQ ID NO:1284), GI No. 92891722 (SEQ ID NO:1285), CeresClone:790881 (SEQ ID NO:1287), CeresClone:299417 (SEQ ID NO:1289), CeresClone:1993894 (SEQ ID NO:1291), GI No. 125539547 (SEQ ID NO:1294), GI No. 48716424 (SEQ ID NO:1295), GI No. 84468278 (SEQ ID NO:1297), and CeresAnnot:6036303 (SEQ ID NO:1300).

FIG. 44 is an alignment of ME13153 (SEQ ID NO:1302) with homologous and/or orthologous amino acid sequences GI No. 70609690 (SEQ ID NO:1303), CeresClone:1927524 (SEQ ID NO:1305), CeresAnnot:1467310 (SEQ ID NO:1311), GI No. 45935270 (SEQ ID NO:1313), CeresClone:718446 (SEQ ID NO:1317), GI No. 92875133 (SEQ ID NO:1318), GI No. 1706318 (SEQ ID NO:1319), GI No. 3252856 (SEQ ID NO:1320), GI No. 1169238 (SEQ ID NO:1326), GI No. 31296711 (SEQ ID NO:1327), CeresClone:1468893 (SEQ ID NO:1330), GI No. 51587340 (SEQ ID NO:1331), CeresClone:1796201 (SEQ ID NO:1333), GI No. 125543034 (SEQ ID NO:1334), GI No. 115476804 (SEQ ID NO:1336), GI No. 75268060 (SEQ ID NO:1339), and GI No. 75268007 (SEQ ID NO:1340).

FIG. 45 is an alignment of ME13177 (SEQ ID NO:1342) with homologous and/or orthologous amino acid sequences CeresAnnot:1443786 (SEQ ID NO:1346), GI No. 15239172 (SEQ ID NO:1355), GI No. 562190 (SEQ ID NO:1363), GI No. 83032266 (SEQ ID NO:1364), CeresClone:602910 (SEQ ID NO:1366), GI No. 7242793 (SEQ ID NO:1370), GI No. 116167 (SEQ ID NO:1371), GI No. 2190259 (SEQ ID NO:1372), GI No. 5420278 (SEQ ID NO:1373), GI No. 1064931 (SEQ ID NO:1374), GI No. 6093215 (SEQ ID NO:1377), GI No. 461726 (SEQ ID NO:1378), GI No. 89111295 (SEQ ID NO:1379), GI No. 82949283 (SEQ ID NO:1380), GI No. 125537180 (SEQ ID NO:1381), GI No. 115489300 (SEQ ID NO:1382), and GI No. 55978000 (SEQ ID NO:1383).

FIG. 46 is an alignment of ME13200 (SEQ ID NO:1385) with homologous and/or orthologous amino acid sequences CeresAnnot:1503394 (SEQ ID NO:1387), GI No. 4914437 (SEQ ID NO:1390), CeresClone:638126 (SEQ ID NO:1393), GI No. 124360540 (SEQ ID NO:1394), GI No. 7981380 (SEQ ID NO:1395), GI No. 118137433 (SEQ ID NO:1396), CeresClone:1723374 (SEQ ID NO:1398), CeresClone:1785379 (SEQ ID NO:1400), GI No. 125553354 (SEQ ID NO:1401), GI No. 115471859 (SEQ ID NO:1404), and CeresAnnot:6040771 (SEQ ID NO:1407).

FIG. 47 is an alignment of ME13204 (SEQ ID NO:1409) with homologous and/or orthologous amino acid sequences CeresClone:1939206 (SEQ ID NO:1413), CeresAnnot:1453316 (SEQ ID NO:1415), GI No. 79319075 (SEQ ID NO:1418), GI No. 124359953 (SEQ ID NO:1419), CeresClone:891431 (SEQ ID NO1421), GI No. 125536578 (SEQ ID NO:1424), and GI No. 20270065 (SEQ ID NO:1425).

FIG. 48 is an alignment of ME14649 (SEQ ID NO:1428) with homologous and/or orthologous amino acid sequences CeresClone:1978733 (SEQ ID NO:1430), CeresAnnot:1476165 (SEQ ID NO:1432), CeresClone:871529 (SEQ ID NO:1436), CeresClone:1043344 (SEQ ID NO:1439), CeresClone:786542 (SEQ ID NO:1442), CeresClone:346115 (SEQ ID NO:1444), CeresClone:1821683 (SEQ ID NO:1452), GI No. 125533171 (SEQ ID NO:1453), and GI No. 77553492 (SEQ ID NO:1457)

FIG. 49 is an alignment of ME16546 (SEQ ID NO:1463) with homologous and/or orthologous amino acid sequences CeresAnnot:1444102 (SEQ ID NO:1465), CeresClone:582439 (SEQ ID NO:1471), CeresClone:579953 (SEQ ID NO:1473), GI No. 125539335 (SEQ ID NO:1474), and GI No. 115445987 (SEQ ID NO:1476).

FIG. 50 is an alignment of ME17567 (SEQ ID NO:1491) with homologous and/or orthologous amino acid sequences CeresClone:1895876 (SEQ ID NO:1493), CeresAnnot:1464522 (SEQ ID NO:1495), CeresClone:968434 (SEQ ID NO:1499), CeresClone:686479 (SEQ ID NO:1501), CeresClone:1564962 (SEQ ID NO:1503), GI No. 125549699 (SEQ ID NO:1504), GI No. 125591612 (SEQ ID NO:1505), and CeresAnnot:6006969 (SEQ ID NO:1508).

FIG. 51 is an alignment of ME17932 (SEQ ID NO:1510) with homologous and/or orthologous amino acid sequences CeresClone:1842178 (SEQ ID NO:1512), CeresAnnot: 1475265 (SEQ ID NO:1516) and CeresClone:1044646 (SEQ ID NO:1520).

FIG. 52 is an alignment of ME17936 (SEQ ID NO:1525) with homologous and/or orthologous amino acid sequences CeresAnnot:1454324 (SEQ ID NO:1527), CeresClone: 1652842 (SEQ ID NO:1534), and GI No. 75214620 (SEQ ID NO:1535).

FIG. 53 is an alignment of ME18275 (SEQ ID NO:1537) with homologous and/or orthologous amino acid sequences CeresAnnot:1514086 (SEQ ID NO:1539), CeresClone: 1087909 (SEQ ID NO:1543), CeresClone:1359070 (SEQ ID NO:1545), GI No. 92880913 (SEQ ID NO:1548), Ceres-Clone:932449 (SEQ ID NO:1550), and CeresClone: 1788695 (SEQ ID NO:1552).

FIG. 54 is an alignment of ME18924 (SEQ ID NO:1554) with homologous and/or orthologous amino acid sequences GI No. 82469976 (SEQ ID NO:1555), CeresAnnot:1533704 (SEQ ID NO:1563), CeresClone:524404 (SEQ ID NO:1565), CeresClone:846541 (SEQ ID NO:1567), Ceres-Clone:1769321 (SEQ ID NO:1571), GI No. 125528559 (SEQ ID NO:1572), GI No. 125572823 (SEQ ID NO:1574), and GI No. 84453208 (SEQ ID NO:1575).

FIG. 55 is an alignment of ME19182 (SEQ ID NO:1577) with homologous and/or orthologous amino acid sequences GI No. 4033417 (SEQ ID NO:1040), GI No. 5669924 (SEQ ID NO:1041), GI No. 40642617 (SEQ ID NO:1440), GI No. 90399018 (SEQ ID NO:1485), GI No. 115464117 (SEQ ID NO:1487), GI No. 75164812 (SEQ ID NO:1578), Ceres-Clone:1794223 (SEQ ID NO:1580), CeresAnnot:1471422 (SEQ ID NO:1590), CeresClone:968096 (SEQ ID NO:1607), GI No. 6752884 (SEQ ID NO:1608), GI No. 47775656 (SEQ ID NO:1609), CeresClone:1020799 (SEQ ID NO:1611), GI No. 87240865 (SEQ ID NO:1622), GI No. 2500047 (SEQ ID NO:1623), CeresClone:705340 (SEQ ID NO:1627), CeresClone:1430456 (SEQ ID NO:1637), GI No. 84619270 (SEQ ID NO:1648), and CeresClone: 1821143 (SEQ ID NO:1651).

FIG. 56 is an alignment of ME20628 (SEQ ID NO:1437) with homologous and/or orthologous amino acid sequences GI No. 113367236 (SEQ ID NO:173), GI No. 115477615 (SEQ ID NO:212), GI No. 125542223 (SEQ ID NO:361), GI No. 1838976 (SEQ ID NO:421), CeresClone:1547185 (SEQ ID NO:443), CeresAnnot:1450452 (SEQ ID NO:740), and GI No. 92870675 (SEQ ID NO:1461).

FIG. 57 is an alignment of ME01821 (SEQ ID NO:97) with homologous and/or orthologous amino acid sequences Public GI ID no. 167480754 (SEQ ID NO:2013) and Public GI ID no. 83830869 (SEQ ID NO:2015).

DETAILED DESCRIPTION

The invention provides methods and materials related to modulating low-nitrogen tolerance levels in plants. In some embodiments, the plants may also have modulated levels of low-nitrogen tolerance. The methods can include transforming a plant cell with a nucleic acid encoding a low nitrogen tolerance-modulating polypeptide, wherein expression of the polypeptide results in a modulated level of low-nitrogen tolerance. Plant cells produced using such methods can be grown to produce plants having an increased tolerance to conditions with limiting exogenous nitrogen sources. Such plants can be used for the production of higher yields and biomasses with existing fertilizer inputs, and/or enable existing yields and biomass of crops to be obtained with lower fertilizer input, or better yields and biomasses on soils of poorer quality.

I. DEFINITIONS

"Amino acid" refers to one of the twenty biologically occurring amino acids and to synthetic amino acids, including D/L optical isomers.

"Cell type-preferential promoter" or "tissue-preferential promoter" refers to a promoter that drives expression preferentially in a target cell type or tissue, respectively, but may also lead to some transcription in other cell types or tissues as well.

"Control plant" refers to a plant that does not contain the exogenous nucleic acid present in a transgenic plant of interest, but otherwise has the same or similar genetic background as such a transgenic plant. A suitable control plant can be a non-transgenic wild type plant, a non-transgenic segregant from a transformation experiment, or a transgenic plant that contains an exogenous nucleic acid other than the exogenous nucleic acid of interest.

"Domains" are groups of substantially contiguous amino acids in a polypeptide that can be used to characterize protein families and/or parts of proteins. Such domains have a "fingerprint" or "signature" that can comprise conserved primary sequence, secondary structure, and/or three-dimensional conformation. Generally, domains are correlated with specific in vitro and/or in vivo activities. A domain can have a length of from 10 amino acids to 400 amino acids, e.g., 10 to 50 amino acids, or 25 to 100 amino acids, or 35 to 65 amino acids, or 35 to 55 amino acids, or 45 to 60 amino acids, or 200 to 300 amino acids, or 300 to 400 amino acids.

"Down-regulation" refers to regulation that decreases production of expression products (mRNA, polypeptide, or both) relative to basal or native states.

"Exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell under consideration. For example, a transgenic plant containing an exogenous nucleic acid can be the progeny of a cross between a stably transformed plant and a non-transgenic plant. Such progeny are considered to contain the exogenous nucleic acid.

"Expression" refers to the process of converting genetic information of a polynucleotide into RNA through transcription, which is catalyzed by an enzyme, RNA polymerase, and into protein, through translation of mRNA on ribosomes.

"Heterologous polypeptide" as used herein refers to a polypeptide that is not a naturally occurring polypeptide in a plant cell, e.g., a transgenic *Panicum virgatum* plant transformed with and expressing the coding sequence for a nitrogen transporter polypeptide from a *Zea mays* plant.

"Isolated nucleic acid" as used herein includes a naturally-occurring nucleic acid, provided one or both of the sequences immediately flanking that nucleic acid in its naturally-occurring genome is removed or absent. Thus, an isolated nucleic acid includes, without limitation, a nucleic acid that exists as a purified molecule or a nucleic acid molecule that is incorporated into a vector or a virus. A nucleic acid existing among hundreds to millions of other nucleic acids within, for example, cDNA libraries, genomic libraries, or gel slices containing a genomic DNA restriction digest, is not to be considered an isolated nucleic acid.

"Low Nitrogen Conditions" as used herein refers to nitrogen concentrations which lead to nitrogen deficiency symptoms such as pale green leaf color, chlorosis and reduced growth and vigor. Typically, low nitrogen conditions lead to a reduction of at least 20%, 25%, 30%, 35%, 40%, 45%, 50%, 60%, 70%, 80% or 90% in growth and/or vigor.

"Modulation" of the level of low-nitrogen tolerance refers to the change in the level of tolerance of a plant to limiting exogenous nitrogen sources that is observed as a result of expression of, or transcription from, an exogenous nucleic acid in a plant cell. The change in low-nitrogen tolerance level is measured by changes in plant size and greenness as well as greater photosynthesis efficiency, relative to the corresponding level in control plants in an environment with limiting nitrogen supply.

"Nucleic acid" and "polynucleotide" are used interchangeably herein, and refer to both RNA and DNA, including cDNA, genomic DNA, synthetic DNA, and DNA or RNA containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, nucleic acid probes and nucleic acid primers. A polynucleotide may contain unconventional or modified nucleotides.

"Operably linked" refers to the positioning of a regulatory region and a sequence to be transcribed in a nucleic acid so that the regulatory region is effective for regulating transcription or translation of the sequence. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site.

"Polypeptide" as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. Full-length polypeptides, truncated polypeptides, point mutants, insertion mutants, splice variants, chimeric proteins, and fragments thereof are encompassed by this definition.

"Progeny" includes descendants of a particular plant or plant line. Progeny of an instant plant include seeds formed on $F_1$, $F_2$, $F_3$, $F_4$, $F_5$, $F_6$ and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. The designation $F_1$ refers to the progeny of a cross between two parents that are genetically distinct. The designations $F_2$, $F_3$, $F_4$, $F_5$ and $F_6$ refer to subsequent generations of self- or sib-pollinated progeny of an $F_1$ plant.

"Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al. (1989) *The Plant Cell*, 1:977-984.

"Up-regulation" refers to regulation that increases the level of an expression product (mRNA, polypeptide, or both) relative to basal or native states.

"Vector" refers to a replicon, such as a plasmid, phage, or cosmid, into which another DNA segment may be inserted so as to bring about the replication of the inserted segment. Generally, a vector is capable of replication when associated with the proper control elements. The term "vector" includes cloning and expression vectors, as well as viral vectors and integrating vectors. An "expression vector" is a vector that includes a regulatory region.

II. POLYPEPTIDES

Polypeptides described herein include low nitrogen tolerance-modulating polypeptides. Low nitrogen tolerance-modulating polypeptides can be effective to modulate low-nitrogen tolerance levels when expressed in a plant or plant cell. Such polypeptides typically contain at least one domain indicative of low nitrogen tolerance-modulating polypeptides, as described in more detail herein. Low nitrogen tolerance-modulating polypeptides typically have an HMM bit score that is greater than 20, as described in more detail herein. In some embodiments, low nitrogen tolerance-modulating polypeptides have greater than 80% identity to SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, or SEQ ID NO:1577, as described in more detail herein.

A. Domains Indicative of Low Nitrogen Tolerance-Modulating Polypeptides

A low nitrogen tolerance-modulating polypeptide can contain a P450 domain, which is characteristic of polypeptides belonging to the Cytochrome P450 superfamily. Cytochrome P450s are haem-thiolate proteins involved in the oxidative degradation of various compounds. They are particularly well known for their role in the degradation of environmental toxins and mutagens. In plants, these proteins are important for the biosynthesis of several compounds such as hormones, defensive compounds and fatty acids. Sequence conservation is relatively low within the family—there are only 3 absolutely conserved residues—but their general topography and structural fold are highly conserved. The conserved core is composed of a coil termed the 'meander', a four-helix bundle, helices J and K, and two sets of beta-sheets. These constitute the haem-binding loop, the proton-transfer groove and the conserved EXXR motif in helix K. While prokaryotic P450s are soluble proteins, most eukaryotic P450s are associated with microsomal membranes. Their general enzymatic function is to catalyse regiospecific and stereospecific oxidation of non-activated hydrocarbons at physiological temperatures. SEQ ID NO:3 and SEQ ID NO:332 set forth the amino acid sequence of Arabidopsis clones, identified herein as ME00919 (SEQ ID NO:3) and ME04587 (SEQ ID NO:332) respectively, that are predicted to encode polypeptides containing a Cytochrome P450 domain.

A low nitrogen tolerance-modulating polypeptide can contain a zf-Dof domain, which is conserved in several DNA-binding proteins of higher plants. Dof domain is a zinc finger DNA-binding domain that shows resemblance to the Cys2 zinc finger, although it has a longer putative loop where an extra Cys residue is typically conserved. The motif is also present in SEQ ID NO:49, which sets forth the amino acid sequence of an Arabidopsis clone, identified herein as Ceres ME01312 (SEQ ID NO:49), that is predicted to encode a polypeptide containing a zf-Dof domain.

A low nitrogen tolerance-modulating polypeptide can contain an Aminotran_3 domain characteristic of polypeptides belonging to the aminotransferase Class-III family. Aminotransferases share certain mechanistic features with other pyridoxalphosphate-dependent enzymes, such as the covalent binding of the pyridoxalphosphate group to a lysine residue. Class-III aminotransferases include acetylornithine aminotransferase, which catalyzes the transfer of an amino group from acetylornithine to alpha-ketoglutarate, yielding N-acetyl-glutamic-5-semi-aldehyde and glutamic acid; ornithine aminotransferase, which catalyzes the transfer of an amino group from ornithine to alpha-ketoglutarate, yielding glutamic-5-semi-aldehyde and glutamic acid; omega-amino acid-pyruvate aminotransferase, which catalyzes transamination between a variety of omega-amino acids, mono- and diamines, and pyruvate; 4-aminobutyrate aminotransferase; GABA transaminase, which catalyzes the transfer of an amino group from GABA to alpha-ketoglutarate, yielding succinate semialdehyde and glutamic acid; DAPA aminotransferase, a bacterial enzyme (bioA), which catalyzes an intermediate step in the biosynthesis of biotin, the transamination of 7-keto-8-aminopelargonic acid to form 7,8-diaminopelargonic acid; 2,2-dialkylglycine decarboxylase, a Burkholderia cepacia (Pseudomonas cepacia) enzyme (dgdA) that catalyzes the decarboxylating amino transfer of 2,2-dialkylglycine and pyruvate to dialkyl ketone, alanine and carbon dioxide; glutamate-1-semialdehyde aminotransferase (GSA); Bacillus subtilis aminotransferases yhxA and yodT; Haemophilus influenzae aminotransferase HI0949; and Caenorhabditis elegans aminotransferase. On the basis of sequence similarity, these various enzymes can be grouped into subfamilies. The aminotran_3 domain is also present in SEQ ID NO:77, which set forth the amino acid sequences of Arabidopsis clone, identified herein as Ceres ME01463 (SEQ ID NO:77), that is predicted to encode polypeptides containing an aminotran_3 domain.

A low nitrogen tolerance-modulating polypeptide can contain a linker histone domain characteristic of polypeptides belonging to the linker histone H1 and H5 family. Linker histone H1 is an essential component of chromatin structure. H1 links nucleosomes into higher order structures. Histone H5 performs the same function as histone H1, and replaces H1 in certain cells. The structure of GH5, the globular domain of the linker histone H5 fold is similar to the DNA-binding domain of the catabolite gene activator protein, CAP, thus providing a possible model for the binding of GH5 to DNA. The domain is also present in SEQ ID NO:100, which sets forth the amino acid sequence of an Arabidopsis clone, identified herein as Ceres ME01910 (SEQ ID NO:100), that is predicted to encode a polypeptide containing a linker histone domain.

A low nitrogen tolerance-modulating polypeptide can contain a zf-C3HC4 domain, which is predicted to be characteristic of proteins belonging to the C3HC4 type zinc finger (RING finger) protein family. The C3HC4 type zinc-finger (RING finger) is a cysteine-rich domain of approximately 40 to 60 residues that coordinates two zinc ions, and is probably involved in mediating protein-protein interactions. Members of the C3HC4 type zinc-finger (RING finger) protein family contain the loosely conserved sequence: C-X2-C-X(9-39)-C-X(1-3)-H-X(2-3)-C-X2-C-X(4-48)-C-X2-C where X is any amino acid. The domain is also present in SEQ ID NOs:166, 746, 976, 1428, which set forth the amino acid sequences of Arabidopsis clones, identified herein as Ceres ME02603 (SEQ ID NO:166), ME05493 (SEQ ID NO:746), ME12954 (SEQ ID NO:976), ME14649 (SEQ ID NO:1428) respectively, that are predicted to encode polypeptides containing a zf-C3HC4 domain.

A low nitrogen tolerance-modulating polypeptide can contain a Gal Lectin domain characteristic of a galactose binding lectin domain protein. SEQ ID NO:208 sets forth the amino acid sequence of an Arabidopsis clone, identified herein as Ceres ME02801 (SEQ ID NO:208), that is predicted to encode a polypeptide containing a galactose binding lectin domain.

A low nitrogen tolerance-modulating polypeptide can contain a TRP_1 domain characteristic of tetratricopeptide repeat (TPR) domain protein. The tetratricopeptide repeat is a structural motif present in a wide range of proteins identified in various different organisms, ranging from bacteria to humans. It mediates protein-protein interactions and the assembly of multiprotein complexes. Sequence alignment of the TPR domains reveals a consensus sequence defined by a pattern of small and large amino acids. Proteins containing TPRs are involved in a variety of biological processes, such as cell cycle regulation, transcriptional control, mitochondrial and peroxisomal protein transport, neurogenesis and protein folding. The X-ray structure of a domain containing three TPRs from protein phosphatase 5 revealed that TPR adopts a helixtumhelix arrangement, with adjacent TPR motifs packing in a parallel fashion, resulting in a spiral of repeating anti-parallel alpha-helices. The two helices are denoted helix A and helix B. The packing angle between helix A and helix B is ~24° within a single TPR and generates a right-handed superhelical shape. Helix A interacts with helix B and with helix A' of the next TPR. Two protein surfaces are generated: the inner concave surface is contributed to mainly by residue on helices A, and the other surface presents residues from both helices A and B.

A low nitrogen tolerance-modulating polypeptide can contain a TRP_2 tetratricopeptide repeat domain, which is predicted to be characteristic of scaffold-proteins in multi-protein complexes. The TPR_2 domain consists of approximately 34-amino-acid motif with a loose consensus and is present, usually as multiple tandem repeats, in proteins with many cellular functions, including mitosis, transcription, protein transport, and development. Structural analysis of the TPR-2 domain demonstrates that it forms two α-helical regions separated by a turn, such that apposed bulky and small side chains form a "knob and hole" structure. In general, the hydrophobic surface of this structure mediates protein-protein interactions between TPR- and non-TPR-containing proteins.

SEQ ID NO:234 sets forth the amino acid sequence of Arabidopsis clone, identified herein as Ceres ME04204 (SEQ ID NO:234), that is predicted to encode a polypeptide containing a TRP_1 tetratricopeptide repeat domain and a TRP 2 tetratricopeptide repeat domain. SEQ ID NO:1510 sets forth the amino acid sequence of Arabidopsis clone, identified herein as Ceres ME17932 (SEQ ID NO:1510), that is predicted to encode a polypeptide containing a TRP_2 tetratricopeptide repeat domain.

A low nitrogen tolerance-modulating polypeptide can contain a zf-AN1 domain characteristic of polypeptides belonging to the AN1-like Zinc finger domain protein family. The AN1-like Zinc finger domain was first identified as a zinc finger at the C-terminus of An1 a ubiquitin-like protein in Xenopus laevis. The following pattern describes the zinc finger: C-X2-C-X(9-12)-C-X(1-2)-C-X4-C-X2-H-X5-H-X-C, where X can be any amino acid, and numbers in brackets indicate the number of residues.

A low nitrogen tolerance-modulating polypeptide can contain a zf-A20 domain, which is characteristic of A20-(an inhibitor of cell death)-like zinc fingers. In animals, A20-like zinc fingers are believed to mediate self-association in A20. These fingers also mediate IL-1-induced NF-kappa B activation. SEQ ID NO: 246 sets forth the amino acid sequence of Arabidopsis clone, identified herein as Ceres ME04477 (SEQ ID NO:246), that is predicted to encode a polypeptide containing an AN1-like Zinc finger domain and zf-A20 domain.

A low nitrogen tolerance-modulating polypeptide can contain an Aa trans domain, or transmembrane amino acid transporter domain, which is predicted to be characteristic of amino acid transporters and amino acid permeases. The domain is also present in SEQ ID NO:300, which sets forth the amino acid sequence of an Arabidopsis clone, identified herein as Ceres ME04507 (SEQ ID NO:300), that is predicted to encode a polypeptide containing an transmembrane amino acid transporter domain.

A low nitrogen tolerance-modulating polypeptide can contain an RNA recognition motif (as known as RRM_1, RRM, RBD, or RNP domain), which is characteristic of polypeptides belonging to the single strand RNA-binding protein superfamily. RRM proteins have a variety of RNA binding preferences and functions, and include heterogeneous nuclear ribonucleoproteins (hnRNPs), proteins implicated in regulation of alternative splicing, protein components of small nuclear ribonucleoproteins, and proteins that regulate RNA stability and translation. The RRM in heterodimeric splicing factor U2 snRNP auxiliary factor (U2AF) appears to have two RRM-like domains with specialized features for protein recognition. The motif also appears in a few single stranded DNA binding proteins. The typical RRM consists of four anti-parallel beta-strands and two alpha-helices arranged in a beta-alpha-beta-beta-alpha-beta fold with side chains that stack with RNA bases. Specificity of RNA binding is determined by multiple contacts with surrounding amino acids. A third helix is present during RNA binding in some cases. The motif is also present in SEQ ID NO:368 and SEQ ID NO:1274, which set forth the amino acid sequences of Arabidopsis clones, identified herein as Ceres ME04753 (SEQ ID NO:368) and ME13151 (SEQ ID NO:1274) respectively, that are predicted to encode polypeptides containing an RNA recognition motif.

A low nitrogen tolerance-modulating polypeptide can contain an NTF2 domain characteristic of a nuclear transport factor 2 (NTF2) polypeptide. NTF2 is a homodimer of approximately 14 kDa subunits which stimulates efficient nuclear import of a cargo protein. NTF2 binds to both RanGDP and FxFG repeat-containing nucleoporins. NTF2 binds to RanGDP sufficiently strongly for the complex to remain intact during transport through nucleopore complexes (NPCs), but the interaction between NTF2 and FxFG nucleoporins is much more transient, which would enable NTF2 to move through the NPC by hopping from one repeat to another. NTF2 folds into a cone with a deep hydrophobic cavity, the opening of which is surrounded by several negatively charged residues. RanGDP binds to NTF2 by inserting a conserved phenylalanine residue into the hydrophobic pocket of NTF2 and making electrostatic interactions with the conserved negatively charged residues that surround the cavity. A structurally similar domain appears in other nuclear import proteins. SEQ ID NO:1274, which sets forth the amino acid sequence of an Arabidopsis clone, identified herein as Ceres ME13151 (SEQ ID NO:1274), that is predicted to encode a polypeptide containing a NTF2 domain.

A low nitrogen tolerance-modulating polypeptide can contain a DUF1218 domain. SEQ ID NO:1274, which sets forth the amino acid sequence of an Arabidopsis clone, identified herein as Ceres ME04772 (SEQ ID NO:510), that is predicted to encode a polypeptide containing a DUF1218 domain.

A low nitrogen tolerance-modulating polypeptide can contain a Myb-like DNA-binding domain characteristic of polypeptides belonging to a protein family whose members contain the DNA binding domains from Myb proteins, as well as the SANT domain family. SEQ ID NO:533, which sets forth the amino acid sequence of an Arabidopsis clone, identified herein as Ceres ME04909 (SEQ ID NO:533), that is predicted to encode a polypeptide containing a Myb-like DNA-binding domain.

A low nitrogen tolerance-modulating polypeptide can contain a FAD_binding_4 domain. This domain is predicted to be characteristic of polypeptides belonging to a family of enzymes that use FAD (flavin adenine dinucleotide) as a co-factor, most of the enzymes are similar to oxygen oxidoreductase, containing a covalently bound FAD group which is attached to a histidine via an 8-alpha-(N3-histidyl)-riboflavin linkage.

A low nitrogen tolerance-modulating polypeptide can contain a BBE domain, which is predicted to be characteristic of a berberine bridge and berberine bridge-like enzyme. BBE enzymes are typically involved in the biosynthesis of numerous isoquinoline alkaloids. They catalyse the transformation of the N-methyl group of (S)-reticuline into the C-8 berberine bridge carbon of (S)-scoulerine. SEQ ID NO:558 sets forth the amino acid sequence of an *Arabidopsis* clone, identified herein as Ceres ME05194 (SEQ ID NO:558), that is predicted to encode a polypeptide containing an FAD_binding_4 domain and a BBE domain.

A low nitrogen tolerance-modulating polypeptide can contain a prefoldin (PFD) domain characteristic of polypeptides belonging to the prefoldin subunit family. Prefoldin (PFD) is a chaperone that typically interacts with type II chaperonins, hetero-oligomers lacking an obligate co-chaperonin that are found in eukaryotes (chaperonin-containing T-complex polypeptide-1 (CCT)) and archaea. Eukaryotic PFD can typically bind both actin and tubulin co-translationally. The chaperone can then delivers the target protein to CCT, interacting with the chaperonin through the tips of the coiled coils. SEQ ID NO:593 sets forth the amino acid sequence of an *Arabidopsis* clone, identified herein as Ceres ME05267 (SEQ ID NO:593), that is predicted to encode a polypeptide containing a prefoldin domain.

A low nitrogen tolerance-modulating polypeptide can contain an HR-lesion domain characteristic of polypeptides belonging to a family of plant proteins can be associated with the hypersensitive response (HR) pathway of defense against plant pathogens. The domain is also present in SEQ ID NO: 646, which sets forth the amino acid sequence of an *Arabidopsis* clone, identified herein as Ceres ME05341 (SEQ ID NO: 646), that is predicted to encode a polypeptide containing an HR-lesion domain.

A low nitrogen tolerance-modulating polypeptide can contain a DUF538 domain. SEQ ID NO:687 sets forth the amino acid sequence of an *Arabidopsis* clone, identified herein as Ceres ME05392 (SEQ ID NO:687), that is predicted to encode a polypeptide containing a DUF538 domain.

A low nitrogen tolerance-modulating polypeptide can contain a zinc finger C-x8-C-x5-C-x3-H type domain (zf-CCCH), which is characteristic of polypeptides belonging to the zinc finger protein superfamily. Members of zinc finger domains proteins are thought to be involved in DNA-binding, and exist as different types. Proteins containing zinc finger domains of the C-x8-C-x5-C-x3-H type include zinc finger proteins from eukaryotes involved in cell cycle or growth phase-related regulation. It has been shown that different CCCH zinc finger proteins interact with the 3' untranslated region of various mRNA. SEQ ID NO:792 sets forth the amino acid sequence of an *Arabidopsis* clone, identified herein as Ceres ME07344 (SEQ ID NO:792), that is predicted to encode a polypeptide containing a zf-CCCH domain.

A low nitrogen tolerance-modulating polypeptide can contain a DUF246 domain. SEQ ID NO:828 sets forth the amino acid sequence of an *Arabidopsis* clone, identified herein as Ceres ME08464 (SEQ ID NO:828), that is predicted to encode a polypeptide containing a DUF246 domain.

A low nitrogen tolerance-modulating polypeptide can contain a C2 domain. The C2 domain is a Ca2+-dependent membrane-targeting module found in many cellular proteins involved in signal transduction or membrane trafficking. C2 domains are unique among membrane targeting domains in that they typically show wide range of lipid selectivity for the major components of cell membranes, including phosphatidylserine and phosphatidylcholine. SEQ ID NO:982 sets forth the amino acid sequence of an *Arabidopsis* clone, identified herein as Ceres ME12970 (SEQ ID NO:982), that is predicted to encode a polypeptide containing an C2 domain.

A low nitrogen tolerance-modulating polypeptide can contain a Cpn60_TCP1 domain characteristic of polypeptides belonging to the TCP-1/cpn60 chaperonin family. This family includes members from the HSP60 chaperone family and the TCP-1 (T-complex protein) family. Chaperonins, a subfamily of molecular chaperones, are typically essential for the correct folding and assembly of polypeptides into oligomeric structures. Chaperonins are typically found in abundance in prokaryotes, chloroplasts and mitochondria. They are typically required for normal cell growth, and are stress-induced, acting to stabilize or protect disassembled polypeptides under heat-shock conditions. SEQ ID NO: 1054 sets forth the amino acid sequence of an *Arabidopsis* clone, identified herein as Ceres ME13021 (SEQ ID NO: 1054), that is predicted to encode a polypeptide containing a Cpn60_TCP1 domain.

A low nitrogen tolerance-modulating polypeptide can contain a zf-C2H2 domain characteristic of a C2H2 zinc finger domain polypeptide. Zinc finger domains are nucleic acid-binding protein structures composed of 25 to 30 amino-acid residues including 2 conserved Cys and 2 conserved His residues in a C-2-C-12-H-3-H type motif. The 12 residues separating the second Cys and the first His are mainly polar and basic, implicating this region in particular in nucleic acid binding. They have the ability to bind to both RNA and DNA, and it has been suggested that the zinc finger may thus represent the original nucleic acid binding protein. It has also been suggested that a Zn-centered domain could be used in a protein interaction, e.g. in protein kinase C. Many classes of zinc fingers are characterized according to the number and positions of the histidine and cysteine residues involved in the zinc atom coordination. In C2H2 zinc finger class, the first pair of zinc coordinating residues are cysteines, while the second pair are histidines. The motif is also present in SEQ ID NO:1116, which sets forth the amino acid sequence of an *Arabidopsis* clone, identified herein as Ceres ME13087 (SEQ ID NO:1116), that is predicted to encode a polypeptide containing a zf-C2H2 domain.

A low nitrogen tolerance-modulating polypeptide can contain a zein domain characteristic of polypeptides belonging to the zein family of seed storage proteins. SEQ ID NO:1159, which sets forth the amino acid sequence of an *Arabidopsis* clone, identified herein as Ceres ME13107 (SEQ ID NO: 1159), that is predicted to encode a polypeptide containing a zein domain.

A low nitrogen tolerance-modulating polypeptide can contain a snf7 domain characteristic of polypeptides belonging to a family of eukaryotic proteins related to yeast SNF7. SEQ ID NO:1185 sets forth the amino acid sequence of an *Arabidopsis* clone, identified herein as Ceres ME13110 (SEQ ID NO:1185), that is predicted to encode a polypeptide containing a snf7 domain.

A low nitrogen tolerance-modulating polypeptide can contain an HhH-GPD domain characteristic of polypeptides belonging to the HhH-GPD base excision DNA repair protein superfamily. Members of the HhH-GPD base excision DNA repair protein superfamily contain helix-hairpin-helix and Gly/Pro rich loop followed by a conserved aspartate. This domain is found in a diverse range of structurally related DNA repair proteins. The domain is also present in SEQ ID NO:1194 sets forth the amino acid sequence of an *Arabidopsis* clone, identified herein as Ceres ME13125

(SEQ ID NO:1194), that is predicted to encode a polypeptide containing an HhH-GPD domain.

A low nitrogen tolerance-modulating polypeptide can contain an Arf domain characteristic of polypeptides belonging to the ADP-ribosylation factor family. The small ADP ribosylation factor (Arf) GTP-binding proteins are major regulators of vesicle biogenesis in intracellular traffic. They are the founding members of a growing family that includes Arl (Arf-like), Arp (Arf-related proteins) and the remotely related Sar (Secretion-associated and Ras-related) proteins. Arf proteins cycle between inactive GDP-bound and active GTP-bound forms that bind selectively to effectors. The classical structural GDP/GTP switch is characterized by conformational changes at the so-called switch 1 and switch 2 regions, which bind tightly to the gamma-phosphate of GTP but poorly or not at all to the GDP nucleotide. Structural studies of Arf1 and Arf6 have revealed that although these proteins feature the switch 1 and 2 conformational changes, they depart from other small GTP-binding proteins in that they use an additional, unique switch to propagate structural information from one side of the protein to the other. The GDP/GTP structural cycles of human Arf1 and Arf6 feature a unique conformational change that affects the beta2beta3 strands connecting switch 1 and switch 2 (inter-switch) and also the amphipathic helical N-terminus. SEQ ID NO: 1210 sets forth the amino acid sequence of an *Arabidopsis* clone, identified herein as Ceres ME13149 (SEQ ID NO:1210), that is predicted to encode a polypeptide containing an Arf domain.

A low nitrogen tolerance-modulating polypeptide can contain a Pyridoxal_deC domain characteristic of pyridoxal-dependent decarboxylase polypeptide. Pyridoxal-dependent decarboxylases typically share regions of sequence similarity, particularly in the vicinity of a conserved lysine residue, which provides the attachment site for the pyridoxal-phosphate (PLP) group. Pyridoxal phosphate is the active form of vitamin B6 (pyridoxine or pyridoxal). PLP is a versatile catalyst, acting as a coenzyme in a multitude of reactions, including decarboxylation, deamination and transamination. PLP-dependent enzymes, including pyridoxal-dependent decarboxylases, are involved in the biosynthesis of amino acids and amino acid-derived metabolites, but they are also found in the biosynthetic pathways of amino sugars and in the synthesis or catabolism of neurotransmitter. SEQ ID NO:1302 sets forth the amino acid sequence of an *Arabidopsis* clone, identified herein as Ceres ME13153 (SEQ ID NO:1302), that is predicted to encode a polypeptide containing a Pyridoxal_deC domain.

A low nitrogen tolerance-modulating polypeptide can contain a Cyclin_C domain, which is characteristic to the C-terminal domain of polypeptides belonging to the Cyclin family. Cyclins are eukaryotic proteins that play an active role in controlling nuclear cell division cycles, and regulate cyclin dependent kinases (CDKs). Cyclins, together with the p34 (cdc2) or cdk2 kinases, form the Maturation Promoting Factor (MPF). There are two main groups of cyclins, G1/S cyclins, which play a role in the control of the cell cycle at the G1/S (start) transition, and G2/M cyclins, which play a role in the control of the cell cycle at the G2/M (mitosis) transition. G2/M cyclins accumulate steadily during G2 and are abruptly destroyed as cells exit from mitosis (at the end of the M-phase). Cyclins typically contain two domains of similar all-alpha fold, of which this family corresponds with the C-terminal domain.

A low nitrogen tolerance-modulating polypeptide can contain a Cyclin N domain, which defines the N-terminal domain of polypeptides belonging to the Cyclin family. SEQ ID NO: 1342 sets forth the amino acid sequence of an *Arabidopsis* clone, identified herein as Ceres ME13177 (SEQ ID NO: 1342), that is predicted to encode a polypeptide containing a Cyclin_C domain and a Cyclin _N domain A low nitrogen tolerance-modulating polypeptide can contain a DUF1442 domain. SEQ ID NO:1463, which sets forth the amino acid sequence of an *Arabidopsis* clone, identified herein as Ceres ME16546 (SEQ ID NO:1463), that is predicted to encode a polypeptide containing a DUF1442 domain.

A low nitrogen tolerance-modulating polypeptide can contain an HLH domain characteristic of polypeptides belonging to the Helix-loop-helix DNA-binding domain superfamily. Basic helix-loop-helix proteins (bHLH) are a group of eukaryotic transcription factors that can exert a determinative influence in a variety of developmental pathways. These transcription factors are characterized by a conserved bHLH domain that mediates specific dimerization. They can facilitate the conversion of inactive monomers to trans-activating dimers at appropriate stages of development. Members of this superfamily can be classified into discrete categories according to dimerization, DNA binding and expression characteristics. SEQ ID NO:1537 sets forth the amino acid sequence of an *Arabidopsis* clone, identified herein as Ceres ME18275 (SEQ ID NO:1537), that is predicted to encode a polypeptide containing an HLH domain.

A low nitrogen tolerance-modulating polypeptide can contain a CRAL_TRIO domain characteristic of the C-terminal of retinaldehyde/retinal-binding protein family. In animals, retinaldehyde/retinal-binding proteins may be functional components of the visual cycle. Cellular retinaldehyde-binding protein (CRALBP) may function as a substrate carrier protein that modulates interaction of these retinoids with visual cycle enzymes. The multidomain protein Trio can bind the LAR transmembrane tyrosine phosphatase, contains a protein kinase domain, and has separate rac-specific and rho-specific guanine nucleotide exchange factor domains. Trio is a multifunctional protein that can integrate and amplify signals involved in coordinating actin remodeling, which is necessary for cell migration and growth. Other members of the family are transfer proteins that include, guanine nucleotide exchange factor that may function as an effector of RAC1, phosphatidylinositol/phosphatidylcholine transfer protein that is required for the transport of secretory proteins from the Golgi complex and alpha-tocopherol transfer protein that enhances the transfer of the ligand between separate membranes.

A low nitrogen tolerance-modulating polypeptide can contain a CRAL_TRIO_N which defines the N-terminal of retinaldehyde/retinal-binding protein family.

A low nitrogen tolerance-modulating polypeptide can contain an EMP24_GP25L domain characteristic of polypeptides belonging to the emp24/gp25L/p24 family/GOLD gene family. Members of this family are implicated in bringing cargo forward from the ER and binding to coat proteins by their cytoplasmic domains. This domain corresponds closely to the beta-strand rich GOLD domain. The GOLD domain is often found combined with lipid- or membrane-association domains. p24 proteins are major membrane components of COPT- and COPII-coated vesicles and are implicated in cargo selectivity of ER to Golgi transport. Multiple members of the p24 family are found in all eukaryotes, from yeast to mammals. Members of the p24 family are type I membrane proteins with a signal peptide at the amino terminus, a lumenal coiled-coil (extra-cytosolic) domain, a single transmembrane domain with conserved amino acids, and a short cytoplasmic tail. They may be grouped into at least three subfamilies based on primary sequence. One subfamily comprises yeast Emp24p and mammalian p24A. Another subfamily comprises yeast Erv25p and mammalian Tmp21, and the third subfamily comprises mammalian gp25L proteins. SEQ ID NO:1554 sets forth the amino acid sequence of an *Arabidopsis* clone, identified herein as Ceres ME18924 (SEQ ID NO:1554), that is predicted to encode a polypeptide containing a CRAL_TRIO domain, a CRAL_TRIO_N domain, and a EMP24_GP25L domain.

A low nitrogen tolerance-modulating polypeptide can contain a Pyrophosphatase domain, which is predicted to be characteristic of an inorganic pyrophosphatase (PPase). PPase is the enzyme responsible for the hydrolysis of pyrophosphate (PPi) which is formed principally as the product of the many biosynthetic reactions that utilize ATP. PPases may require the presence of divalent metal cations, with magnesium conferring the highest activity. Among other residues, a lysine has been postulated to be part of or close to the active site. The sequences of PPases share some regions of similarities, among which is a region that contains three conserved aspartates that are involved in the binding of cations. SEQ ID NO:1577 sets forth the amino acid sequence of an *Arabidopsis* clone, identified herein as Ceres ME19182 (SEQ ID NO:1577), that is predicted to encode a polypeptide containing a Pyrophosphatase domain.

A low nitrogen tolerance-modulating polypeptide can contain a bZIP_1 domain characteristic of polypeptides belonging to the superfamily of basic ZIP transcription factors. Members of the eukaryotic bZIP transcription factor superfamily contain a basic region mediating sequence-specific DNA-binding followed by a leucine zipper region required for dimerization. SEQ ID NO: 1437 sets forth the amino acid sequence of an *Arabidopsis* clone, identified herein as Ceres ME20628 (SEQ ID NO: 1437), that is predicted to encode a polypeptide containing a bZIP_1 domain.

B. Functional Homologs Identified by Reciprocal BLAST

In some embodiments, one or more functional homologs of a reference low nitrogen tolerance-modulating polypeptide defined by one or more of the Pfam descriptions indicated above are suitable for use as low nitrogen tolerance-modulating polypeptides. A functional homolog is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, may themselves be functional homologs. Functional homologs can also be created via site-directed mutagenesis of the coding sequence for a low nitrogen tolerance-modulating polypeptide, or by combining domains from the coding sequences for different naturally-occurring low nitrogen tolerance-modulating polypeptides ("domain swapping"). The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of low nitrogen tolerance-modulating polypeptides. Sequence analysis can involve BLAST, Reciprocal BLAST, or PSI-BLAST analysis of nonredundant databases using a low nitrogen tolerance-modulating polypeptide amino acid sequence as the reference sequence. Amino acid sequence is, in some instances, deduced from the nucleotide sequence. Those polypeptides in the database that have greater than 20% sequence identity are candidates for further evaluation for suitability as a low nitrogen tolerance-modulating polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in low nitrogen tolerance-modulating polypeptides, e.g., conserved functional domains.

Conserved regions can be identified by locating a region within the primary amino acid sequence of a low nitrogen tolerance-modulating polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/and pfam.janelia.org/. A description of the information included at the Pfam database is described in Sonnhammer et al. (1998) *Nucl. Acids Res.*, 26:320-322; Sonnhammer et al. (1997) *Proteins*, 28:405-420; and Bateman et al. (1999) *Nucl. Acids Res.*, 27:260-262. Conserved regions also can be determined by aligning sequences of the same or related polypeptides from closely related species. Closely related species preferably are from the same family. In some embodiments, alignment of sequences from two different species is adequate.

Typically, polypeptides that exhibit at least about 40% amino acid sequence identity are useful to identify conserved regions. Conserved regions of related polypeptides exhibit at least 20% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

Examples of amino acid sequences of functional homologs of the polypeptide set forth in SEQ ID NO:3 are provided in FIG. 1 and in the Sequence Listing. Such functional homologs include SEQ ID NO:4, SEQ ID NO:6, SEQ ID NO:8, SEQ ID NO:10, SEQ ID NO:12, SEQ ID NO:14, SEQ ID NO:16, SEQ ID NO:17, SEQ ID NO:19, SEQ ID NO:20, SEQ ID NO:21, SEQ ID NO:22, SEQ ID NO:24, SEQ ID NO:25, SEQ ID NO:27, SEQ ID NO:29, SEQ ID NO:31, SEQ ID NO:33, SEQ ID NO:35, SEQ ID NO:36, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, and SEQ ID NO:47. In some cases, a functional homolog of SEQ ID NO:3 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:3.

Examples of amino acid sequences of functional homologs of the polypeptide set forth in SEQ ID NO:49 are provided in FIG. 2 and in the Sequence Listing. Such functional homologs include SEQ ID NO:51, SEQ ID NO:53, SEQ ID NO:55, SEQ ID NO:56, SEQ ID NO:58, SEQ ID NO:60, SEQ ID NO:62, SEQ ID NO:63, SEQ ID NO:64, SEQ ID NO:65, SEQ ID NO:67, SEQ ID NO:69, SEQ ID NO:70, SEQ ID NO:71, SEQ ID NO:72, SEQ ID NO:73, and SEQ ID NO:75. In some cases, a functional homolog of SEQ ID NO:49 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:49.

Examples of amino acid sequences of functional homologs of the polypeptide set forth in SEQ ID NO:77 are provided in FIG. 3 and in the Sequence Listing. Such functional homologs include SEQ ID NO:78, SEQ ID NO:80, SEQ ID NO:82, SEQ ID NO:84, SEQ ID NO:85, SEQ ID NO:87, SEQ ID NO:88, SEQ ID NO:90, SEQ ID NO:92, SEQ ID NO:93, SEQ ID NO:95, and CeresAnnot: 839064 (SEQ ID NO:1479). In some cases, a functional homolog of SEQ ID NO:77 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:77.

Examples of amino acid sequences of functional homologs of the polypeptide set forth in SEQ ID NO:100 are provided in FIG. 4 and in the Sequence Listing. Such functional homologs include SEQ ID NO:101, SEQ ID NO:102, SEQ ID NO:104, SEQ ID NO:106, SEQ ID NO:108, SEQ ID NO:110, SEQ ID NO:111, SEQ ID NO:113, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:125, SEQ ID NO:126, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:137, SEQ ID NO:139, SEQ ID NO:141, SEQ ID NO:142, SEQ ID NO:144, SEQ ID NO:145, SEQ ID NO:146, SEQ ID NO:147, SEQ ID NO:148, SEQ ID NO:149, and SEQ ID NO:150. In some cases, a functional homolog of SEQ ID NO:100 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:100.

Examples of amino acid sequences of functional homologs of the polypeptide set forth in SEQ ID NO:152 are provided in FIG. 5 and in the Sequence Listing. Such functional homologs include SEQ ID NO:154, SEQ ID NO:156, SEQ ID NO:158, SEQ ID NO:160, SEQ ID NO:162, and SEQ ID NO:164. In some cases, a functional homolog of SEQ ID NO:152 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:152.

Examples of amino acid sequences of functional homologs of the polypeptide set forth in SEQ ID NO:166 are provided in FIG. 6 and in the Sequence Listing. Such functional homologs include SEQ ID NO:168, SEQ ID NO:170, SEQ ID NO:172, SEQ ID NO:174, SEQ ID NO:177, SEQ ID NO:179, SEQ ID NO:181, SEQ ID NO:182, SEQ ID NO:183, and SEQ ID NO:184. In some cases, a functional homolog of SEQ ID NO:166 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:166.

Examples of amino acid sequences of functional homologs of the polypeptide set forth in SEQ ID NO:186 are provided in FIG. 7 and in the Sequence Listing. Such functional homologs include SEQ ID NO:188, SEQ ID NO:190, SEQ ID NO:191, SEQ ID NO:193, SEQ ID NO:194, SEQ ID NO:196, SEQ ID NO:197, SEQ ID NO:199, SEQ ID NO:201, SEQ ID NO:203, SEQ ID NO:204, SEQ ID NO:205, and SEQ ID NO:206. In some cases, a functional homolog of SEQ ID NO:186 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:186.

Examples of amino acid sequences of functional homologs of the polypeptide set forth in SEQ ID NO:208 are provided in FIG. 8 and in the Sequence Listing. Such functional homologs include SEQ ID NO:209, SEQ ID NO:210, SEQ ID NO:214, and SEQ ID NO:216. In some cases, a functional homolog of SEQ ID NO:208 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:208.

Examples of amino acid sequences of functional homologs of the polypeptide set forth in SEQ ID NO:218 are provided in FIG. 9 and in the Sequence Listing. Such functional homologs include SEQ ID NO:220, SEQ ID NO:222, SEQ ID NO:223, SEQ ID NO:225, SEQ ID NO:227, SEQ ID NO:229, SEQ ID NO:230, SEQ ID NO:231, SEQ ID NO:232, SEQ ID NO:1039, SEQ ID NO:1049, and SEQ ID NO:1052. In some cases, a functional homolog of SEQ ID NO:218 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:218.

Examples of amino acid sequences of functional homologs of the polypeptide set forth in SEQ ID NO:234 are provided in FIG. 10 and in the Sequence Listing. Such functional homologs include SEQ ID NO:236, SEQ ID NO:238, SEQ ID NO:239, SEQ ID NO:241, SEQ ID NO:242, SEQ ID NO:243, and SEQ ID NO:244. In some cases, a functional homolog of SEQ ID NO:234 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:234.

Examples of amino acid sequences of functional homologs of the polypeptide set forth in SEQ ID NO:246 are provided in FIG. 11 and in the Sequence Listing. Such functional homologs include SEQ ID NO:248, SEQ ID NO:249, SEQ ID NO:251, SEQ ID NO:253, SEQ ID NO:255, SEQ ID NO:257, SEQ ID NO:259, SEQ ID NO:260, SEQ ID NO:262, SEQ ID NO:264, SEQ ID NO:265, SEQ ID NO:267, SEQ ID NO:268, SEQ ID NO:270, SEQ ID NO:272, SEQ ID NO:274, SEQ ID NO:276, SEQ ID NO:277, SEQ ID NO:279, SEQ ID NO:281, SEQ ID NO:283, SEQ ID NO:285, SEQ ID NO:286, SEQ ID NO:287, SEQ ID NO:288, SEQ ID NO:290, SEQ ID NO:291, SEQ ID NO:292, SEQ ID NO:293, SEQ ID NO:296, and SEQ ID NO:298. In some cases, a functional homolog of SEQ ID NO:246 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:246.

Examples of amino acid sequences of functional homologs of the polypeptide set forth in SEQ ID NO:300 are provided in FIG. 12 and in the Sequence Listing. Such functional homologs include SEQ ID NO:302, SEQ ID NO:304, SEQ ID NO:306, SEQ ID NO:308, SEQ ID NO:310, SEQ ID NO:312, SEQ ID NO:314, SEQ ID NO:316, SEQ ID NO:318, SEQ ID NO:319, SEQ ID NO:320, SEQ ID NO:321, SEQ ID NO:322, SEQ ID NO:323, SEQ ID NO:325, SEQ ID NO:327, and SEQ ID NO:329. In some cases, a functional homolog of SEQ ID NO:300 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:300.

Examples of amino acid sequences of functional homologs of the polypeptide set forth in SEQ ID NO:332 are provided in FIG. 13 and in the Sequence Listing. Such functional homologs include SEQ ID NO:332, SEQ ID NO:334, SEQ ID NO:335, SEQ ID NO:336, SEQ ID NO:338, SEQ ID NO:339, SEQ ID NO:341, SEQ ID NO:342, SEQ ID NO:343, SEQ ID NO:344, SEQ ID NO:345, SEQ ID NO:346, SEQ ID NO:347, SEQ ID NO:348, SEQ ID NO:349, SEQ ID NO:351, SEQ ID NO:352, SEQ ID NO:353, SEQ ID NO:354, SEQ ID NO:355, SEQ ID NO:356, SEQ ID NO:357, SEQ ID NO:358, SEQ ID NO:359, SEQ ID NO:360, SEQ ID NO:362, SEQ ID NO:363, SEQ ID NO:364, SEQ ID NO:365, SEQ ID NO:366, SEQ ID NO:2541, SEQ ID NO:2542, SEQ ID NO:2543, SEQ ID NO:2544, SEQ ID NO:2546, SEQ ID NO:2548, SEQ ID NO:2549, SEQ ID NO:2550, SEQ ID NO:2551, SEQ ID NO:2552, and SEQ ID NO:2553. In some cases, a functional homolog of SEQ ID NO:332 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:332.

Examples of amino acid sequences of functional homologs of the polypeptide set forth in SEQ ID NO:368 are provided in FIG. 14 and in the Sequence Listing. Such functional homologs include SEQ ID NO:369, SEQ ID NO:370, SEQ ID NO:371, SEQ ID NO:372, SEQ ID NO:373, SEQ ID NO:374, SEQ ID NO:376, SEQ ID NO:378, SEQ ID NO:380, SEQ ID NO:382, SEQ ID NO:384, SEQ ID NO:386, SEQ ID NO:388, SEQ ID NO:390, SEQ ID NO:392, SEQ ID NO:394, SEQ ID NO:396, SEQ ID NO:398, SEQ ID NO:399, SEQ ID NO:401, SEQ ID NO:403, SEQ ID NO:404, SEQ ID NO:406, SEQ ID NO:408, SEQ ID NO:410, SEQ ID NO:412, SEQ ID NO:414, SEQ ID NO:416, SEQ ID NO:418, SEQ ID NO:419, SEQ ID NO:420, SEQ ID NO:422, SEQ ID NO:423, SEQ ID NO:425, SEQ ID NO:427, SEQ ID NO:428, SEQ ID NO:430, SEQ ID NO:432, SEQ ID NO:433, SEQ ID NO:434, SEQ ID NO:435, SEQ ID NO:436, SEQ ID NO:437, SEQ ID NO:438, SEQ ID NO:439, SEQ ID NO:440, SEQ ID NO:441, SEQ ID NO:444, SEQ ID NO:445, SEQ ID NO:446, SEQ ID NO:447, SEQ ID NO:448, SEQ ID NO:449, SEQ ID NO:450, SEQ ID NO:451, SEQ ID NO:452, SEQ ID NO:453, SEQ ID NO:454, SEQ ID NO:455, SEQ ID NO:456, SEQ ID NO:458, SEQ ID NO:459, SEQ ID NO:461, SEQ ID NO:463, SEQ ID NO:465, SEQ ID NO:467, SEQ ID NO:469, SEQ ID NO:471, SEQ ID NO:473, SEQ ID NO:474, SEQ ID NO:475, SEQ ID NO:477, SEQ ID NO:479, SEQ ID NO:481, SEQ ID NO:483, SEQ ID NO:485, SEQ ID NO:487, SEQ ID NO:488, SEQ ID NO:489, SEQ ID NO:490, SEQ ID NO:491, SEQ ID NO:492, SEQ ID NO:494, SEQ ID NO:495, SEQ ID NO:496, SEQ ID NO:497, SEQ ID NO:498, SEQ ID NO:499, SEQ ID NO:500, SEQ ID NO:501, SEQ ID NO:502, SEQ ID NO:504, SEQ ID NO:505, SEQ ID NO:506, SEQ ID NO:507, and SEQ ID NO:508. In some cases, a functional homolog of SEQ ID NO:368 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:368.

Examples of amino acid sequences of functional homologs of the polypeptide set forth in SEQ ID NO:510 are provided in FIG. 15 and in the Sequence Listing. Such functional homologs include SEQ ID NO:511, SEQ ID NO:513, SEQ ID NO:515, SEQ ID NO:517, SEQ ID NO:521, SEQ ID NO:523, SEQ ID NO:525, SEQ ID NO:527, SEQ ID NO:529, SEQ ID NO:530, and SEQ ID NO:531. In some cases, a functional homolog of SEQ ID NO:510 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:510.

Examples of amino acid sequences of functional homologs of the polypeptide set forth in SEQ ID NO:533 are provided in FIG. 16 and in the Sequence Listing. Such functional homologs include SEQ ID NO:535, SEQ ID NO:536, SEQ ID NO:538, SEQ ID NO:539, SEQ ID NO:541, SEQ ID NO:542, SEQ ID NO:543, SEQ ID NO:544, SEQ ID NO:545, SEQ ID NO:546, SEQ ID NO:547, SEQ ID NO:548, SEQ ID NO:550, SEQ ID NO:552, SEQ ID NO:553, and SEQ ID NO:554. In some cases, a functional homolog of SEQ ID NO:533 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:533.

Examples of amino acid sequences of functional homologs of the polypeptide set forth in SEQ ID NO:558 are provided in FIG. 17 and in the Sequence Listing. Such functional homologs include SEQ ID NO:559, SEQ ID NO:560, SEQ ID NO:561, SEQ ID NO:562, SEQ ID NO:563, SEQ ID NO:564, SEQ ID NO:565, SEQ ID NO:566, SEQ ID NO:567, SEQ ID NO:569, SEQ ID NO:571, SEQ ID NO:572, SEQ ID NO:573, SEQ ID NO:575, SEQ ID NO:576, SEQ ID NO:577, SEQ ID NO:578, SEQ ID NO:579, SEQ ID NO:581, SEQ ID NO:583, SEQ ID NO:584, SEQ ID NO:585, SEQ ID NO:586, SEQ ID NO:588, SEQ ID NO:589, SEQ ID NO:590, and SEQ ID NO:591. In some cases, a functional homolog of SEQ ID NO:558 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:558.

Examples of amino acid sequences of functional homologs of the polypeptide set forth in SEQ ID NO:593 are provided in FIG. 18 and in the Sequence Listing. Such functional homologs include SEQ ID NO:595, SEQ ID NO:597, SEQ ID NO:599, SEQ ID NO:601, SEQ ID NO:603, SEQ ID NO:605, SEQ ID NO:607, SEQ ID NO:609, SEQ ID NO:610, and SEQ ID NO:611. In some cases, a functional homolog of SEQ ID NO:593 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:593.

Examples of amino acid sequences of functional homologs of the polypeptide set forth in SEQ ID NO:613 are provided in FIG. 19 and in the Sequence Listing. Such functional homologs include SEQ ID NO:615, SEQ ID NO:617, SEQ ID NO:618, SEQ ID NO:620, SEQ ID NO:622, SEQ ID NO:624, SEQ ID NO:626, SEQ ID NO:628, SEQ ID NO:630, SEQ ID NO:632, SEQ ID NO:634, SEQ ID NO:636, SEQ ID NO:638, SEQ ID NO:640, SEQ ID NO:642, SEQ ID NO:643, and SEQ ID NO:644. In some cases, a functional homolog of SEQ ID NO:613 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:613.

Examples of amino acid sequences of functional homologs of the polypeptide set forth in SEQ ID NO:646 are provided in FIG. 20 and in the Sequence Listing. Such functional homologs include SEQ ID NO:648, SEQ ID NO:650, SEQ ID NO:652, SEQ ID NO:654, SEQ ID NO:656, SEQ ID NO:658, SEQ ID NO:660, SEQ ID NO:662, SEQ ID NO:664, SEQ ID NO:666, SEQ ID NO:668, SEQ ID NO:670, SEQ ID NO:672, SEQ ID NO:674, SEQ ID NO:676, SEQ ID NO:678, SEQ ID NO:679, SEQ ID NO:680, SEQ ID NO:681, SEQ ID NO:682, SEQ ID NO:683, and SEQ ID NO:685. In some cases, a functional homolog of SEQ ID NO:646 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:646.

Examples of amino acid sequences of functional homologs of the polypeptide set forth in SEQ ID NO:687 are provided in FIG. 21 and in the Sequence Listing. Such functional homologs include SEQ ID NO:689, SEQ ID NO:691, SEQ ID NO:693, SEQ ID NO:694, SEQ ID NO:696, SEQ ID NO:697, SEQ ID NO:699, SEQ ID NO:701, SEQ ID NO:703, SEQ ID NO:705, SEQ ID NO:706, SEQ ID NO:708, SEQ ID NO:710, SEQ ID NO:712, SEQ ID NO:714, SEQ ID NO:716, SEQ ID NO:718, SEQ ID NO:720, SEQ ID NO:721, SEQ ID NO:722, SEQ ID NO:723, SEQ ID NO:724, SEQ ID NO:725, SEQ ID NO:726, SEQ ID NO:727, and SEQ ID NO:728. In some cases, a functional homolog of SEQ ID NO:687 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:687.

Examples of amino acid sequences of functional homologs of the polypeptide set forth in SEQ ID NO:730 are provided in FIG. 22 and in the Sequence Listing. Such functional homologs include SEQ ID NO:732, SEQ ID NO:733, SEQ ID NO:735, SEQ ID NO:737, SEQ ID NO:738, and SEQ ID NO:742. In some cases, a functional homolog of SEQ ID NO:730 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:730.

Examples of amino acid sequences of functional homologs of the polypeptide set forth in SEQ ID NO:746 are provided in FIG. 23 and in the Sequence Listing. Such functional homologs include SEQ ID NO:748, SEQ ID NO:750, SEQ ID NO:751, SEQ ID NO:753, SEQ ID NO:755, SEQ ID NO:757, SEQ ID NO:758, SEQ ID NO:760, SEQ ID NO:761, SEQ ID NO:762, SEQ ID NO:763, SEQ ID NO:765, and SEQ ID NO:767. In some cases, a functional homolog of SEQ ID NO:746 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:746.

Examples of amino acid sequences of functional homologs of the polypeptide set forth in SEQ ID NO:769 are provided in FIG. 24 and in the Sequence Listing. Such functional homologs include SEQ ID NO:771, SEQ ID NO:773, SEQ ID NO:775, SEQ ID NO:777, SEQ ID NO:779, SEQ ID NO:781, SEQ ID NO:783, SEQ ID NO:785, SEQ ID NO:787, SEQ ID NO:789, and SEQ ID NO:790. In some cases, a functional homolog of SEQ ID NO:769 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:769.

Examples of amino acid sequences of functional homologs of the polypeptide set forth in SEQ ID NO:792 are provided in FIG. 25 and in the Sequence Listing. Such functional homologs include SEQ ID NO:794, SEQ ID NO:796, SEQ ID NO:798, SEQ ID NO:799, SEQ ID NO:801, SEQ ID NO:803, SEQ ID NO:805, SEQ ID NO:807, SEQ ID NO:808, SEQ ID NO:810, SEQ ID NO:812, SEQ ID NO:814, SEQ ID NO:816, SEQ ID NO:818, SEQ ID NO:819, SEQ ID NO:820, SEQ ID NO821, and SEQ ID NO:822. In some cases, a functional homolog of SEQ ID NO:792 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:792.

Examples of amino acid sequences of functional homologs of the polypeptide set forth in SEQ ID NO:824 are provided in FIG. 26 and in the Sequence Listing. Such functional homologs include, but not limited to, SEQ ID NO:826, SEQ ID NO:1696, SEQ ID NO:1698, SEQ ID NO:1700, SEQ ID NO:1702, SEQ ID NO:1704, SEQ ID NO:1706, SEQ ID NO:1708, SEQ ID NO:1710, SEQ ID NO:1711, SEQ ID NO:1713, SEQ ID NO:1714, SEQ ID NO:1715, and SEQ ID NO:1716. In some cases, a functional homolog of SEQ ID NO:824 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:824.

Examples of amino acid sequences of functional homologs of the polypeptide set forth in SEQ ID NO:828 are provided in FIG. 27 and in the Sequence Listing. Such functional homologs include SEQ ID NO:830, SEQ ID NO:832, SEQ ID NO:834, SEQ ID NO:836, SEQ ID NO:837, SEQ ID NO:838, SEQ ID NO:839, SEQ ID NO:840, SEQ ID NO:842, SEQ ID NO:844, SEQ ID NO:845, SEQ ID NO:846, SEQ ID NO:847, SEQ ID NO:848, SEQ ID NO:849, SEQ ID NO:850, and SEQ ID NO:851. In some cases, a functional homolog of SEQ ID NO:828 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:828.

Examples of amino acid sequences of functional homologs of the polypeptide set forth in SEQ ID NO:855 are provided in FIG. 28 and in the Sequence Listing. Such functional homologs include SEQ ID NO:856, SEQ ID NO:858, SEQ ID NO:860, SEQ ID NO:862, SEQ ID NO:864, SEQ ID NO:866, SEQ ID NO:868, SEQ ID NO:870, SEQ ID NO:872, SEQ ID NO:874, SEQ ID NO:876, SEQ ID NO:878, SEQ ID NO:880, SEQ ID NO:882, SEQ ID NO:884, SEQ ID NO:885, SEQ ID NO:886, SEQ ID NO:887, SEQ ID NO:888, and SEQ ID NO:889. In some cases, a functional homolog of SEQ ID NO:855 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:855.

Examples of amino acid sequences of functional homologs of the polypeptide set forth in SEQ ID NO:891 are provided in FIG. 29 and in the Sequence Listing. Such functional homologs include SEQ ID NO:893, SEQ ID NO:894, SEQ ID NO:895, SEQ ID NO:896, SEQ ID NO:898, SEQ ID NO:900, SEQ ID NO:901, SEQ ID NO:902, SEQ ID NO:903, SEQ ID NO:904, SEQ ID NO:905, SEQ ID NO:907, SEQ ID NO:908, SEQ ID NO:909, SEQ ID NO:910, SEQ ID NO:911, SEQ ID NO:912, SEQ ID NO:913, SEQ ID NO:914, and SEQ ID NO:915. In some cases, a functional homolog of SEQ ID NO:891 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:891.

Examples of amino acid sequences of functional homologs of the polypeptide set forth in SEQ ID NO:917 are provided in FIG. 30 and in the Sequence Listing. Such functional homologs include SEQ ID NO:919, SEQ ID NO:921, SEQ ID NO:923, SEQ ID NO:925, SEQ ID NO:927, SEQ ID NO:929, SEQ ID NO:931, SEQ ID NO:933, SEQ ID NO:935, SEQ ID NO:937, SEQ ID NO:939, and SEQ ID NO:940. In some cases, a functional homolog of SEQ ID NO:917 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:917.

Examples of amino acid sequences of functional homologs of the polypeptide set forth in SEQ ID NO:944 are provided in FIG. 31 and in the Sequence Listing. Such functional homologs include SEQ ID NO:946, SEQ ID NO:947, SEQ ID NO:948, SEQ ID NO:950, SEQ ID NO:952, SEQ ID NO:954, SEQ ID NO:956, SEQ ID NO:958, SEQ ID NO:960, SEQ ID NO:962, SEQ ID NO:964, SEQ ID NO:966, SEQ ID NO:967, SEQ ID NO:968, SEQ ID NO:969, SEQ ID NO:970, SEQ ID NO:972, and SEQ ID NO:974. In some cases, a functional homolog of SEQ ID NO:944 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:944.

Examples of amino acid sequences of functional homologs of the polypeptide set forth in SEQ ID NO:976 are provided in FIG. 32 and in the Sequence Listing. Such functional homologs include, but not limited to, SEQ ID NO:978 and SEQ ID NO:980. In some cases, a functional homolog of SEQ ID NO:976 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:976.

Examples of amino acid sequences of functional homologs of the polypeptide set forth in SEQ ID NO:982 are provided in FIG. 33 and in the Sequence Listing. Such functional homologs include SEQ ID NO:984, SEQ ID NO:985, SEQ ID NO:986, SEQ ID NO:987, SEQ ID NO:988, SEQ ID NO:989, SEQ ID NO:990, SEQ ID NO:991, SEQ ID NO:992, SEQ ID NO:993, SEQ ID NO:995, SEQ ID NO:996, SEQ ID NO:998, SEQ ID NO:1000, SEQ ID NO:1001, SEQ ID NO:1003, SEQ ID NO:1005, SEQ ID NO:1007, SEQ ID NO:1008, SEQ ID NO:1009, SEQ ID NO:1011, SEQ ID NO:1013, SEQ ID NO:1015, SEQ ID NO:1016, SEQ ID NO:1018, SEQ ID NO:1019, SEQ ID NO:1021, SEQ ID NO:1023, SEQ ID NO:1025, SEQ ID NO:1026, SEQ ID NO:1027, SEQ ID NO:1028, SEQ ID NO:1029, SEQ ID NO:1030, SEQ ID NO:1031, SEQ ID NO:1032, and SEQ ID NO:1033. In some cases, a functional homolog of SEQ ID NO:982 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:982.

Examples of amino acid sequences of functional homologs of the polypeptide set forth in SEQ ID NO:1054 are provided in FIG. 34 and in the Sequence Listing. Such functional homologs include SEQ ID NO:1055, SEQ ID NO:1057, SEQ ID NO:1058, SEQ ID NO:1059, SEQ ID NO:1061, SEQ ID NO:1063, SEQ ID NO:1065, SEQ ID NO:1067, SEQ ID NO:1068, SEQ ID NO:1070, SEQ ID NO:1071, SEQ ID NO:1072, SEQ ID NO:1074, SEQ ID NO:1075, SEQ ID NO:1076, SEQ ID NO:1077, SEQ ID NO:1078, SEQ ID NO:1080, SEQ ID NO:1082, SEQ ID NO:1083, SEQ ID NO:1085, SEQ ID NO:1086, SEQ ID NO:1087, SEQ ID NO:1088, SEQ ID NO:1089, SEQ ID NO:1090, SEQ ID NO:1091, SEQ ID NO:1092, SEQ ID NO:1093, SEQ ID NO:1094, SEQ ID NO:1095, and SEQ ID NO:1097. In some cases, a functional homolog of SEQ ID NO:1054 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1054.

Examples of amino acid sequences of functional homologs of the polypeptide set forth in SEQ ID NO:1099 are provided in FIG. 35 and in the Sequence Listing. Such functional homologs include SEQ ID NO:1101, SEQ ID NO:1103, SEQ ID NO:1104, SEQ ID NO:1105, SEQ ID NO:1106, SEQ ID NO:1108, SEQ ID NO:1109, and SEQ ID NO:1110. In some cases, a functional homolog of SEQ ID NO:1099 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1099.

Examples of amino acid sequences of functional homologs of the polypeptide set forth in SEQ ID NO:1112 are provided in FIG. 36 and in the Sequence Listing. Such functional homologs include SEQ ID NO:1113 and SEQ ID NO:1114. In some cases, a functional homolog of SEQ ID NO:1112 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1112.

Examples of amino acid sequences of functional homologs of the polypeptide set forth in SEQ ID NO:1116 are provided in FIG. 37 and in the Sequence Listing. Such functional homologs include SEQ ID NO:1118, SEQ ID NO:1120, SEQ ID NO:1122, SEQ ID NO:1123, SEQ ID NO:1125, SEQ ID NO:1126, SEQ ID NO:1128, SEQ ID NO:1129, SEQ ID NO:1131, SEQ ID NO:1132, SEQ ID NO:1133, SEQ ID NO:1134, SEQ ID NO:1136, SEQ ID NO:1138, SEQ ID NO:1140, SEQ ID NO:1141, SEQ ID NO:1142, SEQ ID NO:1143, SEQ ID NO:1144, SEQ ID NO:1145, SEQ ID NO:1147, SEQ ID NO:1149, SEQ ID NO:1151, SEQ ID NO:1153, and SEQ ID NO:1155. In some cases, a functional homolog of SEQ ID NO:1116 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1116.

Examples of amino acid sequences of functional homologs of the polypeptide set forth in SEQ ID NO:1159 are provided in FIG. 38 and in the Sequence Listing. Such functional homologs include SEQ ID NO:1161, SEQ ID NO:1162, SEQ ID NO:1163, and SEQ ID NO:1164. In some cases, a functional homolog of SEQ ID NO:1159 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1159.

Examples of amino acid sequences of functional homologs of the polypeptide set forth in SEQ ID NO:1166 are provided in FIG. 39 and in the Sequence Listing. Such functional homologs include SEQ ID NO:1167, SEQ ID NO:1169, SEQ ID NO:1171, SEQ ID NO:1173, SEQ ID NO:1175, SEQ ID NO:1177, SEQ ID NO:1179, SEQ ID NO:1180, SEQ ID NO:1182, and SEQ ID NO:1183. In some cases, a functional homolog of SEQ ID NO:1166 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1166.

Examples of amino acid sequences of functional homologs of the polypeptide set forth in SEQ ID NO:1185 are provided in FIG. 40 and in the Sequence Listing. Such functional homologs include SEQ ID NO:1187, SEQ ID NO:1189, SEQ ID NO:1190, SEQ ID NO:1191, and SEQ ID NO:1192. In some cases, a functional homolog of SEQ ID NO:1185 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1185.

Examples of amino acid sequences of functional homologs of the polypeptide set forth in SEQ ID NO:1194 are provided in FIG. 41 and in the Sequence Listing. Such functional homologs include SEQ ID NO:1196, SEQ ID NO:1198, SEQ ID NO:1200, SEQ ID NO:1202, SEQ ID NO:1203, SEQ ID NO:1204, SEQ ID NO:1205, SEQ ID NO:1206, SEQ ID NO:1207, and SEQ ID NO:1208. In some cases, a functional homolog of SEQ ID NO:1194 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1194.

Examples of amino acid sequences of functional homologs of the polypeptide set forth in SEQ ID NO:1210 are provided in FIG. 42 and in the Sequence Listing. Such functional homologs include SEQ ID NO:1211, SEQ ID NO:1213, SEQ ID NO:1215, SEQ ID NO:1216, SEQ ID NO:1218, SEQ ID NO:1220, SEQ ID NO:1222, SEQ ID NO:1224, SEQ ID NO:1226, SEQ ID NO:1228, SEQ ID NO:1229, SEQ ID NO:1230, SEQ ID NO:1232, SEQ ID NO:1233, SEQ ID NO:1234, SEQ ID NO:1235, SEQ ID NO:1236, SEQ ID NO:1237, SEQ ID NO:1238, SEQ ID NO:1239, SEQ ID NO:1240, SEQ ID NO:1241, SEQ ID NO:1242, SEQ ID NO:1243, SEQ ID NO:1244, SEQ ID NO:1245, SEQ ID NO:1246, SEQ ID NO:1247, SEQ ID NO:1248, SEQ ID NO:1249, SEQ ID NO:1251, SEQ ID NO:1253, SEQ ID NO:1255, SEQ ID NO:1257, SEQ ID NO:1259, SEQ ID NO:1261, SEQ ID NO:1263, SEQ ID NO:1264, SEQ ID NO:1265, SEQ ID NO:1266, SEQ ID NO:1267, SEQ ID NO:1268, SEQ ID NO:1269, SEQ ID NO:1270, SEQ ID NO:1271, and SEQ ID NO:1272. In some cases, a functional homolog of SEQ ID NO:1210 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1210.

Examples of amino acid sequences of functional homologs of the polypeptide set forth in SEQ ID NO:1274 are provided in FIG. 43 and in the Sequence Listing. Such functional homologs include SEQ ID NO:1276, SEQ ID NO:1278, SEQ ID NO:1280, SEQ ID NO:1281, SEQ ID NO:1282, SEQ ID NO:1284, SEQ ID NO:1285, SEQ ID NO:1287, SEQ ID NO:1289, SEQ ID NO:1291, SEQ ID NO:1293, SEQ ID NO:1294, SEQ ID NO:1295, SEQ ID NO:1296, SEQ ID NO:1297, SEQ ID NO:1298, and SEQ ID NO:1300. In some cases, a functional homolog of SEQ ID NO:1274 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1274.

Examples of amino acid sequences of functional homologs of the polypeptide set forth in SEQ ID NO:1302 are provided in FIG. 44 and in the Sequence Listing. Such functional homologs include SEQ ID NO:1303, SEQ ID NO:1305, SEQ ID NO:1307, SEQ ID NO:1309, SEQ ID NO:1311, SEQ ID NO:1312, SEQ ID NO:1313, SEQ ID NO:1314, SEQ ID NO:1315, SEQ ID NO:1317, SEQ ID NO:1318, SEQ ID NO:1319, SEQ ID NO:1320, SEQ ID NO:1321, SEQ ID NO:1322, SEQ ID NO:1323, SEQ ID NO:1324, SEQ ID NO:1325, SEQ ID NO:1326, SEQ ID NO:1327, SEQ ID NO:1328, SEQ ID NO:1330, SEQ ID NO:1331, SEQ ID NO:1333, SEQ ID NO:1334, SEQ ID NO:1335, SEQ ID NO:1336, SEQ ID NO:1337, SEQ ID NO:1338, SEQ ID NO:1339, and SEQ ID NO:1340. In some cases, a functional homolog of SEQ ID NO:1302 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1302.

Examples of amino acid sequences of functional homologs of the polypeptide set forth in SEQ ID NO:1342 are provided in FIG. 45 and in the Sequence Listing. Such functional homologs include SEQ ID NO:1344, SEQ ID NO:1346, SEQ ID NO:1348, SEQ ID NO:1350, SEQ ID NO:1352, SEQ ID NO:1354, SEQ ID NO:1355, SEQ ID NO:1357, SEQ ID NO:1358, SEQ ID NO:1360, SEQ ID NO:1361, SEQ ID NO:1362, SEQ ID NO:1363, SEQ ID NO:1364, SEQ ID NO:1366, SEQ ID NO:1367, SEQ ID NO:1369, SEQ ID NO:1370, SEQ ID NO:1371, SEQ ID NO:1372, SEQ ID NO:1373, SEQ ID NO:1374, SEQ ID NO:1375, SEQ ID NO:1376, SEQ ID NO:1377, SEQ ID NO:1378, SEQ ID NO:1379, SEQ ID NO:1380, SEQ ID NO:1381, SEQ ID NO:1382, and SEQ ID NO:1383. In some cases, a functional homolog of SEQ ID NO:1342 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1342.

Examples of amino acid sequences of functional homologs of the polypeptide set forth in SEQ ID NO:1385 are provided in FIG. 46 and in the Sequence Listing. Such functional homologs include SEQ ID NO:1387, SEQ ID NO:1389, SEQ ID NO:1390, SEQ ID NO:1391, SEQ ID NO:1393, SEQ ID NO:1394, SEQ ID NO:1395, SEQ ID NO:1396, SEQ ID NO:1398, SEQ ID NO:1400, SEQ ID NO:1401, SEQ ID NO:1402, SEQ ID NO:1403, SEQ ID NO:1404, SEQ ID NO:1405, and SEQ ID NO:1407. In some cases, a functional homolog of SEQ ID NO:1385 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1385.

Examples of amino acid sequences of functional homologs of the polypeptide set forth in SEQ ID NO:1409 are provided in FIG. 47 and in the Sequence Listing. Such functional homologs include SEQ ID NO:1411, SEQ ID NO:1413, SEQ ID NO:1415, SEQ ID NO:1417, SEQ ID NO:1418, SEQ ID NO:1419, SEQ ID NO:1421, SEQ ID NO:1423, SEQ ID NO:1424, SEQ ID NO:1425, and SEQ ID NO:1426. In some cases, a functional homolog of SEQ ID NO:1409 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1409.

Examples of amino acid sequences of functional homologs of the polypeptide set forth in SEQ ID NO:1428 are provided in FIG. 48 and in the Sequence Listing. Such functional homologs include SEQ ID NO:1430, SEQ ID NO:1432, SEQ ID NO:1434, SEQ ID NO:1436, SEQ ID NO:1439, SEQ ID NO:1442, SEQ ID NO:1444, SEQ ID NO:1446, SEQ ID NO:1448, SEQ ID NO:1450, SEQ ID NO:1452, SEQ ID NO:1453, SEQ ID NO:1454, SEQ ID NO:1455, SEQ ID NO:1456, SEQ ID NO:1457, SEQ ID NO:1458, and SEQ ID NO:1459. In some cases, a functional homolog of SEQ ID NO:1428 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1428.

Examples of amino acid sequences of functional homologs of the polypeptide set forth in SEQ ID NO:1463 are provided in FIG. 49 and in the Sequence Listing. Such functional homologs include SEQ ID NO:1465, SEQ ID NO:1467, SEQ ID NO:1469, SEQ ID NO:1471, SEQ ID NO:1473, SEQ ID NO:1474, SEQ ID NO:1475, SEQ ID NO:1476, and SEQ ID NO:1477. In some cases, a functional homolog of SEQ ID NO:1463 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1463.

Examples of amino acid sequences of functional homologs of the polypeptide set forth in SEQ ID NO:1491 are provided in FIG. 50 and in the Sequence Listing. Such functional homologs include SEQ ID NO:1493, SEQ ID NO:1495, SEQ ID NO:1497, SEQ ID NO:1499, SEQ ID NO:1501, SEQ ID NO:1503, SEQ ID NO:1504, SEQ ID NO:1505, SEQ ID NO:1506, and SEQ ID NO:1508. In some cases, a functional homolog of SEQ ID NO:1491 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1491.

Examples of amino acid sequences of functional homologs of the polypeptide set forth in SEQ ID NO:1510 are provided in FIG. 51 and in the Sequence Listing. Such functional homologs include SEQ ID NO:1512, SEQ ID NO:1514, SEQ ID NO:1516, SEQ ID NO:1518, SEQ ID NO:1520, SEQ ID NO:1522, and SEQ ID NO:1523. In some cases, a functional homolog of SEQ ID NO:1510 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1510.

Examples of amino acid sequences of functional homologs of the polypeptide set forth in SEQ ID NO:1525 are provided in FIG. 52 and in the Sequence Listing. Such functional homologs include SEQ ID NO:1527, SEQ ID NO:1529, SEQ ID NO:1530, SEQ ID NO:1532, SEQ ID NO:1534, and SEQ ID NO:1535. In some cases, a functional homolog of SEQ ID NO:1525 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1525.

Examples of amino acid sequences of functional homologs of the polypeptide set forth in SEQ ID NO:1537 are provided in FIG. 53 and in the Sequence Listing. Such functional homologs include SEQ ID NO:1539, SEQ ID NO:1540, SEQ ID NO:1541, SEQ ID NO:1543, SEQ ID NO:1545, SEQ ID NO:1547, SEQ ID NO:1548, SEQ ID NO:1550, SEQ ID NO:1552, SEQ ID NO:2386, SEQ ID NO:2388, SEQ ID NO:2390, SEQ ID NO:2391, and SEQ ID NO:2392. In some cases, a functional homolog of SEQ ID NO:1537 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1537.

Examples of amino acid sequences of functional homologs of the polypeptide set forth in SEQ ID NO:1554 are provided in FIG. 54 and in the Sequence Listing. Such functional homologs include SEQ ID NO:1555, SEQ ID NO:1557, SEQ ID NO:1559, SEQ ID NO:1561, SEQ ID NO:1563, SEQ ID NO:1565, SEQ ID NO:1567, SEQ ID NO:1569, SEQ ID NO:1571, SEQ ID NO:1572, SEQ ID NO:1573, SEQ ID NO:1574, and SEQ ID NO:1575. In some cases, a functional homolog of SEQ ID NO:1554 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1554.

Examples of amino acid sequences of functional homologs of the polypeptide set forth in SEQ ID NO:1577 are provided in FIG. 55 and in the Sequence Listing. Such functional homologs include SEQ ID NO:1035, SEQ ID NO:1036, SEQ ID NO:1037, SEQ ID NO:1040, SEQ ID NO:1041, SEQ ID NO:1043, SEQ ID NO:1044, SEQ ID NO:1046, SEQ ID NO:1047, SEQ ID NO:1048, SEQ ID NO:1050, SEQ ID NO:1440, SEQ ID NO:1480, SEQ ID NO:1481, SEQ ID NO:1482, SEQ ID NO:1483, SEQ ID NO:1484, SEQ ID NO:1485, SEQ ID NO:1486, SEQ ID NO:1487, SEQ ID NO:1488, SEQ ID NO:1578, SEQ ID NO:1580, SEQ ID NO:1582, SEQ ID NO:1584, SEQ ID NO:1586, SEQ ID NO:1588, SEQ ID NO:1590, SEQ ID NO:1592, SEQ ID NO:1594, SEQ ID NO:1596, SEQ ID NO:1598, SEQ ID NO:1599, SEQ ID NO:1601, SEQ ID NO:1602, SEQ ID NO:1605, SEQ ID NO:1607, SEQ ID NO:1608, SEQ ID NO:1609, SEQ ID NO:1611, SEQ ID NO:1613, SEQ ID NO:1615, SEQ ID NO:1617, SEQ ID NO:1619, SEQ ID NO:1621, SEQ ID NO:1622, SEQ ID NO:1623, SEQ ID NO:1624, SEQ ID NO:1625, SEQ ID NO:1627, SEQ ID NO:1629, SEQ ID NO:1631, SEQ ID NO:1633, SEQ ID NO:1635, SEQ ID NO:1637, SEQ ID NO:1639, SEQ ID NO:1643, SEQ ID NO:1645, SEQ ID NO:1648, SEQ ID NO:1649, SEQ ID NO:1651, and SEQ ID NO:1653. In some cases, a functional homolog of SEQ ID NO:1577 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1577.

Examples of amino acid sequences of functional homologs of the polypeptide set forth in SEQ ID NO:1437 are provided in FIG. 56 and in the Sequence Listing. Such functional homologs include SEQ ID NO:173, SEQ ID NO:212, SEQ ID NO:361, SEQ ID NO:421, SEQ ID NO:443, SEQ ID NO:740, SEQ ID NO:744, SEQ ID NO:942, and SEQ ID NO:1461. In some cases, a functional homolog of SEQ ID NO:1437 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1437.

Examples of amino acid sequences of functional homologs of the polypeptide set forth in SEQ ID NO:97 are provided in FIG. 57 and in the Sequence Listing. Such functional homologs include SEQ ID NO:2010, SEQ ID NO:2011, SEQ ID NO:2013, SEQ ID NO:2015, SEQ ID NO:2017. In some cases, a functional homolog of SEQ ID NO:97 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:97.

The identification of conserved regions in a low nitrogen tolerance-modulating polypeptide facilitates production of variants of low nitrogen tolerance-modulating polypeptides. Variants of low nitrogen tolerance-modulating polypeptides typically have 10 or fewer conservative amino acid substitutions within the primary amino acid sequence, e.g., 7 or fewer conservative amino acid substitutions, 5 or fewer conservative amino acid substitutions, or between 1 and 5 conservative substitutions. A useful variant polypeptide can be constructed based on one of the alignments set forth in FIG. 1-57 and/or homologs identified in the Sequence Listing. Such a polypeptide includes the conserved regions, arranged in the order depicted in the Figure from amino-terminal end to carboxy-terminal end. Such a polypeptide may also include zero, one, or more than one amino acid in positions marked by dashes. When no amino acids are present at positions marked by dashes, the length of such a polypeptide is the sum of the amino acid residues in all conserved regions. When amino acids are present at all positions marked by dashes, such a polypeptide has a length that is the sum of the amino acid residues in all conserved regions and all dashes.

C. Functional Homologs Identified by HMMER

In some embodiments, useful low nitrogen tolerance-modulating polypeptides include those that fit a Hidden Markov Model based on the polypeptides set forth in any one of FIGS. 1-57. A Hidden Markov Model (HMM) is a statistical model of a consensus sequence for a group of functional homologs. See, Durbin et al. (1998) *Biological Sequence Analysis: Probabilistic Models of Proteins and Nucleic Acids*, Cambridge University Press, Cambridge, UK. An HMM is generated by the program HMMER 2.3.2 with default program parameters, using the sequences of the group of functional homologs as input. The multiple sequence alignment is generated by ProbCons (Do et al. (2005) Genome Res., 15(2):330-40) version 1.11 using a set of default parameters: -c, -consistency REPS of 2; -ir, -iterative-refinement REPS of 100; -pre, -pre-training REPS of 0. ProbCons is a public domain software program provided by Stanford University.

The default parameters for building an HMM (hmmbuild) are as follows: the default "architecture prior" (archpri) used by MAP architecture construction is 0.85, and the default cutoff threshold (idlevel) used to determine the effective sequence number is 0.62. HMMER 2.3.2 was released Oct. 3, 2003 under a GNU general public license, and is available from various sources on the World Wide Web such as hmmerjanelia.org; hmmer.wustl.edu; and fr.com/hmmer232/. Hmmbuild outputs the model as a text file.

The HMM for a group of functional homologs can be used to determine the likelihood that a candidate low nitrogen tolerance-modulating polypeptide sequence is a better fit to that particular HMM than to a null HMM generated using a group of sequences that are not structurally or functionally related. The likelihood that a candidate polypeptide sequence is a better fit to an HMM than to a null HMM is indicated by the HMM bit score, a number generated when the candidate sequence is fitted to the HMM profile using the HMMER hmmsearch program. The following default parameters are used when running hmmsearch: the default E-value cutoff (E) is 10.0, the default bit score cutoff (T) is negative infinity, the default number of sequences in a database (Z) is the real number of sequences in the database, the default E-value cutoff for the per-domain ranked hit list (domE) is infinity, and the default bit score cutoff for the per-domain ranked hit list (domT) is negative infinity. A high HMM bit score indicates a greater likelihood that the candidate sequence carries out one or more of the biochemical or physiological function(s) of the polypeptides used to generate the HMM. A high HMM bit score is at least 20, and often is higher. Slight variations in the HMM bit score of a particular sequence can occur due to factors such as the order in which sequences are processed for alignment by multiple sequence alignment algorithms such as the ProbCons program. Nevertheless, such HMM bit score variation is minor.

The low nitrogen tolerance-modulating polypeptides discussed below fit the indicated HMM with an HMM bit score greater than 20 (e.g., greater than 30, 40, 50, 60, 70, 80, 90, 100, 200, 300, 400, or 500). In some embodiments, the HMM bit score of a low nitrogen tolerance-modulating polypeptide discussed below is about 50%, 60%, 70%, 80%, 90%, or 95% of the HMM bit score of a functional homolog provided the Sequence Listing of this application. In some embodiments, a low nitrogen tolerance-modulating polypeptide discussed below fits the indicated HMM with an HMM bit score greater than 20, and has a domain indicative of a low nitrogen tolerance-modulating polypeptide. In some embodiments, a low nitrogen tolerance-modulating polypeptide discussed below fits the indicated HMM with an HMM bit score greater than 20, and has 70% or greater sequence identity (e.g., 75%, 80%, 85%, 90%, 95%, or 100% sequence identity) to an amino acid sequence shown in any one of FIGS. 1-57.

Examples of polypeptides are shown in the sequence listing that have HMM bit scores greater than 800 when fitted to an HMM generated from the amino acid sequences set forth in FIG. 1 are identified in the Sequence Listing of this application. Such polypeptides include SEQ ID NO:3, SEQ ID NO:4, SEQ ID NO:6, SEQ ID NO:8, SEQ ID NO:10, SEQ ID NO:12, SEQ ID NO:14, SEQ ID NO:16, SEQ ID NO:17, SEQ ID NO:19, SEQ ID NO:20, SEQ ID NO:21, SEQ ID NO:22, SEQ ID NO:24, SEQ ID NO:25, SEQ ID NO:27, SEQ ID NO:29, SEQ ID NO:31, SEQ ID NO:33, SEQ ID NO:35, SEQ ID NO:36, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, and SEQ ID NO:47.

Examples of polypeptides are shown in the sequence listing that have HMM bit scores greater than 150 when fitted to an HMM generated from the amino acid sequences set forth in FIG. 2 are identified in the Sequence Listing of this application. Such polypeptides include SEQ ID NO:49, SEQ ID NO:51, SEQ ID NO:53, SEQ ID NO:55, SEQ ID NO:56, SEQ ID NO:58, SEQ ID NO:60, SEQ ID NO:62, SEQ ID NO:63, SEQ ID NO:64, SEQ ID NO:65, SEQ ID NO:67, SEQ ID NO:69, SEQ ID NO:70, SEQ ID NO:71, SEQ ID NO:72, SEQ ID NO:73, and SEQ ID NO:75.

Examples of polypeptides are shown in the sequence listing that have HMM bit scores greater than 540 when fitted to an HMM generated from the amino acid sequences set forth in FIG. 3 are identified in the Sequence Listing of this application. Such polypeptides include SEQ ID NO:77, SEQ ID NO:78, SEQ ID NO:80, SEQ ID NO:82, SEQ ID NO:84, SEQ ID NO:85, SEQ ID NO:87, SEQ ID NO:88, SEQ ID NO:90, SEQ ID NO:92, SEQ ID NO:93, SEQ ID NO:95, and SEQ ID NO:1479.

Examples of polypeptides are shown in the sequence listing that have HMM bit scores greater than 210 when fitted to an HMM generated from the amino acid sequences set forth in FIG. 4 are identified in the Sequence Listing of this application. Such polypeptides include SEQ ID NO:100, SEQ ID NO:101, SEQ ID NO:102, SEQ ID NO:104, SEQ ID NO:106, SEQ ID NO:108, SEQ ID NO:110, SEQ ID NO:111, SEQ ID NO:113, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:125, SEQ ID NO:126, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:137, SEQ ID NO:139, SEQ ID NO:141, SEQ ID NO:142, SEQ ID NO:144, SEQ ID NO:145, SEQ ID NO:146, SEQ ID NO:147, SEQ ID NO:148, SEQ ID NO:149, and SEQ ID NO:150.

Examples of polypeptides are shown in the sequence listing that have HMM bit scores greater than 90 when fitted to an HMM generated from the amino acid sequences set forth in FIG. 5 are identified in the Sequence Listing of this application. Such polypeptides include SEQ ID NO:152, SEQ ID NO:154, SEQ ID NO:156, SEQ ID NO:158, SEQ ID NO:160, SEQ ID NO:162, and SEQ ID NO:164.

Examples of polypeptides are shown in the sequence listing that have HMM bit scores greater than 230 when fitted to an HMM generated from the amino acid sequences set forth in FIG. 6 are identified in the Sequence Listing of this application. Such polypeptides include SEQ ID NO:166, SEQ ID NO:168, SEQ ID NO:170, SEQ ID NO:172, SEQ ID NO:174, SEQ ID NO:177, SEQ ID NO:179, SEQ ID NO:181, SEQ ID NO:182, SEQ ID NO:183, and SEQ ID NO:184.

Examples of polypeptides are shown in the sequence listing that have HMM bit scores greater than 90 when fitted to an HMM generated from the amino acid sequences set forth in FIG. 7 are identified in the Sequence Listing of this application. Such polypeptides include SEQ ID NO:186, SEQ ID NO:188, SEQ ID NO:190, SEQ ID NO:191, SEQ ID NO:193, SEQ ID NO:194, SEQ ID NO:196, SEQ ID NO:197, SEQ ID NO:199, SEQ ID NO:201, SEQ ID NO:203, SEQ ID NO:204, SEQ ID NO:205, and SEQ ID NO:206.

Examples of polypeptides are shown in the sequence listing that have HMM bit scores greater than 380 when fitted to an HMM generated from the amino acid sequences set forth in FIG. 8 are identified in the Sequence Listing of this application. Such polypeptides include SEQ ID NO:208, SEQ ID NO:209, SEQ ID NO:210, SEQ ID NO:214, and SEQ ID NO:216.

Examples of polypeptides are shown in the sequence listing that have HMM bit scores greater than 110 when fitted to an HMM generated from the amino acid sequences set forth in FIG. 9 are identified in the Sequence Listing of this application. Such polypeptides include SEQ ID NO:218, SEQ ID NO:220, SEQ ID NO:222, SEQ ID NO:223, SEQ ID NO:225, SEQ ID NO:227, SEQ ID NO:229, SEQ ID NO:230, SEQ ID NO:231, SEQ ID NO:232, SEQ ID NO:1039, SEQ ID NO:1049, and SEQ ID NO:1052.

Examples of polypeptides are shown in the sequence listing that have HMM bit scores greater than 220 when fitted to an HMM generated from the amino acid sequences set forth in FIG. 10 are identified in the Sequence Listing of this application. Such polypeptides include SEQ ID NO:234, SEQ ID NO:236, SEQ ID NO:238, SEQ ID NO:239, SEQ ID NO:241, SEQ ID NO:242, SEQ ID NO:243, and SEQ ID NO:244.

Examples of polypeptides are shown in the sequence listing that have HMM bit scores greater than 150 when fitted to an HMM generated from the amino acid sequences set forth in FIG. 11 are identified in the Sequence Listing of this application. Such polypeptides include SEQ ID NO:246, SEQ ID NO:248, SEQ ID NO:249, SEQ ID NO:251, SEQ ID NO:253, SEQ ID NO:255, SEQ ID NO:257, SEQ ID NO:259, SEQ ID NO:260, SEQ ID NO:262, SEQ ID NO:264, SEQ ID NO:265, SEQ ID NO:267, SEQ ID NO:268, SEQ ID NO:270, SEQ ID NO:272, SEQ ID NO:274, SEQ ID NO:276, SEQ ID NO:277, SEQ ID NO:279, SEQ ID NO:281, SEQ ID NO:283, SEQ ID NO:285, SEQ ID NO:286, SEQ ID NO:287, SEQ ID NO:288, SEQ ID NO:290, SEQ ID NO:291, SEQ ID NO:292, SEQ ID NO:293, SEQ ID NO:296, and SEQ ID NO:298.

Examples of polypeptides are shown in the sequence listing that have HMM bit scores greater than 950 when fitted to an HMM generated from the amino acid sequences set forth in FIG. 12 are identified in the Sequence Listing of this application. Such polypeptides include SEQ ID NO:300, SEQ ID NO:302, SEQ ID NO:304, SEQ ID NO:306, SEQ ID NO:308, SEQ ID NO:310, SEQ ID NO:312, SEQ ID NO:314, SEQ ID NO:316, SEQ ID NO:318, SEQ ID NO:319, SEQ ID NO:320, SEQ ID NO:321, SEQ ID NO:322, SEQ ID NO:323, SEQ ID NO:325, SEQ ID NO:327, and SEQ ID NO:329.

Examples of polypeptides are shown in the sequence listing that have HMM bit scores greater than 460 when fitted to an HMM generated from the amino acid sequences set forth in FIG. 13 are identified in the Sequence Listing of this application. Such polypeptides include SEQ ID NO:332, SEQ ID NO:334, SEQ ID NO:335, SEQ ID NO:336, SEQ ID NO:338, SEQ ID NO:339, SEQ ID NO:341, SEQ ID NO:342, SEQ ID NO:343, SEQ ID NO:344, SEQ ID NO:345, SEQ ID NO:346, SEQ ID NO:347, SEQ ID NO:348, SEQ ID NO:349, SEQ ID NO:351, SEQ ID NO:352, SEQ ID NO:353, SEQ ID NO:354, SEQ ID NO:355, SEQ ID NO:356, SEQ ID NO:357, SEQ ID NO:358, SEQ ID NO:359, SEQ ID NO:360, SEQ ID NO:362, SEQ ID NO:363, SEQ ID NO:364, SEQ ID NO:365, SEQ ID NO:366, SEQ ID NO:2541, SEQ ID NO:2542, SEQ ID NO:2543, SEQ ID NO:2544, SEQ ID NO:2546, SEQ ID NO:2548, SEQ ID NO:2549, SEQ ID NO:2550, SEQ ID NO:2551, SEQ ID NO:2552, and SEQ ID NO:2553.

Examples of polypeptides are shown in the sequence listing that have HMM bit scores greater than 150 when fitted to an HMM generated from the amino acid sequences set forth in FIG. 14 are identified in the Sequence Listing of this application. Such polypeptides include SEQ ID NO:368, SEQ ID NO:369, SEQ ID NO:370, SEQ ID NO:371, SEQ ID NO:372, SEQ ID NO:373, SEQ ID NO:374, SEQ ID NO:376, SEQ ID NO:378, SEQ ID NO:380, SEQ ID NO:382, SEQ ID NO:384, SEQ ID NO:386, SEQ ID NO:388, SEQ ID NO:390, SEQ ID NO:392, SEQ ID NO:394, SEQ ID NO:396, SEQ ID NO:398, SEQ ID NO:399, SEQ ID NO:401, SEQ ID NO:403, SEQ ID NO:404, SEQ ID NO:406, SEQ ID NO:408, SEQ ID NO:410, SEQ ID NO:412, SEQ ID NO:414, SEQ ID NO:416, SEQ ID NO:418, SEQ ID NO:419, SEQ ID NO:420, SEQ ID NO:422, SEQ ID NO:423, SEQ ID NO:425, SEQ ID NO:427, SEQ ID NO:428, SEQ ID NO:430, SEQ ID NO:432, SEQ ID NO:433, SEQ ID NO:434, SEQ ID NO:435, SEQ ID NO:436, SEQ ID NO:437, SEQ ID NO:438, SEQ ID NO:439, SEQ ID NO:440, SEQ ID NO:441, SEQ ID NO:444, SEQ ID NO:445, SEQ ID NO:446, SEQ ID NO:447, SEQ ID NO:448, SEQ ID NO:449, SEQ ID NO:450, SEQ ID NO:451, SEQ ID NO:452, SEQ ID NO:453, SEQ ID NO:454, SEQ ID NO:455, SEQ ID NO:456, SEQ ID NO:458, SEQ ID NO:459, SEQ ID NO:461, SEQ ID NO:463, SEQ ID NO:465, SEQ ID NO:467, SEQ ID NO:469, SEQ ID NO:471, SEQ ID NO:473, SEQ ID NO:474, SEQ ID NO:475, SEQ ID NO:477, SEQ ID NO:479, SEQ ID NO:481, SEQ ID NO:483, SEQ ID NO:485, SEQ ID NO:487, SEQ ID NO:488, SEQ ID NO:489, SEQ ID NO:490, SEQ ID NO:491, SEQ ID NO:492, SEQ ID NO:494, SEQ ID NO:495, SEQ ID NO:496, SEQ ID NO:497, SEQ ID NO:498, SEQ ID NO:499, SEQ ID NO:500, SEQ ID NO:501, SEQ ID NO:502, SEQ ID NO:504, SEQ ID NO:505, SEQ ID NO:506, SEQ ID NO:507, and SEQ ID NO:508.

Examples of polypeptides are shown in the sequence listing that have HMM bit scores greater than 410 when fitted to an HMM generated from the amino acid sequences set forth in FIG. 15 are identified in the Sequence Listing of this application. Such polypeptides include SEQ ID NO:510, SEQ ID NO:511, SEQ ID NO:513, SEQ ID NO:515, SEQ ID NO:517, SEQ ID NO:521, SEQ ID NO:523, SEQ ID NO:525, SEQ ID NO:527, SEQ ID NO:529, SEQ ID NO:530, and SEQ ID NO:531.

Examples of polypeptides are shown in the sequence listing that have HMM bit scores greater than 520 when fitted to an HMM generated from the amino acid sequences set forth in FIG. 16 are identified in the Sequence Listing of this application. Such polypeptides include SEQ ID NO:533, SEQ ID NO:535, SEQ ID NO:536, SEQ ID NO:538, SEQ ID NO:539, SEQ ID NO:541, SEQ ID NO:542, SEQ ID NO:543, SEQ ID NO:544, SEQ ID NO:545, SEQ ID NO:546, SEQ ID NO:547, SEQ ID NO:548, SEQ ID NO:550, SEQ ID NO:552, SEQ ID NO:553, and SEQ ID NO:554.

Examples of polypeptides are shown in the sequence listing that have HMM bit scores greater than 1150 when fitted to an HMM generated from the amino acid sequences set forth in FIG. 17 are identified in the Sequence Listing of this application. Such polypeptides include SEQ ID NO:558, SEQ ID NO:559, SEQ ID NO:560, SEQ ID NO:561, SEQ ID NO:562, SEQ ID NO:563, SEQ ID NO:564, SEQ ID NO:565, SEQ ID NO:566, SEQ ID NO:567, SEQ ID NO:569, SEQ ID NO:571, SEQ ID NO:572, SEQ ID NO:573, SEQ ID NO:575, SEQ ID NO:576, SEQ ID NO:577, SEQ ID NO:578, SEQ ID NO:579, SEQ ID NO:581, SEQ ID NO:583, SEQ ID NO:584, SEQ ID NO:585, SEQ ID NO:586, SEQ ID NO:588, SEQ ID NO:589, SEQ ID NO:590, and SEQ ID NO:591.

Examples of polypeptides are shown in the sequence listing that have HMM bit scores greater than 340 when fitted to an HMM generated from the amino acid sequences set forth in FIG. 18 are identified in the Sequence Listing of this application. Such polypeptides include SEQ ID NO:593, SEQ ID NO:595, SEQ ID NO:597, SEQ ID NO:599, SEQ ID NO:601, SEQ ID NO:603, SEQ ID NO:605, SEQ ID NO:607, SEQ ID NO:609, SEQ ID NO:610, and SEQ ID NO:611.

Examples of polypeptides are shown in the sequence listing that have HMM bit scores greater than 140 when fitted to an HMM generated from the amino acid sequences set forth in FIG. 19 are identified in the Sequence Listing of this application. Such polypeptides include SEQ ID NO:613, SEQ ID NO:615, SEQ ID NO:617, SEQ ID NO:618, SEQ ID NO:620, SEQ ID NO:622, SEQ ID NO:624, SEQ ID NO:626, SEQ ID NO:628, SEQ ID NO:630, SEQ ID NO:632, SEQ ID NO:634, SEQ ID NO:636, SEQ ID NO:638, SEQ ID NO:640, SEQ ID NO:642, SEQ ID NO:643, and SEQ ID NO:644.

Examples of polypeptides are shown in the sequence listing that have HMM bit scores greater than 250 when fitted to an HMM generated from the amino acid sequences set forth in FIG. 20 are identified in the Sequence Listing of this application. Such polypeptides include SEQ ID NO:646, SEQ ID NO:648, SEQ ID NO:650, SEQ ID NO:652, SEQ ID NO:654, SEQ ID NO:656, SEQ ID NO:658, SEQ ID NO:660, SEQ ID NO:662, SEQ ID NO:664, SEQ ID NO:666, SEQ ID NO:668, SEQ ID NO:670, SEQ ID NO:672, SEQ ID NO:674, SEQ ID NO:676, SEQ ID NO:678, SEQ ID NO:679, SEQ ID NO:680, SEQ ID NO:681, SEQ ID NO:682, SEQ ID NO:683, and SEQ ID NO:685.

Examples of polypeptides are shown in the sequence listing that have HMM bit scores greater than 170 when fitted to an HMM generated from the amino acid sequences set forth in FIG. 21 are identified in the Sequence Listing of this application. Such polypeptides include SEQ ID NO:687, SEQ ID NO:689, SEQ ID NO:691, SEQ ID NO:693, SEQ ID NO:694, SEQ ID NO:696, SEQ ID NO:697, SEQ ID NO:699, SEQ ID NO:701, SEQ ID NO:703, SEQ ID NO:705, SEQ ID NO:706, SEQ ID NO:708, SEQ ID NO:710, SEQ ID NO:712, SEQ ID NO:714, SEQ ID NO:716, SEQ ID NO:718, SEQ ID NO:720, SEQ ID NO:721, SEQ ID NO:722, SEQ ID NO:723, SEQ ID NO:724, SEQ ID NO:725, SEQ ID NO:726, SEQ ID NO:727, and SEQ ID NO:728.

Examples of polypeptides are shown in the sequence listing that have HMM bit scores greater than 210 when fitted to an HMM generated from the amino acid sequences set forth in FIG. 22 are identified in the Sequence Listing of this application. Such polypeptides include SEQ ID NO:730, SEQ ID NO:732, SEQ ID NO:733, SEQ ID NO:735, SEQ ID NO:737, SEQ ID NO:738, and SEQ ID NO:742.

Examples of polypeptides are shown in the sequence listing that have HMM bit scores greater than 230 when fitted to an HMM generated from the amino acid sequences set forth in FIG. 23 are identified in the Sequence Listing of this application. Such polypeptides include SEQ ID NO:746, SEQ ID NO:748, SEQ ID NO:750, SEQ ID NO:751, SEQ ID NO:753, SEQ ID NO:755, SEQ ID NO:757, SEQ ID NO:758, SEQ ID NO:760, SEQ ID NO:761, SEQ ID NO:762, SEQ ID NO:763, SEQ ID NO:765, and SEQ ID NO:767.

Examples of polypeptides are shown in the sequence listing that have HMM bit scores greater than 180 when fitted to an HMM generated from the amino acid sequences set forth in FIG. 24 are identified in the Sequence Listing of this application. Such polypeptides include SEQ ID NO:769, SEQ ID NO:771, SEQ ID NO:773, SEQ ID NO:775, SEQ ID NO:777, SEQ ID NO:779, SEQ ID NO:781, SEQ ID NO:783, SEQ ID NO:785, SEQ ID NO:787, SEQ ID NO:789, and SEQ ID NO:790.

Examples of polypeptides are shown in the sequence listing that have HMM bit scores greater than 300 when fitted to an HMM generated from the amino acid sequences set forth in FIG. 25 are identified in the Sequence Listing of this application. Such polypeptides include SEQ ID NO:792, SEQ ID NO:794, SEQ ID NO:796, SEQ ID NO:798, SEQ ID NO:799, SEQ ID NO:801, SEQ ID NO:803, SEQ ID NO:805, SEQ ID NO:807, SEQ ID NO:808, SEQ ID NO:810, SEQ ID NO:812, SEQ ID NO:814, SEQ ID NO:816, SEQ ID NO:818, SEQ ID NO:819, SEQ ID NO:820, SEQ ID NO:821, and SEQ ID NO:822.

Examples of polypeptides are shown in the sequence listing that have HMM bit scores greater than 190 when fitted to an HMM generated from the amino acid sequences set forth in FIG. 26 are identified in the Sequence Listing of this application. Such polypeptides include SEQ ID NO:824, SEQ ID NO:826, SEQ ID NO:1696, SEQ ID NO:1698, SEQ ID NO:1700, SEQ ID NO:1702, SEQ ID NO:1704, SEQ ID NO:1706, SEQ ID NO:1708, SEQ ID NO:1710, SEQ ID NO:1711, SEQ ID NO:1713, SEQ ID NO:1714, SEQ ID NO:1715, and SEQ ID NO:1716.

Examples of polypeptides are shown in the sequence listing that have HMM bit scores greater than 630 when fitted to an HMM generated from the amino acid sequences set forth in FIG. 27 are identified in the Sequence Listing of this application. Such polypeptides include SEQ ID NO:828, SEQ ID NO:830, SEQ ID NO:832, SEQ ID NO:834, SEQ ID NO:836, SEQ ID NO:837, SEQ ID NO:838, SEQ ID NO:839, SEQ ID NO:840, SEQ ID NO:842, SEQ ID NO:844, SEQ ID NO:845, SEQ ID NO:846, SEQ ID NO:847, SEQ ID NO:848, SEQ ID NO:849, SEQ ID NO:850, and SEQ ID NO:851.

Examples of polypeptides are shown in the sequence listing that have HMM bit scores greater than 95 when fitted to an MCA generated from the amino acid sequences set forth in FIG. 28 are identified in the Sequence Listing of this application. Such polypeptides include SEQ ID NO:855, SEQ ID NO:856, SEQ ID NO:858, SEQ ID NO:860, SEQ ID NO:862, SEQ ID NO:864, SEQ ID NO:866, SEQ ID NO:868, SEQ ID NO:870, SEQ ID NO:872, SEQ ID NO:874, SEQ ID NO:876, SEQ ID NO:878, SEQ ID NO:880, SEQ ID NO:882, SEQ ID NO:884, SEQ ID NO:885, SEQ ID NO:886, SEQ ID NO:887, SEQ ID NO:888, and SEQ ID NO:889.

Examples of polypeptides are shown in the sequence listing that have HMM bit scores greater than 850 when fitted to an HMM generated from the amino acid sequences set forth in FIG. 29 are identified in the Sequence Listing of this application. Such polypeptides include SEQ ID NO:891, SEQ ID NO:893, SEQ ID NO:894, SEQ ID NO:895, SEQ ID NO:896, SEQ ID NO:898, SEQ ID NO:900, SEQ ID NO:901, SEQ ID NO:902, SEQ ID NO:903, SEQ ID NO:904, SEQ ID NO:905, SEQ ID NO:907, SEQ ID NO:908, SEQ ID NO:909, SEQ ID NO:910, SEQ ID NO:911, SEQ ID NO:912, SEQ ID NO:913, SEQ ID NO:914, and SEQ ID NO:915.

Examples of polypeptides are shown in the sequence listing that have HMM bit scores greater than 300 when fitted to an HMM generated from the amino acid sequences set forth in FIG. 30 are identified in the Sequence Listing of this application. Such polypeptides include SEQ ID NO:917, SEQ ID NO:919, SEQ ID NO:921, SEQ ID NO:923, SEQ ID NO:925, SEQ ID NO:927, SEQ ID NO:929, SEQ ID NO:931, SEQ ID NO:933, SEQ ID NO:935, SEQ ID NO:937, SEQ ID NO:939, and SEQ ID NO:940.

Examples of polypeptides are shown in the sequence listing that have HMM bit scores greater than 60 when fitted to an HMM generated from the amino acid sequences set forth in FIG. 31 are identified in the Sequence Listing of this application. Such polypeptides include SEQ ID NO:944, SEQ ID NO:946, SEQ ID NO:947, SEQ ID NO:948, SEQ ID NO:950, SEQ ID NO:952, SEQ ID NO:954, SEQ ID NO:956, SEQ ID NO:958, SEQ ID NO:960, SEQ ID NO:962, SEQ ID NO:964, SEQ ID NO:966, SEQ ID NO:967, SEQ ID NO:968, SEQ ID NO:969, SEQ ID NO:970, SEQ ID NO:972, and SEQ ID NO:974.

Examples of polypeptides are shown in the sequence listing that have HMM bit scores greater than 340 when fitted to an HMM generated from the amino acid sequences set forth in FIG. 32 are identified in the Sequence Listing of this application. Such polypeptides include SEQ ID NO:976, SEQ ID NO:978, and SEQ ID NO:980.

Examples of polypeptides are shown in the sequence listing that have HMM bit scores greater than 180 when fitted to an HMM generated from the amino acid sequences set forth in FIG. 33 are identified in the Sequence Listing of this application. Such polypeptides include SEQ ID NO:982, SEQ ID NO:984, SEQ ID NO:985, SEQ ID NO:986, SEQ ID NO:987, SEQ ID NO:988, SEQ ID NO:989, SEQ ID NO:990, SEQ ID NO:991, SEQ ID NO:992, SEQ ID NO:993, SEQ ID NO:995, SEQ ID NO:996, SEQ ID NO:998, SEQ ID NO:1000, SEQ ID NO:1001, SEQ ID NO:1003, SEQ ID NO:1005, SEQ ID NO:1007, SEQ ID NO:1008, SEQ ID NO:1009, SEQ ID NO:1011, SEQ ID NO:1013, SEQ ID NO:1015, SEQ ID NO:1016, SEQ ID NO:1018, SEQ ID NO:1019, SEQ ID NO:1021, SEQ ID NO:1023, SEQ ID NO:1025, SEQ ID NO:1026, SEQ ID NO:1027, SEQ ID NO:1028, SEQ ID NO:1029, SEQ ID NO:1030, SEQ ID NO:1031, SEQ ID NO:1032, and SEQ ID NO:1033.

Examples of polypeptides are shown in the sequence listing that have HMM bit scores greater than 1060 when fitted to an HMM generated from the amino acid sequences set forth in FIG. 34 are identified in the Sequence Listing of this application. Such polypeptides include SEQ ID NO:1054, SEQ ID NO:1055, SEQ ID NO:1057, SEQ ID NO:1058, SEQ ID NO:1059, SEQ ID NO:1061, SEQ ID NO:1063, SEQ ID NO:1065, SEQ ID NO:1065, SEQ ID NO:1067, SEQ ID NO:1068, SEQ ID NO:1070, SEQ ID NO:1071, SEQ ID NO:1072, SEQ ID NO:1074, SEQ ID NO:1075, SEQ ID NO:1076, SEQ ID NO:1077, SEQ ID NO:1078, SEQ ID NO:1080, SEQ ID NO:1082, SEQ ID NO:1083, SEQ ID NO:1085, SEQ ID NO:1086, SEQ ID NO:1087, SEQ ID NO:1088, SEQ ID NO:1089, SEQ ID NO:1089, SEQ ID NO:1090, SEQ ID NO:1091, SEQ ID NO:1092, SEQ ID NO:1093, SEQ ID NO:1094, SEQ ID NO:1095, and SEQ ID NO:1097.

Examples of polypeptides are shown in the sequence listing that have HIM bit scores greater than 260 when fitted to an HMM generated from the amino acid sequences set forth in FIG. 35 are identified in the Sequence Listing of this application. Such polypeptides include SEQ ID NO:1099, SEQ ID NO:1101, SEQ ID NO:1103, SEQ ID NO:1104, SEQ ID NO:1105, SEQ ID NO:1106, SEQ ID NO:1108, SEQ ID NO:1109, and SEQ ID NO:1110.

Examples of polypeptides are shown in the sequence listing that have HMM bit scores greater than 150 when fitted to an HMM generated from the amino acid sequences set forth in FIG. 36 are identified in the Sequence Listing of this application. Such polypeptides include SEQ ID NO:1112, SEQ ID NO:1113, and SEQ ID NO:1114.

Examples of polypeptides are shown in the sequence listing that have HMM bit scores greater than 40 when fitted to an HMM generated from the amino acid sequences set forth in FIG. 37 are identified in the Sequence Listing of this application. Such polypeptides include SEQ ID NO:1116, SEQ ID NO:1118, SEQ ID NO:1120, SEQ ID NO:1122, SEQ ID NO:1123, SEQ ID NO:1125, SEQ ID NO:1126, SEQ ID NO:1128, SEQ ID NO:1129, SEQ ID NO:1131, SEQ ID NO:1132, SEQ ID NO:1133, SEQ ID NO:1134, SEQ ID NO:1136, SEQ ID NO:1138, SEQ ID NO:1140, SEQ ID NO:1141, SEQ ID NO:1142, SEQ ID NO:1143, SEQ ID NO:1144, SEQ ID NO:1145, SEQ ID NO:1147, SEQ ID NO:1149, SEQ ID NO:1151, SEQ ID NO:1153, and SEQ ID NO:1155.

Examples of polypeptides are shown in the sequence listing that have HMM bit scores greater than 450 when fitted to an HMM generated from the amino acid sequences set forth in FIG. 38 are identified in the Sequence Listing of this application. Such polypeptides include SEQ ID NO:1159, SEQ ID NO:1161, SEQ ID NO:1162, SEQ ID NO:1163, and SEQ ID NO:1164.

Examples of polypeptides are shown in the sequence listing that have HMM bit scores greater than 160 when fitted to an HMM generated from the amino acid sequences set forth in FIG. 39 are identified in the Sequence Listing of this application. Such polypeptides include SEQ ID NO:1166, SEQ ID NO:1167, SEQ ID NO:1169, SEQ ID NO:1171, SEQ ID NO:1173, SEQ ID NO:1175, SEQ ID NO:1177, SEQ ID NO:1179, SEQ ID NO:1180, SEQ ID NO:1182, and SEQ ID NO:1183.

Examples of polypeptides are shown in the sequence listing that have HMM bit scores greater than 180 when fitted to an HMM generated from the amino acid sequences set forth in FIG. 40 are identified in the Sequence Listing of this application. Such polypeptides include SEQ ID NO:1185, SEQ ID NO:1187, SEQ ID NO:1189, SEQ ID NO:1190, SEQ ID NO:1191, and SEQ ID NO:1192.

Examples of polypeptides are shown in the sequence listing that have HMM bit scores greater than 670 when fitted to an HMM generated from the amino acid sequences set forth in FIG. 41 are identified in the Sequence Listing of this application. Such polypeptides include SEQ ID NO:1194, SEQ ID NO:1196, SEQ ID NO:1198, SEQ ID NO:1200, SEQ ID NO:1202, SEQ ID NO:1203, SEQ ID NO:1204, SEQ ID NO:1205, SEQ ID NO:1206, SEQ ID NO:1207, and SEQ ID NO:1208.

Examples of polypeptides are shown in the sequence listing that have HMM bit scores greater than 280 when fitted to an HMM generated from the amino acid sequences set forth in FIG. 42 are identified in the Sequence Listing of this application. Such polypeptides include SEQ ID NO:1210, SEQ ID NO:1211, SEQ ID NO:1213, SEQ ID NO:1215, SEQ ID NO:1216, SEQ ID NO:1218, SEQ ID NO:1220, SEQ ID NO:1222, SEQ ID NO:1224, SEQ ID NO:1226, SEQ ID NO:1228, SEQ ID NO:1229, SEQ ID NO:1230, SEQ ID NO:1232, SEQ ID NO:1233, SEQ ID NO:1234, SEQ ID NO:1235, SEQ ID NO:1236, SEQ ID NO:1237, SEQ ID NO:1238, SEQ ID NO:1239, SEQ ID NO:1240, SEQ ID NO:1241, SEQ ID NO:1242, SEQ ID NO:1243, SEQ ID NO:1244, SEQ ID NO:1245, SEQ ID NO:1246, SEQ ID NO:1247, SEQ ID NO:1248, SEQ ID NO:1249, SEQ ID NO:1251, SEQ ID NO:1253, SEQ ID NO:1255, SEQ ID NO:1257, SEQ ID NO:1259, SEQ ID NO:1261, SEQ ID NO:1263, SEQ ID NO:1264, SEQ ID NO:1265, SEQ ID NO:1266, SEQ ID NO:1267, SEQ ID NO:1268, SEQ ID NO:1269, SEQ ID NO:1270, SEQ ID NO:1271, and SEQ ID NO:1272.

Examples of polypeptides are shown in the sequence listing that have HMM bit scores greater than 700 when fitted to an HMM generated from the amino acid sequences set forth in FIG. 43 are identified in the Sequence Listing of this application. Such polypeptides include SEQ ID NO:1274, SEQ ID NO:1276, SEQ ID NO:1278, SEQ ID NO:1280, SEQ ID NO:1281, SEQ ID NO:1282, SEQ ID NO:1284, SEQ ID NO:1285, SEQ ID NO:1287, SEQ ID NO:1289, SEQ ID NO:1291, SEQ ID NO:1293, SEQ ID NO:1294, SEQ ID NO:1295, SEQ ID NO:1296, SEQ ID NO:1297, SEQ ID NO:1298, and SEQ ID NO:1300.

Examples of polypeptides are shown in the sequence listing that have HMM bit scores greater than 920 when fitted to an HMM generated from the amino acid sequences set forth in FIG. 44 are identified in the Sequence Listing of this application. Such polypeptides include SEQ ID NO:1302, SEQ ID NO:1303, SEQ ID NO:1305, SEQ ID NO:1307, SEQ ID NO:1309, SEQ ID NO:1311, SEQ ID NO:1312, SEQ ID NO:1313, SEQ ID NO:1314, SEQ ID NO:1315, SEQ ID NO:1317, SEQ ID NO:1318, SEQ ID NO:1319, SEQ ID NO:1320, SEQ ID NO:1321, SEQ ID NO:1322, SEQ ID NO:1323, SEQ ID NO:1324, SEQ ID NO:1325, SEQ ID NO:1326, SEQ ID NO:1327, SEQ ID NO:1328, SEQ ID NO:1330, SEQ ID NO:1331, SEQ ID NO:1333, SEQ ID NO:1334, SEQ ID NO:1335, SEQ ID NO:1336, SEQ ID NO:1337, SEQ ID NO:1338, SEQ ID NO:1339, and SEQ ID NO:1340.

Examples of polypeptides are shown in the sequence listing that have HMM bit scores greater than 510 when fitted to an HMM generated from the amino acid sequences set forth in FIG. 45 are identified in the Sequence Listing of this application. Such polypeptides include SEQ ID NO:1342, SEQ ID NO:1344, SEQ ID NO:1346, SEQ ID NO:1348, SEQ ID NO:1350, SEQ ID NO:1352, SEQ ID NO:1354, SEQ ID NO:1355, SEQ ID NO:1357, SEQ ID NO:1358, SEQ ID NO:1360, SEQ ID NO:1361, SEQ ID NO:1362, SEQ ID NO:1363, SEQ ID NO:1364, SEQ ID NO:1366, SEQ ID NO:1367, SEQ ID NO:1369, SEQ ID NO:1370, SEQ ID NO:1371, SEQ ID NO:1372, SEQ ID NO:1373, SEQ ID NO:1374, SEQ ID NO:1375, SEQ ID NO:1376, SEQ ID NO:1377, SEQ ID NO:1378, SEQ ID NO:1379, SEQ ID NO:1380, SEQ ID NO:1381, SEQ ID NO:1382, and SEQ ID NO:1383.

Examples of polypeptides are shown in the sequence listing that have HMM bit scores greater than 140 when fitted to an HMM generated from the amino acid sequences set forth in FIG. 46 are identified in the Sequence Listing of this application. Such polypeptides include SEQ ID NO:1385, SEQ ID NO:1387, SEQ ID NO:1389, SEQ ID NO:1390, SEQ ID NO:1391, SEQ ID NO:1393, SEQ ID NO:1394, SEQ ID NO:1395, SEQ ID NO:1396, SEQ ID NO:1398, SEQ ID NO:1400, SEQ ID NO:1401, SEQ ID. NO:1402, SEQ ID NO:1403, SEQ ID NO:1404, SEQ ID NO:1405, and SEQ ID NO:1407.

Examples of polypeptides are shown in the sequence listing that have HMM bit scores greater than 150 when fitted to an HMM generated from the amino acid sequences set forth in FIG. 47 are identified in the Sequence Listing of this application. Such polypeptides include SEQ ID NO:1409, SEQ ID NO:1411, SEQ ID NO:1413, SEQ ID NO:1415, SEQ ID NO:1417, SEQ ID NO:1418, SEQ ID NO:1419, SEQ ID NO:1421, SEQ ID NO:1423, SEQ ID NO:1424, SEQ ID NO:1425, SEQ ID NO:1426.

Examples of polypeptides are shown in the sequence listing that have HMM bit scores greater than 190 when fitted to an HMM generated from the amino acid sequences set forth in FIG. 48 are identified in the Sequence Listing of this application. Such polypeptides include SEQ ID NO:1428, SEQ ID NO:1430, SEQ ID NO:1432, SEQ ID NO:1434, SEQ ID NO:1436, SEQ ID NO:1439, SEQ ID NO:1442, SEQ ID NO:1444, SEQ ID NO:1446, SEQ ID NO:1448, SEQ ID NO:1450, SEQ ID NO:1452, SEQ ID NO:1453, SEQ ID NO:1454, SEQ ID NO:1455, SEQ ID NO:1456, SEQ ID NO:1457, SEQ ID NO:1458, and SEQ ID NO:1459.

Examples of polypeptides are shown in the sequence listing that have HMM bit scores greater than 450 when fitted to an HMM generated from the amino acid sequences set forth in FIG. 49 are identified in the Sequence Listing of this application. Such polypeptides include SEQ ID NO:1463, SEQ ID NO:1465, SEQ ID NO:1467, SEQ ID NO:1469, SEQ ID NO:1471, SEQ ID NO:1473, SEQ ID NO:1474, SEQ ID NO:1475, SEQ ID NO:1476, and SEQ ID NO:1477.

Examples of polypeptides are shown in the sequence listing that have HMM bit scores greater than 580 when fitted to an HMM generated from the amino acid sequences set forth in FIG. 50 are identified in the Sequence Listing of this application. Such polypeptides include SEQ ID NO:1491, SEQ ID NO:1493, SEQ ID NO:1495, SEQ ID NO:1497, SEQ ID NO:1499, SEQ ID NO:1501, SEQ ID NO:1503, SEQ ID NO:1504, SEQ ID NO:1505, SEQ ID NO:1506, and SEQ ID NO:1508.

Examples of polypeptides are shown in the sequence listing that have HMM bit scores greater than 100 when fitted to an HMM generated from the amino acid sequences set forth in FIG. 51 are identified in the Sequence Listing of this application. Such polypeptides include SEQ ID NO:1510, SEQ ID NO:1512, SEQ ID NO:1514, SEQ ID NO:1516, SEQ ID NO:1518, SEQ ID NO:1520, SEQ ID NO:1522, and SEQ ID NO:1523.

Examples of polypeptides are shown in the sequence listing that have HMM bit scores greater than 800 when fitted to an HMM generated from the amino acid sequences set forth in FIG. 52 are identified in the Sequence Listing of this application. Such polypeptides include SEQ ID NO:1525, SEQ ID NO:1527, SEQ ID NO:1529, SEQ ID NO:1530, SEQ ID NO:1532, SEQ ID NO:1534, and SEQ ID NO:1535.

Examples of polypeptides are shown in the sequence listing that have HMM bit scores greater than 490 when fitted to an HMM generated from the amino acid sequences set forth in FIG. 53 are identified in the Sequence Listing of this application. Such polypeptides include SEQ ID NO:1537, SEQ ID NO:1539, SEQ ID NO:1540, SEQ ID NO:1541, SEQ ID NO:1543, SEQ ID NO:1545, SEQ ID NO:1547, SEQ ID NO:1548, SEQ ID NO:1550, SEQ ID NO:1552, SEQ ID NO:2386, SEQ ID NO:2388, SEQ ID NO:2390, SEQ ID NO:2391, and SEQ ID NO:2392.

Examples of polypeptides are shown in the sequence listing that have HMM bit scores greater than 690 when fitted to an HMM generated from the amino acid sequences set forth in FIG. 54 are identified in the Sequence Listing of this application. Such polypeptides include SEQ ID NO:1554, SEQ ID NO:1555, SEQ ID NO:1557, SEQ ID NO:1559, SEQ ID NO:1561, SEQ ID NO:1563, SEQ ID NO:1565, SEQ ID NO:1567, SEQ ID NO:1569, SEQ ID NO:1571, SEQ ID NO:1572, SEQ ID NO:1573, SEQ ID NO:1574, and SEQ ID NO:1575.

Examples of polypeptides are shown in the sequence listing that have HMM bit scores greater than 380 when fitted to an HMM generated from the amino acid sequences set forth in FIG. 55 are identified in the Sequence Listing of this application. Such polypeptides include SEQ ID NO:1035, SEQ ID NO:1036, SEQ ID NO:1037, SEQ ID NO:1040, SEQ ID NO:1041, SEQ ID NO:1043, SEQ ID NO:1044, SEQ ID NO:1046, SEQ ID NO:1047, SEQ ID NO:1048, SEQ ID NO:1050, SEQ ID NO:1440, SEQ ID NO:1480, SEQ ID NO:1481, SEQ ID NO:1482, SEQ ID NO:1483, SEQ ID NO:1484, SEQ ID NO:1485, SEQ ID NO:1486, SEQ ID NO:1487, SEQ ID NO:1488, SEQ ID NO:1577, SEQ ID NO:1578, SEQ ID NO:1580, SEQ ID NO:1582, SEQ ID NO:1584, SEQ ID NO:1586, SEQ ID NO:1588, SEQ ID NO:1590, SEQ ID NO:1592, SEQ ID NO:1594, SEQ ID NO:1596, SEQ ID NO:1598, SEQ ID NO:1599, SEQ ID NO:1601, SEQ ID NO:1602, SEQ ID NO:1605, SEQ ID NO:1607, SEQ ID NO:1608, SEQ ID NO:1609, SEQ ID NO:1611, SEQ ID NO:1613, SEQ ID NO:1615, SEQ ID NO:1617, SEQ ID NO:1619, SEQ ID NO:1621, SEQ ID NO:1622, SEQ ID NO:1623, SEQ ID NO:1624, SEQ ID NO:1625, SEQ ID NO:1627, SEQ ID NO:1629, SEQ ID NO:1631, SEQ ID NO:1633, SEQ ID NO:1635, SEQ ID NO:1637, SEQ ID NO:1639, SEQ ID NO:1643, SEQ ID NO:1645, SEQ ID NO:1648, SEQ ID NO:1649, SEQ ID NO:1651, and SEQ ID NO:1653.

Examples of polypeptides are shown in the sequence listing that have HMM bit scores greater than 870 when fitted to an HMM generated from the amino acid sequences set forth in FIG. 56 are identified in the Sequence Listing of this application. Such polypeptides include SEQ ID NO:173, SEQ ID NO:212, SEQ ID NO:361, SEQ ID NO:421, SEQ ID NO:443, SEQ ID NO:740, SEQ ID NO:744, SEQ ID NO:942, SEQ ID NO:1437, and SEQ ID NO:1461.

Examples of polypeptides are shown in the sequence listing that have HMM bit scores greater than 140 when fitted to an HMM generated from the amino acid sequences set forth in FIG. 57 are identified in the Sequence Listing of this application. Such polypeptides include SEQ ID NO:97, SEQ ID NO:2010, SEQ ID NO:2011, SEQ ID NO:2013, SEQ ID NO:2015, and SEQ ID NO:2017.

D. Percent Identity

In some embodiments, a low nitrogen tolerance-modulating polypeptide has an amino acid sequence with at least 20% sequence identity, e.g., at least 50%, 52%, 56%, 59%, 61%, 65%, 70%, 75%, 80%, 85%, 90%, 95%, 97%, 98%, or 99% sequence identity, to one of the amino acid sequences set forth in SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, and SEQ ID NO:1577. Polypeptides having such a percent sequence identity often have a domain indicative of a low nitrogen tolerance-modulating polypeptide and/or have an HMM bit score that is greater than 20, as discussed above. Amino acid sequences of low nitrogen tolerance-modulating polypeptides having at least 20% sequence identity to one of the amino acid sequences set forth in SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, and SEQ ID NO:1577 are provided in FIGS. 1-57 and in the Sequence Listing.

"Percent sequence identity" refers to the degree of sequence identity between any given reference sequence, e.g., SEQ ID NO:3, and a candidate low nitrogen tolerance-modulating sequence. A candidate sequence typically has a length that is from 80 percent to 200 percent of the length of the reference sequence, e.g., 82, 85, 87, 89, 90, 93, 95, 97, 99, 100, 105, 110, 115, 120, 130, 140, 150, 160, 170, 180, 190, or 200 percent of the length of the reference sequence. A percent identity for any candidate nucleic acid or polypeptide relative to a reference nucleic acid or polypeptide can be determined as follows. A reference sequence (e.g., a nucleic acid sequence or an amino acid sequence) is aligned to one or more candidate sequences using the computer program ClustalW (version 1.83, default parameters), which allows alignments of nucleic acid or polypeptide sequences to be carried out across their entire length (global alignment). Chenna et al. (2003) *Nucleic Acids Res.*, 31(13): 3497-500.

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site (searchlauncher.bcm.tmc.edu/multi-align/multi-align.html) and at the European Bioinformatics Institute site on the World Wide Web (ebi.ac.uk/clustalw).

To determine percent identity of a candidate nucleic acid or amino acid sequence to a reference sequence, the sequences are aligned using ClustalW, the number of identical matches in the alignment is divided by the length of the reference sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

In some cases, a low nitrogen tolerance-modulating polypeptide has an amino acid sequence with sequence similarity to the amino acid sequence set forth in SEQ ID NO:3, and preferably has at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:3. Amino acid sequences of polypeptides having greater than 20% sequence identity to the polypeptide set forth in SEQ ID NO:3 are provided in FIG. 1 and in the Sequence Listing. Examples of such polypeptides include SEQ ID NO:4, SEQ ID NO:6, SEQ ID NO:8, SEQ ID NO:10, SEQ ID NO:12, SEQ ID NO:14, SEQ ID NO:16, SEQ ID NO:17, SEQ ID NO:19, SEQ ID NO:20, SEQ ID NO:21, SEQ ID NO:22, SEQ ID NO:24, SEQ ID NO:25, SEQ ID NO:27, SEQ ID NO:29, SEQ ID NO:31, SEQ ID NO:33, SEQ ID NO:35, SEQ ID NO:36, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, and SEQ ID NO:47.

In some cases, a low nitrogen tolerance-modulating polypeptide has an amino acid sequence with sequence similarity to the amino acid sequence set forth in SEQ ID 0269667NO:49, and preferably has at least 20%, e.g., %, %, %, %, %, %, %, 75%, 80%, 85%, 90%, 95%, 97%, 98%, or 99% sequence identity, to the amino acid sequence set forth in SEQ ID NO:49. Amino acid sequences of polypeptides having greater than 45% sequence identity to the polypeptide set forth in SEQ ID NO:49 are provided in FIG. 2 and in the Sequence Listing. Examples of such polypeptides include SEQ ID NO:51, SEQ ID NO:53, SEQ ID NO:55, SEQ ID NO:56, SEQ ID NO:58, SEQ ID NO:60, SEQ ID NO:62, SEQ ID NO:63, SEQ ID NO:64, SEQ ID NO:65, SEQ ID NO:67, SEQ ID NO:69, SEQ ID NO:70, SEQ ID NO:71, SEQ ID NO:72, SEQ ID NO:73, and SEQ ID NO:75.

In some cases, a low nitrogen tolerance-modulating polypeptide has an amino acid sequence with sequence similarity to the amino acid sequence set forth in SEQ ID NO:77, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:77. Amino acid sequences of polypeptides having greater than 45% sequence identity to the polypeptide set forth in SEQ ID NO:77 are provided in FIG. 3 and in the Sequence Listing. Examples of such polypeptides include SEQ ID NO:78, SEQ ID NO:80, SEQ ID NO:82, SEQ ID NO:84, SEQ ID NO:85, SEQ ID NO:87, SEQ ID NO:88, SEQ ID NO:90, SEQ ID NO:92, SEQ ID NO:93, SEQ ID NO:95, SEQ ID NO:1479.

In some cases, a low nitrogen tolerance-modulating polypeptide has an amino acid sequence with sequence similarity to the amino acid sequence set forth in SEQ ID NO:100, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:100. Amino acid sequences of polypeptides having greater than 45% sequence identity to the polypeptide set forth in SEQ ID NO: 100 are provided in FIG. 4 and in the Sequence Listing. Examples of such polypeptides include SEQ ID NO:101, SEQ ID NO:102, SEQ ID NO:104, SEQ ID NO:106, SEQ ID NO:108, SEQ ID NO:110, SEQ ID NO:111, SEQ ID NO:113, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:125, SEQ ID NO:126, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:137, SEQ ID NO:139, SEQ ID NO:141, SEQ ID NO:142, SEQ ID NO:144, SEQ ID NO:145, SEQ ID NO:146, SEQ ID NO:147, SEQ ID NO:148, SEQ ID NO:149, and SEQ ID NO:150.

In some cases, a low nitrogen tolerance-modulating polypeptide has an amino acid sequence with sequence similarity to the amino acid sequence set forth in SEQ ID NO:152, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:152. Amino acid sequences of polypeptides having greater than 45% sequence identity to the polypeptide set forth in SEQ ID NO:152 are provided in FIG. 5 and in the Sequence Listing. Examples of such polypeptides include SEQ ID NO:154, SEQ ID NO:156, SEQ ID NO:158, SEQ ID NO:160, SEQ ID NO:162, and SEQ ID NO:164.

In some cases, a low nitrogen tolerance-modulating polypeptide has an amino acid sequence with sequence similarity to the amino acid sequence set forth in SEQ ID NO:166, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:166. Amino acid sequences of polypeptides having greater than 45% sequence identity to the polypeptide set forth in SEQ ID NO:166 are provided in FIG. 6 and in the Sequence Listing. Examples of such polypeptides include SEQ ID NO:166, SEQ ID NO:168, SEQ ID NO:170, SEQ ID NO:172, SEQ ID NO:174, SEQ ID NO:177, SEQ ID NO:179, SEQ ID NO:181, SEQ ID NO:182, SEQ ID NO:183, SEQ ID NO:184.

In some cases, a low nitrogen tolerance-modulating polypeptide has an amino acid sequence with sequence similarity to the amino acid sequence set forth in SEQ ID NO:186, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:186. Amino acid sequences of polypeptides having greater than 45% sequence identity to the polypeptide set forth in SEQ ID NO:186 are provided in FIG. 7 and in the Sequence Listing. Examples of such polypeptides include SEQ ID NO:188, SEQ ID NO:190, SEQ ID NO:191, SEQ ID NO:193, SEQ ID NO:194, SEQ ID NO:196, SEQ ID NO:197, SEQ ID NO:199, SEQ ID NO:201, SEQ ID NO:203, SEQ ID NO:204, SEQ ID NO:205, and SEQ ID NO:206.

In some cases, a low nitrogen tolerance-modulating polypeptide has an amino acid sequence with sequence similarity to the amino acid sequence set forth in SEQ ID NO:208, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:208. Amino acid sequences of polypeptides having greater than 45% sequence identity to the polypeptide set forth in SEQ ID NO:208 are provided in FIG. 8 and in the Sequence Listing. Examples of such polypeptides include SEQ ID NO:209, SEQ ID NO:210, SEQ ID NO:214, and SEQ ID NO:216.

In some cases, a low nitrogen tolerance-modulating polypeptide has an amino acid sequence with sequence similarity to the amino acid sequence set forth in SEQ ID NO:218, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:218. Amino acid sequences of polypeptides having greater than 45% sequence identity to the polypeptide set forth in SEQ ID NO:218 are provided in FIG. 9 and in the Sequence Listing. Examples of such polypeptides include SEQ ID NO:218, SEQ ID NO:220, SEQ ID NO:222, SEQ ID NO:223, SEQ ID NO:225, SEQ ID NO:227, SEQ ID NO:229, SEQ ID NO:230, SEQ ID NO:231, SEQ ID NO:232, SEQ ID NO:1039, SEQ ID NO:1049, and SEQ ID NO:1052.

In some cases, a low nitrogen tolerance-modulating polypeptide has an amino acid sequence with sequence similarity to the amino acid sequence set forth in SEQ ID NO:234, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:234. Amino acid sequences of polypeptides having greater than 45% sequence identity to the polypeptide set forth in SEQ ID NO:234 are provided in FIG. 10 and in the Sequence Listing. Examples of such polypeptides include SEQ ID NO:236, SEQ ID NO:238, SEQ ID NO:239, SEQ ID NO:241, SEQ ID NO:242, SEQ ID NO:243, and SEQ ID NO:244.

In some cases, a low nitrogen tolerance-modulating polypeptide has an amino acid sequence with sequence similarity to the amino acid sequence set forth in SEQ ID NO:246, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:246. Amino acid sequences of polypeptides having greater than 45% sequence identity to the polypeptide set forth in SEQ ID NO:246 are provided in FIG. 11 and in the Sequence Listing. Examples of such polypeptides include SEQ ID NO:248, SEQ ID NO:249, SEQ ID NO:251, SEQ ID NO:253, SEQ ID NO:255, SEQ ID NO:257, SEQ ID NO:259, SEQ ID NO:260, SEQ ID NO:262, SEQ ID NO:264, SEQ ID NO:265, SEQ ID NO:267, SEQ ID NO:268, SEQ ID NO:270, SEQ ID NO:272, SEQ ID NO:274, SEQ ID NO:276, SEQ ID NO:277, SEQ ID NO:279, SEQ ID NO:281, SEQ ID NO:283, SEQ ID NO:285, SEQ ID NO:286, SEQ ID NO:287, SEQ ID NO:288, SEQ ID NO:290, SEQ ID NO:291, SEQ ID NO:292, SEQ ID NO:293, SEQ ID NO:296, and SEQ ID NO:298.

In some cases, a low nitrogen tolerance-modulating polypeptide has an amino acid sequence with sequence similarity to the amino acid sequence set forth in SEQ ID NO:300, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:300. Amino acid sequences of polypeptides having greater than 45% sequence identity to the polypeptide set forth in SEQ ID NO:300 are provided in FIG. 12 and in the Sequence Listing. Examples of such polypeptides include SEQ ID NO:302, SEQ ID NO:304, SEQ ID NO:306, SEQ ID NO:308, SEQ ID NO:310, SEQ ID NO:312, SEQ ID NO:314, SEQ ID NO:316, SEQ ID NO:318, SEQ ID NO:319, SEQ ID NO:320, SEQ ID NO:321, SEQ ID NO:322, SEQ ID NO:323, SEQ ID NO:325, SEQ ID NO:327, and SEQ ID NO:329.

In some cases, a low nitrogen tolerance-modulating polypeptide has an amino acid sequence with sequence similarity to the amino acid sequence set forth in SEQ ID NO:332, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:332. Amino acid sequences of polypeptides having greater than 45% sequence identity to the polypeptide set forth in SEQ ID NO:332 are provided in FIG. 13 and in the Sequence Listing. Examples of such polypeptides include SEQ ID NO:332, SEQ ID NO:334, SEQ ID NO:335, SEQ ID NO:336, SEQ ID NO:338, SEQ ID NO:339, SEQ ID NO:341, SEQ ID NO:342, SEQ ID NO:343, SEQ ID NO:344, SEQ ID NO:345, SEQ ID NO:346, SEQ ID NO:347, SEQ ID NO:348, SEQ ID NO:349, SEQ ID NO:351, SEQ ID NO:352, SEQ ID NO:353, SEQ ID NO:354, SEQ ID NO:355, SEQ ID NO:356, SEQ ID NO:357, SEQ ID NO:358, SEQ ID NO:359, SEQ ID NO:360, SEQ ID NO:362, SEQ ID NO:363, SEQ ID NO:364, SEQ ID NO:365, SEQ ID NO:366, SEQ ID NO:2541, SEQ ID NO:2542, SEQ ID NO:2543, SEQ ID NO:2544, SEQ ID NO:2546, SEQ ID NO:2548, SEQ ID NO:2549, SEQ ID NO:2550, SEQ ID NO:2551, SEQ ID NO:2552, and SEQ ID NO:2553.

In some cases, a low nitrogen tolerance-modulating polypeptide has an amino acid sequence with sequence similarity to the amino acid sequence set forth in SEQ ID NO:368, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:368. Amino acid sequences of polypeptides having greater than 45% sequence identity to the polypeptide set forth in SEQ ID NO:368 are provided in FIG. 14 and in the Sequence Listing. Examples of such polypeptides include SEQ ID NO:369, SEQ ID NO:370, SEQ ID NO:371, SEQ ID NO:372, SEQ ID NO:373, SEQ ID NO:374, SEQ ID NO:376, SEQ ID NO:378, SEQ ID NO:380, SEQ ID NO:382, SEQ ID NO:384, SEQ ID NO:386, SEQ ID NO:388, SEQ ID NO:390, SEQ ID NO:392, SEQ ID NO:394, SEQ ID NO:396, SEQ ID NO:398, SEQ ID NO:399, SEQ ID NO:401, SEQ ID NO:403, SEQ ID NO:404, SEQ ID NO:406, SEQ ID NO:408, SEQ ID NO:410, SEQ ID NO:412, SEQ ID NO:414, SEQ ID NO:416, SEQ ID NO:418, SEQ ID NO:419, SEQ ID NO:420, SEQ ID NO:422, SEQ ID NO:423, SEQ ID NO:425, SEQ ID NO:427, SEQ ID NO:428, SEQ ID NO:430, SEQ ID NO:432, SEQ ID NO:433, SEQ ID NO:434, SEQ ID NO:435, SEQ ID NO:436, SEQ ID NO:437, SEQ ID NO:438, SEQ ID NO:439, SEQ ID NO:440, SEQ ID NO:441, SEQ ID NO:444, SEQ ID NO:445, SEQ ID NO:446, SEQ ID NO:447, SEQ ID NO:448, SEQ ID NO:449, SEQ ID NO:450, SEQ ID NO:451, SEQ ID NO:452, SEQ ID NO:453, SEQ ID NO:454, SEQ ID NO:455, SEQ ID NO:456, SEQ ID NO:458, SEQ ID NO:459, SEQ ID NO:461, SEQ ID NO:463, SEQ ID NO:465, SEQ ID NO:467, SEQ ID NO:469, SEQ ID NO:471, SEQ ID NO:473, SEQ ID NO:474, SEQ ID NO:475, SEQ ID NO:477, SEQ ID NO:479, SEQ ID NO:481, SEQ ID NO:483, SEQ ID NO:485, SEQ ID NO:487, SEQ ID NO:488, SEQ ID NO:489, SEQ ID NO:490, SEQ ID NO:491, SEQ ID NO:492, SEQ ID NO:494, SEQ ID NO:495, SEQ ID NO:496, SEQ ID NO:497, SEQ ID NO:498, SEQ ID NO:499, SEQ ID NO:500, SEQ ID NO:501, SEQ ID NO:502, SEQ ID NO:504, SEQ ID NO:505, SEQ ID NO:506, SEQ ID NO:507, and SEQ ID NO:508.

In some cases, a low nitrogen tolerance-modulating polypeptide has an amino acid sequence with sequence similarity to the amino acid sequence set forth in SEQ ID NO:510, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:510. Amino acid sequences of polypeptides having greater than 45% sequence identity to the polypeptide set forth in SEQ ID NO:510 are provided in FIG. 15 and in the Sequence Listing. Examples of such polypeptides include SEQ ID NO:511, SEQ ID NO:513, SEQ ID NO:515, SEQ ID NO:517, SEQ ID NO:521, SEQ ID NO:523, SEQ ID NO:525, SEQ ID NO:527, SEQ ID NO:529, SEQ ID NO:530, and SEQ ID NO:531.

In some cases, a low nitrogen tolerance-modulating polypeptide has an amino acid sequence with sequence similarity to the amino acid sequence set forth in SEQ ID NO:533, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:533. Amino acid sequences of polypeptides having greater than 45% sequence identity to the polypeptide set forth in SEQ ID NO:533 are provided in FIG. 16 and in the Sequence Listing. Examples of such polypeptides include SEQ ID NO:535, SEQ ID NO:536, SEQ ID NO:538, SEQ ID NO:539, SEQ ID NO:541, SEQ ID NO:542, SEQ ID NO:543, SEQ ID NO:544, SEQ ID NO:545, SEQ ID NO:546, SEQ ID NO:547, SEQ ID NO:548, SEQ ID NO:550, SEQ ID NO:552, SEQ ID NO:553, and SEQ ID NO:554.

In some cases, a low nitrogen tolerance-modulating polypeptide has an amino acid sequence with sequence similarity to the amino acid sequence set forth in SEQ ID NO:558, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:558. Amino acid sequences of polypeptides having greater than 45% sequence identity to the polypeptide set forth in SEQ ID NO:558 are provided in FIG. 17 and in the Sequence Listing. Examples of such polypeptides include SEQ ID NO:559, SEQ ID NO:560, SEQ ID NO:561, SEQ ID NO:562, SEQ ID NO:563, SEQ ID NO:564, SEQ ID NO:565, SEQ ID NO:566, SEQ ID NO:567, SEQ ID NO:569, SEQ ID NO:571, SEQ ID NO:572, SEQ ID NO:573, SEQ ID NO:575, SEQ ID NO:576, SEQ ID NO:577, SEQ ID NO:578, SEQ ID NO:579, SEQ ID NO:581, SEQ ID NO:583, SEQ ID NO:584, SEQ ID NO:585, SEQ ID NO:586, SEQ ID NO:588, SEQ ID NO:589, SEQ ID NO:590, and SEQ ID NO:591.

In some cases, a low nitrogen tolerance-modulating polypeptide has an amino acid sequence with sequence similarity to the amino acid sequence set forth in SEQ ID NO:593, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:593. Amino acid sequences of polypeptides having greater than 45% sequence identity to the polypeptide set forth in SEQ ID NO:593 are provided in FIG. 18 and in the Sequence Listing. Examples of such polypeptides include SEQ ID NO:595, SEQ ID NO:597, SEQ ID NO:599, SEQ ID NO:601, SEQ ID NO:603, SEQ ID NO:605, SEQ ID NO:607, SEQ ID NO:609, SEQ ID NO:610, and SEQ ID NO:611.

In some cases, a low nitrogen tolerance-modulating polypeptide has an amino acid sequence with sequence similarity to the amino acid sequence set forth in SEQ ID NO:613, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:613. Amino acid sequences of polypeptides having greater than 45% sequence identity to the polypeptide set forth in SEQ ID NO:613 are provided in FIG. 19 and in the Sequence Listing. Examples of such polypeptides include SEQ ID NO:615, SEQ ID NO:617, SEQ ID NO:618, SEQ ID NO:620, SEQ ID NO:622, SEQ ID NO:624, SEQ ID NO:626, SEQ ID NO:628, SEQ ID NO:630, SEQ ID NO:632, SEQ ID NO:634, SEQ ID NO:636, SEQ ID NO:638, SEQ ID NO:640, SEQ ID NO:642, SEQ ID NO:643, and SEQ ID NO:644.

In some cases, a low nitrogen tolerance-modulating polypeptide has an amino acid sequence with sequence similarity to the amino acid sequence set forth in SEQ ID NO:646, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:646. Amino acid sequences of polypeptides having greater than 45% sequence identity to the polypeptide set forth in SEQ ID NO:646 are provided in FIG. 20 and in the Sequence Listing. Examples of such polypeptides include SEQ ID NO:648, SEQ ID NO:650, SEQ ID NO:652, SEQ ID NO:654, SEQ ID NO:656, SEQ ID NO:658, SEQ ID NO:660, SEQ ID NO:662, SEQ ID NO:664, SEQ ID NO:666, SEQ ID NO:668, SEQ ID NO:670, SEQ ID NO:672, SEQ ID NO:674, SEQ ID NO:676, SEQ ID NO:678, SEQ ID NO:679, SEQ ID NO:680, SEQ ID NO:681, SEQ ID NO:682, SEQ ID NO:683, and SEQ ID NO:685.

In some cases, a low nitrogen tolerance-modulating polypeptide has an amino acid sequence with sequence similarity to the amino acid sequence set forth in SEQ ID NO:687, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:687. Amino acid sequences of polypeptides having greater than 45% sequence identity to the polypeptide set forth in SEQ ID NO:687 are provided in FIG. 21 and in the Sequence Listing. Examples of such polypeptides include SEQ ID NO:689, SEQ ID NO:691, SEQ ID NO:693, SEQ ID NO:694, SEQ ID NO:696, SEQ ID NO:697, SEQ ID NO:699, SEQ ID NO:701, SEQ ID NO:703, SEQ ID NO:705, SEQ ID NO:706, SEQ ID NO:708, SEQ ID NO:710, SEQ ID NO:712, SEQ ID NO:714, SEQ ID NO:716, SEQ ID NO:718, SEQ ID NO:720, SEQ ID NO:721, SEQ ID NO:722, SEQ ID NO:723, SEQ ID NO:724, SEQ ID NO:725, SEQ ID NO:726, SEQ ID NO:727, and SEQ ID NO:728.

In some cases, a low nitrogen tolerance-modulating polypeptide has an amino acid sequence with sequence similarity to the amino acid sequence set forth in SEQ ID NO:730, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:730. Amino acid sequences of polypeptides having greater than 45% sequence identity to the polypeptide set forth in SEQ ID NO:730 are provided in FIG. 22 and in the Sequence Listing. Examples of such polypeptides include SEQ ID NO:732, SEQ ID NO:733, SEQ ID NO:735, SEQ ID NO:737, SEQ ID NO:738, and SEQ ID NO:742.

In some cases, a low nitrogen tolerance-modulating polypeptide has an amino acid sequence with sequence similarity to the amino acid sequence set forth in SEQ ID NO:746, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:746. Amino acid sequences of polypeptides having greater than 45% sequence identity to the polypeptide set forth in SEQ ID NO:746 are provided in FIG. 23 and in the Sequence Listing. Examples of such polypeptides include SEQ ID NO:748, SEQ ID NO:750, SEQ ID NO:751, SEQ ID NO:753, SEQ ID NO:755, SEQ ID NO:757, SEQ ID NO:758, SEQ ID NO:760, SEQ ID NO:761, SEQ ID NO:762, SEQ ID NO:763, SEQ ID NO:765, and SEQ ID NO:767.

In some cases, a low nitrogen tolerance-modulating polypeptide has an amino acid sequence with sequence similarity to the amino acid sequence set forth in SEQ ID NO:769, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:769. Amino acid sequences of polypeptides having greater than 45% sequence identity to the polypeptide set forth in SEQ ID NO:769 are provided in FIG. 24 and in the Sequence Listing. Examples of such polypeptides include SEQ ID NO:771, SEQ ID NO:773, SEQ ID NO:775, SEQ ID NO:777, SEQ ID NO:779, SEQ ID NO:781, SEQ ID NO:783, SEQ ID NO:785, SEQ ID NO:787, SEQ ID NO:789, and SEQ ID NO:790.

In some cases, a low nitrogen tolerance-modulating polypeptide has an amino acid sequence with sequence similarity to the amino acid sequence set forth in SEQ ID NO:792, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:792. Amino acid sequences of polypeptides having greater than 20% sequence identity to the polypeptide set forth in SEQ ID NO:792 are provided in FIG. 25 and in the Sequence Listing. Examples of such polypeptides include SEQ ID NO:794, SEQ ID NO:796, SEQ ID NO:798, SEQ ID NO:799, SEQ ID NO:801, SEQ ID NO:803, SEQ ID NO:805, SEQ ID NO:807, SEQ ID NO:808, SEQ ID NO:810, SEQ ID NO:812, SEQ ID NO:814, SEQ ID NO:816, SEQ ID NO:818, SEQ ID NO:819, SEQ ID NO:820, SEQ ID NO:821, and SEQ ID NO:822.

In some cases, a low nitrogen tolerance-modulating polypeptide has an amino acid sequence with sequence similarity to the amino acid sequence set forth in SEQ ID NO:824, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:824. Amino acid sequences of polypeptides having greater than 45% sequence identity to the polypeptide set forth in SEQ ID NO:824 are provided in FIG. 26 and in the Sequence Listing. Such polypeptides include, but not limited to, SEQ ID NO:826, SEQ ID NO:1696, SEQ ID NO:1698, SEQ ID NO:1700, SEQ ID NO:1702, SEQ ID NO:1704, SEQ ID NO:1706, SEQ ID NO:1708, SEQ ID NO:1710, SEQ ID NO:1711, SEQ ID NO:1713, SEQ ID NO:1714, SEQ ID NO:1715, and SEQ ID NO:1716.

In some cases, a low nitrogen tolerance-modulating polypeptide has an amino acid sequence with sequence similarity to the amino acid sequence set forth in SEQ ID NO:828, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:828. Amino acid sequences of polypeptides having greater than 20% sequence identity to the polypeptide set forth in SEQ ID NO:828 are provided in FIG. 27 and in the Sequence Listing. Examples of such polypeptides include SEQ ID NO:830, SEQ ID NO:832, SEQ ID NO:834, SEQ ID NO:836, SEQ ID NO:837, SEQ ID NO:838, SEQ ID NO:839, SEQ ID NO:840, SEQ ID NO:842, SEQ ID NO:844, SEQ ID NO:845, SEQ ID NO:846, SEQ ID NO:847, SEQ ID NO:848, SEQ ID NO:849, SEQ ID NO:850, and SEQ ID NO:851.

In some cases, a low nitrogen tolerance-modulating polypeptide has an amino acid sequence with sequence similarity to the amino acid sequence set forth in SEQ ID NO:855, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:855. Amino acid sequences of polypeptides having greater than 20% sequence identity to the polypeptide set forth in SEQ ID NO:855 are provided in FIG. 28 and in the Sequence Listing. Examples of such polypeptides include SEQ ID NO:856, SEQ ID NO:858, SEQ ID NO:860, SEQ ID NO:862, SEQ ID NO:864, SEQ ID NO:866, SEQ ID NO:868, SEQ ID NO:870, SEQ ID NO:872, SEQ ID NO:874, SEQ ID NO:876, SEQ ID NO:878, SEQ ID NO:880, SEQ ID NO:882, SEQ ID NO:884, SEQ ID NO:885, SEQ ID NO:886, SEQ ID NO:887, SEQ ID NO:888, and SEQ ID NO:889.

In some cases, a low nitrogen tolerance-modulating polypeptide has an amino acid sequence with sequence similarity to the amino acid sequence set forth in SEQ ID NO:891, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:891. Amino acid sequences of polypeptides having greater than 20% sequence identity to the polypeptide set forth in SEQ ID NO:891 are provided in FIG. 29 and in the Sequence Listing. Examples of such polypeptides include SEQ ID NO:893, SEQ ID NO:894, SEQ ID NO:895, SEQ ID NO:896, SEQ ID NO:898, SEQ ID NO:900, SEQ ID NO:901, SEQ ID NO:902, SEQ ID NO:903, SEQ ID NO:904, SEQ ID NO:905, SEQ ID NO:907, SEQ ID NO:908, SEQ ID NO:909, SEQ ID NO:910, SEQ ID NO:911, SEQ ID NO:912, SEQ ID NO:913, SEQ ID NO:914, and SEQ ID NO:915.

In some cases, a low nitrogen tolerance-modulating polypeptide has an amino acid sequence with sequence similarity to the amino acid sequence set forth in SEQ ID NO:917, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:917. Amino acid sequences of polypeptides having greater than 20% sequence identity to the polypeptide set forth in SEQ ID NO:917 are provided in FIG. 30 and in the Sequence Listing. Examples of such polypeptides include SEQ ID NO:919, SEQ ID NO:921, SEQ ID NO:923, SEQ ID NO:925, SEQ ID NO:927, SEQ ID NO:929, SEQ ID NO:931, SEQ ID NO:933, SEQ ID NO:935, SEQ ID NO:937, SEQ ID NO:939, and SEQ ID NO:940.

In some cases, a low nitrogen tolerance-modulating polypeptide has an amino acid sequence with sequence similarity to the amino acid sequence set forth in SEQ ID NO:944, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:944. Amino acid sequences of polypeptides having greater than 20% sequence identity to the polypeptide set forth in SEQ ID NO:944 are provided in FIG. 31 and in the Sequence Listing. Examples of such polypeptides include SEQ ID NO:946, SEQ ID NO:947, SEQ ID NO:948, SEQ ID NO:950, SEQ ID NO:952, SEQ ID NO:954, SEQ ID NO:956, SEQ ID NO:958, SEQ ID NO:960, SEQ ID NO:962, SEQ ID NO:964, SEQ ID NO:966, SEQ ID NO:967, SEQ ID NO:968, SEQ ID NO:969, SEQ ID NO:970, SEQ ID NO:972, and SEQ ID NO:974.

In some cases, a low nitrogen tolerance-modulating polypeptide has an amino acid sequence with sequence similarity to the amino acid sequence set forth in SEQ ID NO:976, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:976. Amino acid sequences of polypeptides having greater than 45% sequence identity to the polypeptide set forth in SEQ ID NO:976 are provided in FIG. 32 and in the Sequence Listing. Examples of such polypeptides include SEQ ID NO:978 and SEQ ID NO:980.

In some cases, a low nitrogen tolerance-modulating polypeptide has an amino acid sequence with sequence similarity to the amino acid sequence set forth in SEQ ID NO:982, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:982. Amino acid sequences of polypeptides having greater than 20% sequence identity to the polypeptide set forth in SEQ ID NO:982 are provided in FIG. 33 and in the Sequence Listing. Examples of such polypeptides include SEQ ID NO:984, SEQ ID NO:985, SEQ ID NO:986, SEQ ID NO:987, SEQ ID NO:988, SEQ ID NO:989, SEQ ID NO:990, SEQ ID NO:991, SEQ ID NO:992, SEQ ID NO:993, SEQ ID NO:995, SEQ ID NO:996, SEQ ID NO:998, SEQ ID NO:1000, SEQ ID NO:1001, SEQ ID NO:1003, SEQ ID NO:1005, SEQ ID NO:1007, SEQ ID NO:1008, SEQ ID NO:1009, SEQ ID NO:1011, SEQ ID NO:1013, SEQ ID NO:1015, SEQ ID NO:1016, SEQ ID NO:1018, SEQ ID NO:1019, SEQ ID NO:1021, SEQ ID NO:1023, SEQ ID NO:1025, SEQ ID NO:1026, SEQ ID NO:1027, SEQ ID NO:1028, SEQ ID NO:1029, SEQ ID NO:1030, SEQ ID NO:1031, SEQ ID NO:1032, and SEQ ID NO:1033.

In some cases, a low nitrogen tolerance-modulating polypeptide has an amino acid sequence with sequence similarity to the amino acid sequence set forth in SEQ ID NO:1054, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1054. Amino acid sequences of polypeptides having greater than 20% sequence identity to the polypeptide set forth in SEQ ID NO:1054 are provided in FIG. 34 and in the Sequence Listing. Examples of such polypeptides include SEQ ID NO:1055, SEQ ID NO:1057, SEQ ID NO:1058, SEQ ID NO:1059, SEQ ID NO:1061, SEQ ID NO:1063, SEQ ID NO:1065, SEQ ID NO:1065, SEQ ID NO:1067, SEQ ID NO:1068, SEQ ID NO:1070, SEQ ID NO:1071, SEQ ID NO:1072, SEQ ID NO:1074, SEQ ID NO:1075, SEQ ID NO:1076, SEQ ID NO:1077, SEQ ID NO:1078, SEQ ID NO:1080, SEQ ID NO:1082, SEQ ID NO:1083, SEQ ID NO:1085, SEQ ID NO:1086, SEQ ID NO:1087, SEQ ID NO:1088, SEQ ID NO:1089, SEQ ID NO:1089, SEQ ID NO:1090, SEQ ID NO:1091, SEQ ID NO:1092, SEQ ID NO:1093, SEQ ID NO:1094, SEQ ID NO:1095, and SEQ ID NO:1097.

In some cases, a low nitrogen tolerance-modulating polypeptide has an amino acid sequence with sequence similarity to the amino acid sequence set forth in SEQ ID NO:1099, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1099. Amino acid sequences of polypeptides having greater than 20% sequence identity to the polypeptide set forth in SEQ ID NO:1099 are provided in FIG. 35 and in the Sequence Listing. Examples of such polypeptides include SEQ ID NO:1101, SEQ ID NO:1103, SEQ ID NO:1104, SEQ ID NO:1105, SEQ ID NO:1106, SEQ ID NO:1108, SEQ ID NO:1109, and SEQ ID NO:1110.

In some cases, a low nitrogen tolerance-modulating polypeptide has an amino acid sequence with sequence similarity to the amino acid sequence set forth in SEQ ID NO:1112, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1112. Amino acid sequences of polypeptides having greater than 20% sequence identity to the polypeptide set forth in SEQ ID NO:1112 are provided in FIG. 36 and in the Sequence Listing. Examples of such polypeptides include SEQ ID NO:1113 and SEQ ID NO:1114.

In some cases, a low nitrogen tolerance-modulating polypeptide has an amino acid sequence with sequence similarity to the amino acid sequence set forth in SEQ ID NO:1116, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1116. Amino acid sequences of polypeptides having greater than 20% sequence identity to the polypeptide set forth in SEQ ID NO:1116 are provided in FIG. 37 and in the Sequence Listing. Examples of such polypeptides include SEQ ID NO:1118, SEQ ID NO:1120, SEQ ID NO:1122, SEQ ID NO:1123, SEQ ID NO:1125, SEQ ID NO:1126, SEQ ID NO:1128, SEQ ID NO:1129, SEQ ID NO:1131, SEQ ID NO:1132, SEQ ID NO:1133, SEQ ID NO:1134, SEQ ID NO:1136, SEQ ID NO:1138, SEQ ID NO:1140, SEQ ID NO:1141, SEQ ID NO:1142, SEQ ID NO:1143, SEQ ID NO:1144, SEQ ID NO:1145, SEQ ID NO:1147, SEQ ID NO:1149, SEQ ID NO:1151, SEQ ID NO:1153, and SEQ ID NO:1155.

In some cases, a low nitrogen tolerance-modulating polypeptide has an amino acid sequence with sequence similarity to the amino acid sequence set forth in SEQ ID NO:1159, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1159. Amino acid sequences of polypeptides having greater than 20% sequence identity to the polypeptide set forth in SEQ ID NO:1159 are provided in FIG. 38 and in the Sequence Listing. Examples of such polypeptides include SEQ ID NO:1161, SEQ ID NO:1162, SEQ ID NO:1163, and SEQ ID NO:1164.

In some cases, a low nitrogen tolerance-modulating polypeptide has an amino acid sequence with sequence similarity to the amino acid sequence set forth in SEQ ID NO:1166, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1166. Amino acid sequences of polypeptides having greater than 20% sequence identity to the polypeptide set forth in SEQ ID NO:1166 are provided in FIG. 39 and in the Sequence Listing. Examples of such polypeptides include SEQ ID NO:1167, SEQ ID NO:1169, SEQ ID NO:1171, SEQ ID NO:1173, SEQ ID NO:1175, SEQ ID NO:1177, SEQ ID NO:1179, SEQ ID NO:1180, SEQ ID NO:1182, and SEQ ID NO:1183.

In some cases, a low nitrogen tolerance-modulating polypeptide has an amino acid sequence with sequence similarity to the amino acid sequence set forth in SEQ ID NO:1185, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1185. Amino acid sequences of polypeptides having greater than 20% sequence identity to the polypeptide set forth in SEQ ID NO:1185 are provided in FIG. 40 and in the Sequence Listing. Examples of such polypeptides include SEQ ID NO:1187, SEQ ID NO:1189, SEQ ID NO:1190, SEQ ID NO:1191, and SEQ ID NO:1192.

In some cases, a low nitrogen tolerance-modulating polypeptide has an amino acid sequence with sequence similarity to the amino acid sequence set forth in SEQ ID NO:1194, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1194. Amino acid sequences of polypeptides having greater than 20% sequence identity to the polypeptide set forth in SEQ ID NO:1194 are provided in FIG. 41 and in the Sequence Listing. Examples of such polypeptides include SEQ ID NO:1196, SEQ ID NO:1198, SEQ ID NO:1200, SEQ ID NO:1202, SEQ ID NO:1203, SEQ ID NO:1204, SEQ ID NO:1205, SEQ ID NO:1206, SEQ ID NO:1207, and SEQ ID NO:1208.

In some cases, a low nitrogen tolerance-modulating polypeptide has an amino acid sequence with sequence similarity to the amino acid sequence set forth in SEQ ID NO:1210, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1210. Amino acid sequences of polypeptides having greater than 20% sequence identity to the polypeptide set forth in SEQ ID NO:1210 are provided in FIG. 42 and in the Sequence Listing. Examples of such polypeptides include SEQ ID NO:1211, SEQ ID NO:1213, SEQ ID NO:1215, SEQ ID NO:1216, SEQ ID NO:1218, SEQ ID NO:1220, SEQ ID NO:1222, SEQ ID NO:1224, SEQ ID NO:1226, SEQ ID NO:1228, SEQ ID NO:1229, SEQ ID NO:1230, SEQ ID NO:1232, SEQ ID NO:1233, SEQ ID NO:1234, SEQ ID NO:1235, SEQ ID NO:1236, SEQ ID NO:1237, SEQ ID NO:1238, SEQ ID NO:1239, SEQ ID NO:1240, SEQ ID NO:1241, SEQ ID NO:1242, SEQ ID NO:1243, SEQ ID NO:1244, SEQ ID NO:1245, SEQ ID NO:1246, SEQ ID NO:1247, SEQ ID NO:1248, SEQ ID NO:1249, SEQ ID NO:1251, SEQ ID NO:1253, SEQ ID NO:1255, SEQ ID NO:1257, SEQ ID NO:1259, SEQ ID NO:1261, SEQ ID NO:1263, SEQ ID NO:1264, SEQ ID NO:1265, SEQ ID NO:1266, SEQ ID NO:1267, SEQ ID NO:1268, SEQ ID NO:1269, SEQ ID NO:1270, SEQ ID NO:1271, and SEQ ID NO:1272.

In some cases, a low nitrogen tolerance-modulating polypeptide has an amino acid sequence with sequence similarity to the amino acid sequence set forth in SEQ ID NO:1274, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1274. Amino acid sequences of polypeptides having greater than 20% sequence identity to the polypeptide set forth in SEQ ID NO:1274 are provided in FIG. 43 and in the Sequence Listing. Examples of such polypeptides include SEQ ID NO:1276, SEQ ID NO:1278, SEQ ID NO:1280, SEQ ID NO:1281, SEQ ID NO:1282, SEQ ID NO:1284, SEQ ID NO:1285, SEQ ID NO:1287, SEQ ID NO:1289, SEQ ID NO:1291, SEQ ID NO:1293, SEQ ID NO:1294, SEQ ID NO:1295, SEQ ID NO:1296, SEQ ID NO:1297, SEQ ID NO:1298, and SEQ ID NO:1300.

In some cases, a low nitrogen tolerance-modulating polypeptide has an amino acid sequence with sequence similarity to the amino acid sequence set forth in SEQ ID NO:1302, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1302. Amino acid sequences of polypeptides having greater than 20% sequence identity to the polypeptide set forth in SEQ ID NO:1302 are provided in FIG. 44 and in the Sequence Listing. Examples of such polypeptides include SEQ ID NO:1303, SEQ ID NO:1305, SEQ ID NO:1307, SEQ ID NO:1309, SEQ ID NO:1311, SEQ ID NO:1312, SEQ ID NO:1313, SEQ ID NO:1314, SEQ ID NO:1315, SEQ ID NO:1317, SEQ ID NO:1318, SEQ ID NO:1319, SEQ ID NO:1320, SEQ ID NO:1321, SEQ ID NO:1322, SEQ ID NO:1323, SEQ ID NO:1324, SEQ ID NO:1325, SEQ ID NO:1326, SEQ ID NO:1327, SEQ ID NO:1328, SEQ ID NO:1330, SEQ ID NO:1331, SEQ ID NO:1333, SEQ ID NO:1334, SEQ ID NO:1335, SEQ ID NO:1336, SEQ ID NO:1337, SEQ ID NO:1338, SEQ ID NO:1339, and SEQ ID NO:1340.

In some cases, a low nitrogen tolerance-modulating polypeptide has an amino acid sequence with sequence similarity to the amino acid sequence set forth in SEQ ID NO:1342, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1342. Amino acid sequences of polypeptides having greater than 20% sequence identity to the polypeptide set forth in SEQ ID NO:1342 are provided in FIG. 45 and in the Sequence Listing. Examples of such polypeptides include SEQ ID NO:1344, SEQ ID NO:1346, SEQ ID NO:1348, SEQ ID NO:1350, SEQ ID NO:1352, SEQ ID NO:1354, SEQ ID NO:1355, SEQ ID NO:1357, SEQ ID NO:1358, SEQ ID NO:1360, SEQ ID NO:1361, SEQ ID NO:1362, SEQ ID NO:1363, SEQ ID NO:1364, SEQ ID NO:1366, SEQ ID NO:1367, SEQ ID NO:1369, SEQ ID NO:1370, SEQ ID NO:1371, SEQ ID NO:1372, SEQ ID NO:1373, SEQ ID NO:1374, SEQ ID NO:1375, SEQ ID NO:1376, SEQ ID NO:1377, SEQ ID NO:1378, SEQ ID NO:1379, SEQ ID NO:1380, SEQ ID NO:1381, SEQ ID NO:1382, and SEQ ID NO:1383.

In some cases, a low nitrogen tolerance-modulating polypeptide has an amino acid sequence with sequence similarity to the amino acid sequence set forth in SEQ ID NO:1385, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1385. Amino acid sequences of polypeptides having greater than 20% sequence identity to the polypeptide set forth in SEQ ID NO:1385 are provided in FIG. 46 and in the Sequence Listing. Examples of such polypeptides include SEQ ID NO:1387, SEQ ID NO:1389, SEQ ID NO:1390, SEQ ID NO:1391, SEQ ID NO:1393, SEQ ID NO:1394, SEQ ID NO:1395, SEQ ID NO:1396, SEQ ID NO:1398, SEQ ID NO:1400, SEQ ID NO:1401, SEQ ID NO:1402, SEQ ID NO:1403, SEQ ID NO:1404, SEQ ID NO:1405, and SEQ ID NO:1407.

In some cases, a low nitrogen tolerance-modulating polypeptide has an amino acid sequence with sequence similarity to the amino acid sequence set forth in SEQ ID NO:1409, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1409. Amino acid sequences of polypeptides having greater than 20% sequence identity to the polypeptide set forth in SEQ ID NO:1409 are provided in FIG. 47 and in the Sequence Listing. Examples of such polypeptides include SEQ ID NO:1411, SEQ ID NO:1413, SEQ ID NO:1415, SEQ ID NO:1417, SEQ ID NO:1418, SEQ ID NO:1419, SEQ ID NO:1421, SEQ ID NO:1423, SEQ ID NO:1424, SEQ ID NO:1425, and SEQ ID NO:1426.

In some cases, a low nitrogen tolerance-modulating polypeptide has an amino acid sequence with sequence similarity to the amino acid sequence set forth in SEQ ID NO:1428, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1428. Amino acid sequences of polypeptides having greater than 20% sequence identity to the polypeptide set forth in SEQ ID NO:1428 are provided in FIG. 48 and in the Sequence Listing. Examples of such polypeptides include SEQ ID NO:1430, SEQ ID NO:1432, SEQ ID NO:1434, SEQ ID NO:1436, SEQ ID NO:1439, SEQ ID NO:1442, SEQ ID NO:1444, SEQ ID NO:1446, SEQ ID NO:1448, SEQ ID NO:1450, SEQ ID NO:1452, SEQ ID NO:1453, SEQ ID NO:1454, SEQ ID NO:1455, SEQ ID NO:1456, SEQ ID NO:1457, SEQ ID NO:1458, and SEQ ID NO:1459.

In some cases, a low nitrogen tolerance-modulating polypeptide has an amino acid sequence with sequence similarity to the amino acid sequence set forth in SEQ ID NO:1463, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1463. Amino acid sequences of polypeptides having greater than 20% sequence identity to the polypeptide set forth in SEQ ID NO:1463 are provided in FIG. 49 and in the Sequence Listing. Examples of such polypeptides include SEQ ID NO:1465, SEQ ID NO:1467, SEQ ID NO:1469, SEQ ID NO:1471, SEQ ID NO:1473, SEQ ID NO:1474, SEQ ID NO:1475, SEQ ID NO:1476, and SEQ ID NO:1477.

In some cases, a low nitrogen tolerance-modulating polypeptide has an amino acid sequence with sequence similarity to the amino acid sequence set forth in SEQ ID NO:1491, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1491. Amino acid sequences of polypeptides having greater than 20% sequence identity to the polypeptide set forth in SEQ ID NO:1491 are provided in FIG. 50 and in the Sequence Listing. Examples of such polypeptides include SEQ ID NO:1493, SEQ ID NO:1495, SEQ ID NO:1497, SEQ ID NO:1499, SEQ ID NO:1501, SEQ ID NO:1503, SEQ ID NO:1504, SEQ ID NO:1505, SEQ ID NO:1506, and SEQ ID NO:1508.

In some cases, a low nitrogen tolerance-modulating polypeptide has an amino acid sequence with sequence similarity to the amino acid sequence set forth in SEQ ID NO:1510, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1510. Amino acid sequences of polypeptides having greater than 20% sequence identity to the polypeptide set forth in SEQ ID NO:1510 are provided in FIG. 51 and in the Sequence Listing. Examples of such polypeptides include SEQ ID NO:1512, SEQ ID NO:1514, SEQ ID NO:1516, SEQ ID NO:1518, SEQ ID NO:1520, SEQ ID NO:1522, and SEQ ID NO:1523.

In some cases, a low nitrogen tolerance-modulating polypeptide has an amino acid sequence with sequence similarity to the amino acid sequence set forth in SEQ ID NO:1525, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1525. Amino acid sequences of polypeptides having greater than 20% sequence identity to the polypeptide set forth in SEQ ID NO:1525 are provided in FIG. 52 and in the Sequence Listing. Examples of such polypeptides include SEQ ID NO:1527, SEQ ID NO:1529, SEQ ID NO:1530, SEQ ID NO:1532, SEQ ID NO:1534, and SEQ ID NO:1535.

In some cases, a low nitrogen tolerance-modulating polypeptide has an amino acid sequence with sequence similarity to the amino acid sequence set forth in SEQ ID NO:1537, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1537. Amino acid sequences of polypeptides having greater than 20% sequence identity to the polypeptide set forth in SEQ ID NO:1537 are provided in FIG. 53 and in the Sequence Listing. Examples of such polypeptides include SEQ ID NO:1539, SEQ ID NO:1540, SEQ ID NO:1541, SEQ ID NO:1543, SEQ ID NO:1545, SEQ ID NO:1547, SEQ ID NO:1548, SEQ ID NO:1550, SEQ ID NO:1552, SEQ ID NO:2386, SEQ ID NO:2388, SEQ ID NO:2390, SEQ ID NO:2391, and SEQ ID NO:2392.

In some cases, a low nitrogen tolerance-modulating polypeptide has an amino acid sequence with sequence similarity to the amino acid sequence set forth in SEQ ID NO:1554, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1554. Amino acid sequences of polypeptides having greater than 20% sequence identity to the polypeptide set forth in SEQ ID NO:1554 are provided in FIG. 54 and in the Sequence Listing. Examples of such polypeptides include SEQ ID NO:1555, SEQ ID NO:1557, SEQ ID NO:1559, SEQ ID NO:1561, SEQ ID NO:1563, SEQ ID NO:1565, SEQ ID NO:1567, SEQ ID NO:1569, SEQ ID NO:1571, SEQ ID NO:1572, SEQ ID NO:1573, SEQ ID NO:1574, and SEQ ID NO:1575.

In some cases, a low nitrogen tolerance-modulating polypeptide has an amino acid sequence with sequence similarity to the amino acid sequence set forth in SEQ ID NO:1577, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1577. Amino acid sequences of polypeptides having greater than 20% sequence identity to the polypeptide set forth in SEQ ID NO:1577 are provided in FIG. 55 and in the Sequence Listing. Examples of such polypeptides include SEQ ID NO:1035, SEQ ID NO:1036, SEQ ID NO:1037, SEQ ID NO:1040, SEQ ID NO:1041, SEQ ID NO:1043, SEQ ID NO:1044, SEQ ID NO:1046, SEQ ID NO:1047, SEQ ID NO:1048, SEQ ID NO:1050, SEQ ID NO:1440, SEQ ID NO:1480, SEQ ID NO:1481, SEQ ID NO:1482, SEQ ID NO:1483, SEQ ID NO:1484, SEQ ID NO:1485, SEQ ID NO:1486, SEQ ID NO:1487, SEQ ID NO:1488, SEQ ID NO:1578, SEQ ID NO:1580, SEQ ID NO:1582, SEQ ID NO:1584, SEQ ID NO:1586, SEQ ID NO:1588, SEQ ID NO:1590, SEQ ID NO:1592, SEQ ID NO:1594, SEQ ID NO:1596, SEQ ID NO:1598, SEQ ID NO:1599, SEQ ID NO:1601, SEQ ID NO:1602, SEQ ID NO:1605, SEQ ID NO:1607, SEQ ID NO:1608, SEQ ID NO:1609, SEQ ID NO:1611, SEQ ID NO:1613, SEQ ID NO:1615, SEQ ID NO:1617, SEQ ID NO:1619, SEQ ID NO:1621, SEQ ID NO:1622, SEQ ID NO:1623, SEQ ID NO:1624, SEQ ID NO:1625, SEQ ID NO:1627, SEQ ID NO:1629, SEQ ID NO:1631, SEQ ID NO:1633, SEQ ID NO:1635, SEQ ID NO:1637, SEQ ID NO:1639, SEQ ID NO:1643, SEQ ID NO:1645, SEQ ID NO:1648, SEQ ID NO:1649, SEQ ID NO:1651, SEQ ID NO:1653.

In some cases, a low nitrogen tolerance-modulating polypeptide has an amino acid sequence with sequence similarity to the amino acid sequence set forth in SEQ ID NO:1437, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1437. Amino acid sequences of polypeptides having greater than 20% sequence identity to the polypeptide set forth in SEQ ID NO:1437 are provided in FIG. 56 and in the Sequence Listing. Examples of such polypeptides include SEQ ID NO:173, SEQ ID NO:212, SEQ ID NO:361, SEQ ID NO:421, SEQ ID NO:443, SEQ ID NO:740, SEQ ID NO:744, SEQ ID NO:942, SEQ ID NO:1461.

In some cases, a low nitrogen tolerance-modulating polypeptide has an amino acid sequence with sequence similarity to the amino acid sequence set forth in SEQ ID NO:97, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:97. Amino acid sequences of polypeptides having greater than 20% sequence identity to the polypeptide set forth in SEQ ID NO:1437 are provided in FIG. 57 and in the Sequence Listing. Examples of such polypeptides include SEQ ID NO:2010, SEQ ID NO:2011, SEQ ID NO:2013, SEQ ID NO:2015, and SEQ ID NO:2017

E. Other Sequences

It should be appreciated that a low nitrogen tolerance-modulating polypeptide can include additional amino acids that are not involved in low nitrogen tolerance-modulation, and thus such a polypeptide can be longer than would otherwise be the case. For example, a low nitrogen tolerance-modulating polypeptide can include a purification tag, a chloroplast transit peptide, a mitochondrial transit peptide, an amyloplast peptide, or a leader sequence added to the amino or carboxy terminus. In some embodiments, a low nitrogen tolerance-modulating polypeptide includes an amino acid sequence that functions as a reporter, e.g., a green fluorescent protein or yellow fluorescent protein

III. NUCLEIC ACIDS

Nucleic acids described herein include nucleic acids that are effective to modulate low-nitrogen tolerance levels when transcribed in a plant or plant cell. Such nucleic acids include, without limitation, those that encode a low nitrogen tolerance-modulating polypeptide and those that can be used to inhibit expression of low nitrogen tolerance-modulating polypeptide via a nucleic acid based method.

A. Nucleic acids encoding low nitrogen tolerance-modulating polypeptides

Nucleic acids encoding low nitrogen tolerance-modulating polypeptides are described herein. Examples of such nucleic acids include SEQ ID NO:1, SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, and SEQ ID NO:1576, as described in more detail below. A nucleic acid also can be a fragment that is at least 40% (e.g., at least 45, 50, 55, 60, 65, 70, 75, 80, 85, 90, 95, or 99%) of the length of the full-length nucleic acid set forth in SEQ ID NO:1, SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, and SEQ ID NO:1576.

A low nitrogen tolerance-modulating nucleic acid can comprise the nucleotide sequence set forth in SEQ ID NO:1. Alternatively, a low nitrogen tolerance-modulating nucleic acid can be a variant of the nucleic acid having the nucleotide sequence set forth in SEQ ID NO:2. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:2.

A low nitrogen tolerance-modulating nucleic acid can comprise the nucleotide sequence set forth in SEQ ID NO: 48. Alternatively, a low nitrogen tolerance-modulating nucleic acid can be a variant of the nucleic acid having the nucleotide sequence set forth in SEQ ID NO: 48. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 48.

A low nitrogen tolerance-modulating nucleic acid can comprise the nucleotide sequence set forth in SEQ ID NO:76. Alternatively, a low nitrogen tolerance-modulating nucleic acid can be a variant of the nucleic acid having the nucleotide sequence set forth in SEQ ID NO:76. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:76.

A low nitrogen tolerance-modulating nucleic acid can comprise the nucleotide sequence set forth in SEQ ID NO:96. Alternatively, a low nitrogen tolerance-modulating nucleic acid can be a variant of the nucleic acid having the nucleotide sequence set forth in SEQ ID NO:96. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:96.

A low nitrogen tolerance-modulating nucleic acid can comprise the nucleotide sequence set forth in SEQ ID NO:99. Alternatively, a low nitrogen tolerance-modulating nucleic acid can be a variant of the nucleic acid having the nucleotide sequence set forth in SEQ ID NO:99. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:99.

A low nitrogen tolerance-modulating nucleic acid can comprise the nucleotide sequence set forth in SEQ ID NO:151. Alternatively, a low nitrogen tolerance-modulating nucleic acid can be a variant of the nucleic acid having the nucleotide sequence set forth in SEQ ID NO:151. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:151.

A low nitrogen tolerance-modulating nucleic acid can comprise the nucleotide sequence set forth in SEQ ID NO:165. Alternatively, a low nitrogen tolerance-modulating nucleic acid can be a variant of the nucleic acid having the nucleotide sequence set forth in SEQ ID NO:165. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:165.

A low nitrogen tolerance-modulating nucleic acid can comprise the nucleotide sequence set forth in SEQ ID NO:175. Alternatively, a low nitrogen tolerance-modulating nucleic acid can be a variant of the nucleic acid having the nucleotide sequence set forth in SEQ ID NO:175. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:175.

A low nitrogen tolerance-modulating nucleic acid can comprise the nucleotide sequence set forth in SEQ ID NO:185. Alternatively, a low nitrogen tolerance-modulating nucleic acid can be a variant of the nucleic acid having the nucleotide sequence set forth in SEQ ID NO:185. For example, a low nitrogen tolerance-modulating nucleic acid can have a nucleotide sequence with at least 80% sequence identity, e.g.; 81%, 85%, 90%, 95%, 97%, 98%, or 99% sequence identity, to the nucleotide sequence set forth in SEQ ID NO:185.

A low nitrogen tolerance-modulating nucleic acid can comprise the nucleotide sequence set forth in SEQ ID NO:207. Alternatively, a low nitrogen tolerance-modulating nucleic acid can be a variant of the nucleic acid having the nucleotide sequence set forth in SEQ ID NO:207. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:207.

A low nitrogen tolerance-modulating nucleic acid can comprise the nucleotide sequence set forth in SEQ ID NO:217. Alternatively, a low nitrogen tolerance-modulating nucleic acid can be a variant of the nucleic acid having the nucleotide sequence set forth in SEQ ID NO:217. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:217.

A low nitrogen tolerance-modulating nucleic acid can comprise the nucleotide sequence set forth in SEQ ID NO:233. Alternatively, a low nitrogen tolerance modulating nucleic acid can be a variant of the nucleic acid having the nucleotide sequence set forth in SEQ ID NO:233. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:233.

A low nitrogen tolerance-modulating nucleic acid can comprise the nucleotide sequence set forth in SEQ ID NO:245. Alternatively, a low nitrogen tolerance-modulating nucleic acid can be a variant of the nucleic acid having the nucleotide sequence set forth in SEQ ID NO:245. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:245.

A low nitrogen tolerance-modulating nucleic acid can comprise the nucleotide sequence set forth in SEQ ID NO:299. Alternatively, a low nitrogen tolerance-modulating nucleic acid can be a variant of the nucleic acid having the nucleotide sequence set forth in SEQ ID NO:299. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:299.

A low nitrogen tolerance-modulating nucleic acid can comprise the nucleotide sequence set forth in SEQ ID NO:331. Alternatively, a low nitrogen tolerance modulating nucleic acid can be a variant of the nucleic acid having the nucleotide sequence set forth in SEQ ID NO:331. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:331.

A low nitrogen tolerance-modulating nucleic acid can comprise the nucleotide sequence set forth in SEQ ID NO:367. Alternatively, a low nitrogen tolerance-modulating nucleic acid can be a variant of the nucleic acid having the nucleotide sequence set forth in SEQ ID NO:367. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:367.

A low nitrogen tolerance-modulating nucleic acid can comprise the nucleotide sequence set forth in SEQ ID NO:509. Alternatively, a low nitrogen tolerance-modulating nucleic acid can be a variant of the nucleic acid having the nucleotide sequence set forth in SEQ ID NO:509. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:509.

A low nitrogen tolerance-modulating nucleic acid can comprise the nucleotide sequence set forth in SEQ ID NO:532. Alternatively, a low nitrogen tolerance-modulating nucleic acid can be a variant of the nucleic acid having the nucleotide sequence set forth in SEQ ID NO:532. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:532.

A low nitrogen tolerance-modulating nucleic acid can comprise the nucleotide sequence set forth in SEQ ID NO:555. Alternatively, a low nitrogen tolerance-modulating nucleic acid can be a variant of the nucleic acid having the nucleotide sequence set forth in SEQ ID NO:555. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:555.

A low nitrogen tolerance-modulating nucleic acid can comprise the nucleotide sequence set forth in SEQ ID NO:557. Alternatively, a low nitrogen tolerance-modulating nucleic acid can be a variant of the nucleic acid having the nucleotide sequence set forth in SEQ ID NO:557. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:557.

A low nitrogen tolerance-modulating nucleic acid can comprise the nucleotide sequence set forth in SEQ ID NO:592. Alternatively, a low nitrogen tolerance-modulating nucleic acid can be a variant of the nucleic acid having the nucleotide sequence set forth in SEQ ID NO:592. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:592.

A low nitrogen tolerance-modulating nucleic acid can comprise the nucleotide sequence set forth in SEQ ID NO:612. Alternatively, a low nitrogen tolerance-modulating nucleic acid can be a variant of the nucleic acid having the nucleotide sequence set forth in SEQ ID NO:612. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:612.

A low nitrogen tolerance-modulating nucleic acid can comprise the nucleotide sequence set forth in SEQ ID NO:645. Alternatively, a low nitrogen tolerance-modulating nucleic acid can be a variant of the nucleic acid having the nucleotide sequence set forth in SEQ ID NO:645. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:645.

A low nitrogen tolerance-modulating nucleic acid can comprise the nucleotide sequence set forth in SEQ ID NO:686. Alternatively, a low nitrogen tolerance-modulating nucleic acid can be a variant of the nucleic acid having the nucleotide sequence set forth in SEQ ID NO:686. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:686.

A low nitrogen tolerance-modulating nucleic acid can comprise the nucleotide sequence set forth in SEQ ID NO:729. Alternatively, a low nitrogen tolerance-modulating nucleic acid can be a variant of the nucleic acid having the nucleotide sequence set forth in SEQ ID NO:729. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:729.

A low nitrogen tolerance-modulating nucleic acid can comprise the nucleotide sequence set forth in SEQ ID NO:745. Alternatively, a low nitrogen tolerance-modulating nucleic acid can be a variant of the nucleic acid having the nucleotide sequence set forth in SEQ ID NO:745. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:745.

A low nitrogen tolerance-modulating nucleic acid can comprise the nucleotide sequence set forth in SEQ ID NO:768. Alternatively, a low nitrogen tolerance-modulating nucleic acid can be a variant of the nucleic acid having the nucleotide sequence set forth in SEQ ID NO:768. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:768.

A low nitrogen tolerance-modulating nucleic acid can comprise the nucleotide sequence set forth in SEQ ID NO:791. Alternatively, a low nitrogen tolerance-modulating nucleic acid can be a variant of the nucleic acid having the nucleotide sequence set forth in SEQ ID NO:791. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:791.

A low nitrogen tolerance-modulating nucleic acid can comprise the nucleotide sequence set forth in SEQ ID NO:823. Alternatively, a low nitrogen tolerance-modulating nucleic acid can be a variant of the nucleic acid having the nucleotide sequence set forth in SEQ ID NO:823. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:823.

A low nitrogen tolerance-modulating nucleic acid can comprise the nucleotide sequence set forth in SEQ ID NO:827. Alternatively, a low nitrogen tolerance-modulating nucleic acid can be a variant of the nucleic acid having the nucleotide sequence set forth in SEQ ID NO:827. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:827.

A low nitrogen tolerance-modulating nucleic acid can comprise the nucleotide sequence set forth in SEQ ID NO:852. Alternatively, a low nitrogen tolerance-modulating nucleic acid can be a variant of the nucleic acid having the nucleotide sequence set forth in SEQ ID NO:852. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:852.

A low nitrogen tolerance-modulating nucleic acid can comprise the nucleotide sequence set forth in SEQ ID NO:854. Alternatively, a low nitrogen tolerance-modulating nucleic acid can be a variant of the nucleic acid having the nucleotide sequence set forth in SEQ ID NO:854. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:854.

A low nitrogen tolerance-modulating nucleic acid can comprise the nucleotide sequence set forth in SEQ ID NO:890. Alternatively, a low nitrogen tolerance-modulating nucleic acid can be a variant of the nucleic acid having the nucleotide sequence set forth in SEQ ID NO:890. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:890.

A low nitrogen tolerance-modulating nucleic acid can comprise the nucleotide sequence set forth in SEQ ID NO:916. Alternatively, a low nitrogen tolerance-modulating nucleic acid can be a variant of the nucleic acid having the nucleotide sequence set forth in SEQ ID NO:916. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:916.

A low nitrogen tolerance-modulating nucleic acid can comprise the nucleotide sequence set forth in SEQ ID NO:943. Alternatively, a low nitrogen tolerance-modulating nucleic acid can be a variant of the nucleic acid having the nucleotide sequence set forth in SEQ ID NO:943. For example, a low nitrogen tolerance-modulating nucleic acid can have a nucleotide sequence with at least 80% sequence A low nitrogen tolerance-modulating nucleic acid can comprise the nucleotide sequence set forth in SEQ ID NO:975. Alternatively, a low nitrogen tolerance-modulating nucleic acid can be a variant of the nucleic acid having the nucleotide sequence set forth in SEQ ID NO:975. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:975.

A low nitrogen tolerance-modulating nucleic acid can comprise the nucleotide sequence set forth in SEQ ID NO:981. Alternatively, a low nitrogen tolerance-modulating nucleic acid can be a variant of the nucleic acid having the nucleotide sequence set forth in SEQ ID NO:981. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:981.

A low nitrogen tolerance-modulating nucleic acid can comprise the nucleotide sequence set forth in SEQ ID NO: 1034. Alternatively, a low nitrogen tolerance-modulating nucleic acid can be a variant of the nucleic acid having the nucleotide sequence set forth in SEQ ID NO: 1034. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 1034.

A low nitrogen tolerance-modulating nucleic acid can comprise the nucleotide sequence set forth in SEQ ID NO:1053. Alternatively, a low nitrogen tolerance-modulating nucleic acid can be a variant of the nucleic acid having the nucleotide sequence set forth in SEQ ID NO:1053. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1053.

A low nitrogen tolerance-modulating nucleic acid can comprise the nucleotide sequence set forth in SEQ ID NO:1098. Alternatively, a low nitrogen tolerance-modulating nucleic acid can be a variant of the nucleic acid having the nucleotide sequence set forth in SEQ ID NO:1098. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1098.

A low nitrogen tolerance-modulating nucleic acid can comprise the nucleotide sequence set forth in SEQ ID NO:1111. Alternatively, a low nitrogen tolerance-modulating nucleic acid can be a variant of the nucleic acid having the nucleotide sequence set forth in SEQ ID NO:1111. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1111.

A low nitrogen tolerance-modulating nucleic acid can comprise the nucleotide sequence set forth in SEQ ID NO:1115. Alternatively, a low nitrogen tolerance-modulating nucleic acid can be a variant of the nucleic acid having the nucleotide sequence set forth in SEQ ID NO:1115. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1115.

A low nitrogen tolerance-modulating nucleic acid can comprise the nucleotide sequence set forth in SEQ ID NO:1156. Alternatively, a low nitrogen tolerance-modulating nucleic acid can be a variant of the nucleic acid having the nucleotide sequence set forth in SEQ ID NO:1156. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1156.

A low nitrogen tolerance-modulating nucleic acid can comprise the nucleotide sequence set forth in SEQ ID NO:1158. Alternatively, a low nitrogen tolerance-modulating nucleic acid can be a variant of the nucleic acid having the nucleotide sequence set forth in SEQ ID NO:1158. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1158.

A low nitrogen tolerance-modulating nucleic acid can comprise the nucleotide sequence set forth in SEQ ID NO:1165. Alternatively, a low nitrogen tolerance-modulating nucleic acid can be a variant of the nucleic acid having the nucleotide sequence set forth in SEQ ID NO:1165. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1165.

A low nitrogen tolerance-modulating nucleic acid can comprise the nucleotide sequence set forth in SEQ ID NO:1184. Alternatively, a low nitrogen tolerance-modulating nucleic acid can be a variant of the nucleic acid having the nucleotide sequence set forth in SEQ ID NO:1184. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1184.

A low nitrogen tolerance-modulating nucleic acid can comprise the nucleotide sequence set forth in SEQ ID NO:1193. Alternatively, a low nitrogen tolerance-modulating nucleic acid can be a variant of the nucleic acid having the nucleotide sequence set forth in SEQ ID NO:1193. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1193.

A low nitrogen tolerance-modulating nucleic acid can comprise the nucleotide sequence set forth in SEQ ID NO: 1209. Alternatively, a low nitrogen tolerance-modulating nucleic acid can be a variant of the nucleic acid having the nucleotide sequence set forth in SEQ ID NO: 1209. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 1209.

A low nitrogen tolerance-modulating nucleic acid can comprise the nucleotide sequence set forth in SEQ ID NO:1273. Alternatively, a low nitrogen tolerance-modulating nucleic acid can be a variant of the nucleic acid having the nucleotide sequence set forth in SEQ ID NO:1273. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1273.

A low nitrogen tolerance-modulating nucleic acid can comprise the nucleotide sequence set forth in SEQ ID NO:1301. Alternatively, a low nitrogen tolerance-modulating nucleic acid can be a variant of the nucleic acid having the nucleotide sequence set forth in SEQ ID NO:1301. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1301.

A low nitrogen tolerance-modulating nucleic acid can comprise the nucleotide sequence set forth in SEQ ID NO:1341. Alternatively, a low nitrogen tolerance-modulating nucleic acid can be a variant of the nucleic acid having the nucleotide sequence set forth in SEQ ID NO:1341. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1341.

A low nitrogen tolerance-modulating nucleic acid can comprise the nucleotide sequence set forth in SEQ ID NO:1384. Alternatively, a low nitrogen tolerance-modulating nucleic acid can be a variant of the nucleic acid having the nucleotide sequence set forth in SEQ ID NO:1384. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1384.

A low nitrogen tolerance-modulating nucleic acid can comprise the nucleotide sequence set forth in SEQ ID NO:1408. Alternatively, a low nitrogen tolerance-modulating nucleic acid can be a variant of the nucleic acid having the nucleotide sequence set forth in SEQ ID NO:1408. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1408.

A low nitrogen tolerance-modulating nucleic acid can comprise the nucleotide sequence set forth in SEQ ID NO:1427. Alternatively, a low nitrogen tolerance-modulating nucleic acid can be a variant of the nucleic acid having the nucleotide sequence set forth in SEQ ID NO:1427. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1427.

A low nitrogen tolerance-modulating nucleic acid can comprise the nucleotide sequence set forth in SEQ ID NO:1462. Alternatively, a low nitrogen tolerance-modulating nucleic acid can be a variant of the nucleic acid having the nucleotide sequence set forth in SEQ ID NO:1462. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1462.

A low nitrogen tolerance-modulating nucleic acid can comprise the nucleotide sequence set forth in SEQ ID NO:1490. Alternatively, a low nitrogen tolerance-modulating nucleic acid can be a variant of the nucleic acid having the nucleotide sequence set forth in SEQ ID NO:1490. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1490.

A low nitrogen tolerance-modulating nucleic acid can comprise the nucleotide sequence set forth in SEQ ID NO:1509. Alternatively, a low nitrogen tolerance-modulating nucleic acid can be a variant of the nucleic acid having the nucleotide sequence set forth in SEQ ID NO:1509. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1509.

A low nitrogen tolerance-modulating nucleic acid can comprise the nucleotide sequence set forth in SEQ ID NO:1524. Alternatively, a low nitrogen tolerance-modulating nucleic acid can be a variant of the nucleic acid having the nucleotide sequence set forth in SEQ ID NO:1524. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1524.

A low nitrogen tolerance-modulating nucleic acid can comprise the nucleotide sequence set forth in SEQ ID NO:1536. Alternatively, a low nitrogen tolerance-modulating nucleic acid can be a variant of the nucleic acid having the nucleotide sequence set forth in SEQ ID NO:1536. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1536.

A low nitrogen tolerance-modulating nucleic acid can comprise the nucleotide sequence set forth in SEQ ID NO:1553. Alternatively, a low nitrogen tolerance-modulating nucleic acid can be a variant of the nucleic acid having the nucleotide sequence set forth in SEQ ID NO:1553. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1553.

A low nitrogen tolerance-modulating nucleic acid can comprise the nucleotide sequence set forth in SEQ ID NO:1576. Alternatively, a low nitrogen tolerance-modulating nucleic acid can be a variant of the nucleic acid having the nucleotide sequence set forth in SEQ ID NO:1576. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1576.

Isolated nucleic acid molecules can be produced by standard techniques. For example, polymerase chain reaction (PCR) techniques can be used to obtain an isolated nucleic acid containing a nucleotide sequence described herein. PCR can be used to amplify specific sequences from DNA as well as RNA, including sequences from total genomic DNA or total cellular RNA. Various PCR methods are described, for example, in PCR Primer: A Laboratory Manual, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid. Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids of the invention also can be obtained by mutagenesis of, e.g., a naturally occurring DNA.

B. Use of Nucleic Acids to Modulate Expression of Polypeptides i. Expression of a Low Nitrogen Tolerance-Modulating Polypeptide A nucleic acid encoding one of the low nitrogen tolerance-modulating polypeptides described herein can be used to express the polypeptide in a plant species of interest, typically by transforming a plant cell with a nucleic acid having the coding sequence for the polypeptide operably linked in sense orientation to one or more regulatory regions. It will be appreciated that because of the degeneracy of the genetic code, a number of nucleic acids can encode a particular low nitrogen tolerance-modulating polypeptide; i.e., for many amino acids, there is more than one nucleotide triplet that serves as the codon for the amino acid. Thus, codons in the coding sequence for a given low nitrogen tolerance-modulating polypeptide can be modified such that optimal expression in a particular plant species is obtained, using appropriate codon bias tables for that species.

In some cases, expression of a low nitrogen tolerance-modulating polypeptide inhibits one or more functions of an endogenous polypeptide. For example, a nucleic acid that encodes a dominant negative polypeptide can be used to inhibit protein function. A dominant negative polypeptide typically is mutated or truncated relative to an endogenous wild type polypeptide, and its presence in a cell inhibits one or more functions of the wild type polypeptide in that cell, i.e., the dominant negative polypeptide is genetically dominant and confers a loss of function. The mechanism by which a dominant negative polypeptide confers such a phenotype can vary but often involves a protein-protein interaction or a protein-DNA interaction. For example, a dominant negative polypeptide can be an enzyme that is truncated relative to a native wild type enzyme, such that the truncated polypeptide retains domains involved in binding a first protein but lacks domains involved in binding a second protein. The truncated polypeptide is thus unable to properly modulate the activity of the second protein. See, e.g., US 2007/0056058. As another example, a point mutation that results in a non-conservative amino acid substitution in a catalytic domain can result in a dominant negative polypeptide. See, e.g., US 2005/032221. As another example, a dominant negative polypeptide can be a transcription factor that is truncated relative to a native wild type transcription factor, such that the truncated polypeptide retains the DNA binding domain(s) but lacks the activation domain(s). Such a truncated polypeptide can inhibit the wild type transcription factor from binding DNA, thereby inhibiting transcription activation.

ii. Inhibition of Expression of a Low Nitrogen Tolerance-Modulating Polypeptide

Polynucleotides and recombinant constructs described herein can be used to inhibit expression of a low nitrogen tolerance-modulating polypeptide in a plant species of interest. See, e.g., Matzke and Birchler, *Nature Reviews Genetics* 6:24-35 (2005); Akashi et al., *Nature Reviews Mol. Cell Biology* 6:413-422 (2005); Mittal, *Nature Reviews Genetics* 5:355-365 (2004); Dorsett and Tuschl, *Nature Reviews Drug Discovery* 3: 318-329 (2004); and *Nature Reviews RNA interference collection*, October 2005 at nature.com/reviews/focus/mai. A number of nucleic acid based methods, including antisense RNA, ribozyme directed RNA cleavage, post-transcriptional gene silencing (PTGS), e.g., RNA interference (RNAi), and transcriptional gene silencing (TGS) are known to inhibit gene expression in plants. Suitable polynucleotides include full-length nucleic acids encoding low nitrogen tolerance-modulating polypeptides or fragments of such full-length nucleic acids. In some embodiments, a complement of the full-length nucleic acid or a fragment thereof can be used. Typically, a fragment is at least 10 nucleotides, e.g., at least 12, 13, 14, 15, 16, 17, 18, 19, 20, 21, 22, 23, 24, 25, 26, 27, 30, 35, 40, 50, 80, 100, 200, 500 nucleotides or more. Generally, higher homology can be used to compensate for the use of a shorter sequence.

Antisense technology is one well-known method. In this method, a nucleic acid of a gene to be repressed is cloned and operably linked to a regulatory region and a transcription termination sequence so that the antisense strand of RNA is transcribed. The recombinant construct is then transformed into plants, as described herein, and the antisense strand of RNA is produced. The nucleic acid need not be the entire sequence of the gene to be repressed, but typically will be substantially complementary to at least a portion of the sense strand of the gene to be repressed.

In another method, a nucleic acid can be transcribed into a ribozyme, or catalytic RNA, that affects expression of an mRNA. See, U.S. Pat. No. 6,423,885. Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman et al. (1995) *Proc. Natl. Acad. Sci. USA*, 92(13):6175-6179; de Feyter and Gaudron, Methods in Molecular Biology, Vol. 74, Chapter 43, "Expressing Ribozymes in Plants", Edited by Turner, P.C., Humana Press Inc., Totowa, N.J. RNA endoribonucleases which have been described, such as the one that occurs naturally in *Tetrahymena thermophila*, can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence or a fragment thereof of a low nitrogen tolerance-modulating polypeptide, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises a sequence that is similar or identical to the antisense strand or a fragment thereof of the coding sequence of the low nitrogen tolerance-modulating polypeptide, and can have a length that is shorter, the same as, or longer than the corresponding length of the sense sequence. In some cases, one strand of the stem portion of a double stranded RNA comprises a sequence that is similar or identical to the 3' or 5' untranslated region, or a fragment thereof, of an mRNA encoding a low nitrogen tolerance-modulating polypeptide, and the other strand of the stem portion of the double stranded RNA comprises a sequence that is similar or identical to the sequence that is complementary to the 3' or 5' untranslated region, respectively, or a fragment thereof, of the mRNA encoding the low nitrogen tolerance-modulating polypeptide. In other embodiments, one strand of the stem portion of a double stranded RNA comprises a sequence that is similar or identical to the sequence of an intron, or a fragment thereof, in the pre-mRNA encoding a low nitrogen tolerance-modulating polypeptide, and the other strand of the stem portion comprises a sequence that is similar or identical to the sequence that is complementary to the sequence of the intron, or a fragment thereof, in the pre-mRNA.

The loop portion of a double stranded RNA can be from 3 nucleotides to 5,000 nucleotides, e.g., from 3 nucleotides to 25 nucleotides, from 15 nucleotides to 1,000 nucleotides, from 20 nucleotides to 500 nucleotides, or from 25 nucleotides to 200 nucleotides. The loop portion of the RNA can include an intron or a fragment thereof. A double stranded RNA can have zero, one, two, three, four, five, six, seven, eight, nine, ten, or more stem-loop structures.

A construct including a sequence that is operably linked to a regulatory region and a transcription termination sequence, and that is transcribed into an RNA that can form a double stranded RNA, is transformed into plants as described herein. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330, and 20030180945.

Constructs containing regulatory regions operably linked to nucleic acid molecules in sense orientation can also be used to inhibit the expression of a gene. The transcription product can be similar or identical to the sense coding sequence, or a fragment thereof, of a low nitrogen tolerance-modulating polypeptide. The transcription product also can be unpolyadenylated, lack a 5' cap structure, or contain an unspliceable intron. Methods of inhibiting gene expression using a full-length cDNA as well as a partial cDNA sequence are known in the art. See, e.g., U.S. Pat. No. 5,231,020.

In some embodiments, a construct containing a nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary. The sense or antisense sequence can be a sequence that is identical or complementary to the sequence of an mRNA, the 3' or 5' untranslated region of an mRNA, or an intron in a pre-mRNA encoding a low nitrogen tolerance-modulating polypeptide, or a fragment of such sequences. In some embodiments, the sense or antisense sequence is identical or complementary to a sequence of the regulatory region that drives transcription of the gene encoding a low nitrogen tolerance-modulating polypeptide. In each case, the sense sequence is the sequence that is complementary to the antisense sequence.

The sense and antisense sequences can be any length greater than about 10 nucleotides (e.g., 12, 13, 14, 15, 16, 17, 18, 19, 20, 21, 22, 23, 24, 25, 26, 27, 28, 29, 30, or more nucleotides). For example, an antisense sequence can be 21 or 22 nucleotides in length. Typically, the sense and antisense sequences range in length from about 15 nucleotides to about 30 nucleotides, e.g., from about 18 nucleotides to about 28 nucleotides, or from about 21 nucleotides to about 25 nucleotides.

In some embodiments, an antisense sequence is a sequence complementary to an mRNA sequence, or a fragment thereof, encoding a low nitrogen tolerance-modulating polypeptide described herein. The sense sequence complementary to the antisense sequence can be a sequence present within the mRNA of the low nitrogen tolerance-modulating polypeptide. Typically, sense and antisense sequences are designed to correspond to a 15-30 nucleotide sequence of a target mRNA such that the level of that target mRNA is reduced.

In some embodiments, a construct containing a nucleic acid having at least one strand that is a template for more than one sense sequence (e.g., 2, 3, 4, 5, 6, 7, 8, 9, 10 or more sense sequences) can be used to inhibit the expression of a gene. Likewise, a construct containing a nucleic acid having at least one strand that is a template for more than one antisense sequence (e.g., 2, 3, 4, 5, 6, 7, 8, 9, 10 or more antisense sequences) can be used to inhibit the expression of a gene. For example, a construct can contain a nucleic acid having at least one strand that is a template for two sense sequences and two antisense sequences. The multiple sense sequences can be identical or different, and the multiple antisense sequences can be identical or different. For example, a construct can have a nucleic acid having one strand that is a template for two identical sense sequences and two identical antisense sequences that are complementary to the two identical sense sequences. Alternatively, an isolated nucleic acid can have one strand that is a template for (1) two identical sense sequences 20 nucleotides in length, (2) one antisense sequence that is complementary to the two identical sense sequences 20 nucleotides in length, (3) a sense sequence 30 nucleotides in length, and (4) three identical antisense sequences that are complementary to the sense sequence 30 nucleotides in length. The constructs provided herein can be designed to have any arrangement of sense and antisense sequences. For example, two identical sense sequences can be followed by two identical antisense sequences or can be positioned between two identical antisense sequences.

A nucleic acid having at least one strand that is a template for one or more sense and/or antisense sequences can be operably linked to a regulatory region to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand, and one from the bottom strand. See, for example, Yan et al., *Plant Physiol.*, 141: 1508-1518 (2006). The two regulatory regions can be the same or different. The two transcripts can form double-stranded RNA molecules that induce degradation of the target RNA. In some cases, a nucleic acid can be positioned within a T-DNA or plant-derived transfer DNA (P-DNA) such that the left and right T-DNA border sequences, or the left and right border-like sequences of the P-DNA, flank or are on either side of the nucleic acid. See, US 2006/0265788. The nucleic acid sequence between the two regulatory regions can be from about 15 to about 300 nucleotides in length. In some embodiments, the nucleic acid sequence between the two regulatory regions is from about 15 to about 200 nucleotides in length, from about 15 to about 100 nucleotides in length, from about 15 to about 50 nucleotides in length, from about 18 to about 50 nucleotides in length, from about 18 to about 40 nucleotides in length, from about 18 to about 30 nucleotides in length, or from about 18 to about 25 nucleotides in length.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller (1997) *Antisense Nucleic Acid Drug Dev.*, 7:187-195; Hyrup et al. (1996) *Bioorgan. Med. Chem.*, 4:5-23. In addition, the deoxyphosphate backbone can be replaced with, for example, phosphorothioate or phosphorodithioate backbone, a phosphoroamidite, or an alkyl phosphotriester backbone.

C. Constructs/Vectors

Recombinant constructs provided herein can be used to transform plants or plant cells in order to modulate low-nitrogen tolerance levels. A recombinant nucleic acid construct can comprise a nucleic acid encoding a low nitrogen tolerance-modulating polypeptide as described herein, operably linked to a regulatory region suitable for expressing the low nitrogen tolerance-modulating polypeptide in the plant or cell. Thus, a nucleic acid can comprise a coding sequence that encodes any of the low nitrogen tolerance-modulating polypeptides as set forth in SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, and SEQ ID NO:1577. Examples of nucleic acids encoding low nitrogen tolerance-modulating polypeptides are set forth in SEQ ID NO:1, SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, and SEQ ID NO:1576. The low nitrogen tolerance-modulating polypeptide encoded by a recombinant nucleic, acid can be a native low nitrogen tolerance-modulating polypeptide, or can be heterologous to the cell. In some cases, the recombinant construct contains a nucleic acid that inhibits expression of a low nitrogen tolerance-modulating polypeptide, operably linked to a regulatory region. Examples of suitable regulatory regions are described in the section entitled "Regulatory Regions."

Vectors containing recombinant nucleic acid constructs such as those described herein also are provided. Suitable vector backbones include, for example, those routinely used in the art such as plasmids, viruses, artificial chromosomes, BACs, YACs, or PACs. Suitable expression vectors include, without limitation, plasmids and viral vectors derived from, for example, bacteriophage, baculoviruses, and retroviruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

The vectors provided herein also can include, for example, origins of replication, scaffold attachment regions (SARs), and/or markers. A marker gene can confer a selectable phenotype on a plant cell. For example, a marker can confer biocide resistance, such as resistance to an antibiotic (e.g., kanamycin, G418, bleomycin, or hygromycin), or an herbicide (e.g., glyphosate, chlorsulfuron or phosphinothricin). In addition, an expression vector can include a tag sequence designed to facilitate manipulation or detection (e.g., purification or localization) of the expressed polypeptide. Tag sequences, such as luciferase, β-glucuronidase (GUS), green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus.

D. Regulatory Regions

The choice of regulatory regions to be included in a recombinant construct depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning regulatory regions relative to the coding sequence. Transcription of a nucleic acid can be modulated in a similar manner.

Some suitable regulatory regions initiate transcription only, or predominantly, in certain cell types. Methods for identifying and characterizing regulatory regions in plant genomic DNA are known, including, for example, those described in the following references: Jordano et al. (1989) *Plant Cell*, 1:855-866; Bustos et al. (1989) *Plant Cell*, 1:839-854; Green et al. (1988) *EMBO J.*, 7:4035-4044; Meier et al. (1991) *Plant Cell*, 3:309-316; and Zhang et al. (1996) *Plant Physiology*, 110:1069-1079.

Examples of various classes of regulatory regions are described below. Some of the regulatory regions indicated below as well as additional regulatory regions are described in more detail in U.S. Patent Application Ser. Nos. 60/505,689; 60/518,075; 60/544,771; 60/558,869; 60/583,691; 60/619,181; 60/637,140; 60/757,544; 60/776,307; 10/957,569; 11/058,689; 11/172,703; 11/208,308; 11/274,890; 60/583,609; 60/612,891; 11/097,589; 11/233,726; 11/408,791; 11/414,142; 10/950,321; 11/360,017; PCT/US05/011105; PCT/US05/23639; PCT/US05/034308; PCT/US05/034343; and PCT/US06/038236; PCT/US06/040572; and PCT/US07/62762.

For example, the sequences of regulatory regions p326, YP0144, YP0190, p13879, YP0050, p32449, 21876, YP0158, YP0214, YP0380, PT0848, PT0633, YP0128, YP0275, PT0660, PT0683, PT0758, PT0613, P10672, PT0688, PT0837, YP0092, PT0676, PT0708, YP0396, YP0007, YP0111, YP0103, YP0028, YP0121, YP0008, YP0039, YP0115, YP0119, YP0120, YP0374, YP0101, YP0102, YP0110, YP0117, YP0137, YP0285, YP0212, YP0097, YP0107, YP0088, YP0143, YP0156, PT0650, PT0695, PT0723, PT0838, PT0879, PT0740, PT0535, PT0668, PT0886, PT0585, YP0381, YP0337, PT0710, YP0356, YP0385, YP0384, YP0286, YP0377, PD1367, PT0863, PT0829, PT0665, PT0678, YP0086, YP0188, YP0263, PT0743 and YP0096 are set forth in the sequence listing of PCT/US06/040572; the sequence of regulatory region PT0625 is set forth in the sequence listing of PCT/US05/034343; the sequences of regulatory regions PT0623, YP0388, YP0087, YP0093, YP0108, YP0022 and YP0080 are set forth in the sequence listing of U.S. patent application Ser. No. 11/172,703; the sequence of regulatory region PR0924 is set forth in the sequence listing of PCT/US07/62762; and the sequences of regulatory regions p530c10, pOsFIE2-2, pOsMEA, pOsYp102, and pOsYp285 are set forth in the sequence listing of PCT/US06/038236.

It will be appreciated that a regulatory region may meet criteria for one classification based on its activity in one plant species, and yet meet criteria for a different classification based on its activity in another plant species.

i. Broadly Expressing Promoters

A promoter can be said to be "broadly expressing" when it promotes transcription in many, but not necessarily all, plant tissues. For example, a broadly expressing promoter can promote transcription of an operably linked sequence in one or more of the shoot, shoot tip (apex), and leaves, but weakly or not at all in tissues such as roots or stems. As another example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. Non-limiting examples of broadly expressing promoters that can be included in the nucleic acid constructs provided herein include the p326, YP0144, YP0190, p13879, YP0050, p32449, 21876, YP0158, YP0214, YP0380, P10848, and PT0633 promoters. Additional examples include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter, and ubiquitin promoters such as the maize ubiquitin-1 promoter. In some cases, the CaMV 35S promoter is excluded from the category of broadly expressing promoters.

ii. Root Promoters

Root-active promoters confer transcription in root tissue, e.g., root endodermis, root epidermis, or root vascular tissues. In some embodiments, root-active promoters are root-preferential promoters, i.e., confer transcription only or predominantly in root tissue. Root-preferential promoters include the YP0128, YP0275, PT0625, PT0660, PT0683, and PT0758 promoters. Other root-preferential promoters include the PT0613, PT0672, PT0688, and PT0837 promoters, which drive transcription primarily in root tissue and to a lesser extent in ovules and/or seeds. Other examples of root-preferential promoters include the root-specific subdomains of the CaMV 35S promoter (Lam et al. (1989) *Proc. Natl. Acad. Sci. USA*, 86:7890-7894), root cell specific promoters reported by Conkling et al. (1990) *Plant Physiol.*, 93:1203-1211, and the tobacco RD2 promoter.

iii. Maturing Endosperm Promoters

In some embodiments, promoters that drive transcription in maturing endosperm can be useful. Transcription from a maturing endosperm promoter typically begins after fertilization and occurs primarily in endosperm tissue during seed development and is typically highest during the cellularization phase. Most suitable are promoters that are active predominantly in maturing endosperm, although promoters that are also active in other tissues can sometimes be used. Non-limiting examples of maturing endosperm promoters that can be included in the nucleic acid constructs provided herein include the napin promoter, the Arcelin-5 promoter, the phaseolin promoter (Bustos et al. (1989) *Plant Cell*, 1(9):839-853), the soybean trypsin inhibitor promoter (Riggs et al. (1989) *Plant Cell*, 1(6):609-621), the ACP promoter (Baerson et al. (1993) *Plant Mol. Biol.*, 22(2):255-267), the stearoyl-ACP desaturase promoter (Slocombe et al. (1994) *Plant Physiol.*, 104(4):167-176), the soybean α' subunit of β-conglycinin promoter (Chen et al. (1986) *Proc. Natl. Acad. Sci. USA*, 83:8560-8564), the oleosin promoter (Hong et al. (1997) *Plant Mol. Biol.*, 34(3):549-555), and zein promoters, such as the 15 kD zein promoter, the 16 kD zein promoter, 19 kD zein promoter, 22 kD zein promoter and 27 kD zein promoter. Also suitable are the Osgt-1 promoter from the rice glutelin-1 gene (Zheng et al. (1993) *Mol. Cell Biol.*, 13:5829-5842), the beta-amylase promoter, and the barley hordein promoter. Other maturing endosperm promoters include the YP0092, PT0676, and PT0708 promoters iv. Ovary Tissue Promoters Promoters that are active in ovary tissues such as the ovule wall and mesocarp can also be useful, e.g., a polygalacturonidase promoter, the banana TRX promoter, the melon actin promoter, YP0396, and PT0623. Examples of promoters that are active primarily in ovules include YP0007, YP0111, YP0092, YP0103, YP0028, YP0121, YP0008, YP0039, YP0115, YP0119, YP0120, and YP0374.

v. Embryo Sac/Early Endosperm Promoters

To achieve expression in embryo sac/early endosperm, regulatory regions can be used that are active in polar nuclei and/or the central cell, or in precursors to polar nuclei, but not in egg cells or precursors to egg cells. Most suitable are promoters that drive expression only or predominantly in polar nuclei or precursors thereto and/or the central cell. A pattern of transcription that extends from polar nuclei into early endosperm development can also be found with embryo sac/early endosperm-preferential promoters, although transcription typically decreases significantly in later endosperm development during and after the cellularization phase. Expression in the zygote or developing embryo typically is not present with embryo sac/early endosperm promoters.

Promoters that may be suitable include those derived from the following genes: *Arabidopsis* viviparous-1 (see, GenBank No. U93215); *Arabidopsis* atmycl (see, Urao (1996) *Plant Mol. Biol.*, 32:571-57; Conceicao (1994) *Plant*, 5:493-505); *Arabidopsis* FIE (GenBank No. AF129516); *Arabidopsis* MEA; *Arabidopsis* FIS2 (GenBank No. AF096096); and FIE 1.1 (U.S. Pat. No. 6,906,244). Other promoters that may be suitable include those derived from the following genes: maize MAC1 (see, Sheridan (1996) *Genetics*, 142: 1009-1020); maize Cat3 (see, GenBank No. L05934; Abler (1993) *Plant Mol. Biol.*, 22:10131-1038). Other promoters include the following *Arabidopsis* promoters: YP0039, YP0101, YP0102, YP0110, YP0117, YP0119, YP0137, DME, YP0285, and YP0212. Other promoters that may be useful include the following rice promoters: p530c10, pOs-FIE2-2, pOsMEA, pOsYp102, and pOsYp285.

vi. Embryo Promoters

Regulatory regions that preferentially drive transcription in zygotic cells following fertilization can provide embryo-preferential expression. Most suitable are promoters that preferentially drive transcription in early stage embryos prior to the heart stage, but expression in late stage and maturing embryos is also suitable. Embryo-preferential promoters include the barley lipid transfer protein (Ltp1) promoter (*Plant Cell Rep* (2001) 20:647-654), YP0097, YP0107, YP0088, YP0143, YP0156, PT0650, PT0695, PT0723, PT0838, PT0879, and PT0740.

vii. Photosynthetic Tissue Promoters

Promoters active in photosynthetic tissue confer transcription in green tissues such as leaves and stems. Most suitable are promoters that drive expression only or predominantly in such tissues. Examples of such promoters include the ribulose-1,5-bisphosphate carboxylase (RbcS) promoters such as the RbcS promoter from eastern larch (*Larix laricina*), the pine cab6 promoter (Yamamoto et al. (1994) *Plant Cell Physiol.*, 35:773-778), the Cab-1 promoter from wheat (Fejes et al. (1990) *Plant Mol. Biol.*, 15:921-932), the CAB-1 promoter from spinach (Lubberstedt et al. (1994) *Plant Physiol.*, 104:997-1006), the cablR promoter from rice (Luan et al. (1992) *Plant Cell*, 4:971-981), the pyruvate orthophosphate dikinase (PPDK) promoter from corn (Matsuoka et al. (1993) *Proc. Natl. Acad. Sci. USA*, 90:9586-9590), the tobacco Lhcb1*2 promoter (Cerdan et al. (1997) *Plant Mol. Biol.*, 33:245-255), the *Arabidopsis thaliana* SUC2 sucrose-H+ symporter promoter (Truernit et al. (1995) *Planta*, 196:564-570), and thylakoid membrane protein promoters from spinach (psaD, psaF, psaE, PC, FNR, atpC, atpD, cab, rbcS). Other photosynthetic tissue promoters include PT0535, PT0668, PT0886, YP0144, YP0380 and PT0585.

viii. Vascular Tissue Promoters

Examples of promoters that have high or preferential activity in vascular bundles include YP0087, YP0093, YP0108, YP0022, and YP0080. Other vascular tissue-preferential promoters include the glycine-rich cell wall protein GRP 1.8 promoter (Keller and Baumgartner (1991) *Plant Cell*, 3(10):1051-1061), the Commelina yellow mottle virus (CoYMV) promoter (Medberry et al. (1992) *Plant Cell*, 4(2):185-192), and the rice tungro bacilliform virus (RTBV) promoter (Dai et al. (2004) *Proc. Natl. Acad. Sci. USA*, 101(2):687-692).

ix. Inducible Promoters

Inducible promoters confer transcription in response to external stimuli such as chemical agents or environmental stimuli. For example, inducible promoters can confer transcription in response to hormones such as giberellic acid or ethylene, or in response to light or drought. Examples of drought-inducible promoters include YP0380, PT0848, YP0381, YP0337, PT0633, YP0374, PT0710, YP0356, YP0385, YP0396, YP0388, YP0384, PT0688, YP0286, YP0377, PD1367, and PD0901. Examples of nitrogen-inducible promoters include PT0863, PT0829, PT0665, and PT0886. Examples of shade-inducible promoters include PR0924 and PT0678. An example of a promoter induced by salt is rd29A (Kasuga et al. (1999) *Nature Biotech* 17: 287-291).

x. Basal Promoters

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

xi. Stem Promoters

A stem promoter may be specific to one or more stem tissues or specific to stem and other plant parts. Stem promoters may have high or preferential activity in, for example, epidermis and cortex, vascular cambium, procambium, or xylem. Examples of stem promoters include YP0018 which is disclosed in US20060015970 and CryIA (b) and CryIA(c) (Braga et al. 2003, *Journal of New Seeds* 5:209-221).

xii. Other Promoters

Other classes of promoters include, but are not limited to, shoot-preferential, callus-preferential, trichome cell-preferential, guard cell-preferential such as PT0678, tuber-preferential, parenchyma cell-preferential, and senescence-preferential promoters. Promoters designated YP0086, YP0188, YP0263, PT0758, PT0743, PT0829, YP0119, and YP0096, as described in the above-referenced patent applications, may also be useful.

xiii. Other Regulatory Regions

A 5' untranslated region (UTR) can be included in nucleic acid constructs described herein. A 5' UTR is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a recombinant polynucleotide, e.g., introns, enhancers, upstream activation regions, transcription terminators, and inducible elements. Thus, for example, more than one regulatory region can be operably linked to the sequence of a polynucleotide encoding a low nitrogen tolerance-modulating polypeptide.

Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

IV. TRANSGENIC PLANTS AND PLANT CELLS

A. Transformation

The invention also features transgenic plant cells and plants comprising at least one recombinant nucleic acid construct described herein. A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

Transgenic plant cells used in methods described herein can constitute part or all of a whole plant. Such plants can be grown in a manner suitable for the species under consideration, either in a growth chamber, a greenhouse, or in a field. Transgenic plants can be bred as desired for a particular purpose, e.g., to introduce a recombinant nucleic acid into other lines, to transfer a recombinant nucleic acid to other species, or for further selection of other desirable traits. Alternatively, transgenic plants can be propagated vegetatively for those species amenable to such techniques. As used herein, a transgenic plant also refers to progeny of an initial transgenic plant provided the progeny inherits the transgene. Seeds produced by a transgenic plant can be grown and then selfed (or outcrossed and selfed) to obtain seeds homozygous for the nucleic acid construct.

Transgenic plants can be grown in suspension culture, or tissue or organ culture. For the purposes of this invention, solid and/or liquid tissue culture techniques can be used. When using solid medium, transgenic plant cells can be placed directly onto the medium or can be placed onto a filter that is then placed in contact with the medium. When using liquid medium, transgenic plant cells can be placed onto a flotation device, e.g., a porous membrane that contacts the liquid medium. A solid medium can be, for example, Murashige and Skoog (MS) medium containing agar and a suitable concentration of an auxin, e.g., 2,4-dichlorophenoxyacetic acid (2,4-D), and a suitable concentration of a cytokinin, e.g., kinetin.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days, or about 1-3 days. The use of transient assays is particularly convenient for rapid analysis in different species, or to confirm expression of a heterologous low nitrogen tolerance-modulating polypeptide whose expression has not previously been confirmed in particular recipient cells.

Techniques for introducing nucleic acids into monocotyledonous and dicotyledonous plants are known in the art, and include, without limitation, Agrobacterium-mediated transformation, viral vector-mediated transformation, electroporation and particle gun transformation, e.g., U.S. Pat. Nos. 5,538,880; 5,204,253; 6,329,571 and 6,013,863. If a cell or cultured tissue is used as the recipient tissue for transformation, plants can be regenerated from transformed cultures if desired, by techniques known to those skilled in the art.

B. Screening/Selection

A population of transgenic plants can be screened and/or selected for those members of the population that have a trait or phenotype conferred by expression of the transgene. For example, a population of progeny of a single transformation event can be screened for those plants having a desired level of expression of a low nitrogen tolerance-modulating polypeptide or nucleic acid. Physical and biochemical methods can be used to identify expression levels. These include Southern analysis or PCR amplification for detection of a polynucleotide; Northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known. As an alternative, a population of plants comprising independent transformation events can be screened for those plants having a desired trait, such as a modulated level of low-nitrogen tolerance. Selection and/or screening can be carried out over one or more generations, and/or in more than one geographic location. In some cases, transgenic plants can be grown and selected under conditions which induce a desired phenotype or are otherwise necessary to produce a desired phenotype in a transgenic plant. In addition, selection and/or screening can be applied during a particular developmental stage in which the phenotype is expected to be exhibited by the plant. Selection and/or screening can be carried out to choose those transgenic plants having a statistically significant difference in low nitrogen tolerance level relative to a control plant that lacks the transgene. Selected or screened transgenic plants have an altered phenotype as compared to a corresponding control plant, as described in the "Transgenic Plant Phenotypes" section herein.

C. Plant Species

The polynucleotides and vectors described herein can be used to transform a number of monocotyledonous and dicotyledonous plants and plant cell systems, including species from one of the following families: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

Suitable species may include members of the genus *Abelmoschus*, *Abies*, *Acer*, *Agrostis*, *Allium*, *Alstroemeria*, *Ananas*, *Andrographis*, *Andropogon*, *Artemisia*, *Arundo*, *Atropa*, *Berberis*, *Beta*, *Bixa*, *Brassica*, *Calendula*, *Camellia*, *Camptotheca*, *Cannabis*, *Capsicum*, *Carthamus*, *Catharanthus*, *Cephalotaxus*, *Chrysanthemum*, *Cinchona*, *Citrullus*, *Coffea*, *Colchicum*, *Coleus*, *Cucumis*, *Cucurbita*, *Cynodon*, *Datura*, *Dianthus*, *Digitalis*, *Dioscorea*, *Elaeis*, *Ephedra*, *Erianthus*, *Erythroxylum*, *Eucalyptus*, *Festuca*, *Fragaria*, *Galanthus*, *Glycine*, *Gossypium*, *Helianthus*, *Hevea*, *Hordeum*, *Hyoscyamus*, *Jatropha*, *Lactuca*, *Linum*, *Lolium*, *Lupinus*, *Lycopersicon*, *Lycopodium*, *Manihot*, *Medicago*, *Mentha*, *Miscanthus*, *Musa*, *Nicotiana*, *Oryza*, *Panicum*, *Papaver*, *Parthenium*, *Pennisetum*, *Petunia*, *Phalaris*, *Phleum*, *Pinus*, *Poa*, *Poinsettia*, *Populus*, *Rauwolfia*, *Ricinus*, *Rosa*, *Saccharum*, *Salix*, *Sanguinaria*, *Scopolia*, *Secale*, *Solanum*, *Sorghum*, *Spartina*, *Spinacea*, *Tanacetum*, *Taxus*, *Theobroma*, *Triticosecale*, *Triticum*, *Uniola*, *Veratrum*, *Vinca*, *Vitis*, and *Zea*.

Suitable species include *Panicum* spp. or hybrid thereof, *Sorghum* spp. or hybrid thereof, sudangrass, *Miscanthus* spp. or hybrid thereof, *Saccharum* spp. or hybrid thereof, *Erianthus* spp., *Populus* spp., *Andropogon gerardii* (big bluestem), *Pennisetum purpureum* (elephant grass)) or hybrid thereof (e.g., *Pennisetum purpureum*×*Pennisetum typhoidum*), *Phalaris arundinacea* (reed canarygrass), *Cynodon dactylon* (bermudagrass), *Festuca arundinacea* (tall fescue), *Spartina pectinata* (prairie cord-grass), *Medicago sativa* (alfalfa), *Arundo donax* (giant reed) or hybrid thereof, *Secale cereale* (rye), *Salix* spp. (willow), *Eucalyptus* spp. (eucalyptus), *Triticosecale* (*triticum*-wheat X rye), *Tripsicum dactyloides* (Eastern gammagrass), *Leymus cinereus* (basin wildrye), *Leymus condensatus* (giant wildrye) and bamboo.

In some embodiments, a suitable species can be a wild, weedy, or cultivated sorghum species such as, but not limited to, *Sorghum almum*, *Sorghum amplum*, *Sorghum angustum*, *Sorghum arundinaceum*, *Sorghum bicolor* (such as bicolor, guinea, caudatum, kafir, and durra), *Sorghum brachypodum*, *Sorghum bulbosum*, *Sorghum burmahicum*, *Sorghum controversum*, *Sorghum drummondii*, *Sorghum ecarinatum*, *Sorghum exstans*, *Sorghum grande*, *Sorghum halepense*, *Sorghum interjectum*, *Sorghum intrans*, *Sorghum laxiflorum*, *Sorghum leiocladum*, *Sorghum macrospermum*, *Sorghum matarankense*, *Sorghum miliaceum*, *Sorghum nigrum*, *Sorghum nitidum*, *Sorghum plumosum*, *Sorghum propinquum*, *Sorghum purpureosericeum*, *Sorghum stipoideum*, *Sorghum sudanensese*, *Sorghum timorense*, *Sorghum trichocladum*, *Sorghum versicolor*, *Sorghum virgatum*, *Sorghum vulgare*, or hybrids such as *Sorghum*×*almum*, *Sorghum*×*sudangrass* or *Sorghum*×*drummondii*.

Suitable species also include *Helianthus annuus* (sunflower), *Carthamus tinctorius* (safflower), *Jatropha curcas* (jatropha), *Ricinus communis* (castor), *Elaeis guineensis* (palm), *Linum usitatissimum* (flax), and *Brassica juncea*.

Suitable species also include *Beta vulgaris* (sugarbeet), and *Manihot esculenta* (cassava).

Suitable species also include *Lycopersicon esculentum* (tomato), *Lactuca sativa* (lettuce), *Musa paradisiaca* (banana), *Solanum tuberosum* (potato), *Brassica oleracea* (broccoli, cauliflower, Brussels sprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), and *Solanum melongena* (eggplant).

Suitable species also include *Papaver somniferum* (opium poppy), *Papaver orientale*, *Taxus baccata*, *Taxus brevifolia*, *Artemisia annua*, *Cannabis sativa*, *Camptotheca acuminate*, *Catharanthus roseus*, *Vinca rosea*, *Cinchona officinalis*, *Colchicum autumnale*, *Veratrum californica*, *Digitalis lanata*, *Digitalis purpurea*, *Dioscorea* spp., *Andrographis paniculata*, *Atropa belladonna*, *Datura stomonium*, *Berberis* spp., *Cephalotaxus* spp., *Ephedra sinica*, *Ephedra* spp., *Erythroxylum coca*, *Galanthus wornorii*, *Scopolia* spp., *Lycopodium serratum* (=*Huperzia serrata*), *Lycopodium* spp., *Rauwolfia serpentina*, *Rauwolfia* spp., *Sanguinaria canadensis*, *Hyoscyamus* spp., *Calendula officinalis*, *Chrysanthemum parthenium*, *Coleus forskohlii*, and *Tanacetum parthenium*.

Suitable species also include *Parthenium argentatum* (guayule), *Hevea* spp. (rubber), *Mentha spicata* (mint), *Mentha piperita* (mint), *Bixa orellana*, and Alstroemeria spp.

Suitable species also include *Rosa* spp. (rose), *Dianthus caryophyllus* (carnation), *Petunia* spp. (*petunia*) and *Poinsettia pulcherrima* (poinsettia).

Suitable species also include *Nicotiana tabacum* (tobacco), *Lupinus albus* (lupin), *Uniola paniculata* (oats), bentgrass (*Agrostis* spp.), *Populus tremuloides* (aspen), *Pinus* spp. (pine), *Abies* spp. (fir), *Acer* spp. (maple), *Hordeum vulgare* (barley), *Poa pratensis* (bluegrass), *Lolium* spp. (ryegrass) and *Phleum pratense* (timothy).

Thus, the methods and compositions can be used over a broad range of plant species, including species from the dicot genera *Brassica*, *Carthamus*, *Glycine*, *Gossypium*, *Helianthus*, *Jatropha*, *Parthenium*, *Populus*, and *Ricinus*; and the monocot genera *Elaeis*, *Festuca*, *Hordeum*, *Lolium*, *Oryza*, *Panicum*, *Pennisetum*, *Phleum*, *Poa*, *Saccharum*, *Secale*, *Sorghum*, *Triticosecale*, *Triticum*, and *Zea*. In some embodiments, a plant is a member of the species *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

In certain embodiments, the polynucleotides and vectors described herein can be used to transform a number of monocotyledonous and dicotyledenous plants and plant cell systems, wherein such plants are hybrids of different species or varieties of a specific species (e.g., *Saccharum* sp. X *Miscanthus* sp., *Panicum virgatum*×*Panicum amarum*, *Panicum virgatum*×*Panicum amarulum*, and *Pennisetum purpureum*×*Pennisetum typhoidum*).

D. Transgenic Plant Phenotypes

In some embodiments, a plant in which expression of a low nitrogen tolerance-modulating polypeptide is modulated can have increased levels of photosynthetic efficiency in seedlings. For example, a low nitrogen tolerance-modulating polypeptide described herein can be expressed in a transgenic plant, resulting in increased levels of photosynthetic efficiency in growth conditions with low nitrogen sources. The level of photosynthetic efficiency can be increased by at least 0.25 percent, e.g., 0.25, 1, 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the level of photosynthetic efficiency in a corresponding control plant that does not express the transgene. In some embodiments, a plant in which expression of a low nitrogen tolerance-modulating polypeptide is modulated can have decreased levels of photosynthetic efficiency. The level of photosynthetic efficiency can be decreased by at least 0.25 percent, e.g., 0.25, 1, 2, 3, 4, 5, 10, 15, 20, 25, 30, 35, or more than 35 percent, as compared to the level of photosynthetic in a corresponding control plant that does not express the transgene.

In some embodiments, a plant in which expression of a low nitrogen tolerance-modulating polypeptide is modulated can have increased or decreased levels of photosynthetic efficiency in one or more green tissues, e.g., leaves, stems, bulbs, flowers, fruits, young seeds. For example, the level of photosynthetic efficiency can be increased by at least 0.25 percent, e.g., 0.25, 1, 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the level of photosynthetic efficiency in a corresponding control plant that does not express the transgene. In some embodiments, a plant in which expression of a low nitrogen tolerance-modulating polypeptide is modulated can have decreased levels of photosynthetic efficiency in one or more green tissues. The level of photosynthetic efficiency can be decreased by at least 0.25 percent, e.g., 0.25, 1, 2, 3, 4, 5, 10, 15, 20, 25, 30, 35, or more than 35 percent, as compared to the level of photosynthetic efficiency in a corresponding control plant that does not express the transgene.

Increases in photosynthetic efficiency in low-nitrogen growth conditions in such plants can provide improved plant growth in geographic locales where plant's intake of nitrogenous fertilizers is often insufficient. Decreases in photosynthetic efficiency, and hence less tolerance to low-nitrogen growth conditions in such plants can be useful for removing weeds and such from the environment, by applying to weeds and such. For example, a plant capable of inducing the decrease in photosynthetic efficiency can be prepared to apply for land improvements and such.

Typically, a difference in the level of photosynthetic efficiency in a transgenic plant or cell relative to a control plant or cell is considered statistically significant at $p \leq 0.05$ with an appropriate parametric or non-parametric statistic, e.g., Chi-square test, Student's t-test, Mann-Whitney test, or F-test. In some embodiments, a difference in the level of photosynthetic is statistically significant at $p < 0.01$, $p < 0.005$, or $p < 0.001$. A statistically significant difference in, for example, the level of photosynthetic efficiency in a transgenic plant compared to the amount in cells of a control plant indicates that the recombinant nucleic acid present in the transgenic plant results in altered levels of photosynthetic efficiency.

In some embodiments, a plant in which expression of a low nitrogen tolerance-modulating polypeptide is modulated can have increased growth rates in seedlings. For example, a low nitrogen tolerance-modulating polypeptide described herein can be expressed in a transgenic plant, resulting in increased growth rate in growth conditions of limiting nitrogen sources. The growth rate can be increased by at least 2 percent, e.g., 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the growth rate in a corresponding control plant that does not express the transgene. In some embodiments, a plant in which expression of a low nitrogen tolerance-modulating polypeptide is modulated can have decreased growth rates. The growth rate can be decreased by at least 2 percent, e.g., 2, 3, 4, 5, 10, 15, 20, 25, 30, 35, or more than 35 percent, as compared to the growth rate in a corresponding control plant that does not express the transgene. Growth rate can be measured in seedlings, developing, or mature plants and measured for periods of time such as about 1 hour, 3 hours, 6 hours, 12 hours, 1 day, 3 days, 5 days, 10 days, 1 month, 3 months, 6 months, 12 months, or the entire lifespan of a plant.

In some embodiments, a plant in which expression of a low nitrogen tolerance-modulating polypeptide is modulated can have increased or decreased growth rates in one or more vegetative and reproductive tissues, e.g., leaves, stems, flowers, bulbs, fruits, young seeds. For example, the growth rate can be increased by at least 2 percent, e.g., 2, 3, 4, 5, 6; 7, 8, 9, 10, 11, 12, 13, 14, 15, 16, 17, 18, 19, 20, 25, 30, 35, 40, 45, 50, 55, 60, or more than 60 percent, as compared to the growth rate in a corresponding control plant that does not express the transgene. In some embodiments, a plant in which expression of a low nitrogen tolerance-modulating polypeptide is modulated can have decreased levels of growth rate in one or more vegetative tissues. The growth rate can be decreased by at least 2 percent, e.g., 2, 3, 4, 5, 10, 15, 20, 25, 30, 35, or more than 35 percent, as compared to the growth rate in a corresponding control plant that does not express the transgene.

Increases in growth rate in low-nitrogen conditions in such plants can provide improved plant growth and initial establishment in geographic locales where plant's intake of nitrogenous fertilizers is often insufficient. Decreases in growth rate, and hence less tolerance to low-nitrogen growth conditions in such plants can be useful for engineering slow-growing plants, by applying to ornamentals and such. For example, a plant capable of inducing the decrease in growth rate can be prepared to apply for land improvements and such.

Typically, a difference in the growth rate of a transgenic plant or cell relative to a control plant or cell is considered statistically significant at $p \leq 0.05$ with an appropriate parametric or non-parametric statistic, e.g., Chi-square test, Student's t-test, Mann-Whitney test, or F-test. In some embodiments, a difference in the growth rate is statistically significant at $p < 0.01$, $p < 0.005$, or $p < 0.001$. A statistically significant difference in, for example, the growth rate of a transgenic plant compared to the growth rate of a control plant indicates that the recombinant nucleic acid present in the transgenic plant results in altered growth rates.

The phenotype of a transgenic plant is evaluated relative to a control plant. A plant is said "not to express" a polypeptide when the plant exhibits less than 10%, e.g., less than 9%, 8%, 7%, 6%, 5%, 4%, 3%, 2%, 1%, 0.5%, 0.1%, 0.01%, or 0.001%, of the amount of polypeptide or mRNA encoding the polypeptide exhibited by the plant of interest. Expression can be evaluated using methods including, for example, RT-PCR, Northern blots, S1 RNase protection, primer extensions, Western blots, protein gel electrophoresis, immunoprecipitation, enzyme-linked immunoassays, chip assays, and mass spectrometry. It should be noted that if a polypeptide is expressed under the control of a tissue-preferential or broadly expressing promoter, expression can be evaluated in the entire plant or in a selected tissue. Similarly, if a polypeptide is expressed at a particular time, e.g., at a particular time in development or upon induction, expression can be evaluated selectively at a desired, time period.

V. PLANT BREEDING

Genetic polymorphisms are discrete allelic sequence differences in a population. Typically, an allele that is present at 1% or greater is considered to be a genetic polymorphism. The discovery that polypeptides disclosed herein can modulate photosynthetic efficiency and/or nitrogen content is useful in plant breeding, because genetic polymorphisms exhibiting a degree of linkage with loci for such polypeptides are more likely to be correlated with variation in a low-nitrogen tolerance trait. For example, genetic polymorphisms linked to the loci for such polypeptides are more likely to be useful in marker-assisted breeding programs to create lines having a desired modulation in the low-nitrogen tolerance trait.

Thus, one aspect of the invention includes methods of identifying whether one or more genetic polymorphisms are associated with variation in a low-nitrogen tolerance trait. Such methods involve determining whether genetic polymorphisms in a given population exhibit linkage with the locus for one of the polypeptides depicted in FIGS. 1-57, SEQ ID NO:556, SEQ ID NO:853, SEQ ID NO:1157 and/or a functional homolog thereof, such as, but not limited to those identified in the Sequence Listing of this application. The correlation is measured between variation in the low-nitrogen tolerance trait in plants of the population and the presence of the genetic polymorphism(s) in plants of the population, thereby identifying whether or not the genetic polymorphism(s) are associated with variation for the trait. If the presence of a particular allele is statistically significantly correlated with a desired modulation in the low-nitrogen tolerance trait, the allele is associated with variation for the trait and is useful as a marker for the trait. If, on the other hand, the presence of a particular allele is not significantly correlated with the desired modulation, the allele is not associated with variation for the trait and is not useful as a marker.

Such methods are applicable to populations containing the naturally occurring endogenous polypeptide rather than an exogenous nucleic acid encoding the polypeptide, i.e., populations that are not transgenic for the exogenous nucleic acid. It will be appreciated, however, that populations suitable for use in the methods may contain a transgene for another, different trait, e.g., herbicide resistance.

Genetic polymorphisms that are useful in such methods include simple sequence repeats (SSRs, or microsatellites), rapid amplification of polymorphic DNA (RAPDs), single nucleotide polymorphisms (SNPs), amplified fragment length polymorphisms (AFLPs) and restriction fragment length polymorphisms (RFLPs). SSR polymorphisms can be identified, for example, by making sequence specific probes and amplifying template DNA from individuals in the population of interest by PCR. If the probes flank an SSR in the population, PCR products of different sizes will be produced. See, e.g., U.S. Pat. No. 5,766,847. Alternatively, SSR polymorphisms can be identified by using PCR product(s) as a probe against Southern blots from different individuals in the population. See, U. H. Refseth et al. (1997) *Electrophoresis* 18: 1519. The identification of RFLPs is discussed, for example, in Alonso-Blanco et al. (Methods in Molecular Biology, vol. 82, "*Arabidopsis* Protocols", pp. 137-146, J. M. Martinez-Zapater and J. Salinas, eds., c. 1998 by Humana Press, Totowa, N.J.); Burr ("Mapping Genes with Recombinant Inbreds", pp. 249-254, in Freeling, M. and V. Walbot (Ed.), *The Maize Handbook*, c. 1994 by Springer-Verlag New York, Inc.: New York, N.Y., USA; Berlin Germany; Burr et al. (1998) *Genetics* 118: 519; and Gardiner, J. et al. (1993) *Genetics* 134: 917). The identification of AFLPs is discussed, for example, in EP 0 534 858 and U.S. Pat. No. 5,878,215.

In some embodiments, the methods are directed to breeding a plant line. Such methods use genetic polymorphisms identified as described above in a marker assisted breeding program to facilitate the development of lines that have a desired alteration in the low-nitrogen tolerance trait. Once a suitable genetic polymorphism is identified as being associated with variation for the trait, one or more individual plants are identified that possess the polymorphic allele correlated with the desired variation. Those plants are then used in a breeding program to combine the polymorphic allele with a plurality of other alleles at other loci that are correlated with the desired variation. Techniques suitable for use in a plant breeding program are known in the art and include, without limitation, backcrossing, mass selection, pedigree breeding, bulk selection, crossing to another population and recurrent selection. These techniques can be used alone or in combination with one or more other techniques in a breeding program. Thus, each identified plants is selfed or crossed a different plant to produce seed which is then germinated to form progeny plants. At least one such progeny plant is then selfed or crossed with a different plant to form a subsequent progeny generation. The breeding program can repeat the steps of selfing or outcrossing for an additional 0 to 5 generations as appropriate in order to achieve the desired uniformity and stability in the resulting plant line, which retains the polymorphic allele. In most breeding programs, analysis for the particular polymorphic allele will be carried out in each generation, although analysis can be carried out in alternate generations if desired.

In some cases, selection for other useful traits is also carried out, e.g., selection for fungal resistance or bacterial resistance. Selection for such other traits can be carried out before, during or after identification of individual plants that possess the desired polymorphic allele.

VI. ARTICLES OF MANUFACTURE

Transgenic plants provided herein have various uses in the agricultural and energy production industries. For example, transgenic plants described herein can be used to make animal feed and food products. Such plants, however, are often particularly useful as a feedstock for energy production. Transgenic plants described herein often produce higher yields of grain and/or biomass per hectare, relative to control plants that lack the exogenous nucleic acid. In some embodiments, such transgenic plants provide equivalent or even increased yields of grain and/or biomass per hectare relative to control plants when grown under conditions of reduced inputs such as fertilizer and/or water. Thus, such transgenic plants can be used to provide yield stability at a lower input cost and/or under environmentally stressful conditions such as drought or limiting nitrogen sources. In some embodiments, plants described herein have a composition that permits more efficient processing into free sugars, and subsequently ethanol, for energy production. In some embodiments, such plants provide higher yields of ethanol, butanol, dimethyl ether, other biofuel molecules, and/or sugar-derived co-products per kilogram of plant material, relative to control plants. Such processing efficiencies are believed to be derived from the nitrogenous composition of the plant material. By providing higher yields at an equivalent or even decreased cost of production, the transgenic plants described herein improve profitability for farmers and processors as well as decrease costs to consumers.

Seeds from transgenic plants described herein can be conditioned and bagged in packaging material by means known in the art to form an article of manufacture. Packaging material such as paper and cloth are well known in the art. A package of seed can have a label, e.g., a tag or label secured to the packaging material, a label printed on the packaging material, or a label inserted within the package, that describes the nature of the seeds therein.

The invention will be further described in the following examples, which do not limit the scope of the invention described in the claims.

VII. EXAMPLES

Example 1—Transgenic *Arabidopsis* Plants

The following symbols are used in the Examples with respect to *Arabidopsis* transformation: $T_1$: first generation transformant; $T_2$: second generation, progeny of self-pollinated $T_1$ plants; $T_3$: third generation, progeny of self-pollinated $T_2$ plants; $T_4$: fourth generation, progeny of self-pollinated $T_3$ plants. Independent transformations are referred to as events.

The following is a list of nucleic acids that were isolated from *Arabidopsis thaliana* plants, CeresClone:29661 (SEQ ID NO:1), CeresClone:251343 (SEQ ID NO:48), CeresClone:19586 (SEQ ID NO:76), CeresClone:25136 (SEQ ID NO:96), CeresClone:1820 (SEQ ID NO:99), CeresClone:13102 (SEQ ID NO:151), CeresClone:15457 (SEQ ID NO:165), Ceres Annot:859276 (SEQ ID NO:175), CeresClone:17883 (SEQ ID NO:185), CeresClone:251590 (SEQ ID NO:207), CeresClone:4898 (SEQ ID NO:217), CeresClone:148977 (SEQ ID NO:233), CeresClone:24255 (SEQ ID NO:245), CeresClone:38432 (SEQ ID NO:299), Ceres Annot:553243 (SEQ ID NO:331), CeresClone:1011900 (SEQ ID NO:367), CeresClone:5232 (SEQ ID NO:509), CeresClone:29302 (SEQ ID NO:532), CeresClone:93971 (SEQ ID NO:555), Ceres Annot:12669619_cDNA (SEQ ID NO:557), CeresClone:21608 (SEQ ID NO:592), CeresClone:2031 (SEQ ID NO:612), CeresClone:94503 (SEQ ID NO:645), CeresClone:21740 (SEQ ID NO:686), CeresClone:5609 (SEQ ID NO:729), CeresClone:3137 (SEQ ID NO:745), CeresClone:32430 (SEQ ID NO:768), CeresClone:101255 (SEQ ID NO:791), Ceres Annot:573161 (SEQ ID NO:854), Ceres Annot:552727 (SEQ ID NO:890), CeresClone:732 (SEQ ID NO:1193), CeresClone:2267 (SEQ ID NO:1209), CeresClone:39358 (SEQ ID NO:1273), CeresClone:115046 (SEQ ID NO:1301), Ceres Annot:850581 (SEQ ID NO:1427), Ceres Annot:862321 (SEQ ID NO:1462), Ceres Annot:839064 (SEQ ID NO:1478), Ceres Annot:864666 (SEQ ID NO:1490), Ceres Annot:875012 (SEQ ID NO:1509), Ceres Annot:874016 (SEQ ID NO:1524), Ceres Annot:827304 (SEQ ID NO:1536), Ceres Annot:869192 (SEQ ID NO:1553), and Ceres Annot:876419 (SEQ ID NO:1576). The nucleic acid designated Ceres Clone:968180 (SEQ ID NO:1115) was isolated from the species *Brassica napus*. The nucleic acid designated Ceres Clone:1017441 (SEQ ID NO:224) was isolated from the species *Triticum aesticum*. The following is a list of nucleic acids that were isolated from *Zea mays* plants, CeresClone:1387146 (SEQ ID NO:981), CeresClone:1408950 (SEQ ID NO:1098, CeresClone:208453 (SEQ ID NO:1111), CeresClone:208995 (SEQ ID NO:943), CeresClone:225681 (SEQ ID NO:975), CeresClone:239806 (SEQ ID NO:916), CeresClone:244306 (SEQ ID NO:1053), CeresClone:276809 (SEQ ID NO:823), CeresClone:324216 (SEQ ID NO:852), CeresClone:339439 (SEQ ID NO:1341), CeresClone:424522 (SEQ ID NO:827), CeresClone:896483 (SEQ ID NO:1384), CeresClone:986438 (SEQ ID NO:1156), CeresClone:988083 (SEQ ID NO:1184), CeresClone:995409 (SEQ ID NO:1408), CeresClone:996227 (SEQ ID NO:1158), and CeresClone:996263 (SEQ ID NO:1165).

With the exception of Ceres Clone:29661 (SEQ ID NO:1), each isolated nucleic acid described above was cloned into a Ti plasmid vector, CRS338, containing a phosphinothricin acetyltransferase gene which confers FINALE™ resistance to transformed plants. Constructs were made using CRS338 that contained SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, or SEQ ID NO:1576, each operably linked to a 355 promoter. Ceres Clone:29661 (SEQ ID NO:1) was cloned into a Ti plasmid vector, CRS 311, containing a phosphinothricin acetyltransferase gene, which confers FINALE™ resistance to transformed plants. SEQ ID NO:1 was operably linked to a p32449 promoter in the constructs made using the CRS 331 vector. Wild-type *Arabidopsis thaliana* ecotype Wassilewskija (Ws) plants were transformed separately with each construct. The transformations were performed essentially as described in Bechtold et al. (1993) *C.R. Acad. Sci. Paris,* 316:1194-1199.

Transgenic *Arabidopsis* lines containing SEQ ID NO:1, SEQ ID NO:48, SEQ ID NO:76, SEQ ID NO:96, SEQ ID NO:99, SEQ ID NO:151, SEQ ID NO:165, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:224, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1478, SEQ ID NO:1490, SEQ ID NO:1509, SEQ ID NO:1524, SEQ ID NO:1536, SEQ ID NO:1553, SEQ ID NO:1576, or SEQ ID NO:175 were designated ME00919, ME01312, ME01463, ME01821, ME01910, ME02538, ME02603, ME02613, ME02801, ME03123, ME04204, ME04477, ME04507, ME04587, ME04753, ME04772, ME04909, ME05033, ME05194, ME05267, ME05300, ME05341, ME05392, ME05429, ME05493, ME05885, ME07344, ME07859, ME08464, ME09939, ME11735, ME12910, ME12927, ME12929, ME12954, ME12970, ME13006, ME13021, ME13064, ME13071, ME13087, ME13106, ME13107, ME13108, ME13110, ME13125, ME13149, ME13151, ME13153, ME13177, ME13200, ME13204, ME14649, ME16546, ME17457, ME17567, ME17932, ME17936, ME18275, ME18924, ME19182, or ME20628, respectively. The presence of each vector containing a nucleic acid described above in the respective transgenic *Arabidopsis* line transformed with the vector was confirmed by FINALE™ resistance, PCR amplification from green leaf tissue extract, and/or sequencing of PCR products. As controls, wild-type *Arabidopsis* ecotype Ws plants were transformed with the empty vector, either CRS338 or CRS311.

Example 2—Screening for Transgenic Plants Tolerant to Low-Nitrogen Growth Conditions A low-nitrogen tolerance screen was carried out on seedlings in order to identify transgenic lines that showed increased photosynthesis efficiency or seedling size or greenness under limiting nitrogen conditions relative to the internal control plants. The media used for the low-nitrogen tolerance assay contained 0.5% sucrose, 0.5× MS without nitrogen media (PhytoTech), 0.05% MES Hydrate, and 0.8% Phytagar. In addition, for low ammonium nitrate assay, 240 µM NH4NO3 was used as nitrogen source. For low nitrate assay, nitrogen source was 300 µM KNO3. pH of the media was adjusted to pH 5.7 using 10N KOH. Sterilized seeds were plated on agar plates and stratified for 2 days in the dark at 4° C. to promote uniform germination. Agar plates with germinating seedlings were placed horizontally in a CONVIRON® growth chamber set at 22° C., 16:8 hour light:dark cycle, 70% humidity with a combination of incandescent and fluorescent lamps emitting a light intensity of ~100 µEinsteins. The control plates were placed randomly within the set. Screen the seedlings daily starting at 14 days. In this screen, seedlings that were larger or greener relative to the internal controls on low nitrogen growth media were selected. As they were found each day, candidate seedlings were aseptically transplanted to standard MS germination plates for recovery. This intermediate recovery step was necessary before transplanting to soil to minimize the overall candidate mortality rate. The scoring and transplanting of candidates were continued until all remaining plants were small and yellowed from nitrogen stress. On the very last day of scoring, each plate was scanned for photosynthetic efficiency (Fv/Fm) on the chlorophyll fluorescence (CF) imager and scored as candidates and transplanted any extreme outliers on the high end of Fv/Fm scores. Fv/Fm ratio typically provides an estimate of the photosystem II (PSII) maximum efficiency within dark-adapted material where Fv is variable fluorescence, i.e. difference between minimum (Fo) and maximum (Fm) fluorescence signal, from dark-adapted material. This could be done visually by looking at the false color image for each seedling using the CF image analysis software (plants with high end Fv/Fm scores appear red). This step was typically done at ~24 days after germination. Seven days after being transferred to MS recovery plates, candidates were transplanted to soil (standard Sunshine:vermiculite 3:2 mix; Osmocote; Marathon). Five days after being transplanted to soil, candidates were sprayed with FINALE® [5 mL FINALE®/48 oz. water] to eliminate non-transgenics from the population. Two days after spraying with FINALE®, cauline leaf tissue of each candidate was collected for genomic DNA extraction, PCR, and sequencing to determine the identity of the transgene for each candidate.

Example 3—Validation Plate Assay

This assay was designed to validate transgenic lines that showed increased photosynthesis or size under limiting nitrogen conditions relative to the internal control. The media used for the low-nitrogen tolerance assay contained 0.5% sucrose, 0.5× MS without nitrogen media (PhytoTech), 0.05% MES Hydrate, and 0.8% Phytagar. pH of the media was adjusted to pH 5.7 using 10N KOH. In addition, for low ammonium nitrate assay, 240 µM NH$_4$NO$_3$ was used as nitrogen source. For low nitrate assay, nitrogen source was 300 µM KNO$_3$. Sterilized seeds were plated on agar plates and stratified for 2 days in the dark at 4° C. to promote uniform germination. Agar plates with germinating seedlings were placed horizontally in a CONVIRON® growth chamber set at 22° C., 16:8 hour light:dark cycle, 70% humidity with a combination of incandescent and fluorescent lamps emitting a light intensity of ~100 µEinsteins. The control plates were placed randomly within the set. Plates were scanned every other day using the CF Imager (after 45 minute of dark-acclimation) and were completed after all wild-type plants have completely yellowed. After the plates were scanned on the last day, they were sprayed with FINALE® (10 mL FINALE® into 48 oz. full-strength MS liquid media). Two days after spraying, each plate was dark-acclimated for 45 minutes and scanned for Fv/Fm on the CF imager and scored for each of the plants at each time point. For each separate time point, the data for all the T$_2$ transgenic plants across an event was pooled and a one-tailed t-test was used to compare both the Fv/Fm ratios and rosette areas relative to the pooled non-transgenics across the same plate. Whenever possible, this process was repeated for the T$_3$ generation plants. A low nitrogen tolerant candidate was confirmed when the transgenic Fv/Fm ratio and/or rosette area was greater than the wild-type segregants with a p-value≤0.05 in 2 or more events in both generations Example 4—Validation Soil Assay A Low, Medium, and High Nitrogen experiment on soil was carried out to assess phenotypic characteristics at a mature point in the life cycle of *Arabidopsis*, as compared to seedling screens. The lines to be tested were originally identified through superpool screens for low nitrate and low ammonium nitrate tolerance. These lines were later individually assayed as seedlings on low nitrate and low ammonium nitrate agar. For this assay, MetroMix200 soil was mixed with vermiculite and Marathon™ (MetroMix200: vermiculite 3:2 mix; Osmocote; Marathon) autoclaved and cooled before use. Experimental plants and controls were randomized across the flats. Prior to sowing seed, each flat was watered with 3L filtered water. Flats with 24 wells were filled with the following 3:2 ratios of MetroMix200 to Thermorock vermiculite. At the beginning of the experiment no nitrogen was provided until 2 weeks after germination when ¼ Hoaglands supplemented with KNO₃ at 25 ppm, 250 ppm, and 1500 ppm were used to water the flats from beneath.

Seeds were stratified on soil and in the dark at 4° C. for 3 days. After the cold treatment, flats were transferred to the growth chamber. Plants were grown for approximately 5 weeks, or until full grown/mature. Plants were then dark-acclimated for one hour. Chlorophyll fluorescence images were taken using a CF-Imager (Technologica, UK) according to the manufacturer's protocol to measure the performance and efficiency of photosystem II: 1) Fv/Fm, maximum photosystem II efficiency 2) Fq'/Fm', operating efficiency and 3) non-photochemical quenching (NPQ).

One week after watering with ¼ Hoaglands supplemented with various $KNO_3$ concentrations, plant rosette area measurements were taken using the WhinRhizo imaging software (Reagent Instruments, Canada). The plants were then collected in manila envelopes, placed in a 125° C. drying oven for 1-2 days and weighed

Example 5—Analysis of ME00919 Events

ME00919 contains Ceres Clone:29661 (At3g61880, SEQ ID NO:1) from *Arabidopsis thaliana*, which encodes a 534 amino acid cytochrome P450 protein. Evaluation of low-nitrogen tolerance for ME00919 in $T_2$ and $T_3$ was conducted under the same conditions as described in Example 2. In this study, the seedling photosynthetic efficiency was measured as Fv/Fm comparing transgenic plants within an event to non-transgenic segregants pooled across the same plate. Two events, -01 and -03, showed significantly increased photosynthetic efficiency relative to the internal controls in both generations at p≤0.05 using a one-tailed t-test assuming unequal variance. A summary of photosynthetic efficiency of ME00919 seedlings on low ammonium nitrate-containing media are shown in Table 1. Events-01 and -03 segregated 15:1 and 3:1 (R:S), respectively, for FINALE™ resistance in the $T_2$ generation. ME00919 events were also tested for enhanced growth on the low ammonium nitrate media. No significant differences between the transgenics and the controls were observed.

TABLE 1 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME00919 | ME00919-01 ($T_2$) | 0.65641304 | 46 | 0.595818 | 11 | $2.48 \times 10^{-2}$ |
| ME00919 | ME00919-01 ($T_3$) | 0.66348780 | 41 | 0.595818 | 11 | $1.55 \times 10^{-2}$ |
| ME00919 | ME00919-03 ($T_2$) | 0.67212195 | 41 | 0.634026 | 38 | $3.35 \times 10^{-3}$ |
| ME00919 | ME00919-03 ($T_3$) | 0.69278947 | 19 | 0.634026 | 38 | $2.39 \times 10^{-5}$ |

Events-01 and -03 of ME00919 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 6—Analysis of ME01312 Events

ME01312 contains Ceres Clone:251343 (At3g21270, SEQ ID NO:48) from *Arabidopsis thaliana*, which encodes a 204 amino acid Dof zinc finger protein. Ceres Clone: 251343 shares approximately 40% amino acid identity to the corn Dof1 gene, which when overexpressed in *Arabidopsis*, has shown to confer tolerance to plants receiving low nitrogen stress (Yanagisawa et al., 2004). Evaluation of low-nitrogen tolerance for ME01312 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -03 and -11, showed significantly enhanced photosynthetic efficiency on either low nitrate or low ammonium nitrate-containing media after 16 and 17 days compared to the internal controls in both generations at p≤0.05 using a one-tailed t-test assuming unequal variance. Event-03 had a slightly greater p-value than 0.05 in the $T_3$ generation for the low nitrate screen, significant at p≤0.10. A summary of photosynthetic efficiency of ME01312 seedlings on either low nitrate or low ammonium nitrate-containing media is shown in Table 2. Events-03 and -11 segregated 3:1 (R:S), respectively, for FINALE™ resistance in the $T_2$ generation.

TABLE 2A

T-test comparison of photosynthetic efficiency between transgenic seedlings and pooled non-transgenic segregants after 16 days of growth on low nitrate.

| | | Transgenic | | Pooled Non-Transgenics | | t-test |
|---|---|---|---|---|---|---|
| Line | Events | Fv/Fm | n | Fv/Fm | n | p-value |
| ME01312 | ME01312-03 ($T_2$) | 0.63 | 38 | 0.60 | 58 | 0.03 |
| ME01312 | ME01312-03 ($T_3$) | 0.63 | 38 | 0.60 | 58 | 0.07 |
| ME01312 | ME01312-11 ($T_2$) | 0.64 | 41 | 0.60 | 58 | 0.019 |
| ME01312 | ME01312-11 ($T_3$) | 0.64 | 47 | 0.60 | 58 | $9.89 \times 10^{-3}$ |

TABLE 2B

T-test comparison of photosynthetic efficiency between transgenic seedlings and pooled non-transgenic segregants after 17 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME01312 | ME01312-03 ($T_2$) | 0.64 | 36 | 0.61 | 88 | $2.64 \times 10^{-3}$ |
| ME01312 | ME01312-03 ($T_3$) | 0.66 | 27 | 0.61 | 88 | $1.87 \times 10^{-5}$ |
| ME01312 | ME01312-11 ($T_2$) | 0.65 | 35 | 0.61 | 88 | $7.06 \times 10^{-4}$ |
| ME01312 | ME01312-11 ($T_3$) | 0.64 | 37 | 0.61 | 88 | 0.011 |

Events-03-11 of ME01312 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 7—Analysis of ME01463 Events

ME01463 contains Ceres Clone:19586 (At1g80600, SEQ ID NO:76) from *Arabidopsis thaliana*, which encodes a 457 acetylornithine aminotransferase, a member of the Class-III aminotransferase family. Evaluation of low-nitrogen tolerance for ME01463 in two generations was conducted under the same conditions as described in Examples 2 and 3. In this study, the seedling photosynthetic efficiency was measured as Fv/Fm comparing transgenic plants within an event to non-transgenic segregants pooled across the same plate. Three events, -02, -06, and -10, showed significantly increased photosynthetic efficiency on low ammonium nitrate containing-media relative to the internal controls in both generations at $p \leq 0.05$ using a one-tailed t-test assuming unequal variance. A summary of photosynthetic efficiency of ME01463 seedlings is shown in Table 3. Events-02, -06, and -10 segregated 2:1, 2:1 and 3:1 (R:S), respectively, for FINALE™ resistance in the $T_2$ generation. ME01463 events were also tested for enhanced growth on the low ammonium nitrate media. No significant differences between the transgenics and the controls were observed (data not shown).

TABLE 3

T-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME01463 | ME01463-02 ($T_3$) | 0.6815 | 26 | 0.6376 | 122 | $2.47 \times 10^{-4}$ |
| ME01463 | ME01463-02 ($T_4$) | 0.6701 | 41 | 0.6376 | 122 | $1.57 \times 10^{-3}$ |
| ME01463 | ME01463-06 ($T_3$) | 0.6615 | 31 | 0.6376 | 122 | $2.37 \times 10^{-2}$ |
| ME01463 | ME01463-06 ($T_4$) | 0.6881 | 35 | 0.6376 | 122 | $5.85 \times 10^{-6}$ |
| ME01463 | ME01463-10 ($T_2$) | 0.6699 | 33 | 0.6376 | 122 | $2.25 \times 10^{-3}$ |
| ME01463 | ME01463-10 ($T_3$) | 0.6809 | 18 | 0.6376 | 122 | $4.60 \times 10^{-4}$ |

Events-02, -06, and -10 of ME01463 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 8—Analysis of ME01821 Events

ME01821 contains Ceres Clone:25136 (At1g65500, SEQ ID NO:96) from *Arabidopsis thaliana*, which encodes a 86 amino acid protein of unknown function. Evaluation of low-nitrogen tolerance for ME01821 in $T_2$ generation was conducted under the same conditions as described in Examples 2 and 3. In this study, the seedling photosynthetic efficiency was measured as Fv/Fm comparing transgenic plants within an event to non-transgenic segregants pooled across the same plate. Three events, -01, -04 and -05, showed significantly increased photosynthetic efficiency on low nitrate-containing media relative to the internal controls in $T_2$ generation. Two events, -04 and -05, showed significantly increased photosynthetic efficiency on low ammonium nitrate-containing media relative to the internal controls in $T_2$ generation at $p \leq 0.05$ using a one-tailed t-test assuming unequal variance. A summary of photosynthetic efficiency of ME01821 seedlings is shown in Table 4.

TABLE 4A

T-test comparison of seedling photosynthetic efficiency between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Fv/Fm | n | Fv/Fm | n | p-value |
| ME01821 | ME01821-01 ($T_2$) | 0.6745 | 15 | 0.6520 | 33 | $3.76 \times 10^{-2}$ |
| ME01821 | ME01821-04 ($T_2$) | 0.6826 | 17 | 0.6614 | 14 | $2.76 \times 10^{-2}$ |
| ME01821 | ME01821-05 ($T_2$) | 0.6826 | 20 | 0.6614 | 14 | $3.74 \times 10^{-2}$ |

TABLE 4B

T-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME01821 | ME01821-04($T_2$) | 0.7422 | 13 | 0.7166 | 21 | $5.20 \times 10^{-3}$ |
| ME01821 | ME01821-05($T_2$) | 0.7426 | 19 | 0.7166 | 21 | $6.07 \times 10^{-3}$ |

A summary of the enhanced growth of ME01812 events on either low nitrate- or low ammonium nitrate-containing media is shown in Table 5. For two events-01 and -05, transgenic seedlings were found significantly larger than the pooled non-transgenic segregants after 14 days of growth on low nitrate-containing media (Table 5A). Transgenic seedlings of two events-02 and -05 were found significantly larger than the pooled non-transgenic segregants after 14 days of growth on low ammonium nitrate-containing media (Table 5B). In this study, the seedling area for transgenic plants within an event was compared to the seedling area for non-transgenic segregants pooled across the same line.

TABLE 5A

T-test comparison of seedling area between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Area | n | Area | n | p-value |
| ME01821 | ME01821-01 ($T_2$) | 0.0608 | 15 | 0.0555 | 33 | $3.97 \times 10^{-2}$ |
| ME01821 | ME01821-05 ($T_2$) | 0.0666 | 20 | 0.0530 | 14 | $3.05 \times 10^{-6}$ |

TABLE 5B

T-test comparison of seedling area between transgenic
seedlings and pooled non-transgenic segregants
after 18 days of growth on low ammonium nitrate.

| Line | Events | Transgenic Area | n | Pooled Non-Transgenics Area | n | t-test p-value |
|---|---|---|---|---|---|---|
| ME01821 | ME01821-02 ($T_2$) | 0.0750 | 19 | 0.0567 | 21 | $8.94 \times 10^{-5}$ |
| ME01821 | ME01821-05 ($T_2$) | 0.0680 | 19 | 0.0567 | 21 | $7.89 \times 10^{-3}$ |

Example 9—Analysis of ME01910 Events

ME01910 contains Ceres Clone:1820 (At2g30620, SEQ ID NO:99) from *Arabidopsis thaliana*, which encodes a 273 amino acid linker histone H1 and H5 family protein. Evaluation of low-nitrogen tolerance for ME01910 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -02, showed significantly increased photosynthetic efficiency relative to the internal controls in both generations at p≤0.05 using a one-tailed t-test assuming unequal variance. A summary of photosynthetic efficiency of ME01910 seedlings is shown in Table 6. Events-01 and -02 segregated 3:1 (R:S) for FINALE™ resistance in the $T_2$ generation. ME01910 events were also tested for enhanced growth on the low ammonium nitrate media. No significant differences between the transgenics and the controls were observed.

TABLE 6 t-test comparison of seedling photosynthetic efficiency
between transgenic seedlings and pooled non-transgenic
segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME01910 | ME01910-01 ($T_2$) | 0.60433 | 39 | 0.56396 | 27 | $2.03 \times 10^{-2}$ |
| ME01910 | ME01910-01 ($T_3$) | 0.61274 | 31 | 0.56396 | 27 | $9.23 \times 10^{-3}$ |
| ME01910 | ME01910-02 ($T_2$) | 0.62705 | 37 | 0.58083 | 29 | $7.39 \times 10^{-3}$ |
| ME01910 | ME01910-02 ($T_3$) | 0.64146 | 24 | 0.58083 | 29 | $9.23 \times 10^{-4}$ |

Events-01 and -02 of ME01910 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 10—Analysis of ME02538 Events

ME02538 contains Ceres Clone:13102 (At1g67920, SEQ ID NO:151) from *Arabidopsis thaliana*, which encodes a 67 amino acid protein of unknown function. Evaluation of low-nitrogen tolerance for ME02538 in $T_2$ generation was conducted under the same conditions as described in Example 2. In this study, the seedling photosynthetic efficiency was measured as Fv/Fm comparing transgenic plants within an event to non-transgenic segregants pooled across the same plate. Two events, -04 and -05, showed significantly increased photosynthetic efficiency relative to the internal controls in $T_2$ generation on both low nitrate-containing and ammonium nitrate-containing media at p 0.05 using a one-tailed t-test assuming unequal variance. A summary of photosynthetic efficiency of ME01821 seedlings is shown in Table 7.

TABLE 7A

T-test comparison of seedling photosynthetic efficiency between transgenic
seedlings and pooled non-transgenic segregants after 14 days of growth on low nitrate.

| Line | Events | Transgenic Fv/Fm | n | Pooled Non-Transgenics Fv/Fm | n | t-test p-value |
|---|---|---|---|---|---|---|
| ME02538 | ME02538-04 ($T_2$) | 0.6686 | 15 | 0.6171 | 24 | $1.92 \times 10^{-4}$ |
| ME02538 | ME02538-05 ($T_2$) | 0.6420 | 20 | 0.6171 | 24 | $4.84 \times 10^{-2}$ |

TABLE 7B

T-test comparison of seedling photosynthetic efficiency between transgenic seedlings and
pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME02538 | ME02538-04 ($T_2$) | 0.7345 | 13 | 0.7080 | 22 | $4.45 \times 10^{-3}$ |
| ME02538 | ME02538-05 ($T_2$) | 0.7356 | 20 | 0.7080 | 22 | $5.93 \times 10^{-3}$ |

ME02538 events were also tested for enhanced growth on the low ammonium nitrate media. A summary of the growth assay performed on ME01812 events is shown in Table 8. Transgenic seedlings of two events-01 and -02 were found significantly larger than the pooled non-transgenic segregants on both low nitrate—(Table 8A) and low ammonium nitrate-containing media (Table 8B).

TABLE 8A

T-test comparison of seedling area between transgenic seedlings and pooled non-transgenic segregants after 14 days of growth on low nitrate.

| Line | Events | Transgenic | | Pooled Non-Transgenics | | t-test |
| --- | --- | --- | --- | --- | --- | --- |
| | | Area | n | Area | n | p-value |
| ME02538 | ME02538-01 ($T_2$) | 0.0655 | 16 | 0.0558 | 36 | $2.80 \times 10^{-4}$ |
| ME02538 | ME02538-02 ($T_2$) | 0.0651 | 13 | 0.0601 | 20 | $1.32 \times 10^{-2}$ |

TABLE 8B

T-test comparison of seedling area between transgenic seedlings and pooled non-transgenic segegants after 18 days of growth on low ammonium nitrate.

| Line | Events | Transgenic | | Pooled Non-Transgenics | | t-test |
| --- | --- | --- | --- | --- | --- | --- |
| | | Area | n | Area | n | p-value |
| ME02538 | ME02538-01 ($T_2$) | 0.0856 | 15 | 0.0737 | 39 | $8.60 \times 10^{-3}$ |
| ME02538 | ME02538-02 ($T_2$) | 0.0864 | 14 | 0.0776 | 22 | $3.13 \times 10^{-2}$ |

Example 11—Analysis of ME02603 Events

ME02603 contains Ceres Clone:15457 (At5g47610, SEQ ID NO:165) from *Arabidopsis thaliana*, which encodes a 166 amino acid zinc ion binding protein. Evaluation of low-nitrogen tolerance for ME02603 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -04, showed significantly increased photosynthetic efficiency on low ammonium nitrate-containing media relative to the internal controls in both generations at p≤0.05 using a one-tailed t-test assuming unequal variance. A summary of photosynthetic efficiency of ME02603 seedlings is shown in Table 9. Events-01 and -04 segregated 3:1 (R:S) for FINALE™ resistance in the $T_2$ generation. Transgenic plants of two events-01 and -04—were also tested for enhanced photosynthetic efficiency on the low nitrate media. No significant differences between the transgenics and the controls were observed.

TABLE 9

T-test comparison of photosynthetic efficiency between transgenic seedlings and pooled non-transgenic segregants after 17 days (21 days for the $T_2$ generation of ME02603-01) of growth on low ammonium nitrate.

| Line | Events | Transgenic | | Pooled Non-Transgenics | | t-test |
| --- | --- | --- | --- | --- | --- | --- |
| | | Fv/Fm | n | Fv/Fm | n | p-value |
| ME02603 | ME02603-01 ($T_2$) | 0.61 | 10 | 0.54 | 32 | $9.00 \times 10^{-4}$ |
| ME02603 | ME02603-01 ($T_3$) | 0.67 | 28 | 0.65 | 62 | $6.11 \times 10^{-3}$ |
| ME02603 | ME02603-04 ($T_2$) | 0.69 | 25 | 0.65 | 62 | $4.45 \times 10^{-5}$ |
| ME02603 | ME02603-04 ($T_3$) | 0.68 | 24 | 0.65 | 62 | $7.53 \times 10^{-3}$ |

Events-01 and -04 of ME02603 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 12—Analysis of ME02613 Events

ME02613 contains Ceres Clone:17883 (At3g13910, SEQ ID NO:185) from *Arabidopsis thaliana*, which encodes a 102 amino acid protein of unknown function. Evaluation of low-nitrogen tolerance for ME02613 in $T_2$ generation was conducted under the same conditions as described in Examples 2 and 3. In this study, the seedling photosynthetic efficiency was measured as Fv/Fm comparing transgenic plants within an event to non-transgenic segregants pooled across the same plate. In $T_2$ generation, two events, -01 and -04, showed significantly increased photosynthetic efficiency on low nitrate containing-media relative to the internal controls in $T_2$ generation at $p \leq 0.05$ using a one-tailed t-test assuming unequal variance. Two events, -03 and -04, showed significantly increased photosynthetic efficiency on low ammonium nitrate containing-media relative to the internal controls in $T_2$ generation at $p \leq 0.05$ using a one-tailed t-test assuming unequal variance. A summary of photosynthetic efficiency of ME02613 seedlings is shown in Table 10.

TABLE 10A

T-test comparison of seedling photosynthetic efficiency between transgenic seedlings and pooled non-transgenic segregants after 14 days of growth on low nitrate.

| Line | Events | Transgenic | | Pooled Non-Transgenics | | t-test |
| --- | --- | --- | --- | --- | --- | --- |
| | | Fv/Fm | n | Fv/Fm | n | p-value |
| ME02613 | ME02613-01 ($T_2$) | 0.6979 | 16 | 0.6630 | 21 | $1.45 \times 10^{-2}$ |
| ME02613 | ME02613-04 ($T_2$) | 0.7046 | 13 | 0.6630 | 21 | $5.73 \times 10^{-4}$ |

TABLE 10B

T-test comparison of seedling photosynthetic efficiency between transgenic seedlings and pooled non-transgenic segregants after 18 days of growth on low ammonium nitrate.

| Line | Events | Transgenic | | Pooled Non-Transgenics | | t-test |
| --- | --- | --- | --- | --- | --- | --- |
| | | Fv/Fm | n | Fv/Fm | n | p-value |
| ME02613 | ME02613-03 ($T_2$) | 0.7270 | 9 | 0.7068 | 29 | $4.34 \times 10^{-2}$ |
| ME02613 | ME02613-04 ($T_2$) | 0.7485 | 15 | 0.7068 | 29 | $7.09 \times 10^{-5}$ |

A summary of the enhanced growth of ME02613 events on either low nitrate- or low ammonium nitrate-containing media is shown in Table 11. For two events-01 and -03, transgenic seedlings were found significantly larger than the pooled non-transgenic segregants after 14 days of growth on low nitrate-containing media (Table 11A). Transgenic seedlings of two events-02 and -03 were found significantly larger than the pooled non-transgenic segregants after 14 days of growth on low ammonium nitrate-containing media (Table 11B).

TABLE 11A

T-test comparison of seedling area between transgenic seedlings and pooled non-transgenic segregants after 14 days of growth on low nitrate.

| Line | Events | Transgenic | | Pooled Non-Transgenics | | t-test |
| --- | --- | --- | --- | --- | --- | --- |
| | | Area | n | Area | n | p-value |
| ME02613 | ME02613-01 ($T_2$) | 0.05706 | 16 | 0.05259 | 31 | $4.71 \times 10^{-2}$ |
| ME02613 | ME02613-03 ($T_2$) | 0.06236 | 12 | 0.05789 | 29 | $2.39 \times 10^{-2}$ |

TABLE 1

T-test comparison of seedling area between transgenic seedlings and pooled non-transgenic segregants after 18 days of growth on low ammonium nitrate.

| Line | Events | Transgenic | | Pooled Non-Transgenics | | t-test |
|---|---|---|---|---|---|---|
| | | Area | n | Area | n | p-value |
| ME02613 | ME02613-02 ($T_2$) | 0.08324 | 14 | 0.07018 | 29 | $2.72 \times 10^{-4}$ |
| ME02613 | ME02613-03 ($T_2$) | 0.08273 | 9 | 0.07018 | 29 | $1.41 \times 10^{-2}$ |

Example 13—Analysis of ME02801 Events le;2qME02801 contains Ceres Clone:251590 (At3g53080, SEQ ID NO:207) from *Arabidopsis thaliana*, which encodes a 155 amino acid protein of unknown function. Evaluation of low-nitrogen tolerance for ME02801 in $T_2$ and $T_3$ was conducted under the same conditions as described in Example 2 and 3. In this study, the seedling photosynthetic efficiency was measured as Fv/Fm comparing transgenic plants within an event to non-transgenic segregants pooled across the same plate. Two events, -02 and -04, showed significantly increased photosynthetic efficiency on low nitrate-containing media relative to the internal controls in both generations at $p \leq 0.05$ using a one-tailed t-test assuming unequal variance. A summary of photosynthetic efficiency of ME02801 seedlings is shown in Table 12. Events-02 and -04 segregated 3:1 (R:S) for FINALE™ resistance in the $T_2$ generation. ME02801 events were also tested for enhanced growth on the low nitrate media and enhanced photosynthetic efficiency and growth on low ammonium nitrate media. No significant differences between the transgenics and the controls were observed.

TABLE 12 t-test comparison of seedling photosynthetic efficiency between transgenic seedlings and pooled non-transgenic segregants after 14 days of growth on low nitrate.

| Line | Events | Transgenic | | Pooled Non-Transgenics | | t-test |
|---|---|---|---|---|---|---|
| | | Fv/Fm | n | Fv/Fm | n | p-value |
| ME02801 | ME02801-02 ($T_2$) | 0.536385 | 39 | 0.465903 | 113 | $5.49 \times 10^{-7}$ |
| ME02801 | ME02801-02 ($T_3$) | 0.536465 | 43 | 0.465903 | 113 | $5.11 \times 10^{-7}$ |
| ME02801 | ME02801-04 ($T_2$) | 0.532419 | 31 | 0.465903 | 113 | $1.28 \times 10^{-5}$ |
| ME02801 | ME02801-04 ($T_3$) | 0.510406 | 32 | 0.465903 | 113 | $1.74 \times 10^{-2}$ |

Events-02 and -04 of ME02801 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 14—Analysis of ME03123 Events

ME03123 contains Ceres Clone:4898 (At1g29970, SEQ ID NO:217) from *Arabidopsis thaliana*, which encodes a 158 amino acid protein of unknown function. Evaluation of low-nitrogen tolerance for ME03123 in $T_2$ and/or $T_3$ was conducted under the same conditions as described in Examples 2 and 3. In this study, the seedling photosynthetic efficiency was measured as Fv/Fm comparing transgenic plants within an event to non-transgenic segregants pooled across the same plate. A summary of photosynthetic efficiency of ME03123 seedlings is shown in Table 13. Two events, -01 and -10, showed significantly increased photosynthetic efficiency on low nitrate- or low ammonium nitrate-containing media relative to the internal controls in $T_2$ or $T_3$ generation at $p \leq 0.05$ using a one-tailed t-test assuming unequal variance.

TABLE 13A

T-test comparison of seedling photosynthetic efficiency between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Fv/Fm | n | Fv/Fm | n | p-value |
| ME03123 | ME03123-01 ($T_2$) | 0.6282 | 15 | 0.5732 | 26 | $6.60 \times 10^{-5}$ |
| ME03123 | ME03123-10 ($T_3$) | 0.6069 | 12 | 0.5732 | 26 | $1.05 \times 10^{-2}$ |

TABLE 13B

T-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME03123 | ME03123-01 ($T_2$) | 0.6736 | 17 | 0.6315 | 16 | $1.74 \times 10^{-2}$ |
| ME03123 | ME03123-10 ($T_3$) | 0.6699 | 20 | 0.6315 | 16 | $1.60 \times 10^{-2}$ |

ME03123 events were also tested for enhanced growth on the low ammonium nitrate media. In this assay, transgenic seedlings of ME03123-02 and ME03123-04 ($T_2$) were significantly larger than the pooled non-transgenic segregants after 14 days of growth on low nitrate (Table 14).

TABLE 14

T-test comparison of seedling area between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Area | n | Area | n | p-value |
| ME03123 | ME03123-02 ($T_2$) | 0.07235 | 19 | 0.05623 | 20 | $1.41 \times 10^{-6}$ |
| ME03123 | ME03123-04 ($T_3$) | 0.06571 | 7 | 0.05729 | 41 | $7.74 \times 10^{-3}$ |

Example 15—Analysis of ME04204 Events

ME04204 contains Ceres Clone:148977 (At1g78770, SEQ ID NO:233) from *Arabidopsis thaliana*, which encodes a 159 amino acid anaphase promoting complex/cyclosome subunit protein. However, it is also possible that this is natural variant transcript produced by the plant, because multiple annotations for locus At1g78770 were found in public domain. Evaluation of low-nitrogen tolerance for ME04204 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -05, showed significantly increased photosynthetic efficiency relative to the internal controls in both generations at p≤0.05 using a one-tailed t-test assuming unequal variance. A summary of photosynthetic efficiency of ME04204 seedlings is shown in Table 15. Events-01 and -05 segregated 3:1 (R:S) for FINALE™ resistance in the $T_2$ generation. ME04204 events were also tested for enhanced growth on the low nitrate media. No significant differences between the transgenics and the controls were observed.

TABLE 15

T-test comparison of seedling photosynthetic efficiency between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Fv/Fm | n | Fv/Fm | n | p-value |
| ME04204 | ME04204-01 ($T_2$) | 0.623676 | 34 | 0.585504 | 121 | $2.15 \times 10^{-4}$ |
| ME04204 | ME04204-01 ($T_3$) | 0.627706 | 17 | 0.585504 | 121 | $8.22 \times 10^{-5}$ |
| ME04204 | ME04204-05 ($T_2$) | 0.615857 | 35 | 0.585504 | 121 | $9.41 \times 10^{-3}$ |
| ME04204 | ME04204-05 ($T_3$) | 0.611419 | 43 | 0.585504 | 121 | $1.25 \times 10^{-2}$ |

Events-01 and -05 of ME04204 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 16—Analysis of ME04477 Events

ME04477 contains Ceres Clone:24255 (At2g36320, SEQ ID NO:245) from *Arabidopsis thaliana*, which encodes a 161 amino acid DNA binding/zinc ion binding protein. Evaluation of low-nitrogen tolerance for ME04477 in $T_2$ and $T_3$ was conducted under the same conditions as described in Example 2. In this study, the seedling photosynthetic efficiency was measured as Fv/Fm comparing transgenic plants within an event to non-transgenic segregants pooled across the same plate. Two events, -01 and -05, showed significantly increased photosynthetic efficiency on low nitrate-containing media relative to the internal controls in both generations at $p \leq 0.05$ using a one-tailed t-test assuming unequal variance. A summary of photosynthetic efficiency of ME04477 seedlings is shown in Table 16. Events-01 and -05 segregated 3:1 (R:S) for FINALE™ resistance in the $T_2$ generation. ME04477 events were also tested for enhanced growth on the low nitrate media. No significant differences between the transgenics and the controls were observed.

TABLE 16

T-test comparison of seedling photosynthetic efficiency between transgenic seedlings and pooled non-transgenic segegants after 14 days of growth on low nitrate.

| | | Transgenic | | Pooled Non-Transgenics | | t-test |
|---|---|---|---|---|---|---|
| Line | Events | Fv/Fm | n | Fv/Fm | n | p-value |
| ME04204 | ME04204-01 ($T_2$) | 0.623676 | 34 | 0.585504 | 121 | $2.15 \times 10^{-4}$ |
| ME04204 | ME04204-01 ($T_3$) | 0.627706 | 17 | 0.585504 | 121 | $8.22 \times 10^{-5}$ |
| ME04204 | ME04204-05 ($T_2$) | 0.615857 | 35 | 0.585504 | 121 | $9.41 \times 10^{-3}$ |
| ME04204 | ME04204-05 ($T_3$) | 0.611419 | 43 | 0.585504 | 121 | $1.25 \times 10^{-2}$ |

Events-01 and -05 of ME04477 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 17—Analysis of ME04507 Events

ME04507 contains Ceres Clone:38432 (At4g38250, SEQ ID NO:299) from *Arabidopsis thaliana*, which encodes a 436 amino acid transmembrane amino acid transporter protein. Evaluation of low-nitrogen tolerance for ME04507 in $T_2$ and $T_3$ was conducted under the same conditions as described in Example 2. In this study, the seedling photosynthetic efficiency was measured as Fv/Fm comparing transgenic plants within an event to non-transgenic segregants pooled across the same plate. Two events, -03 and -04, showed significantly increased photosynthetic efficiency on low nitrate-containing media relative to the internal controls in both generations at $p \leq 0.05$ using a one-tailed t-test assuming unequal variance. A summary of photosynthetic efficiency of ME04507 seedlings is shown in Table 17. Events-03 and -04 segregated 15:1 and 3:1 (R:S), respectively, for FINALE™ resistance in the $T_2$ generation. ME04507 events were also tested for enhanced growth on the low nitrate media. No significant differences between the transgenics and the controls were observed.

TABLE 17

T-test comparison of seedling photosynthetic efficiency between transgenic seedlings and pooled non-transgenic segregants after 14 days of growth on low nitrate media.

| | | Transgenic | | Pooled Non-Transgenics | | t-test |
|---|---|---|---|---|---|---|
| Line | Events | Fv/Fm | n | Fv/Fm | n | p-value |
| ME04507 | ME04507-03 ($T_2$) | 0.57753 | 40 | 0.53084 | 103 | $4.90 \times 10^{-4}$ |
| ME04507 | ME04507-03 ($T_3$) | 0.56318 | 39 | 0.53084 | 103 | $2.64 \times 10^{-2}$ |
| ME04507 | ME04507-04 ($T_2$) | 0.57708 | 38 | 0.53084 | 103 | $6.12 \times 10^{-3}$ |
| ME04507 | ME04507-04 ($T_3$) | 0.57277 | 22 | 0.53084 | 103 | $2.35 \times 10^{-2}$ |

Events-03 and -04 of ME04507 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 18—Analysis of ME04587 Events

ME04587 contains Ceres Annot:553243 (At2g27010, SEQ ID NO:331) from *Arabidopsis thaliana*, which encodes a 516 amino acid cytochrome P450 protein. Evaluation of low-nitrogen tolerance for ME04587 in $T_2$ and $T_3$ was conducted under the same conditions as described in Example 2. In this study, the seedling photosynthetic efficiency was measured as Fv/Fm comparing transgenic plants within an event to non-transgenic segregants pooled across the same plate. Two events, -01 and -02, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME04587 seedlings is shown in Table 18. In $T_2$ generation, events-01 and -02 segregated 1:1 and 47:1 respectively (R:S) for FINALE™ resistance. These two events segregated 2:1 and 7:1 respectively (R:S) for FINALE® resistance in the $T_3$ generation.

TABLE 18

T-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME04587 | ME04587-01 ($T_2$) | 0.6424 | 10 | 0.5437 | 30 | $2.48 \times 10^{-3}$ |
| ME04587 | ME04587-01 ($T_3$) | 0.6165 | 25 | 0.5437 | 30 | $1.24 \times 10^{-2}$ |
| ME04587 | ME04587-02 ($T_2$) | 0.6022 | 47 | 0.5437 | 30 | $3.08 \times 10^{-2}$ |
| ME04587 | ME04587-02 ($T_3$) | 0.6310 | 43 | 0.5437 | 30 | $3.68 \times 10^{-3}$ |

ME04587 events were also tested for enhanced growth on the low ammonium nitrate media. In addition, these events were tested on low nitrate media for increased seedling area and photosynthetic efficiency. No statistically significant differences between the transgenics and the controls were observed.

Events-01 and -02 of ME04587 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 19—Analysis of ME04753 Events

ME04753 contains Ceres Clone:1011900 (At2g21660, SEQ ID NO:367) from *Arabidopsis thaliana*, which encodes a 130 amino acid glycine-rich RNA binding protein. Evaluation of low-nitrogen tolerance for ME04753 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -02, showed significantly increased photosynthetic efficiency on low nitrate-containing media relative to the internal controls in both generations at p≤0.05 using a one-tailed t-test assuming unequal variance. A summary of photosynthetic efficiency of ME04753 seedlings is shown in Table 19. Events-01 and -02 segregated 3:1 and 2:1 respectively (R:S) for FINALE™ resistance in the $T_2$ generation. ME04753 events were also tested for enhanced growth on the low nitrate media. No significant differences between the transgenics and the controls were observed.

TABLE 19

T-test comparison of seedling photosynthetic efficiency between transgenic seedlings and pooled non-transgenic segregants after 14 days of growth on low nitrate media.

| Line | Events | Transgenic Fv/Fm | n | Pooled Non-Transgenics Fv/Fm | n | t-test p-value |
|---|---|---|---|---|---|---|
| ME04753 | ME04753-01 ($T_2$) | 0.49323 | 39 | 0.45917 | 66 | $3.17 \times 10^{-2}$ |
| ME04753 | ME04753-01 ($T_3$) | 0.50942 | 26 | 0.45917 | 66 | $1.80 \times 10^{-2}$ |
| ME04753 | ME04753-02 ($T_2$) | 0.49856 | 34 | 0.45917 | 66 | $2.43 \times 10^{-2}$ |
| ME04753 | ME04753-02 ($T_3$) | 0.51274 | 27 | 0.45917 | 66 | $1.15 \times 10^{-2}$ |

Events-01 and -02 of ME04753 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 20—Analysis of ME04772 Events

ME04772 contains Ceres Clone:5232 (At1g13380, SEQ ID NO:509) from *Arabidopsis thaliana*, which encodes a 188 amino acid protein of unknown function. Evaluation of low-nitrogen tolerance for ME04772 in $T_2$ and $T_3$ was conducted under the same conditions as described in Example 2. In this study, the seedling photosynthetic efficiency was measured as Fv/Fm comparing transgenic plants within an event to non-transgenic segregants pooled across the same plate. Two events, -02 and -04, showed significantly increased photosynthetic efficiency on low nitrate-containing media relative to the internal controls in both generations at p≤0.05 using a one-tailed t-test assuming unequal variance. A summary of photosynthetic efficiency of ME04772 seedlings is shown in Table 20. Events-02 and -04 segregated 2:1 and 3:1 respectively (R:S) for FINALE™ resistance in the $T_2$ generation. ME04772 events were also tested for enhanced growth on the low nitrate media. No significant differences between the transgenics and the controls were observed.

TABLE 20

T-test comparison of seedling photosynthetic efficiency between transgenic seedlings and pooled non-transgenic segregants after 14 days of growth on low nitrate media.

| Line | Events | Transgenic Fv/Fm | n | Pooled Non-Transgenics Fv/Fm | n | t-test p-value |
|---|---|---|---|---|---|---|
| ME04772 | ME04772-02 ($T_2$) | 0.53708 | 25 | 0.46204 | 53 | $3.36 \times 10^{-5}$ |
| ME04772 | ME04772-02 ($T_3$) | 0.53121 | 34 | 0.46204 | 53 | $1.27 \times 10^{-4}$ |
| ME04772 | ME04772-04 ($T_2$) | 0.52921 | 34 | 0.46204 | 53 | $3.71 \times 10^{-4}$ |
| ME04772 | ME04772-04 ($T_3$) | 0.50272 | 36 | 0.46204 | 53 | $2.73 \times 10^{-2}$ |

Events-02 and -04 of ME04772 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 21—Analysis of ME04772 Events

ME04909 contains Ceres Clone:29302 (At1g49010, SEQ ID NO:532) from *Arabidopsis thaliana*, which encodes a 314 amino acid Myb-like DNA-binding domain protein. Evaluation of low-nitrogen tolerance for ME04909 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -03, showed significantly increased photosynthetic efficiency on low nitrate-containing media relative to the internal controls in both generations at p≤0.05 using a one-tailed t-test assuming unequal variance. A summary of photosynthetic efficiency of ME04909 seedlings is shown in Table 21. Events-01 and -03 segregated 15:1 (R:S) for FINALE™ resistance in the $T_2$ generation. ME04909 events were also tested for enhanced growth on the low nitrate media. No significant differences between the transgenics and the controls were observed.

TABLE 21 t-test comparison of seedling photosynthetic efficiency between transgenic seedlings and pooled non-transgenic segregants after 14 days of growth on low nitrate.

| Line | Events | Transgenic | | Pooled Non-Transgenics | | t-test |
|---|---|---|---|---|---|---|
| | | Fv/Fm | n | Fv/Fm | n | p-value |
| ME04909 | ME04909-01 ($T_2$) | 0.587774 | 31 | 0.550342 | 111 | $1.36 \times 10^{-2}$ |
| ME04909 | ME04909-01 ($T_3$) | 0.607452 | 31 | 0.550342 | 111 | $1.28 \times 10^{-3}$ |
| ME04909 | ME04909-03 ($T_2$) | 0.581537 | 41 | 0.550342 | 111 | $1.8 \times 10^{-2}$ |
| ME04909 | ME04909-03 ($T_3$) | 0.609806 | 31 | 0.550342 | 111 | $4.3 \times 10^{-5}$ |

Events-01 and -03 of ME04909 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 22—Analysis of ME05033 Events

ME05033 contains Ceres Clone:93971 (At4g19095, SEQ ID NO:555) from *Arabidopsis thaliana*, which encodes a 188 amino acid protein of unknown function. Evaluation of low-nitrogen tolerance for ME05033 in $T_2$ and $T_3$ was conducted under the same conditions as described in Example 2. In this study, the seedling photosynthetic efficiency was measured as Fv/Fm comparing transgenic plants within an event to non-transgenic segregants pooled across the same plate. Two events, -03 and -05, showed significantly increased photosynthetic efficiency on low nitrate-containing media relative to the internal controls in both generations at p≤0.05 using a one-tailed t-test assuming unequal variance. A summary of photosynthetic efficiency of ME05033 seedlings is shown in Table 22. Events-03 and -05 segregated 15:1 and 2:1 respectively (R:S) for FINALE™ resistance in the $T_2$ generation. ME05033 events were also tested for enhanced growth on the low nitrate media. No significant differences between the transgenics and the controls were observed.

TABLE 22

T-test comparison of seedling photosynthetic efficiency between transgenic seedlings and pooled non-transgenic segregants after 14 days of growth on low nitrate media.

| Line | Events | Transgenic | | Pooled Non-Transgenics | | t-test |
|---|---|---|---|---|---|---|
| | | Fv/Fm | n | Fv/Fm | n | p-value |
| ME05033 | ME05033-03 ($T_2$) | 0.65717 | 46 | 0.62621 | 132 | $9.20 \times 10^{-5}$ |
| ME05033 | ME05033-03 ($T_3$) | 0.64956 | 39 | 0.62621 | 132 | $4.52 \times 10^{-3}$ |
| ME05033 | ME05033-05 ($T_2$) | 0.64448 | 29 | 0.62621 | 132 | $3.46 \times 10^{-2}$ |
| ME05033 | ME05033-05 ($T_3$) | 0.65537 | 30 | 0.62621 | 132 | $2.38 \times 10^{-4}$ |

Events-03 and -05 of ME05033 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 23—Analysis of ME05194 Events

ME05194 contains Ceres cDNA:12669619 (At1g30710, SEQ ID NO:557) from *Arabidopsis thaliana*, which encodes a 531 amino acid electron carrier protein. Evaluation of low-nitrogen tolerance for ME05194 in $T_2$ and $T_3$ was conducted under the same conditions as described in Examples 2 and 3. Two events, -03 and -05, showed significantly enhanced growth on low nitrate-containing media relative to the internal controls in both generations at p≤0.05 using a one-tailed t-test assuming unequal variance. In this study, the seedling area at 14 days for transgenic plants within an event was compared to the seedling area for non-transgenic segregants pooled across the same line. A summary of enhanced growth under low nitrate growth conditions of ME05194 seedlings is shown in Table 23. Events-03 and -05 segregated 1:1 (R:S) for FINALE™ resistance in the $T_2$ generation. ME05194 events were also tested for increased photosynthetic efficiency on the low nitrate media. No significant differences between the transgenics and the controls were observed.

TABLE 23 t-test comparison of seedling area between transgenic seedlings
and pooled non-transgenic segregants after
14 days of growth on low nitrate.

| Line | Events | Transgenic | | Pooled Non-Transgenics | | t-test |
| --- | --- | --- | --- | --- | --- | --- |
| | | Area | n | Area | n | p-value |
| ME05194 | ME05194-03 ($T_2$) | 0.051216 | 38 | 0.040874 | 82 | $2.54 \times 10^{-5}$ |
| ME05194 | ME05194-03 ($T_3$) | 0.047042 | 45 | 0.040874 | 82 | $2.61 \times 10^{-2}$ |
| ME05194 | ME05194-05 ($T_2$) | 0.048746 | 26 | 0.040874 | 82 | $6.15 \times 10^{-3}$ |
| ME05194 | ME05194-05 ($T_3$) | 0.048457 | 14 | 0.040874 | 82 | $3.03 \times 10^{-2}$ |

Events-03 and -05 of ME05194 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 24—Analysis of ME05267 Events

ME05267 contains Ceres Clone:21608 (At5g49510, SEQ ID NO:592) from *Arabidopsis thaliana*, which encodes a 195 amino acid von Hippel-Lindau binding protein. Evaluation of low-nitrogen tolerance for ME05267 in $T_2$ and $T_3$ was conducted under the same conditions as described in Examples 2 and 3. Two events, -01 and -04, showed significantly enhanced growth on low nitrate-containing media relative to the internal controls in both generations at $p \leq 0.05$ using a one-tailed t-test assuming unequal variance. In this study, the seedling area at 14 days for transgenic plants within an event was compared to the seedling area for non-transgenic segregants pooled across the same line. A summary of enhanced growth under low nitrate growth conditions of ME05194 seedlings is shown in Table 24. Events-01 and -04 segregated 15:1 (R:S) for FINALE™ resistance in the $T_2$ generation. ME05267 events were also tested for increased photosynthetic efficiency on the low nitrate media. No significant differences between the transgenics and the controls were observed.

Events-01 and -04 of ME05267 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 25—Analysis of ME05300 Events

ME05300 contains Ceres Clone:2031 (At1g72020, SEQ ID NO:612) from *Arabidopsis thaliana*, which encodes a 97 amino acid protein of unknown function. Evaluation of low-nitrogen tolerance for ME05300 in $T_2$ generation was conducted under the same conditions as described in Examples 2 and 3. A summary of photosynthetic efficiency of ME05300 seedlings is shown in Table 25. Two events, -04 and -05, showed significantly increased photosynthetic efficiency on low nitrate- and low ammonium nitrate-containing media relative to the internal controls in $T_2$ generation at $p \leq 0.05$ using a one-tailed t-test assuming unequal variance. In this study, the seedling photosynthetic efficiency was measured as Fv/Fm comparing transgenic plants within an event to non-transgenic segregants pooled across the same plate. In addition, two events, -01 and -05, showed significantly enhanced growth on low nitrate- and low ammonium nitrate-containing media relative to the internal controls in $T_2$ generation at $p \leq 0.05$ using a one-tailed t-test assuming unequal variance. In this study, the seedling area for transgenic plants within an event was compared to the seedling area for non-transgenic segregants pooled across the same line. A summary of enhanced growth under low nitrate and low ammonium nitrate growth conditions of ME05300 seedlings is shown in Table 26.

TABLE 24 t-test comparison of seedling area between
transgenic seedlings and pooled non-
transgenic segregants after 14 days of growth on low nitrate.

| Line | Events | Transgenic | | Pooled Non-Transgenics | | t-test |
| --- | --- | --- | --- | --- | --- | --- |
| | | Area | n | Area | n | p-value |
| ME05267 | ME05267-01 ($T_2$) | 0.053263 | 46 | 0.0450197 | 122 | $4.4 \times 10^{-5}$ |
| ME05267 | ME05267-01 ($T_3$) | 0.051135 | 26 | 0.0450197 | 122 | $5.0 \times 10^{-2}$ |
| ME05267 | ME05267-04 ($T_2$) | 0.049977 | 44 | 0.0450197 | 122 | $6.4 \times 10^{-3}$ |
| ME05267 | ME05267-04 ($T_3$) | 0.053084 | 38 | 0.0450197 | 122 | $8.4 \times 10^{-4}$ |

TABLE 25A

T-test comparison of seedling photosynthetic efficiency between transgenic seedlings and pooled non-transgenic segregants after 14 days of growth on low nitrate.

| Line | Events | Transgenic Fv/Fm | n | Pooled Non-Transgenics Fv/Fm | n | t-test p-value |
|---|---|---|---|---|---|---|
| ME05300 | ME05300-04 ($T_2$) | 0.6867 | 7 | 0.6488 | 27 | $1.65 \times 10^{-2}$ |
| ME05300 | ME05300-05 ($T_2$) | 0.6839 | 16 | 0.6488 | 27 | $2.50 \times 10^{-3}$ |

TABLE 25B

T-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME05300 | ME05300-04 ($T_2$) | 0.6767 | 6 | 0.6323 | 32 | $1.68 \times 10^{-2}$ |
| ME05300 | ME05300-05 ($T_2$) | 0.6934 | 11 | 0.6323 | 32 | $7.04 \times 10^{-4}$ |

TABLE 26A

T-test comparison of seedling area between transgenic seedlings and pooled non-transgenic segregants after 14 days of growth on low nitrate.

| Line | Events | Transgenic Area | n | Pooled Non-Transgenics Area | n | t-test p-value |
|---|---|---|---|---|---|---|
| ME05300 | ME05300-01 ($T_2$) | 0.0737 | 18 | 0.0588 | 21 | $3.80 \times 10^{-3}$ |
| ME05300 | ME05300-05 ($T_2$) | 0.0655 | 16 | 0.0570 | 27 | $1.59 \times 10^{-2}$ |

TABLE 26B

T-test comparison of seedling area between transgenic seedlings and pooled non-transgenic segregants after 18 days of growth on low ammonium nitrate.

| Line | Events | Transgenic Area | n | Pooled Non-Transgenics Area | n | t-test p-value |
|---|---|---|---|---|---|---|
| ME05300 | ME05300-01 ($T_2$) | 0.0987 | 17 | 0.0776 | 29 | $3.89 \times 10^{-3}$ |
| ME05300 | ME05300-05 ($T_2$) | 0.1082 | 11 | 0.0776 | 29 | $1.57 \times 10^{-3}$ |

Example 26—Analysis of ME05341 Events

ME05341 contains Ceres Clone:94503 (At4g14420, SEQ ID NO:645) from *Arabidopsis thaliana*, which encodes a 158 amino acid elicitor-like protein. Evaluation of low-nitrogen tolerance for ME05341 in $T_2$ and $T_3$ was conducted under the same conditions as described in Examples 2 and 3. Two events, -01 and -02, showed significantly enhanced growth on low nitrate-containing media relative to the internal controls in both generations at $p \leq 0.05$ using a one-tailed t-test assuming unequal variance. In this study, the seedling area at 14 days for transgenic plants within an event was compared to the seedling area for non-transgenic segregants pooled across the same line. A summary of photosynthetic efficiency of ME05341 seedlings is shown in Table 27. Events-01 and -02 segregated 15:1 (R:S) for FINALE™ resistance in the $T_2$ generation. ME05341 events were also tested for increased photosynthetic efficiency on the low nitrate media. No significant differences between the transgenics and the controls were observed.

TABLE 27 t-test comparison of seedling area between transgenic seedlings and pooled non-transgenic segregants after 14 days of growth on low nitrate.

| Line | Events | Transgenic Area | n | Pooled Non-Transgenics Area | n | t-test p-value |
|---|---|---|---|---|---|---|
| ME05341 | ME05341-01 ($T_2$) | 0.06253 | 46 | 0.04988 | 143 | $4.17 \times 10^{-10}$ |
| ME05341 | ME05341-01 ($T_3$) | 0.05876 | 38 | 0.04988 | 143 | $4.13 \times 10^{-4}$ |
| ME05341 | ME05341-02 ($T_2$) | 0.06152 | 46 | 0.04988 | 143 | $2.91 \times 10^{-7}$ |
| ME05341 | ME05341-02 ($T_3$) | 0.05572 | 48 | 0.04988 | 143 | $2.90 \times 10^{-3}$ |

Events-01 and -02 of ME05341 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 27—Analysis of ME05392 Events

ME05392 contains Ceres Clone:21740 (At5g01610, SEQ ID NO:686) from *Arabidopsis thaliana*, which encodes a 170 amino acid protein of unknown function. Evaluation of low-nitrogen tolerance for ME05392 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -03, showed significantly increased photosynthetic efficiency on low nitrate-containing media relative to the internal controls in both generations at $p \leq 0.05$ using a one-tailed t-test assuming unequal variance. A summary of photosynthetic efficiency of ME05392 seedlings is shown in Table 20. Events-01 and -03 segregated 2:1 (R:S) for FINALE™ resistance in the $T_2$ generation. ME05392 events were also tested for enhanced growth on the low nitrate media. No significant differences between the transgenics and the controls were observed.

TABLE 28

T-test comparison of seedling photosynthetic efficiency between transgenic seedlings and pooled non-transgenic segregants after 14 days of growth on low nitrate media.

| Line | Events | Transgenic Fv/Fm | n | Pooled Non-Transgenics Fv/Fm | n | t-test p-value |
|---|---|---|---|---|---|---|
| ME05392 | ME05392-01 ($T_2$) | 0.61759 | 32 | 0.60093 | 107 | $3.70 \times 10^{-2}$ |
| ME05392 | ME05392-01 ($T_3$) | 0.63388 | 40 | 0.60093 | 107 | $5.05 \times 10^{-5}$ |
| ME05392 | ME05392-03 ($T_2$) | 0.64335 | 23 | 0.60093 | 107 | $5.81 \times 10^{-5}$ |
| ME05392 | ME05392-03 ($T_3$) | 0.63397 | 36 | 0.60093 | 107 | $4.30 \times 10^{-5}$ |

Events-01 and -03 of ME05392 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 28—Analysis of ME05429 Events

ME05429 contains Ceres Clone:5609 (At3g60480, SEQ ID NO:729) from *Arabidopsis thaliana*, which encodes a 188 amino acid protein of unknown function. Evaluation of low-nitrogen tolerance for ME05429 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -06 and -08, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME05429 seedlings is shown in Table 29. Events-06 and -08 segregated 3:1 and 2:1 respectively (R:S) for FINALE™ resistance in the $T_2$ generation. ME05429 events were tested for enhanced growth on the low ammonium nitrate media. In addition, these events were also tested for enhanced growth and photosynthetic efficiency on low nitrate media. No significant differences between the transgenics and the controls were observed.

TABLE 29 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME05429 | ME05429-06 ($T_2$) | 0.62521 | 28 | 0.59991 | 78 | $2.85 \times 10^{-2}$ |
| ME05429 | ME05429-06 ($T_3$) | 0.63031 | 39 | 0.59991 | 78 | $8.49 \times 10^{-3}$ |
| ME05429 | ME05429-08 ($T_2$) | 0.64526 | 23 | 0.59991 | 78 | $1.67 \times 10^{-3}$ |
| ME05429 | ME05429-08 ($T_3$) | 0.65076 | 17 | 0.59991 | 78 | $2.76 \times 10^{-4}$ |

Events-06 and -08 of ME05429 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 29—Analysis of ME05493 Events

ME05493 contains Ceres Clone:3137 (At3g43430, SEQ ID NO:745) from *Arabidopsis thaliana*, which encodes a 169 amino acid zinc finger family protein. Evaluation of low-nitrogen tolerance for ME05493 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -05, showed significantly increased photosynthetic efficiency on low nitrate-containing media relative to the internal controls in both generations at $p \leq 0.05$ using a one-tailed t-test assuming unequal variance. A summary of photosynthetic efficiency of ME05493 seedlings is shown in Table 30. Events-01 and -05 segregated 15:1 (R:S) for FINALE™ resistance in the $T_2$ generation. ME05493 events were also tested for enhanced growth on the low nitrate media. No significant differences between the transgenics and the controls were observed.

TABLE 30 t-test comparison of seedling photosynthetic efficiency between transgenic seedlings and pooled non-transgenic segregants after 14 days of growth on low nitrate media.

| Line | Events | Transgenic Fv/Fm | n | Pooled Non-Transgenics Fv/Fm | n | t-test p-value |
|---|---|---|---|---|---|---|
| ME05493 | ME05493-01 ($T_2$) | 0.64121 | 32 | 0.61097 | 92 | $1.13 \times 10^{-3}$ |
| ME05493 | ME05493-01 ($T_3$) | 0.64250 | 46 | 0.61097 | 92 | $3.03 \times 10^{-4}$ |
| ME05493 | ME05493-05 ($T_2$) | 0.62865 | 43 | 0.61097 | 92 | $1.75 \times 10^{-2}$ |
| ME05493 | ME05493-05 ($T_3$) | 0.63936 | 42 | 0.61097 | 92 | $1.21 \times 10^{-4}$ |

Events-01 and -05 of ME05493 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 30—Analysis of ME05885 Event

ME05885 contains Ceres Clone:32430 (At1g16170, SEQ ID NO:768) from *Arabidopsis thaliana*, which encodes a 92 amino acid protein of unknown function. Evaluation of low-nitrogen tolerance for ME05885 in $T_3$ generation was conducted under the same conditions as described in Examples 2 and 3. A summary of photosynthetic efficiency of ME05885 seedlings is shown in Table 31. In this study, the seedling photosynthetic efficiency was measured as Fv/Fm comparing transgenic plants within an event to non-transgenic segregants pooled across the same plate. Two events, -01 and -05, showed significantly increased photosynthetic efficiency on low nitrate-containing media and low ammonium nitrate-containing media relative to the internal controls in $T_3$ generation at $p \leq 0.05$ using a one-tailed t-test assuming unequal variance.

TABLE 31

A. T-test comparison of seedling photosynthetic efficiency between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Fv/Fm | n | Fv/Fm | n | p-value |
| ME05885 | ME05885-01 ($T_3$) | 0.6759 | 12 | 0.6533 | 28 | $4.32 \times 10^{-2}$ |
| ME05885 | ME05885-05 ($T_3$) | 0.6831 | 7 | 0.6530 | 52 | $3.68 \times 10^{-6}$ |

B. T-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME05885 | ME05885-01 ($T_3$) | 0.6490 | 13 | 0.6135 | 30 | $3.06 \times 10^{-2}$ |
| ME05885 | ME05885-05 ($T_3$) | 0.6810 | 9 | 0.6133 | 43 | $6.77 \times 10^{-5}$ |

ME05885 events were also tested for enhanced growth on the low nitrate and low ammonium nitrate media. A summary of enhanced growth under low nitrate and low ammonium nitrate growth conditions of ME05885 seedlings in $T_3$ generation is shown in Table 32. Two events, -03 and -05, showed significantly enhanced growth on low nitrate-containing media. Two events, -02 and -05, showed significantly enhanced growth on low ammonium nitrate-containing media relative to the internal controls at p≤0.05 using a one-tailed t-test assuming unequal variance. In this study, the seedling area for transgenic plants within an event was compared to the seedling area for non-transgenic segregants pooled across the same line.

TABLE 32

A. T-test comparison of seedling area between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Area | n | Area | n | p-value |
| ME05885 | ME05885-03 ($T_3$) | 0.06245 | 6 | 0.05286 | 14 | $1.42 \times 10^{-2}$ |
| ME05885 | ME05885-05 ($T_3$) | 0.05893 | 7 | 0.04725 | 12 | $5.61 \times 10^{-3}$ |

B. T-test comparison of seedling area between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Area | n | Area | n | p-value |
| ME05885 | ME05885-02 ($T_3$) | 0.0744 | 14 | 0.05595 | 6 | $3.28 \times 10^{-5}$ |
| ME05885 | ME05885-05 ($T_3$) | 0.0753 | 9 | 0.06179 | 11 | $5.08 \times 10^{-3}$ |

Example 31—Analysis of ME07344 Events

ME07344 contains Ceres Clone:101255 (At2g19810, SEQ ID NO:791) from *Arabidopsis thaliana*, which encodes a 359 amino acid CCCH-type zinc finger protein. Evaluation of low-nitrogen tolerance for ME07344 in $T_2$ and $T_3$ was conducted under the same conditions as described in Example 4. In this study, the 4$^{th}$ true leaf from each plant was collected on day 38 and analyzed on the CF imager for its Fv/Fm value. Transgenic plants within an event were compared to all non-transgenic plants, including the non-transgenic segregants and external controls. Two events, -02 and -03, showed significantly increased photosynthetic efficiency relative to the internal controls in both generations at p 0.05 using a one-tailed t-test assuming unequal variance. A summary of photosynthetic efficiency of ME07344 seedlings is shown in Table 33. Events-02 and -03 segregated 3:1 (R:S) for FINALE™ resistance in the $T_2$ generation. ME07344 events were also tested for enhanced growth on the low nitrate media. No significant differences between the transgenics and the controls were observed.

TABLE 33

T-test comparison of photosynthetic efficiency between transgenic plants and non-transgenic controls after 38 days of growth on nitrogen-depleted soil.

| | | Transgenic | | Non-Transgenic Controls | | t-test |
|---|---|---|---|---|---|---|
| Line | Events | Fv/Fm | n | Fv/Fm | n | p-value |
| ME07344 | ME07344-02 ($T_2$) | 0.752 | 17 | 0.729 | 50 | $2.86 \times 10^{-4}$ |
| ME07344 | ME07344-02 ($T_3$) | 0.750 | 16 | 0.729 | 50 | $1.11 \times 10^{-4}$ |
| ME07344 | ME07344-03 ($T_2$) | 0.741 | 13 | 0.729 | 50 | 0.018 |
| ME07344 | ME07344-03 ($T_3$) | 0.754 | 17 | 0.729 | 50 | $4.62 \times 10^{-6}$ |

Events-02 and -03 of ME07344 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 32—Analysis of ME07859 Events

ME07859 contains Ceres Clone:276809 (SEQ ID NO:823) from *Zea mays*, which encodes a 135 amino acid sterol desaturase protein. Evaluation of low-nitrogen tolerance for ME07859 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -02 and -04, showed significantly increased photosynthetic efficiency on low nitrate-containing media relative to the internal controls in both generations at p≤0.05 using a one-tailed t-test assuming unequal variance. A summary of photosynthetic efficiency of ME07859 seedlings is shown in Table 34. Events-02 and -04 segregated 1:1 and 2:1 respectively (R:S) for FINALE™ resistance in the $T_2$ generation. ME07859 events were also tested for enhanced growth on the low nitrate media as well as for enhanced growth and photosynthetic efficiency on low ammonium nitrate media. No significant differences between the transgenics and the controls were observed.

TABLE 34 t-test comparison of seedling photosynthetic efficiency between transgenic seedlings and pooled non-transgenic segregants after 14 days of growth on low nitrate media.

| Line | Events | Transgenic Fv/Fm | n | Pooled Non-Transgenics Fv/Fm | n | t-test p-value |
|---|---|---|---|---|---|---|
| ME07859 | ME07859-02 ($T_2$) | 0.6598 | 24 | 0.6378 | 127 | 0.03 |
| ME07859 | ME07859-02 ($T_3$) | 0.6825 | 14 | 0.6378 | 127 | $1.3 \times 10^{-3}$ |
| ME07859 | ME07859-04 ($T_2$) | 0.6539 | 33 | 0.6378 | 127 | 0.05 |
| ME07859 | ME07859-04 ($T_3$) | 0.6601 | 17 | 0.6378 | 127 | 0.05 |

Events-02 and -04 of ME07859 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 33—Analysis of ME08464 Events

ME08464 contains Ceres Clone:424522 (SEQ ID NO:827) from *Zea mays*, which encodes a 500 amino acid unknown protein. Evaluation of low-nitrogen tolerance for ME08464 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -02 and -03, showed significantly increased photosynthetic efficiency on low ammonium nitrate-containing media relative to the internal controls in both generations at p≤0.05 using a one-tailed t-test assuming unequal variance. A summary of photosynthetic efficiency of ME07859 seedlings is shown in Table 35. Events-02 and -03 segregated 3:1 (R:S) for FINALE™ resistance in the $T_2$ generation. ME08464 events were also tested for increased photosynthetic efficiency on the low nitrate media. No significant differences between the transgenics and the controls were observed.

TABLE 35

T-test comparison of photosynthetic efficiency between transgenic seedlings and pooled non-transgenic segregants after 15 days of growth on low ammonium nitrate.

| Line | Events | Transgenic Fv/Fm | n | Pooled Non-Transgenics Fv/Fm | n | t-test p-value |
|---|---|---|---|---|---|---|
| ME08464 | ME08464-02 ($T_2$) | 0.65 | 41 | 0.62 | 40 | 0.015 |
| ME08464 | ME08464-02 ($T_3$) | 0.67 | 32 | 0.62 | 40 | $2.32 \times 10^{-4}$ |
| ME08464 | ME08464-03 ($T_2$) | 0.65 | 43 | 0.62 | 40 | 0.013 |
| ME08464 | ME08464-03 ($T_3$) | 0.65 | 42 | 0.62 | 40 | $6.85 \times 10^{-3}$ |

Events-02 and -03 of ME08464 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill)

Example 34—Analysis of ME09939 Events

ME09939 contains Ceres Clone:324216 (SEQ ID NO:852) from *Zea mays*, which encodes a 38 amino acid protein of unknown function. Evaluation of low-nitrogen tolerance for ME09939 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -04 and -05, showed significantly increased photosynthetic efficiency on low ammonium nitrate-containing media relative to the internal controls in both generations at p≤0.05 using a one-tailed t-test assuming unequal variance. A summary of photosynthetic efficiency of ME09939 seedlings is shown in Table 36. Events-04 and -05 segregated 15:1 and 3:1 respectively (R:S) for FINALE™ resistance in the $T_2$ generation. ME09939 events were also tested for enhanced growth on the low ammonium nitrate media. No significant differences between the transgenics and the controls were observed.

TABLE 36

T-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME09939 | ME09939-04 ($T_2$) | 0.49285 | 40 | 0.38571 | 7 | 0.05 |
| ME09939 | ME09939-04 ($T_3$) | 0.50697 | 34 | 0.38571 | 7 | $3.50 \times 10^{-2}$ |
| ME09939 | ME09939-05 ($T_2$) | 0.53487 | 39 | 0.47492 | 24 | $1.19 \times 10^{-2}$ |
| ME09939 | ME09939-05 ($T_3$) | 0.55341 | 32 | 0.47492 | 24 | $1.82 \times 10^{-3}$ |

Events-04 and -05 of ME09939 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 35—Analysis of ME1 1735 Events

ME11735 contains Ceres Annot:573161 (At5g43260, SEQ ID NO:854) from *Arabidopsis thaliana*, which encodes a 97 amino acid DnaJ-related chaperone protein. Evaluation of low-nitrogen tolerance for ME11735 in $1_2$ and $T_3$ was conducted under the same conditions as described in Example 2 and 3. A summary of the enhanced growth of ME11735 events on low nitrate-containing media is shown in Table 37. In this study, the seedling area for transgenic plants within an event was compared to the seedling area for non-transgenic segregants pooled across the same line. Two events, -04 and -05, were found significantly larger than the pooled non-transgenic segregants after 14 days of growth on low nitrate-containing media relative to the internal controls in both generations at $p \leq 0.05$ using a one-tailed t-test assuming unequal variance. ME11735 events were also tested for increased photosynthetic efficiency on the low nitrate media. No significant differences between the transgenics and the controls were observed. Events-04 and -05 segregated 40:1 and 4:1 respectively (R:S) for FINALE™ resistance in the $T_2$ generation.

TABLE 37 t-test comparison of seedling area between transgenic seedlings and pooled non-transgenic segregants after 14 days of growth on low nitrate.

| Line | Events | Transgenic Area | n | Pooled Non-Transgenics Area | n | t-test p-value |
|---|---|---|---|---|---|---|
| ME11735 | ME11735-04 ($T_2$) | 0.05820 | 41 | 0.04994 | 127 | $5.91 \times 10^{-5}$ |
| ME11735 | ME11735-04 ($T_3$) | 0.05553 | 42 | 0.04994 | 127 | $1.26 \times 10^{-2}$ |
| ME11735 | ME11735-05 ($T_2$) | 0.05788 | 37 | 0.04994 | 127 | $1.59 \times 10^{-3}$ |
| ME11735 | ME11735-05 ($T_3$) | 0.06011 | 13 | 0.04994 | 127 | $1.64 \times 10^{-2}$ |

Events-04 and -05 of ME11735 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 36—Analysis of ME12910 Events

ME12910 contains Ceres Annot:552727 (At2g22930, SEQ ID NO:890) from *Arabidopsis thaliana*, which encodes a 442 amino acid UDP-glucoronosyl and UDP-glucosyl transferase family protein. Evaluation of low-nitrogen tolerance for ME12910 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -03 and -05, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME12910 seedlings is shown in Table 38. ME12910 events were also tested for enhanced growth on the low ammonium nitrate media. No significant differences between the transgenics and the controls were observed.

TABLE 38 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME12910 | ME12910-03 ($T_2$) | 0.5851 | 39 | 0.5191 | 29 | $1.54 \times 10^{-3}$ |
| ME12910 | ME12910-03 ($T_3$) | 0.5861 | 22 | 0.5191 | 29 | $2.17 \times 10^{-3}$ |
| ME12910 | ME12910-05 ($T_2$) | 0.5523 | 44 | 0.4251 | 7 | $1.23 \times 10^{-2}$ |
| ME12910 | ME12910-05 ($T_3$) | 0.5600 | 42 | 0.4251 | 7 | $9.6 \times 10^{-3}$ |

Events-03 and -05 segregated 3:1 and 15:1 respectively (R:S) for FINALE™ resistance in the $T_2$ generation.

Events-03 and -05 of ME12910 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill)

Example 37—Analysis of ME12927 Event

ME12927 contains Ceres Clone:239806 (SEQ ID NO:916) from *Zea mays*, which encodes a 201 amino acid lipoprotein amino terminal region. Evaluation of low-nitrogen tolerance for ME12927 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Three events, -02, -03 and -05, showed significantly increased photosynthetic efficiency on low ammonium nitrate-containing media relative to the internal controls in both generations at $p \leq 0.05$, using a one-tailed t-test assuming unequal variance. A summary of photosynthetic efficiency of ME12927 seedlings is shown in Table 39.

TABLE 39 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME12927 | ME12927-02 ($T_2$) | 0.60843 | 44 | 0.47813 | 8 | $4.88 \times 10^{-3}$ |
| ME12927 | ME12927-02 ($T_3$) | 0.60867 | 36 | 0.47813 | 8 | $5.23 \times 10^{-3}$ |
| ME12927 | ME12927-03 ($T_2$) | 0.61906 | 32 | 0.57929 | 38 | $8.96 \times 10^{-3}$ |
| ME12927 | ME12927-03 ($T_3$) | 0.63437 | 19 | 0.57929 | 38 | $5.35 \times 10^{-4}$ |
| ME12927 | ME12927-05 ($T_2$) | 0.60581 | 43 | 0.53982 | 22 | $7.26 \times 10^{-3}$ |
| ME12927 | ME12927-05 ($T_3$) | 0.63145 | 29 | 0.53982 | 22 | $5.83 \times 10^{-4}$ |

ME12927 events were also tested for enhanced growth on the low ammonium nitrate media. A summary of the enhanced growth of ME11735 events on low ammonium nitrate-containing media is shown in Table 40. In this study, the seedling area for transgenic plants within an event was compared to the seedling area for non-transgenic segregants pooled across the same line. Three events, -02, -03 and -05, were found significantly larger than the pooled non-transgenic segregants after 18 days of growth on low ammonium nitrate-containing media relative to the internal controls in both generations at $p \leq 0.05$, using a one-tailed t-test assuming unequal variance.

TABLE 40 t-test comparison of seedling area between transgenic seedlings and pooled non-transgenic segregants after 18 days of growth on low ammonium nitrate.

| Line | Events | Transgenic Area | n | Pooled Non-Transgenics Area | n | t-test p-value |
|---|---|---|---|---|---|---|
| ME12927 | ME12927-02 ($T_2$) | 0.066920 | 44 | 0.056585 | 117 | $1.65 \times 10^{-4}$ |
| ME12927 | ME12927-02 ($T_3$) | 0.062119 | 36 | 0.056585 | 117 | $3.51 \times 10^{-2}$ |
| ME12927 | ME12927-03 ($T_2$) | 0.068972 | 32 | 0.056585 | 117 | $1.18 \times 10^{-5}$ |
| ME12927 | ME12927-03 ($T_3$) | 0.063716 | 19 | 0.056585 | 117 | $1.98 \times 10^{-2}$ |
| ME12927 | ME12927-05 ($T_2$) | 0.069972 | 43 | 0.056585 | 117 | $4.25 \times 10^{-6}$ |
| ME12927 | ME12927-05 ($T_3$) | 0.064014 | 29 | 0.056585 | 117 | $8.49 \times 10^{-3}$ |

Events 02, -03 and -05 segregated 15:1, 2:1 and 15:1 respectively (R:S) for FINALE™ resistance in the $T_2$ generation.

Events 02, -03 and -05 of ME12927 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill) in $T_1$ generation.

Example 38—Analysis of ME12929 Events

ME12929 contains Ceres Clone:208995 (SEQ ID NO:943) from *Zea mays*, which encodes a 94 amino acid protein of unknown function. Evaluation of low-nitrogen tolerance for ME12929 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -03 and -04, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME12929 seedlings is shown in Table 41. ME12929 events were also tested for enhanced growth on the low ammonium nitrate media. No significant differences between the transgenics and the controls were observed. Events-03 and -04 segregated 1:1 and 3:1 respectively (R:S) for FINALE™ resistance in the $T_2$ generation.

TABLE 41 t-test comparison of seedling photosynthetic efficiency between transgenic seedlings and pooled non-transgenic segregants after 14 days of growth on low ammonium nitrate.

| Line | Events | Transgenic Fv/Fm | n | Pooled Non-Transgenics Fv/Fm | n | t-test p-value |
|---|---|---|---|---|---|---|
| ME12929 | ME12929-03 ($T_2$) | 0.6410 | 33 | 0.5736 | 24 | $9.44 \times 10^{-4}$ |
| ME12929 | ME12929-03 ($T_3$) | 0.6610 | 41 | 0.5736 | 24 | $4.38 \times 10^{-5}$ |
| ME12929 | ME12929-04 ($T_2$) | 0.6544 | 47 | 0.5790 | 9 | $3.68 \times 10^{-2}$ |
| ME12929 | ME12929-04 ($T_3$) | 0.6663 | 43 | 0.5790 | 9 | $2.15 \times 10^{-2}$ |

Events-03 and -04 of ME12929 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill)

Example 39—Analysis of ME12954 Events

ME12954 contains Ceres Clone:225681 (SEQ ID NO:975) from *Zea mays*, which encodes a 286 amino acid protein of unknown function. Evaluation of low-nitrogen tolerance for ME12954 in $T_2$ and $T_3$ was conducted under the same conditions as described in Examples 2 and 3. Two events, -04 and -05, showed significantly increased photosynthetic efficiency on low ammonium nitrate-containing media relative to the internal controls in both generations at $p \leq 0.05$ using a one-tailed t-test assuming unequal variance. In this study, the seedling photosynthetic efficiency was measured as Fv/Fm comparing transgenic plants within an event to non-transgenic segregants pooled across the same plate. A summary of photosynthetic efficiency of ME12954 seedlings is shown in Table 42.

TABLE 42 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME12954 | ME12954-04 ($T_2$) | 0.6236 | 40 | 0.5973 | 152 | $6.61 \times 10^{-3}$ |
| ME12954 | ME12954-04 ($T_3$) | 0.6200 | 39 | 0.5973 | 152 | $1.97 \times 10^{-2}$ |
| ME12954 | ME12954-05 ($T_2$) | 0.6280 | 45 | 0.5973 | 152 | $1.79 \times 10^{-2}$ |
| ME12954 | ME12954-05 ($T_3$) | 0.6315 | 35 | 0.5973 | 152 | $2.85 \times 10^{-2}$ |

ME12954 events were also tested for enhanced growth on the low ammonium nitrate media. A summary of the enhanced growth of ME12954 events on low ammonium nitrate-containing media is shown in Table 43. In this study, the seedling area for transgenic plants within an event was compared to the seedling area for non-transgenic segregants pooled across the same line. Two events, -02 and -04, were found significantly larger than the pooled non-transgenic segregants after 18 days of growth on low ammonium nitrate-containing media relative to the internal controls in both generations at $p \leq 0.05$, using a one-tailed t-test assuming unequal variance.

TABLE 43 t-test comparison of seedling area between
transgenic seedlings and pooled non-transgenic segregants
after 18 days of growth on low ammonium nitrate.

| | | Transgenic | | Pooled Non-Transgenics | | t-test |
|---|---|---|---|---|---|---|
| Line | Events | Area | n | Area | n | p-value |
| ME12954 | ME12954-02 ($T_2$) | 0.06883 | 31 | 0.05579 | 152 | $1.86 \times 10^{-5}$ |
| ME12954 | ME12954-02 ($T_3$) | 0.06604 | 26 | 0.05579 | 152 | $1.48 \times 10^{-3}$ |
| ME12954 | ME12954-04 ($T_2$) | 0.06469 | 40 | 0.05579 | 152 | $1.95 \times 10^{-4}$ |
| ME12954 | ME12954-04 ($T_3$) | 0.06301 | 39 | 0.05579 | 152 | $3.32 \times 10^{-3}$ |

Events-02, -04 and -05 segregated 2:1, 3:1 and 15:1 respectively (R:S) for FINALE™ resistance in the T2 generation.

Events-02, -04 and -05 of ME12954 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 40 Analysis of ME12970 Events

ME12970 contains Ceres Clone:1387146 (SEQ ID NO:981) from *Zea mays*, which encodes a 147 amino acid C2 domain-containing protein. Evaluation of low-nitrogen tolerance for ME12970 in $T_2$ and $T_3$ was conducted under the same conditions as described in Examples 2 and 3. Two events, -02 and -03, showed significantly increased photosynthetic efficiency on low ammonium nitrate-containing media relative to the internal controls in both generations at p≤0.05 using a one-tailed t-test assuming unequal variance. In this study, the seedling photosynthetic efficiency was measured as Fv/Fm comparing transgenic plants within an event to non-transgenic segregants pooled across the same plate. A summary of photosynthetic efficiency of ME12970 seedlings is shown in Table 44. ME12970 events were also tested for enhanced growth on the low ammonium nitrate media. No significant differences between the transgenics and the controls were observed.

TABLE 44 t-test comparison of seedling photosynthetic efficiency
between transgenic seedlings and pooled non-transgenic
segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME12970 | ME12970-02 ($T_2$) | 0.55136 | 44 | 0.52401 | 108 | $3.78 \times 10^{-2}$ |
| ME12970 | ME12970-02 ($T_3$) | 0.58305 | 43 | 0.52401 | 108 | $1.89 \times 10^{-5}$ |
| ME12970 | ME12970-03 ($T_2$) | 0.58759 | 37 | 0.52401 | 108 | $2.14 \times 10^{-6}$ |
| ME12970 | ME12970-03 ($T_3$) | 0.59131 | 29 | 0.52401 | 108 | $3.05 \times 10^{-6}$ |

Events-02 and -03 segregated 15:1 and 3:1 respectively (R:S) for FINALE™ resistance in the T2 generation.

Events-02 and -03 of ME12970 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 41—Analysis of ME13006 Events

ME13006 contains Ceres Clone:1017441 (SEQ ID NO:224) from *Triticum aestivum*, which encodes a 143 amino acid polypeptide, predicted to be a homolog of Ceres Clone:4898 (ME03123, SEQ ID NO:217). Evaluation of low-nitrogen tolerance for ME13006 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -03, showed significantly increased photosynthetic efficiency on low ammonium nitrate-containing media relative to the internal controls in both generations at p≤0.05 using a one-tailed t-test assuming unequal variance. A summary of photosynthetic efficiency of ME13006 seedlings is shown in Table 45. ME13006 events were also tested for enhanced growth on the low nitrate media. No significant differences between the transgenics and the controls were observed.

TABLE 45 t-test comparison of seedling area between transgenic
seedlings and pooled non-transgenic segregants
after 14 days of growth on low ammonium nitrate.

| | | Transgenic | | Pooled Non-Transgenics | | t-test |
|---|---|---|---|---|---|---|
| Line | Events | Area | n | Area | n | p-value |
| ME13006 | ME13006-01 ($T_2$) | 0.0777 | 42 | 0.0648 | 7 | $3.29 \times 10^{-2}$ |
| ME13006 | ME13006-01 ($T_3$) | 0.0660 | 28 | 0.0540 | 19 | $1.49 \times 10^{-3}$ |
| ME13006 | ME13006-03 ($T_2$) | 0.0706 | 21 | 0.0601 | 29 | $4.83 \times 10^{-3}$ |
| ME13006 | ME13006-03 ($T_3$) | 0.0758 | 14 | 0.0617 | 33 | $2.60 \times 10^{-3}$ |

Events-01 and -03 segregated 3:1 and 1:1 respectively (R:S) for FINALE™ resistance in the $1'_2$ generation.

Events-01 and -03 of ME13006 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 42—Analysis of ME13021 Events

ME13021 contains Ceres Clone:244306 (SEQ ID NO:1053) from *Zea mays*, which encodes a 572 amino acid TCP-1/cpn60 chaperonin family protein. Evaluation of low-nitrogen tolerance for ME in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -04 and -05, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME13021 seedlings is shown in Table 46. ME13021 events were also tested for enhanced growth on the low ammonium nitrate media. No significant differences between the transgenics and the controls were observed.

TABLE 46 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME13021 | ME13021-04 ($T_2$) | 0.56697 | 39 | 0.49440 | 10 | $2.47 \times 10^{-2}$ |
| ME13021 | ME13021-04 ($T_3$) | 0.59916 | 37 | 0.48685 | 13 | $1.54 \times 10^{-3}$ |
| ME13021 | ME13021-05 ($T_2$) | 0.60575 | 32 | 0.50344 | 18 | $6.05 \times 10^{-4}$ |
| ME13021 | ME13021-05 ($T_3$) | 0.64400 | 23 | 0.55638 | 26 | $3.86 \times 10^{-6}$ |

Events-04 and -05 segregated 3:1 and 2:1 respectively (R:S) for FINALE™ resistance in the T2 generation.

Events-04 and -05 of ME13021 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill) in T1 generation.

Example 43—Analysis of ME13064 Events

ME13064 contains Ceres Clone:1408950 (SEQ ID NO:1098) from *Zea mays*, which encodes a 152 amino acid protein of unknown function. Evaluation of low-nitrogen tolerance for ME13064 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -03 and -04, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME13064 seedlings is shown in Table 47. ME13064 events were also tested for enhanced growth on the low ammonium nitrate media. No significant differences between the transgenics and the controls were observed.

TABLE 47 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME13064 | ME13064-03 ($T_2$) | 0.59444 | 27 | 0.54793 | 28 | $5.84 \times 10^{-3}$ |
| ME13064 | ME13064-03 ($T_3$) | 0.59676 | 29 | 0.54793 | 28 | $1.25 \times 10^{-2}$ |

TABLE 47-continued t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME13064 | ME13064-04 ($T_2$) | 0.58577 | 31 | 0.51053 | 40 | $2.05 \times 10^{-3}$ |
| ME13064 | ME13064-04 ($T_3$) | 0.59128 | 25 | 0.51053 | 40 | $8.93 \times 10^{-4}$ |

Events-03 and -04 segregated 2:1 (R:S) for FINALE™ resistance in the T2 generation.

Events-03 and -04 of ME13064 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill) in T1 generation.

Example 44—Analysis of ME13071 Events

ME13071 contains Ceres Clone:208453 (SEQ ID NO:1111) from *Zea mays*, which encodes a 74 amino acid protein of unknown function. Evaluation of low-nitrogen tolerance for ME13071 in $1_2$ and $T_3$ was conducted under the same conditions as described in Examples 2 and 3. Two events, -03 and -05, showed significantly enhanced growth on low nitrate- and low ammonium nitrate-containing media relative to the internal controls in $T_2$ generation at $p \leq 0.05$ using a one-tailed t-test assuming unequal variance. In this study, the seedling area for transgenic plants within an event was compared to the seedling area for non-transgenic segregants pooled across the same line. A summary of enhanced growth under low ammonium nitrate growth conditions of ME13071 seedlings is shown in Table 48. ME13071 events were also tested for photosynthetic efficiency on the low ammonium nitrate media. No significant differences between the transgenics and the controls were observed.

TABLE 48 t-test comparison of seedling area between transgenic seedlings and pooled non-transgenic segregants after 18 days of growth on low ammonium nitrate.

| Line | Events | Transgenic Area | n | Pooled Non-Transgenics Area | n | t-test p-value |
|---|---|---|---|---|---|---|
| ME13071 | ME13071-03 ($T_2$) | 0.06694 | 26 | 0.05915 | 19 | $3.55 \times 10^{-3}$ |
| ME13071 | ME13071-03 ($T_3$) | 0.07787 | 24 | 0.07040 | 22 | $3.65 \times 10^{-2}$ |
| ME13071 | ME13071-05 ($T_2$) | 0.06232 | 32 | 0.05491 | 16 | $2.07 \times 10^{-3}$ |
| ME13071 | ME13071-05 ($T_3$) | 0.06335 | 22 | 0.05626 | 28 | $1.09 \times 10^{-2}$ |

Events-03 and -05 segregated 1:1 and 2:1 respectively (R:S) for FINALE™ resistance in the T2 generation.

Events-03 and -05 of ME13071 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 45—Analysis of ME13087 Events

ME13087 contains Ceres Clone:968180 (SEQ ID NO:1115) from *Brassica napus*, which encodes a 159 amino acid zinc finger protein. Evaluation of low-nitrogen tolerance for ME13087 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Four events, -01, -02, -03 and -04, showed significantly increased photosynthetic efficiency on low ammonium nitrate-containing media relative to the internal controls in both generations at p≤0.05 using a one-tailed t-test assuming unequal variance. A summary of photosynthetic efficiency of ME13087 seedlings is shown in Table 49. ME13087 events were also tested for enhanced growth on the low ammonium nitrate media. No significant differences between the transgenics and the controls were observed.

TABLE 49 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME13087 | ME13087-01 ($T_2$) | 0.59761 | 23 | 0.56163 | 38 | $9.61 \times 10^{-3}$ |
| ME13087 | ME13087-01 ($T_3$) | 0.61247 | 15 | 0.56163 | 38 | $5.99 \times 10^{-4}$ |
| ME13087 | ME13087-02 ($T_2$) | 0.63400 | 39 | 0.58532 | 34 | $9.30 \times 10^{-3}$ |
| ME13087 | ME13087-02 ($T_3$) | 0.63442 | 26 | 0.58532 | 34 | $1.22 \times 10^{-2}$ |
| ME13087 | ME13087-03 ($T_2$) | 0.61429 | 38 | 0.55533 | 24 | $5.04 \times 10^{-3}$ |
| ME13087 | ME13087-03 ($T_3$) | 0.62283 | 35 | 0.55533 | 24 | $3.31 \times 10^{-3}$ |
| ME13087 | ME13087-04 ($T_2$) | 0.62714 | 28 | 0.60068 | 56 | $3.02 \times 10^{-2}$ |
| ME13087 | ME13087-04 ($T_3$) | 0.64543 | 7 | 0.60068 | 56 | $9.04 \times 10^{-3}$ |

Events-01, -02, -03 and -04 segregated 2:1, 3:1, 3:1 and 2:1 respectively (R:S) for FINALE™ resistance in the T2 generation.

Events-01, -02, -03 and -04 of ME13087 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill) in T1 generation Example 46—Analysis of ME13106 Events ME13106 contains Ceres Clone:986438 (SEQ ID NO:1156) from *Zea mays*, which encodes a 188 amino acid protein of unknown function. Evaluation of low-nitrogen tolerance for ME13106 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -03 and -04, showed significantly increased photosynthetic efficiency on low ammonium nitrate-containing media relative to the internal controls in both generations at p≤0.05 using a one-tailed t-test assuming unequal variance. A summary of photosynthetic efficiency of ME13106 seedlings is shown in Table 50. ME13106 events were also tested for enhanced growth on the low ammonium nitrate media. No significant differences between the transgenics and the controls were observed.

TABLE 50 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME13106 | ME13106-03 ($T_2$) | 0.62726 | 27 | 0.58600 | 43 | $1.50 \times 10^{-2}$ |
| ME13106 | ME13106-03 ($T_3$) | 0.65163 | 30 | 0.58600 | 43 | $1.69 \times 10^{-4}$ |
| ME13106 | ME13106-04 ($T_2$) | 0.60836 | 36 | 0.55876 | 25 | $2.62 \times 10^{-2}$ |
| ME13106 | ME13106-04 ($T_3$) | 0.64250 | 38 | 0.55876 | 25 | $5.01 \times 10^{-4}$ |

Events-03 and -04 segregated 1:1 and 3:1 respectively (R:S) for FINALE™ resistance in the $T_2$ generation.

Events-03 and -04 of ME13106 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill)

Example 47—Analysis of ME13107 Events

ME13107 contains Ceres Clone:996227 (SEQ ID NO:1158) from *Zea mays*, which encodes a 240 amino acid zein seed storage protein. Evaluation of low-nitrogen tolerance for ME13107 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Three events, -02, -04 and -05, showed significantly increased photosynthetic efficiency on low ammonium nitrate-containing media relative to the internal controls in both generations at p≤0.05 using a one-tailed t-test assuming unequal variance. A summary of photosynthetic efficiency of ME13107 seedlings is shown in Table 51.

TABLE 51 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME13107 | ME13107-02 ($T_2$) | 0.63122 | 37 | 0.56643 | 21 | $1.07 \times 10^{-2}$ |
| ME13107 | ME13107-02 ($T_3$) | 0.63848 | 29 | 0.56643 | 21 | $6.03 \times 10^{-3}$ |
| ME13107 | ME13107-04 ($T_2$) | 0.62948 | 27 | 0.55918 | 50 | $2.07 \times 10^{-5}$ |

TABLE 51-continued t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME13107 | ME13107-04 ($T_3$) | 0.63019 | 21 | 0.55918 | 50 | $6.72 \times 10^{-5}$ |
| ME13107 | ME13107-05 ($T_2$) | 0.61952 | 29 | 0.54440 | 48 | $7.85 \times 10^{-5}$ |
| ME13107 | ME13107-05 ($T_3$) | 0.62185 | 20 | 0.54440 | 48 | $4.02 \times 10^{-5}$ |

ME13107 events were also tested for enhanced growth on the low ammonium nitrate media. Two events, -02 and -04, showed significantly enhanced growth on low ammonium nitrate-containing media relative to the internal controls in $T_2$ generation at p 0.05 using a one-tailed t-test assuming unequal variance. In this study, the seedling area for transgenic plants within an event was compared to the seedling area for non-transgenic segregants pooled across the same line. A summary of enhanced growth under low ammonium nitrate growth conditions of ME13071 seedlings is shown in Table 52.

TABLE 52 t-test comparison of seedling area between transgenic seedlings and pooled non-transgenic segregants after 18 days of growth on low ammonium nitrate.

| Line | Events | Transgenic Area | n | Pooled Non-Transgenics Area | n | t-test p-value |
|---|---|---|---|---|---|---|
| ME13107 | ME13107-02 ($T_2$) | 0.07738 | 37 | 0.06919 | 203 | $3.63 \times 10^{-2}$ |
| ME13107 | ME13107-02 ($T_3$) | 0.07688 | 29 | 0.06919 | 203 | $4.60 \times 10^{-2}$ |
| ME13107 | ME13107-04 ($T_2$) | 0.07514 | 27 | 0.06919 | 203 | $3.18 \times 10^{-2}$ |
| ME13107 | ME13107-04 ($T_3$) | 0.07585 | 21 | 0.06919 | 203 | $2.27 \times 10^{-2}$ |

Events-02, -04 and -05 segregated 3:1, 1:1 and 2:1 respectively (R:S) for FINALE™ resistance in the $T_2$ generation.

Events-02, -04 and -05 of ME13107 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 48—Analysis of ME13108 Events

ME13108 contains Ceres Clone:996263 (SEQ ID NO:1165) from *Zea mays*, which encodes an 84 amino acid BRICK1 protein. Evaluation of low-nitrogen tolerance for ME13108 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Three events, -01, -04 and -05, showed significantly increased photosynthetic efficiency on low ammonium nitrate-containing media relative to the internal controls in both generations at p≤0.05 using a one-tailed t-test assuming unequal variance. A summary of photosynthetic efficiency of ME13108 seedlings is shown in Table 53. ME13108 events were also tested for enhanced growth on the low ammonium nitrate media. No significant differences between the transgenics and the controls were observed.

TABLE 53 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME13108 | ME13108-01 ($T_2$) | 0.56703 | 36 | 0.53932 | 195 | $1.97 \times 10^{-2}$ |
| ME13108 | ME13108-01 ($T_3$) | 0.59250 | 26 | 0.53932 | 195 | $3.64 \times 10^{-4}$ |
| ME13108 | ME13108-04 ($T_2$) | 0.60032 | 37 | 0.53932 | 195 | $3.37 \times 10^{-7}$ |
| ME13108 | ME13108-04 ($T_3$) | 0.60463 | 30 | 0.53932 | 195 | $4.10 \times 10^{-5}$ |
| ME13108 | ME13108-05 ($T_2$) | 0.60727 | 30 | 0.53932 | 195 | $4.97 \times 10^{-9}$ |
| ME13108 | ME13108-05 ($T_3$) | 0.61850 | 32 | 0.53932 | 195 | $2.35 \times 10^{-9}$ |

Events-01, -04 and -05 segregated 3:1 (R:S) for FINALE™ resistance in the $T_2$ generation.

Events-01, -04 and -05 of ME13108 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 49—Analysis of ME13110 Events

ME13110 contains Ceres Clone:988083 (SEQ ID NO:1184) from *Zea mays*, which encodes a 188 amino acid protein of unknown function. Evaluation of low-nitrogen tolerance for ME13110 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Three events, -03, -04 and -05, showed significantly increased photosynthetic efficiency on low ammonium nitrate-containing media relative to the internal controls in both generations at p≤0.05 using a one-tailed t-test assuming unequal variance. A summary of photosynthetic efficiency of ME13110 seedlings is shown in Table 54. ME13110 events were also tested for enhanced growth on the low ammonium nitrate media. No significant differences between the transgenics and the controls were observed.

TABLE 54 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME13110 | ME13110-03 ($T_2$) | 0.5721 | 34 | 0.3948 | 16 | $8.92 \times 10^{-3}$ |
| ME13110 | ME13110-03 ($T_3$) | 0.5773 | 24 | 0.4583 | 26 | $4.58 \times 10^{-4}$ |
| ME13110 | ME13110-04 ($T_2$) | 0.5651 | 35 | 0.4243 | 15 | $4.34 \times 10^{-2}$ |

TABLE 54-continued t-test comparison of seedling photosynthetic efficiency
between transgenic seedlings and pooled non-transgenic
segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME13110 | ME13110-04 ($T_3$) | 0.6000 | 10 | 0.4594 | 40 | $3.29 \times 10^{-3}$ |
| ME13110 | ME13110-05 ($T_2$) | 0.5143 | 28 | 0.3809 | 22 | $2.24 \times 10^{-2}$ |
| ME13110 | ME13110-05 ($T_3$) | 0.5278 | 28 | 0.3688 | 21 | $1.28 \times 10^{-2}$ |

Events-03, -04 and -05 segregated 3:1, 1:1 and 3:1 respectively (R:S) for FINALE™ resistance in the $T_2$ generation.

Events-03, -04 and -05 of ME13110 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 50—Analysis of ME13125 Events

ME13125 contains Ceres Clone:732 (At3g50880, SEQ ID NO:1193) from *Arabidopsis thaliana*, which encodes a 188 amino acid protein of unknown function. Evaluation of low-nitrogen tolerance for ME13125 in $T_2$ and $T_3$ was conducted under the same conditions as described in Examples 2 and 3. In this study, the seedling photosynthetic efficiency was measured as Fv/Fm comparing transgenic plants within an event to non transgenic segregants pooled across the same plate. Three events, -01, -03 and -05, showed significantly increased photosynthetic efficiency on low ammonium nitrate-containing media relative to the internal controls in both generations at p≤0.05 using a one-tailed t-test assuming unequal variance. A summary of photosynthetic efficiency of ME13125 seedlings is shown in Table 55. ME13125 events were also tested for enhanced growth on the low ammonium nitrate media. No significant differences between the transgenics and the controls were observed.

TABLE 55 t-test comparison of seedling photosynthetic efficiency
between transgenic seedlings and pooled non-transgenic
segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME13125 | ME13125-01 ($T_2$) | 0.61129 | 42 | 0.53829 | 125 | $4.82 \times 10^{-7}$ |
| ME13125 | ME13125-01 ($T_3$) | 0.61929 | 38 | 0.53829 | 125 | $1.96 \times 10^{-7}$ |
| ME13125 | ME13125-03 ($T_2$) | 0.63360 | 45 | 0.53829 | 125 | $3.05 \times 10^{-13}$ |
| ME13125 | ME13125-03 ($T_3$) | 0.62218 | 44 | 0.53829 | 125 | $3.81 \times 10^{-9}$ |
| ME13125 | ME13125-05 ($T_2$) | 0.61565 | 31 | 0.53829 | 125 | $4.12 \times 10^{-8}$ |
| ME13125 | ME13125-05 ($T_3$) | 0.58469 | 16 | 0.53829 | 125 | 0.05 |

Events-01, -03 and -05 segregated 3:1, 15:1 and 2:1 respectively (R:S) for FINALE™ resistance in the $T_2$ generation.

Events-01, -03 and -05 of ME13125 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 51—Analysis of ME13149 Events

ME13149 contains Ceres Clone:2267 (At2g24765, SEQ ID NO:1209) from *Arabidopsis thaliana*, which encodes a 182 amino acid ADP-ribosylation factor 3 protein. Evaluation of low-nitrogen tolerance for ME13149 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -02 and -03, showed significantly increased photosynthetic efficiency on low ammonium nitrate-containing media relative to the internal controls in both generations at p≤0.05 using a one-tailed t-test assuming unequal variance. A summary of photosynthetic efficiency of ME13149 seedlings is shown in Table 56. ME13149 events were also tested for enhanced growth on the low ammonium nitrate media. No significant differences between the transgenics and the controls were observed.

TABLE 56 t-test comparison of seedling photosynthetic efficiency
between transgenic seedlings and pooled non-transgenic
segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME13149 | ME13149-02 ($T_2$) | 0.55623 | 30 | 0.51138 | 55 | $2.29 \times 10^{-2}$ |
| ME13149 | ME13149-02 ($T_3$) | 0.54818 | 17 | 0.51138 | 55 | $4.56 \times 10^{-2}$ |
| ME13149 | ME13149-03 ($T_2$) | 0.55998 | 42 | 0.51138 | 55 | $5.11 \times 10^{-3}$ |
| ME13149 | ME13149-03 ($T_3$) | 0.58450 | 24 | 0.51138 | 55 | $2.77 \times 10^{-4}$ |

Events-02 and -03 segregated 2:1 and 15:1 respectively (R:S) for FINALE™ resistance in the $1'_2$ generation.

Events-02 and -03 of ME13149 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 52—Analysis of ME13151 Events

ME13151 contains Ceres Clone:39358 (At3g25150, SEQ ID NO:1273) from *Arabidopsis thaliana*, which encodes a 488 amino acid nuclear transport factor 2 (NTF2) domain protein. Evaluation of low-nitrogen tolerance for ME13151 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -02, showed significantly increased photosynthetic efficiency on low ammonium nitrate-containing media relative to the internal controls in both generations at p≤0.05 using a one-tailed t-test assuming unequal variance. A summary of photosynthetic efficiency of ME13151 seedlings is shown in Table 57. ME13151 events were also tested for enhanced growth on the low ammonium nitrate media. No significant differences between the transgenics and the controls were observed.

TABLE 57

T-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME13151 | ME13151-01 ($T_2$) | 0.62593 | 44 | 0.53141 | 17 | $8.58 \times 10^{-4}$ |
| ME13151 | ME13151-01 ($T_3$) | 0.59936 | 33 | 0.53141 | 17 | $1.21 \times 10^{-2}$ |
| ME13151 | ME13151-02 ($T_2$) | 0.59879 | 39 | 0.46956 | 16 | $3.08 \times 10^{-5}$ |
| ME13151 | ME13151-02 ($T_3$) | 0.59566 | 32 | 0.46956 | 16 | $4.28 \times 10^{-5}$ |

Events-01 and -02 segregated 9:1 and 6:1 respectively (R:S) for FINALE™ resistance in the T2 generation.

Events-01 and -02 of ME13151 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 53—Analysis of ME13153 Events

ME13153 contains Ceres Clone:115046 (At3g17760, SEQ ID NO:1301) from *Arabidopsis thaliana*, which encodes a 494 amino acid glutamate decarboxylase. Evaluation of low-nitrogen tolerance for ME13153 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -03 and -04, showed significantly increased photosynthetic efficiency on low ammonium nitrate-containing media relative to the internal controls in both generations at p≤0.05 using a one-tailed t-test assuming unequal variance. A summary of photosynthetic efficiency of ME13153 seedlings is shown in Table 58. ME13153 events were also tested for increased photosynthetic efficiency on the low nitrate media. No significant differences between the transgenics and the controls were observed.

TABLE 58

T-test comparison of seedling photosynthetic efficiency between transgenic seedlings and non-transgenic segregants after 14 days of growth on low ammonium nitrate.

| Line | Events | Transgenic Fv/Fm | n | Pooled Non-Transgenics Fv/Fm | n | t-test p-value |
|---|---|---|---|---|---|---|
| ME13153 | ME13153-03 ($T_2$) | 0.62 | 34 | 0.56 | 16 | $3.0 \times 10^{-2}$ |
| ME13153 | ME13153-03 ($T_3$) | 0.60 | 19 | 0.54 | 22 | $2.9 \times 10^{-2}$ |
| ME13153 | ME13153-04 ($T_2$) | 0.57 | 32 | 0.50 | 18 | $4.3 \times 10^{-2}$ |
| ME13153 | ME13153-04 ($T_3$) | 0.61 | 24 | 0.55 | 24 | $2.1 \times 10^{-2}$ |

Events-03 and -04 segregated 3:1 (R:S) for FINALE™ resistance in the $T_2$ generation.

Events-03 and -04 of ME13153 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting. Events-03 and -04 yielded slightly less seed per plant compared to the controls, but these differences are not significant at p≤0.10.

Example 54—Analysis of ME13177 Events

ME13177 contains Ceres Clone:339439 (SEQ ID NO:1341) from *Zea mays*, which encodes a 345 amino acid cyclin C-terminal domain protein. Evaluation of low-nitrogen tolerance for ME13177 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -02, showed significantly increased photosynthetic efficiency on low ammonium nitrate-containing media relative to the internal controls in both generations at p≤0.05 using a one-tailed t-test assuming unequal variance. A summary of photosynthetic efficiency of ME13177 seedlings is shown in Table 59. ME13177 events were also tested for enhanced growth on the low ammonium nitrate media. No significant differences between the transgenics and the controls were observed.

TABLE 59 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME13177 | ME13177-01 ($T_2$) | 0.6315 | 32 | 0.6112 | 175 | $2.43 \times 10^{-2}$ |
| ME13177 | ME13177-01 ($T_3$) | 0.6407 | 29 | 0.6112 | 175 | $7.33 \times 10^{-3}$ |
| ME13177 | ME13177-02 ($T_2$) | 0.6400 | 41 | 0.6112 | 175 | $1.23 \times 10^{-3}$ |
| ME13177 | ME13177-02 ($T_3$) | 0.6499 | 20 | 0.6112 | 175 | $6.47 \times 10^{-3}$ |

Events-01 and -02 segregated 2:1 and 3:1 respectively (R:S) for FINALE™ resistance in the $T_2$ generation.

Events-01 and -02 of ME13177 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 55—Analysis of ME13200 Events

ME13200 contains Ceres Clone:896483 (SEQ ID NO:1384) from *Zea mays*, which encodes an 85 amino acid myb family transcription factor. Evaluation of low-nitrogen tolerance for ME13200 in $T_2$ and $T_3$ was conducted under the same conditions as described in Examples 2 and 3. A summary of the enhanced growth of ME13200 events on low ammonium nitrate-containing media is shown in Table 60. In this study, the seedling area for transgenic plants within an event was compared to the seedling area for non-transgenic segregants pooled across the same line. Two events, -03 and -04, were found significantly larger than the pooled non-transgenic segregants after 18 days of growth on low ammonium nitrate-containing media relative to the internal controls in both generations at $p \leq 0.05$ using a one-tailed t-test assuming unequal variance. ME13200 events were also tested for increased photosynthetic efficiency on the low ammonium nitrate media as well as for enhanced photosynthesis and growth on low nitrate media. No significant differences between the transgenics and the controls were observed.

TABLE 60 t-test comparison of seedling area between transgenic seedlings and pooled non-transgenic segregants after 18 days of growth on low ammonium nitrate.

| Line | Events | Transgenic | | Pooled Non-Transgenics | | t-test |
|------|--------|------|---|------|---|---------|
| | | Area | n | Area | n | p-value |
| ME13200 | ME13200-03 ($T_2$) | 0.07366 | 43 | 0.06342 | 35 | $4.09 \times 10^{-4}$ |
| ME13200 | ME13200-03 ($T_3$) | 0.08193 | 34 | 0.06342 | 35 | $2.37 \times 10^{-3}$ |
| ME13200 | ME13200-04 ($T_2$) | 0.07377 | 48 | 0.06342 | 35 | $4.87 \times 10^{-4}$ |
| ME13200 | ME13200-04 ($T_3$) | 0.07530 | 47 | 0.06342 | 35 | $1.88 \times 10^{-4}$ |

Events-03 and -04 segregated 3:1 and 15:1 respectively respectively (R:S) for FINALE™ resistance in the $T_2$ generation.

Events-03 and -04 of ME13200 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 56 Analysis of ME13204 Events

ME13204 contains Ceres Clone:995409 (SEQ ID NO:1408) from *Zea mays*, which encodes a 178 amino acid protein of unknown function. Evaluation of low-nitrogen tolerance for ME13204 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -05, showed significantly increased photosynthetic efficiency on low nitrate-containing media relative to the internal controls in both generations at $p \leq 0.05$ using a one-tailed t-test assuming unequal variance. A summary of photosynthetic efficiency of ME13204 seedlings is shown in Table 61. ME13204 events were also tested for enhanced growth on the low nitrate media as well as for enhanced growth and photosynthetic efficiency on low ammonium nitrate media. No significant differences between the transgenics and the controls were observed.

TABLE 61

T-test comparison of seedling photosynthetic efficiency between transgenic seedlings and pooled non-transgenic segregants after 14 days of growth on low nitrate media.

| Line | Events | Transgenic | | Pooled Non-Transgenics | | t-test |
|------|--------|------|---|------|---|---------|
| | | Fv/Fm | n | Fv/Fm | n | p-value |
| ME13204 | ME13204-01 ($T_2$) | 0.5874 | 45 | 0.5354 | 46 | $1.41 \times 10^{-2}$ |
| ME13204 | ME13204-01 ($T_3$) | 0.5932 | 36 | 0.5354 | 46 | $9.85 \times 10^{-3}$ |
| ME13204 | ME13204-05 ($T_2$) | 0.5855 | 34 | 0.5354 | 46 | $2.00 \times 10^{-2}$ |
| ME13204 | ME13204-05 ($T_3$) | 0.5998 | 20 | 0.5354 | 46 | $5.58 \times 10^{-3}$ |

Events-01 and -05 segregated 9:1 and 3:1 respectively (R:S) for FINALE™ resistance in the $T_2$ generation.

Events-01 and -05 of ME13204 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 57—Analysis of ME14649 Events

ME14649 contains Ceres Annot:850581 (At5g01880, SEQ ID NO:1427) from *Arabidopsis thaliana*, which encodes a 159 amino acid zinc finger protein. Evaluation of low-nitrogen tolerance for ME14649 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -02 and -03, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME14649 seedlings is shown in Table 62. ME14649 events were also tested for enhanced growth on the low ammonium nitrate media. No significant differences between the transgenics and the controls were observed.

TABLE 62 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME14649 | ME14649-02 ($T_2$) | 0.59789 | 35 | 0.54533 | 30 | $1.54 \times 10^{-4}$ |
| ME14649 | ME14649-02 ($T_3$) | 0.58154 | 26 | 0.54533 | 30 | $3.42 \times 10^{-2}$ |
| ME14649 | ME14649-03 ($T_2$) | 0.61875 | 28 | 0.56539 | 33 | $2.03 \times 10^{-3}$ |
| ME14649 | ME14649-03 ($T_3$) | 0.62630 | 27 | 0.56539 | 33 | $9.18 \times 10^{-4}$ |

Events-02 and -03 segregated 3:1 and 2:1 respectively (R:S) for FINALE™ resistance in the $T_2$ generation.

Events-02 and -03 of ME14649 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill) in T1 generation.

Example 58—Analysis of ME16546 Events

ME16546 contains Ceres Annot:862321 (At2g45360, SEQ ID NO:1462) from *Arabidopsis thaliana*, which encodes a 215 amino acid protein of unknown function. Evaluation of low-nitrogen tolerance for ME16546 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -04 and -05, showed significantly increased photosynthetic efficiency on low ammonium nitrate-containing media relative to the internal controls in both generations at p≤0.05 using a one-tailed t-test assuming unequal variance. A summary of photosynthetic efficiency of ME16546 seedlings is shown in Table 63. ME16546 events were also tested for enhanced growth on the low ammonium nitrate media. No significant differences between the transgenics and the controls were observed.

TABLE 63 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME16546 | ME16546-04 ($T_2$) | 0.59891 | 33 | 0.56124 | 130 | $2.21 \times 10^{-4}$ |
| ME16546 | ME16546-04 ($T_3$) | 0.57924 | 41 | 0.56124 | 130 | $3.77 \times 10^{-2}$ |
| ME16546 | ME16546-05 ($T_2$) | 0.58861 | 36 | 0.56124 | 130 | $7.17 \times 10^{-3}$ |
| ME16546 | ME16546-05 ($T_3$) | 0.61763 | 27 | 0.56124 | 130 | $3.25 \times 10^{-6}$ |

Events-04 and -05 segregated 2:1 and 3:1 respectively (R:S) for FINALE™ resistance in the $1'_2$ generation.

Events-04 and -05 of ME16546 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 59—Analysis of ME17457 Events

ME17457 contains Ceres Annot:839064 (At1g80600, SEQ ID NO:1478) from *Arabidopsis thaliana*, which encodes a 457 acetylornithine aminotransferase, a member of the Class-III aminotransferase family. This is a homolog of Ceres Clone:19586 (ME01463, SEQ ID NO:76). Evaluation of low-nitrogen tolerance for ME17457 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Four events, -02, -03, -05 and -06, showed significantly increased photosynthetic efficiency on low ammonium nitrate-containing media relative to the internal controls in both generations at p≤0.05 using a one-tailed t-test assuming unequal variance. A summary of photosynthetic efficiency of ME17457 seedlings is shown in Table 64. ME17457 events were also tested for enhanced growth on the low ammonium nitrate media. No significant differences between the transgenics and the controls were observed.

TABLE 64 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME17457 | ME17457-02 ($T_2$) | 0.60800 | 21 | 0.50878 | 46 | $6.99 \times 10^{-4}$ |
| ME17457 | ME17457-02 ($T_3$) | 0.59539 | 18 | 0.50878 | 46 | $9.02 \times 10^{-3}$ |
| ME17457 | ME17457-03 ($T_2$) | 0.55164 | 11 | 0.49673 | 45 | $3.45 \times 10^{-2}$ |
| ME17457 | ME17457-03 ($T_3$) | 0.57356 | 18 | 0.49673 | 45 | $2.49 \times 10^{-3}$ |
| ME17457 | ME17457-05 ($T_2$) | 0.52928 | 18 | 0.42672 | 32 | $2.23 \times 10^{-3}$ |
| ME17457 | ME17457-05 ($T_3$) | 0.56660 | 25 | 0.42672 | 32 | $5.97 \times 10^{-5}$ |
| ME17457 | ME17457-06 ($T_2$) | 0.54088 | 33 | 0.47350 | 30 | $3.59 \times 10^{-4}$ |
| ME17457 | ME17457-06 ($T_3$) | 0.52210 | 21 | 0.47350 | 30 | $2.03 \times 10^{-2}$ |

Events-02, -03 and -05 segregated 1:1, and Event -06 segregated 3:1 (R:S) for FINALE™ resistance in the $T_2$ generation.

Events-02, -03, -05 and -06 of ME17457 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 60—Analysis of ME17567 Events

ME17567 contains Ceres Annot:864666 (At1g16320, SEQ ID NO:1490) from *Arabidopsis thaliana*, which encodes a 273 amino acid protein of unknown function.

Evaluation of low-nitrogen tolerance for ME17567 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -04, showed significantly increased photosynthetic efficiency on low nitrate-containing media relative to the internal controls in both generations at $p \leq 0.05$ using a one-tailed t-test assuming unequal variance. A summary of photosynthetic efficiency of ME17567 seedlings is shown in Table 65. ME17567 events were also tested for enhanced growth on the low nitrate media as well as enhanced photosynthetic efficiency and growth on low ammonium nitrate media. No significant differences between the transgenics and the controls were observed.

TABLE 65 t-test comparison of seedling photosynthetic efficiency between transgenic seedlings and pooled non-transgenic segregants after 14 days of growth on low nitrate.

| Line | Events | Transgenic Fv/Fm | n | Pooled Non-Transgenics Fv/Fm | n | t-test p-value |
|---|---|---|---|---|---|---|
| ME17567 | ME17567-01 ($T_2$) | 0.605455 | 33 | 0.474791 | 67 | $9.69 \times 10^{-10}$ |
| ME17567 | ME17567-01 ($T_3$) | 0.6244 | 20 | 0.474791 | 67 | $6.79 \times 10^{-13}$ |
| ME17567 | ME17567-04 ($T_2$) | 0.57727 | 37 | 0.474791 | 67 | $1.22 \times 10^{-7}$ |
| ME17567 | ME17567-04 ($T_3$) | 0.615143 | 35 | 0.474791 | 67 | $5.95 \times 10^{-13}$ |

Events-01 and -04 segregated 2:1 and 3:1 respectively (R:S) for FINALE™ resistance in the $T_2$ generation.

Events-01 and -04 of ME17567 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 61—Analysis of ME17932 Events

ME17932 contains Ceres Annot:875012 (At3g53560, SEQ ID NO:1509) from *Arabidopsis thaliana*, which encodes a 340 amino acid chloroplast lumen common family protein. Evaluation of low-nitrogen tolerance for ME17932 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Four events, -01, -02, -03 and -05, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME17932 seedlings is shown in Table 66. ME17932 events were also tested for enhanced growth on the low ammonium nitrate media. No significant differences between the transgenics and the controls were observed.

TABLE 66 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME17932 | ME17932-01 ($T_2$) | 0.6292 | 36 | 0.6094 | 194 | 0.050 |
| ME17932 | ME17932-01 ($T_3$) | 0.6640 | 22 | 0.6094 | 194 | $2.82 \times 10^{-6}$ |
| ME17932 | ME17932-02 ($T_2$) | 0.6351 | 32 | 0.6094 | 194 | $1.05 \times 10^{-2}$ |
| ME17932 | ME17932-02 ($T_3$) | 0.6373 | 20 | 0.6094 | 194 | $2.82 \times 10^{-2}$ |
| ME17932 | ME17932-03 ($T_2$) | 0.6504 | 45 | 0.6094 | 194 | $1.80 \times 10^{-5}$ |
| ME17932 | ME17932-03 ($T_3$) | 0.6708 | 20 | 0.6094 | 194 | $8.38 \times 10^{-4}$ |
| ME17932 | ME17932-05 ($T_2$) | 0.6349 | 24 | 0.6094 | 194 | $3.23 \times 10^{-2}$ |
| ME17932 | ME17932-05 ($T_3$) | 0.6615 | 11 | 0.6094 | 194 | $1.16 \times 10^{-3}$ |

Events-01, -02, -03 and -05 segregated 3:1, 2:1, 15:1 and 1:1 respectively (R:S) for FINALE™ resistance in the $T_2$ generation.

Events-01, -02, -03 and -05 of ME17932 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 62—Analysis of ME17936 Events

ME17936 contains Ceres Annot:874016 (At3g42800, SEQ ID NO:1524) from *Arabidopsis thaliana*, which encodes a 341 amino acid protein of unknown function. Evaluation of low-nitrogen tolerance for ME17936 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -05, showed significantly increased photosynthetic efficiency on low nitrate-containing media relative to the internal controls in both generations at $p \leq 0.05$ using a one-tailed t-test assuming unequal variance. A summary of photosynthetic efficiency of ME17936 seedlings is shown in Table 67. ME17936 events were also tested for for enhanced growth on the low nitrate media as well as for increased photosynthetic efficiency and enhanced growth on low ammonium nitrate media. No significant differences between the transgenics and the controls were observed.

TABLE 67 t-test comparison of seedling photosynthetic efficiency between transgenic seedlings and pooled non-transgenic segregants after 14 days of growth on low nitrate media.

| Line | Events | Transgenic Fv/Fm | n | Pooled Non-Transgenics Fv/Fm | n | t-test p-value |
|---|---|---|---|---|---|---|
| ME17936 | ME17936-01 ($T_2$) | 0.64778 | 36 | 0.61762 | 39 | $4.68 \times 10^{-3}$ |
| ME17936 | ME17936-01 ($T_3$) | 0.66081 | 21 | 0.61762 | 39 | $4.33 \times 10^{-5}$ |
| ME17936 | ME17936-05 ($T_2$) | 0.63189 | 35 | 0.61444 | 50 | $2.73 \times 10^{-2}$ |
| ME17936 | ME17936-05 ($T_3$) | 0.64257 | 14 | 0.61444 | 50 | $2.56 \times 10^{-2}$ |

Events-01 and -05 segregated 3:1 (R:S) for FINALE™ resistance in the $T_2$ generation.

Events-01 and -05 of ME17936 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 63—Analysis of ME18275 Events

ME18275 contains Ceres Annot:827304 (At2g18300, SEQ ID NO:1536) from *Arabidopsis thaliana*, which encodes a 335 amino acid helix-loop-helix DNA-binding domain. Evaluation of low-nitrogen tolerance for ME18275 in $T_2$ and $T_3$ was conducted under the same conditions as described in Examples 2 and 3. A summary of the enhanced growth of ME18275 events on low nitrate-containing media is shown in Table 68. In this study, the seedling area for transgenic plants within an event was compared to the seedling area for non-transgenic segregants pooled across the same line. Three events, -01, -02 and -03, were found significantly larger than the pooled non-transgenic segregants after 14 days of growth on low nitrate-containing media relative to the internal controls in both generations at p≤0.05, using a one-tailed t-test assuming unequal variance. ME18275 events were also tested for photosynthetic efficiency on the low nitrate media as well as for increased photosynthetic efficiency and enhanced growth on low ammonium nitrate media. No significant differences between the transgenics and the controls were observed.

TABLE 68 t-test comparison of seedling area between transgenic seedlings and pooled non-transgenic segregants after 14 days of growth on low nitrate.

| Line | Events | Transgenic Area | n | Pooled Non-Transgenics Area | n | t-test p-value |
|---|---|---|---|---|---|---|
| ME18275 | ME18275-01 ($T_2$) | 0.09574 | 40 | 0.05961 | 10 | $3.24 \times 10^{-10}$ |
| ME18275 | ME18275-01 ($T_3$) | 0.07807 | 32 | 0.05142 | 15 | $3.71 \times 10^{-4}$ |
| ME18275 | ME18275-02 ($T_2$) | 0.11903 | 33 | 0.05884 | 16 | $6.21 \times 10^{-14}$ |
| ME18275 | ME18275-02 ($T_3$) | 0.08552 | 22 | 0.04208 | 24 | $2.82 \times 10^{-5}$ |
| ME18275 | ME18275-03 ($T_2$) | 0.10281 | 39 | 0.06789 | 9 | $9.48 \times 10^{-8}$ |
| ME18275 | ME18275-03 ($T_3$) | 0.09136 | 20 | 0.05646 | 26 | $9.46 \times 10^{-4}$ |

Events-01, -02 and -03 segregated 3:1 (R:S) for FINALE™ resistance in the $T_2$ generation.

Events-01, -02 and -03 of ME18275 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 64—Analysis of ME18924 Events

ME18924 contains Ceres Annot:869192 (At1g72160, SEQ ID NO:1553) from *Arabidopsis thaliana*, which encodes a 490 amino acid emp24/gp25L/p24 family protein. Evaluation of low-nitrogen tolerance for ME18924 in $T_2$ and $T_3$ was conducted under the same conditions as described in Examples 2 and 3. A summary of photosynthetic efficiency of ME18924 seedlings is shown in Table 69. In this study, the seedling photosynthetic efficiency was measured as Fv/Fm comparing transgenic plants within an event to non-transgenic segregants pooled across the same plate. Three events, -02, -04 and -05, showed significantly increased photosynthetic efficiency on low ammonium nitrate-containing media relative to the internal controls in both generations at p≤0.05, using a one-tailed t-test assuming unequal variance.

TABLE 69 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME18924 | ME18924-02 ($T_2$) | 0.6515 | 46 | 0.6223 | 138 | $6.43 \times 10^{-3}$ |
| ME18924 | ME18924-02 ($T_3$) | 0.6639 | 45 | 0.6223 | 138 | $1.52 \times 10^{-4}$ |
| ME18924 | ME18924-04 ($T_2$) | 0.6489 | 33 | 0.6223 | 138 | $2.72 \times 10^{-3}$ |
| ME18924 | ME18924-04 ($T_3$) | 0.6517 | 21 | 0.6223 | 138 | $1.58 \times 10^{-2}$ |
| ME18924 | ME18924-05 ($T_2$) | 0.6602 | 35 | 0.6223 | 138 | $5.55 \times 10^{-5}$ |
| ME18924 | ME18924-05 ($T_3$) | 0.6488 | 31 | 0.6223 | 138 | $4.25 \times 10^{-2}$ |

ME18924 events were also tested for enhanced growth on the low ammonium nitrate media. A summary of the enhanced growth of ME18924 events on low nitrate-containing media is shown in Table 70. In this study, the seedling area for transgenic plants within an event was compared to the seedling area for non-transgenic segregants pooled across the same line. Two events, -01 and -04, were found significantly larger than the pooled non-transgenic segregants after 18 days of growth on low ammonium nitrate-containing media relative to the internal controls in both generations at p≤0.05, using a one-tailed t-test assuming unequal variance.

TABLE 70 t-test comparison of seedling area between transgenic seedlings and pooled non-transgenic segregants after 18 days of growth on low ammonium nitrate.

| Line | Events | Transgenic Area | n | Pooled Non-Transgenics Area | n | t-test p-value |
|---|---|---|---|---|---|---|
| ME18924 | ME18924-01 ($T_2$) | 0.06881 | 37 | 0.06311 | 138 | $1.31 \times 10^{-2}$ |
| ME18924 | ME18924-01 ($T_3$) | 0.07164 | 34 | 0.06311 | 138 | $7.43 \times 10^{-3}$ |
| ME18924 | ME18924-04 ($T_2$) | 0.08401 | 33 | 0.06311 | 138 | $5.64 \times 10^{-8}$ |
| ME18924 | MEI 8924-04 ($T_3$) | 0.07365 | 21 | 0.06311 | 138 | $3.82 \times 10^{-2}$ |

Events-01, -02, -04 and -05 segregated 3:1, 15:1, 2:1 and 2:1 respectively (R:S) for FINALE™ resistance in the $1_2$ generation.

Events-01, -02, -04 and -05 of ME18924 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 65—Analysis of ME19182 Events

ME19182 contains Ceres Annot:876419 (At4g01480, SEQ ID NO:1576) from *Arabidopsis thaliana*, which encodes a 216 amino acid inorganic pyrophosphatase protein. Evaluation of low-nitrogen tolerance for ME19182 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -03, showed significantly increased photosynthetic efficiency on low ammonium nitrate-containing media relative to the internal controls in both generations at p≤0.05 using a one-tailed t-test assuming unequal variance. A summary of photosynthetic efficiency of ME19182 seedlings is shown in Table 71. ME19182 events were also tested for enhanced growth on the low ammonium nitrate media. No significant differences between the transgenics and the controls were observed.

TABLE 71 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME19182 | ME19182-01 ($T_2$) | 0.64938 | 24 | 0.61988 | 154 | $2.47 \times 10^{-2}$ |
| ME19182 | ME19182-01 ($T_3$) | 0.65546 | 13 | 0.61988 | 154 | $1.08 \times 10^{-2}$ |
| ME19182 | ME19182-03 ($T_2$) | 0.64797 | 37 | 0.61988 | 154 | $3.84 \times 10^{-3}$ |
| ME19182 | ME19182-03 ($T_3$) | 0.65388 | 26 | 0.61988 | 154 | $3.15 \times 10^{-3}$ |

Events-01 and -03 segregated 2:1 and 3:1 respectively (R:S) for FINALE™ resistance in the T2 generation.

Events-01 and -03 of ME19182 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 66—Analysis of ME20628 Events

ME20628 contains Ceres Annot:859276 (At2g21230, SEQ ID NO:175) from *Arabidopsis thaliana*, which encodes a 188 amino acid protein of unknown function. Evaluation of low-nitrogen tolerance for ME20628 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -03 and -04, showed significantly increased photosynthetic efficiency on low nitrate-containing media relative to the internal controls in both generations at p≤0.05 using a one-tailed t-test assuming unequal variance. A summary of photosynthetic efficiency of ME20628 seedlings is shown in Table 72. ME20628 events were also tested for enhanced growth on the low nitrate media as well as for increased photosynthetic efficiency and enhanced growth on low ammonium nitrate media. No significant differences between the transgenics and the controls were observed.

TABLE 72 t-test comparison of seedling photosynthetic efficiency between transgenic seedlings and pooled non-transgenic segregants after 14 days of growth on low nitrate media.

| Line | Events | Transgenic Fv/Fm | n | Pooled Non-Transgenics Fv/Fm | n | t-test p-value |
|---|---|---|---|---|---|---|
| ME20628 | ME20628-03 ($T_2$) | 0.62771 | 42 | 0.58957 | 7 | $9.94 \times 10^{-3}$ |
| ME20628 | ME20628-03 ($T_3$) | 0.64375 | 20 | 0.61914 | 28 | $2.97 \times 10^{-2}$ |
| ME20628 | ME20628-04 ($T_2$) | 0.62439 | 38 | 0.59667 | 12 | $4.78 \times 10^{-2}$ |
| ME20628 | ME20628-04 ($T_3$) | 0.64768 | 22 | 0.61360 | 25 | $9.93 \times 10^{-4}$ |

Events-03 and -04 segregated 3:1 (R:S) for FINALE™ resistance in the $T_2$ generation.

Events-03 and -04 of ME20628 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 67—Determination of Functional Homologs by Reciprocal BLAST

A candidate sequence was considered a functional homolog of a reference sequence if the candidate and reference sequences encoded proteins having a similar function and/or activity. A process known as Reciprocal BLAST (Rivera et al. (1998) *Proc. Natl. Acad. Sci. USA*, 95:6239-6244) was used to identify potential functional homolog sequences from databases consisting of all available public and proprietary peptide sequences, including NR from NCBI and peptide translations from Ceres clones.

Before starting a Reciprocal BLAST process, a specific reference polypeptide was searched against all peptides from its source species using BLAST in order to identify polypeptides having BLAST sequence identity of 80% or greater to the reference polypeptide and an alignment length of 85% or greater along the shorter sequence in the alignment. The reference polypeptide and any of the aforementioned identified polypeptides were designated as a cluster.

The BLASTP version 2.0 program from Washington University at Saint Louis, Mo., USA was used to determine BLAST sequence identity and E-value. The BLASTP version 2.0 program includes the following parameters: 1) an E-value cutoff of 1.0e-5; 2) a word size of 5; and 3) the -postsw option. The BLAST sequence identity was calculated based on the alignment of the first BLAST HSP (High-scoring Segment Pairs) of the identified potential functional homolog sequence with a specific reference polypeptide. The number of identically matched residues in the BLAST HSP alignment was divided by the HSP length, and then multiplied by 100 to get the BLAST sequence identity. The HSP length typically included gaps in the alignment, but in some cases gaps were excluded.

The main Reciprocal BLAST process consists of two rounds of BLAST searches; forward search and reverse search. In the forward search step, a reference polypeptide sequence, "polypeptide A," from source species SA was BLASTed against all protein sequences from a species of interest. Top hits were determined using an E-value cutoff of $10^{-5}$ and a sequence identity cutoff of 35%. Among the top hits, the sequence having the lowest E-value was designated as the best hit, and considered a potential functional homolog or ortholog. Any other top hit that had a sequence identity of 80% or greater to the best hit or to the original reference polypeptide was considered a potential functional homolog or ortholog as well. This process was repeated for all species of interest.

In the reverse search round, the top hits identified in the forward search from all species were BLASTed against all protein sequences from the source species SA. A top hit from the forward search that returned a polypeptide from the aforementioned cluster as its best hit was also considered as a potential functional homolog.

Functional homologs were identified by manual inspection of potential functional homolog sequences. Representative functional homologs for SEQ ID NO:3, SEQ ID NO:49, SEQ ID NO:77, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1463, SEQ ID NO:1491, SEQ ID NO:1510, SEQ ID NO:1525, SEQ ID NO:1537, SEQ ID NO:1554, SEQ ID NO:1577, and SEQ ID NO:1437 are shown in FIGS. 1-57, respectively. Additional exemplary homologs are correlated to certain Figures in the Sequence Listing.

Example 68—Determination of Functional Homologs by Hidden Markov Models

Hidden Markov Models (HMMs) were generated by the program HMMER 2.3.2. To generate each HMM, the default HMMER 2.3.2 program parameters, configured for global alignments, were used.

An HMM was generated using the sequences shown in FIG. 1 as input. These sequences were fitted to the model and a representative HMM bit score for each sequence is shown in the Sequence Listing. Additional sequences were fitted to the model, and representative HMM bit scores for any such additional sequences are shown in the Sequence Listing. The results indicate that these additional sequences are functional homologs of SEQ ID NO:3.

The procedure above was repeated and an HMM was generated for each group of sequences shown in FIGS. 2-57, using the sequences shown in each Figure as input for that HMM. A representative bit score for each sequence is shown in the Sequence Listing. Additional sequences were fitted to certain HMMs, and representative HMM bit scores for such additional sequences are shown in the Sequence Listing. The results indicate that these additional sequences are functional homologs of the sequences used to generate that HMM.

VIII. OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11396659B2). An electronic copy of the "Sequence Listing" will also be available from the USPTO upon request and payment of the fee set forth in 37 CFR 1.19(b)(3).

What is claimed is:

1. A method of producing a plant, said method comprising regenerating a plant from a plant cell comprising an exogenous nucleic acid molecule, said exogenous nucleic acid molecule comprising a regulatory region operably linked to a nucleotide sequence, wherein the nucleotide sequence comprises a polynucleotide sequence having 95 percent or greater sequence identity to the nucleic acid sequence of SEQ ID NO:151, or wherein the nucleotide sequence encodes a polypeptide, said polypeptide comprising an amino acid sequence having 95 percent or greater sequence identity to the amino acid sequence of SEQ ID NO:152, and wherein said plant has an increased level of low-nitrogen tolerance as compared to the corresponding level of low-nitrogen tolerance of a control plant that does not comprise said nucleic acid molecule.

2. The method of claim 1, wherein the polypeptide comprises the amino acid sequence of SEQ ID NO:152.

3. A method of increasing the level of low-nitrogen tolerance in a plant, said method comprising introducing into a plant cell an exogenous nucleic acid molecule, said exogenous nucleic acid molecule comprising a regulatory region operably linked to a nucleotide sequence, wherein the nucleotide sequence comprises a polynucleotide sequence having 95 percent or greater sequence identity to the nucleic acid sequence of SEQ ID NO:151, or wherein the nucleotide sequence encodes a polypeptide, said polypeptide comprising an amino acid sequence having 95 percent or greater sequence identity to the amino acid sequence of SEQ ID NO:152, and wherein a plant produced from said plant cell has an increased level of low-nitrogen tolerance as compared to the corresponding level of low-nitrogen tolerance of a control plant that does not comprise said exogenous nucleic acid molecule.

4. The method claim 3, wherein said polypeptide comprises the amino acid sequence of SEQ ID NO:152.

5. The method of claim 3, wherein the nucleic acid molecule comprises the nucleic acid sequence of SEQ ID NO:151.

6. A plant cell comprising an exogenous nucleic acid molecule, said exogenous nucleic acid molecule comprising a regulatory region operably linked to a nucleotide sequence, wherein the nucleotide sequence comprises a polynucleotide sequence having 95 percent or greater sequence identity to the nucleic acid sequence of SEQ ID NO:151, or wherein the nucleotide sequence encodes a polypeptide, said polypeptide comprising an amino acid sequence having 95 percent or greater sequence identity to the amino acid sequence of SEQ ID NO:152, and wherein a plant regenerated from said plant cell has an increased level of low-nitrogen tolerance as compared to the corresponding level of low-nitrogen tolerance of a control plant that does not comprise said nucleic acid molecule.

7. A transgenic plant comprising the plant cell of claim 6.

8. The transgenic plant of claim 7, wherein said plant is a member of a species selected from the group consisting of *Panicum virgatum* (switchgrass), *Sorghum bicolor* (sorghum, sudangrass), *Miscanthus giganteus* (*miscanthus*), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

9. A product comprising plant tissue from the transgenic plant according to claim 8.

10. The plant cell of claim 6, wherein the polypeptide comprises the amino acid sequence of SEQ ID NO:152.

11. The plant cell of claim 6, wherein the nucleotide sequence comprises the nucleic acid sequence of SEQ ID NO:151.

* * * * *